(12) United States Patent
Lu et al.

(10) Patent No.: US 10,806,785 B2
(45) Date of Patent: Oct. 20, 2020

(54) IMMUNOMODULATOR COMPOUNDS AND METHODS OF USE

(71) Applicant: Incyte Corporation, Wilmington, DE (US)

(72) Inventors: Liang Lu, Hockessin, DE (US); Wenyu Zhu, Media, PA (US); Ding-Quan Qian, Newark, DE (US); Kaijiong Xiao, Clark, NJ (US)

(73) Assignee: Incyte Corporation, Wilmington, DE (US)

( * ) Notice: Subject to any disclaimer, the term of this patent is extended or adjusted under 35 U.S.C. 154(b) by 231 days.

(21) Appl. No.: 15/851,497

(22) Filed: Dec. 21, 2017

(65) Prior Publication Data

US 2018/0177870 A1 Jun. 28, 2018

Related U.S. Application Data

(60) Provisional application No. 62/487,457, filed on Apr. 19, 2017, provisional application No. 62/569,936, (Continued)

(51) Int. Cl.
*A61K 39/39* (2006.01)
*A61P 37/00* (2006.01)
(Continued)

(52) U.S. Cl.
CPC .............. *A61K 39/39* (2013.01); *A61K 45/06* (2013.01); *A61P 35/00* (2018.01); *A61P 37/00* (2018.01);
(Continued)

(58) Field of Classification Search
CPC .......... A61P 37/00; A61P 37/04; A61P 35/00; C07D 213/81; C07D 263/57;
(Continued)

(56) References Cited

U.S. PATENT DOCUMENTS 3,272,781 A 9/1966 Goodrow
4,208,328 A 6/1980 Lavallee et al.
(Continued)

FOREIGN PATENT DOCUMENTS

CA 2355249 6/2000
CL 2018001531 7/2018
(Continued)

OTHER PUBLICATIONS

Abdellaoui et al., "Palladium-catalyzed non-directed C-H bond acylation of difluorobenzenes and dichlorobenzenes bearing benzoxazole or benzothiazole," Catalysis Communications, 2015, 71:13-16.
(Continued)

*Primary Examiner* — Angela C Brown-Pettigrew
(74) *Attorney, Agent, or Firm* — Fish & Richardson P.C.

(57) ABSTRACT

Compositions and methods for inducing PD-L1 internalization are disclosed. The methods include reducing the amount of cell surface PD-L1 by contacting a cell expressing PD-L1 with a compound that binds to cell surface PD-L1 and induces PD-L1 internalization. Compounds that induce PD-L1 internalization can be used to enhance, stimulate and/or increase an immune response and treat a PD-1-related disease or condition.

17 Claims, 4 Drawing Sheets

Related U.S. Application Data filed on Oct. 9, 2017, provisional application No. 62/438,001, filed on Dec. 22, 2016, provisional application No. 62/487,341, filed on Apr. 19, 2017, provisional application No. 62/438,009, filed on Dec. 22, 2016, provisional application No. 62/487,336, filed on Apr. 19, 2017, provisional application No. 62/551,033, filed on Aug. 28, 2017, provisional application No. 62/438,020, filed on Dec. 22, 2016, provisional application No. 62/487,356, filed on Apr. 19, 2017, provisional application No. 62/438,038, filed on Dec. 22, 2016, provisional application No. 62/487,362, filed on Apr. 19, 2017, provisional application No. 62/551,011, filed on Aug. 28, 2017, provisional application No. 62/437,998, filed on Dec. 22, 2016, provisional application No. 62/487,365, filed on Apr. 19, 2017.

(51) Int. Cl.

| | |
|---|---|
| *A61P 37/04* | (2006.01) |
| *A61P 35/00* | (2006.01) |
| *A61K 45/06* | (2006.01) |
| *C07D 213/81* | (2006.01) |
| *C07D 263/57* | (2006.01) |
| *C07D 413/06* | (2006.01) |
| *C07D 413/14* | (2006.01) |
| *C07D 471/04* | (2006.01) |
| *C07D 519/00* | (2006.01) |
| *G01N 33/50* | (2006.01) |
| *A61K 39/00* | (2006.01) |

(52) U.S. Cl.
CPC ............ *A61P 37/04* (2018.01); *C07D 213/81* (2013.01); *C07D 263/57* (2013.01); *C07D 413/06* (2013.01); *C07D 413/14* (2013.01); *C07D 471/04* (2013.01); *C07D 519/00* (2013.01); *G01N 33/5026* (2013.01); *A61K 2039/55511* (2013.01)

(58) Field of Classification Search
CPC .. C07D 413/06; C07D 413/14; C07D 471/04; C07D 519/00
See application file for complete search history.

(56) References Cited

U.S. PATENT DOCUMENTS

| | | | |
|---|---|---|---|
| 4,789,711 | A | 12/1988 | Monnier et al. |
| 5,077,164 | A | 12/1991 | Ueda et al. |
| 6,114,497 | A | 9/2000 | Tada et al. |
| 6,297,351 | B1 | 10/2001 | Murayama et al. |
| 6,372,907 | B1 | 4/2002 | Lee et al. |
| 6,521,618 | B2 | 2/2003 | Boschelli et al. |
| 6,867,200 | B1 | 3/2005 | Allen et al. |
| 7,320,989 | B2 | 1/2008 | Anderson et al. |
| 8,541,424 | B2 | 9/2013 | DeGoey et al. |
| 8,993,604 | B2 | 3/2015 | Byrd et al. |
| 9,163,017 | B2 | 10/2015 | DeGoey et al. |
| 9,540,322 | B2 | 1/2017 | Jorgensen et al. |
| 9,643,922 | B2 | 5/2017 | Jorgensen et al. |
| 10,017,520 | B2 | 7/2018 | Koehler et al. |
| 10,202,343 | B2 | 2/2019 | Jorgensen et al. |
| 10,308,644 | B2 | 6/2019 | Wu et al. |
| 2002/0082266 | A1 | 6/2002 | Gallant et al. |
| 2003/0134843 | A1 | 7/2003 | Lubisch et al. |
| 2004/0058938 | A1 | 3/2004 | Cullmann et al. |
| 2004/0063963 | A1 | 4/2004 | Ueno et al. |
| 2004/0082635 | A1 | 4/2004 | Hashimoto et al. |
| 2004/0186114 | A1 | 9/2004 | Cirillo et al. |
| 2004/0214040 | A1 | 10/2004 | Lee et al. |
| 2005/0187230 | A1 | 8/2005 | Ding et al. |
| 2005/0245536 | A1 | 11/2005 | Hao et al. |
| 2005/0260126 | A1 | 11/2005 | Kudo et al. |
| 2005/0288295 | A1 | 12/2005 | Currie et al. |
| 2006/0004010 | A1 | 1/2006 | Habashita et al. |
| 2006/0089362 | A1 | 4/2006 | Seno et al. |
| 2006/0178367 | A1 | 8/2006 | Currie et al. |
| 2006/0229337 | A1 | 10/2006 | Brittelli et al. |
| 2006/0270686 | A1 | 11/2006 | Kelly et al. |
| 2007/0099938 | A1 | 5/2007 | Ohmoto et al. |
| 2007/0191395 | A1 | 8/2007 | Kawakami et al. |
| 2008/0139557 | A1 | 6/2008 | Blomgren et al. |
| 2008/0153834 | A1 | 6/2008 | Blomgren et al. |
| 2008/0280891 | A1 | 11/2008 | Kelly et al. |
| 2009/0253735 | A1 | 10/2009 | Almario-Garcia et al. |
| 2009/0281075 | A1 | 11/2009 | Roughton et al. |
| 2009/0281120 | A1 | 11/2009 | Nakai et al. |
| 2009/0304821 | A1 | 12/2009 | Notoya et al. |
| 2010/0155712 | A1 | 6/2010 | Kitamura |
| 2010/0160292 | A1 | 6/2010 | Whitney et al. |
| 2010/0249151 | A1 | 9/2010 | Klein et al. |
| 2010/0267775 | A1 | 10/2010 | Negoro et al. |
| 2010/0267778 | A1 | 10/2010 | Kusuda et al. |
| 2010/0273832 | A1 | 10/2010 | Jung et al. |
| 2010/0292227 | A1 | 11/2010 | Yoakim et al. |
| 2011/0053915 | A1 | 3/2011 | Ivaschenko et al. |
| 2011/0062858 | A1 | 3/2011 | Yersin et al. |
| 2011/0065699 | A1 | 3/2011 | De Peretti et al. |
| 2011/0065700 | A1 | 3/2011 | De Peretti et al. |
| 2011/0065745 | A1 | 3/2011 | De Peretti et al. |
| 2011/0124640 | A1 | 5/2011 | Liu et al. |
| 2011/0294781 | A1 | 12/2011 | Yamamoto et al. |
| 2011/0301145 | A1 | 12/2011 | Barbosa, Jr. et al. |
| 2012/0058996 | A1 | 3/2012 | Liu et al. |
| 2012/0295884 | A1 | 11/2012 | Altmann et al. |
| 2012/0323002 | A1 | 12/2012 | Yamamoto et al. |
| 2012/0328569 | A1 | 12/2012 | McComas et al. |
| 2013/0096118 | A1 | 4/2013 | Liu et al. |
| 2013/0131063 | A1 | 5/2013 | Castro et al. |
| 2013/0203741 | A1 | 8/2013 | Suzuki et al. |
| 2013/0203747 | A1 | 8/2013 | Yoakim et al. |
| 2013/0203754 | A1 | 8/2013 | Yang et al. |
| 2013/0253011 | A1 | 9/2013 | Jung et al. |
| 2014/0058097 | A1 | 2/2014 | Kobayashi et al. |
| 2014/0088117 | A1 | 3/2014 | Burch et al. |
| 2014/0128382 | A1 | 5/2014 | Wu et al. |
| 2014/0243306 | A1 | 8/2014 | Heng et al. |
| 2014/0275058 | A1 | 9/2014 | Minatti et al. |
| 2014/0288094 | A1 | 9/2014 | Bennett et al. |
| 2014/0378447 | A1 | 12/2014 | Okano et al. |
| 2015/0005279 | A1 | 1/2015 | Bonafoux et al. |
| 2015/0011751 | A1 | 1/2015 | Kawakami et al. |
| 2015/0073024 | A1 | 3/2015 | Sasikumar et al. |
| 2015/0181880 | A1 | 7/2015 | Takahashi |
| 2015/0210680 | A1 | 7/2015 | Kobayashi et al. |
| 2015/0232478 | A1 | 8/2015 | Ishida et al. |
| 2015/0239868 | A1 | 8/2015 | Pais et al. |
| 2015/0252011 | A1 | 9/2015 | Minatti et al. |
| 2015/0258505 | A1 | 9/2015 | Hironaka et al. |
| 2015/0291549 | A1 | 10/2015 | Chupak et al. |
| 2015/0299227 | A1 | 10/2015 | Wolkenberg et al. |
| 2015/0307465 | A1 | 10/2015 | Scott et al. |
| 2015/0376172 | A1 | 12/2015 | Guba et al. |
| 2016/0015690 | A1 | 1/2016 | Babaoglu et al. |
| 2016/0046648 | A1 | 2/2016 | Petrukhin et al. |
| 2016/0130251 | A1 | 5/2016 | Graupe et al. |
| 2016/0229816 | A1 | 8/2016 | Sato et al. |
| 2017/0107216 | A1 | 4/2017 | Wu et al. |
| 2017/0145025 | A1 | 5/2017 | Li et al. |
| 2017/0174671 | A1 | 6/2017 | Wu et al. |
| 2017/0174679 | A1 | 6/2017 | Lajkiewicz et al. |
| 2017/0320875 | A1 | 11/2017 | Li et al. |
| 2017/0342060 | A1 | 11/2017 | Lu et al. |
| 2017/0362253 | A1 | 12/2017 | Xiao et al. |
| 2018/0016260 | A1 | 1/2018 | Yu et al. |
| 2018/0057486 | A1 | 3/2018 | Wu et al. |
| 2018/0177784 | A1 | 6/2018 | Wu et al. |
| 2018/0179179 | A1 | 6/2018 | Wu et al. |
| 2018/0179197 | A1 | 6/2018 | Wu et al. |

(56) References Cited

U.S. PATENT DOCUMENTS

| | | |
|---|---|---|
| 2018/0179201 A1 | 6/2018 | Wu et al. |
| 2018/0179202 A1 | 6/2018 | Wu et al. |
| 2018/0273519 A1 | 9/2018 | Wu et al. |
| 2019/0040082 A1 | 2/2019 | Xiao et al. |
| 2019/0062345 A1 | 2/2019 | Xiao et al. |
| 2019/0071439 A1 | 3/2019 | Li et al. |
| 2019/0144439 A1 | 5/2019 | Wu et al. |
| 2019/0202824 A1 | 7/2019 | Wu et al. |
| 2019/0225601 A1 | 7/2019 | Wu et al. |
| 2019/0270706 A1 | 9/2019 | Jorgensen et al. |
| 2019/0300524 A1 | 10/2019 | Wu et al. |
| 2019/0345170 A1 | 11/2019 | Wu et al. |

FOREIGN PATENT DOCUMENTS

| | | |
|---|---|---|
| CL | 2018003734 | 2/2019 |
| CL | 2018003697 | 5/2019 |
| CN | 101891895 | 11/2010 |
| CN | 103933036 | 7/2014 |
| CN | 104045552 | 9/2014 |
| CN | 104211726 | 12/2014 |
| EP | 0644460 | 3/1995 |
| EP | 1505068 | 2/2005 |
| EP | 1942105 | 7/2008 |
| EP | 2233474 | 9/2010 |
| EP | 2402345 | 1/2012 |
| EP | 2871179 | 5/2015 |
| EP | 2824099 | 1/2018 |
| FR | 1425700 | 1/1966 |
| JP | H 10316853 | 12/1998 |
| JP | 2000128986 | 5/2000 |
| JP | 2000128987 | 5/2000 |
| JP | 2000212281 | 8/2000 |
| JP | 2001114893 | 4/2001 |
| JP | 2001163975 | 6/2001 |
| JP | 3461397 | 10/2003 |
| JP | 2003287634 | 10/2003 |
| JP | 2004059761 | 2/2004 |
| JP | 2004294556 | 10/2004 |
| JP | 2005002330 | 1/2005 |
| JP | 2005248082 | 9/2005 |
| JP | 2005290301 | 10/2005 |
| JP | 2006-290883 A | 10/2006 |
| JP | 2008218327 | 9/2008 |
| JP | 2010202530 | 9/2010 |
| JP | 2013084945 | 5/2013 |
| JP | 2015155397 | 8/2015 |
| JP | 2015193612 | 11/2015 |
| JP | 2016135778 | 7/2016 |
| KR | 1715090 | 3/2015 |
| KR | 1717601 | 12/2015 |
| KR | 1653560 | 2/2016 |
| WO | WO 98/27108 | 6/1998 |
| WO | WO 1999/018096 | 4/1999 |
| WO | WO 99/44992 A1 | 9/1999 |
| WO | WO 00/35886 | 6/2000 |
| WO | WO 2001/047883 | 7/2001 |
| WO | WO 01/74815 | 10/2001 |
| WO | WO 2002/000196 | 1/2002 |
| WO | WO 02/14321 | 2/2002 |
| WO | WO 02/48147 | 6/2002 |
| WO | WO 02/066477 | 8/2002 |
| WO | WO 02/071827 | 9/2002 |
| WO | WO 02/078700 | 10/2002 |
| WO | WO 02/083672 | 10/2002 |
| WO | WO 02/088124 | 11/2002 |
| WO | WO 03/022845 | 3/2003 |
| WO | WO 03/031587 | 4/2003 |
| WO | WO 2004/006906 | 1/2004 |
| WO | WO 2004/033454 | 4/2004 |
| WO | WO 2004/035588 | 4/2004 |
| WO | WO 2004/085385 | 10/2004 |
| WO | WO 2005/000833 | 1/2005 |
| WO | WO 2005/014543 | 2/2005 |
| WO | WO 2005/023761 | 3/2005 |
| WO | WO 2005/034869 | 4/2005 |
| WO | WO 2005/063710 | 7/2005 |
| WO | WO 2005/077948 | 8/2005 |
| WO | WO 2005/079802 | 9/2005 |
| WO | WO 2005/080316 | 9/2005 |
| WO | WO 2005/086808 | 9/2005 |
| WO | WO 2005/086904 | 9/2005 |
| WO | WO 2005/097751 | 10/2005 |
| WO | WO 2005/103022 | 11/2005 |
| WO | WO 2005/105798 | 11/2005 |
| WO | WO 2006/050803 | 5/2006 |
| WO | WO 2006/053121 | 5/2006 |
| WO | WO 2006/094235 | 9/2006 |
| WO | WO 2006/125101 | 11/2006 |
| WO | WO 2007/004954 | 1/2007 |
| WO | WO 2007/034282 | 3/2007 |
| WO | WO 2007/067711 | 6/2007 |
| WO | WO 2007/069565 | 6/2007 |
| WO | WO 2007/096764 | 8/2007 |
| WO | WO 2007/113226 | 10/2007 |
| WO | WO 2007/146712 | 12/2007 |
| WO | WO 2008/011560 | 1/2008 |
| WO | WO 2008/027812 | 3/2008 |
| WO | WO 2008/033854 | 3/2008 |
| WO | WO 2008/033857 | 3/2008 |
| WO | WO 2008/033858 | 3/2008 |
| WO | WO 2008/062182 | 5/2008 |
| WO | WO 2008/104077 | 9/2008 |
| WO | WO 2008/104278 | 9/2008 |
| WO | WO 2008/104279 | 9/2008 |
| WO | WO 2008/118122 | 10/2008 |
| WO | WO 2008/134553 | 11/2008 |
| WO | WO 2008/141249 | 11/2008 |
| WO | WO 2009/027733 | 3/2009 |
| WO | WO 2009/038759 | 3/2009 |
| WO | WO 2009/039397 | 3/2009 |
| WO | WO 2009/059162 | 5/2009 |
| WO | WO 2009/062059 | 5/2009 |
| WO | WO 2009/077197 | 6/2009 |
| WO | WO 2009/079683 | 7/2009 |
| WO | WO 2009/106539 | 9/2009 |
| WO | WO 2009/123986 | 10/2009 |
| WO | WO 2009/143156 | 11/2009 |
| WO | WO 2009/146358 | 12/2009 |
| WO | WO 2010/011837 | 1/2010 |
| WO | WO 2010/029950 | 3/2010 |
| WO | WO 2010/056875 | 5/2010 |
| WO | WO 2010/064020 | 6/2010 |
| WO | WO 2010/071885 | 6/2010 |
| WO | WO 2010/075376 | 7/2010 |
| WO | WO 2010/104306 | 9/2010 |
| WO | WO 2010/115736 | 10/2010 |
| WO | WO 2010/119264 | 10/2010 |
| WO | WO 2011/002635 | 1/2011 |
| WO | WO 2011/008709 | 1/2011 |
| WO | WO 2011/018170 | 2/2011 |
| WO | WO 2011/044181 | 4/2011 |
| WO | WO 2011/047129 | 4/2011 |
| WO | WO 2011/047319 | 4/2011 |
| WO | WO 2011/050245 | 4/2011 |
| WO | WO 2011/082400 | 7/2011 |
| WO | WO 2011/097607 | 8/2011 |
| WO | WO 2011/113606 | 9/2011 |
| WO | WO 2011/117264 | 9/2011 |
| WO | WO 2011/140202 | 11/2011 |
| WO | WO 2012/016133 | 2/2012 |
| WO | WO 2012/033735 | 3/2012 |
| WO | WO 2012/034363 | 3/2012 |
| WO | WO 2012/047856 | 4/2012 |
| WO | WO 2012/052730 | 4/2012 |
| WO | WO 2012/052745 | 4/2012 |
| WO | WO 2012/068406 | 5/2012 |
| WO | WO 2012/080376 | 6/2012 |
| WO | WO 2012/088411 | 6/2012 |
| WO | WO 2012/100342 | 8/2012 |
| WO | WO 2012/125886 | 9/2012 |
| WO | WO 2012/129562 | 9/2012 |
| WO | WO 2012/139425 | 10/2012 |
| WO | WO 2012/159565 | 11/2012 |

(56) References Cited

FOREIGN PATENT DOCUMENTS

| | | |
|---|---|---|
| WO | WO 2012/166951 | 12/2012 |
| WO | WO 2012/168733 | 12/2012 |
| WO | WO 2012/175991 | 12/2012 |
| WO | WO 2013/008095 | 1/2013 |
| WO | WO 2013/033901 | 3/2013 |
| WO | WO 2013/040528 | 3/2013 |
| WO | WO 2013/057650 | 4/2013 |
| WO | WO 2013/059594 | 4/2013 |
| WO | WO 2013/120040 | 8/2013 |
| WO | WO 2013/134113 | 9/2013 |
| WO | WO 2013/157021 | 10/2013 |
| WO | WO 2013/163404 | 10/2013 |
| WO | WO 2014/009295 | 1/2014 |
| WO | WO 2014/009296 | 1/2014 |
| WO | WO 2014/017087 | 1/2014 |
| WO | WO 2014/039595 | 3/2014 |
| WO | WO 2014/061693 | 4/2014 |
| WO | WO 2014/081878 | 5/2014 |
| WO | WO 2014/113388 | 7/2014 |
| WO | WO 2014/114532 | 7/2014 |
| WO | WO 2014/133046 | 9/2014 |
| WO | WO 2014/138484 | 9/2014 |
| WO | WO 2014/138791 | 9/2014 |
| WO | WO 2014/152536 | 9/2014 |
| WO | WO 2014/159959 | 10/2014 |
| WO | WO 2014/181287 | 11/2014 |
| WO | WO 2015/000715 | 1/2015 |
| WO | WO 2015/013635 | 1/2015 |
| WO | WO 2015/018940 | 2/2015 |
| WO | WO 2015/033299 | 3/2015 |
| WO | WO 2015/033301 | 3/2015 |
| WO | WO 2015/034820 | 3/2015 |
| WO | WO 2015/036927 | 3/2015 |
| WO | WO 2015/086499 | 6/2015 |
| WO | WO 2015/086502 | 6/2015 |
| WO | WO 2015/086512 | 6/2015 |
| WO | WO 2015/095337 | 6/2015 |
| WO | WO 2015/101622 | 7/2015 |
| WO | WO 2015/120364 | 8/2015 |
| WO | WO 2015/150097 | 10/2015 |
| WO | WO 2015/160641 | 10/2015 |
| WO | WO 2015/197028 | 12/2015 |
| WO | WO 2016/044604 | 3/2016 |
| WO | WO 2016/094688 | 6/2016 |
| WO | WO 2016/116525 | 7/2016 |
| WO | WO 2016/118404 | 7/2016 |
| WO | WO 2016/156282 | 10/2016 |
| WO | WO 2017/035405 | 3/2017 |
| WO | WO 2017/066227 | 4/2017 |
| WO | WO 2017/070089 | 4/2017 |
| WO | WO 2017/070320 | 4/2017 |
| WO | WO 2017/087777 | 5/2017 |
| WO | WO 2017/106634 | 6/2017 |
| WO | WO 2017/108569 | 6/2017 |
| WO | WO 2017/109041 | 6/2017 |
| WO | WO 2017/112617 | 6/2017 |
| WO | WO 2017/112730 | 6/2017 |
| WO | WO 2017/192961 | 11/2017 |
| WO | WO 2017/205464 | 11/2017 |
| WO | WO 2017/222976 | 12/2017 |
| WO | WO 2018/013789 | 1/2018 |
| WO | WO 2018/026971 | 2/2018 |
| WO | WO 2018/044783 | 3/2018 |
| WO | WO 2016/057500 | 4/2018 |
| WO | WO 2018/119221 | 6/2018 |
| WO | WO 2018/119224 | 6/2018 |
| WO | WO 2018/119236 | 6/2018 |
| WO | WO 2018/119263 | 6/2018 |
| WO | WO 2018/119266 | 6/2018 |
| WO | WO 2018/119286 | 6/2018 |
| WO | WO 2018/195321 | 10/2018 |
| WO | WO 2019/023575 | 1/2019 |
| WO | WO 2019/032547 | 2/2019 |
| WO | WO 2019/034172 | 2/2019 |
| WO | WO 2019/191707 | 10/2019 |
| WO | WO 2019/192506 | 10/2019 |
| WO | WO 2019/204609 | 10/2019 |

OTHER PUBLICATIONS

Ahmed et al., "Enantioselective Polymerization of Epoxides Using Biaryl-Linked Bimetallic Cobalt Catalysts: A Mechanistic Study," J Am Chem Soc., 2013, 135(50):18901-18911.

Amaya et al., "Synthesis of three-dimensionally arranged bis-biphenol ligand on hexaaryl benzene scaffold and its application for cross-pinacol coupling reaction," Tetrahedron Letters, 2011, 52(35):4567-4569.

Anyika et al., "Point-to-Axial Chirality Transfer-A New Probe for "Sensing" the Absolute Configurations of Monoamines," J Am Chem Soc., 2014, 136(2):550-553.

Arkin et al., "Small-Molecule Inhibitors of Protein-Protein Interactions: Progressing toward the Reality," Chemistry & Biology, Sep. 2014, 21:1102-1114.

Arkin et al., "Small-Molecule Inhibitors of Protein—Protein Interactions: Progressing Towards the Dream," Nature Reviews, Apr. 2004, 3:301-317.

Artz et al., "Host-guest complexation. 28. Hemispherands with four self-organizing units," J Am Chem Soc., 1984, 106(7):2160-2171.

Atzrodt et al., The Renaissance of H/D Exchange, Angew Chem Int Ed., 2007, 7744-7765.

Barakat, "Do We Need Small Molecule Inhibitors for the Immune Checkpoints?" J. Pharma. Care Health Sys., 2014, 1(4):1000e119.

Barber et al, "Restoring function in exhausted CD8 T cells during chronic viral infection," Nature, Feb. 2006, 439:682-687.

Bentley et al., "Antenna Biphenols: Development of Extended Wavelength Chiroptical Reporters," J Org Chem., 2016, 81(3):1185-1191.

Berg, "Modulation of Protein—Protein Interactions with Small Organic Molecules," Angew. Chem. Int. Ed., 2003, 42:2462-2481.

Berge et al., "Pharmaceutical Salts," J. Pharm. Sci., Jan. 1977, 66(1):1-19.

Blank et al, "PD-L1/B7H-1 Inhibits the Effector Phase of Tumor Rejection by T Cell Receptor (TCR) Transgenic CD8+ T Cells," Cancer Res., Feb. 2004, 64(3):1140-5.

Blom et al., "Optimizing Preparative LC-MS Configurations and Methods for Parallel Synthesis Purification", J. Combi. Chem., 2003, 5:670-83.

Blom et al., "Preparative LC-MS Purification: Improved Compound Specific Method Optimization", J. Combi. Chem., Nov. 2004, 6:874-883.

Blom, "Two-Pump at Column Dilution Configuration for Preparative LC-MS", K. Blom, J. Combi. Chem., 2002, 4:295-301.

Bross et al., "Radiation damage to 2-(2'-hydroxyphenyl)benzothiazoles," Radiation Physics and Chemistry, Jul. 1992, 41:379-387.

Buisman et al., "Chiral Cooperativity in Diastereomeric Diphosphite Ligands: Effects on the Rhodium-Catalyzed Enantioselective Hydroformylation of Styrene," Organometallics, 1997, 16(13):2929-2939.

Carter et al, "PD-1:PD-L inhibitory pathway affects both CD4+ and CD8+ T cells and is overcome By IL-2," Eur. J. Immunol., 2002, 32(3):634-643.

Chang et al., "Blocking of the PD-1/PD-L1 Interaction by a d-Peptide Antagonist for Cancer Immunotherapy," Angew. Chem. Int. Ed., 2015, 127(40):11926-11930.

Chang et al., "Blocking of the PD-1/PD-L1 Interaction by a d-Peptide Antagonist for Cancer Immunotherapy: Supporting Information" Angew. Chem. Int. Ed., 2015, 26 pages.

Chen et al., "Anti-PD-1/PD-L1 therapy of human cancer: past, present, and future," J. Clin. Invest., Sep. 2015, 125(9):3384-3391.

Cheng et al., "Synthetic connections to the aromatic directed metalation reaction. Iterative ortho metalation-cross coupling tactics for the construction of polyphenyls," Tetrahedron Letters, 1978, 28(43):5097-5098.

Cheng et al., "Recent Advances in Small Molecule Based Cancer Immunotherapy," Eur J Med Chem., 2018, 157:582-598.

(56) References Cited

OTHER PUBLICATIONS

Cheng et al., "Structure and Interactions of the Human Programmed Cell Death 1 Receptor," J. Bio. Chem., Apr. 2013, 288(17):11771-11785.
Chilean Office Action in Chilean Application No. 201801685, dated Aug. 20, 2019, 18 pages.
Chilean Office Action in Chilean Application No. 201803701, dated Nov. 22, 2019, 18 page.
Clayden et al., "Conformational Preference and Remote (1,10) Stereocontrol in Biphenyl-2,2'-dicalboxamides," Org. Lett., 2001, 3(26):4133-4136.
Cram et al., "Host-guest complexation. 32. Spherands composed of cyclic urea and anisyl units," J Am Chem Soc., 1984, 106(23):7150-7167.
Cram et al., "Host-guest complexation. 29. Expanded hemispherands," J Am Chem Soc., 1984, 106(11):6386-3292.
Cram et al., "Host-guest complexation. 26. Cavitands composed of fluorobenzene units bonded in their 2,6-positions to form macrocycles," J Am Chem Soc., 1984, 106(3):695-701.
Cram et al., "Spherand hosts containing cyclic urea units," J Am Chem Soc., 1982, 104(24):6828-6830.
Curis, "Overview and Path for Growth," Aurigene Strategic Collaboration, Jan. 21, 2015, 13 slides.
Database Accession No. 1590700-72-3 abstract, Apr. 27, 2014, 1 page.
Database Accession No. 1581556-71-9 abstract, Apr. 8, 2014, 1 page.
Database Accession No. 1580823-55-7 abstract, Apr. 6, 2014, 1 page.
Database Accession No. 1568738-04-4 abstract, Mar. 14, 2014, 1 page.
Database Accession No. 1478989-52-4 abstract, Nov. 22, 2013, 1 page.
Database Accession No. 2013:447446 abstract, 2013, 1 page.
De Lucca et al., "Small Molecule Reversible Inhibitors of Bruton's Tyrosine Kinase (BTK): Structure-Activity Relationships Leading to the Identification of 7-(2-Hydroxypropan-2-yl)-4[2-methy1-3-(4-oxo-3,4-dihydroquinazolin-3-yl)pheny1]-9H-carbazole-1-carboxamide (BMS-935177),"Journal of Medicinal Chemistry, 2016, 59(17):7915-7935.
Differding, "AUNP-12—A Novel Peptide Therapeutic Targeting PD-1 Immune Checkpoint Pathway for Cancer Immunotherapy—Structure Activity Relationships & Peptide / Peptidomimetic Analogs," Differding Consulting s.p.r.l. (Belgium), Feb. 26, 2014, 12 pages.
Dhanunjayarao et al., "Synthesis and Optical Properties of Salicylaldimine-Based Diboron Complexes," Eur J Inorg Chem., 2014, 3:539-545.
Dolan et al., "PD-1 Pathway Inhibitors: Changing the Landscape of Cancer Immunotherapy," Cancer Control, Jul. 2014, 21(3):231-237.
Domling et al., "Programmed Death-1: Therapeutic Success after More than 100 Years of Cancer Immunotherapy," Angew. Chem. Int. Ed., 2014, 53:2283-2288.
Ecuador Opposition in Ecuador Application No. SENADI-2019-3773, dated Oct. 10, 2019, 29 pages.
Escarcega-Bobadilla et al., "A Recyclable Trinuclear Bifunctional Catalyst Derived from a Tetraoxo Bis-Zn(salphen) Metalloligand," Chemistry—A European Journal, 2013, 19(8):2641-2648.
Escarcega-Bobadilla et al., "Metal-directed assembly of chiral bis-Zn(II) Schiff base structures," Dalton Transactions, 2012, 41(32):9766-9772.
Escarcega-Bobadilla et al., "Versatile Switching in Substrate Topicity: Supramolecular Chirality Induction in Di- and Trinuclear Host Complexes," Chemistry—A European Journal, 2012:8(22):6805-6810.
Eurasian Office Action in Eurasian Application No. 201990074/28, dated Oct. 3, 2019, 5 pages.
European Communication in European Application No. 16805690.1, dated Jul. 10, 2018, 6 pages.

Fabris et al., "Central to Axial Transfer of Chirality in Menthone or Camphor-Derived 2,2'-Biphenols," J of Org Chem., 1997, 62(21):7156-7164.
FDA Report, "22 Case Studies Where Phase 2 and Phase 3 Trials Had Divergent Results," U.S. Food and Drug Administration, Jan. 2017, 44 pages.
Francisco et al., "The PD-1 Pathway in Tolerance and Autoimmunity," Immunol. Rev., Jul. 2010, 236:219-242.
Freeman et al, "Engagement of the Pd-1 Immunoinhibitoiy Receptor by a Novel B7 Family Member Leads to Negative Regulation of Lymphocyte Activation," J. Exp. Med., Oct. 2000, 192(7):1027-34.
Freeman, "Structures of PD-1 with its ligands: Sideways and dancing cheek to cheek," PNAS, Jul. 2008, 105(30):10275-10276.
Freindorf, M., "Vibronic couplings in an excited state of hydrogen bond dimeric systems," Acta Physica Polonica, 1990, A78(6):825-839.
Gong et al., "Rhodium(I)-catalyzed regiospecific dimerization of aromatic acids: two direct C—H bond activations in water," Angewandte Chemie, 2015, 54(19):5718-5721.
Goswami et al., "A turn on ESIPT probe for rapid and ratiometric fluorogenic detection of homocysteine and cysteine in water with live cell-imaging," Tetrahedron Letters, 2014, 55(2):490-494.
Green et al., "Synthesis and investigation of the configurational stability of some dimethylammonium borate salts," Perkins 1, 2000, 24:4403-4408.
Greenwald et al, "The B7 Family Revisited," Annu. Rev. Immunol., 2005, 23:515-548.
Han et al., "Synthesis of binuclear phenoxyimino organoaluminum complexes and their use as the catalyst precursors for efficient ring-opening polymerisation of E-caprolactone," Dalton Trans., Sep. 14, 2013; 42(34):12346-53.
Helgeson et al., "Host-guest complexation. 66. 18-Membered-ring spherands containing five anisyl groups," J of Am Chem Soc., 1993, 1115(24):11506-11511.
Hu et al., "Syntheses and Ethylene Polymerization Behavior of Supported Salicylaldimine-Based Neutral Nickel(II) Catalysts," Organometallics, 2007, 26(10):2609-2615.
Hu et al., "Synthesis and Ethylene Polymerization Activity of a Novel, Highly Active Single-Component Binuclear Neutral Nickel(II) Catalyst," Organometallics, 2005, 24(11):2628-2632.
Hu et al., "Novel highly active binuclear neutral nickel and palladium complexes as precatalysts for norbornene polymerization," Journal of Molecular Catalysis A: Chemical, 2006, 253(1-):155-164.
Huang et al, "The prognostic significance of PD-L1 in bladder cancer," Oncol. Rep., 2015, 33:3075-3084.
Huddle et al., "Reactions of alkyl-lithium compounds with aryl halides ," J Chem Soc., 1980, 12:2617-2625.
HuGEMM™ and HuCELL™ Models, "FactSheet," CrownBio, Oct. 2016, 8 pages.
International Preliminary Report on Patentability in International Application No. PCT/US2016/057487, dated May 3, 2018, 7 pages.
International Preliminary Report on Patentability in International Application No. PCT/US2016/062730, dated May 31, 2018, 7 pages.
International Preliminary Report on Patentability in International Application No. PCT/US2016/067155, dated Jun. 19, 2018, 10 pages.
International Preliminary Report on Patentability in International Application No. PCT/US2016/067925, dated Jun. 26, 2018, 8 pages.
International Preliminary Report on Patentability in International Application No. PCT/US2017/031242, dated Nov. 6, 2018, 7 pages.
International Preliminary Report on Patentability in International Application No. PCT/US2017/034173, dated Nov. 27, 2018, 8 pages.
International Preliminary Report on Patentability in International Application No. PCT/US2017/038120, dated Dec. 25, 2018, 6 pages.
International Preliminary Report on Patentability in International Application No. PCT/US2017/041899, dated Jan. 15, 2019, 7 pages.
International Preliminary Report on Patentability in International Application No. PCT/US2017/048880, dated Mar. 5, 2019, 9 pages.

(56) References Cited

OTHER PUBLICATIONS

International Preliminary Report on Patentability in International Application No. PCT/US2017/067904, dated Jun. 25, 2019, 7 pages.
International Preliminary Report on Patentability in International Application No. PCT/US2017/067951, dated Jun. 25, 2019, 8 pages.
International Preliminary Report on Patentability in International Application No. PCT/US2017/067880, dated Jun. 25, 2019, 7 pages.
International Preliminary Report on Patentability in International Application No. PCT/US2017/067984, dated Jun. 25, 2019, 7 pages.
International Preliminary Report on Patentability in International Application No. PCT/US2017/067946, dated Jun. 25, 2019, 9 pages.
International Preliminary Report on Patentability in International Application No. PCT/US2017/067886, dated Jun. 25, 2019, 9 pages.
International Search Report and Written Opinion in International Application No. PCT/US2016/057487, dated Dec. 8, 2016, 11 pages.
International Search Report and Written Opinion in International Application No. PCT/US2016/062730, dated Feb. 9, 2017, 12 pages.
International Search Report and Written Opinion in International Application No. PCT/US2016/067925, dated Mar. 27, 2017, 13 pages.
International Search Report and Written Opinion in International Application No. PCT/US2016/067155, dated Apr. 24, 2017, 26 pages.
International Search Report and Written Opinion in International Application No. PCT/US2017/031242, dated Jun. 20, 2017, 22 pages.
International Search Report and Written Opinion in International Application No. PCT/US2017/034173, dated Aug. 8, 2017, 15 pages.
International Search Report and Written Opinion in International Application No. PCT/US2017/041899, dated Sep. 5, 2017, 12 pages.
International Search Report and Written Opinion in International Application No. PCT/US2017/038120, dated Aug. 1, 2017, 14 pages.
International Search Report and Written Opinion in International Application No. PCT/US2017/067904, dated Mar. 22, 2018, 14 pages.
International Search Report and Written Opinion in International Application No. PCT/US2017/067880, dated Mar. 21, 2018, 13 pages.
International Search Report and Written Opinion in International Application No. PCT/US2017/067984, dated Mar. 22, 2018, 14 pages.
International Search Report and Written Opinion in International Application No. PCT/US2017/067886, dated Mar. 23, 2018, 24 pages.
International Search Report and Written Opinion in International Application No. PCT/US2017/067946, dated May 22, 2018, 16 Pages.
International Search Report and Written Opinion in International Application No. PCT/US2017/067951, dated Mar. 27, 2018, 15 pages.
International Search Report and Written Opinion in International Application No. PCT/US2017/048880, dated Oct. 23, 2017, 15 pages.
International Search Report and Written Opinion in International Application No. PCT/US2019/031728, dated Jun. 25, 2019, 12 pages.
International Search Report and Written Opinion in International Application No. PCT/US2019/025036, dated Jul. 3, 2019, 12 pages.

Iwai et al, "Involvement of PD-L1 on tumor cells in the escape from host immune system and tumor immunotherapy by PD-L1 blockade," PNAS, Sep. 2002, 99(19):12293-12297.
Jiang et al., "Self-immobilizing binuclear neutral nickel catalyst for ethylene polymerization: Synthesis and catalytic studies," J of Mol Cat., 2013, 380:139-143.
Kayal et al., "3,3'-Bis(triphenylsilyl)biphenoxide as a Sterically Hindered Ligand on Fe(II), Fe(III), and Cr(II)," Inorg Chem., 2002, 41(2):321-330.
Keir et al., "PD-1 and Its Ligands in Tolerance and Immunity," Annu Rev. Immunol., 2008, 26:677-704.
Kerekes et al., "Aurora kinase inhibitors based on the imidazo[1,2-a]pyrazine core: fluorine and deuterium incorporation improve oral absorption and exposure," J Med Chem., 2011, 54(1):201-210.
Koch et al., "Nucleophilic reactions of pyridines and imidazoles with vinyl and aromatic halides," J. Org Chem., 1993, 58(6):1409-1414.
Komiyama et al, "IL-17 Plays an Important Role in the Development of Experimental Autoimmune Encephalomyelitis," J. Immunol., Jul. 2006, 177:566-73.
Latchman et al, "PD-L2 is a second ligand for PD-1 and inhibits T cell activation," Nat. Immunol., Mar. 2001, 2(3):261-268.
Lazar-Molnar et al., "Crystal structure of the complex between programmed death-1 (PD-1) and its ligand PD-L2," PNAS, Jul. 2008, 105(30):10483-10488.
Legon'kova et al., "Interaction of o,o-dihalo o'-hydroxy azo compounds with metallic copper. II. Preparation of oligomeric azo compounds from monoazo compounds," Mosk Khim-Tekhnol Inst im Mendeleeva., 1968, 11(11):1281-1284 Machine Translation.
Legon'kova et al., "Interaction of o,o-dihalogeno o-hydroxy azo compounds with metallic copper," Trudy Instituta—Moskovskii Khimiko—Tekhnologicheskii Institut imeni D. I. Mendeleeva, 1965, 48:120-125 Machine Translation.
Lehtonen et al., "Comparison of quaternary methyl-, ethyl- and butylammonium hydroxides as alkylating reagents in pyrolysis-GC/MS studies of aquatic fulvic acid," Journal of Analytical and Applied Pyrolysis, 2003, 68-69:315-329.
Li et al., "A Mini-Review for Cancer Immunotherapy: Molecular Understanding of PD-1/PD-L1 Pathway & Translational Blockade of Immune Checkpoints," Int. J. Mol. Soc., 2016, 17:1151, 22 pages.
Li et al., "Analysis of Receptor Tyrosine Kinase Internalization Using Flow Cytometry," Methods Mol. Biol., 2008, 457:305-317.
Li et al., "Asymmetric Alternating Copolymerization of Meso-epoxides and Cyclic Anhydrides: Efficient Access to Enantiopure Polyesters," J Am Chem Soc, 2016, 138(36):11493-11496.
Li et al., "A 3D Mesomeric Supramolecular Structure of a Cu(II) Coordination Polymer with 1,1'-Biphenyl-2,2',3,3'-tetracarboxylic Acid and 5,5'-Dimethyl-2,2'-bipyridine Ligands," J of Inorg and Organomet Poly Mat., 2012, 22(6):1320-1324.
Li et al., "Discovery of peptide inhibitors targeting human programmed death 1 (PD-1) receptor," Oncotarget, Aug. 2016, 7(40):64967-64976.
Lin et al., "The PD-1/PD-L1 complex resembles the antigen-binding Fv domains of antibodies and T cell receptors," PNAS, Feb. 2008, 105(8):3011-3016.
Lipson et al., "From Discovery to Development: Blocking PD-1 and its Ligands," The Melanoma Letter, A Publication of the Skin Cancer Foundation, vol. 31, Summer 2013, 6 pages.
Liu et al., "Asymmetric Copolymerization of CO2 with meso-Epoxides Mediated by Dinuclear Cobalt(III) Complexes: Unprecedented Enantioselectivity and Activity," Angewandte Chemie, 2013, 52(44):11594-11598.
Liu et al., "Development of amino- and dimethylcarbamate-substituted resorcinol as programmed cell death-1 (PD-1) inhibitor," European Journal of Pharmaceutical Sciences, 2016, 88:50-58.
Mahoney et al., "The Next Immune-Checkpoint Inhibitors: PD-1/PD-L1 Blockade in Melanoma," Clin. Therapeutics, Nov. 2015, 37(4):761-782.
Maier et al., "Effects of the stationary phase and the solvent on the stereodynamics of biphep ligands quantified by dynamic three-column HPLC," Angewante Chemie, 2012, 51(12):2985-2988.

(56) References Cited

OTHER PUBLICATIONS

Manecke et al., "Preparation and properties of monomeric and polymeric Schiff bases derived from salicylaldehyde and 2,5-dihydroxyterephthalaldehyde. II. Electrical conductivity," Makromolekulare Chemie, 1972, 160:111-126 English Abstract.

Manecke et al., "Preparation and properties of chelate-forming monomeric and polymeric Schiff bases derived from salicylaldehyde and 2,5-dihydroxyterephthalaldehyde. I," Makromolekulare Chemie, 1970, 133:61-82 English Abstract.

Mochida et al., "Rhodium-Catalyzed Regio selective Olefination Directed by a Carboxylic Group," J Org Chem, 2011, 76(9):3024-3033.

Moneta et al., "Boron templated synthesis of macrocyclic hosts containing convergent hydroxy or methoxy groups," Bulletin de la Societe Chimique de France, 1988, 6:995-1004 (English Abstract).

Nallasivam et al., "Development of Unimolecular Tetrakis(piperidin-4-ol) as a Ligand for Suzuki-Miyaura Cross-Coupling Reactions: Synthesis of Incrustoporin and Preclamol," 2015, Euro J Org Chem., 2015(16):3558-3567.

Nero et al., "Oncogenic protein interfaces: small molecules, big challenges," Nature Reviews, Apr. 2014, 14:248-262.

Nishimura et al, "Autoimmune Dilated Cardiomyopathy in PD-1 Receptor-Deficient Mice," Science, Jan. 2001, 291:319-322.

Nishimura et al, "Development of Lupus-like Autoimmune Diseases by Disruption of the PD-1 Gene Encoding an ITIM Motif-Carrying Immunoreceptor," Immunity, Aug. 1999, 11:141-151.

Nishimura et al., "PD-1: an inhibitory immunoreceptor involved in peripheral tolerance," Trends in Immunology, May 2001, 22(5):265-268.

Nishino et al., "Copper-Mediated C—H/C—H Biaryl Coupling of Benzoic Acid Derivatives and 1,3-Azoles," Angew. Chem. Int. Ed., 2013, 52:4457-4461.

Normand et al., "Dinuclear vs. mononuclear complexes: accelerated, metal-dependent ring-opening polymerization of lactide," 2013, 49(99):11692-11694.

Okazaki and Honjo, "The PD-1-PD-L pathway in immunological tolerance," Trends Immunol., Apr. 2006, 4:195-201.

Okazaki et al., "A rheostat for immune responses: the unique properties of PD-1 and their advantages for clinical application," Nature Immunology, Dec. 2013, 14(12):1212-1218.

Paek et al.., "Facile syntheses and multi-orthofunctionalizations of tertiary benzamides," Bulletin of The Korean Chemical Society, 1993, 14(6):732-739.

Paek et al., "Chiral host. Attempted synthesis using McMurray reaction as a final ring closure method," Bulletin of the Korean Chemical Society, 1989, 10(6):572-577.

Pardoll, "The blockade of immune checkpoints in cancer immunotherapy," Nature, Apr. 2012, 12:252-264.

Parry et al, "CTLA-4 and PD-1 Receptors Inhibit T-Cell Activation by Distinct Mechanisms," Mol. Cell. Biol., Nov. 2005, 25(21):9543-9553.

Parsons et al., "Directed ortho metalation reactions. Expedient synthesis of 3,3'-disubstituted 1,1'-bi-(2-phenols) (BIPOLS)," Tetrahedron Letters, 1994, 35(41):7537-7540.

Pascolutti et al., "Structure and Dynamics of PD-L1 and an Ultra-High-Affinity PD-1 Receptor Mutant," Structure, Oct. 2016, 24:1719-1728.

Paulini et al., "Orthogonal Multipolar Interactions in Structural Chemistry and Biology," Angew. Chem. Int. Ed., 2005, 44:1788-1805.

Pearson et al., "The formation of complexes between aza-derivatives of crown ethers and primary alkylammonium salts. Part 5. Chiral macrocyclic diamines," J Chem Soc., Perkin Trans. 1, 1979, 12:3113-3126.

Pfeiffer et al., "Inner complex salts of the aldimine and azo series," Journal fuer Praktische Chemie, 1937, 149:217-296 Machine Translation.

Pierre et al., "Synthesis of a new macrobicyclic siderophoric host molecule with six converging phenolate groups," Angewandte Chemie, 1991, 103(1):75-76 Machine Translation.

Postow et al, "Immune Checkpoint Blockade in Cancer Therapy," J. Clinical Oncology, Jun. 2015, 33(17):1974-1982.

Press Release Archive, "Boehringer Ingelheim and Yale University collaborate to investigate novel immunotherapy targets across several therapeutic areas," Boehringer Ingelheim, Jan. 13, 2015, 2 pages.

Puehlhofer et al., "SASAPOS cascades of pefluorinated aromatic carboxylic acids: low-temperature decarboxylation triggered by electrostatic effects of polycationic ligand sets," Euro J Org Chem., 2004, 5:1002-1007.

Punniyamurthy et al., "Enantiomerically pure bicyclo[3.3.1]nona-2,6-diene as the sole source of enantioselectivity in BIPHEP-Rh asymmetric hydrogenation," Chem Comm., 2008, 41:5092-5094.

Sabatier et al, "Prognostic and predictive value of PDL1 expression in breast cancer," Oncotarget, Mar. 2015, 6(7):5449-5464.

Sharpe et al, "The function of programmed cell death 1 and its ligands in regulating autoimmunity and infection," Nat. Immunol., Mar. 2007 8(3):239-245.

Sharpe et al., "The B7—CD28 Superfamily," Nature Reviews, Feb. 2002, 2:116-126.

Sharma et al., "Palladium-Catalyzed Decarboxylative Acylation of O-Phenyl Carbamates with Alpha-Oxocarboxylic Acids at Room Temperature," Advanced Synthesis & Catalysis, 2013, 355(4):667-672.

STN Search Report dated Apr. 14 2016, 79 pages.
STN Search Report dated Apr. 29, 2016, 69 pages.
STN Search Report dated Aug. 30, 2016, 4 pages.
STN Search Report dated Jun. 6, 2016, 115 pages.
STN Search Report dated Sep. 2 2016, 115 pages.
STN Search Report dated Jul. 12, 2016, 4 pages.
Search Report, dated May 1, 2016, 12 pages.
Search Report dated May 24, 2016, 92 pages.
Search Report dated Sep. 12, 2016, 4 pages.
Search Report dated Jun. 16, 2016, 8 pages.
Search Report dated Sep. 12, 2016, 17 pages.
Search Report dated Jul. 12, 2016, 4 pages.
Search Report dated Aug. 19, 2016, 23 pages.
Search Report dated Dec. 15, 2016, 4 pages (0505P01).
Search Report dated Dec. 15, 2016, 4 pages (0506P01).
Search Report dated Dec. 19, 2016, 11 pages.
Search Report dated Dec. 16, 2016, 25 pages.
Search Report dated Dec. 16, 2016, 4 pages.
Search Report dated Dec. 20, 2016, 117 pages.
Search Report dated Sep. 27, 2017, 4 pages.
Search Report dated Mar. 27, 2018, 4 pages.
Search Report dated Apr. 30, 2018, 8 pages.

Sorrell et al., "3,3'-Disubstituted 2,2'-biphenols. Synthesis of nonplanar, tetradentate chelating ligands," J of Org Chem., 1985, 50(26):5765-5769.

Storz, "Intellectual property issues of immune checkpoint inhibitors," MAbs, Jan. 2016, 8(1):10-26.

Sumrit et al., "Aluminum complexes containing salicylbenzoxazole ligands and their application in the ring-opening polymerization of rac-lactide and ε-caprolactone," Dalton Transactions (2016), 45(22), 9250-9266.

Tang et al., "Facile synthesis of enantioenriched phenol-sulfoxides and their aluminum complexes," Org Biomol Chem., 2016, 14(24):5580-5585.

Thiel et al., "Small-Molecule Stabilization of Protein—Protein Interactions: An Underestimated Concept in Drug Discovery?" Angew. Chem. Int. Ed., 2012, 51:2012-2018.

Tucker et al., "Host-guest complexation. 52. Bridged and chiral hemispherands," J Org Chem., 1989, 54(23):5460-5482.

Unrau et al., "Directed ortho metalation. Suzuki cross coupling connections. Convenient regiospecific routes to functionalized m- and p-teraryls and m-quinquearyls," Tetrahedron Letters, 1992, 33(20):2773-2776.

Velcheti et al., "Programmed death-1/programmed death-1 ligand axis as a therapeutic target in oncology: current insights," Journal of Receptor Ligand and Channel Research, Dec. 2014, 8(23): 1-7.

Wang et al, "The prognostic value of PD-L1 expression for non-small cell lung cancer patients: A meta-analysis," Eur. J. Surg. Oncol., 2015, 41:450-456.

(56) References Cited

OTHER PUBLICATIONS

Wang et al., "A binuclear Zn(II)-Zn(II) complex from a 2-hydroxybenzohydrazide-derived Schiff base for selective detection of pyrophosphate," Dalton Transactions, Oct. 2014, 43(37):14142-14146.
Wang et al., "Molecular Modeling and Functional Mapping of B7-H1 and B7-DC Uncouple Costimulatory Function from PD-1 Interaction," J. Exp. Med., Apr. 2013, 197(3):1083-1091.
Wei et al., "Strength of PD-1 signaling differentially affects T-cell effector functions," PNAS, Apr. 2013, E2480-E2489.
Weinmann, "Cancer Immunotherapy: Selected Targets and Small-Molecule Modulators," Chem. Med. Chem., 2016, 11:450-466.
Weiss et al., "Electrostatics and color: Massive electrostatic perturbation of chromophores by ion cluster ligands," J Am Chem Soc., 2007, 129(3):547-553.
Weiss et al., "Electrostatic activation of SNAr-reactivity by sulfonylonio substituents," Zeitschrift fuer Naturforschung, 2001, 56(12):1360-1368 English Abstract.
Weiss et al., "First-ever per(onio) substitution of benzene: the role of the counterion," Angewandte Chemie, 1995, 34(12):1319-1321.
Weiss et al., "Massive electrostatic effects on heteropolar C-C disconnections: Transforming a phenyl anion into a potent leaving group," Eur J Org Chem., 2005, 16:3530-3535.
Weiss et al., "Poly-onio substituted quinones as strong electron acceptors," Angewandte Chemie Int. Ed., 1986, 25(10):917-919.
Weiss et al., "SASAPOS, not Sisyphus: highly efficient 20-step one-pot synthesis of a discrete organic-inorganic ion cluster with a porphyrin core," Angewandte Chemie International Edition, 41(20):3815-3817.
Weiss et al., "Syntheses and Reactions of Polycationically Substituted Azido- and Diazidobenzenes," Eur J Org Chem., Nov. 2007, 31:5270-5276.
Wells et al., "Reaching for high-hanging fruit in drug discovery at protein-protein interfaces," Nature, Dec. 2007, 450:1001-1009.
Wu et al., "Targeting the BACE1 Active Site Flap Leads to a Potent Inhibitor That Elicits Robust Brain Aβ Reduction in Rodents," ACS Medicinal Chemistry Letters, 2016, 7(3):271-276.
www.medscape.com' [online]. "The 'Family Business' Behind the Flurry of PD-1 Inhibitors," Sep. 10, 2014. [Retrieved on Jan. 1, 2015]. Retrieved from the Internet: URL<http://www.medscape.com/viewarticle/831448_print>. 3 pages.
Xiong et al., "Biaryl-Bridged Salalen Ligands and Their Application in Titanium-Catalyzed Asymmetric Epoxidation of Olefins with Aqueous H2O2," Euro J Org Chem., 2011, 23:4289-4292.
Xu et al., "Quantitative structure-activity relationship study on BTK inhibitors by modified multivariate adaptive regression spline and CoMSIA methods," SAR QSAR Environ Res., 2015, 26(4):279-300.
Xu et al., "Design, synthesis and biological evaluation of deuterated nintedanib for improving pharmacokinetic properties," J Label Compd RadioPharm., Jun. 15, 2015, 58(7):308-312.
Yin et al., "Strategies for Targeting Protein-Protein Interactions With Synthetic Agents," Angew. Chem. Int. Ed., 2005, 44:4130-4163.
Young et al., "Discovery of highly potent and selective Bruton's tyrosine kinase inhibitors: Pyridazinone analogs with improved metabolic stability," Bioorganic & Medicinal Chemistry Letters, 2016, 26(2):575-579.
Young et al., "Potent and selective Bruton's tyrosine kinase inhibitors: Discovery of GDC-0834, Bioorganic & Medicinal Chemistry Letters ," 2015, 25(6):1333-1337.
Zarganes-Tzitzikas, "Inhibitors of programmed cell death 1 (PD-1): a patent review (2010-2015)," Expert Opinion on Therapeutic Patents, Sep. 19, 2016, 26(9):973-977.
Zak et al., "Structural basis for small molecule targeting of the programmed death ligand 1 (PD-L1)," Oncotarget, 2016, 7(21):30323-30335.
Zak et al., "Structural basis for small molecule targeting of the programmed death ligand 1 (PD-L1): Supplementary Material" Oncotarget, Apr. 2016, 19 pages.
Zak et al., "Structure of the Complex of Human Programmed Death 1, PD-1, and Its Ligand PD-L1: with Supplemental Information," Structure, Dec. 2015, 23:2341-2348.
Zang et al., "Four 2D metal-organic networks incorporating Cd-cluster SUBs: hydrothermal synthesis, structures and photoluminescent properties," CrystEngComm, 2009, 11(1):122-129.
Zhan et al., "From monoclonal antibodies to small molecules: the development of inhibitors targeting the PD-1/PD-L1 pathway," Drug Discovery Today, Apr. 2016, 10 pages.
Zhang et al., "Electrospray mass spectrum of a per(onio)-substituted benzene: retention of Coulombic charge upon collisionally activated decomposition," J Am Soc. Mass Spectrom., 1998, 9(1):15-20.
Zhang et al., "Non-symmetrical diarylcarboxylic acids via rhodium(I)-catalyzed regiospecific cross-dehydrogenation coupling of aromatic acids: twofold direct C-H bond activations in water," RSC Advances, 2016, 6(64):91617-91620.
Zhang et al., "Structural and Functional Analysis of the Costimulatory Receptor Programmed Death-1," Immunity, Mar. 2004, 20:337-347.
Zhang et al., "Biaryl-Based Macrocyclic and Polymeric Chiral (Salophen)Ni(II) Complexes: Synthesis and Spectroscopic Study," J Org Chem., 2001, 66(2):481-487.
Zhao et al., "Design, synthesis and organocatalysis of 2,2'-biphenol-based prolinamide organocatalysts in the asymmetric direct aldol reaction in water," Synlett, 2013, 24(20):2743-2747.

IMMUNOMODULATOR COMPOUNDS AND METHODS OF USE

TECHNICAL FIELD

The present application is concerned with pharmaceutically active compounds as well as their compositions and methods of use. The compounds cause internalization of PD-L1 from the cell surface and are useful in the treatment of various diseases including cancer.

BACKGROUND

The immune system plays an important role in controlling and eradicating diseases such as cancer. However, cancer cells often develop strategies to evade or to suppress the immune system in order to favor their growth. One such mechanism is altering the expression of co-stimulatory and co-inhibitory molecules expressed on immune cells (Postow et al, J. Clinical Oncology 2015, 1-9). Blocking the signaling of an inhibitory immune checkpoint, such as Programmed cell death-1 (PD-1), has proven to be a promising and effective treatment modality.

PD-1, also known as CD279, is a cell surface receptor expressed on activated T cells, natural killer T cells, B cells, and macrophages (Greenwald et al, Annu. Rev. Immunol 2005, 23:515-548; Okazaki and Honjo, Trends Immunol 2006, (4): 195-201). It functions as an intrinsic negative feedback system to prevent the activation of T-cells, which in turn reduces autoimmunity and promotes self-tolerance. In addition, PD-1 is also known to play a critical role in the suppression of antigen-specific T cell response in diseases like cancer and viral infection (Sharpe et al, Nat Immunol 2007 8, 239-245; Postow et al, J. Clinical Oncol 2015, 1-9).

The structure of PD-1 consists of an extracellular immunoglobulin variable-like domain followed by a transmembrane region and an intracellular domain (Parry et al, Mol Cell Biol 2005, 9543-9553). The intracellular domain contains two phosphorylation sites located in an immunoreceptor tyrosine-based inhibitory motif and an immunoreceptor tyrosine-based switch motif, which suggests that PD-1 negatively regulates T cell receptor-mediated signals. PD-1 has two ligands, PD-L1 and PD-L2 (Parry et al, Mol Cell Biol 2005, 9543-9553; Latchman et al, Nat Immunol 2001, 2, 261-268), and they differ in their expression patterns. PD-L1 protein is upregulated on macrophages and dendritic cells in response to lipopolysaccharide and GM-CSF treatment, and on T cells and B cells upon T cell receptor and B cell receptor signaling. PD-L1 is also highly expressed on almost all tumor cells, and the expression is further increased after IFN-γ treatment (Iwai et al, PNAS2002, 99(19): 12293-7; Blank et al, Cancer Res 2004, 64(3): 1140-5). In fact, tumor PD-L1 expression status has been shown to be prognostic in multiple tumor types (Wang et al, Eur J Surg Oncol 2015; Huang et al, Oncol Rep 2015; Sabatier et al, Oncotarget 2015, 6(7): 5449-5464). PD-L2 expression, in contrast, is more restricted and is expressed mainly by dendritic cells (Nakae et al, J Immunol 2006, 177:566-73). Ligation of PD-1 with its ligands PD-L1 and PD-L2 on T cells delivers a signal that inhibits IL-2 and IFN-γ production, as well as cell proliferation induced upon T cell receptor activation (Carter et al, Eur J Immunol 2002, 32(3):634-43; Freeman et al, J Exp Med 2000, 192(7): 1027-34). The mechanism involves recruitment of SHP-2 or SHP-1 phosphatases to inhibit T cell receptor signaling such as Syk and Lck phosphorylation (Sharpe et al, Nat Immunol 2007, 8, 239-245). Activation of the PD-1 signaling axis also attenuates PKC-θ activation loop phosphorylation, which is necessary for the activation of NF-κB and API pathways, and for cytokine production such as IL-2, IFN-γ and TNF (Sharpe et al, Nat Immunol 2007, 8, 239-245; Carter et al, Eur J Immunol 2002, 32(3):634-43; Freeman et al, J Exp Med 2000, 192(7): 1027-34).

Several lines of evidence from preclinical animal studies indicate that PD-1 and its ligands negatively regulate immune responses. PD-1-deficient mice have been shown to develop lupus-like glomerulonephritis and dilated cardiomyopathy (Nishimura et al, Immunity 1999, 11:141-151; Nishimura et al, Science 2001, 291:319-322). Using an LCMV model of chronic infection, it has been shown that PD-1/PD-L1 interaction inhibits activation, expansion and acquisition of effector functions of virus-specific CD8 T cells (Barber et al, Nature 2006, 439, 682-7). Antibodies that block the PD-1 signaling by either binding to PD-1 or binding to PD-L1 have been shown to be effective in the treatment of cancer. Together, these data support the development of a therapeutic approach to block the PD-1-mediated inhibitory signaling cascade in order to augment or "rescue" T cell response. Accordingly, there is a need for new compounds that prevent PD-1/PD-L1 protein/protein interaction.

SUMMARY

The present disclosure provides, inter alia, compounds that cause internalization of cell surface PD-L1. The compounds of this disclosure can be represented by any of the formulae and/or embodiments described herein. Reducing cell surface expression of PD-L1 results in reduced PD-L1 available for ligand engagement with PD-1 on an opposing cell and thereby reduces the inhibitory signaling that results from the PD-1-PD-L1 interaction. By reducing PD-1 inhibitory signaling, the compounds of the present disclosure increase an immune response and can be used to treat a PD-1-related disease or condition such as cancer.

In one aspect, the disclosure features a method of treating a PD-1-related disease or condition in a human subject in need thereof by administering to the human subject a therapeutically effective amount of a compound that binds to cell surface PD-L1 and induces PD-L1 internalization.

As used herein "internalization" refers to the transport of PD-L1 proteins from the surface of a cell to the interior of the cell. As used herein, a compound induces PD-L1 internalization if it causes PD-L1 internalization in the CHO/PD-L1 internalization assay described in Example 3A or causes PD-L1 internalization in primary cells from cancer patients as described in Example 12A. In some embodiments, the compound causes at least 50%, (e.g., at least 60%, at least 70%, at least 75%, at least 80%, at least 85%, at least 90%, at least 95%, at least 98%, or at least 99%) of cell surface PD-L1 to be internalized. In some embodiments, a compound induces PD-L1 internalization if it causes PD-L1 internalization in the MDA-MB231/PD-L1 internalization assay described in Example 3A. In some embodiments, a compound induces PD-L1 internalization if it causes PD-L1 internalization in primary cells from cancer patients described in the example herein.

In some embodiments, the PD-1-related disease or condition is a cancer (e.g., melanoma, renal cancer, prostate cancer, breast cancer, colon cancer, lung cancer, squamous cell cancer, head and neck cancer, urothelial cancer, or a cancer with high microsatellite instability ($MSI^{high}$)).

In some embodiments, the PD-1-related disease or condition is sepsis.

In some embodiments, the PD-1-related disease or condition is a viral, bacterial, fungal, or parasitic infection.

In another aspect, the disclosure features a method of reducing the amount of cell surface PD-L1 by contacting a cell expressing PD-L1 with an effective amount of a compound that binds to cell surface PD-L1 and induces PD-L1 internalization.

In another aspect, the disclosure features a method of decreasing or reducing the interaction of PD-1 and PD-L1 by contacting a cell expressing PD-L1 with an effective amount of a compound that binds to cell surface PD-L1 and induces PD-L1 internalization.

In some embodiments, the cell is an immune cell (e.g., a monocyte or macrophage) or a tumor cell.

In another aspect, the disclosure features a method of enhancing, stimulating and/or increasing an immune response in a human subject in need thereof by administering to the human subject a therapeutically effective amount of a compound that binds to cell surface PD-L1 and induces PD-L1 internalization.

In some embodiments, the immune response is a T cell immune response (e.g., a cytotoxic or effector T cell response).

In some embodiments of any of the methods described herein, a second therapeutic agent (e.g., a chemotherapeutic, an immunomodulatory agent, or a kinase inhibitor) is administered in combination with the compound.

In another aspect, the disclosure features a method for assessing the ability of a compound to induce internalization of PD-L1 in a cell, wherein the method includes: contacting a cell expressing PD-L1 with a compound; and determining the amount of PD-L1 internalized in the cell in the presence of the compound as compared to the absence of the compound.

In another aspect, the disclosure features a method for assessing the ability of a compound to induce internalization of PD L1 in a cell, wherein the method includes: identifying a compound that binds to PD-L1; contacting a cell with the compound; and determining the amount of PD-L1 internalized in the cell in the presence of the compound as compared to the absence of the compound.

In another aspect, the disclosure features a method for assessing the ability of a compound to induce dimerization and internalization of PD-L1 in a cell, wherein the method includes: measuring the ability of a compound to induce dimerization of PD-L1; contacting a cell expressing PD-L1 with the compound; and determining the amount of PD-L1 internalized in the cell in the presence of the compound as compared to the absence of the compound.

In another aspect, the disclosure features a method for assessing the ability of a compound to induce dimerization and internalization of PD-L1 in a cell, wherein the method includes: identifying a compound that binds to PD-L1; measuring the ability of the compound to induce dimerization of PD-L1; contacting a cell expressing PD-L1 with the compound; and determining the amount of PD-L1 internalized in the cell in the presence of the compound as compared to the absence of the compound.

In some embodiments, the ability of the compound to induce internalization of cell surface PD-L1 is measured by contacting a PD-L1-expressing cell with the compound and detecting the amount of PD-L1 internalized in the cell after incubation of the cell with the compound.

In some embodiments, the ability of the compound to induce internalization of cell surface PD-L1 is measured by contacting a PD-L1-expressing cell with the compound and detecting the amount of PD-L1 remaining on the surface of the cell after incubation of the cell with the compound.

In some embodiments, the method further entails formulating the compound into a sterile pharmaceutical composition suitable for administration to a human subject.

In some embodiments, the pharmaceutical composition is a tablet, pill, capsule, or intravenous formulation.

In some embodiments, the pharmaceutical composition is suitable for oral, intravenous, subcutaneous administration.

In some embodiments of any of the methods described herein, the compound is a small molecule. In some embodiments, the compound has a molecular weight of less than 1000 daltons. In some embodiments, the compound has a molecular weight between 300 and 700 daltons.

In some embodiments of any of the methods described herein, the compound induces PD-L1 internalization with an $IC_{50}$ of 500 nM or lower.

In some embodiments of any of the methods described herein, the compound induces PD-L1 internalization with an $IC_{50}$ of 100 nM or lower.

In some embodiments of any of the methods described herein, the compound induces PD-L1 internalization with an $IC_{50}$ of 50 nM or lower.

Internalization can optionally be measured in the whole blood indirect internalization assay described in Example 3A.

In some embodiments of any of the methods described herein, the compound induces PD-L1 dimerization, and the dimerization occurs prior to PD-L1 internalization.

As used herein, a compound induces PD-L1 dimerization if it yields a score in the range of 1.75 to 2.29 in the PD-L1 homogeneous time-resolved fluorescence dimerization assay described in Example 2A.

In some embodiments of any of the methods described herein, the compound induces PD-L1 dimerization with a score in the range of 2.0 to 2.2 in the PD-L1 homogeneous time-resolved fluorescence dimerization assay described in Example 2A.

In some embodiments of any of the methods described herein, the compound inhibits binding between PD-L1 and PD-1. In some embodiments, the compound inhibits binding between PD-L1 and PD-1 with an $IC_{50}$ of less than 10 nM, less than 1 nM, or less than 0.5 nM.

All publications, patent applications, patents, and other references mentioned herein are incorporated by reference in their entirety. Unless otherwise defined, all technical and scientific terms used herein have the same meaning as commonly understood by one of ordinary skill in the art to which this invention belongs. In case of conflict, the present specification, including definitions, will control. Suitable methods and materials are described below, although methods and materials similar or equivalent to those described herein can also be used in the practice or testing of the present invention. The materials, methods, and examples are illustrative only and not intended to be limiting.

Other features and advantages of the invention will be apparent from the following detailed description, and from the claims.

DETAILED DESCRIPTION

Figure 1:
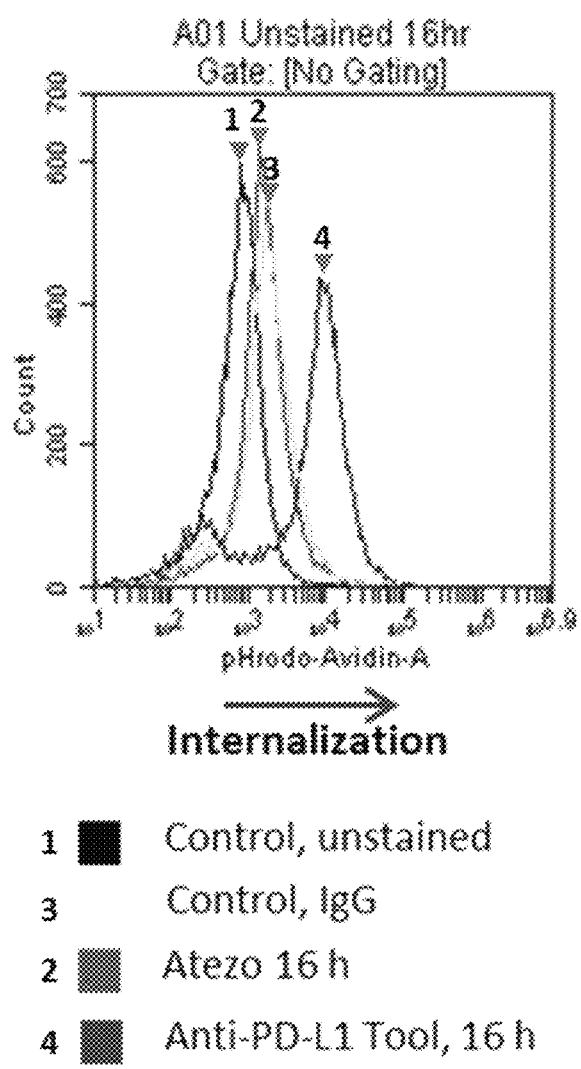
FIG. 1 is a graph depicting the effect of Atezolizumab and control antibodies on PD-L1 internalization.

PD-1 negatively regulates immune responses upon interaction with its ligand PD-L1. The present disclosure provides compounds that cause internalization of cell surface PD-L1, thereby reducing inhibitory signaling that results from the PD-1-PD-L1 interaction.

Compounds

Compounds used according to the methods described herein bind to cell surface PD-L1 and induce PD-L1 internalization. Compounds can be assessed for their ability to induce PD-L1 internalization by, for example, the indirect or direct PD-L1 internalization assays described in Example 3A. Optionally, compounds can also be assessed for their ability to induce PD-L1 dimerization, by, for example, the dimerization assay described in Example 2A. Dimerization of PD-L1 protein can result in the formation of various dimerized conformations. Only a subset of the conformations are capable of, configured to, or indicative of causing internalization of the cell surface PD-L1. A score in the range from about 1.75 to 2.29 according to the dimerization assay described in Example 2A indicates that a compound induces a structural conformation in PD-L1 that has a tendency towards PD-L1 internalization. Not all compounds that bind to PD-L1 and induce PD-L1 dimerization are able to also induce PD-L1 internalization. For example, some compounds that score outside the range of range of 1.75 to 2.29 in the PD-L1 dimerization assay are able to induce PD-L1 dimerization but are unable to induce PD-L1 internalization.

Examples of compounds that can be used to induce PD-L1 internalization in the methods described herein are described in Example 4A (see, e.g., compounds 7-26 in Table 2 and compounds 60-183 in Table 29) and Example 8A (see e.g., compounds in Examples 1-189).

In certain embodiments, compounds can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bio net (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, NH), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

The compounds of the present disclosure can have pseudo-symmetry with, or around, the core or central ring structure or structures (e.g., "BC"). As used herein the term "pseudo-symmetry" refers to the quality of the compounds of the present disclosure being made up of similar substituents around the core or central ring structure or structures. For example, the compounds can contain a core or central ring structure or structures including a bicyclic core or a spirocyclic core. The compounds can exhibit pseudo-symmetry by having, or the placement of, linking group-ring structures substituted on one or more of the central ring structure or structures. For example, each ring of a biphenyl core or central structure can be substituted with a linking group-ring structure.

The similarity of the substituents (e.g., the linking group-ring structure, substitute or unsubstituted) around the core or central ring structure or structures can have comparable molecular weights. The molecular weight of each of the substituents can be about 50, 100, 150, 200, 250, 300, 350, 400, 450, 500, 550, 600, 650, 700 and about 750 Daltons. These values can be used to define a range, such as from about 50 Daltons to about 500 Daltons. The difference between the molecular weights of the substituents can be less than about 500, 450, 400, 350, 300, 250, 200, 150, 100 and about 50 Daltons. These values can be used to define a range, such as from about 200 Daltons to about 50 Daltons.

The similarity of the substituents (e.g., the linking group-ring structure, substitute or unsubstituted) around the core or central ring structure or structures can have a comparable number of non-hydrogen atoms. The number of non-hydrogen atoms of each substituent can be about 4, 5, 6, 7, 8, 9, 10, 11, 12, 13, 14, 15, 16, 17, 18, 19, 20, 21, 22, 23, 24, 25, 26, 27 or about 28 atoms. These values can be used to define a range, such as from about 4 atoms to about 24 atoms. The difference between the number of non-hydrogen atoms of the substituents can be less than about 20, 19, 18, 17, 16, 15, 14, 13, 12, 11, 10, 9, 8, 7, 6, 5, 4, 3, 2 or about 1 atom. These values can be used to define a range, such as from about 12 atoms to about 2 atoms.

The similarity of the substituents (e.g., the linking group-ring structure, substitute or unsubstituted) around the core or central ring structure or structures can have a comparable number of ring structures. Each substituent can contain 1, 2 (e.g., two monocyclic rings or a bicyclic ring), 3 or 4 different ring structures. The difference in the number of ring structures of each substitute can be about, or less than about, 3, 2, 1 or 0. These values can be used to define a range, such as from about 3 rings to about 0 rings.

The compounds of the present disclosure can also have symmetry with, or around, the core or central ring structure or structures. As used, herein the term "symmetry" refers to the quality of the compounds of the present disclosure being made up of the same substituents around the core or central ring structure or structures. The compounds can exhibit symmetry by having a same linking group-ring structure substituted on one or more of the central ring structure or structures. For example, each ring of a biphenyl core or central structure can be substituted with the same linking group-ring structure.

In one embodiment, the compound used in a method described herein has Formula (I):

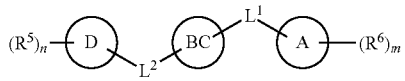
(I)

or a pharmaceutically acceptable salt or a stereoisomer thereof, wherein:

ring A is a $C_{6-10}$ aryl, a 5- to 14-membered heteroaryl comprising carbon and 1, 2, 3, or 4 heteroatoms selected from N, O and S, a 4- to 14-membered heterocycloalkyl comprising carbon and 1, 2, 3, or 4 heteroatoms selected from N, O and S, or a $C_{3-14}$ cycloalkyl;

ring BC is of formula (Ia) or (Ib):

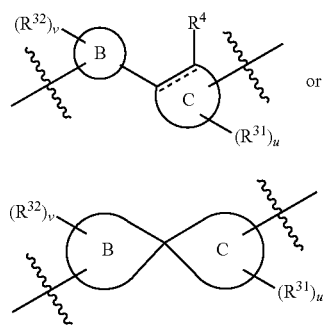

provided when ring BC is of formula (Ia) then ring B is a $C_{6-10}$ aryl, a 5- to 14-membered heteroaryl comprising carbon and 1, 2, 3, or 4 heteroatoms selected from N, O and S, a 4- to 14-membered heterocycloalkyl comprising carbon and 1, 2, 3, or 4 heteroatoms selected from N, O and S, or a $C_{3-14}$ cycloalkyl, and ring C is $C_{6-10}$ aryl, a 5- to 14-membered heteroaryl comprising carbon and 1, 2, 3, or 4 heteroatoms selected from N, O and S, a 4- to 14-membered heterocycloalkyl comprising carbon and 1, 2, 3, or 4 heteroatoms selected from N, O and S, or $C_{3-14}$ cycloalkyl; and the atoms on ring C, to which the substituent $R^4$ and ring B are attached can be either carbon or nitrogen;

----- is a single bond or a double bond;

provided when ring BC is of formula (Ib) then ring B and ring C are each independently a 4-to 14-membered heterocycloalkyl comprising carbon and 1, 2, 3, or 4 heteroatoms selected from N, O and S, or $C_{344}$ cycloalkyl; and ring B and ring C are joined together through a quaternary ring carbon atom to form a spiro structure;

ring D is a $C_{6-10}$ aryl, a 5- to 14-membered heteroaryl comprising carbon and 1, 2, 3, or 4 heteroatoms selected from N, O and S, a 4- to 14-membered heterocycloalkyl comprising carbon and 1, 2, 3, or 4 heteroatoms selected from N, O and S, or a $C_{3-14}$ cycloalkyl;

$L^1$ is a bond, $-(CR^{14}R^{15})_tC(O)NR^{13}(CR^{14}R^{15})_t-$, $-(CR^{14}R^{15})_tNR^{13}C(O)(CR^{14}R^{15})_t-$, $-O-$, $-(CR^{14}R^{15})_p-$, $-(CR^{14}R^{15})_p-O-$, $-O(CR^{14}R^{15})_p-$, $-(CR^{14}R^{15})_p-O-(CR^{14}R^{15})_p-$, $-NR^{13}-$, $-(CR^{14}R^{15})_tNR^{13}(CR^{14}R^{15})_t-$, $-NH-$, $-(CR^{14}R^{15})_wNH(CR^{14}R^{15})_w-$, $-CR^{13}=CR^{13}-$, $-C\equiv C-$, $-SO_2-$, $-(CR^{14}R^{15})_tSO_2(CR^{14}R^{15})_t-$, $-(CR^{14}R^{15})_tSO_2NR^{13}(CR^{14}R^{15})_t-$, $-(CR^{14}R^{15})_tNR^{13}SO_2(CR^{14}R^{15})_t-$, $-(CR^{14}R^{15})_tNR^{13}SO_2NR^{13}(CR^{14}R^{15})_t-$, $NR^{13}C(O)O(CR^{14}R^{15})_t-$, $-NR^{13}C(O)O-$, $-(CR^{14}R^{15})_tO(CO)NR^{13}(CR^{14}R^{15})_t-O(CO)NR^{13}-$, $-NR^{13}C(O)NR^{13}-$ or $-(CR^{14}R^{15})_tNR^{13}C(O)NR^{13}(CR^{14}R^{15})_t$;

$L^2$ is a bond, $-(CR^{29}R^{30})_tC(O)NR^{28}(CR^{29}R^{30})_t-$, $-(CR^{29}R^{30})_tNR^{28}C(O)(CR^{29}R^{30})_t-O-$, $-(CR^{29}R^{30})_q-$, $-(CR^{29}R^{30})_q-O-$, $-O(CR^{29}R^{30})_q-$, $-(CR^{29}R^{30})_q-O-(CR^{29}R^{30})_q-$, $-NR^{28}-$, $-(CR^{29}R^{30})_qNR^{28}(CR^{29}R^{30})_q-$, $-NH-$, $-(CR^{29}R^{30})_wNH(CR^{29}R^{30})_w-$, $-CR^{28}=CR^{28}-$, $-C\equiv C-$, $-SO_2-$, $-(CR^{29}R^{30})_wSO_2(CR^{29}R^{30})_w-$, $-(CR^{29}R^{30})_wSO_2NR^{28}(CR^{29}R^{30})_w-$, $-(CR^{29}R^{30})_wNR^{28}SO_2(CR^{29}R^{30})_w-$, $-(CR^{29}R^{30})_wNR^{28}SO_2NR^{28}(CR^{29}R^{30})_w-$, $-(CR^{29}R^{30})_wNR^{28}C(O)O(CR^{29}R^{30})_w-$, $-NR^{28}C(O)O-$, $-(CR^{29}R^{30})_wO(CO)NR^{28}(CR^{29}R^{30})_w-$, $-O(CO)NR^{28}-$, $-NR^{28}C(O)NR^{28}-$ or $-(CR^{29}R^{30})_wNR^{28}C(O)NR^{28}(CR^{29}R^{30})_w-$;

each $R^{13}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, $-COOH$, $NH_2$, $-NHC_{1-4}$ alkyl and $-N(C_{1-4}$ alkyl$)_2$;

$R^{14}$ and $R^{15}$ are each independently selected from H, halo, CN, OH, $-COOH$, $NH_2$, $C_{1-4}$ alkyl, $C_{1-4}$ alkoxy, $-NHC_{1-4}$ alkyl, $-N(C_{1-4}$ alkyl$)_2$, $C_{1-4}$ haloalkyl, and $C_{1-4}$ haloalkoxy;

each $R^{28}$ is independently H, $C_{1-6}$ haloalkyl or $C_{1-6}$ alkyl optionally substituted with a substituent selected from $C_{1-4}$ alkyl, $C_{1-4}$ alkoxy, $C_{1-4}$ haloalkyl, $C_{1-4}$ haloalkoxy, CN, halo, OH, $-COOH$, $NH_2$, $-NHC_{1-4}$ alkyl and $-N(C_{1-4}$ alkyl$)_2$;

$R^{29}$ and $R^{30}$ are each independently selected from H, halo, CN, OH, $NH_2$, $-COOH$, $C_{1-4}$ alkyl, $C_{1-4}$ alkoxy, $-NHC_{1-4}$ alkyl, $-N(C_{1-4}$ alkyl$)_2$, $C_{1-4}$ haloalkyl, and $C_{1-4}$ haloalkoxy;

$R^4$ is halo, oxo, CN, $C_{1-6}$ alkyl, $C_{1-6}$ alkoxy, $C_{2-6}$ alkenyl, $C_{2-6}$ alkynyl, $C_{1-6}$ haloalkyl, or $C_{1-4}$ haloalkoxy;

$R^5$, $R^6$, $R^{31}$ and $R^{32}$ are each independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-14 membered heteroaryl)-$C_{1-4}$ alkyl-, (4-10 membered heterocycloalkyl)-$C_{1-4}$ alkyl-, CN, $NO_2$, $OR^a$, $SR^a$, $NHOR^a$, $C(O)R^a$, $C(O)NR^aR^a$, $C(O)OR^a$, $OC(O)R^a$, $OC(O)NR^aR^a$, $NHR^a$, $NR^aR^a$, $NR^aC(O)R^a$, $NR^aC(O)OR^a$, $NR^aC(O)NR^aR^a$, $C(=NR^a)R^a$, $C(=NR^a)NR^aR^a$, $NR^aC(=NR^a)NR^aR^a$, $NR^aC(=NOH)NR^aR^a$, $NR^aC(=NCN)NR^aR^a$, $NR^aS(O)R^aNR^aS(O)_2R^a$, $NR^aS(O)_2NR^aR^a$, $S(O)R^a$, $S(O)NR^aR^a$, $S(O)_2R^a$, and $S(O)_2NR^aR^a$, wherein the $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl-, $C_{3-10}$cycloalkyl-$C_{1-4}$ alkyl-, (5-14 membered heteroaryl)-$C_{1-4}$ alkyl-, and (4-10 membered heterocycloalkyl)-$C_{1-4}$ alkyl- of $R^5$, $R^6$, $R^{31}$ and $R^{32}$ are each optionally substituted with 1, 2, 3, 4 or 5 substituents independently selected from $R^b$;

alternatively, two adjacent $R^5$ substituents on ring D, taken together with the atoms to which they are attached, form a fused phenyl ring, a fused 4-, 5-, 6- or 7-membered heterocycloalkyl ring, a fused 5- or 6-membered heteroaryl ring or a fused $C_{3-6}$ cycloalkyl ring, wherein the fused 4-, 5-, 6- or 7-membered heterocycloalkyl ring and fused 5- or 6-membered heteroaryl ring each have 1-4 heteroatoms as ring members selected from N, O and S, and wherein the fused phenyl ring, fused 4-, 5-, 6- or 7-membered heterocycloalkyl ring, fused 5- or 6-membered heteroaryl ring and fused $C_{3-6}$ cycloalkyl ring are each optionally substituted with 1, 2 or 3 substituents independently selected from $R^b$;

alternatively, two $R^5$ substituents on the same ring carbon atom of ring D, taken together with the carbon atom to which they are attached, form a spiro 4-, 5-, 6- or 7-membered heterocycloalkyl ring, or a spiro $C_{3-6}$ cycloalkyl ring, wherein the spiro 4-, 5-, 6- or 7-membered heterocycloalkyl ring has 1-4 heteroatoms as ring members selected from N, O and S and wherein the spiro 4-, 5-, 6- or 7-membered heterocycloalkyl ring and spiro $C_{3-6}$ cycloalkyl ring are each optionally substituted with 1, 2 or 3 substituents independently selected from $R^b$;

alternatively, two adjacent $R^6$ substituents on ring A, taken together with the atoms to which they are attached, form a fused phenyl ring, a fused 4-, 5-, 6- or 7-membered heterocycloalkyl ring, a fused 5- or 6-membered heteroaryl ring, or a fused $C_{3-6}$ cycloalkyl ring, wherein the fused 4-, 5-, 6- or 7-membered heterocycloalkyl ring and fused 5- or 6-membered heteroaryl ring each have 1-4 heteroatoms as ring members selected from N, O and S, and wherein the fused phenyl ring, fused 4-, 5-, 6- or 7-membered heterocycloalkyl ring, fused 5- or 6-membered heteroaryl ring, and fused $C_{3-6}$ cycloalkyl ring are each optionally substituted with 1, 2 or 3 substituents independently selected from $R^b$;

alternatively, two $R^6$ substituents on the same ring carbon atom of the ring A, taken together with the carbon atom to which they are attached, form a spiro 4-, 5-, 6- or 7-membered heterocycloalkyl ring, or a spiro $C_{3-6}$ cycloalkyl ring, wherein the spiro 4-, 5-, 6- or 7-membered heterocycloalkyl ring has 1-4 heteroatoms as ring members selected from N, O and S, and wherein the spiro 4-, 5-, 6- or 7-membered heterocycloalkyl ring and spiro $C_{3-6}$ cycloalkyl ring are each optionally substituted with 1, 2 or 3 substituents independently selected from $R^b$;

alternatively, two adjacent $R^{31}$ substituents on ring C, taken together with the atoms to which they are attached, form a fused phenyl ring, a fused 4-, 5-, 6- or 7-membered heterocycloalkyl ring, a fused 5- or 6-membered heteroaryl ring, or a fused $C_{3-6}$ cycloalkyl ring, wherein the fused 4-, 5-, 6- or 7-membered heterocycloalkyl ring and fused 5- or 6-membered heteroaryl ring each have 1-4 heteroatoms as ring members selected from N, O and S, and wherein the fused phenyl ring, fused 4-, 5-, 6- or 7-membered heterocycloalkyl ring, fused 5- or 6-membered heteroaryl ring and fused $C_{3-6}$ cycloalkyl ring are each optionally substituted with 1, 2 or 3 substituents independently selected from $R^b$;

alternatively, two $R^{31}$ substituents on the same ring carbon atom of ring C, taken together with the carbon atom to which they are attached, form a spiro 4-, 5-, 6- or 7-membered heterocycloalkyl ring, or a spiro $C_{3-6}$ cycloalkyl ring, wherein the spiro 4-, 5-, 6- or 7-membered heterocycloalkyl ring has 1-4 heteroatoms as ring members selected from N, O and S, and wherein the spiro 4-, 5-, 6- or 7-membered heterocycloalkyl ring and spiro $C_{3-6}$ cycloalkyl ring are each optionally substituted with 1, 2 or 3 substituents independently selected from $R^b$; alternatively, two adjacent $R^{32}$ substituents on ring B, taken together with the atoms to which they are attached, form a fused phenyl ring, a fused 4-, 5-, 6- or 7-membered heterocycloalkyl ring, a fused 5- or 6-membered heteroaryl ring, or a fused $C_{3-6}$ cycloalkyl ring, wherein the fused 4-, 5-, 6- or 7-membered heterocycloalkyl ring and fused 5- or 6-membered heteroaryl ring each have 1-4 heteroatoms as ring members selected from N, O and S, and wherein the fused phenyl ring, fused 4-, 5-, 6- or 7-membered heterocycloalkyl ring, fused 5- or 6-membered heteroaryl ring and fused $C_{3-6}$ cycloalkyl ring are each optionally substituted with 1, 2 or 3 substituents independently selected from $R^b$;

alternatively, two $R^{32}$ substituents on the same ring carbon atom of ring B, taken together with the carbon atom to which they are attached, form a spiro 4-, 5-, 6- or 7-membered heterocycloalkyl ring, or a spiro $C_{3-6}$ cycloalkyl ring, wherein the spiro 4-, 5-, 6- or 7-membered heterocycloalkyl ring has 1-4 heteroatoms as ring members selected from N, O and S, and wherein the spiro 4-, 5-, 6- or 7-membered heterocycloalkyl ring and spiro $C_{3-6}$ cycloalkyl ring are each optionally substituted with 1, 2 or 3 substituents independently selected from $R^b$;

each $R^a$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-membered heterocycloalkyl)-$C_{1-4}$ alkyl-, wherein the $C_{1-6}$ alkyl, $C_{1-6}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^a$ are each optionally substituted with 1, 2 or 3 substituents independently selected from $R^d$;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)$ $NR^cR^c$, $NR^cC(=NR^c)NR^cR^c$, $NR^cC(=NOH)NR^cR^c$, $NR^cC(=NCN)NR^cR^c$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$ and $S(O)_2NR^cR^c$; wherein the $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^b$ are each further optionally substituted with 1, 2, or 3 substituents independently selected from $R^d$;

alternatively, two $R^b$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 substituents independently selected from $R^f$;

each $R^c$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^c$ are each optionally substituted with 1, 2 or 3 $R^f$ substituents;

each $R^f$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $NR^gC(=NOH)$ $NR^gR^g$, $NR^gC(=NCN)NR^gR^g$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$;

wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{1-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of R$^f$ are each optionally substituted with 1, 2 or 3 R'' substituents;

each R'' is independently selected from $C_{1-6}$ alkyl, $C_{1-6}$ haloalkyl, halo, CN, $C_{6-10}$ aryl, $C_{3-10}$ cycloalkyl, 5-10 membered heteroaryl, 4-10 membered heterocycloalkyl, $C_{1-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR$^o$)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, and S(O)$_2$NR$^o$R$^o$, wherein the $C_{1-6}$ alkyl, $C_{1-6}$ haloalkyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of R'' is optionally substituted with 1, 2 or 3 R$^q$ substituents;

each R$^d$ is independently selected from $C_{1-6}$ alkyl, $C_{1-6}$ haloalkyl, halo, $C_{6-10}$ aryl, 5-10 membered heteroaryl, $C_{3-10}$ cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, CN, NH$_2$, NHOR$^e$, OR$^e$, SR$^e$, C(O)R$^e$, C(O)NR$^e$R$^e$, C(O)OR$^e$, OC(O)R$^e$, OC(O)NR$^e$R$^e$, NHR$^c$, NR$^e$R$^e$, NR$^e$C(O)R$^e$, NR$^e$C(O)NR$^e$R$^e$, NR$^e$C(O)OR$^e$, C(=NR$^e$)NR$^e$R$^c$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^c$, S(O)$_2$R$^e$, NR$^e$S(O)$_2$R$^e$, NR$^e$S(O)$_2$NR$^e$R$^e$, and S(O)$_2$NR$^e$R$^e$, wherein the $C_{1-6}$ alkyl, $C_{1-6}$haloalkyl, $C_{6-10}$ aryl, 5-10 membered heteroaryl, $C_{3-10}$cycloalkyl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of R$^d$ are each optionally substituted with 1, 2, or 3 substituents independently selected from R$^f$;

each R$^e$ is independently selected from H, $C_{1-6}$ alkyl, $C_{1-6}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^e$ are each optionally substituted with 1, 2 or 3 substituents independently selected from R$^f$;

each R$^g$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$cycloalkyl-$C_{1-4}$alkyl-, (5-10 membered heteroaryl)-$C_{1-4}$ alkyl- and (4-10 membered heterocycloalkyl)-$C_{1-4}$ alkyl- of R$^g$ are each optionally substituted with 1, 2, or 3 R$^p$ substituents;

each R$^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$ and S(O)$_2$NR$^r$R$^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$cycloalkyl-$C_{1-4}$ alkyl-, (5-10 membered heteroaryl)-$C_{1-4}$ alkyl- and (4-10 membered heterocycloalkyl)-$C_{1-4}$ alkyl- of R$^p$ is optionally substituted with 1, 2 or 3 R$^q$ substituents;

alternatively, any two R$^a$ substituents together with the nitrogen atom to which they are attached form a 4-, 5-, 6-, 7-, 8-, 9- or 10-membered heterocycloalkyl group optionally substituted with 1, 2 or 3 R$^h$ substituents;

each R$^h$ is independently selected from $C_{1-6}$ alkyl, $C_{1-6}$ haloalkyl, $C_{1-6}$ haloalkoxy, $C_{3-10}$ cycloalkyl, 4-10 membered heterocycloalkyl, $C_{6-10}$ aryl, 5-10 membered heteroaryl, $C_{3-10}$ cycloalkyl-Cm alkyl-, (5-10 membered heteroaryl)-$C_{1-4}$ alkyl-, (4-10 membered heterocycloalkyl)-$C_{1-4}$ alkyl-, $C_{6-10}$ aryl-$C_{1-4}$ alkyl-, $C_{2-6}$ alkenyl, $C_{2-6}$ alkynyl, halo, CN, OR$^i$, SR$^i$, NHOR$^i$, C(O)R$^i$, C(O)NR$^i$R$^i$, C(O)OR$^i$, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$, R$^i$, NR$^i$C(=NR$^i$)NR$^i$R$^i$, NR$^i$C(=NOH)NR$^i$R$^i$, NR$^i$C(=NCN)NR$^i$R$^i$, S(O)R$^i$, S(O)NR$^i$R$^i$, S(O)$_2$R$^i$, NR$^i$S(O)$_2$R$^i$, NR$^i$S(O)$_2$NR$^i$R$^i$, and S(O)$_2$NR$^i$R$^i$, wherein the $C_{1-6}$ alkyl, $C_{1-6}$ haloalkyl, $C_{1-6}$ haloalkoxy, $C_{3-10}$ cycloalkyl, 4-10 membered heterocycloalkyl, $C_{6-10}$ aryl, 5-10 membered heteroaryl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of R$^h$ are each optionally substituted by 1, 2, or 3 R$^j$ substituents;

each R$^j$ is independently selected from $C_{1-4}$ alkyl, $C_{3-10}$ cycloalkyl, $C_{6-10}$ aryl, 5-10 membered heteroaryl, 4-10 membered heterocycloalkyl, $C_{2-4}$ alkenyl, $C_{2-4}$ alkynyl, halo, $C_{1-4}$ haloalkyl, $C_{1-4}$ haloalkoxy, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, and S(O)$_2$NR$^k$R$^k$, wherein the $C_{1-4}$ alkyl, $C_{3-10}$ cycloalkyl, $C_{6-10}$ aryl, 5-10 membered heteroaryl, 4-10 membered heterocycloalkyl, $C_{2-4}$ alkenyl, $C_{1-4}$ haloalkyl, and $C_{1-4}$ haloalkoxy of R$^j$ are each optionally substituted with 1, 2 or 3 substituents independently selected from R$^q$;

alternatively, two R$^h$ groups attached to the same carbon atom of the 4- to 10-membered heterocycloalkyl, taken together with the carbon atom to which they are attached, form a $C_{3-6}$ cycloalkyl or 4- to 6-membered heterocycloalkyl having 1-2 heteroatoms as ring members selected from O, N or S;

alternatively, any two R$^c$ substituents together with the nitrogen atom to which they are attached form a 4-, 5-, 6-, 7-, 8-, 9-, or 10-membered heterocycloalkyl group optionally substituted with 1, 2, or 3 substituents independently selected from R$^f$;

alternatively, any two R$^e$ substituents together with the nitrogen atom to which they are attached form a 4-, 5-, 6-, 7-, 8-, 9-, or 10-membered heterocycloalkyl group optionally substituted with 1, 2, or 3 substituents independently selected from $R^j$;

alternatively, any two $R^g$ substituents together with the nitrogen atom to which they are attached form a 4-, 5-, 6-, 7-, 8-, 9-, or 10-membered heterocycloalkyl group optionally substituted with 1, 2, or 3 substituents independently selected from $R^p$;

alternatively, any two $R^i$ substituents together with the nitrogen atom to which they are attached form a 4-, 5-, 6-, 7-, 8-, 9-, or 10-membered heterocycloalkyl group optionally substituted with 1, 2, or 3 substituents independently selected from $R^q$;

alternatively, any two $R^k$ substituents together with the nitrogen atom to which they are attached form a 4-, 5-, 6-, 7-, 8-, 9-, or 10-membered heterocycloalkyl group optionally substituted with 1, 2, or 3 substituents independently selected from $R^q$;

alternatively, any two $R^o$ substituents together with the nitrogen atom to which they are attached form a 4-, 5-, 6-, 7-, 8-, 9-, or 10-membered heterocycloalkyl group optionally substituted with 1, 2, or 3 substituents independently selected from $R^q$; and alternatively, any two $R^r$ substituents together with the nitrogen atom to which they are attached form a 4-, 5-, 6-, 7-, 8-, 9-, or 10-membered heterocycloalkyl group optionally substituted with 1, 2, or 3 substituents independently selected from $R^q$;

each $R^i$, $R^k$, $R^o$ or $R^r$ is independently selected from H, $C_{1-6}$ alkyl, $C_{1-6}$ haloalkyl, $C_{3-6}$ cycloalkyl, $C_{6-10}$ aryl, 4-6 membered heterocycloalkyl, 5 or 6-membered heteroaryl, $C_{1-4}$ haloalkyl, $C_{2-4}$ alkenyl, and $C_{2-4}$ alkynyl, wherein the $C_{1-4}$ alkyl, $C_{1-6}$ haloalkyl, $C_{3-6}$ cycloalkyl, $C_{6-10}$ aryl, 4-6 membered heterocycloalkyl, 5 or 6-membered heteroaryl, $C_{2-4}$ alkenyl, and $C_{2-4}$ alkynyl of $R^i$, $R^k$, $R^o$ or $R^r$ are each optionally substituted with 1, 2 or 3 $R^q$ substituents;

each $R^q$ is independently selected from OH, CN, —COOH, $NH_2$, halo, $C_{1-6}$ haloalkyl, $C_{1-6}$ alkyl, $C_{1-6}$alkoxy, $C_{1-6}$haloalkoxy, $C_{1-6}$ alkylthio, phenyl, 5-6 membered heteroaryl, 4-6 membered heterocycloalkyl, $C_{3-6}$ cycloalkyl, $NHR^{12}$ and $NR^{12}R^{12}$, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, 5-6 membered heteroaryl, $C_{3-10}$ cycloalkyl and 4-6 membered heterocycloalkyl and each $R^{12}$ is independently $C_{1-6}$ alkyl;

the subscript n is an integer of 0, 1, 2, or 3;

the subscript m is an integer of 0, 1, 2, or 3;

the subscript u is an integer of 0, 1, 2, or 3;

the subscript v is an integer of 0, 1, 2, or 3;

each subscript p is independently an integer of 1, 2, or 3;

each subscript t is independently an integer of 0, 1, 2, or 3;

each subscript q is independently an integer of 1, 2, or 3; and each subscript w is independently an integer of 0, 1, 2, or 3.

In one embodiment, combinable with any other embodiment disclosed herein, the compound used in a method described herein is the compound of Formula (II):

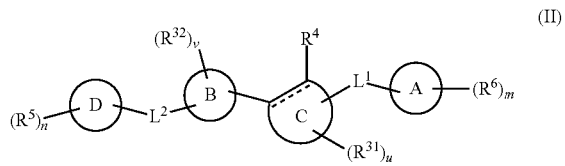

or a pharmaceutically acceptable salt or a stereoisomer thereof.

In one embodiment, combinable with any other embodiment disclosed herein, the compound used in a method described herein is the compound of Formula (II):

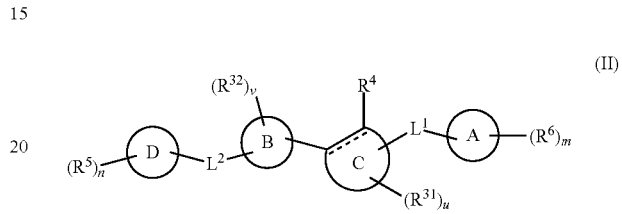

or a pharmaceutically acceptable salt or a stereoisomer thereof, wherein ring B is a $C_{6-10}$ aryl, a 5- to 10-membered heteroaryl comprising carbon and 1, 2, 3, or 4 heteroatoms selected from N, O and S, a 4- to 10-membered heterocycloalkyl comprising carbon and 1, 2, 3, or 4 heteroatoms selected from N, O and S, or a $C_{3-10}$ cycloalkyl;

ring C is $C_{6-10}$ aryl, a 5- to 10-membered heteroaryl comprising carbon and 1, 2, 3, or 4 heteroatoms selected from N, O and S, a 4- to 10-membered heterocycloalkyl comprising carbon and 1, 2, 3, or 4 heteroatoms selected from N, O and S, or $C_{3-10}$ cycloalkyl; the atoms on ring C, to which the substituent $R^4$ and ring B are attached are carbon; and ---- is a single bond or a double bond.

In one embodiment, combinable with any other embodiment disclosed herein, the compound used in a method described herein is the compound of Formula (II):

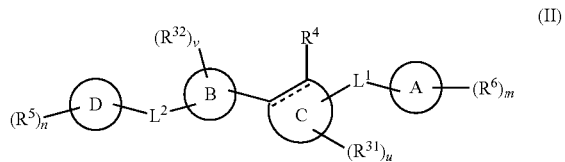

or a pharmaceutically acceptable salt or a stereoisomer thereof, wherein ring B is a phenyl, a 5- to 6-membered heteroaryl comprising carbon and 1, 2, or 3 heteroatoms selected from N, O and S, a 4- to 6-membered heterocycloalkyl comprising carbon and 1, 2, or 3 heteroatoms selected from N, O and S, or a $C_{3-6}$ cycloalkyl;

ring C is phenyl, a 5- to 6-membered heteroaryl comprising carbon and 1, 2, or 3 heteroatoms selected from N, O and S, a 4- to 6-membered heterocycloalkyl comprising carbon and 1, 2, or 3 heteroatoms selected from N, O and S, or a $C_{3-6}$ cycloalkyl;

the atoms on ring C, to which the substituent $R^4$ and ring B are attached are carbon; and ---- is a single bond or a double bond.

In one embodiment, combinable with any other embodiment disclosed herein, the compound used in a method described herein is the compound of Formula (III):

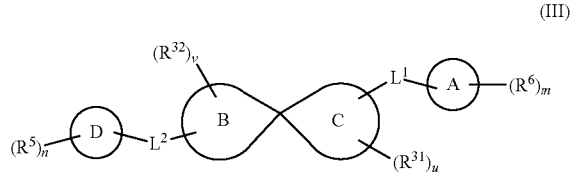

(III)

or a pharmaceutically acceptable salt or a stereoisomer thereof, wherein ring B and ring C are each independently 4- to 11-membered heterocycloalkyl or $C_{3-10}$ cycloalkyl.

In one embodiment, combinable with any other embodiment described herein, the compound used in a method described herein is the compound of Formula (III):

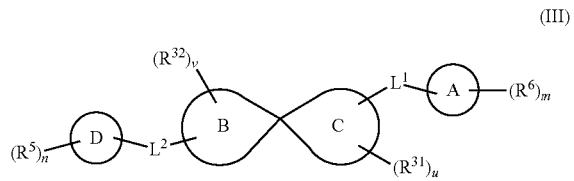

(III)

or a pharmaceutically acceptable salt or a stereoisomer thereof, wherein ring B and ring C are each independently 4- to 7-membered heterocycloalkyl or $C_{3-7}$ cycloalkyl.

In one embodiment, combinable with any other embodiment described herein, the compound used in a method described herein is the compound of Formula (IIa):

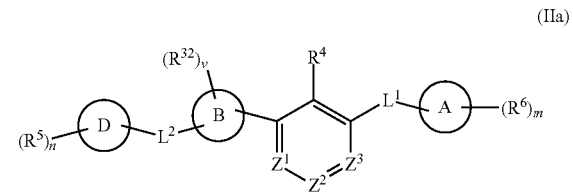

(IIa)

or a pharmaceutically acceptable salt or a stereoisomer thereof, wherein:
$Z^1$ is N or $CR^1$;
$Z^2$ is N or $CR^2$;
$Z^3$ is N or $CR^3$;
ring B is a phenyl, a 5- to 6-membered heteroaryl comprising carbon and 1, 2, or 3 heteroatoms selected from N, O and S, a 4- to 6-membered heterocycloalkyl comprising carbon and 1, 2, or 3 heteroatoms selected from N, O and S, or a $C_{3-6}$ cycloalkyl;
$R^1$, $R^2$ and $R^3$ are each independently selected from H, $C_{1-4}$ alkyl, $C_{1-4}$ alkoxy, $C_{3-10}$ cycloalkyl, $C_{3-10}$cycloalkyl-$C_{1-4}$ alkyl-, $C_{6-10}$ aryl, $C_{1-10}$ aryl-$C_{1-4}$ alkyl-, 5-10 membered heteroaryl, 4-10 membered heterocycloalkyl, (5-10 membered heteroaryl)-$C_{1-4}$ alkyl-, (4-10 membered heterocycloalkyl)-$C_{1-4}$ alkyl-, $C_{2-4}$ alkenyl, $C_{2-4}$ alkynyl, halo, CN, $OR^7$, $C_{1-4}$ haloalkyl, $C_{1-4}$ haloalkoxy, $NH_2$, —$NHR^7$, —$NR^7R^7$, $NHOR^7$, $C(O)R^7$, $C(O)NR^7R^7$, $C(O)OR^7$, $OC(O)R^7$, $OC(O)NR^7R^7$, $NR^7C(O)R^7$, $NR^7C(O)OR^7$, $NR^7C(O)NR^7R^7$, $C(=NR^7)R^7$, $C(=NR^7)NR^7R^7$, $NR^7C(=NR^7)NR^7R^7$, $NR^7S(O)R^7$, $NR^7S(O)_2R^7$, $NR^7S(O)_2NR^7R^7$, $S(O)R^7$, $S(O)NR^7R^7$, $S(O)_2R^7$, and $S(O)_2NR^7R^7$, wherein each $R^7$ is independently selected from H, $C_{1-4}$ alkyl, $C_{2-4}$ alkenyl, $C_{2-4}$ alkynyl, $C_{1-4}$alkoxy, $C_{3-10}$ cycloalkyl, $C_{3-10}$ cycloalkyl-$C_{1-4}$ alkyl-, $C_{6-10}$ aryl, $C_{6-10}$ aryl-$C_{1-4}$ alkyl, 5-10 membered heteroaryl, 4-10 membered heterocycloalkyl, (5-10 membered heteroaryl)-$C_{1-4}$ alkyl-, and (4-10 membered heterocycloalkyl)-$C_{1-4}$ alkyl-, wherein the $C_{1-4}$ alkyl, $C_{1-4}$ alkoxy, $C_{3-10}$ cycloalkyl, $C_{3-10}$ cycloalkyl-$C_{3-10}$ alkyl-, $C_{6-10}$ aryl, $C_{6-10}$ aryl-$C_{1-4}$ alkyl-, 5-10 membered heteroaryl, 4-10 membered heterocycloalkyl, (5-10 membered heteroaryl)-$C_{1-4}$ alkyl-, and (4-10 membered heterocycloalkyl)-$C_{1-4}$ alkyl- of $R^1$, $R^2$, $R^3$ and $R^7$ are each optionally substituted with 1 or 2 independently selected $R^d$ substituents.

In one embodiment, combinable with any other embodiment described herein, the compound used in a method described herein is the compound of Formula (IIb):

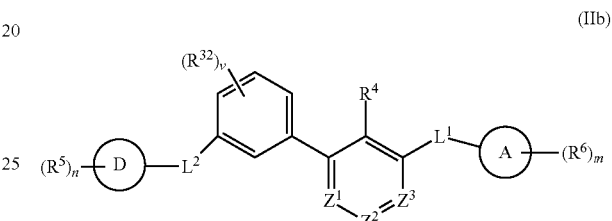

(IIb)

or a pharmaceutically acceptable salt or a stereoisomer thereof.

In one embodiment, combinable with any other embodiment described herein, the compound is the compound, or a pharmaceutically acceptable salt or a stereoisomer thereof, wherein:

substituent

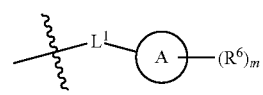

is

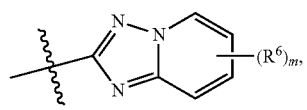

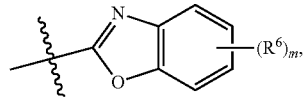

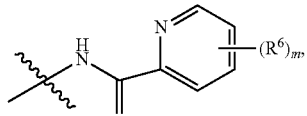

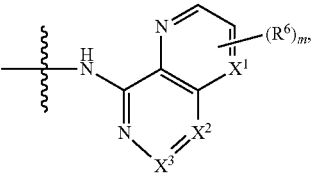

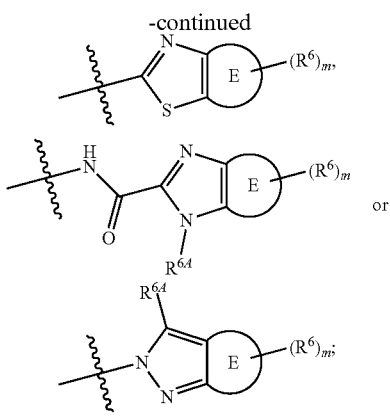

wherein $X^1$, $X^2$ and $X^3$ are each independently N or CH; ring E is fused 5- or 6-membered heterocycloalkyl; $R^{6A}$ is H or $C_{1-6}$ alkyl; and each subscript m is independently an integer of 0, 1, or 2.

In one embodiment, combinable with any other embodiment described herein, the compound used in a method described herein is the compound, or a pharmaceutically acceptable salt or a stereoisomer thereof, wherein each $R^{32}$ is independently $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{0-4}$ alkyl$)_2$.

In one embodiment, combinable with any other embodiment described herein, the compound used in a method described herein is the compound, or a pharmaceutically acceptable salt or a stereoisomer thereof, wherein $Z^1$ is $CR^1$, $Z^2$ is $CR^2$ and $Z^3$ is $CR^3$.

In one embodiment, combinable with any other embodiment described herein, the compound used in a method described herein is the compound, or a pharmaceutically acceptable salt or a stereoisomer thereof, wherein $Z^1$, $Z^2$ and $Z^3$ are each CH.

In one embodiment, combinable with any other embodiment described herein, the compound used in a method described herein is the compound, or a pharmaceutically acceptable salt or a stereoisomer thereof, wherein
$L^1$ is a bond, —$(CR^{14}R^{15})_tC(O)NR^{13}(CR^{14}R^{15})_t$—, —$(CR^{14}R^{15})_tNR^{13}C(O)(CR^{14}R^{15})_t$—, —O—, —$(CR^{14}R^{15})_p$—, —$(CR^{14}R^{15})_p$—O—, —O$(CR^{14}R^{15})_p$—, —$(CR^{14}R^{15})_p$—O—$(CR^{14}R^{15})_p$—, —$NR^{13}$—, —$(CR^{14}R^{15})_tNR^{13}(CR^{14}R^{15})_t$—, —NH—, —$(CR^{14}R^{15})_tNH(CR^{14}R^{15})_t$—, —$CR^{13}$=$CR^{13}$—, —C≡C—, —$SO_2$—, —$(CR^{14}R^{15})_tSO_2(CR^{14}R^{15})_t$—, —$(CR^{14}R^{15})_tSO_2NR^{13}(CR^{14}R^{15})_t$—, —$(CR^{14}R^{15})_tNR^{13}SO_2(CR^{14}R^{15})_t$—, —$(CR^{14}R^{15})_tNR^{13}SO_2NR^{13}(CR^{14}R^{15})_t$—, —$(CR^{14}R^{15})_tNR^{13}C(O)O(CR^{14}R^{15})_t$—, —$NR^{13}C(O)O$—, —$(CR^{14}R^{15})_tO(CO)NR^{13}(CR^{14}R^{15})_t$—, —$O(CO)NR^{13}$—, —$NR^{13}C(O)NR^{13}$— or —$(CR^{14}R^{15})_tNR^{13}C(O)NR^{13}(CR^{14}R^{15})_t$—;

each subscript p is independently an integer of 1 or 2; and each subscript t is independently an integer of 0, 1, or 2.

In one embodiment, combinable with any other embodiment described herein, the compound used in a method described herein is the compound, or a pharmaceutically acceptable salt or a stereoisomer thereof, wherein $R^{13}$ is H, $R^{14}$ is H, and $R^{15}$ is H.

In one embodiment, combinable with any other embodiment described herein, the compound used in a method described herein is the compound, or a pharmaceutically acceptable salt or a stereoisomer thereof, wherein $L^1$ is a bond, —C(O)NH—, —NHC(O)—, —O—, —NH—, —CH=CH—, —C≡C—, —$SO_2$—, —$SO_2NH$—, —$NHSO_2$—, —$NHSO_2NH$—, —NHC(O)O—, —NHC(O)O—, —O(CO)NH—, —O(CO)NH—, —NHC(O)NH— or —NHC(O)NH.

In one embodiment, combinable with any other embodiment described herein, the compound used in a method described herein is the compound, or a pharmaceutically acceptable salt or a stereoisomer thereof, wherein
$L^2$ is a bond, —$(CR^{29}R^{30})_tC(O)NR^{28}(CR^{29}R^{30})_t$—, —$(CR^{29}R^{30})_tNR^{28}C(O)(CR^{29}R^{30})_t$—, —O—, —$(CR^{29}R^{30})_q$—, —$(CR^{29}R^{30})_q$—O—, —O$(CR^{29}R^{30})_q$—, —$(CR^{29}R^{30})_q$—O—$(CR^{29}R^{30})_q$—, —$NR^{28}$—, —$(CR^{29}R^{30})_qNR^{28}(CR^{29}R^{30})_q$—, —NH—, —$(CR^{29}R^{30})_wNH(CR^{29}R^{30})_w$—, —$CR^{28}$=$CR^{28}$—, —C≡C—, —$SO_2$—, —$(CR^{29}R^{30})_wSO_2(CR^{29}R^{30})_w$—, —$(CR^{29}R^{30})_wSO_2NR^{28}(CR^{29}R^{30})_w$—, —$(CR^{29}R^{30})_wNR^{28}SO_2(CR^{29}R^{30})_w$—, —$(CR^{29}R^{30})_wNR^{28}SO_2NR^{28}(CR^{29}R^{30})_w$—, —$(CR^{29}R^{30})_wNR^{28}C(O)O(CR^{29}R^{30})_w$—, —$NR^{28}C(O)O$—, —$(CR^{29}R^{30})_wO(CO)NR^{28}(CR^{29}R^{30})_w$—, —O(CO)NR^{28}—, —$NR^{28}C(O)NR^{28}$— or —$(CR^{29}R^{30})_wNR^{28}C(O)NR^{28}(CR^{29}R^{30})_w$—;

each subscript t is independently an integer of 0, 1, or 2; each subscript q is independently an integer of 1 or 2; and each subscript w is independently an integer of 0, 1, or 2.

In one embodiment, combinable with any other embodiment described herein, the compound used in a method described herein is the compound, or a pharmaceutically acceptable salt or a stereoisomer thereof, wherein $R^{28}$ is H, $R^{29}$ is H, and $R^{30}$ is H.

In one embodiment, combinable with any other embodiment described herein, the compound used in a method described herein is the compound, or a pharmaceutically acceptable salt or a stereoisomer thereof, wherein $L^2$ is a bond, —C(O)NH—, —NHC(O)—, —O—, —NH—, —CH=CH—, —C≡C—, —$SO_2$—, —$SO_2NH$—, —$NHSO_2$—, —$NHSO_2NH$—, —NHC(O)O—, —NHC(O)O—, —O(CO)NH—, —O(CO)NH—, —NHC(O)NH— or —NHC(O)NH.

In some embodiments, the present disclosure provides compounds of Formula (IV):

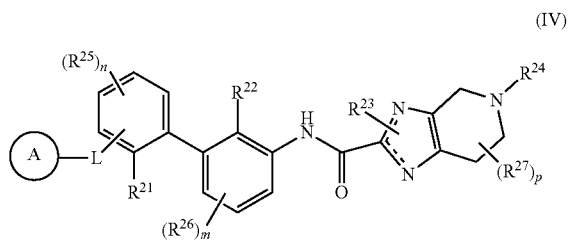

or a pharmaceutically acceptable salt or a stereoisomer thereof, wherein:

ring A is 5- to 14-membered heteroaryl, 4- to 14-membered heterocycloalkyl, $C_{6-10}$ aryl or $C_{3-10}$ cycloalkyl, wherein the 5- to 14-membered heteroaryl and 4- to 14-membered heterocycloalkyl each has 1-4 heteroatoms as ring members selected from B, P, N, O and S, wherein the N, P or S atom as ring members is optionally oxidized and one or more carbon atoms as ring members are each optionally replaced by a carbonyl group; and wherein ring A is optionally substituted with 1, 2, 3, 4 or 5 $R^{20}$ substituents;

L is a bond, —NH—, —O—, —C(O)NH—, —C(=S)NH—, —C(=NH)NH—, —C(=NOH)NH—, —C(=NCN)NH—, —$CH_2O$— or —$OCH_2$—, wherein the carbonyl group in the —C(O)NH— linkage is attached to ring A;

$R^{21}$ and $R^{22}$ are each independently halo, $C_{1-6}$ alkyl or CN;

$R^{23}$ is H, $C_{1-6}$ alkyl or $C_{1-6}$ haloalkyl;

$R^{25}$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

$R^{26}$ is $C_{1-4}$ alkyl, $C_{1-4}$ alkoxy, $C_{1-4}$ haloalkyl, $C_{1-4}$ haloalkoxy, CN, halo, OH, —COOH, $NH_2$, —$NHC_{1-4}$ alkyl or —$N(C_{1-4}$ alkyl$)_2$;

$R^{24}$ is selected from H, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, $C(O)R^a$, $C(O)NR^aR^a$, $C(O)OR^a$, $C(=NR^a)R^a$, $C(=NOH)R^a$, $C(=NOH)NR^a$, $C(=NCN)NR^aR^a$, $C(=NR^a)NR^aR^a$, $S(O)R^a$, $S(O)NR^aR^a$, $S(O)_2R^a$, —$P(O)R^aR^a$, —$P(O)(OR^a)(OR^a)$, —$B(OH)_2$, —$B(OR^a)_2$ and $S(O)_2NR^aR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^{24}$ are each optionally substituted with 1, 2, 3, 4 or 5 independently selected $R^b$ substituents;

$R^{20}$ is each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^{a1}$, $SR^{a1}$, $NHOR^{a1}$, $C(O)R^{a1}$, $C(O)NR^{a1}R^{a1}$, $C(O)OR^{a1}$, $C(O)NR^{a1}S(O)_2R^{a1}$, $OC(O)R^{a1}$, $OC(O)NR^{a1}R^{a1}$, $NHR^{a1}$, $NR^{a1}R^{a1}$, $NR^{a1}C(O)R^{a1}$, $NR^{a1}C(=NR^{a1})R^{a1}$, $NR^{a1}C(O)OR^{a1}$, $NR^{a1}C(O)NR^{a1}R^{a1}$, $C(=NR^{a1})R^{a1}$, $C(=NOH)R^{a1}$, $C(=NOH)NR^{a1}$, $C(=NCN)NR^{a1}R^{a1}$, $NR^{a1}C(=NCN)NR^{a1}R^{a1}$, $C(=NR^{a1})NR^{a1}R^{a1}$, $NR^{a1}C(=NR^{a1})NR^{a1}R^{a1}$, $NR^{a1}S(O)R^{a1}$, $NR^{a1}S(O)_2R^{a1}$, $NR^{a1}S(O)_2NR^{a1}R^{a1}$, $S(O)R^{a1}$, $S(O)NR^{a1}R^{a1}$, $S(O)_2R^{a1}$, $S(O)_2NR^{a1}C(O)R^{a1}$, —$P(O)R^{a1}R^{a1}$, —$P(O)(OR^{a1})(OR^{a1})$, —$B(OH)_2$, —$B(OR^{a1})_2$ and $S(O)_2NR^{a1}R^{a1}$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^{20}$ are each optionally substituted with 1, 2, 3, 4 or 5 independently selected $R^b$ substituents;

$R^{27}$ is each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NO_2$, $OR^{a2}$, $SR^{a2}$, $NHOR^{a2}$, $C(O)R^{a2}$, $C(O)NR^{a2}R^{a2}$, $C(O)OR^{a2}$, $C(O)NR^{a2}S(O)_2R^{a2}$, $OC(O)R^{a2}$, $OC(O)NR^{a2}R^{a2}$, $NHR^{a2}$, $NR^{a2}R^{a2}$, $NR^{a2}C(O)R^{a2}$, $NR^{a2}C(=NR^{a2})R^{a2}$, $NR^{a2}C(O)OR^{a2}$, $NR^{a2}C(O)NR^{a2}R^{a2}$, $C(=NR^{a2})R^{a2}$, $C(=NOH)R^{a2}$, $C(=NOH)NR^{a2}$, $C(=NCN)NR^{a2}R^{a2}$, $NR^{a2}C(=NCN)NR^{a2}R^{a2}$, $C(=NR^{a2})NR^{a2}R^{a2}$, $NR^{a2}C(=NR^{a2})NR^{a2}R^{a2}$, $NR^{a2}S(O)R^{a2}$, $NR^{a2}S(O)_2R^{a2}$, $NR^{a2}S(O)_2NR^{a2}R^{a2}$, $S(O)R^{a2}$, $S(O)NR^{a2}R^{a2}$, $S(O)_2R^{a2}$, $S(O)_2NR^{a2}C(O)R^{a2}$, —$P(O)R^{a2}R^{a2}$, —$P(O)(OR^{a2})(OR^{a2})$, —$B(OH)_2$, —$B(OR^{a2})_2$ and $S(O)_2NR^{a2}R^{a2}$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$alkyl-, (5-14 membered heteroaryl)-$C_{1-4}$ alkyl- and (4-14 membered heterocycloalkyl)-$C_{1-4}$ alkyl- of $R^{27}$ are each optionally substituted with 1, 2, 3, 4 or 5 independently selected $R^b$ substituents;

or two $R^{20}$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

or two $R^{27}$ substituents attached to the same ring carbon atom taken together with the ring carbon atom to which they are attached form spiro $C_{3-6}$ cycloalkyl or spiro 4- to 7-membered heterocycloalkyl, each of which is optionally substituted with 1, 2, or 3 independently selected $R^f$ substituents;

each of $R^a$, $R^{a1}$ and $R^{a2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-14}$cycloalkyl, 5-14 membered heteroaryl, 4-14 membered heterocycloalkyl, $C_{6-10}$ aryl-$C_{1-4}$ alkyl-, $C_{3-14}$cycloalkyl-$C_{1-4}$ alkyl-, (5-14 membered heteroaryl)-$C_{1-4}$ alkyl- and (4-14 membered heterocycloalkyl)-$C_{1-4}$ alkyl- of R $R^{a1}$ and $R^{a2}$ are each optionally substituted with 1, 2, 3, 4, or 5 independently selected $R^d$ substituents;

each $R^d$ is independently selected from $C_{1-6}$ alkyl, $C_{1-6}$haloalkyl, halo, $C_{6-10}$ aryl, 5-14 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $NH_2$, $NHOR^e$, $OR^e$, $SR^e$, $C(O)R^e$, $C(O)NR^eR^e$, $C(O)OR^e$, $C(O)NR^eS(O)_2R^e$, $OC(O)R^c$, $OC(O)NR^cR^e$, $NHR^c$, $NR^eR^e$, $NR^cC(O)R^e$, $NR^cC(=NR^e)R^e$, $NR^eC(O)NR^eR^e$, $NR^eC(O)OR^c$, $C(=NR^c)NR^eR^e$, $NR^eC(=NR^e)NR^eR^e$, $NR^eC(=NOH)NR^eR^c$, $NR^eC(=NCN)NR^eR^e$, $S(O)R^e$, $S(O)NR^eR^e$, $S(O)_2R^e$, $S(O)_2NR^eC(O)R^e$, $NR^eS(O)_2R^e$, $NR^eS(O)_2NR^eR^e$, —$P(O)R^eR^e$, —$P(O)(OR^e)(OR^e)$, —$B(OH)_2$, —$B(OR^e)_2$ and $S(O)_2NR^eR^e$, wherein the $C_{1-6}$ alkyl, $C_{1-6}$ haloalkyl, $C_{6-10}$ aryl, 5-14 membered heteroaryl, $C_{3-14}$ cycloalkyl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, and (4-14 membered heterocycloalkyl)-$C_{1-4}$ alkyl- of $R^d$ are each optionally substituted with 1, 2, or 3 independently selected $R^f$ substituents;

each $R^e$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^e$ are each optionally substituted with 1, 2 or 3 independently selected $R^f$ substituents;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, OH, $NH_2$, $NO_2$, $NHOR^c$, $OR^c$, $SR^c$, $C(O)R^c$, $C(O)NR^cR^c$, $C(O)OR^c$, $C(O)NR^cS(O)_2R^c$, $OC(O)R^c$, $OC(O)NR^cR^c$, $C(=NOH)R^c$, $C(=NOH)NR^cR^c$, $C(=NCN)NR^cR^c$, $NR^cC(=NCN)NR^cR^c$, $C(=NR^c)NR^cR^c$, $NR^cC(=NR^c)NR^cR^c$, $NHR^c$, $NR^cR^c$, $NR^cC(O)R^c$, $NR^cC(=NR^c)R^c$, $NR^cC(O)OR^c$, $NR^cC(O)NR^cR^c$, $NR^cS(O)R^c$, $NR^cS(O)_2R^c$, $NR^cS(O)_2NR^cR^c$, $S(O)R^c$, $S(O)NR^cR^c$, $S(O)_2R^c$, $S(O)_2NR^cC(O)R^c$, —$P(O)R^cR^c$, —$P(O)(OR^c)(OR^c)$, —$B(OH)_2$, —$B(OR^c)_2$ and $S(O)_2NR^cR^c$; wherein the $C_{1-6}$ alkyl, $C_{1-6}$ haloalkyl, $C_{1-6}$ haloalkoxy, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^b$ are each further optionally substituted with 1, 2 or 3 independently selected $R^d$ substituents;

each $R^c$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$cycloalkyl-$C_{1-4}$ alkyl-, (5-14 membered heteroaryl)-$C_{1-4}$alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^c$ are each optionally substituted with 1, 2, 3, 4, or 5 independently selected $R^f$ substituents;

each $R^f$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^g$, $OR^g$, $SR^g$, $C(O)R^g$, $C(O)NR^gR^g$, $C(O)OR^g$, $C(O)NR^gS(O)_2R^g$, $OC(O)R^g$, $OC(O)NR^gR^g$, $NHR^g$, $NR^gR^g$, $NR^gC(O)R^g$, $NR^gC(=NR^g)R^g$, $NR^gC(O)NR^gR^g$, $NR^gC(O)OR^g$, $C(=NR^g)NR^gR^g$, $NR^gC(=NR^g)NR^gR^g$, $S(O)R^g$, $S(O)NR^gR^g$, $S(O)_2R^g$, $S(O)_2NR^gC(O)R^g$, $NR^gS(O)_2R^g$, $NR^gS(O)_2NR^gR^g$, —$P(O)R^gR^g$, —$P(O)(OR^g)(OR^g)$, —$B(OH)_2$, —$B(OR^g)_2$ and $S(O)_2NR^gR^g$; wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^f$ are each optionally substituted with 1, 2, 3, 4, or 5 independently selected $R^n$ substituents;

each $R^n$ is substituents independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^o$, $OR^o$, $SR^o$, $C(O)R^o$, $C(O)NR^oR^o$, $C(O)OR^o$, $C(O)NR^oS(O)_2R^o$, $OC(O)R^o$, $OC(O)NR^oR^o$, $NHR^o$, $NR^oR^o$, $NR^oC(O)R^o$, $NR^oC(=NR^o)R^o$, $NR^oC(O)NR^oR^o$, $NR^oC(O)OR^o$, $C(=NR^o)NR^oR^o$, $NR^oC(=NR^o)NR^oR^o$, $S(O)R^o$, $S(O)NR^oR^o$, $S(O)_2R^o$, $S(O)_2NR^oC(O)R^o$, $NR^oS(O)_2 R^o$, $NR^oS(O)_2NR^oR^o$, —$P(O)R^oR^o$, —$P(O)(OR^o)(OR^o)$, —$B(OH)_2$, —$B(OR^o)_2$ and $S(O)_2NR^oR^o$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl- of $R^n$ are each optionally substituted with 1, 2 or 3 independently selected $R^q$ substituents;

each $R^g$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, and (4-10 membered heterocycloalkyl)-$C_{1-4}$ alkyl-, wherein the $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^g$ are each optionally substituted with 1, 2, or 3 independently selected $R^p$ substituents;

each $R^p$ is independently selected from $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, halo, CN, $NHOR^r$, $OR^r$, $SR^r$, $C(O)R^r$, $C(O)NR^rR^r$, $C(O)OR^r$, $C(O)NR^rS(O)_2R^r$, $OC(O)R^r$, $OC(O)NR^rR^r$, $NHR^r$, $NR^rR^r$, $NR^rC(O)R^r$, $NR^rC(=NR^r)R^r$, $NR^rC(O)NR^rR^r$, $NR^rC(O)OR^r$, $C(=NR^r)NR^rR^r$, $NR^rC(=NR^r)NR^rR^r$, $NR^rC(=NOH)NR^rR^r$, $NR^rC(=NCN)NR^rR^r$, $S(O)R^r$, $S(O)NR^rR^r$, $S(O)_2R^r$, $S(O)_2NR^rC(O)R^r$, $NR^rS(O)_2R^r$, $NR^rS(O)_2NR^rR^r$, —$P(O)R^rR^r$, —$P(O)(OR^r)(OR^r)$, —$B(OH)_2$, —$B(OR^r)_2$ and $S(O)_2NR^rR^r$, wherein the $C_{1-6}$ alkyl, $C_{1-6}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl- and (4-10 membered heterocycloalkyl)-$C_{1-4}$ alkyl- of $R^p$ is optionally substituted with 1, 2 or 3 independently selected $R^q$ substituents;

or any two $R^a$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected $R^h$ substituents;

or any two $R^{a1}$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected $R^h$ substituents;

or any two $R^{a2}$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected $R^h$ substituents;

each $R^h$ is independently selected from $C_{1-4}$ alkyl, $C_{3-10}$ cycloalkyl, 4-10 membered heterocycloalkyl, $C_{6-10}$ aryl, 5-10 membered heteroaryl, $C_{6-10}$ aryl-$C_{1-4}$ alkyl-, $C_{3-10}$ cycloalkyl-$C_{1-4}$ alkyl-, (5-10 membered heteroaryl)-$C_{1-4}$ alkyl-, (4-10 membered heterocycloalkyl)-$C_{1-4}$ alkyl-, $C_{1-6}$ haloalkyl, $C_{1-6}$haloalkoxy, $C_{2-6}$ alkenyl, $C_{2-6}$ alkynyl, halo, CN, $OR^i$, $SR^i$, $NHOR^i$, $C(O)R^i$, $C(O)NR^iR^i$, $C(O)OR^i$, $C(O)NR^iS(O)_2R^i$, $OC(O)R^i$, $OC(O)NR^iR^i$, $NHR^i$, $NR^iR^i$, $NR^iC(O)R^i$, $NR^iC(=NR^i)R^i$, $NR^iC(O)NR^iR^i$, $NR^iC(O)OR^i$, $C(=NR^i)NR^iR^i$, $NR^iC(=NR^i)NR^iR^i$, $S(O)R^i$, $S(O)NR^iR^i$, $S(O)_2R^i$, $S(O)_2NR^iC(O)R^i$, $NR^iS(O)_2R^i$, $NR^iS(O)_2NR^iR^i$, —$P(O)R^iR^i$, —$P(O)(OR^i)(OR^i)$, —$B(OH)_2$, —$B(OR^i)_2$ and $S(O)_2NR^iR^i$, wherein the $C_{1-6}$ alkyl, $C_{2-6}$ alkenyl, $C_{2-6}$ alkynyl, $C_{3-10}$ cycloalkyl, 4-10 membered heterocycloalkyl, $C_{6-10}$ aryl, 5-10 membered heteroaryl, $C_{6-10}$ aryl-$C_{1-4}$ alkyl-, $C_{3-10}$ cycloalkyl-$C_{1-4}$ alkyl-, (5-10 membered heteroaryl)-

$C_{1-4}$ alkyl-, and (4-10 membered heterocycloalkyl)-$C_{1-4}$ alkyl- of $R^h$ are each optionally substituted by 1, 2, or 3 independently selected $R^j$ substituents;

each $R^j$ is independently selected from $C_{3-6}$ cycloalkyl, $C_{6-10}$ aryl, 5 or 6-membered heteroaryl, 4-7 membered heterocycloalkyl, $C_{2-4}$ alkenyl, $C_{2-4}$ alkynyl, halo, $C_{1-4}$ alkyl, $C_{1-4}$ haloalkyl, $C_{1-4}$ haloalkoxy, CN, NHOR$^k$, OR$^k$, SR$^k$, C(O)R$^k$, C(O)NR$^k$R$^k$, C(O)OR$^k$, C(O)NR$^k$S(O)$_2$R$^k$, OC(O)R$^k$, OC(O)NR$^k$R$^k$, NHR$^k$, NR$^k$R$^k$, NR$^k$C(O)R$^k$, NR$^k$C(=NR$^k$)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, S(O)$_2$NR$^k$C(O)R$^k$, NR$^k$S(O)$_2$R$^k$, NR$^k$S(O)$_2$NR$^k$R$^k$, —P(O)R$^k$R$^k$, —P(O)(OR$^k$)(OR$^k$), —B(OH)$_2$, —B(OR$^k$)$_2$ and S(O)$_2$NR$^k$R$^k$, wherein the $C_{1-4}$ alkyl, $C_{3-6}$ cycloalkyl, $C_{6-10}$ aryl, 5- or 6-membered heteroaryl, 4-7 membered heterocycloalkyl, $C_{2-4}$ alkenyl, $C_{2-4}$ alkynyl, $C_{1-4}$ haloalkyl, and $C_{1-4}$ haloalkoxy of $R^j$ are each optionally substituted with 1, 2 or 3 independently selected $R^q$ substituents;

or two $R^h$ groups attached to the same carbon atom of the 4- to 10-membered heterocycloalkyl taken together with the carbon atom to which they are attached form a $C_{3-6}$ cycloalkyl or 4- to 6-membered heterocycloalkyl having 1-2 heteroatoms as ring members selected from O, N or S;

or any two $R^c$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^c$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^g$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^i$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^k$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^o$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-4}$ alkyl, $C_{3-6}$ cycloalkyl, $C_{6-10}$ aryl, or 6-membered heteroaryl, 4-7 membered heterocycloalkyl, $C_{1-4}$ haloalkyl, $C_{1-4}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 independently selected $R^q$ substituents;

each $R^q$ is independently selected from halo, OH, CN, —COOH, B(OH)$_2$, NH$_2$, —NH—$C_{1-6}$ alkyl, —N($C_{1-6}$ alky)$_2$, $C_{1-6}$ alkyl, $C_{1-6}$ alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2 or 3 substituents independently selected from halo, OH, CN, —COOH, NH$_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

the subscript p is an integer of 1, 2, 3, 4, 5 or 6; and

=== is a single bond or a double bond to maintain the 5-membered imidazole ring being aromatic.

In certain embodiments, ring A is 5- to 14-membered heteroaryl, 4- to 14-membered heterocycloalkyl, $C_{6-10}$ aryl or $C_{3-10}$ cycloalkyl, wherein the 5- to 14-membered heteroaryl and 4-to 14-membered heterocycloalkyl each has 1-4 heteroatoms as ring members selected from B, P, N, O and S, wherein the N, P or S atom as ring members is optionally oxidized and one or more carbon atoms as ring members are each optionally replaced by a carbonyl group; and wherein ring A is optionally substituted with 1, 2, 3, 4 or 5 $R^{20}$ substituents;

L is a bond, —NH—, —O—, —C(O)NH—, —CH$_2$O— or —OCH$_2$—, wherein the carbonyl group in the —C(O)NH— linkage is attached to ring A;

$R^{21}$ and $R^{22}$ are each independently halo, $C_{1-6}$ alkyl or CN;

$R^{23}$ is H, $C_{1-6}$ alkyl or $C_{1-6}$ haloalkyl;

$R^{25}$ is $C_{1-4}$ alkyl, $C_{1-4}$ alkoxy, $C_{1-4}$ haloalkyl, $C_{1-4}$ haloalkoxy, CN, halo, OH, —COOH, NH$_2$, —NHC$_{1-4}$ alkyl or —N(C$_{1-4}$ alkyl)$_2$;

$R^{26}$ is $C_{1-4}$ alkyl, $C_{1-4}$ alkoxy, $C_{1-4}$ haloalkyl, $C_{1-4}$ haloalkoxy, CN, halo, OH, —COOH, NH$_2$, —NHC$_{1-4}$ alkyl or —N(C$_{1-4}$ alkyl)$_2$;

$R^{24}$ is selected from H, $C_{1-6}$ alkyl, $C_{2-6}$ alkenyl, $C_{2-6}$ alkynyl, $C_{1-6}$ haloalkyl, $C_{1-6}$ haloalkoxy, $C_{1-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, C(O)R$^a$, C(O)NR$^a$R$^a$, C(O)OR$^a$, C(=NR$^a$)R$^a$, C(=NOH)R$^a$, C(=NOH)NR$^a$, C(=NCN)NR$^a$R$^a$, C(=NR$^a$)NR$^a$R$^a$, S(O)R$^a$, S(O)NR$^a$R$^a$, S(O)$_2$R$^a$, —P(O)R$^a$R$^a$, —P(O)(OR$^a$)(OR$^a$), —B(OH)$_2$, —B(OR$^a$)$_2$ and S(O)$_2$NR$^a$R$^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^{24}$ are each optionally substituted with 1, 2, 3, 4 or 5 independently selected $R^b$ substituents;

$R^{20}$ is each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{1-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, NO$_2$, OR$^{a1}$, SR$^{a1}$, NHOR$^{a1}$, C(O)R$^{a1}$, C(O)NR$^{a1}$R$^{a1}$, C(O)OR$^{a1}$, OC(O)R$^{a1}$, OC(O)NR$^{a1}$R$^{a1}$, NHR$^{a1}$, NR$^{a1}$R$^{a1}$, NR$^{a1}$C(O)R$^{a1}$, NR$^{a1}$C(O)OR$^{a1}$, NR$^{a1}$C(O)NR$^{a1}$R$^{a1}$, C(=NR$^{a1}$)R$^{a1}$, C(=NOH)R$^{a1}$, C(=NOH)NR$^{a1}$, C(=NCN)NR$^{a1}$R$^{a1}$, NR$^{a1}$C(=NCN)NR$^{a1}$R$^{a1}$, C(=NR$^{a1}$)

NR$^{a1}$R$^{a1}$, NR$^{a1}$C(=NR$^{a1}$)NR$^{a1}$R$^{a1}$, NR$^{a1}$S(O)R$^{a1}$, NR$^{a1}$S(O)$_2$R$^{a1}$, NR$^{a1}$S(O)$_2$NR$^{a1}$R$^{a1}$, S(O)R$^{a1}$, S(O)NR$^{a1}$R$^{a1}$, S(O)$_2$R$^{a1}$, —P(O)R$^{a1}$R$^{a1}$, —P(O)(OR$^{a1}$)(OR$^{a1}$), —B(OH)$_2$, —B(OR$^{a1}$)$_2$ and S(O)$_2$NR$^{a1}$R$^{a1}$, wherein the C$_{1-6}$ alkyl, C$_{2-6}$ alkenyl, C$_{2-6}$ alkynyl, C$_{6-10}$ aryl, C$_{3-14}$ cycloalkyl, 5-14 membered heteroaryl, 4-14 membered heterocycloalkyl, C$_{6-10}$ aryl-C$_{1-4}$ alkyl-, C$_{3-14}$ cycloalkyl-C$_{1-4}$ alkyl-, (5-14 membered heteroaryl)-C$_{1-4}$ alkyl- and (4-14 membered heterocycloalkyl)-C$_{1-4}$ alkyl- of R$^{20}$ are each optionally substituted with 1, 2, 3, 4 or 5 independently selected R$^b$ substituents;

R$^{27}$ is each independently selected from H, halo, C$_{1-6}$ alkyl, C$_{2-6}$ alkenyl, C$_{2-6}$ alkynyl, C$_{1-6}$ haloalkyl, C$_{1-6}$ haloalkoxy, C$_{6-10}$ aryl, C$_{3-14}$ cycloalkyl, 5-14 membered heteroaryl, 4-14 membered heterocycloalkyl, C$_{6-10}$ aryl-C$_{1-4}$ alkyl-, C$_{3-14}$ cycloalkyl-C$_{1-4}$ alkyl-, (5-14 membered heteroaryl)-C$_{1-4}$ alkyl-, (4-14 membered heterocycloalkyl)-C$_{1-4}$ alkyl-, CN, NO$_2$, OR$^{a2}$, SR$^{a2}$, NHOR$^{a2}$, C(O)R$^{a2}$, C(O)NR$^{a2}$R$^{a2}$, C(O)OR$^{a2}$, OC(O)R$^{a2}$, OC(O)NR$^{a2}$R$^{a2}$, NHR$^{a2}$, NR$^{a2}$R$^{a2}$, NR$^{a2}$C(O)R$^{a}$, NR$^{a2}$C(O)OR$^{a2}$, NR$^{a2}$C(O)NR$^{a2}$R$^{a2}$, C(=NR$^{a2}$)R$^{a2}$, C(=NOH)R$^{a2}$, C(=NOH)NR$^{a2}$, C(=NCN)NR$^{a2}$R$^{a2}$, NR$^{a2}$C(=NCN)NR$^{a2}$R$^{a2}$, C(=NR$^{a2}$)NR$^{a2}$R$^{a2}$, NR$^{a2}$C(=NR$^{a2}$)NR$^{a2}$R$^{a2}$, NR$^{a2}$S(O)R$^{a2}$, NR$^{a2}$S(O)$_2$R$^{a2}$, NR$^{a2}$S(O)$_2$NR$^{a2}$R$^{a2}$, S(O)R$^{a2}$, S(O)NR$^{a2}$R$^{a2}$, S(O)$_2$R$^{a2}$, —P(O)R$^{a2}$R$^{a2}$, —P(O)(OR$^{a2}$)(OR$^{a2}$), —B(OH)$_2$, —B(OR$^{a2}$)$_2$ and S(O)$_2$NR$^{a2}$R$^{a2}$, wherein the C$_{1-6}$ alkyl, C$_{2-6}$ alkenyl, C$_{2-6}$ alkynyl, C$_{6-10}$ aryl, C$_{3-14}$ cycloalkyl, 5-14 membered heteroaryl, 4-14 membered heterocycloalkyl, C$_{6-10}$ aryl-C$_{1-4}$ alkyl-, C$_{3-14}$ cycloalkyl-C$_{1-4}$ alkyl-, (5-14 membered heteroaryl)-C$_{1-4}$ alkyl- and (4-14 membered heterocycloalkyl)-C$_{1-4}$ alkyl- of R$^{27}$ are each optionally substituted with 1, 2, 3, 4 or 5 independently selected R$^b$ substituents;

or two R$^{20}$ substituents attached to the same ring carbon atom taken together with the ring carbon atom to which they are attached form spiro C$_{3-6}$ cycloalkyl or spiro 4- to 7-membered heterocycloalkyl, each of which is optionally substituted with 1, 2, or 3 independently selected R$^f$ substituents;

or two R$^{27}$ substituents attached to the same ring carbon atom taken together with the ring carbon atom to which they are attached form spiro C$_{3-6}$ cycloalkyl or spiro 4- to 7-membered heterocycloalkyl, each of which is optionally substituted with 1, 2, or 3 independently selected R$^f$ substituents;

each of R$^a$, R$^{a1}$, and R$^{a2}$ is independently selected from H, C$_{1-6}$ alkyl, C$_{1-6}$haloalkyl, C$_{2-6}$ alkenyl, C$_{2-6}$ alkynyl, C$_{6-10}$ aryl, C$_{3-14}$ cycloalkyl, 5-14 membered heteroaryl, 4-14 membered heterocycloalkyl, C$_{6-10}$ aryl-C$_{1-4}$alkyl-, C$_{3-14}$cycloalkyl-C$_{1-4}$alkyl-, (5-14 membered heteroaryl)-C$_{1-4}$ alkyl-, and (4-14 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-14}$ cycloalkyl, 5-14 membered heteroaryl, 4-14 membered heterocycloalkyl, C$_{6-10}$ aryl-C$_{1-4}$ alkyl-, C$_{3-14}$cycloalkyl-C$_{1-4}$ alkyl-, (5-14 membered heteroaryl)-C$_{1-4}$alkyl- and (4-14 membered heterocycloalkyl)-C$_{1-4}$alkyl- of R$^a$, R$^{a1}$, and R$^{a2}$ are each optionally substituted with 1, 2, 3, 4, or 5 independently selected R$^d$ substituents;

each R$^d$ is independently selected from C$_{1-6}$ alkyl, C$_{1-6}$haloalkyl, halo, C$_{6-10}$ aryl, 5-14 membered heteroaryl, C$_{3-14}$ cycloalkyl, 4-14 membered heterocycloalkyl, C$_{6-10}$ aryl-C$_{1-4}$ alkyl-, C$_{3-14}$ cycloalkyl-C$_{1-4}$ alkyl-, (5-14 membered heteroaryl)-C$_{1-4}$alkyl-, (4-14 membered heterocycloalkyl)-C$_{1-4}$ alkyl-, CN, NH$_2$, NHOR$^e$, OR$^e$, SR$^e$, C(O)R$^e$, C(O)NR$^e$R$^e$, C(O)OR$^e$, OC(G)R$^e$, OC(O)NR$^e$R$^e$, NHR$^e$, NR$^e$R$^e$, NR$^e$C(O)R$^e$, NR$^e$C(O)NR$^e$R$^e$, NR$^e$C(O)OR$^e$, C(=NR$^e$)NR$^e$R$^e$, NR$^e$C(=NR$^e$)NR$^e$R$^e$, NR$^e$C(=NOH)NR$^e$R$^e$, NR$^e$C(=NCN)NR$^e$R$^e$, S(O)R$^e$, S(O)NR$^e$R$^e$, S(O)$_2$R$^e$, NR$^e$S(O)$_2$R$^e$, NR$^e$S(O)$_2$NR$^e$R$^e$, —P(O)R$^e$R$^e$, —P(O)(OR$^e$) (OR$^e$), —B(OH)$_2$, —B(OR$^e$)$_2$ and S(O)$_2$NR$^e$R$^e$, wherein the C$_{1-6}$ alkyl, C$_{1-6}$haloalkyl, C$_{6-10}$ aryl, 5-14 membered heteroaryl, 4-14 membered heterocycloalkyl, C$_{6-10}$ aryl-C$_{1-4}$ alkyl-, C$_{3-14}$cycloalkyl-C$_{1-4}$ alkyl-, (5-14 membered heteroaryl)-C$_{1-4}$ alkyl-, and (4-14 membered heterocycloalkyl)-C$_{1-4}$ alkyl- of R$^d$ are each optionally substituted with 1, 2, or 3 independently selected R$^f$ substituents;

each R$^e$ is independently selected from H, C$_{1-6}$ alkyl, C$_{1-6}$haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^e$ are each optionally substituted with 1, 2 or 3 independently selected R$^f$ substituents;

each R$^b$ substituent is independently selected from halo, C$_{1-6}$ alkyl, C$_{2-6}$ alkenyl, C$_{2-6}$ alkynyl, C$_{1-6}$ haloalkyl, C$_{1-6}$haloalkoxy, C$_{6-10}$ aryl, C$_{3-14}$ cycloalkyl, 5-14 membered heteroaryl, 4-14 membered heterocycloalkyl, C$_{6-10}$ aryl-C$_{1-4}$ alkyl-, C$_{3-14}$ cycloalkyl-C$_{1-4}$ alkyl-, (5-14 membered heteroaryl)-C$_{1-4}$ alkyl-, (4-14 membered heterocycloalkyl)-C$_{1-4}$ alkyl-, CN, OH, NH$_2$, NO$_2$, NHOR$^c$, OR$^c$, SR$^c$, C(O)R$^c$, C(O)NR$^c$R$^c$, C(O)OR$^c$, OC(O)R$^c$, OC(O)NR$^c$R$^c$, C(=NOH)R$^c$, C(=NOH)NR$^c$, C(=NCN)NR$^c$R$^c$, NR$^c$C(=NCN)NR$^c$R$^c$, C(=NR$^c$)NR$^c$R$^c$, NR$^c$C(=NR$^c$)NR$^c$R$^c$, NHR$^c$, NR$^c$R$^c$, NR$^c$C(O)R$^c$, NR$^c$C(O)OR$^c$, NR$^c$C(O)NR$^c$R$^c$, NR$^c$S(O)R$^c$, NR$^c$S(O)$_2$R$^c$, NR$^c$S(O)$_2$NR$^c$R$^c$, S(O)R$^c$, S(O)NR$^c$R$^c$, S(O)$_2$R$^c$, —P(O)R$^c$R$^c$, —P(O)(OR$^c$)(OR$^c$), —B(OH)$_2$, —B(OR$^c$)$_2$ and S(O)$_2$NR$^c$R$^c$; wherein the C$_{1-6}$ alkyl, C$_{1-6}$ haloalkyl, C$_{1-6}$ haloalkoxy, C$_{2-6}$ alkenyl, C$_{2-6}$ alkynyl, C$_{6-10}$ aryl, C$_{3-14}$ cycloalkyl, 5-14 membered heteroaryl, 4-14 membered heterocycloalkyl, C$_{6-10}$ aryl-C$_{1-4}$alkyl-, C$_{3-14}$ cycloalkyl-C$_{1-4}$ alkyl-, (5-14 membered heteroaryl)-C$_{1-4}$ alkyl- and (4-14 membered heterocycloalkyl)-C$_{1-4}$ alkyl- of R$^b$ are each further optionally substituted with 1, 2 or 3 independently selected R$^d$ substituents;

each R$^c$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-14}$ cycloalkyl, 5-14 membered heteroaryl, 4-14 membered heterocycloalkyl, C$_{6-10}$ aryl-C$_{1-4}$ alkyl-, C$_{3-14}$cycloalkyl-C$_{1-4}$ alkyl-, (5-14 membered heteroaryl)-C$_{1-4}$ alkyl-, and (4-14 membered heterocycloalkyl)-C$_{1-4}$ alkyl-, wherein the C$_{1-6}$ alkyl, C$_{2-6}$ alkenyl, C$_{2-6}$ alkynyl, C$_{1-10}$ aryl, C$_{3-14}$ cycloalkyl, 5-14 membered heteroaryl, 4-14 membered heterocycloalkyl, C$_{6-10}$ aryl-C$_{1-4}$ alkyl-, C$_{3-14}$ cycloalkyl-C$_{1-4}$ alkyl-, (5-14 membered heteroaryl)-C$_{1-4}$ alkyl- and (4-14 membered heterocycloalkyl)-C$_{1-4}$ alkyl- of R$^c$ are each optionally substituted with 1, 2, 3, 4, or 5 independently selected R$^f$ substituents;

each R$^f$ is independently selected from C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halo, CN, NHOR$^g$, OR$^g$, SR$^g$, C(O)R$^g$, C(O)NR$^g$R$^g$, C(O)OR$^g$, OC(O)R$^g$, OC(O)NR$^g$R$^g$, NHR$^g$, NR$^g$R$^g$, NR$^g$C(O)R$^g$, NR$^g$C(O)N-R$^g$R$^g$, NR$^g$C(O)OR$^g$, C(=NR$^g$)NR$^g$R$^g$, NR$^g$C(=NR$^g$)NR$^g$R$^g$, S(O)R$^g$, S(O)NR$^g$R$^g$, S(O)$_2$R$^g$, NR$^g$S(O)$_2$R$^g$, NR$^g$S(O)$_2$NR$^g$R$^g$, —P(O)R$^g$R$^g$, —P(O)(OR$^g$)(OR$^g$), —B(OH)$_2$, —B(OR$^g$)$_2$ and S(O)$_2$NR$^g$R$^g$; wherein the C$_{1-6}$ alkyl, C$_{1-6}$ haloalkyl, C$_{2-6}$ alkenyl, C$_{2-6}$ alkynyl, C$_{1-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- of R$^f$ are each optionally substituted with 1, 2, 3, 4, or 5 independently selected R$^n$ substituents;

each R$^n$ is substituents independently selected from C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_6$.m aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_{1-4}$ alkyl-, halo, CN, NHOR$^o$, OR$^o$, SR$^o$, C(O)R$^o$, C(O)NR$^o$R$^o$, C(O)OR$^o$, OC(O)R$^o$, OC(O)NR$^o$R$^o$, NHR$^o$, NR$^o$R$^o$, NR$^o$C(O)R$^o$, NR$^o$C(O)NR$^o$R$^o$, NR$^o$C(O)OR$^o$, C(=NR$^o$)NR$^o$R$^o$, NR$^o$C(=NR$^o$)NR$^o$R$^o$, S(O)R$^o$, S(O)NR$^o$R$^o$, S(O)$_2$R$^o$, NR$^o$S(O)$_2$R$^o$, NR$^o$S(O)$_2$NR$^o$R$^o$, —P(O)R$^o$R$^o$, —P(O)(OR$^o$)(OR$^o$), —B(OH)$_2$, —B(OR$^o$)$_2$ and S(O)$_2$NR$^o$R$^o$, wherein the C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- of R$^n$ are each optionally substituted with 1, 2 or 3 independently selected R$^q$ substituents;

each R$^g$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl-, wherein the C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^g$ are each optionally substituted with 1, 2, or 3 independently selected R$^p$ substituents;

each R$^p$ is independently selected from C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, (4-10 membered heterocycloalkyl)-C$_M$ alkyl-, halo, CN, NHOR$^r$, OR$^r$, SR$^r$, C(O)R$^r$, C(O)NR$^r$R$^r$, C(O)OR$^r$, OC(O)R$^r$, OC(O)NR$^r$R$^r$, NHR$^r$, NR$^r$R$^r$, NR$^r$C(O)R$^r$, NR$^r$C(O)NR$^r$R$^r$, NR$^r$C(O)OR$^r$, C(=NR$^r$)NR$^r$R$^r$, NR$^r$C(=NR$^r$)NR$^r$R$^r$, NR$^r$C(=NOH)NR$^r$R$^r$, NR$^r$C(=NCN)NR$^r$R$^r$, S(O)R$^r$, S(O)NR$^r$R$^r$, S(O)$_2$R$^r$, NR$^r$S(O)$_2$R$^r$, NR$^r$S(O)$_2$NR$^r$R$^r$, —P(O)R$^r$R$^r$, —P(G)(OR$^r$)(OR$^r$), —B(OH)$_2$, —B(OR$^r$)$_2$ and S(O)$_2$NR$^r$R$^r$, wherein the C$_{1-6}$ alkyl, C$_{1-6}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl- and (4-10 membered heterocycloalkyl)-C$_{1-4}$ alkyl- of R$^p$ is optionally substituted with 1, 2 or 3 independently selected R$^q$ substituents;

or any two R$^a$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected R$^h$ substituents;

or any two R$^{a1}$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected R$^h$ substituents;

or any two R$^{a2}$ substituents together with the boron, phosphorus or nitrogen atom to which they are attached form a 4-, 5-, 6-, 7-, 8-, 9- or 10-membered heterocycloalkyl group optionally substituted with 1, 2 or 3 independently selected R$^h$ substituents;

each R$^h$ is independently selected from C$_{1-4}$ alkyl, C$_{3-10}$ cycloalkyl, 4-10 membered heterocycloalkyl, C$_{6-10}$ aryl, 5-10 membered heteroaryl, C$_{6-10}$ aryl-C$_{1-4}$ alkyl-, C$_{3-10}$cycloalkyl-C$_{1-4}$ alkyl-, (5-10 membered heteroaryl)-C$_{1-4}$ alkyl-, (4-10 membered heterocycloalkyl)-C$_{1-4}$ alkyl-, C$_{1-6}$ haloalkyl, C$_{1-6}$ haloalkoxy, C$_{2-6}$ alkenyl, C$_{2-6}$ alkynyl, halo, CN, OR$^i$, SR$^i$, NHOR$^i$, C(O)R$^i$, C(O)NR$^i$R$^i$, C(O)OR, OC(O)R$^i$, OC(O)NR$^i$R$^i$, NHR$^i$, NR$^i$R$^i$, NR$^i$C(O)R$^i$, NR$^i$C(O)NR$^i$R$^i$, NR$^i$C(O)OR$^i$, C(=NR$^i$)NR$^i$R$^i$, NR$^i$C(=NR$^i$)NR$^i$R$^i$, S(O)R$^i$, S(O)NR$^i$R$^i$, S(O)$_2$R, NR$^i$S(O)$_2$R$^i$, NR$^i$S(O)$_2$NR$^i$R$^i$, —P(O)R$^i$R$^i$, —P(O)(OR$^i$)(OR$^i$), —B(OH)$_2$, —B(OR$^i$)$_2$ and S(O)$_2$NR$^i$R$^i$, wherein the C$_{1-6}$ alkyl, C$_{2-6}$alkenyl, C$_{2-6}$alkynyl, C$_{3-10}$cycloalkyl, 4-10 membered heterocycloalkyl, C$_{6-10}$ aryl, 5-10 membered heteroaryl, C$_{6-10}$ aryl-C$_{1-4}$ alkyl-, C$_{3-10}$ cycloalkyl-C$_{1-4}$ alkyl-, (5-10 membered heteroaryl)-C$_{1-4}$ alkyl-, and (4-10 membered heterocycloalkyl)-C$_{1-4}$ alkyl- of R$^h$ are each optionally substituted by 1, 2, or 3 independently selected R$^j$ substituents;

each R$^j$ is independently selected from C$_{3-6}$ cycloalkyl, C$_{6-10}$ aryl, 5 or 6-membered heteroaryl, 4-7 membered heterocycloalkyl, C$_{24}$ alkenyl, C$_{24}$ alkynyl, halo, C$_{1-4}$ alkyl, C$_{1-4}$ haloalkyl, C$_{1-4}$ haloalkoxy, CN, NHOR$^k$, OR$^k$, SR$^k$, C(O)R$^k$, C(O)NR$^k$R$^k$, C(O)OR$^k$, OC(O)R$^k$, OC(O)NR$^k$R$^k$, NHR$^k$, NR$^k$R$^k$, NR$^k$C(O)R$^k$, NR$^k$C(O)NR$^k$R$^k$, NR$^k$C(O)OR$^k$, C(=NR$^k$)NR$^k$R$^k$, NR$^k$C(=NR$^k$)NR$^k$R$^k$, S(O)R$^k$, S(O)NR$^k$R$^k$, S(O)$_2$R$^k$, NR$^k$S(O)$_2$R$^k$, NR$^k$S(O)$_2$NR$^k$R$^k$, —P(O)R$^k$R$^k$, —P(O)(OR$^k$)(OR$^k$), —B(OH)$_2$, —B(OR$^k$)$_2$ and S(O)$_2$NR$^k$R$^k$, wherein the C$_{1-4}$ alkyl, C$_{3-6}$ cycloalkyl, C$_{6-10}$ aryl, 5- or 6-membered heteroaryl, 4-7 membered heterocycloalkyl, C$_{24}$ alkenyl, C$_{24}$ alkynyl, C$_{1-4}$ haloalkyl, and C$_{1-4}$ haloalkoxy of R$^j$ are each optionally substituted with 1, 2 or 3 independently selected R$^q$ substituents;

or two R$^h$ groups attached to the same carbon atom of the 4- to 10-membered heterocycloalkyl taken together with the carbon atom to which they are attached form a C$_{3-6}$ cycloalkyl or 4- to 6-membered heterocycloalkyl having 1-2 heteroatoms as ring members selected from O, N or S;

or any two R$^c$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^c$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^g$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^h$ substituents;

or any two R$^i$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected R$^q$ substituents;

or any two R$^k$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^q$ substituents;

or any two $R^o$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

or any two $R^r$ substituents together with the boron, phosphorus or nitrogen atom to which they are attached form a 4-, 5-, 6-, 7-, 8-, 9- or 10-membered heterocycloalkyl group optionally substituted with 1, 2, or 3 independently selected $R^h$ substituents;

each $R^i$, $R^k$, $R^o$ or $R^r$ is independently selected from H, $C_{1-64}$ alkyl, $C_{3-6}$ cycloalkyl, $C_{6-10}$ aryl, 5 or 6-membered heteroaryl, 4-7 membered heterocycloalkyl, $C_{1-4}$ haloalkyl, $C_{1-4}$ haloalkoxy, $C_{2-4}$ alkenyl, and $C_{2-4}$ alkynyl, wherein the $C_{1-4}$ alkyl, $C_{3-6}$ cycloalkyl, $C_{6-10}$ aryl, 5 or 6-membered heteroaryl, 4-7 membered heterocycloalkyl, $C_{2-4}$ alkenyl, and $C_{2-4}$ alkynyl of $R^i$, $R^k$, $R^o$ or $R^r$ are each optionally substituted with 1, 2 or 3 independently selected $R^q$ substituents;

each $R^q$ is independently selected from halo, OH, CN, —COOH, $B(OH)_2$, $NH_2$, —NH—$C_{1-6}$ alkyl, —N($C_{1-6}$ alky)$_2$, $C_{1-6}$ alkyl, $C_{1-6}$alkoxy, $C_{1-6}$ alkylthio, $C_{1-6}$ haloalkyl, $C_{1-6}$ haloalkoxy, phenyl, 5-6 membered heteroaryl, 4-6 membered heterocycloalkyl and $C_{3-6}$ cycloalkyl, wherein the $C_{1-6}$ alkyl, phenyl, $C_{3-6}$ cycloalkyl, 4-6 membered heterocycloalkyl, and 5-6 membered heteroaryl of $R^q$ are each optionally substituted with 1, 2 or 3 substituents independently selected from halo, OH, CN, —COOH, $NH_2$, $C_{1-4}$ alkyl, $C_{1-4}$ alkoxy, $C_{1-4}$ haloalkyl, $C_{1-4}$ haloalkoxy, phenyl, $C_{3-10}$ cycloalkyl, 5-6 membered heteroaryl and 4-6 membered heterocycloalkyl;

the subscript m is an integer of 0, 1, 2 or 3;

the subscript n is an integer of 0, 1, 2 or 3;

the subscript p is an integer of 1, 2, 3, 4, 5, or 6; and

⚌ is 3 single bond or a double bond to maintain the 5-membered imidazole ring being aromatic.

In some embodiments of compounds of Formula (IV), (1) when L is a bond, ring A is not 2-benzoxazolyl; (2) when L is a bond, ring A is not [1,2,4]triazolo[1,5-a]pyridin-2-yl; (3) when L is —NH—, ring A is not 1,7-naphthyridin-8-yl or pyrido[3,2-d]pyrimidin-4-yl; and (4) when L is —C(O)NH—, ring A is not 2-pyridyl.

In some embodiments of compounds of Formula (IV), (1) when L is a bond, ring A is not 2-benzoxazolyl; (2) when L is —NH—, ring A is not 1,7-naphthyridin-8-yl or pyrido[3,2-d]pyrimidin-4-yl; and (3) when L is —C(O)NH—, ring A is not 2-pyridyl.

In some embodiments of compounds of Formula (IV), (1) when L is a bond, ring A is not 2-benzoxazolyl; (2) when L is a bond, ring A is not [1,2,4]triazolo[1,5-a]pyridin-2-yl; (3) when L is —NH—, ring A is not 1,7-naphthyridin-8-yl or pyrido[3,2-d]pyrimidin-4-yl; or (4) when L is —C(O)NH—, ring A is not 2-pyridyl.

In some embodiments of compounds of Formula (IV), (1) when L is a bond, ring A is not 2-benzoxazolyl; (2) when L is —NH—, ring A is not 1,7-naphthyridin-8-yl or pyrido[3, 2-d]pyrimidin-4-yl; or (3) when L is —C(O)NH—, ring A is not 2-pyridyl.

In some embodiments, compounds of Formula (IV) have subformula (V):

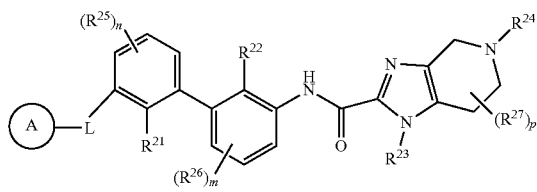

(V)

where ring A, linker L, the substituents $R^{20}$, $R^{21}$, $R^{22}$, $R^{23}$, $R^{24}$, $R^{25}$, $R^{26}$ and $R^{27}$ and the subscripts m, n and p are as defined in any embodiments of compounds of Formula (IV) or any embodiment as disclosed herein.

In some embodiments, compounds of Formula (IV) or (V) have subformula (Va):

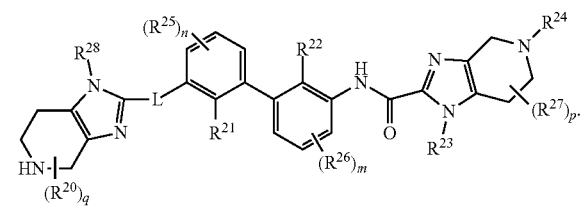

(Va)

$R^{28}$ is H or $C_{1-6}$ alkyl. The subscript q is an integer of 1, 2 or 3. The subscript p is an integer of 1, 2, 3, 4, 5 or 6. In some embodiments, $R^{28}$ is H. In other embodiments, $R^{28}$ is methyl. In some embodiments, the subscript q is 1. Linker L, the substituents $R^{20}$, $R^{21}$, $R^{22}$, $R^{23}$, $R^{24}$, $R^{25}$, $R^{26}$ and $R^{27}$ and the subscripts m, n and p are as defined in any embodiments of compounds of Formula (IV) or any embodiment as disclosed herein.

In some embodiments, compounds of Formula (IV), (V) or (Va) have subformula (Va-1):

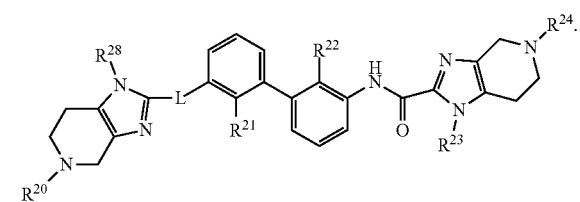

(Va-1)

$R^{28}$ is H or $C_{1-6}$ alkyl. In some instances, $R^{28}$ is H. In other instances, $R^{28}$ is methyl. Linker L and the substituents $R^{20}$, $R^{21}$, $R^{22}$, $R^{23}$ and $R^{24}$ are as defined in any embodiments of compounds of Formula (IV) or any embodiment as disclosed herein.

In some embodiments, compounds of Formula (IV) or (V) have subformula (Vb):

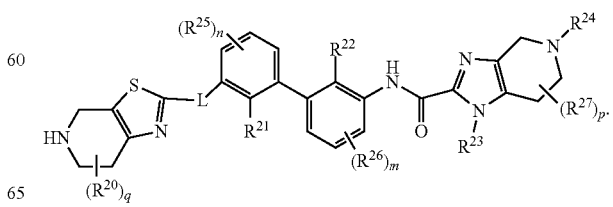

(Vb)

The subscript q is an integer of 1, 2 or 3. In some embodiments, the subscript q is 1. Linker L, the substituents $R^{20}$, $R^{21}$, $R^{22}$, $R^{23}$, $R^{24}$, $R^{25}$, $R^{26}$ and $R^{27}$ and the subscripts m, n and p are as defined in any embodiments of compounds of Formula (IV) or any embodiment as disclosed herein.

In some embodiments, compounds of Formula (IV), (V) or (Vb) have subformula (Vb-1):

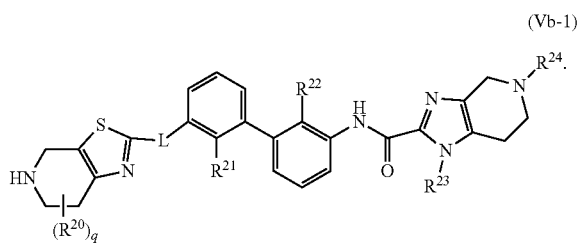

(Vb-1)

The subscript q is an integer of 1, 2 or 3. In some embodiments, the subscript q is 1. Linker L and the substituents $R^{20}$, $R^{21}$, $R^{22}$, $R^{23}$ and $R^{24}$ are as defined in any embodiments of compounds of Formula (IV) or any embodiment as disclosed herein.

In some embodiments, compounds of Formula (IV) or (V) have subformula (Vc):

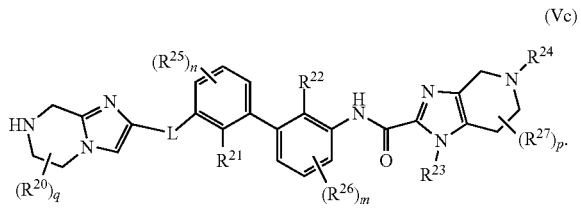

(Vc)

The subscript q is an integer of 1, 2 or 3. In some embodiments, the subscript q is 1. Linker L, the substituents $R^{20}$, $R^{21}$, $R^{22}$, $R^{23}$, $R^{24}$, $R^{25}$, $R^{26}$ and $R^{27}$ and the subscripts m, n and p are as defined in any embodiments of compounds of Formula (IV) or any embodiment as disclosed herein.

In some embodiments, compounds of Formula (IV), (V) or (Vc) have subformula (Vc-1):

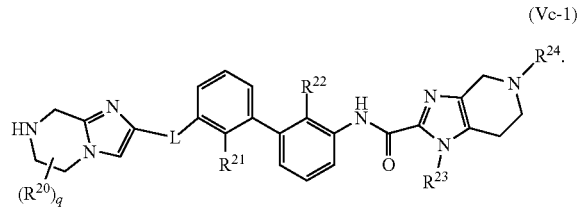

(Vc-1)

The subscript q is an integer of 1, 2 or 3. In some embodiments, the subscript q is 1. Linker L and the substituents $R^{20}$, $R^{21}$, $R^{22}$, $R^{23}$ and $R^{24}$ are as defined in any embodiments of compounds of Formula (IV) or any embodiment as disclosed herein.

In some embodiments, compounds of Formula (IV) or (V) have subformula (Vd):

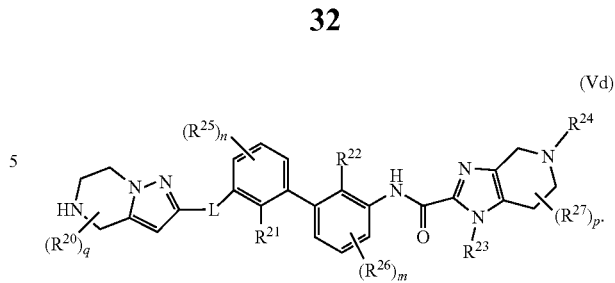

(Vd)

The subscript q is an integer of 1, 2 or 3. In some embodiments, the subscript q is 1. Linker L, the substituents $R^{20}$, $R^{21}$, $R^{22}$, $R^{23}$, $R^{24}$, $R^{25}$, $R^{26}$ and $R^{27}$ and the subscripts m, n and p are as defined in any embodiments of compounds of Formula (IV) or any embodiment as disclosed herein.

In some embodiments, compounds of Formula (IV), (V) or (Vd) have subformula (Vd-1):

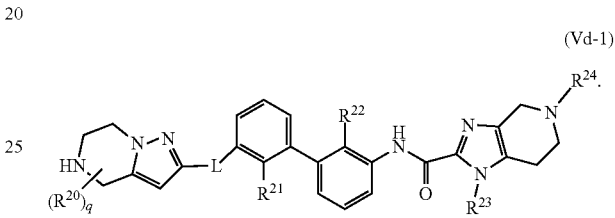

(Vd-1)

The subscript q is an integer of 1, 2 or 3. In some embodiments, the subscript q is 1. Linker L and the substituents $R^{20}$, $R^{21}$, $R^{22}$, $R^{23}$ and $R^{24}$ are as defined in any embodiments of compounds of Formula (IV) or any embodiment as disclosed herein.

In some embodiments, compounds of Formula (IV) or (V) have subformula (Ve):

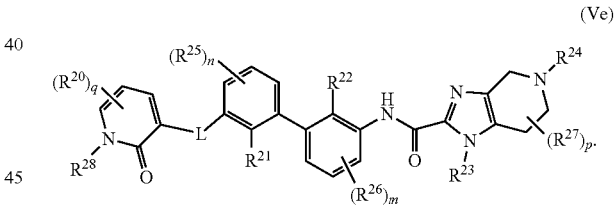

(Ve)

$R^{28}$ is H or $C_{1-6}$ alkyl. The subscript q is an integer of 1, 2 or 3. In some instances, $R^{28}$ is H. In other instances, $R^{28}$ is methyl. In some instances, the subscript q is 1. Linker L, the substituents $R^{20}$, $R^{21}$, $R^{22}$, $R^{23}$, $R^{24}$, $R^{25}$, $R^{26}$ and $R^{27}$ and the subscripts m, n and p are as defined in any embodiments of compounds of Formula (IV) or any embodiment as disclosed herein.

In some embodiments, compounds of Formula (IV), (V) or (Ve) have subformula (Ve-1):

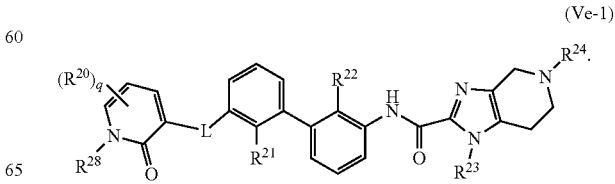

(Ve-1)

$R^{28}$ is H or $C_{1-6}$ alkyl. The subscript q is an integer of 1, 2 or 3. In some instances, $R^{28}$ is H. In other instances, $R^{28}$ is methyl. In some instances, the subscript q is 1. Linker L and the substituents $R^{20}$, $R^{21}$, $R^{22}$, $R^{23}$ and $R^{24}$ are as defined in any embodiments of compounds of Formula (IV) or any embodiment as disclosed herein.

In some embodiments, compounds of Formula (IV) or (V) have subformula (Vf):

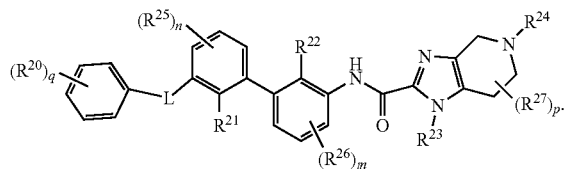

(Vf)

The subscript q is an integer of 1, 2 or 3. In some embodiments, the subscript q is 1. Linker L, the substituents $R^{20}$, $R^{21}$, $R^{22}$, $R^{23}$, $R^{24}$, $R^{25}$, $R^{26}$ and $R^{27}$ and the subscripts m, n and p are as defined in any embodiments of compounds of Formula (IV) or any embodiment as disclosed herein.

In some embodiments, compounds of Formula (IV), (V) or (Vf) have subformula (Vf-1):

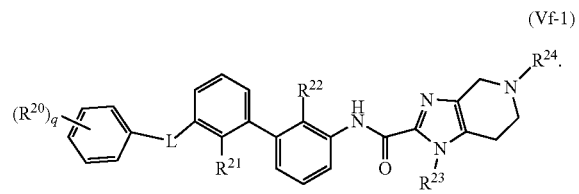

(Vf-1)

The subscript q is an integer of 1, 2 or 3. In some embodiments, the subscript q is 1. Linker L and the substituents $R^{20}$, $R^{21}$, $R^{22}$, $R^{23}$ and $R^{24}$ are as defined in any embodiments of compounds of Formula (IV) or any embodiment as disclosed herein.

In some embodiments, compounds of Formula (IV) or (V) have subformula (Vg):

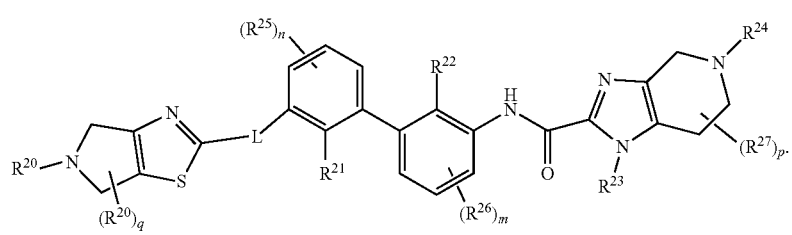

(Vg)

The subscript q is an integer of 1, 2 or 3. In some embodiments, the subscript q is 1. Linker L, the substituents $R^{20}$, $R^{21}$, $R^{22}$, $R^{23}$, $R^{24}$, $R^{25}$, $R^{26}$ and $R^{27}$ and the subscripts m, n and p are as defined in any embodiments of compounds of Formula (IV) or any embodiment as disclosed herein.

In some embodiments, compounds of Formula (IV), (V) or (Vg) have subformula (Vg-1):

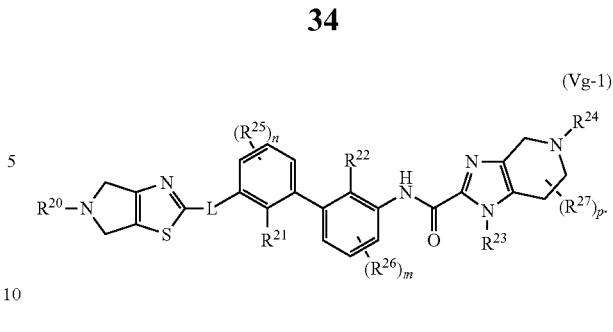

(Vg-1)

Linker L, the substituents $R^{20}$, $R^{21}$, $R^{22}$, $R^{23}$, $R^{24}$, $R^{25}$, $R^{26}$ and $R^{27}$ and the subscripts m, n and p are as defined in any embodiments of compounds of Formula (IV) or any embodiment as disclosed herein.

In some embodiments, compounds of Formula (IV), (V) or (Vg) have subformula (Vg-2):

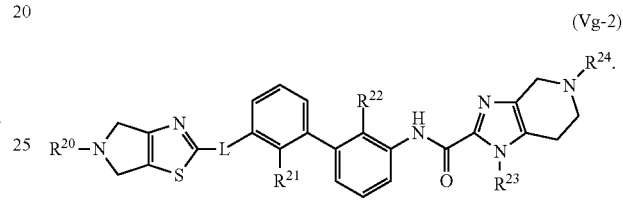

(Vg-2)

Linker L and the substituents $R^{20}$, $R^{21}$, $R^{22}$, $R^{23}$ and $R^{24}$ are as defined in any embodiments of compounds of Formula (IV) or any embodiment as disclosed herein.

In some embodiments, compounds of Formula (IV) or (V) have subformula (Vh):

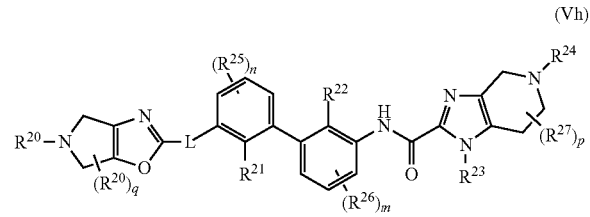

(Vh)

or a pharmaceutically acceptable salt or a stereoisomer thereof. Linker L, the substituents $R^{20}$, $R^{21}$, $R^{22}$, $R^{23}$, $R^{24}$, $R^{25}$, $R^{26}$, and $R^{27}$, and the subscripts m, n, p, and q are as defined in any embodiments of compounds of Formula (IV) or any embodiment as disclosed herein.

In some embodiments, compounds of Formula (IV), (V) or (Vh) have subformula (Vh-1):

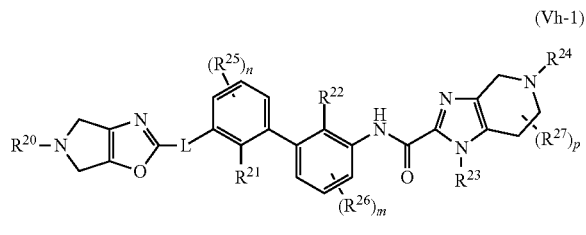

(Vh-1)

or a pharmaceutically acceptable salt or a stereoisomer thereof. Linker L, the substituents $R^{20}$, $R^{21}$, $R^{22}$, $R^{23}$, $R^{24}$, $R^{25}$, $R^{26}$, and $R^{27}$ and the subscripts m, n, and p are as defined in any embodiments of compounds of Formula (IV) or any embodiment as disclosed herein.

In some embodiments, compounds of Formula (IV), (V) or (Vh) have subformula (Vh-2):

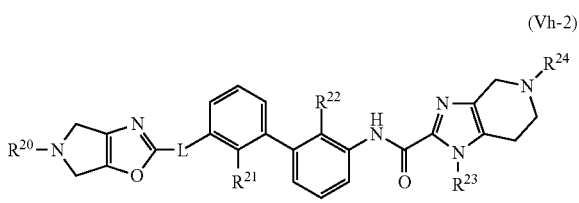

(Vh-2)

or a pharmaceutically acceptable salt or a stereoisomer thereof. Linker L and the substituents $R^{20}$, $R^{21}$, $R^{22}$, $R^{23}$, and $R^{24}$ are as defined in any embodiments of compounds of Formula (IV) or any embodiment as disclosed herein.

In some embodiments, ring A is 5- to 14-membered heteroaryl, 4- to 14-membered heterocycloalkyl, or $C_{6-10}$ aryl, wherein the 5- to 14-membered heteroaryl and 4- to 14-membered heterocycloalkyl each has 1-4 heteroatoms as ring members selected from B, P, N, O and S, wherein the N, P or S atom as ring members is optionally oxidized and one or more carbon atoms as ring members are each optionally replaced by a carbonyl group; and wherein ring A is optionally substituted with 1, 2, or 3 $R^{20}$ substituents.

In some embodiments, ring A is 5- to 14-membered heteroaryl or 4- to 14-membered heterocycloalkyl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^{20}$ substituents.

In some embodiments, ring A is 5- to 14-membered heteroaryl, wherein the 5- to 14-membered heteroaryl has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^{20}$ substituents. In some embodiments, ring A is 4- to 14-membered heterocycloalkyl, wherein the 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^{20}$ substituents.

In some embodiments of compounds of Formula (IV) or (V), or any embodiment disclosed herein, ring A is selected from:

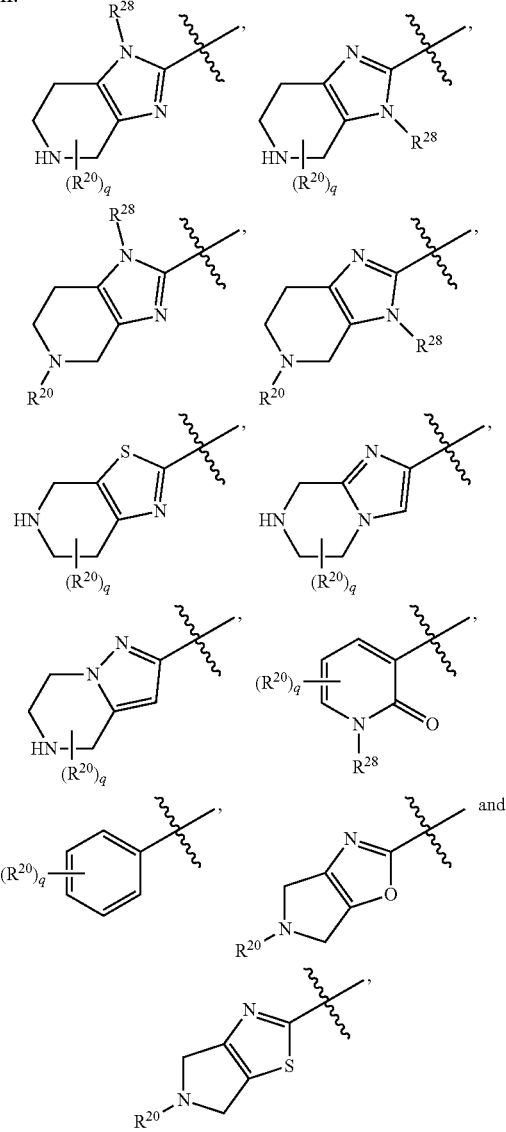

wherein each subscript q is independently an integer of 1, 2, 3 or 4; each $R^{28}$ is independently H or $C_{1-6}$ alkyl; and the wavy line indicates the point of attachment to L. In some instances, q is 1. In other instances, $R^{28}$ is H. In other instances, $R^{28}$ is methyl.

In some embodiments of compounds of Formula (IV) or (V), or any embodiment disclosed herein, ring A is

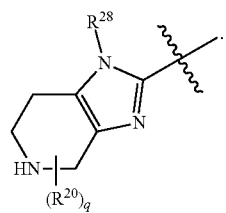

In some embodiments of compounds of Formula (IV) or (V), or any embodiment disclosed herein, ring A is

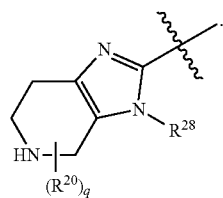

In some embodiments of compounds of Formula (IV) or (V), or any embodiment disclosed herein, ring A is

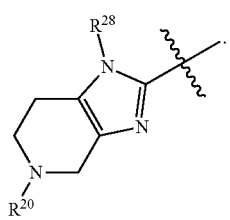

In some embodiments of compounds of Formula (IV) or (V), or any embodiment disclosed herein, ring A is

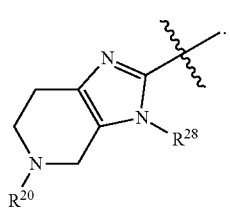

In some embodiments of compounds of Formula (IV) or (V), or any embodiment disclosed herein, ring A is

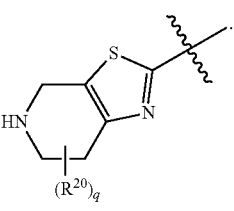

In some embodiments of compounds of Formula (IV) or (V), or any embodiment disclosed herein, ring A is

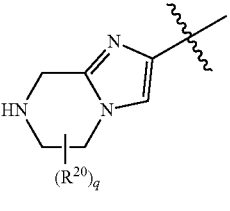

In some embodiments of compounds of Formula (IV) or (V), or any embodiment disclosed herein, ring A is

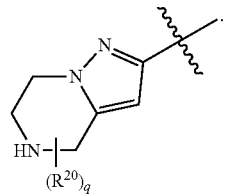

In some embodiments of compounds of Formula (IV) or (V), or any embodiment disclosed herein, ring A is

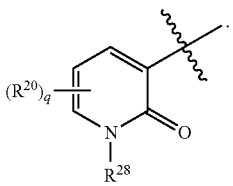

In some embodiments of compounds of Formula (IV) or (V), or any embodiment disclosed herein, ring A is

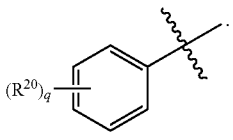

In some embodiments of compounds of Formula (IV) or (V), or any embodiment disclosed herein, ring A is

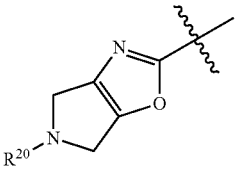

In some embodiments of compounds of Formula (IV) or (V), or any embodiment disclosed herein, ring A is

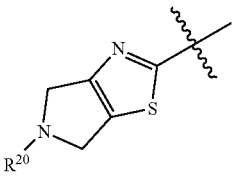

In some embodiments of compounds of Formula (IV), (V), (Va), (Va-1), (Vb), (Vb-1), (Vc), (Vc-1), (Vd), (Vd-1), (Ve), (Ve-1), (Vf), (Vf-1), (Vg), (Vg-1), (Vg-2), (Vh), (Vh-1), or (Vh-2), or any embodiment disclosed herein, L is —C(O)NH—, wherein the carbonyl group in the —C(O)NH— linkage is attached to ring A. In other embodiments, L is NH. In other embodiments, L is a bond. In other embodiments, L is —OCH$_2$—, wherein the oxygen atom in the —OCH$_2$-linkage is attached to ring A. In some embodiments, L is a bond, —C(O)NH—, or —OCH$_2$—, wherein the carbonyl group in the —C(O)NH— linkage and the oxygen atom in the —OCH$_2$-linkage is attached to ring A. In some embodiments, L is a bond or —C(O)NH—, wherein the carbonyl group in the —C(O)NH— linkage is attached to ring A. In some embodiments, L is a bond, —NH—, or —C(O)NH—, wherein the carbonyl group in the —C(O)NH— linkage is attached to ring A.

In some embodiments of compounds of Formula (IV), (V), (Va), (Va-1), (Vb), (Vb-1), (Vc), (Vc-1), (Vd), (Vd-1), (Ve), (Ve-1), (Vf), (Vf-1), (Vg), (Vg-1), (Vg-2), (Vh), (Vh-1), or (Vh-2), or any embodiment disclosed herein, $R^{21}$ and $R^{22}$ are each independently Cl, CN or methyl. In some instances, $R^{21}$ and $R^{22}$ are each $C_{1-6}$ alkyl. In other instances, $R^{21}$ and $R^{22}$ are each methyl. In other instances, $R^{21}$ and $R^{22}$ are each halo. In other instances, $R^{21}$ and $R^{22}$ are each Cl. In other instances, $R^{21}$ is halo and $R^{22}$ is $C_{1-6}$ alkyl. In other instances, $R^{21}$ is $C_{1-6}$ alkyl and $R^{22}$ is halo. In other instances, $R^{21}$ is methyl and $R^{22}$ is Cl. In other instances, $R^{21}$ is Cl and $R^{22}$ is methyl. In some instances, substituents $R^{21}$ and $R^{22}$ are the same (e.g., both $R^{21}$ and $R^{22}$ are methyl, Cl, or CN). In some instances, substituents $R^{21}$ and $R^{22}$ are different.

In some embodiments of compounds of Formula (IV), (V), (Va), (Va-1), (Vb), (Vb-1), (Vc), (Vc-1), (Vd), (Vd-1), (Ve), (Ve-1), (Vf), (Vf-1), (Vg), (Vg-1), (Vg-2), (Vh), (Vh-1), or (Vh-2), or any embodiment disclosed herein, $R^{20}$ is H, $C_{1-6}$ alkyl optionally substituted with 1, 2 or 3 independently selected $R^b$ substituents, halo, CN, $C_{3-6}$ cycloalkyl optionally substituted with 1, 2 or 3 independently selected $R^b$ substituents, 4-6 membered heterocycloalkyl optionally substituted with 1, 2 or 3 independently selected $R^b$ substituents, phenyl optionally substituted with 1, 2 or 3 independently selected $R^b$ substituents or 5-6 membered heteroaryl optionally substituted with 1, 2 or 3 independently selected $R^b$ substituents. In some embodiments, each $R^{20}$ is independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{3-14}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, NO$_2$, OR$^{a1}$, SR$^{a1}$, NHOR$^{a1}$, C(O)R$^{a1}$, C(O)NR$^{a1}$R$^{a1}$, C(O)OR$^{a1}$, OC(O)R$^{a1}$, OC(O)NR$^{a1}$R$^{a1}$, NHR$^{a1}$, NR$^{a1}$R$^{a1}$, NR$^{a1}$C(O)R$^{a1}$, and NR$^{a1}$C(O)OR$^{a1}$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^{20}$ are each optionally substituted with 1, 2, or 3 independently selected $R^b$ substituents. In some embodiments, each $R^{20}$ is independently selected from H, halo, $C_{1-6}$ alkyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, OR$^{a1}$, and C(O)R$^{a1}$, wherein the $C_{1-6}$ alkyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^{20}$ are each optionally substituted with 1, 2, or 3 independently selected $R^b$ substituents.

In some instances, $R^{20}$ is H, $C_{1-6}$ alkyl, 2-hydroxypropyl, (R)-2-hydroxypropyl, (S)-2-hydroxypropyl, 2-hydroxyethyl, 1-(methylsulfonyl)piperidin-4-yl, tetrahydro-2H-pyran-4-yl, (tetrahydro-2H-pyran-4-yl)methyl, 1-(hydroxymethyl)cyclopropyl)methyl, (S)-(2,3-dihydroxypropyl)-1-methyl, (2,3-dihydroxypropyl)-1-methyl, (R)-(2,3-dihydroxypropyl)-1-methyl, carboxymethyl, 1-acetylpiperidin-4-yl, 4-carboxy-4-methylcyclohexyl, 3-(methylsulfonamido)propyl, trans-(4-carboxycyclohexyl)methyl, cis-(4-carboxycyclohexyl)methyl, (3-carboxypyrrolidin-1-yl)methyl, (R)-(3-carboxypyrrolidin-1-yl)methyl, (S)-(3-carboxypyrrolidin-1-yl)methyl, (3-hydroxypyrrolidin-1-yl)methyl, (R)-(3-hydroxypyrrolidin-1-yl)methyl, (S)-(3-hydroxypyrrolidin-1-yl)methyl, pyrrolidin-1-ylmethyl, 2-(dimethylamino)acetyl, (5-cyanopyridin-3-yl)methoxy, (2-carboxypiperidin-1-yl)methyl, (R)-(2-carboxypiperidin-1-yl)methyl, (S)-(2-carboxypiperidin-1-yl)methyl, halo, cyclobutyl, cyclopropylmethyl, or CN. In other instances, $R^{20}$ is $C_{1-6}$ alkyl, 2-hydroxypropyl, (R)-2-hydroxypropyl, (S)-2-hydroxypropyl, 2-hydroxyethyl, 1-(methylsulfonyl)piperidin-4-yl, tetrahydro-2H-pyran-4-yl, (tetrahydro-2H-pyran-4-yl)methyl, 1-(hydroxymethyl)cyclopropyl)methyl, (S)-(2,3-dihydroxypropyl)-1-methyl, (2,3-dihydroxypropyl)-1-methyl, (R)-(2,3-dihydroxypropyl)-1-methyl, carboxymethyl, 1-acetylpiperidin-4-yl, 4-carboxy-4-methylcyclohexyl, 3-(methylsulfonamido)propyl, trans-(4-carboxycyclohexyl)methyl, cis-(4-carboxycyclohexyl)methyl, (3-carboxypyrrolidin-1-yl)methyl, (R)-(3-carboxypyrrolidin-1-yl)methyl, (S)-(3-carboxypyrrolidin-1-yl)methyl, (3-hydroxypyrrolidin-1-yl)methyl, (R)-(3-hydroxypyrrolidin-1-yl)methyl, (S)-(3-hydroxypyrrolidin-1-yl)methyl, pyrrolidin-1-ylmethyl, 2-(dimethylamino)acetyl, (5-cyanopyridin-3-yl)methoxy, (2-carboxypiperidin-1-yl)methyl, (R)-(2-carboxypiperidin-1-yl)methyl, (S)-(2-carboxypiperidin-1-yl)methyl, halo, cycle butyl, cyclopropylmethyl, or CN. In some instances, $R^{20}$ is H, $C_{1-6}$ alkyl (e.g., methyl) or 2-hydroxypropyl (e.g., (R)-2-hydroxypropyl and (S)-2-hydroxypropyl). In some instances, $R^{20}$ is $C_{1-6}$ alkyl (e.g., methyl). In other instances, $R^{20}$ is (R)-2-hydroxypropyl or (S)-2-hydroxypropyl.

In some instances, $R^{20}$ is H, $C_{1-6}$ alkyl, 2-hydroxypropyl, (R)-2-hydroxypropyl, (S)-2-hydroxypropyl, 2-hydroxyethyl, 1-(methylsulfonyl)piperidin-4-yl, tetrahydro-2H-pyran-4-yl, (tetrahydro-2H-pyran-4-yl)methyl, 1-(hydroxymethyl)cyclopropyl)methyl, (S)-(2,3-dihydroxypropyl)-1-methyl, (2,3-dihydroxypropyl)-1-methyl, (R)-(2,3-dihydroxypropyl)-1-methyl, carboxymethyl, 1-acetylpiperidin-4-yl, 4-carboxy-4-methylcyclohexyl, 3-(methylsulfonamido)propyl, trans-(4-carboxycyclohexyl)methyl, cis-(4-carboxycyclohexyl)methyl, (3-carboxypyrrolidin-1-yl)methyl, (R)-(3-carboxypyrrolidin-1-yl)methyl, (S)-(3-carboxypyrrolidin-1-yl)methyl, (3-hydroxypyrrolidin-1-yl)methyl, (R)-(3-hydroxypyrrolidin-1-yl)methyl, (S)-(3-hydroxypyrrolidin-1-yl)methyl, pyrrolidin-1-ylmethyl, 2-(dimethylamino)acetyl, (5-cyanopyridin-3-yl)methoxy, (2-carboxypiperidin-1-yl)methyl, (R)-(2-carboxypiperidin-1-yl)methyl, (S)-(2-carboxypiperidin-1-yl)methyl, halo, cyclobutyl, cyclopropylmethyl, CN, trans-(4-carboxycyclohexyl)ethyl, cis-(4-carboxycyclohexyl)ethyl, 4-carboxycyclohexyl, trans-4-carboxycyclohexyl, cis-4-carboxycyclohexyl, 4-carboxybenzyl, 4-carboxyphenethyl, 2-(4-carboxy-4-methylcyclohexyl)methyl, 2-(4-carboxy-4-methylcyclohexyl)ethyl, (4-carboxybicyclo[2.2.2]octan-1-yl)methyl, 4-carboxybicyclo[2.2.1]heptan-1-yl, (4-carboxybicyclo[2.2.1]heptan-1-yl)methyl, 4-carboxy-4-methylcyclohexyl, (S)-3-hydroxypyrrolidin-1-yl)acetyl, (R)-3-hydroxypyrrolidin-1-yl)acetyl, 4-carboxy-4-ethylcyclohexyl, N-isopropyl-N-methylglycyl, (R)-3-carboxy-3-methylpyrrolidin-1-yl, (S)-3-carboxy-3-methylpyrrolidin-1-yl, (S)-1-hydroxypropan-2-yl)glycyl, (R)-1-hydroxypropan-2-yl)glycyl, (3-hydroxycyclobutyl)glycyl, cis-(3-hydroxycyclobutyl)

glycyl, trans-(3-hydroxycyclobutyl)glycyl, dimethylglycyl, N-ethyl-N-methylglycyl, ethyl(methyl)amino)propanoyl, or 1-carboxyadamant-4-yl.

In some embodiments of compounds of Formula (IV), (V), (Va), (Va-1), (Vb), (Vb-1), (Vc), (Vc-1), (Vd), (Vd-1), (Ve), (Ve-1), (VI), (Vf-1), (Vg), (Vg-1), (Vg-2), (Vh), (Vh-1), or (Vh-2), or any embodiment disclosed herein, $R^{23}$ is H, methyl, $CF_3$, $CF_2H$, or $CH_2F$. In some instances, $R^{23}$ is H. In other instances, $R^{23}$ is $C_{1-6}$ alkyl. In other instances, $R^{23}$ is methyl. In other instances, $R^{23}$ is $C_{1-6}$ haloalkyl.

In some embodiments of compounds of Formula (IV), or any embodiment disclosed herein, $R^{24}$ is selected from H, $C_{1-6}$ alkyl, $C_{6-10}$ aryl, $C_{3-14}$ cycloalkyl, 5-14 membered heteroaryl, 4-14 membered heterocycloalkyl, $C_{6-10}$ aryl-$C_{3-14}$ alkyl-, $C_{3-14}$cycloalkyl-$C_{1-4}$ alkyl-, (5-14 membered heteroaryl)-$C_{1-4}$ alkyl-, (4-14 membered heterocycloalkyl)-$C_{1-4}$ alkyl-, $C(O)R^a$, $C(O)NR^aR^a$, and $C(O)OR^a$, wherein the $C_{1-6}$ alkyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^{24}$ are each optionally substituted with 1, 2, or 3 independently selected $R^b$ substituents. In some embodiments of compounds of Formula (IV), or any embodiment disclosed herein, $R^{24}$ is selected from H, $C_{1-6}$ alkyl, $C_{3-14}$ cycloalkyl, 4-14 membered heterocycloalkyl, $C_{3-14}$cycloalkyl-$C_{1-4}$ alkyl-, (4-14 membered heterocycloalkyl)-$C_{1-4}$ alkyl-, and $C(O)R^a$, wherein the $C_{1-6}$ alkyl, $C_{3-14}$ cycloalkyl, 4-14 membered heterocycloalkyl, $C_{3-14}$ cycloalkyl-$C_{1-4}$ alkyl- and (4-14 membered heterocycloalkyl)-$C_{1-4}$ alkyl- of $R^{24}$ are each optionally substituted with 1 or 2 independently selected $R^b$ substituents.

In some embodiments of compounds of Formula (IV), or any embodiment disclosed herein, $R^{24}$ is H, $C_{1-6}$ alkyl optionally substituted with 1, 2 or 3 independently selected $R^b$ substituents, halo, CN, $C_{3-6}$ cycloalkyl optionally substituted with 1, 2 or 3 independently selected $R^b$ substituents, 4-6 membered heterocycloalkyl optionally substituted with 1, 2 or 3 independently selected $R^b$ substituents, phenyl optionally substituted with 1, 2 or 3 independently selected $R^b$ substituents or 5-6 membered heteroaryl optionally substituted with 1, 2 or 3 independently selected $R^b$ substituents. In some instances, $R^{24}$ is H, $C_{1-6}$ alkyl optionally substituted with 1, 2 or 3 independently selected $R^b$ substituents. In other instances, $R^{24}$ is H. In other instances, $R^{24}$ is $C_{1-6}$ alkyl (e.g., methyl). In other instances, $R^{24}$ is $C_{1-6}$ alkyl substituted with 1, 2 or 3 independently selected $R^b$ substituents. In other instances, $R^{24}$ is H, $C_{1-6}$ alkyl, 2-hydroxypropyl, (R)-2-hydroxypropyl, (S)-2-hydroxypropyl, 2-hydroxyethyl, $C_{3-6}$ cycloalkyl, $C_{3-6}$ cycloalkyl-$C_{1-4}$ alkyl-, 1-(methylsulfonyl)piperidin-4-yl or tetrahydro-2H-pyran-4-yl. In some instances, $R^{24}$ is H, $C_{1-6}$ alkyl, 2-hydroxypropyl, (R)-2-hydroxypropyl, (S)-2-hydroxypropyl, 2-hydroxyethyl, 1-(methylsulfonyl)piperidin-4-yl, tetrahydro-2H-pyran-4-yl, (tetrahydro-2H-pyran-4-yl)methyl, 1-(hydroxymethyl)cyclopropyl)methyl, (S)-(2,3-dihydroxypropyl)-1-methyl, (2,3-dihydroxypropyl)-1-methyl, (R)-(2,3-dihydroxypropyl)-1-methyl, carboxymethyl, 1-acetylpiperidin-4-yl, 4-carboxy-4-methylcyclohexyl, 3-(methylsulfonamido)propyl, trans-(4-carboxycyclohexyl)methyl, cis-(4-carboxycyclohexyl)methyl, (3-carboxypyrrolidin-1-yl)methyl, (R)-(3-carboxypyrrolidin-1-yl)methyl, (S)-(3-carboxypyrrolidin-1-yl)methyl, (3-hydroxypyrrolidin-1-yl)methyl, (R)-(3-hydroxypyrrolidin-1-yl)methyl, (S)-(3-hydroxypyrrolidin-1-yl)methyl, pyrrolidin-1-ylmethyl, 2-(dimethylamino)acetyl, (5-cyanopyridin-3-yl)methoxy, (2-carboxypiperidin-1-yl)methyl, (R)-(2-carboxypiperidin-1-yl)methyl, (S)-(2-carboxypiperidin-1-yl)methyl, halo, cyclobutyl, cyclopropylmethyl, or CN. In some instances, $R^{24}$ is $C_{1-6}$ alkyl, 2-hydroxypropyl, (R)-2-hydroxypropyl, (S)-2-hydroxypropyl, 2-hydroxyethyl, 1-(methylsulfonyl)piperidin-4-yl, tetrahydro-2H-pyran-4-yl, (tetrahydro-2H-pyran-4-yl)methyl, 1-(hydroxymethyl)cyclopropyl)methyl, (S)-(2,3-dihydroxypropyl)-1-methyl, (2,3-dihydroxypropyl)-1-methyl, (R)-(2,3-dihydroxypropyl)-1-methyl, carboxymethyl, 1-acetylpiperidin-4-yl, 4-carboxy-4-methylcyclohexyl, 3-(methylsulfonamido)propyl, trans-(4-carboxycyclohexyl)methyl, cis-(4-carboxycyclohexyl)methyl, (3-carboxypyrrolidin-1-yl)methyl, (R)-(3-carboxypyrrolidin-1-yl)methyl, (S)-(3-carboxypyrrolidin-1-yl)methyl, (3-hydroxypyrrolidin-1-yl)methyl, (R)-(3-hydroxypyrrolidin-1-yl)methyl, (S)-(3-hydroxypyrrolidin-1-yl)methyl, pyrrolidin-1-ylmethyl, 2-(dimethylamino)acetyl, (5-cyanopyridin-3-yl)methoxy, (2-carboxypiperidin-1-yl)methyl, (R)-(2-carboxypiperidin-1-yl)methyl, (S)-(2-carboxypiperidin-1-yl)methyl, halo, cyclobutyl, cyclopropylmethyl, or CN. In some instances, $R^{24}$ is H, $C_{1-6}$ alkyl (e.g., methyl) or 2-hydroxypropyl (e.g., (R)-2-hydroxypropyl and (S)-2-hydroxypropyl). In other instances, $R^{24}$ is (R)-2-hydroxypropyl or (S)-2-hydroxypropyl.

In some instances, $R^{24}$ is H, $C_{1-6}$ alkyl, 2-hydroxypropyl, (R)-2-hydroxypropyl, (S)-2-hydroxypropyl, 2-hydroxyethyl, $C_{3-6}$ cycloalkyl, $C_{3-6}$ cycloalkyl-$C_{1-4}$ alkyl-, 1-(methylsulfonyl)piperidin-4-yl, or tetrahydro-2H-pyran-4-yl, 4-hydroxycyclohexyl, trans-(4-carboxycyclohexyl)methyl, cis-(4-carboxycyclohexyl)methyl, (4-carboxycyclohexyl)ethyl, 4-carboxy-4-methylcyclohexyl, or 2-(4-carboxycyclohexyl)ethyl.

In some embodiments, substituents $R^{20}$ and $R^{24}$ are the same. In some embodiments, substituents $R^{20}$ and $R^{24}$ are different.

In some embodiments of compounds of Formula (IV), (V), (Va), (Vb), (Vc), (Vd), (Ve), (VI), (Vg), (Vg-1), (Vh), or (Vh-1), or any embodiment disclosed herein, $R^{25}$ and $R^{26}$ are each H. In some embodiments, m and n are each 0.

In some embodiments of compounds of Formula (IV), (V), (Va), (Vb), (Vc), (Vd), (Ve), (Vf), (Vg), (Vg-1), (Vh), or (Vh-1), or any embodiment disclosed herein, the subscript m, n and p are each an integer of 1.

In some embodiments of compounds of Formula (IV), (V), (Va), (Vb), (Vc), (Vd), (Ve), (Vf), (Vg), (Vg-1), (Vh), or (Vh-1), or any embodiment disclosed herein, $R^{25}$, $R^{26}$ and $R^{27}$ are each H.

In some embodiments, each of $R^a$ $R^{a1}$, and $R^{a2}$ is independently selected from H, $C_{1-6}$ alkyl, $C_{1-6}$ haloalkyl, 5-14 membered heteroaryl, 4-14 membered heterocycloalkyl, (5-14 membered heteroaryl)-$C_{1-4}$ alkyl-, and (4-14 membered heterocycloalkyl)-$C_{1-4}$ alkyl-, wherein the $C_{1-6}$ alkyl, 5-14 membered heteroaryl, 4-14 membered heterocycloalkyl, (5-14 membered heteroaryl)-$C_{1-4}$ alkyl- and (4-14 membered heterocycloalkyl)-$C_{1-4}$ alkyl- of $R^a$, $R^{a1}$ and $R^{a2}$ are each optionally substituted with 1, 2 or 3 independently selected $R^d$ substituents. In some embodiments, each of $R^a$, $R^{a1}$ and $R^{a2}$ is independently selected from H, $C_{1-6}$ alkyl and (5-14 membered heteroaryl)-$C_{1-4}$ alkyl-, wherein the $C_{1-6}$ alkyl and (5-14 membered heteroaryl)-$C_{1-4}$ alkyl- of $R^a$, $R^{a1}$ and $R^{a2}$ are each optionally substituted with 1 or 2 independently selected $R^d$ substituents.

In some embodiments, each $R^d$ is independently selected from $C_{1-6}$ alkyl, $C_{1-6}$ haloalkyl, halo, CN, $NH_2$, $OR^e$, $SR^e$, $C(O)R^e$, $C(O)NR^eR^e$, $C(O)OR^e$, and $NR^eS(O)_2R^c$. In some embodiments, each $R^d$ is independently selected from $C_{1-6}$ alkyl, $C_{1-6}$ haloalkyl, halo, CN, $NH_2$, $OR^e$, and $NR^eS(O)_2R^e$.

In some embodiments, each $R^e$ is independently selected from H, $C_{1-6}$ alkyl, $C_{1-6}$ haloalkyl, $C_{2-6}$ alkenyl, and $C_{2-6}$ alkynyl. In some embodiments, each $R^e$ is independently selected from H and $C_{1-6}$ alkyl. In some embodiments, $R^e$ is H. In other embodiments, $R^e$ is $C_{1-6}$ alkyl.

In some embodiments, each $R^b$ substituent is independently selected from halo, $C_{1-6}$ alkyl, CN, OH, $NH_2$, $OR^c$, $SR^c$, $C(O)R^c$, $C(O)NR^cR^c$, $C(O)OR^c$, $NR^cR^c$, $NR^cC(O)R^c$, $S(O)NR^cR^c$, and $S(O)_2R^c$; wherein the $C_{1-6}$ alkyl of $R^b$ is optionally substituted with 1 or 2 independently selected $R^d$ substituents. In some embodiments, each $R^b$ substituent is independently selected from $C_{1-6}$ alkyl, OH, $OR^c$, $C(O)R^c$, $C(O)OR^c$, and $S(O)_2R^c$; wherein the $C_{1-6}$ alkyl of $R^b$ is optionally substituted with 1 or 2 independently selected $R^d$ substituents.

In some embodiments, each $R^c$ is independently selected from H, $C_{1-6}$ alkyl, $C_{1-6}$haloalkyl, $C_{2-6}$ alkenyl, and $C_{2-6}$ alkynyl. In some embodiments, each $R^c$ is independently selected from H and $C_{1-6}$ alkyl. In some embodiments, $R^c$ is H. In other embodiments, $R^c$ is $C_{1-6}$ alkyl.

In some embodiments of compounds of Formula (IV), or any embodiment disclosed herein, or a pharmaceutically acceptable salt or a stereoisomer thereof, wherein:

ring A is 5- to 14-membered heteroaryl, 4- to 14-membered heterocycloalkyl, or $C_{6-10}$ aryl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^{20}$ substituents;

L is a bond, —C(O)NH—, —CH$_2$O— or —OCH$_2$—, wherein the carbonyl group in the —C(O)NH— linkage is attached to ring A;

$R^{21}$ and $R^{22}$ are each independently halo, $C_{1-6}$ alkyl or CN;

$R^{23}$ is H, $C_{1-6}$ alkyl or $C_{1-6}$ haloalkyl;

$R^{24}$ is selected from H, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{3-14}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, $C(O)R^a$, $C(O)NR^aR^a$, and $C(O)OR^a$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^{24}$ are each optionally substituted with 1, 2, or 3 independently selected $R^b$ substituents;

$R^{20}$ is each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $OR^{a1}$, $SR^{a1}$, $NHOR^{a1}$, $C(O)R^{a1}$, $C(O)NR^{a1}R^{a1}$, and $C(O)OR^{a1}$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$alkyl- and (4-14 membered heterocycloalkyl)-$C_{1-4}$ alkyl- of $R^{20}$ are each optionally substituted with 1, 2, or 3 independently selected $R^b$ substituents;

$R^{27}$ is each independently selected from H, halo, $C_{1-6}$ alkyl, $C_{2-6}$ alkenyl, $C_{2-6}$ alkynyl, $C_{1-6}$ haloalkyl, $C_{1-6}$ haloalkoxy, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl-, (4-14 membered heterocycloalkyl)-$C_{1-4}$ alkyl-, CN, $OR^{a2}$, $SR^{a2}$, $NHOR^{a2}$, $C(O)R^{a2}$, $C(O)NR^{a2}R^{a2}$, and $C(O)OR^{a2}$, wherein the $C_{1-6}$ alkyl, $C_{2-6}$ alkenyl, $C_{2-6}$ alkynyl, $C_{6-10}$ aryl, $C_{3-14}$ cycloalkyl, 5-14 membered heteroaryl, 4-14 membered heterocycloalkyl, $C_{6-10}$ aryl-$C_{1-4}$ alkyl-, $C_{3-14}$ cycloalkyl-$C_{1-4}$ alkyl-, (5-14 membered heteroaryl)-$C_{1-4}$ alkyl- and (4-14 membered heterocycloalkyl)-$C_{1-4}$ alkyl- of $R^{27}$ are each optionally substituted with 1, 2, or 3 independently selected $R^b$ substituents;

each of $R^a$, $R^{a1}$, and $R^{a2}$ is independently selected from H, $C_{1-6}$ alkyl, $C_{1-6}$ haloalkyl, $C_{2-6}$ alkenyl, $C_{2-6}$ alkynyl, 5-14 membered heteroaryl, 4-14 membered heterocycloalkyl, (5-14 membered heteroaryl)-$C_{1-4}$ alkyl-, and (4-14 membered heterocycloalkyl)-$C_{1-4}$ alkyl-, wherein the $C_{1-6}$ alkyl, $C_{2-6}$ alkenyl, $C_{2-6}$ alkynyl, 5-14 membered heteroaryl, 4-14 membered heterocycloalkyl, (5-14 membered heteroaryl)-$C_{1-4}$ alkyl- and (4-14 membered heterocycloalkyl)-$C_{1-4}$ alkyl- of $R^a$, $R^{a1}$ and $R^{a2}$ are each optionally substituted with 1, 2, or 3 independently selected $R^d$ substituents;

each $R^d$ is independently selected from $C_{1-4}$ alkyl, $C_{1-6}$ haloalkyl, halo, CN, $NH_2$, $OR^e$, $SR^e$, $C(O)R^e$, $C(O)NR^eR^e$, $C(O)OR^e$, $NHR^c$, $NR^eR^e$, $NR^eC(G)R^e$, $S(O)R^e$, $S(O)NR^eR^e$, $S(O)_2R^e$, $NR^eS(O)_2R^e$, and $S(O)_2NR^eR^e$, wherein the $C_{1-4}$ alkyl of $R^d$ is optionally substituted with 1, 2, or 3 independently selected $R^f$ substituents;

each $R^e$ is independently selected from H, $C_{1-6}$ alkyl, $C_{1-6}$haloalkyl, $C_{2-6}$ alkenyl, and $C_{2-6}$ alkynyl;

each $R^b$ substituent is independently selected from halo, $C_{1-6}$ alkyl, $C_{2-6}$ alkenyl, $C_{2-6}$ alkynyl, $C_{1-6}$ haloalkyl, $C_{1-6}$ haloalkoxy, CN, OH, $NH_2$, $OR^c$, $SR^c$, $C(O)R^c$, $C(O)NR^cR^c$, $C(O)OR^c$, $S(O)R^c$, $S(O)NR^cR^c$, $S(O)_2R^c$, and $S(O)_2NR^cR^c$; wherein the $C_{1-6}$ alkyl of $R^b$ is optionally substituted with 1, 2 or 3 independently selected $R^d$ substituents;

each $R^c$ is independently selected from H, $C_{1-6}$ alkyl, $C_{1-6}$ haloalkyl, $C_{2-6}$ alkenyl, and $C_{2-6}$ alkynyl;

the subscript m is an integer of 0;

the subscript n is an integer of 0;

the subscript p is an integer of 1, 2, 3, 4, 5 or 6; and

==== is a single bond or a double bond to maintain the 5-membered imidazole ring being aromatic.

In some embodiments of compounds of Formula (IV), or any embodiment disclosed herein, or a pharmaceutically acceptable salt or a stereoisomer thereof, wherein:

ring A is 5- to 14-membered heteroaryl, 4- to 14-membered heterocycloalkyl, or $C_{6-10}$ aryl, wherein the 5- to 14-membered heteroaryl and 4- to 14-membered heterocycloalkyl each has 1-4 heteroatoms as ring members selected from N, O and S, wherein the N or S atom as ring members is optionally oxidized and one or more carbon atoms as ring members are each optionally replaced by a carbonyl group; and wherein ring A is optionally substituted with 1, 2, or 3 $R^{20}$ substituents;

L is a bond, —C(O)NH—, —CH$_2$O— or —OCH$_2$—, wherein the carbonyl group in the —C(O)NH— linkage is attached to ring A;

$R^{21}$ and $R^{22}$ are each independently halo, $C_{1-6}$ alkyl or CN;

$R^{23}$ is H or $C_{1-6}$ alkyl;

$R^{24}$ is selected from H, $C_{1-6}$ alkyl, $C_{3-14}$ cycloalkyl, 4-14 membered heterocycloalkyl, $C_{3-14}$ cycloalkyl-$C_{1-4}$ alkyl-, (4-14 membered heterocycloalkyl)-$C_{1-4}$ alkyl-, and $C(O)R^a$, wherein the $C_{1-6}$ alkyl, $C_{3-14}$ cycloalkyl, 4-14 membered heterocycloalkyl, $C_{3-14}$cycloalkyl-$C_{1-4}$ alkyl-, and (4-14 membered heterocycloalkyl)-$C_{1-4}$ alkyl- of $R^{24}$ are each optionally substituted with 1 or 2 independently selected $R^b$ substituents;

$R^{20}$ is each independently selected from H, halo, $C_{1-6}$ alkyl, $C_{3-14}$ cycloalkyl, 4-14 membered heterocycloalkyl, $C_{3-14}$ cycloalkyl-$C_{1-4}$ alkyl-, (4-14 membered heterocycloalkyl)-$C_{1-4}$ alkyl-, CN, $OR^{a1}$, and $C(O)R^{a1}$, wherein the $C_{1-6}$ alkyl, $C_{3-14}$ cycloalkyl, 4-14 membered heterocycloalkyl, $C_{3-14}$cycloalkyl-$C_{1-4}$ alkyl-, and (4-14 membered heterocycloalkyl)-$C_{1-4}$alkyl- of $R^{20}$ are each optionally substituted with 1 or 2 independently selected $R^b$ substituents;

$R^{27}$ are each independently selected from H, halo, $C_{1-6}$ alkyl, $C_{3-14}$ cycloalkyl, 4-14 membered heterocycloalkyl, $C_{3-14}$ cycloalkyl-$C_{1-4}$ alkyl-, (4-14 membered heterocycloalkyl)-$C_{1-4}$ alkyl-, CN, $OR^{a2}$, and $C(O)R^{a2}$, wherein the $C_{1-6}$ alkyl, $C_{3-14}$ cycloalkyl, 4-14 membered heterocycloalkyl, $C_{3-14}$ cycloalkyl-$C_{1-4}$ alkyl-, and (4-14 membered heterocycloalkyl)-$C_{1-4}$alkyl- of $R^{27}$ are each optionally substituted with 1 or 2 independently selected $R^b$ substituents;

each of $R^a$, $R^{a1}$, and $R^{a2}$ is independently selected from H, $C_{1-6}$ alkyl, 5-14 membered heteroaryl, and (5-14 membered heteroaryl)-$C_{1-4}$ alkyl-, wherein the $C_{1-6}$ alkyl, 5-14 membered heteroaryl, and (5-14 membered heteroaryl)-$C_{1-4}$ alkyl- of $R^a$, $R^{a1}$, and $R^{a2}$ are each optionally substituted with 1 or 2 independently selected $R^d$ substituents;

each $R^d$ is independently selected from $C_{1-6}$ alkyl, $C_{1-6}$haloalkyl, halo, CN, $NH_2$, $OR^e$, $NHR^e$, $NR^cR^c$, and $NR^c$ $S(O)_2R^e$;

each $R^e$ is independently selected from H and $C_{1-6}$ alkyl;

each $R^b$ substituent is independently selected from halo, $C_{1-6}$ alkyl, CN, OH, $NH_2$, $OR^c$, $SR^c$, $C(O)R^c$, $C(O)NR^cR^c$, $C(O)OR^c$, and $S(O)_2R^c$; wherein the $C_{1-6}$ alkyl of $R^b$ is optionally substituted with 1 or 2 independently selected $R^d$ substituents;

each $R^c$ is independently selected from H and $C_{1-6}$ alkyl, the subscript m is an integer of 0;

the subscript n is an integer of 0;

the subscript p is an integer of 1, 2, 3, 4, 5, or 6; and

≡≡≡ is a single bond or a double bond to maintain the 5-membered imidazole ring being aromatic.

In some embodiments, the present disclosure provides any of the compounds set forth in Table 2 and described in the examples, such as Examples 1-189, or pharmaceutically acceptable salts or stereoisomers thereof. In certain embodiments, the present disclosure provides any of the compounds in Examples 13-54, or pharmaceutically acceptable salts or stereoisomers thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of the Formulas of the present disclosure (e.g., Formula (I)) can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, —NR(CR'R")$_n$— includes both —NR(CR'R")$_n$— and —(CR'R")$_n$NR— and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted", unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, indanyl, indenyl and the like. In some embodiments, aryl groups have from 6 to about 10 carbon atoms. In some embodiments, aryl groups have 6 carbon atoms. In some embodiments, aryl groups have 10 carbon atoms. In some embodiments, the aryl group is phenyl. In some embodiments, the aryl group is naphthyl.

The term "heteroaryl," employed alone or in combination with other terms, refers to a monocyclic or polycyclic aromatic heterocycle having at least one heteroatom ring member selected from boron, phosphorus, sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, benzothiophenyl, benzofuranyl, benzisoxazolyl, imidazo[1,2-6]thiazolyl, purinyl, and the like.

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from B, P, N, O and S. Exemplary six-membered ring heteroaryls are pyridyl, pyrazinyl, pyrimidinyl, triazinyl and pyridazinyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from boron, phosphorus, nitrogen, sulfur oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or S(O)$_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include azetidinyl, azepanyl, dihydrobenzofuranyl, dihydrofuranyl, dihydropyranyl, morpholino, 3-oxa-9-azaspiro[5.5]undecanyl, 1-oxa-8-azaspiro[4.5]decanyl, piperidinyl, piperazinyl, oxopiperazinyl, pyranyl, pyrrolidinyl, quinuclidinyl, tetrahydrofuranyl, tetrahydropyranyl, 1,2,3,4-tetrahydroquinolinyl, tropanyl, 4,5,6,7-tetrahydrothiazolo[5,4-c]pyridinyl, 4,5,6,7-tetrahydro-1H-imidazo[4,5-c]pyridine, and thiomorpholino.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "haloalkyl" as used herein refers to an alkyl group in which one or more of the hydrogen atoms has been replaced by a halogen atom. The term "$C_{n-m}$ haloalkyl" refers to a $C_{n-m}$ alkyl group having n to m carbon atoms and from at least one up to {2(n to m)+1} halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$ and the like. In some embodiments, the haloalkyl group is a fluoroalkyl group.

The term "alkyl" employed alone or in combination with other terms, refers to a saturated hydrocarbon group that may be straight-chained or branched. The term "$C_{n-m}$ alkyl", refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homo logs such as 2-methyl-1-butyl, w-pentyl, 3-pentyl, w-hexyl, 1,2,2-trimethylpropyl and the like. The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, w-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkoxy", employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms.

The term "haloalkoxy", employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The terms "halo" or "halogen", used alone or in combination with other terms, refers to fluoro, chloro, bromo and iodo. In some embodiments, "halo" refers to a halogen atom selected from F, Cl, or Br. In some embodiments, halo groups are F.

The term "oxo" refers to an oxygen atom as a divalent substituent, forming a carbonyl group when attached to carbon, or attached to a heteroatom forming a sulfoxide or sulfone group, or an Y-oxide group. In some embodiments, heterocyclic groups may be optionally substituted by 1 or 2 oxo (=O) substituents.

The term "fused" refers to having a bond in common with, such as a fused ring. The term "alkylthio" refers to an —S-alkyl group. Example alkylthio groups include meththio, ethylthio, propylthio (e.g., n-propylthio and isopropylthio), and the like.

The term "sulfido" refers to a sulfur atom as a divalent substituent, forming a thiocarbonyl group (C=S) when attached to carbon.

The term "heteroatom" used herein is meant to include boron, phosphorus, sulfur, oxygen and nitrogen.

As used herein, the term "about" generally refers to that the actual value is within 10%, 5%, 1%, or 0.5% of a particular value or range. The term "about" means herein that the actual value is within an acceptable standard error of the mean, depending on the considerations of those ordinary skill in the art to which this invention belongs. Besides the experimental examples, or unless stated specifically otherwise, it should be understood that the ranges, amounts, numerical values, and percentages used herein are modified by "about". Therefore, unless stated otherwise, the numerical values or parameters disclosed in the specification and claims are all rough values and may be varied as desired.

Compounds of the present disclosure can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the present disclosure can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art.

The term, "compound," as used herein is meant to include all stereoisomers, geometric isomers, tautomers and isotopes of the structures depicted. The term is also meant to refer to compounds of the present disclosure, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the present disclosure, or salts thereof, are substantially isolated. By "substantially isolated" is meant that the compound is at least partially or substantially separated from the environment in which it was formed or detected. Partial separation can include, e.g., a composition enriched in the compounds of the present disclosure. Substantial separation can include compositions containing at least about 50%, at least about 60%, at least about 70%, at least about 80%, at least about 90%, at least about 95%, at least about 97%, or at least about 99% by weight of the compounds of the present disclosure, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present disclosure also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present disclosure include the non-toxic salts of the parent compound formed, e.g., from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, $17^{th}$ Ed., (Mack Publishing Company, Easton, 1985), p. 1418, Berge et al., *J. Pharm. Sci.*, 1977, 66(1), 1-19 and in Stahl et at., *Handbook of Pharmaceutical Salts: Properties, Selection, and Use*, (Wiley, 2002). In some embodiments, the compounds described herein include the N-oxide forms.

Uses of the Compounds

Compounds of the present disclosure can reduce PD-1/PD-L1 protein/protein interaction and, thus, are useful in treating diseases and disorders associated with activity of PD-1 and the diseases and disorders associated with PD-L1 including its interaction with other proteins such as PD-1 and B7-1 (CD80). Collectively, these are referred to herein as "PD-1-related diseases or conditions." In certain embodiments, the compounds of the present disclosure, or pharmaceutically acceptable salts or stereoisomers thereof, are useful for therapeutic administration to enhance, stimulate and/or increase immunity in cancer, chronic infection, or sepsis, including enhancement of response to vaccination. In some embodiments, the present disclosure provides a method for reducing the PD-1/PD-L1 protein/protein interaction. The method includes administering to an individual or a patient a compound described herein or a pharmaceutically acceptable salt or a stereoisomer thereof. The compounds of the present disclosure can be used alone, in combination with other agents or therapies or as an adjuvant or neoadjuvant for the treatment of diseases or disorders, including cancer or infection diseases. For the uses described herein, any of the compounds of the disclosure, including any of the embodiments thereof, may be used.

The compounds of the present disclosure reduce the PD-1/PD-L1 protein/protein interaction, resulting in a PD-1 pathway blockade. The blockade of PD-1 can enhance the immune response to cancerous cells and infectious diseases in mammals, including humans. In some embodiments, the present disclosure provides treatment of an individual or a patient in vivo using a compound described herein or a salt or stereoisomer thereof such that growth of cancerous tumors is inhibited. A compound described herein or a salt or stereoisomer thereof, can be used to inhibit the growth of cancerous tumors. Alternatively, a compound described herein or a salt or stereoisomer thereof, can be used in conjunction with other agents or standard cancer treatments, as described below. In one embodiment, the present disclosure provides a method for inhibiting growth of tumor cells in vitro. The method includes contacting the tumor cells in vitro with a compound described herein or of a salt or stereoisomer thereof. In another embodiment, the present disclosure provides a method for inhibiting growth of tumor cells in an individual or a patient. The method includes administering to the individual or patient in need thereof a therapeutically effective amount of a compound described herein or a salt or a stereoisomer thereof.

In some embodiments, provided herein is a method for treating cancer. The method includes administering to a patient in need thereof, a therapeutically effective amount of a compound described herein or a salt thereof. Examples of cancers include those whose growth may be inhibited using compounds of the disclosure and cancers typically responsive to immunotherapy.

In some embodiments, the present disclosure provides a method of enhancing, stimulating and/or increasing the immune response in a patient. The method includes administering to the patient in need thereof a therapeutically effective amount of a compound described herein or a salt thereof.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers, especially metastatic cancers that express PD-L1.

In some embodiments, cancers treatable with compounds of the present disclosure include melanoma (e.g., metastatic malignant melanoma), renal cancer (e.g., clear cell carcinoma), prostate cancer (e.g. hormone refractory prostate adenocarcinoma), breast cancer, triple-negative breast cancer, colon cancer, lung cancer (e.g., non-small cell lung cancer and small cell lung cancer), squamous cell head and neck cancer, urothelial cancer (e.g., bladder) and cancers with high micro satellite instability ($MSI^{high}$). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma, Ewing's sarcoma, brain cancer, brain tumor, astrocytoma, neuroblastoma, neurofibroma, basal cell carcinoma, chondrosarcoma, epithelioid sarcoma, eye cancer, Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronffoma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

PD-1 pathway blockade with compounds of the present disclosure can also be used for treating infections such as viral, bacteria, fungus and parasite infections. The present disclosure provides a method for treating infections such as viral infections. The method includes administering to a patient in need thereof, a therapeutically effective amount of a compound described herein or a salt thereof. Examples of viruses causing infections treatable by methods of the present disclosure include, but are not limit to, human immunodeficiency virus, human papillomavirus, influenza, hepatitis A, B, C or D viruses, adenovirus, poxvirus, herpes simplex viruses, human cytomegalovirus, severe acute respiratory syndrome virus, ebola virus, and measles virus. In some embodiments, viruses causing infections treatable by methods of the present disclosure include, but are not limit to, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, comovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

The present disclosure provides a method for treating bacterial infections. The method includes administering to a patient in need thereof, a therapeutically effective amount of a compound described herein or a salt thereof. Non-limiting examples of pathogenic bacteria causing infections treatable by methods of the disclosure include chlamydia, rickettsial bacteria, mycobacteria, staphylococci, streptococci, pneumonococci, meningococci and conococci, klebsiella, proteus, serratia, *pseudomonas*, legionella, diphtheria, salmonella, bacilli, cholera, tetanus, botulism, anthrax, plague, leptospirosis, and Lyme's disease bacteria.

The present disclosure provides a method for treating fungus infections. The method includes administering to a patient in need thereof, a therapeutically effective amount of a compound described herein or a salt thereof. Non-limiting examples of pathogenic fungi causing infections treatable by methods of the disclosure include *Candida* (*albicans, krusei, glabrata, tropicalis*, etc.), *Cryptococcus neoformans, Aspergillus* (*fumigatus, niger*, etc.), Genus Mucorales (mucor, absidia, rhizophus), *Sporothrix schenkii, Blastomyces dermatitidis, Paracoccidioides brasiliensis, Coccidioides immitis* and *Histoplasma capsulatum*.

The present disclosure provides a method for treating parasite infections. The method includes administering to a patient in need thereof, a therapeutically effective amount of a compound described herein or a salt thereof. Non-limiting examples of pathogenic parasites causing infections treatable by methods of the disclosure include *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

The present disclosure provides a method for treating sepsis. The method includes treating sepsis by administering to a patient in need thereof, a therapeutically effective amount of a compound described herein or a salt thereof.

The terms "individual" or "patient," used interchangeably, refer to any animal, including mammals, preferably mice, rats, other rodents, rabbits, dogs, cats, swine, cattle, sheep, horses, or primates, and most preferably humans.

The phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein, the term "treating" or "treatment" refers to one or more of (1) inhibiting the disease; e.g., inhibiting a disease, condition or disorder in an individual who is experiencing or displaying the pathology or symptomatology of the disease, condition or disorder (i.e., arresting further development of the pathology and/or symptomatology); and (2) ameliorating the disease; e.g., ameliorating a disease, condition or disorder in an individual who is experiencing or displaying the pathology or symptomatology of the disease, condition or disorder (i.e., reversing the pathology and/or symptomatology) such as decreasing the severity of disease.

In some embodiments, the compounds of the present disclosure are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

Combination Therapies

Cancer cell growth and survival can be impacted by multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

The compounds of the present disclosure can be used in combination with one or more other enzyme/protein/receptor inhibitors or one or more therapies for the treatment of diseases, such as cancer or infections. Examples of diseases and indications treatable with combination therapies include those as described herein. Examples of cancers include solid tumors and liquid tumors, such as blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, PI3K (alpha, beta, gamma, delta), CSFIR, KIT, FLK-II, KDR/FLK-1, FLK-4, flt-1, FGFR1, FGFR2, FGFR3, FGFR4, c-Met, Ron, Sea, TRKA, TRKB, TRKC, TAM kinases (Axl, Mer, Tyro3), FLT3, VEGFR/FU2, Flt4, EphA1, EphA2, EphA3, EphB2, EphB4, Tie2, Src, Fyn, Lck, Fgr, Btk, Fak, SYK, FRK, JAK, ABE, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., INCB54828, INCB62079 and INCB63904), a JAK inhibitor (JAK1 and/or JAK2, e.g., ruxolitinib, baricitinib or INCB39110), an IDO inhibitor (e.g., epacadostat, NLG919, and BMS-986205), an ESDI inhibitor (e.g., INCB59872 and INCB60003), a TDO inhibitor, a PI3K-delta inhibitor (e.g., INCB50797 and INCB50465), a PI3K-gamma inhibitor such as a PI3K-gamma selective inhibitor, a Pim inhibitor (INCB53914), a CSF1R inhibitor, a TAM receptor tyrosine kinases (Tyro-3, Axl, and Mer), a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), a poly ADP ribose polymerase (PARP) inhibitor such as rucaparib, olaparib, niraparib, veliparib, or talazoparib, and an adenosine receptor antagonist and an arginase inhibitor (INCB01158) or combinations thereof.

Compounds of the present disclosure can be used in combination with one or more immune checkpoint inhibitors. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-IBB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is nivolumab. In some embodiments, the anti-PD1 antibody is pembrolizumab. In some embodiments, the anti PD-1 antibody is SHR-1210.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab.

In some embodiments, the inhibitor of an immune checkpoint molecule is an inhibitor of LAG3, e.g., an anti-LAG3 antibody. In some embodiments, the anti-LAG3 antibody is BMS-986016, LAG525 or INCAGN2385.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of GITR, e.g., an anti-GITR antibody. In some embodiments, the anti-GITR antibody is TRX518 or MK-4166, INCAGN1876, MK-1248, AMG228, BMS-986156, GWN323, MEDI1873. In some embodiments, the inhibitor of an immune checkpoint molecule is an inhibitor of OX40, e.g., an anti-OX40 antibody or OX40L fusion protein. In some embodiments, the anti-OX40 antibody is MEDI0562, MOXR-0916, PF-04518600, GSK3174998, BMS-986178. In some embodiments, the OX40L fusion protein is MEDI6383.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, adoptive T cell transfer, Toll receptor agonists, STING agonists, oncolytic virotherapy and immunomodulating small molecules, including thalidomide or JAK1/2 inhibitor and the like. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fialvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, olaparib, oxaliplatin, paclitaxel, pamidronate, panitumumab, pegaspargase, pegfdgrastim, pemetrexed disodium, pentostatin, pipobroman, plicamycin, procarbazine, quinacrine, rasburicase, rituximab, ruxolitinib, rucaparib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, niraparib, veliparib, talazoparib and zoledronate.

Other anti-cancer agent(s) include antibody therapeutics such as trastuzumab (Herceptin), antibodies to costimulatory molecules such as CTLA-4 (e.g., ipilimumab), 4-IBB (e.g., urelumab, utomilumab), antibodies to PD-1 and PD-L1, or antibodies to cytokines (IL-10, TGF-β, etc.). Examples of antibodies to PD-1 and/or PD-L1 that can be combined with compounds of the present disclosure for the treatment of cancer or infections such as viral, bacteria, fungus and parasite infections include, but are not limited to, nivolumab, pembrolizumab, MPDL3280A, MEDI-4736 and SHR-1210.

The compounds of the present disclosure can further be used in combination with one or more anti-inflammatory agents, steroids, immunosuppressants or therapeutic antibodies.

The compounds described herein or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds described herein or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds described herein or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

The compounds of the present disclosure can be used in combination with bone marrow transplant for the treatment of a variety of tumors of hematopoietic origin.

The compounds described herein or salts thereof can be used in combination with vaccines, to stimulate the immune response to pathogens, toxins, and self antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, *Giardia, Malaria, Leishmania, Staphylococcus aureus, Pseudomonas Aeruginosa*.

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, ebola virus, measles virus, herpes virus (e.g., VZV, HSV-1, HAV-6, HSV-II, and CMV, Epstein Barr virus), flaviviruses, echovirus, rhinovirus, coxsackie virus, comovirus, respiratory syncytial virus, mumpsvirus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, chlamydia, rickettsial bacteria, mycobacteria, staphylococci, streptococci, pneumonococci, meningococci and conococci, klebsiella, proteus, serratia, *pseudomonas*, legionella, diphtheria, salmonella, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus Mucorales (*mucor, absidia*, rhizophus), *Sporothrix schenkii, Blastomyces dermatitidis, Paracoccidioides brasiliensis, Coccidioides immitis* and *Histoplasma capsulatum*.

Pathogenic parasites causing infections treatable by methods of the disclosure include, but are not limited to, *Entamoeba histolytica, Balantidium coli, Naegleriafowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis*.

When more than one pharmaceutical agent is administered to a patient, they can be administered simultaneously, separately, sequentially, or in combination (e.g., for more than two agents).

Formulation, Dosage Forms and Administration

When employed as pharmaceuticals, the compounds of the present disclosure can be administered in the form of pharmaceutical compositions. Thus the present disclosure provides a composition comprising a compound described herein or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This present disclosure also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the present disclosure, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g, up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the present disclosure may be milled using known milling procedures such as wet milling to obtain a particle size appropriate for tablet formation and for other formulation types. Finely divided (nanoparticulate) preparations of the compounds of the present disclosure can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the present disclosure can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 0.5 to about 1,000 mg, or from about 5 to about 1,000 mg (1 g), or from about 100 mg to about 500 mg, of the active ingredient. In some embodiments, each dosage contains about 1 mg of the active ingredient. In some embodiments, each dosage contains about 5 mg of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present disclosure can vary according to, e.g., the particular use for which the treatment is made, the manner of administration of the compound, the health and condition of the patient, and the judgment of the prescribing physician. The proportion or concentration of a compound of the present disclosure in a pharmaceutical composition can vary depending upon a number of factors including dosage, chemical characteristics (e.g., hydrophobicity), and the route of administration. For example, the compounds of the present disclosure can be provided in an aqueous physiological buffer solution containing from about 0.01 to about 10% w/v, or from about 0.1 to about 10% w/v, of the compound for parenteral administration. Some typical dose ranges are from about 0.1 µg/kg to about 1 g/kg, or from about 1 µg/kg to about 1 g/kg, of body weight per day. In some embodiments, the dose range is from about 0.001 mg/kg to about 100 mg/kg, or from about 0.01 mg/kg to about 100 mg/kg, of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.01 to about 1000 mg, or about 0.1 to about 1000 mg, of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.01, at least about 0.05, at least about 0.1, at least about 0.25, at least about 0.5, at least about 1, at least about 2 or at least about 5 wt % of the compound of the present disclosure. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present disclosure can vary according to, e.g., the particular use for which the treatment is made, the manner of administration of the compound, the health and condition of the patient, and the judgment of the prescribing physician. The proportion or concentration of a compound of the present disclosure in a pharmaceutical composition can vary depending upon a number of factors including dosage, chemical characteristics (e.g., hydrophobicity), and the route of administration. For example, the compounds of the present disclosure can be provided in an aqueous physiological buffer solution containing about 0.01 to about 10% w/v, or from about 0.1 to about 10% w/v of the compound for parenteral administration. Some typical dose ranges are from about 0.1 µg/kg to about 1 g/kg, or from about 1 µg/kg to about 1 g/kg, of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

The compounds of the present disclosure can further be useful in investigations of biological processes in normal and abnormal tissues. Thus, another aspect of the present invention relates to labeled compounds of the invention (radio-labeled, fluorescent-labeled, etc.) that would be useful not only in imaging techniques but also in assays, both in vitro and in vivo, for localizing and quantitating PD-1 or PD-L1 protein in tissue samples, including human, and for identifying PD-L1 ligands by inhibition binding of a labeled compound. Accordingly, the present invention includes PD-1/PD-L1 binding assays that contain such labeled compounds.

The present invention further includes isotopically-substituted compounds of the disclosure. An "isotopically-substituted" compound is a compound of the invention where one or more atoms are replaced or substituted by an atom having the same atomic number but a different atomic mass or mass number e.g., a different atomic mass or mass number from the atomic mass or mass number typically found in nature (i.e., naturally occurring). It is to be understood that a "radio-labeled" compound is a compound that has incorporated at least one isotope that is radioactive (e.g., radionuclide). Suitable radionuclides that may be incorporated in compounds of the present invention include but are not limited to $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro PD-L1 protein labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

In some embodiments the radionuclide is selected from the group consisting of $^3$H, $^{14}$C, $^{125}$I, $^{35}$S and $^{82}$Br. Synthetic methods for incorporating radio-isotopes into organic compounds are known in the art.

Specifically, a labeled compound of the invention can be used in a screening assay to identify and/or evaluate compounds. For example, a newly synthesized or identified compound (i.e., test compound) which is labeled can be evaluated for its ability to bind a PD-L1 protein by monitoring its concentration variation when contacting with the PD-L1 protein, through tracking of the labeling. For example, a test compound (labeled) can be evaluated for its ability to reduce binding of another compound which is known to bind to a PD-L1 protein (i.e., standard compound). Accordingly, the ability of a test compound to compete with the standard compound for binding to the PD-L1 protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of PD-L1 including its interaction with other proteins such as PD-1 and B7-1 (CD80), such as cancer or infections, which include one or more containers containing a pharmaceutical composition comprising a therapeutically effective amount of a compound of Formula (I), or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following are examples of the practice of the invention. They are not to be construed as limiting the scope of the invention in any way.

EXAMPLES

Examples 1A and 1B: PD-1/PD-L1 Binding Assay

Example 1A: Alphascreen

Binding assays were conducted in a low volume white 384-well polystyrene plate in a final volume of 20 µL. Compounds to be analyzed were first serially diluted in DMSO and added to the plate wells before the addition of other reaction components. The final concentration of DMSO in the assay was 1%. The assay was carried out at 25° C. in the PBS buffer (pH 7.4) with 0.05% Tween-20 and 0.1% BSA. Recombinant human PD-L1 protein (19-238) with a His-tag at the C-terminus was purchased from Acro-Biosystems (PD1-H5229). Recombinant human PD-1 protein (25-167) with Fc tag at the C-terminus was also from AcroBiosystems (PD1-H5257). PD-L1 and PD-1 proteins were diluted in the assay buffer (final concentration ~0.67 and 0.20 nM respectively) and 10 µL was added to the plate well. Plates were centrifuged and proteins were preincubated with compounds for 40 minutes. The incubation was followed by the addition of 10 µL of assay buffer supplemented with Alphascreen Ni chelate donor beads (PerkinElmer-AS101D) and Protein A Acceptor beads (PerkinElmer-6760137) at final concentration 2.5 µg/mL under reduced light. After plate sealing, the plate was incubated in the dark at room temperature for 120 minutes before reading on a PHERAstar FS plate reader (BMG Labtech). $IC_{50}$ determination was performed by fitting the curve of percent control activity versus the log of the compound concentration using the GraphPad Prism 5.0 software.

Example 1B; Homogeneous Time-Resolved Fluorescence (HERF)

The assays were conducted in a standard black 384-well polystyrene plate with a final volume of 20 µL. Inhibitors were first serially diluted in DMSO and then added to the plate wells before the addition of other reaction components. The final concentration of DMSO in the assay was 1%. The assays were carried out at 25° C. in the PBS buffer (pH 7.4) with 0.05% Tween-20 and 0.1% BSA. Recombinant human PD-L1 protein (19-238) with a His-tag at the C-terminus was purchased from AcroBiosystems (PD1-H5229). Recombinant human PD-1 protein (25-167) with Fc tag at the C-terminus was also purchased from AcroBiosystems (PD1-H5257). PD-L1 and PD-1 proteins were diluted in the assay buffer and 10 µL was added to the plate well. Plates were centrifuged and proteins were preincubated with inhibitors for 40 minutes. The incubation was followed by the addition of 10 µL of HTRF detection buffer supplemented with Europium cryptate-labeled anti-human IgG (PerkinElmer-AD0212) specific for Fc and anti-His antibody conjugated to SureLight®-Allophycocyanin (APC, PerkinElmer-AD0059H). After centrifugation, the plate was incubated at 25° C. for 60 min. before reading on a PHERAstar FS plate reader (665 nm/620 nm ratio). Final concentrations in the assay were ~3 nM PD1, 10 nM PD-L1, 1 nM europium anti-human IgG and 20 nM anti-His-Allophycocyanin. $IC_{50}$ determination was performed by fitting the curve of percent control activity versus the log of the inhibitor concentration using the GraphPad Prism 5.0 software.

Example 2A: PD-L1 Homogeneous Time-Resolved Fluorescence (HTRF) Dimerization

Assay Dimerization assays were conducted in a standard black 384-we 11 polystyrene plate in a final volume of 20 µL. Compounds to be analyzed were diluted in DMSO and added to the plate wells before the addition of other reaction components. The final concentration of tested compounds was 10 µM and DMSO was at 1%. The assays were carried out at 25° C. in PBS buffer (pH 7.4) with 0.05% Tween-20 and 0.1% BSA. Recombinant human PD-L1 protein (19-238) with a His-tag at the C-terminus was purchased from AcroBiosystems (PD1-H5229). Recombinant human PD-L1 protein (19-239) with Fc tag at the C-terminus was purchased from BPS Bioscience (#71104). PD-L1 proteins were diluted in the assay buffer, mixed, and 10 ul was added to the plate well. Plates were centrifuged and proteins were preincubated with compounds for 40 minutes. The incubation was followed by the addition of 10 µL of HTRF detection buffer supplemented with Europium cryptate-labeled anti-human IgG (PerkinElmer-AD0074) specific for Fc and anti-His antibody conjugated to SureLight®-Allophycocyanin (APC, PerkinElmer-AD0059H). Final concentrations in the assay were: 30 nM PD-L1 (Fc-tag), 100 nM PD-L1 (His-tag), 10 nM europium anti-human IgG and 200 nM anti-His-Allophycocyanin. After centrifugation, the plate was incubated at 25° C. for 60 minutes before reading on a PHERAstar FS plate reader (665 nm/620 nm ratio). The dimerization ratio was calculated based on the assay signal in the presence of compound divided by the signal in the presence of DMSO.

Example 3A: PD-L1 Internalization Assays

Endocytosis or internalization of PD-L1 was measured by two different methods, one direct and the other indirect. In the direct method, an anti PD-L1 antibody labeled with a pH sensitive fluorophore is incubated with PD-L1 expressing cells. Upon internalization and trafficking of the antibody-PD-L1 complex to low pH endosomes, fluorescence is emitted. In the indirect method, cell surface PD-L1 is measured using an anti PD-L1 antibody after incubation with a compound to determine remaining, non-internalized receptor.

Direct Method Assessing for PD-L1 Internalization

For the direct measurement, biotinylated anti-PD-L1 antibody (BPS Biosciences) or Atezolizumab, biotinylated with a 20-fold excess of biotin using the EZ-Link™ Sulfo-NHS-LC-Biotin reagents (ThermoFisher), were labeled with pHrodo™ Red Avidin (Life Technologies) conjugate. Equimolar solutions of the antibody and pHrodo™ Red avidin (4.2 uM each) were incubated on ice for 2 hours in the dark in a buffer composed of 40 mM Tris-HCl, pH 8.0, 110 mM NaCl, 2.2 mM KCl, 20% glycerol, and 1% bovine serum albumin. The mixture was centrifuged for 1 minute at 1000 rpm, and the clarified supernatant was used in subsequent assays. As an isotype control, a biotinylated Human IgG1κ antibody (Ancell) was labeled using the same protocol. For the assay, $2\times10^5$ CHO-PD-L1 cells (Promega) were seeded into each well of a 6-well tissue culture plate in 2 ml of F-12 medium supplemented with 10% FBS, 200 µg/ml Hydromycin and 250 µg/ml Geneticin. Cells were allowed to attach for 24 hours, and then 40 nM of the anti-PD-L1-biotin/pHrodo-Avidin, Atezolizumab/pHrodo-Avidin or IgG-biotin/pHrodo-Avidin complex was added to the cells and allowed to incubate at 37° C. for 5 to 16 hours. The cells were washed twice with PBS (Mg, Ca free) and harvested using non-enzymatic lift buffer (10 mM Tris (pH 7.5), 140 mM NaCl, 1 mM EDTA), collected by centrifugation, and re-suspended in 400 µL of PBS. The cells were analyzed by flow cytometry, and internalized antibody-receptor complex was detected using a C6 Accuri Flow Cytometer (excitation with 488 nM laser and emission collected with a 585/40 bandpass filter). There was no difference between IgG control and Atezolizumab, demonstrating that Atezolizumab dos not cause PD-L1 internalization.

Indirect Method for Assessing for PD-L1 Internalization

For the indirect analysis, cell surface PD-L1 was detected with fluorescently labeled anti-PD-L1 (CD274) antibodies. CHO-PD-L1 cells were seeded at $2\times10^5$ cells per well of a 6-well tissue culture plate in 2 ml of F-12 medium supplemented with 10% FBS, 200 µg/ml Hydromycin and 250 µg/ml Geneticin and allowed to attach for 24 hours. After 24 hours, test compounds were added to a final concentration of 1 uM from DMSO stocks, and an equal volume of DMSO was added to control wells. Cells were incubated in the presence of a compound for 16 hours at 37° C. 5% CO2. Prior to analysis, the cells were washed twice with 1 mL of Ca, Mg free PBS and detached with 1 mL of lift buffer (10 mM Tris, 140 mM NaCl, 1 mM EDTA). The collected cells were stained with PE-conjugated mouse anti-human CD274 antibody according to manufacturer instructions: BD Pharmigen #557924 Clone MIH1 (20 µL of Ab per 100 uL of BSA based staining buffer) or eBioscience #12-5983 Clone MIH1 (2 µl per 100 ul of BSA based staining buffer). Cells were incubated at room temperature for 20 minutes, protected from light, washed twice with Ca, Mg free PBS and resuspended in 400 µL of PBS. Antibody binding was detected by flow cytometry using an Accuri C6 instrument. Isotype control antibody-stained cells were used as a negative control. To test that lack of PD-L1 cell surface staining was not due to inhibition of detection antibody binding by the test article, an acid-wash procedure was used. After 16 hours of incubation in the presence of a compound or anti-PD-L1 antibody, the remaining, non-internalized acompound or antibody was stripped from the cell surface using freshly prepared, ice-cold acid stripping buffer (DMEM/ 0.2% BSA, pH 3.5). Cells were washed in this manner three times for 5 minutes each on a shaking platform. The stripped cells were then washed with ice-cold PBS three times for 5 minutes each with gentle shaking, harvested with lift buffer and stained with PE-mouse anti human CD274 antibodies as described.

For the indirect method of assessing PD-L1 internalization using the MDA-MB231 breast cancer cell line, the procedure for the assays was the same as described for the CHO-PD-L1 cells with the following changes. MDA-MB231 were seeded at $2\times10^5$ cells per well of a 6-well tissue culture plate in 2 ml of RPMI1640 medium supplemented with 10% FBS. After compound treatment for 16 hrs, the cells were treated with the stripping buffer (DMEM/ 0.2% BSA, pH 3.5) prior to staining with the anti-CD274 antibodies as described.

Indirect Whole Blood Assay

To determine PD-L1 internalization in human whole blood, normal human blood (Biological Specialty Corp, Colmar. Pa.) was incubated in the presence or absence of a concentration range of test compounds and 1 ng/ml human interferon γ (R&D Systems Inc. Minn. Minn.) in a 96 well round bottom plate (Corning, Corning, N.Y.) for 18 hours at 37° C. Blood was then transferred into 96 well "2 ml Assay Block" (Corning, Corning N.Y.) and stained with PD-L1 (MIH1, eBioscience; or BD Biosciences San Jose, Calif.), CD14 (Life Technologies, Carlsbad, Calif.) for 30 minutes in the dark at room temperature. Whole Blood/red cells were lysed/fixed (lysis buffer BD Biosciences) for 5 minutes at 37° C. in dark and then centrifuged at 1600 RPM for 5 minutes and cells were transferred into 96 well round bottom plates (Corning). Cells were gated on CD14+ (BD Biosciences) and PD-L1 expression determined by mean fluorescence intensity (MFI) (BD LSRFortessa™ X-20). $IC_{50}$ determination was performed by fitting the curve of compound percent inhibition versus the log of the compound concentration using the GraphPad Prism 7.0 software.

Example 4A: Results of Binding, Dimerization, and Internalization Assays

Several compounds were assessed in each of the PD-1-PD-L1 Alphascreen binding assay (Example 1A), the PD-L1 dimerization assay (Example 2A), the indirect CHO/PD-L1 internalization assay (Example 3A), the indirect whole blood PD-L1 internalization assay (Example 3A), and the internalization assays using the MDA-MB231 breast cancer cell line (Example 3A). Compounds described herein were also assessed in PD-1-PD-L1 HTRF binding assay (Example 1B). The cutoffs for ranges of values observed in each of the assays is shown in Table 1. The results obtained for the tested compounds are shown in Table 2, Table 3, and Table 4.

TABLE 1

| Cutoffs | + | ++ | +++ | ++++ |
|---|---|---|---|---|
| PD-1-PD-L1 Binding $IC_{50}$ (nM) (Alphascreen) | <=0.1 nM | >0.1 to <= 1 nM | >1 nM | |
| PD-1-PD-L1 Binding $IC_{50}$ (nM) (HTRF) | <=10 nM | >10 to <= 100 | | |

TABLE 1-continued
| Cutoffs | + | ++ | +++ | ++++ |
|---|---|---|---|---|
| PD-L1 Dimerization ratio | >=1.88 to <= 2.16 | >=1.75 to < 1.88 or > 2.16 to <= 2.29 | <1.75 or > 2.29 | |
| Indirect PD-L1 Internalization Assay using CHO-PD-L1 cells | >90 % internalized | <=90% internalized | | |
| Indirect PD-L1 Internalization Assay using MDA-MB231 cells IC$_{50}$ (nM) | <10 nM | >=10 nM to < 100 nM | >=100 nM to <= 500 nM | >500 nM |
| PD-L1 Whole Blood Internalization IC$_{50}$ (nM) | <100 nM | >=100 nM to < 1000 nM | >=1000 nM to <= 5000 nM | >5000 nM |
TABLE 2
| Cpd | Structure |
|---|---|
| 1 | 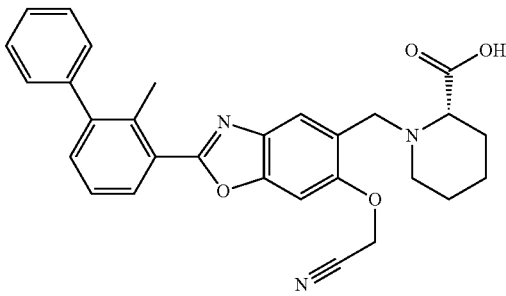 [SMILES: Cc1c(-c2ccccc2)cccc1-c1nc2cc(CN3CCCC[C@H]3C(=O)O)c(OCC#N)cc2o1] |
| 2 | 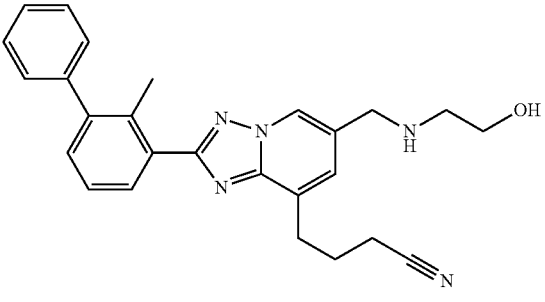 [SMILES: Cc1c(-c2ccccc2)cccc1-c1nc2c(CCCC#N)cc(CNCCO)cn2n1] |
| 3 | 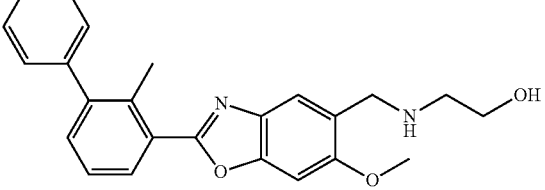 |
| 4 | 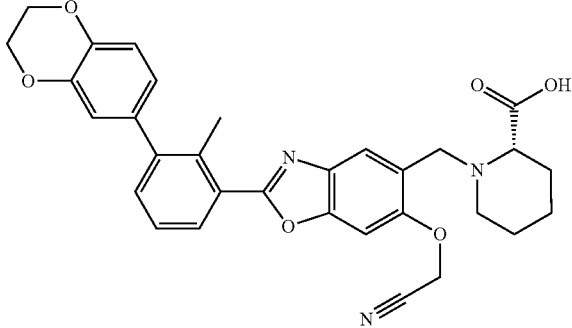 [SMILES: Cc1c(-c2ccc3c(c2)OCCO3)cccc1-c1nc2cc(CN3CCCC[C@H]3C(=O)O)c(OCC#N)cc2o1] |

TABLE 2-continued
5 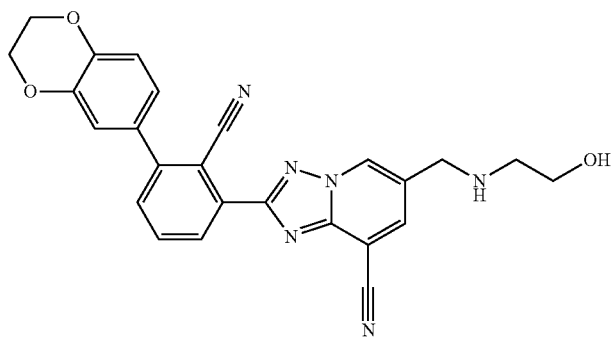 [SMILES: N#Cc1c(-c2ccc3c(c2)OCCO3)cccc1-c1nc2c(C#N)cc(CNCCO)cn2n1]
6 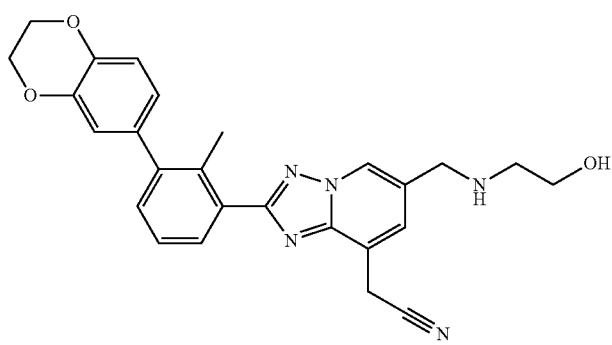 [SMILES: Cc1c(-c2ccc3c(c2)OCCO3)cccc1-c1nc2c(CC#N)cc(CNCCO)cn2n1]
7 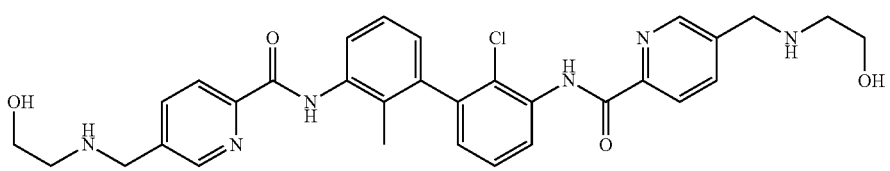 [SMILES: Cc1c(NC(=O)c2ccc(CNCCO)cn2)cccc1-c1cccc(NC(=O)c2ccc(CNCCO)cn2)c1Cl]
8 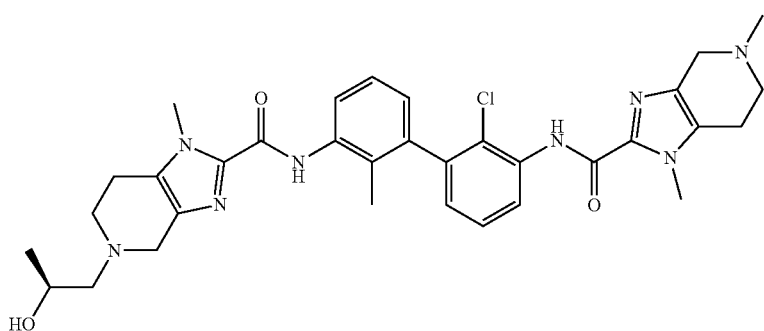 [SMILES: Cc1c(NC(=O)c2nc3c(n2C)CCN(C[C@H](C)O)C3)cccc1-c1cccc(NC(=O)c2nc3c(n2C)CCN(C)C3)c1Cl]
9 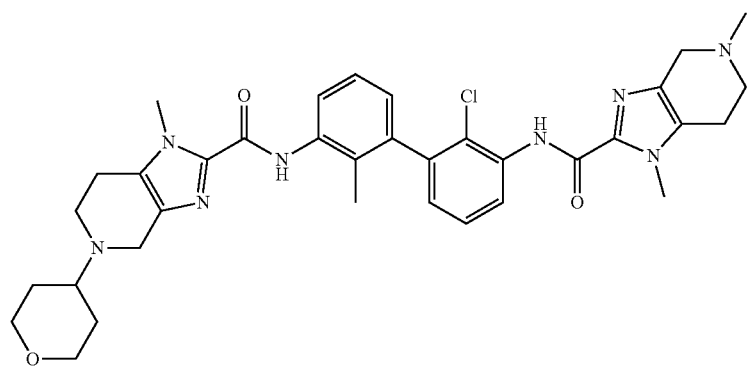 [SMILES: Cc1c(NC(=O)c2nc3c(n2C)CCN(C2CCOCC2)C3)cccc1-c1cccc(NC(=O)c2nc3c(n2C)CCN(C)C3)c1Cl]

TABLE 2-continued
10
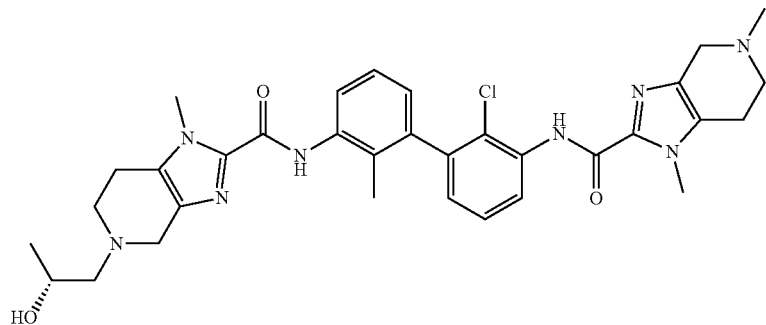 [SMILES: Cc1c(NC(=O)c2nc3c(n2C)CCN(C[C@@H](C)O)C3)cccc1-c1cccc(NC(=O)c2nc3c(n2C)CCN(C)C3)c1Cl]
11
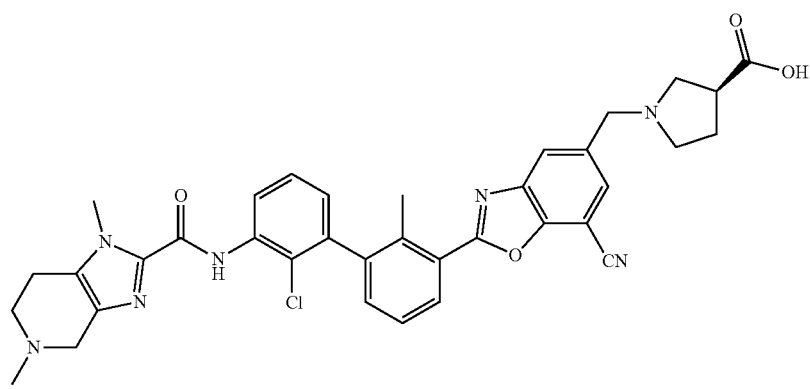 [SMILES: Cc1c(-c2nc3cc(CN4CC[C@H](C(=O)O)C4)cc(C#N)c3o2)cccc1-c1cccc(NC(=O)c2nc3c(n2C)CCN(C)C3)c1Cl]
12
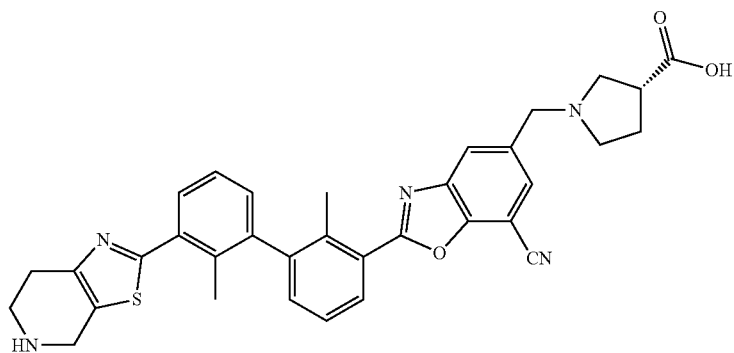 [SMILES: Cc1c(-c2nc3cc(CN4CC[C@@H](C(=O)O)C4)cc(C#N)c3o2)cccc1-c1cccc(-c2nc3c(s2)CNCC3)c1C]
13
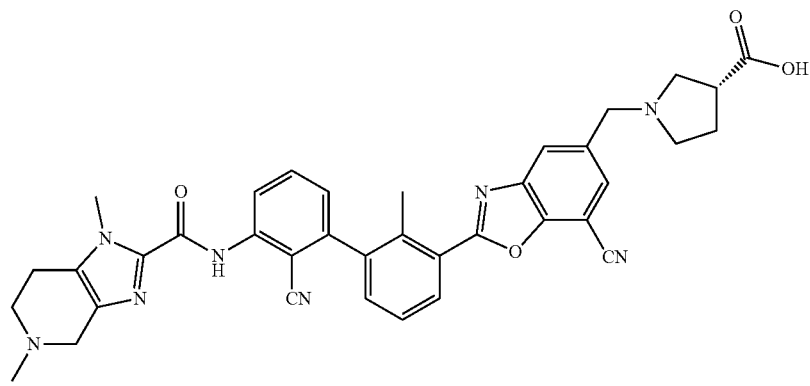 [SMILES: Cc1c(-c2nc3cc(CN4CC[C@@H](C(=O)O)C4)cc(C#N)c3o2)cccc1-c1cccc(NC(=O)c2nc3c(n2C)CCN(C)C3)c1C#N]

TABLE 2-continued
14
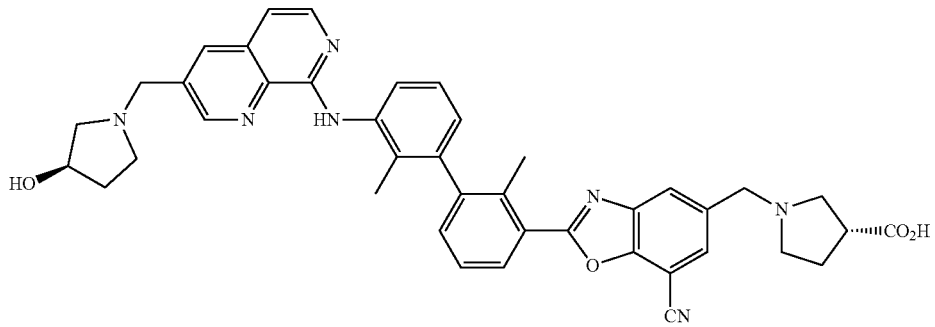 [SMILES: Cc1c(Nc2nccc3cc(CN4CC[C@@H](O)C4)cnc23)cccc1-c1cccc(-c2nc3cc(CN4CC[C@@H](C(=O)O)C4)cc(C#N)c3o2)c1C]
15
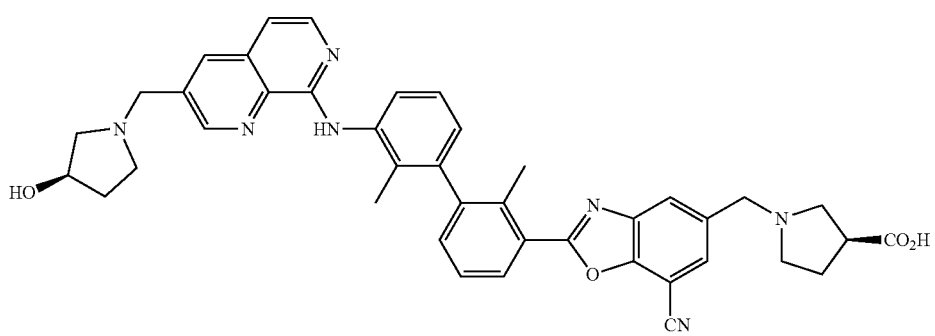 [SMILES: Cc1c(Nc2nccc3cc(CN4CC[C@@H](O)C4)cnc23)cccc1-c1cccc(-c2nc3cc(CN4CC[C@H](C(=O)O)C4)cc(C#N)c3o2)c1C]
16
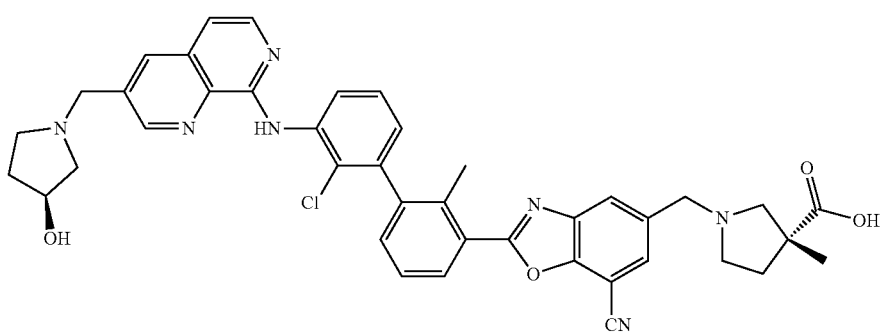 [SMILES: Cc1c(-c2nc3cc(CN4CC[C@@](C)(C(=O)O)C4)cc(C#N)c3o2)cccc1-c1cccc(Nc2nccc3cc(CN4CC[C@H](O)C4)cnc23)c1Cl]
17
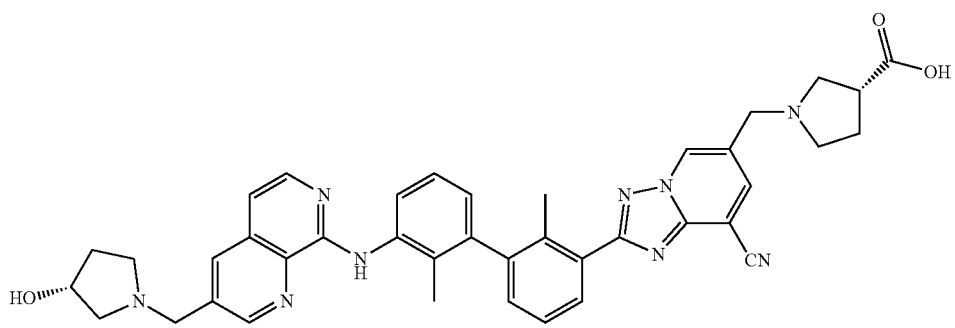 [SMILES: Cc1c(Nc2nccc3cc(CN4CC[C@@H](O)C4)cnc23)cccc1-c1cccc(-c2nc3c(C#N)cc(CN4CC[C@@H](C(=O)O)C4)cn3n2)c1C]
18
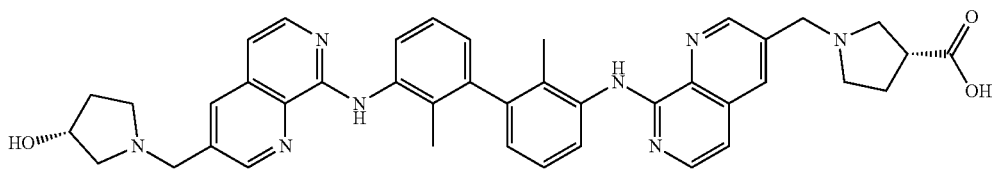 [SMILES: Cc1c(Nc2nccc3cc(CN4CC[C@@H](O)C4)cnc23)cccc1-c1cccc(Nc2nccc3cc(CN4CC[C@@H](C(=O)O)C4)cnc23)c1C]

TABLE 2-continued
19
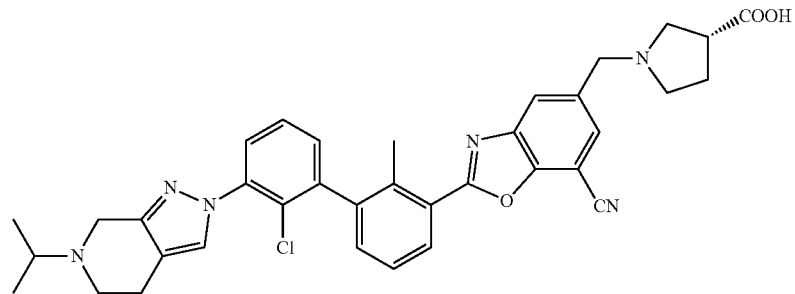 [SMILES: Cc1c(-c2nc3cc(CN4CC[C@@H](C(=O)O)C4)cc(C#N)c3o2)cccc1-c1cccc(-n2cc3c(n2)CN(C(C)C)CC3)c1Cl]
20
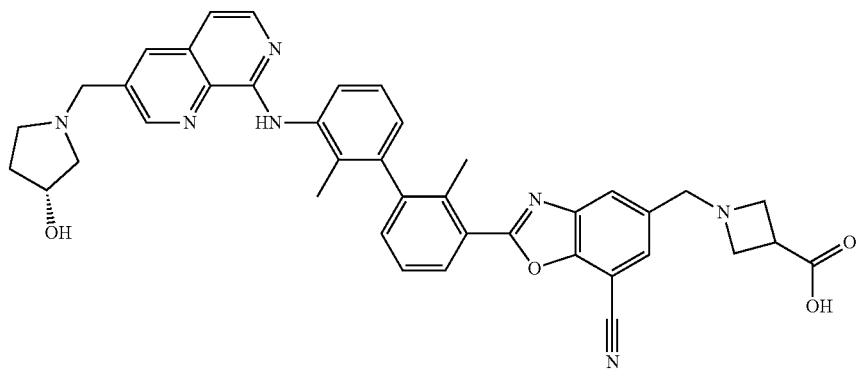 [SMILES: Cc1c(Nc2nccc3cc(CN4CC[C@@H](O)C4)cnc23)cccc1-c1cccc(-c2nc3cc(CN4CC(C(=O)O)C4)cc(C#N)c3o2)c1C]
21
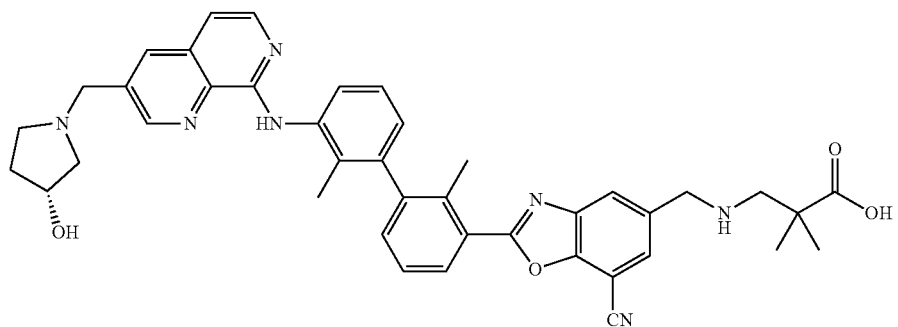 [SMILES: Cc1c(Nc2nccc3cc(CN4CC[C@@H](O)C4)cnc23)cccc1-c1cccc(-c2nc3cc(CNCC(C)(C)C(=O)O)cc(C#N)c3o2)c1C]
22
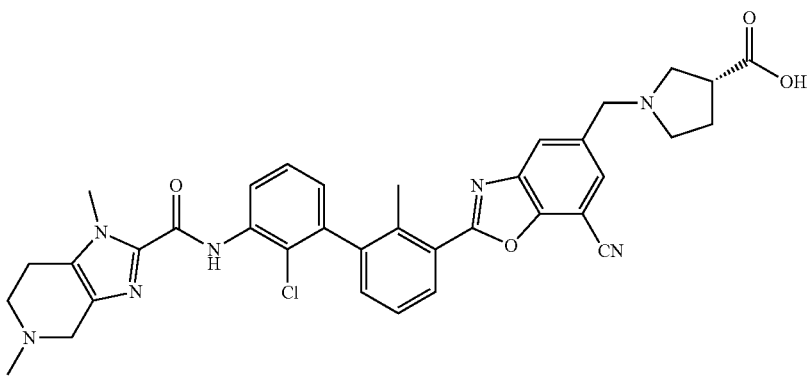 [SMILES: Cc1c(-c2nc3cc(CN4CC[C@@H](C(=O)O)C4)cc(C#N)c3o2)cccc1-c1cccc(NC(=O)c2nc3c(n2C)CCN(C)C3)c1Cl]
23
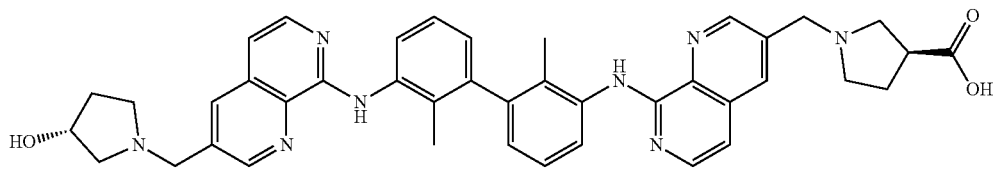 [SMILES: Cc1c(Nc2nccc3cc(CN4CC[C@@H](O)C4)cnc23)cccc1-c1cccc(Nc2nccc3cc(CN4CC[C@H](C(=O)O)C4)cnc23)c1C]

TABLE 2-continued

24 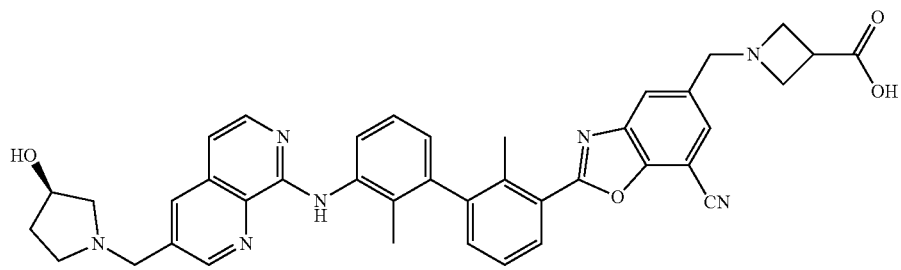 [SMILES: Cc1c(Nc2nccc3cc(CN4CC[C@@H](O)C4)cnc23)cccc1-c1cccc(-c2nc3cc(CN4CC(C(=O)O)C4)cc(C#N)c3o2)c1C]

25 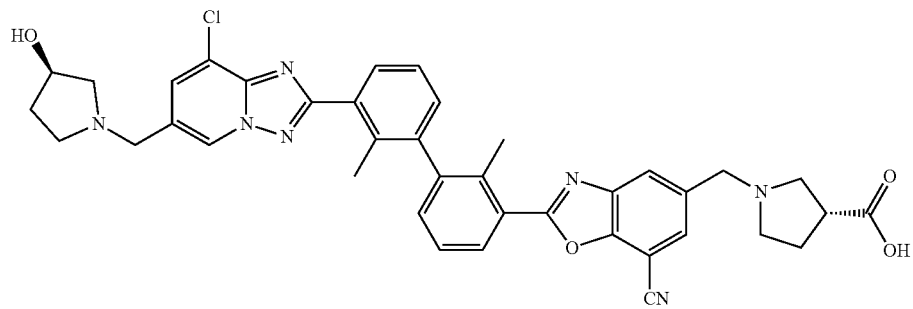 [SMILES: Cc1c(-c2nc3c(Cl)cc(CN4CC[C@@H](O)C4)cn3n2)cccc1-c1cccc(-c2nc3cc(CN4CC[C@@H](C(=O)O)C4)cc(C#N)c3o2)c1C]

26 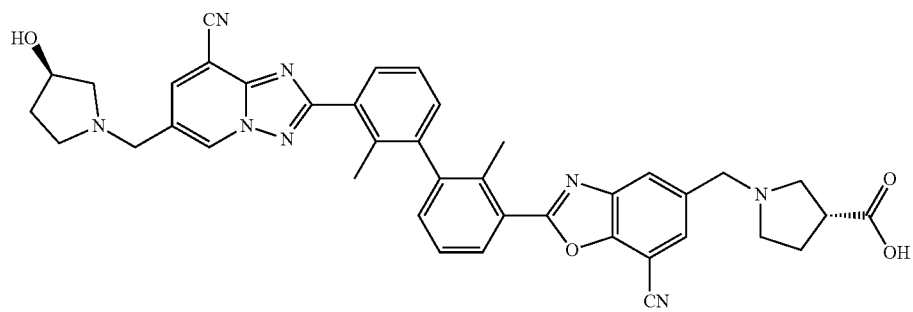 [SMILES: Cc1c(-c2nc3c(C#N)cc(CN4CC[C@@H](O)C4)cn3n2)cccc1-c1cccc(-c2nc3cc(CN4CC[C@@H](C(=O)O)C4)cc(C#N)c3o2)c1C]

27 ***

| Cpd | PD-1-PD-L1 Binding IC$_{50}$ (nM) (Alphascreen) | PD-L1 Dimerization Cpd/DMSO ratio | PD-L1 Indirect Internalization Assay using CHO-PD-L1 cells | PD-L1 Whole Blood Internalization IC$_{50}$ (nM) |
|---|---|---|---|---|
| 1 | ++ | +++ | ++ | ++++ |
| 2 | +++ | +++ | ++ | ++++ |
| 3 | +++ | +++ | ++ | ++++ |
| 4 | ++ | +++ | ++ | ++++ |
| 5 | +++ | +++ | ++ | ++++ |
| 6 | +++ | +++ | ++ | ++++ |
| 7 | + | + | + | + |
| 8 | ++ | + | + | + |
| 9 | ++ | + | + | + |
| 10 | ++ | + | + | + |
| 11 | + | ++ | + | + |
| 12 | ++ | ++ | + | ++ |
| 13 | ++ | ++ | + | ++ |
| 14 | ++ | ++ | + | + |
| 15 | ++ | + | + | ++ |
| 16 | ++ | + | + | ++ |
| 17 | ++ | ++ | + | ++ |
| 18 | ++ | + | + | ++ |
| 19 | ++ | + | + | ++ |
| 20 | ++ | + | + | ++ |
| 21 | ++ | + | + | ++ |
| 22 | ++ | ++ | + | + |
| 23 | ++ | + | + | ++ |
| 24 | ++ | + | + | ++ |
| 25 | ++ | + | + | +++ |

TABLE 2-continued

| | | | | |
|---|---|---|---|---|
| 26 | ++ | + | + | ++ |
| 27 | +++ | +++ | ++ | NA |

***The structure of compound 27 is:

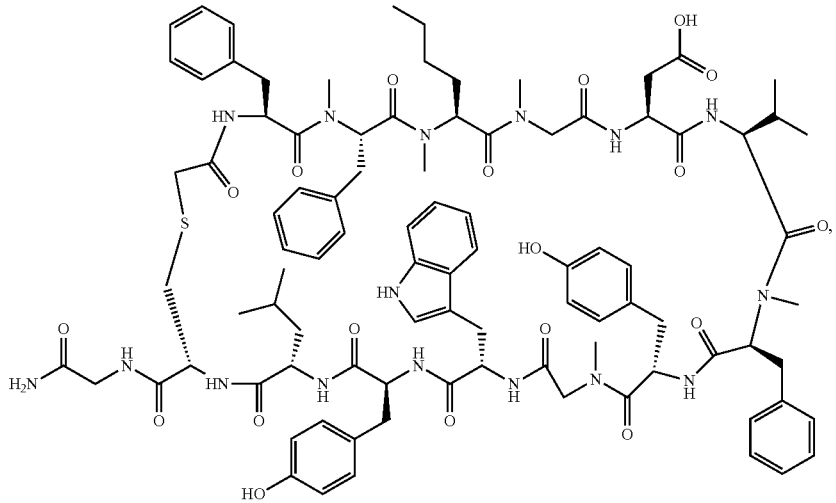 [SMILES: CCCC[C@H]1C(=O)N(C)CC(=O)N[C@@H](CC(=O)O)C(=O)N[C@@H](C(C)C)C(=O)N(C)[C@@H](Cc2ccccc2)C(=O)N[C@@H](Cc2ccc(O)cc2)C(=O)N(C)CC(=O)N[C@@H](Cc2c[nH]c3ccccc23)C(=O)N[C@@H](Cc2ccc(O)cc2)C(=O)N[C@@H](CC(C)C)C(=O)N[C@H](C(=O)NCC(N)=O)CSCC(=O)N[C@@H](Cc2ccccc2)C(=O)N(C)[C@@H](Cc2ccccc2)C(=O)N1C]

see WO 2014/151634, the content of which is incorporated herein by reference.

TABLE 3

| Compound from Example Number | PD-1-PD-L1 Binding IC$_{50}$ (nM) (HTRF) |
|---|---|
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | + |
| 51 | + |
| 52 | + |

TABLE 3-continued

| Compound from Example Number | PD-1-PD-L1 Binding IC$_{50}$ (nM) (HTRF) |
|---|---|
| 53 | + |
| 54 | + |

TABLE 4

| Compound from Table 2 | Indirect PD-L1 Internalization Assay using MDA-MB231 cells IC$_{50}$ (nM) |
|---|---|
| 7 | + |
| 8 | + |
| 9 | + |
| 10 | + |
| 11 | + |
| 12 | ++ |
| 13 | ++ |
| 14 | + |
| 15 | + |
| 16 | ++ |
| 17 | +++ |
| 18 | + |
| 19 | ++++ |
| 20 | + |
| 21 | ++ |
| 22 | + |
| 23 | ++ |
| 24 | ++ |
| 25 | ++ |
| 26 | ++ |

Example 5A: Effects of Antibodies on PD-L1 Internalization

In addition to small molecules disclosed as PD-1-PD-L1 inhibitors, a monoclonal antibody disclosed as a PD-1-PD-L1 inhibitor was also tested. Atezolizumab is a folly humanized, engineered monoclonal antibody of IgG1 iso type against the PD-L1. Atezolizumab was tested in the direct method for assessing PD-L1 internalization described in Example 3A. The commercially available tool anti PD-L1 antibody (BPS Biosciences) was used as a control. The tool anti-PD-L1 antibody is known to cause internalization. Atezolizumab was tested against tool anti-PD-L1 antibody to determine if it would also cause PD-L1 internalization. FIG. 1 show the internalization results. The tool anti-PD-L1 antibody resulted in an increase in mean fluorescence relative to the control IgG, indicative of internalization. Atezolizumab produced no intensity shift relative to the control IgG antibody. These results demonstrate that the tool anti-PD-L1 antibody results in PD-L1 internalization and Atezolizumab does not result in PD-L1 internalization.

The test involved a 40 nM Atezolizumab/pHrodo-Avidin complex incubated with CHO/PD-L1 cells for 5 or 16 hr. FACS analysis was performed as described in the direct method with internalization being measured by increased fluorescence as assessed by a rightward shift in the curve relative to IgG control (3). FIG. 1 shows the PD-L1 fluorescence—shown on X-axis in LOG 10 scale. No difference was observed between IgG control (Curve 3) and Atezolizumab (Curve 2) demonstrating that Atezolizumab does not cause PD-L1 internalization.

Example 6A: Whole Blood Interferon γ Assay

To determine the increase of Interferon γ in whole blood, normal human blood (Biological Specialty Corp, Colmar. Pa.) diluted 1/10 in AIM-V media (Life Technologies) is incubated in the presence or absence of a concentration range of test compounds and 5 ng/ml *Staphylococcal enterotoxin* B (Toxin Technologies Sarasota, Fla.) in a 96 well U bottom Tissue Culture Plate (Corning) for 3 days at 37° C. Plates are centrifuged at 1400 RPM for 5 minutes, and supernatants collected and tested for presence of Interferon γ in a commercial Interferon γ ELISA kit (R&D Human IFN-γ Quantikine ELISA (R&D Systems, Minneapolis, Minn.).

Example 7A: Animal Models

Studies to assess pharmacokinetics, pharmacodynamics, and efficacy are conducted in mice engrafted with human CD34+ cells and mice engineered to express human checkpoint molecules. Both preclinical models have been validated with approved therapeutics targeting the PD-1:PD-L1-axis Humanized CD34+ Mice Humanized CD34+ mice have been used commonly to study immune-oncology, infectious diseases and graft rejection research. In brief, immune-compromised NSG mice (NOD sc id IL2Rg$^{null}$; Jackson Laboratory) receive total body irradiation to deplete existing bone marrow cells. CD34+ human stem cells derived from umbilical cord blood are then engrafted to establish a fully human immune system over a 12-14 week period. Alternative mouse strains may also be used to improve the engraftment of stem cells and enhance the development of myeloid lineage cells, which are the main PD-L1-expressing host immune cells. For example, the NSG-SGM3 mice were engineered to produce human cytokines (SCF, IL-3 and GM-CSF) that allow full differentiation of the myeloid lineage [Jackson Laboratory], Cell-derived xenograft models are selected based on tumor and host PD-L1 expression, as well as their response to anti-PD-L1 antibody treatment. PD-L1 internalization induced by small molecules targeting PD-L1 are the main pharmacodynamic bio marker and are determined by measuring the remaining PD-L1 expression on both tumor and host immune cells Human Checkpoint Molecule Knock-in Mice Human-mouse chimeric models have been developed to allow binding of human-specific antibodies to the human protein while using fully intact mouse immune biology. This approach is utilized to evaluate small molecules targeting PD-L1. To this end, the relevant extracellular domain of the human gene is integrated into the locus of the mouse gene by homologous recombination ('knock-in'). For example, the HuGEMM model for PD-1 and PD-L1 uses a human PD-1 knock-in strain that is engrafted with the mouse colon carcinoma cell line MC38 recombinantly expressing human PD-L1 [HuCELL; Crown Bioscience]. Human PD-L1 and PD-1 double knock-in animals with engraftment of MC38-huPD-L1 are developed and used to evaluate PD-L1 internalization induced by small molecules targeting PD-L1 in both tumor and host immune cells.

Example 8A: Synthesis of Exemplary Compounds

Compounds of the invention, including salts thereof, can be prepared using known organic synthesis techniques and can be synthesized according to any of numerous possible synthetic routes. Synthesis of exemplary compounds are provided herein.

Example 1

(S)-1-((2-(2'-chloro-3'-(1,5-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)pyrrolidine-3-carboxylic Acid

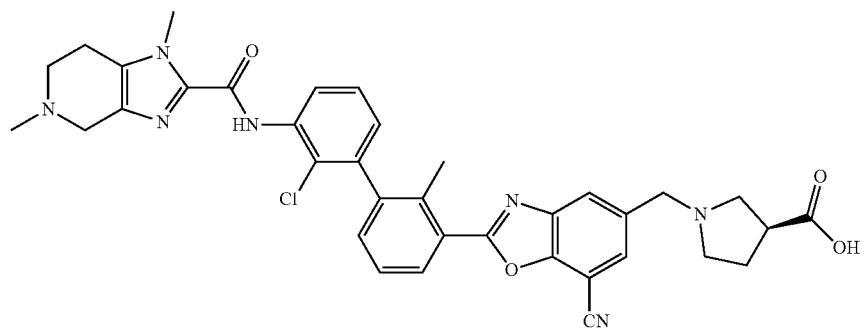 [SMILES: Cc1c(-c2nc3cc(CN4CC[C@H](C(=O)O)C4)cc(C#N)c3o2)cccc1-c1cccc(NC(=O)c2nc3c(n2C)CCN(C)C3)c1Cl]

Step 1: methyl 3-chloro-4-hydroxy-5-nitrobenzoate

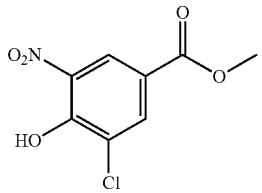

To a solution of methyl 3-chloro-4-hydroxybenzoate (Alfa Aesar, # A512389: 10.0 g, 53.6 mmol) in acetic acid (20.0 mL, 352 mmol) was added a mixture of acetic acid (20.0 mL, 352 mmol) and nitric acid (4.72 mL, 112 mmol) dropwise at 0° C. Then the ice bath was removed and the thick mixture was stirred at room temperature for 2 hrs. Then an equal volume of water was added to the reaction suspension at 0° C. The mixture was filtered and washed with cold water. The resulting yellow solid was used directly in the next step without further purification. LC-MS calculated for $C_8H_7ClNO_5$ $(M+H)^+$: m/z=232.0; found 232.0.

Step 2: methyl 3-amino-5-chloro-4-hydroxybenzoate

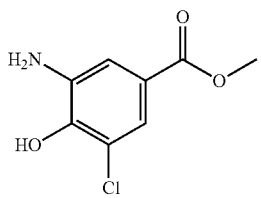

Methyl 3-chloro-4-hydroxy-5-nitrobenzoate (2.08 g, 8.98 mmol) was hydrogenated under ambient pressure of hydrogen using palladium on carbon (10 wt %, 0.57 g, 0.539 mmol) in ethyl acetate (15 mL) for 1 h. The resulting suspension was filtered through a pad of Celite®, washed with EtOAc, and the solvent was removed under reduced pressure. The crude product was purified by column chromatography (eluting with MeOH/DCM 0%-10%). LC-MS calculated for $C_8H_9ClNO_3$ $(M+H)^+$: m/z=202.0; found 202.0.

Step 3: methyl 2-(3-bromo-2-methylphenyl)-7-chlorobenzo[d]oxazole-5-carboxylate

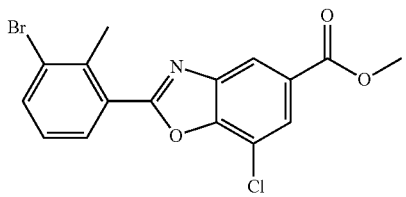 [SMILES: COC(=O)c1cc(Cl)c2oc(-c3cccc(Br)c3C)nc2c1]

A mixture of methyl 3-amino-5-chloro-4-hydroxybenzoate (1.04 g, 5.16 mmol), 3-bromo-2-methylbenzaldehyde (AstaTech, #52940: 0.98 g, 4.92 mmol) in EtOH (25 ml) was placed in a vial and stirred at room temperature for 1 h. The mixture was then concentrated. The residue was redissovled in methylene chloride (25 mL) and dichlorodicyanoquinone (1.12 g, 4.92 mmol) was added. The mixture was stirred at room temperature for 30 min. The reaction was diluted with methylene chloride and washed with an aqueous $Na_2S_2O_3$ solution and $NaHCO_3$ solution. The organic phase was dried over $MgSO_4$, filtered and the filtrate was concentrated. The crude residue was used directly in the next step without further purification. LC-MS calculated for $C_{16}H_{12}BrClNO_3$ $(M+H)^+$: m/z=380.0, 382.0; found 379.9, 381.9.

Step 4: (2-(3-bromo-2-methylphenyl)-7-chlorobenzo[d]oxazol-5-yl)methanol

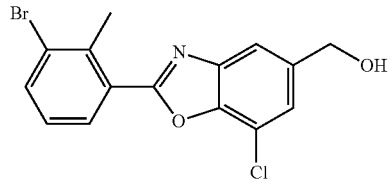 [SMILES: Cc1c(Br)cccc1-c1nc2cc(CO)cc(Cl)c2o1]

To a solution of methyl 2-(3-bromo-2-methylphenyl)-7-chlorobenzo[d]oxazole-5-carboxylate (395.0 mg, 1.04 mmol) in DCM (10.0 ml) was added diisobutylaluminum hydride in DCM (1.0 M, 2.08 ml, 2.08 mmol) dropwise at −78° C. The mixture was slowly warmed up to 0° C. Then the mixture was quenched with EtOAc and DCM, followed by addition of an aqueous Rochelle salt solution. The mixture was stirred vigorously at room temperature for 1 h. The organic phase was dried over $MgSO_4$ before filtering through a short pad of Celite® to remove solids. The filtrate was concentrated and purified by column chromatography (eluting with 0-5% MeOH/DCM) to give the desired product. LC-MS calculated for $C_{15}H_{12}BrClNO_2$ $(M+H)^+$: m/z=352.0, 354.0; found 352.0, 354.0.

Step 5: (7-chloro-2-(2-methyl-3-(4,4,5,5-tetramethyl-1,3,2-dioxaborolan-2-yl)phenyl)benzo[d]oxazol-5-yl) methanol

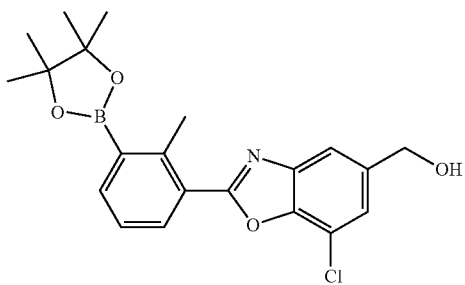 [SMILES: Cc1c(B2OC(C)(C)C(C)(C)O2)cccc1-c1nc2cc(CO)cc(Cl)c2o1]

A mixture of (2-(3-bromo-2-methylphenyl)-7-chlorobenzo[d]oxazol-5-yl)methanol (113 mg, 0.322 mmol), bis(pinacolato)diboron (98 mg, 0.386 mmol), dichloro[1,1'-bis(diphenylphosphino)ferrocene]palladium (II) dichloromethane adduct (26.3 mg, 0.032 mmol) and anhydrous potassium acetate (79 mg, 0.804 mmol) in 1,4-dioxane (3 mL) was purged with nitrogen then stirred at 110° C. for 2 h. The crude was diluted with DCM, and then filtered through Celite®. The filtrate was concentrated, and the resulting residue was purified by flash chromatography (eluting with EtOAc/Hexanes, 0-40%). LC-MS calculated for $C_{21}H_{24}BClNO_4$ $(M+H)^+$: m/z=400.1; found 400.2.

Step 6: tert-butyl 1-methyl-1,4,6,7-tetrahydro-5H-imidazo[4,5-c]pyridine-5-carboxylate

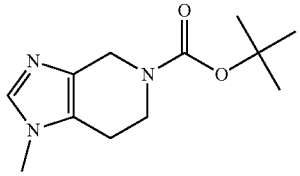 [SMILES: Cn1cnc2c1CCN(C(=O)OC(C)(C)C)C2]

A solution of 1-methyl-4,5,6,7-tetrahydro-1H-imidazo[4,5-c]pyridine (Accela, cat # SY032476: 2.0 g, 14.58 mmol) and (Boc)$_2$O (3.38 mL, 14.58 mmol) in dichloromethane (60 mL) was stirred at room temperature for 1 h. The reaction was quenched with saturated aqueous NaHCO$_3$ solution, and extracted with ethyl acetate. The combined organic layers were washed with brine, dried over Na$_2$SO$_4$, filtered, and concentrated under reduced pressure. The crude product was used directly in the next step without further purification. LC-MS calculated for C$_{12}$H$_{20}$N$_3$O$_2$ (M+H)$^+$: m/z=238.2; found 238.2.

Step 7: 5-tert-butyl 2-methyl 1-methyl-6,7-dihydro-1H-imidazo[4,5-c]pyridine-2,5(4H)-dicarboxylate

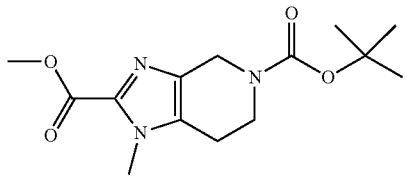

n-Butyllithium in hexanes (2.5 M, 7.00 mL, 17.49 mmol) was added to a cold (−78° C.) solution of tert-butyl 1-methyl-1,4,6,7-tetrahydro-5H-imidazo[4,5-c]pyridine-5-carboxylate (crude product from Step 6) in tetrahydrofuran (60.0 mL). The reaction mixture was stirred at −78° C. for 10 min prior to the addition of methyl chloroformate (1.7 mL, 21.9 mmol). After being stirred at −78° C. for 30 min, the reaction was then quenched with saturated aqueous NaHCO$_3$ solution, and extracted with ethyl acetate, dried over Na$_2$SO$_4$, filtered, and concentrated under reduced pressure. The residue was purified by flash chromatography on a silica gel column eluting with 0 to 100% ethyl acetate in hexanes to afford the desired product. LC-MS calculated for C$_{14}$H$_{22}$N$_3$O$_4$ (M+H)$^+$: m/z=296.2; found 296.3.

Step 8: tert-butyl 2-((3-bromo-2-chlorophenyl)carbamoyl)-1-methyl-1,4,6,7-tetrahydro-5H imidazo[4,5-c]pyridine-5-carboxylate

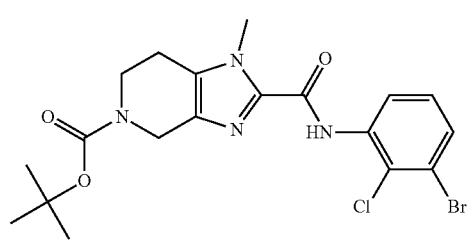 [SMILES: Cn1c(C(=O)Nc2cccc(Br)c2Cl)nc2c1CCN(C(=O)OC(C)(C)C)C2]

Potassium tert-butoxide in THF (1.0 M, 3.39 mL, 3.39 mmol) was added to a solution of 5-tert-butyl 2-methyl 1-methyl-6,7-dihydro-1H-imidazo[4,5-c]pyridine-2,5(4H)-dicarboxylate (500 mg, 1.69 mmol) and 3-bromo-2-chloroaniline (Astatech, cat # CL9068; 348 mg, 1.69 mmol) in tetrahydrofuran (12.0 mL). After being stirred at room temperature for 1 h, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 50% ethyl acetate in hexanes to afford the desired product. LC-MS calculated for C$_{19}$H$_{23}$BrClN$_4$O$_3$ (M+H)$^+$: m/z=469.1; found 469.1.

Step 9: N-(3-bromo-2-chlorophenyl)-1,5-dimethyl-4,5,6,7-tetrahydro-1H-imidazo[4,5-c]pyridine-2-carboxamide

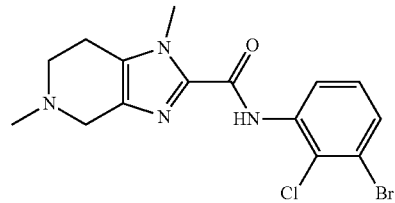 [SMILES: CN1CCc2c(nc(C(=O)Nc3cccc(Br)c3Cl)n2C)C1]

A solution of tert-butyl 2-((3-bromo-2-chlorophenyl)carbamoyl)-1-methyl-1,4,6,7-tetrahydro-5H-imidazo[4,5-c]pyridine-5-carboxylate (300 mg, 0.64 mmol) in trifluoroacetic acid (0.2 mL) and dichloromethane (0.4 mL) was stirred at room temperature for 1 h. The solvent was evaporated, and the residue was dissolved in THF (1.0 mL). 37 wt % Formaldehyde in water (0.48 mL, 6.39 mmol) and sodium triacetoxyborohydride (406 mg, 1.92 mmol) were successively added. After being stirred at room temperature for 1 h, the mixture was quenched with sat. NaHCO$_3$ solution and extracted with ethyl acetate. The combined organic layers were washed with brine, dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{15}$H$_{17}$BrClN$_4$O (M+H)$^+$: m/z=383.0; found 383.0.

Step 10: N-(2-chloro-3'-(7-chloro-5-(hydroxymethyl)benzo[d]oxazol-2-yl)-2'-methylbiphenyl-3-yl)-1,5-dimethyl-4,5,6,7-tetrahydro-1H-imidazo[4,5-c]pyridine-2-carboxamide

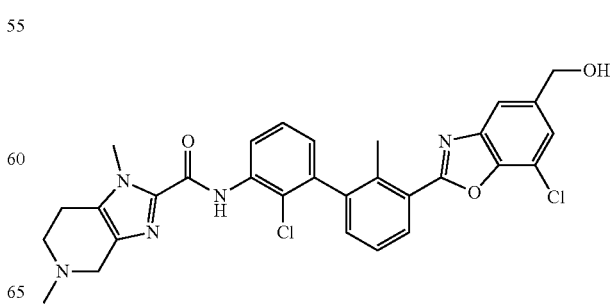

A mixture of N-(3-bromo-2-chlorophenyl)-1,5-dimethyl-4,5,6,7-tetrahydro-1H-imidazo[4,5-c]pyridine-2-carboxamide (150 mg, 0.391 mmol), (7-chloro-2-(2-methyl-3-(4,4,5,5-tetramethyl-1,3,2-dioxaborolan-2-yl)phenyl)benzo[d]oxazol-5-yl)methanol (Step 5: 188 mg, 0.469 mmol), and Dichloro[1,1'-bis(dicyclohexylphosphino)ferrocene]palladium(II) (17.7 mg, 0.023 mmol) in t-BuOH (5 ml) was added cesium carbonate (255 mg, 0.782 mmol) and a few drops of water. The reaction mixture was purged with nitrogen and then stirred at 100° C. for 5 hrs. After being cooled to room temperature, the reaction mixture was extracted with ethyl acetate. The combined organic layers were washed with brine, dried over $Na_2SO_4$, filtered and concentrated under reduced pressure. The residue was purified by flash chromatography on a silica gel column eluting with 0 to 10% methanol in DCM to afford the desired product. LC-MS calculated for $C_{30}H_{28}Cl_2N_5O_3$ $(M+H)^+$: m/z=576.2; found 576.1.

Step 11: N-(2-chloro-3'-(7-cyano-5-(hydroxymethyl)benzo[d]oxazol-2-yl)-2'-methylbiphenyl-3-yl)-1,5-dimethyl-4,5,6,7-tetrahydro-1H-imidazo[4,5-c]pyridine-2-carboxamide

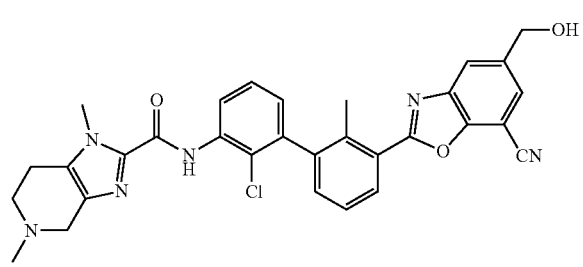 [SMILES: Cc1c(-c2nc3cc(CO)cc(C#N)c3o2)cccc1-c1cccc(NC(=O)c2nc3c(n2C)CCN(C)C3)c1Cl]

A mixture of N-(2-chloro-3'-(7-chloro-5-(hydroxymethyl)benzo[d]oxazol-2-yl)-2'-methyl-[1,1'-biphenyl]-3-yl)-1,5-dimethyl-4,5,6,7-tetrahydro-1H-imidazo[4,5-c]pyridine-2-carboxamide (140 mg, 0.24 mmol), tBuXPhos Pd G3 (19.3 mg, 0.024 mmol), potassium hexacyanoferrate(II) trihydrate (103 mg, 0.24 mmol) and potassium acetate (4.8 mg, 0.049 mmol) in 1,4-dioxane (3.0 mL)/Water (3.0 mL) was purged with nitrogen and then stirred at 100° C. for 1 h. After being cooled to room temperature, the reaction was extracted with ethyl acetate. The combined organic phases was dried over $Na_2SO_4$ and concentrated under reduced pressure. The crude was used directly in the next step without further purification. LC-MS calculated for $C_{31}H_{28}ClN_6O_3$ $(M+H)^+$: m/z=567.2; found 567.2.

Step 12: N-(2-chloro-3'-(7-cyano-5-formylbenzo[d]oxazol-2-yl)-2'-methylbiphenyl-3-yl)-1,5-dimethyl-4,5,6,7-tetrahydro-1H-imidazo[4,5-c]pyridine-2-carboxamide

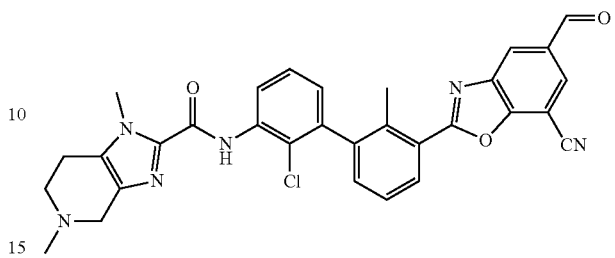

To a stirred solution of N-(2-chloro-3'-(7-cyano-5-(hydroxymethyl)benzo[d]oxazol-2-yl)-2'-methyl-[1,1'-biphenyl]-3-yl)-1,5-dimethyl-4,5,6,7-tetrahydro-1H-imidazo[4,5-c]pyridine-2-carboxamide (140.0 mg, 0.247 mmol) in DCM (3.0 ml) was added sodium bicarbonate (207 mg, 2.47 mmol) and dess-martin periodinane (157 mg, 0.370 mmol). The resulted mixture was stirred at rt for 2 hrs, then filtered. The filtrate was concentrated under reduced pressure. The residue was used in the next step directly without further purification. LC-MS calculated for $C_{31}H_{26}ClN_6O_3$ $(M+H)^+$: m/z=565.2; found 565.1.

Step 13: (S)-1-((2-(2'-chloro-3'-(1,5-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)pyrrolidine-3-carboxylic Acid To a solution of N-(2-chloro-3'-(7-cyano-5-formylbenzo[d]oxazol-2-yl)-2'-methyl-[1,1'-biphenyl]-3-yl)-1,5-dimethyl-4,5,6,7-tetrahydro-1H-imidazo[4,5-c]pyridine-2-carboxamide (65 mg, 0.115 mmol) in DCM (1 ml) was added (S)-pyrrolidine-3-carboxylic acid (66.2 mg, 0.575 mmol) and DIEA (0.161 ml, 0.920 mmol). The mixture was stirred at r.t. for 60 min, then sodium triacetoxyborohydride (73.1 mg, 0.345 mmol) was added. The resulting mixture was stirred at r.t. overnight then concentrated. The residue was purified via prep-HPLC (pH=2, MeCN/water with TFA) to give the desired product as the TFA salt. LC-MS calculated for $C_{36}H_{35}ClN_7O_4$ $(M+H)^+$: m/z=664.2; found 664.2.

Example 2

(R)-1-((2-(2'-chloro-3'-(1,5-dimethyl-4,5,6,7-tetrahydro-1H-imidazo[4,5-c]pyridine-2-carboxamido)-2-methylbiphenyl-3-yl)-7-cyanobenzo[d]oxazol-5-yl)methyl)pyrrolidine-3-carboxylic Acid

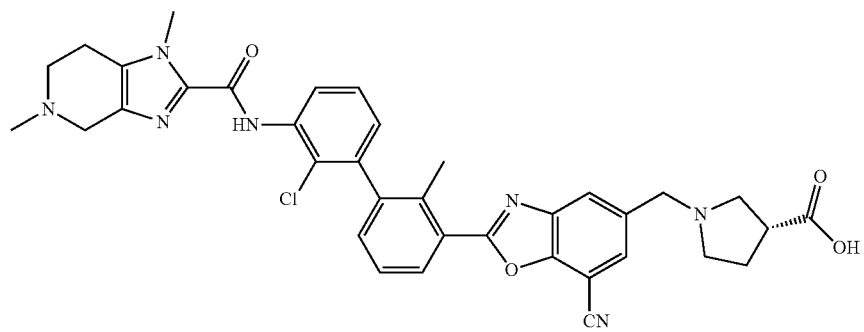 [SMILES: Cc1c(-c2nc3cc(CN4CC[C@@H](C(=O)O)C4)cc(C#N)c3o2)cccc1-c1cccc(NC(=O)c2nc3c(n2C)CCN(C)C3)c1Cl]

This compound was prepared using similar procedure as described for Example 1 with (R)-pyrrolidine-3-carboxylic acid replacing (S)-pyrrolidine-3-carboxylic acid in Step 13. It was purified via pH 2 preparative HPLC (MeCN/water with TFA) to give the desired product as its TFA salt. LC-MS calculated for $C_{36}H_{35}ClN_7O_4$ (M+H)$^+$: m/z=664.2; found 664.3.

Example 3

(R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic Acid

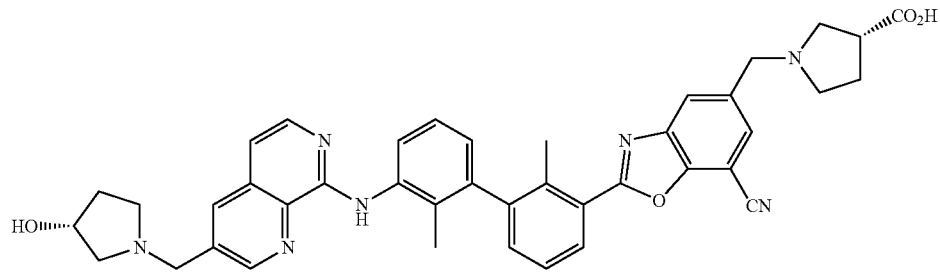 [SMILES: Cc1c(Nc2nccc3cc(CN4CC[C@@H](O)C4)cnc23)cccc1-c1cccc(-c2nc3cc(CN4CC[C@@H](C(=O)O)C4)cc(C#N)c3o2)c1C]

Step 1: 8-chloro-3-vinyl-1,7-naphthyridine

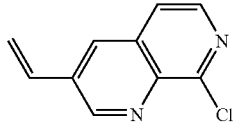

A mixture of 3-bromo-8-chloro-1,7-naphthyridine (PharmaBlock, cat # PBLJ2743: 1221 mg, 5.01 mmol), 4,4,5,5-tetramethyl-2-vinyl-1,3,2-dioxaborolane (927 mg, 6.02 mmol), sodium carbonate (1329 mg, 12.54 mmol) and tetrakis(triphenylphosphine)palladium(0) (290 mg, 0.25 mmol) in f-butanol (12 ml) and water (12 ml) was purged with nitrogen and sealed. It was stirred at 90° C. for 2 h. The reaction mixture was cooled to room temperature then extracted with ethyl acetate. The combined organic layers were washed with brine, dried over MgSO$_4$, filtered and concentrated under reduced pressure. The crude residue was used directly in the next step without further purification. LC-MS calculated for $C_{10}H_8ClN_2$ (M+H)$^+$: m/z=191.0; found 191.0.

Step 2: N-(3-bromo-2-methylphenyl)-3-vinyl-1,7-naphthyridin-8-amine

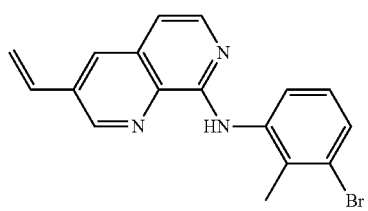 [SMILES: C=Cc1cnc2c(Nc3cccc(Br)c3C)nccc2c1]

A mixture of 3-bromo-2-methylaniline (139 mg, 0.74 mmol), 8-chloro-3-vinyl-1,7-naphthyridine (142 mg, 0.74 mmol) and HCl in dioxane (4.0 M, 186 µL, 0.74 mmol) in t-butanol (3.7 mL) was heated at 130° C. for 2 h. The reaction mixture was then cooled to room temperature and diluted with DCM. The reaction was quenched by aqueous NaHCO$_3$ solution, extracted with DCM. The organic phase was dried over MgSO$_4$, filtered and the filtrate was concentrated. The residue was used directly for next step. LC-MS calculated for $C_{17}H_{15}BrN_3$ (M+H)$^+$: m/z=340.0; found 340.1.

Step 3; 8-(3-bromo-2-methylphenylamino)-1,7-naphthyridine-3-carbaldehyde

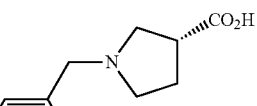

A vial was charged with N-(3-bromo-2-methylphenyl)-3-vinyl-1,7-naphthyridin-8-amine (281 mg, 0.826 mmol), a stir bar, 1,4-dioxane (6.2 ml) and water (2.0 ml). To this suspension was added osmium tetroxide (4% w/w in water, 324 µl, 0.041 mmol). The reaction was stirred for 5 min then sodium periodate (883 mg, 4.13 mmol) was added. After stirring at room temperature for 1 h, the reaction mixture was quenched with a saturated aqueous solution of sodium thiosulfate. The mixture was then extracted with ethyl acetate, and the combined organic layers were separated, washed with brine, dried over Na$_2$SO$_4$, filtered, and concentrated in vacuo. The crude residue was used directly in the next step without further purification. LC-MS calculated for $C_{16}H_{13}BrN_3O$ (M+H)+: m/z=342.0; found 342.0.

Step 4: (R)-1-((8-(3-bromo-2-methylpkenylamino)-1,7-naphthyridin-3-yl)methyl)pyrrolidin-3-ol

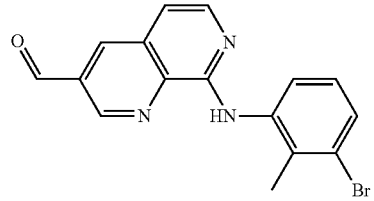 [SMILES: Cc1c(Br)cccc1Nc1nccc2cc(C=O)cnc12]

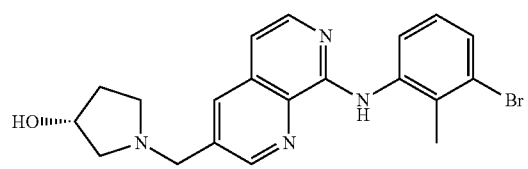 [SMILES: Cc1c(Br)cccc1Nc1nccc2cc(CN3CC[C@@H](O)C3)cnc12]

A mixture of 8-((3-bromo-2-methylphenyl)amino)-1,7-naphthyridine-3-carbaldehyde (102 mg, 0.298 mmol) and (R)-pyrrolidin-3-ol (51.9 mg, 0.596 mmol) in DCM (1490 µl) was stirred at room temperature for 0.5 h. Then sodium triacetoxyborohydride (95 mg, 0.447 mmol) and acetic acid (25.0 µl, 0.447 mmol) were added. The mixture was further stirred at room temperature for 1 h. The reaction mixture was quenched by NH$_4$OH aqueous solution then extracted with DCM. The organic phases were combined and dried over MgSO$_4$, then filtered. The filtrate was concentrated and used directly in the next step without further purification. LC-MS calculated for $C_{20}H_{22}BrN_4O$ (M+H)$^+$: m/z=413.1; found 413.1.

Step 5: (R)-1-((8-(3'-(7-chloro-5-(hydroxymethyl)benzo[d]oxazol-2-yl)-2,2'-dimethylbiphenyl-3-ylamino)-1,7-naphthyridin-3-yl)methyl)pyrrolidin-3-ol

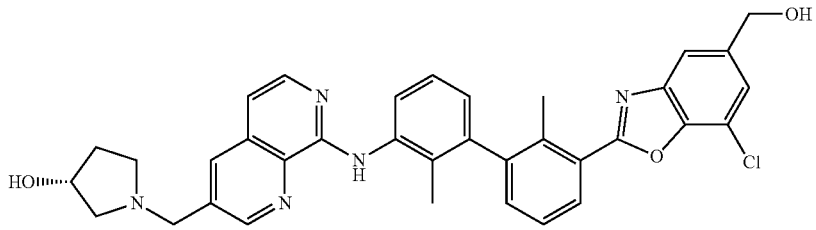 [SMILES: Cc1c(Nc2nccc3cc(CN4CC[C@@H](O)C4)cnc23)cccc1-c1cccc(-c2nc3cc(CO)cc(Cl)c3o2)c1C]

A mixture of (R)-1-((8-((3-bromo-2-methylphenyl)amino)-1,7-naphthyridin-3-yl)methyl)pyrrolidin-3-ol (419 mg, 1.01 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 611 mg, 1.12 mmol), sodium carbonate (269 mg, 2.53 mmol) and tetrakis(triphenylphosphine)palladium(0) (117 mg, 0.101 mmol) in water (1.7 mL) and 1,4-dioxane (8.4 mL) was purged with N$_2$ and then stirred at 100° C. for 4 h. The reaction mixture was cooled to room temperature, diluted with ethyl acetate and then washed with H2O. The organic layer was dried over MgSO$_4$ and filtered. The filtrate was concentrated to give a crude residue, which was purified by flash chromatography on a silica gel column eluting with 0 to 15% MeOH/DCM to give the desired product. LC-MS calculated for $C_{35}H_{33}ClN_5O_3$ (M+H)$^+$: m/z=606.2; found 606.4.

Step 6: (R)-5-(hydroxymethyl)-2-(3'-(3-((3-hydroxypyrrolidin-1-yl)methyl)-f 7-naphthyridin-8-ylamino)-2,2'-dimethylbiphenyl-3-yl)benzo[d]oxazole-7-carbonitrile

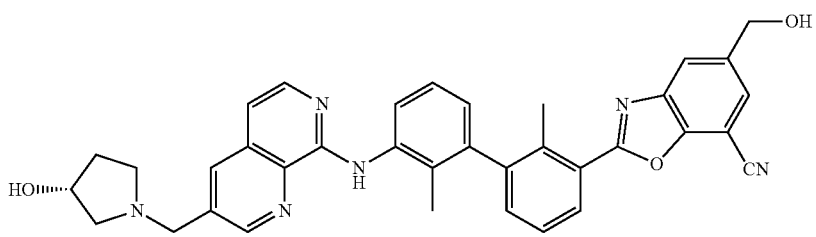 [SMILES: Cc1c(Nc2nccc3cc(CN4CC[C@@H](O)C4)cnc23)cccc1-c1cccc(-c2nc3cc(CO)cc(C#N)c3o2)c1C]

A mixture of (7?)-1-((8-((3'-(7-chloro-5-(hydroxymethyl)benzo[d]oxazol-2-yl)-2,2'-dimethyl-[1,1'-biphenyl]-3-yl)amino)-1,7-naphthyridin-3-yl)methyl)pyrrolidin-3-ol (79 mg, 0.13 mmol), [(2-di-tert-butylphosphino-2',4',6'-triisopropyl-1,1'-biphenyl)-2-(2'-amino-1,1'-biphenyl)]palladium(II) methanesulfonate (10.4 mg, 0.013 mmol), potassium hexacyanoferrate(II) trihydrate (55.1 mg, 0.130 mmol) and potassium acetate (2.6 mg, 0.026 mmol) in 1,4-dioxane (650 µl) and water (650 µl) was stirred and heated at 100° C. for 4 h. After cooling to room temperature, the reaction mixture was diluted with EtOAc and water, extracted with EtOAc. The combined organic phases was dried over MgSO$_4$, and then filtered. The filtrate was concentrated. The crude material was purified by column chromatography (0-8% MeOH in DCM) to give the desired product. LC-MS calculated for $C_{36}H_{33}N_6O_3$ (M+H)$^+$: m/z=597.3; found 597.2.

Step 7: (R)-5-formyl-2-(3'-(3-((3-hydroxypyrrolidin-1-yl)methyl)-1,7-naphthyridin-8-ylamino)-2,2'-dimethylbiphenyl-3-yl)benzo[d]oxazole-7-carbonitrile

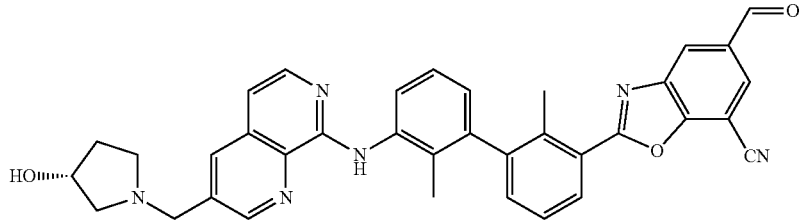 [SMILES: Cc1c(Nc2nccc3cc(CN4CC[C@@H](O)C4)cnc23)cccc1-c1cccc(-c2nc3cc(C=O)cc(C#N)c3o2)c1C]

A suspension of (R)-5-(hydroxymethyl)-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazole-7-carbonitrile (72 mg, 0.12 mmol) and manganese dioxide (231 mg, 2.65 mmol) in DCM (1.2 mL) was stirred at 45° C. for 25 min. The reaction mixture was cooled to room temperature, filtered through a short pad of Celite® and then concentrated to yield a crude residue, which was used directly in the next step without further purification. LC-MS calculated for $C_{36}H_{31}N_6O_3$ $(M+H)^+$: m/z=595.2; found 595.2.

Step 8: (R)-1-((7-cyano-2-(3'-(3-(((R)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic Acid A mixture of (7?)-5-formyl-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazole-7-carbonitrile (72 mg, 0.12 mmol), (R)-pyrrolidine-3-carboxylic acid (27.9 mg, 0.242 mmol) and triethylamine (34 μl, 0.24 mmol) in DCM (800 μl) was stirred at room temperature for 2 h. Then sodium triacetoxyborohydride (38.5 mg, 0.182 mmol) and acetic acid (10.5 μl, 0.18 mmol) were added. The mixture was further stirred at room temperature for 1 h. The reaction mixture was diluted with MeOH and then purified by prep-HPLC (pH=2, acetonitrile/water+TFA) to give the desired product as its TFA salt. LC-MS calculated for $C_{41}H_{40}N_7O_4$ $(M+H)^+$: m/z=694.3; found 694.3. $^1H$ NMR (500 MHz, DMSO) δ 9.07 (s, 1H), 8.55-8.48 (m, 1H), 8.40 (d, J=1.5 Hz, 1H), 8.25-8.10 (m, 3H), 8.04 (d, J=5.8 Hz, 1H), 7.59 (t, J=7.7 Hz, 1H), 7.48 (dd, J=7.6, 1.4 Hz, 1H), 7.41 (t, J=7.8 Hz, 1H), 7.23 (d, J=6.0 Hz, 1H), 7.06 (d, J=7.3 Hz, 1H), 4.86-4.36 (m, 5H), 3.88-3.00 (m, 9H), 2.49 (s, 3H), 2.42-2.15 (m, 2H), 2.06 (s, 3H), 2.02-1.80 (m, 2H).

Example 4

(S)-1-((7-cyano-2-(3'-(3-(((j?)-3-hydroxypyrrolidin-1-yl)methyl)-1,7-naphthyridin-8-ylamino)-2,2'-dimethylbiphenyl-3-yl)benzo[d]oxazol-5-yl)methyl)pyrrolidine-3-carboxylic acid

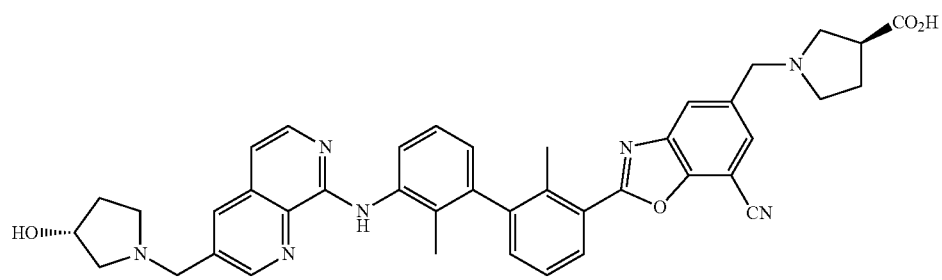 [SMILES: Cc1c(Nc2nccc3cc(CN4CC[C@@H](O)C4)cnc23)cccc1-c1cccc(-c2nc3cc(CN4CC[C@H](C(=O)O)C4)cc(C#N)c3o2)c1C]

This compound was prepared using similar procedures as described for Example 3 with (S)-pyrrolidine-3-carboxylic acid replacing (R)-pyrrolidine-3-carboxylic acid in Step 8. The reaction mixture was diluted with MeOH and then purified by prep-HPLC (pH=2, acetonitrile/water+TFA) to give the desired product as its TFA salt. LC-MS calculated for $C_{41}H_{40}N_7O_4$ $(M+H)^+$: m/z=694.3; found 694.3. $^1H$ NMR (500 MHz, DMSO) δ 9.09 (s, 1H), 8.53 (s, 1H), 8.40 (d, J=1.6 Hz, 1H), 8.20 (dd, J=8.0, 1.4 Hz, 1H), 8.17-8.06 (m, 2H), 8.01 (d, J=6.8 Hz, 1H), 7.59 (t, J=7.7 Hz, 1H), 7.48 (dd, J=7.7, 1.4 Hz, 1H), 7.43 (t, J=7.8 Hz, 1H), 7.24 (d, J=6.0 Hz, 1H), 7.09 (d, J=7.7 Hz, 1H), 4.82-4.37 (m, 5H), 3.77-3.06 (m, 9H), 2.50 (s, 3H), 2.43-1.82 (m, 4H), 2.06 (s, 3H).

Example 5

(R)-1-((7-Cyano-2-(3'-(3-((3-Hydroxypyrrolidin-1-Yl)Methyl)-1,7-Naphthyridin-8-Ylamino)-2,2'-Dimethylbiphenyl-3-Yl)Benzo[d]Oxazol-5-Yl)Methyl)Azetidine-3-Carboxylic Acid

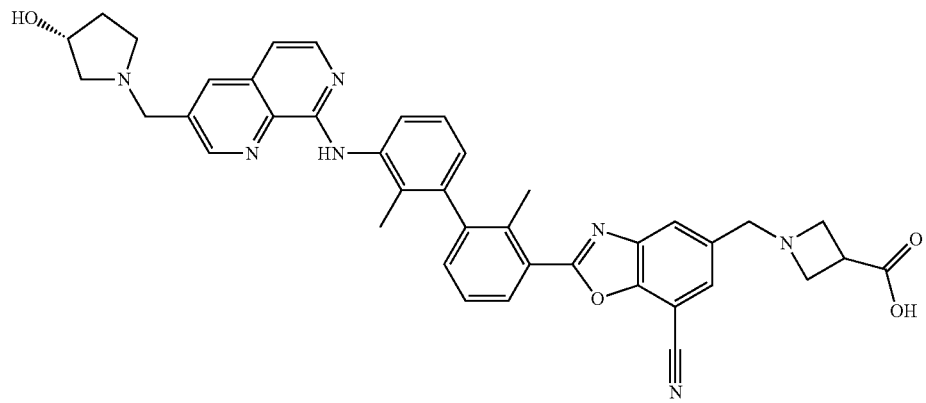 [SMILES: Cc1c(Nc2nccc3cc(CN4CC[C@@H](O)C4)cnc23)cccc1-c1cccc(-c2nc3cc(CN4CC(C(=O)O)C4)cc(C#N)c3o2)c1C]

This compound was prepared using similar procedures as described for Example 3 with azetidine-3-carboxylic acid replacing (R)-pyrrolidine-S-carboxylic acid in Step 8. The reaction mixture was diluted with MeOH and then purified by prep-HPLC (pH=10, acetonitrile/water+NH$_4$OH) to give the desired product. LC-MS calculated for C$_{40}$H$_{38}$N$_7$O$_4$ (M+H)$^+$: m/z=680.3; found 680.3.

Example 6

(R)-3-((7-cyano-2-(3'-(3-((3-hydroxypyrrolidin-1-yl)methyl)-1,7-naphthyridin-8-ylamino)-2,2'-dimethylbiphenyl-3-yl)benzo[d]oxazol-5-yl)methylamino)-2,2-dimethylpropanoic Acid

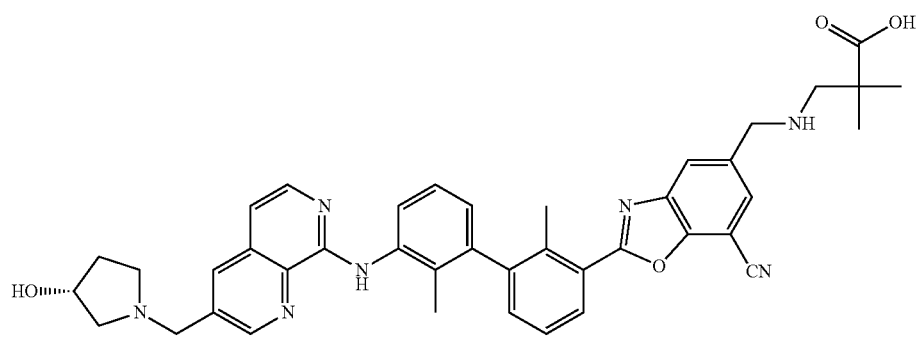 [SMILES: Cc1c(Nc2nccc3cc(CN4CC[C@@H](O)C4)cnc23)cccc1-c1cccc(-c2nc3cc(CNCC(C)(C)C(=O)O)cc(C#N)c3o2)c1C]

This compound was prepared using similar procedures as described for Example 3 with 3-amino-2,2-dimethylpropanoic acid replacing (R)-pyrrolidine-3-carboxylic acid in Step 8. The reaction mixture was diluted with MeOH and then purified by prep-HPLC (pH=10, acetonitrile/water+NH$_4$OH) to give the desired product. LC-MS calculated for C$_{41}$H$_{42}$N$_{42}$N$_7$O$_4$ (M+H)$^+$: m/z=696.3; found 696.3.

Example 7

(R)-1-((2-(2'-chloro-3'-(3-(((S)-3-hydroxypyrrolidin-1-yl)methyl)-1,7-naphthyridin-8-ylamino)-2-methyl-biphenyl-3-yl)-7-cyanobenzo[d]oxazol-5-yl)methyl)-3-methylpyrrolidine-3-carboxylic Acid

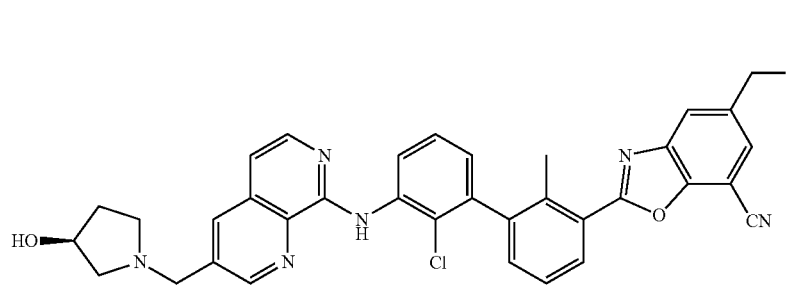

Step 1: 8-chloro-3-vinyl-1,7-naphthyridine

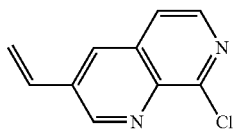

A mixture of 3-bromo-8-chloro-1,7-naphthyridine (PharmaBlock, cat # PBLJ2743: 770 mg, 3.16 mmol), 4,4,5,5-tetramethyl-2-vinyl-1,3,2-dioxaborolane (584 mg, 3.79 mmol), sodium carbonate (838 mg, 7.91 mmol) and tetrakis(triphenylphosphine)palladium(0) (183 mg, 0.158 mmol) in t-butanol (8 ml) and water (8 ml) was degassed and sealed. It was stirred at 80° C. for 2 h. The reaction mixture was cooled then extracted with ethyl acetate. The combined organic layers were washed with brine, dried over MgSO$_4$, and filtered. The filtrate was concentrated under reduced pressure. The crude residue was used directly in the next step without further purification. LC-MS calculated for C$_{10}$H$_8$ClN$_2$ (M+H)$^+$: m/z=191.0; found 191.0.

Step 2: N-(3-bromo-2-chlorophenyl)-3-vinyl-1,7-naphthyridin-8-amine

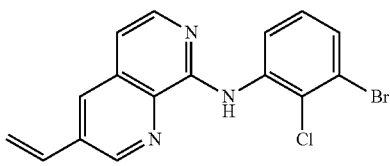 [SMILES: C=Cc1cnc2c(Nc3cccc(Br)c3Cl)nccc2c1]

A mixture of 3-bromo-2-chloroaniline (Astatech, cat # CL9068; 536 mg, 2.59 mmol), 8-chloro-3-vinyl-1,7-naphthyridine (471 mg, 2.47 mmol) and 4M HCl in dioxane (618 µl, 2.47 mmol) in t-butanol (12.4 mL) was heated at 120° C. for 2 h. The reaction mixture was cooled to room temperature, diluted with DCM then quenched by aqueous NaHCO$_3$ solution and extracted with DCM. The organic phase was dried over MgSO$_4$, filtered and the filtrate was concentrated. The residue was used directly in the next step without further purification. LC-MS calculated for C$_{16}$H$_{12}$BrClN$_3$ (M+H)$^+$: m/z=360.0; found 360.0.

Step 3: 8-(3-bromo-2-chlorophenylamino)-1,7-naphthyridine-3-carbaldehyde

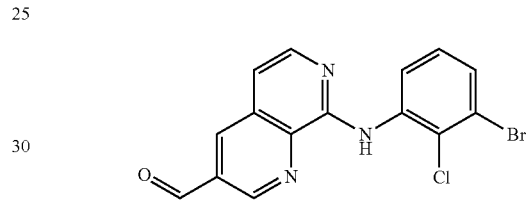

To the solution of N-(3-bromo-2-chlorophenyl)-3-vinyl-1,7-naphthyridin-8-amine (135 mg, 0.374 mmol) in 1,4-dioxane (2.8 mL) and water (0.9 mL) was added osmium tetroxide (4% w/w in water, 147 µl, 0.019 mmol). The mixture was stirred at room temperature for 5 min then sodium periodate (400 mg, 1.872 mmol) was added. After stirring at room temperature for 1 h, the reaction mixture was quenched with a saturated aqueous solution of sodium thiosulfate. The mixture was then extracted with ethyl acetate, and the combined organic layers were separated, washed with brine, dried over Na$_2$SO$_4$, filtered, and concentrated in vacuo. The crude residue was used directly in the next step without further purification. LC-MS calculated for C$_{15}$H$_{10}$BrClN$_3$O (M+H)$^+$: m/z=362.0; found 362.0.

Step 4: (S)-1-((8-(3-bromo-2-chlorophenylamino)-1,7-naphthyridin-3-yl)methyl)pyrrolidin-3-ol

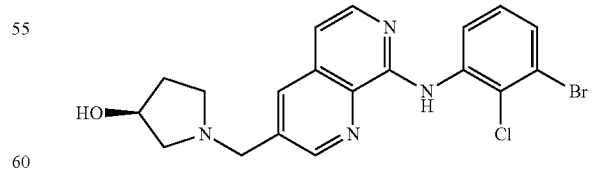

A mixture of 8-((3-bromo-2-chlorophenyl)amino)-1,7-naphthyridine-3-carbaldehyde (384 mg, 1.06 mmol) and (S)-pyrrolidin-3-ol (185 mg, 2.12 mmol) in DCM (5.3 mL) was stirred at room temperature for 0.5 h. Then sodium triacetoxyborohydride (337 mg, 1.59 mmol) and acetic acid (91 µl, 1.59 mmol) were added. The mixture was further stirred at room temperature for 1 h. The reaction mixture was quenched by NH₄OH aqueous solution and extracted with DCM. The organic phases were combined and dried over MgSO₄, then filtered. The filtrate was concentrated and the residue was purified by column chromatography on a silica gel column eluting with 0 to 8% MeOH/DCM to give the desired product. LC-MS calculated for C₁₉H₁₉BrClN₄O (M+H)⁺: m/z=433.0; found 433.0.

Step 5: (S)-1-((8-(2-chloro-3'-(7-chloro-5-(hydroxymethyl)benzo[d]oxazol-2-yl)-24 methylbiphenyl-3-ylamino)-1,7-naphthyridin-3-yl)methyl)pyrrolidin-3-ol A mixture of (5)-1-((8-((2-chloro-3'-(7-chloro-5-(hydroxymethyl)benzo[d]oxazol-2-yl)-2'-methyl-[1,1'-biphenyl]-3-yl)amino)-1,7-naphthyridin-3-yl)methyl)pyrrolidin-3-ol (114 mg, 0.182 mmol), [(2-di-tert-butylphosphino-2',4',6'-triisopropyl-1,1'-biphenyl)-2-(2'-amino-1,1'-biphenyl)]palladium(II) methanesulfonate (14.4 mg, 0.018 mmol), potassium hexacyanoferrate(II) trihydrate (77 mg, 0.18 mmol) and potassium acetate (3.6 mg, 0.036 mmol) in 1,4-dioxane (910 μl) and water (910 μl) was stirred and heated at 100° C. for 1 h. After cooling to room temperature, the reaction mixture was diluted with EtOAc and water, and the layers were separated. The aqueous layer was further extracted with EtOAc and the combined organic phases

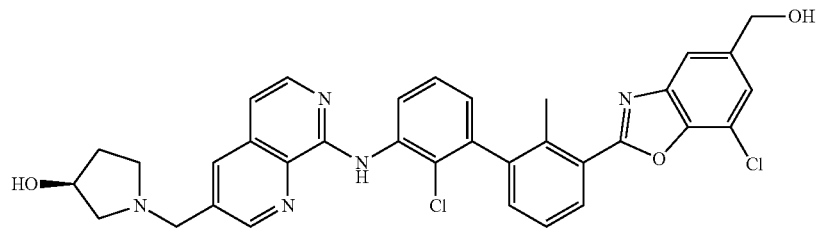 [SMILES: Cc1c(-c2nc3cc(CO)cc(Cl)c3o2)cccc1-c1cccc(Nc2nccc3cc(CN4CC[C@H](O)C4)cnc23)c1Cl]

A mixture of (5)-1-((8-(3-bromo-2-chlorophenylamino)-1,7-naphthyridin-3-yl)methyl)pyrrolidin-3-ol (10.3 mg, 0.024 mmol), (7-chloro-2-(2-methyl-3-(4,4,5,5-tetramethyl-1,3,2-dioxaborolan-2-yl)phenyl)benzo[d]oxazol-5-yl)methanol (Example 1, Step 5: 9.5 mg, 0.024 mmol), sodium carbonate (6.30 mg, 0.059 mmol) and tetrakis(triphenylphosphine) palladium(O) (2.75 mg, 2.377 μmol) in water (40 μl) and 1,4-dioxane (200 μl) was purged with N₂ and then stirred at 100° C. for 1 h. The reaction mixture was cooled to room temperature, diluted with ethyl acetate and then washed with H₂O. The organic layer was dried MgSO₄ and filtered. The filtrate was concentrated to give a crude residue, which was purified by flash chromatography on a silica gel column eluting with 0 to 15% MeOH/DCM to give the desired product. LC-MS calculated for C₃₄H30Cl₂N₅O₃ (M+H)⁺: m/z=626.2; found 626.2.

were dried over MgSO₄, and then filtered. The filtrate was concentrated and the crude material was purified by column chromatography (0-8% MeOH in DCM) to give the desired product. LC-MS calculated for C₃₅H₃₀ClN₆O₃ (M+H)⁺: m/z=617.2; found 617.4.

Step 6: (S)-2-(2'-chloro-3'-(3-((3-hydroxypyrrolidin-1-yl)methyl)-1,7-naphthyridin-8-ylamino)-2-methyl biphenyl-3-yl)-5-(hydroxymethyl)benzo[d]oxazole-7-carbonitrile

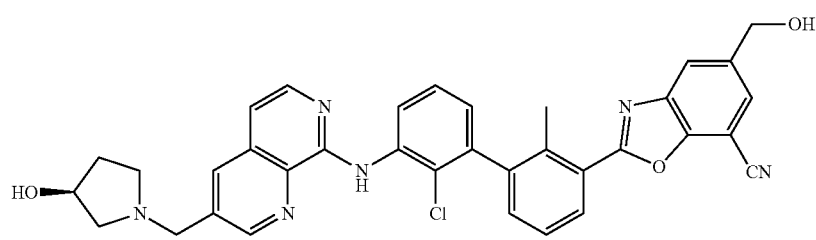 [SMILES: Cc1c(-c2nc3cc(CO)cc(C#N)c3o2)cccc1-c1cccc(Nc2nccc3cc(CN4CC[C@H](O)C4)cnc23)c1Cl]

Step 7: (S)-2-(2'-chloro-3'-(3-((3-hydroxypyrrolidin-1-yl)methyl)-1,7-naphthyridin-8-ylamino)-2-methyl-biphenyl-3-yl)-5-formylbenzo[d]oxazole-7-carbonitrile

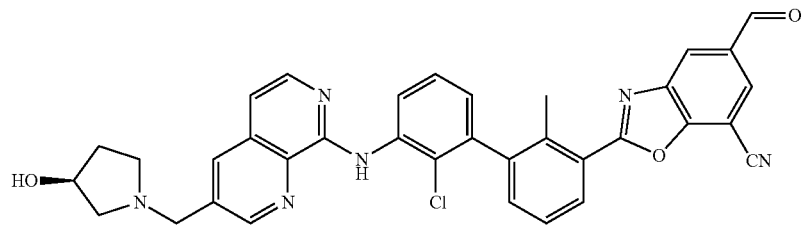 [SMILES: Cc1c(-c2nc3cc(C=O)cc(C#N)c3o2)cccc1-c1cccc(Nc2nccc3cc(CN4CC[C@H](O)C4)cnc23)c1Cl]

A suspension of (S)-2-(2'-chloro-3'-((3-((3-hydroxypyrrolidin-1-yl)methyl)-1,7-naphthyridin-8-yl)amino)-2-methyl-[1,1'-biphenyl]-3-yl)-5-(hydroxymethyl)benzo[d]oxazole-7-carbonitrile (64 mg, 0.104 mmol) and manganese dioxide (198 mg, 2.28 mmol) in DCM (1.0 mL) was stirred at 45° C. for 15 min. The reaction was filtered through a short pad of Celite® and then concentrated to yield a crude residue, which was used directly in the next step without further purification. LC-MS calculated for $C_{35}H_{28}ClN_6O_3$ (M+H)$^+$: m/z=615.2; found 615.2.

Step 8: (R)-1-((2-(2'-chloro-3'-(3-(((S)-3-hydroxypyrrolidin-1-yl)methyl)-1,7-naphthyridin-8-ylamino)-2-methylbiphenyl-3-yl)-7-cyanobenzo[d]oxazol-5-yl)methyl)-3-methylpyrrolidine-3-carboxylic acid A mixture of (S)-2-(2'-chloro-3'-((3-((3-hydroxypyrrolidin-1-yl)methyl)-1,7-naphthyridin-8-yl)amino)-2-methyl-[1,1'-biphenyl]-3-yl)-5-formylbenzo[d]oxazole-7-carbonitrile (10.2 mg, 0.017 mmol), (R)-3-methylpyrrolidine-3-carboxylic acid (J&W Pharmlab, #75R0495: 6.4 mg, 0.050 mmol) and triethylamine (6.9 µl, 0.050 mmol) in DCM (120 µl) was stirred at rt for 2 h. Then sodium triacetoxyborohydride (10.5 mg, 0.050 mmol) and acetic acid (3.0 µl, 0.050 mmol) were added. The mixture was further stirred at rt for 1 h. The reaction was diluted with MeOH and then purified by prep-HPLC (pH=2, acetonitrile/water+TFA) to give the desired product as its TFA salt. LC-MS calculated for $C_{41}H_{39}ClN_7O_4$ (M+H)$^+$: m/z=728.3; found 728.3.

Example 8

(R)-1-((8-((3'-((3-(((R)-3-hydroxypyrrolidin-1-yl)methyl)-1,7-naphthyridin-8-yl)amino)-2,2'-dimethyl-[1,1'-biphenyl]-3-yl)amino)-1,7-naphthyridin-3-yl)methyl)pyrrolidine-3-carboxylic Acid

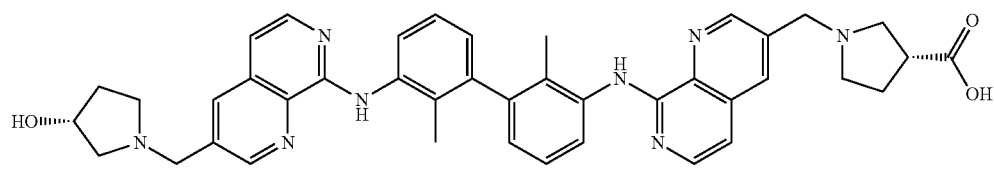 [SMILES: Cc1c(Nc2nccc3cc(CN4CC[C@@H](O)C4)cnc23)cccc1-c1cccc(Nc2nccc3cc(CN4CC[C@@H](C(=O)O)C4)cnc23)c1C]

Step 1: (R)-1-((8-((3-bromo-2-methylphenyl)amino)-1,7-naphthyridin-3-yl)methyl)pyrrolidin-3-ol

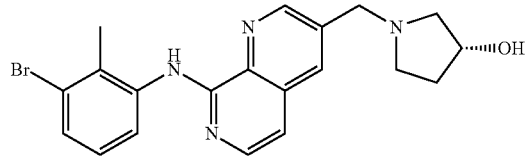 [SMILES: Cc1c(Br)cccc1Nc1nccc2cc(CN3CC[C@@H](O)C3)cnc12]

A mixture of 8-((3-bromo-2-methylphenyl)amino)-1,7-naphthyridine-3-carbaldehyde (Example 3, Step 3; 0.100 g, 0.292 mmol) and (R)-3-hydroxypyrrolidine (Combi-Blocks, # AM-2005: 0.025 g, 0.292 mmol) in 1,2-dichloroethane (1.461 ml) and N,N-diisopropylethylamine (0.051 ml, 0.292 mmol) was stirred at rt for 1 h. Sodium triacetoxyborohydride (0.093 g, 0.438 mmol) was carefully added in portions. The reaction was stirred at rt for 2 h, then quenched with a saturated aqueous solution of sodium bicarbonate. The mixture was then extracted with a 3:1 mixture of chlorofom/IPA. The combined organic layers were dried over sodium sulfate, and then concentrated in vacuo. The crude residue was purified by silica gel chromatography (0→30% methanol/DCM). LC-MS calculated for $C_{20}H_{22}BrN_4O$ (M+H)$^+$: m/z=413.1; found 413.1.

Step 2: (8-((2-methyl-3-(4,4,5,5-tetramethyl-1,3,2-dioxaborolan-2-yl)phenyl)amino)-1,7-naphthyridin-3-yl)methanol

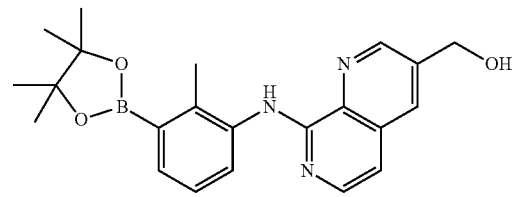 [SMILES: Cc1c(Nc2nccc3cc(CO)cnc23)cccc1B1OC(C)(C)C(C)(C)O1]

A mixture of (8-((3-bromo-2-methylphenyl)amino)-1,7-naphthyridin-3-yl)methanol (Affinity Research Chemicals, #

ARI-0169: 0.300 g, 0.872 mmol), bis(pinacolato)diboron (Aldrich, #473294: 0.266 g, 1.046 mmol), dichloro[1,1'-bis(diphenylphosphino)ferrocene]palladium (II) dichloromethane adduct (0.071 g, 0.087 mmol) and potassium acetate (0.214 g, 2.179 mmol) was charged with nitrogen and stirred at 110° C. for 2 h. The crude was diluted with DCM, and then filtered through Celite®. The filtrate was concentrated, and the resulting residue was used directly in the next step without further purification. LC-MS calculated for $C_{22}H_{27}BN_3O_3$ (M+H)$^+$: m/z=392.2; found 392.3.

Step 3: (R)-1-((8-((3'-((3-(hydroxymethyl)-1,7-naphthyridin-8-yl)amino)-2,2'-dimethyl-[1,1-biphenyl]-3-yl)amino)-1,7-naphthyridin-3-yl)methyl)pyrrolidin-3-ol To a solution of (R)-1-((8-((3'-((3-(hydroxymethyl)-1,7-naphthyridin-8-yl)amino)-2,2'-dimethyl-[1,1'-biphenyl]-3-yl)amino)-1,7-naphthyridin-3-yl)methyl)pyrrolidin-3-ol (0.0715 g, 0.120 mmol) in DCM (1.196 ml) was added manganese dioxide (0.208 g, 2.392 mmol). The resulting mixture was heated at 45° C. for 30 min. After cooling, the mixture was filtered through Celite® and the filtrate was concentrated. The crude orange solid was used directly in the next step without further purification. LC-MS calculated for $C_{36}H_{34}N_7O_2$ (M+H)$^+$: m/z=596.3; found 596.5.

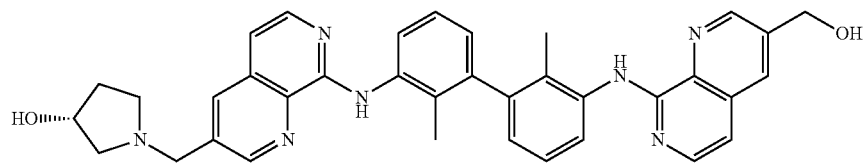 [SMILES: Cc1c(Nc2nccc3cc(CO)cnc23)cccc1-c1cccc(Nc2nccc3cc(CN4CC[C@@H](O)C4)cnc23)c1C]

To a vial was added (8-((2-methyl-3-(4,4,5,5-tetramethyl-1,3,2-dioxaborolan-2-yl)phenyl)amino)-1,7-naphthyridin-3-yl)methanol (0.162 g, 0.414 mmol), (R)-1-((8-((3-bromo-2-methylphenyl)amino)-1,7-naphthyridin-3-yl)methyl)pyrrolidin-3-ol (0.163 g, 0.394 mmol), 1 M aqueous sodium carbonate (0.789 mmol), [1,1'-bis(di-cyclohexylphosphino)ferrocene]-dichloropalladium (II) (0.029 g, 0.039 mmol), and 1,4-dioxane (3.48 ml). The mixture was degassed, sealed, and heated to 90° C. whilst stirring for 2 h. The mixture was cooled, diluted with EtOAc and filtered through Celite®. The filtrate was concentrated and purified using silica gel chromatography (20% MeOH/DCM) to provide the desired compound as an orange solid. LC-MS calculated for $C_{36}H_{36}N_7O_2$ (M+H)$^+$: m/z=598.3; found 598.4.

Step 4: (R)-8-((3'-((3-((3-hydroxypyrrolidin-1-yl)methyl)-1,7-naphthyridin-8-yl)amino)-2,2'-dimethyl-[1,1'-biphenyl]-3-yl)amino)-1,7-naphthyridine-3-carbaldehyde Step 5: (R)-1-((8-((3'-((3-(((R)-3-hydroxypyrrolidin-1-yl)methyl)-1,7-naphthyridin-8-yl)amino)-2,2'-dimethyl-[1,1'-biphenyl]-3-yl)amino)-1,7-naphthyridin-3-yl)methyl)pyrrolidine-3-carboxylic acid To a vial was added (R)-8-((3'-((3-((3-hydroxypyrrolidin-1-yl)methyl)-1,7-naphthyridin-8-yl)amino)-2,2'-dimethyl-[1,1'-biphenyl]-3-yl)amino)-1,7-naphthyridine-3-carbaldehyde (0.013 g, 0.022 mmol), (R)-pyrrolidine-3-carboxylic acid (Combi-Blocks, # ST-7698: 7.5 mg, 0.065 mmol), 1,2-dichloroethane (0.336 ml) and triethylamine (9.13 µl, 0.065 mmol). The reaction was stirred at rt for 2 h, then sodium triacetoxyborohydride (0.023 g, 0.109 mmol) and acetic acid (3.75 µl, 0.065 mmol) were added. The reaction was stirred for 2 h, then the mixture was diluted with methanol and purified by prep-HPLC (pH=2, acetonitrile/water+TFA) to give the desired product as TFA salt. LC-MS calculated for $C_{41}H_{43}N_8O_3$ (M+H)$^+$: m/z=695.3; found 695.3. $^1$H NMR (500 MHz, DMSO) δ 10.72 (br s, 2H), 9.11 (m, 2H), 8.54 (m, 2H), 8.02 (m, 4H), 7.42 (m, 2H), 7.26 (m, 2H), 7.11 (m, 2H), 4.70 (m, 4H), 4.47 (m, 1H), 3.82-3.08 (m, 10H), 2.38-2.18 (m, 2H), 2.10 (s, 6H), 2.05-1.82 (m, 2H).

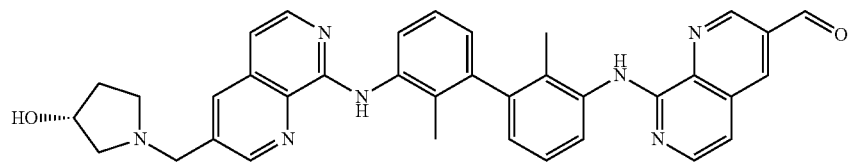 [SMILES: Cc1c(Nc2nccc3cc(C=O)cnc23)cccc1-c1cccc(Nc2nccc3cc(CN4CC[C@@H](O)C4)cnc23)c1C]

Example 9

(S)-1-((8-((3'-((3-(((R)-3-hydroxypyrrolidin-1-yl)methyl)-1,7-naphthyridin-8-yl)amino)-2,2'-dimethyl-[1,1'-biphenyl]-3-yl)amino)-1,7-naphthyridin-3-yl)methyl)pyrrolidine-3-carboxylic acid

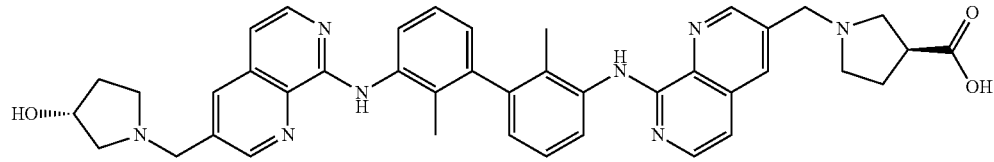 [SMILES: Cc1c(Nc2nccc3cc(CN4CC[C@@H](O)C4)cnc23)cccc1-c1cccc(Nc2nccc3cc(CN4CC[C@H](C(=O)O)C4)cnc23)c1C]

This compound was prepared using similar procedures as described for Example 8 with (5)-pyrrolidine-3-carboxylic acid (Combi-Blocks, # ST-1381) replacing (R)-pyrrolidine-3-carboxylic acid in Step 5. The reaction was diluted with MeOH and then purified by prep-HPLC (pH=2, acetonitrile/water+TFA) to give the desired product as the TEA salt. LC-MS calculated for $C_{41}H_{43}N_8O_3$ (M+H)$^+$: m/z=695.3; found 695.3.

Example 10

(R)-1-((7-cyano-2-(2,2'-dimethyl-3'-(4,5,6,7-tetrahydrothiazolo[5,4-c]pyridin-2-yl)biphenyl-3-yl)benzo[d]oxazol-5-yl)methyl)pyrrolidine-3-carboxylic Acid

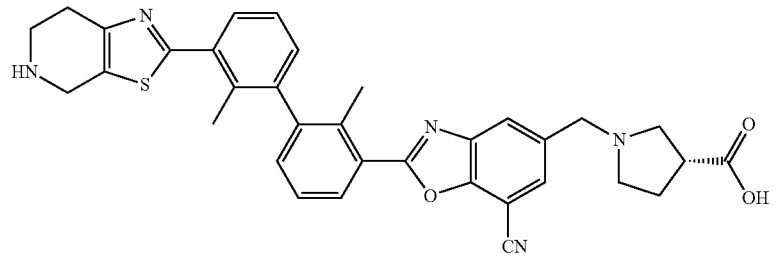 [SMILES: Cc1c(-c2nc3cc(CN4CC[C@@H](C(=O)O)C4)cc(C#N)c3o2)cccc1-c1cccc(-c2nc3c(s2)CNCC3)c1C]

To a solution of (7-chloro-2-(2-methyl-3-(4,4,5,5-tetramethyl-1,3,2-dioxaborolan-2-yl)phenyl)benzo[d]oxazol-5-yl)methanol (Example 1, Step 5: 11.3 g, 28.4 mmol) and 1,3-dibromo-2-methylbenzene (14.17 g, 56.7 mmol) in H$_2$O (30 mL) and 1,4-dioxane (120 ml) was added Na$_2$CO$_3$ (6.01 g, 56.7 mmol) and PdCl$_2$(dppf)-CH$_2$Cl$_{1-2}$ adduct (2.316 g, 2.84 mmol). The resulted mixture was stirred in a closed vial flushed with argon at 100° C. for 1.5 h. The reaction mixture was concentrated, followed by extraction with dichloromethane (25 mL×3). The combined organic layers were dried Na$_2$SO$_4$, filtered and concentrated. The crude product was added to a silica gel column and was eluted with ethyl acetate/dichloromethane from 0% to 40% to give (2-(3'-bromo-2,2'-dimethyl-[1,1'-biphenyl]-3-yl)-7-chlorobenzo[d]oxazol-5-yl)methanol (10.2 g, 23.0 mmol, 81% yield). LC-MS calculated for $C_{22}H_{18}BrClNO_2$ (M+H)$^+$: m/z=442.0; found 442.1.

Step 1: (2-(3'-bromo-2,2'-dimethyl-[1,1'-biphenyl]-3-yl)-7-chlorobenzo[d]oxazol-5-yl)methanol

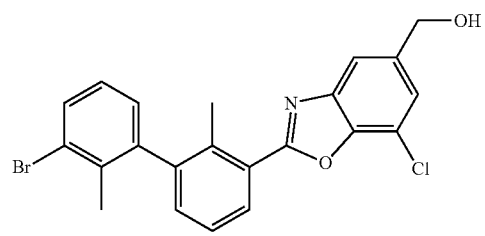 [SMILES: Cc1c(Br)cccc1-c1cccc(-c2nc3cc(CO)cc(Cl)c3o2)c1C]

Step 2: (7-chloro-2-(2,2'-dimethyl-3'-(4,4,5,5-tetramethyl-1,3,2-dioxaborolan-2-yl)-[1,1'-biphenyl]-3-yl)benzo[d]oxazol-5-yl)methanol

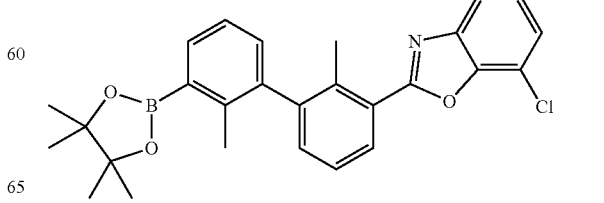

(2-(3'-bromo-2,2'-dimethyl-[1,1'-biphenyl]-3-yl)-7-chlorobenzo[d]oxazol-5-yl)methanol (6.52 g, 14.7 mmol) was dissolved in dioxane (14.7 mL) to give a pale yellow solution. B₂Pin₂ (4.49 g, 17.7 mmol), potassium acetate (2.89 g, 29.5 mmol) and PdCl₂(dppf)-CH₂Cl₂ adduct (1.20 g, 1.47 mmol) were added to the reaction mixture. The reaction mixture was heated to 100° C. After 12 h, saturated NaHCO₃ (25 mL) was added to the reaction mixture followed by extraction with dichloromethane (25 mL×3). The combined organic layers were dried over Na₂SO₄, filtered and concentrated. The crude product was added to a silica gel column and was eluted with ethyl acetate/hexane from 0% to 60% to give (7-chloro-2-(2,2'-dimethyl-3'-(4,4,5,5-tetramethyl-1,3,2-dioxaborolan-2-yl)-[1,1'-biphenyl]-3-yl)benzo[d]oxazol-5-yl)methanol (6.33 g, 12.9 mmol, 88% yield) as a yellow foam. LC-MS calculated for C₂₈H₃₀BClNO₄ (M+H)⁺: m/z=490.2; found 490.1.

Step 3: tert-butyl 2-(3'-(7-chloro-5-(hydroxymethyl)benzo[d]oxazol-2-yl)-2,2'-dimethyl-[1,1 biphenyl]-3-yl)-6,7-dihydrothiazolo[5,4-c]pyridine-5(4H)-carboxylate

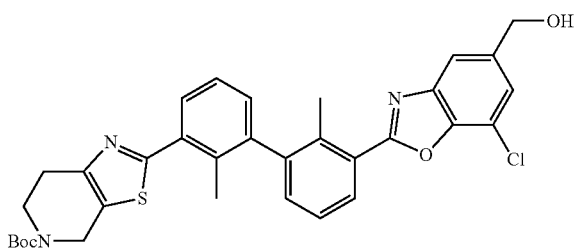 [SMILES: Cc1c(-c2nc3cc(CO)cc(Cl)c3o2)cccc1-c1cccc(-c2nc3c(s2)CN(C(=O)OC(C)(C)C)CC3)c1C]

(7-chloro-2-(2,2'-dimethyl-3'-(4,4,5,5-tetramethyl-1,3,2-dioxaborolan-2-yl)-[1,1'-biphenyl]-3-yl)benzo[d]oxazol-5-yl)methanol (2.98 g, 6.08 mmol), tert-butyl 2-bromo-6,7-dihydrothiazolo[5,4-c]pyridine-5(4H)-carboxylate (AstaTech, cat # AB 1021: 2.33 g, 7.29 mmol), Na₂CO₃ (1.29 g, 12.2 mmol) and PdCl₂(dppf)-CH₂Cl₂ adduct (496 mg, 0.608 mmol) in 1,4-dioxane (60 ml) and water (15 mL) were stirred in a closed vial flushed with argon at 100° C. for 1 h. Saturated NaHCO₃ (50 mL) was added to the reaction mixture followed by extraction with dichloromethane (25 mL×4). The combined organic layers were dried over Na₂SO₄, filtered and concentrated. The crude product was added to a silica gel column and was eluted with ethyl acetate/hexane from 0% to 60% to give tert-butyl 2-(3'-(7-chloro-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate (1.80 g, 2.99 mmol, 49.2% yield) as a yellow oil. LC-MS calculated for C₃₃H₃₃ClN₃O₄S (M+H)⁺: m/z=602.2; found 602.1.

Step 4: tert-butyl 2-(3'-(7-cyano-5-(hydroxymethyl)benzo[d]oxazol-2-yl)-2,2'-dimethyl-[1,1'-biphenyl]-3-yl)-6,7-dihydrothiazolo[5,4-c]pyridine-5 (4H)-carboxylate

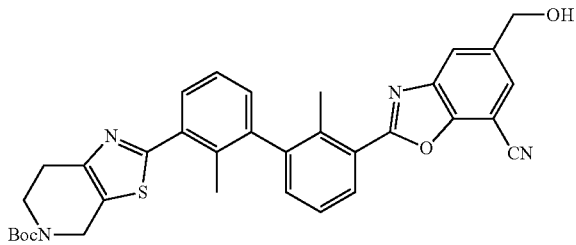 [SMILES: Cc1c(-c2nc3cc(CO)cc(C#N)c3o2)cccc1-c1cccc(-c2nc3c(s2)CN(C(=O)OC(C)(C)C)CC3)c1C]

In a 4 dram vial tert-butyl 2-(3'-(7-chloro-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate (900 mg, 1.50 mmol) and potassium ferrocyanide(II) hydrate (947 mg, 2.24 mmol) were dissolved in 1,4-dioxane (10 ml) and water (4.5 ml). Potassium acetate (367 mg, 3.74 mmol) and [(2-di-tert-butylphosphino-2',4',6'-triisopropyl-1,1'-biphenyl)-2-(2'-amino-1,1'-biphenyl)] palladium(II) methanesulfonate (119 mg, 0.15 mmol) were added to the reaction mixture. The reaction mixture was heated to 100° C. After 2 h, saturated NaHCO₃ (15 mL) was added to the reaction mixture followed by extraction with dichloromethane (10 mL×4). The combined organic layers were dried Na₂SO₄, filtered and concentrated. The crude product was added to a silica gel column and was eluted with ethyl acetate/hexane from 10% to 60% to give tert-butyl 2-(3'-(7-cyano-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate (702 mg, 1.18 mmol, 79% yield) as a yellow oil. LC-MS calculated for C₃₄H₃₃N₄O₄S (M+H)⁺: m/z=593.2; found 593.1.

Step 5: tert-butyl 2-(3'-(7-cyano-5-formylbenzo[d]oxazol-2-yl)-2,2'-dimethyl-[1,1'-biphenyl]-3-yl)-6,7-dihydrothiazolo[5,4-c]pyridine-5(4H)-carboxylate

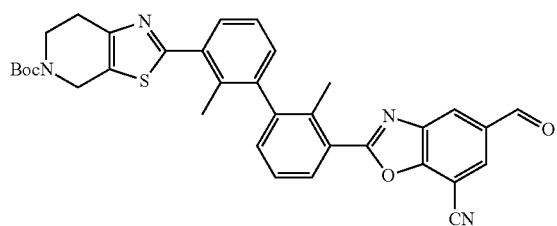 [SMILES: Cc1c(-c2nc3cc(C=O)cc(C#N)c3o2)cccc1-c1cccc(-c2nc3c(s2)CN(C(=O)OC(C)(C)C)CC3)c1C]

To a solution of tert-butyl 2-(3'-(7-cyano-5-(hydroxymethyl)benzo[d]oxazol-2-yl)-2,2'-dimethyl-[1,1'-biphenyl]-3-yl)-6,7-dihydrothiazolo[5,4-c]pyridine-5(4H)-carboxylate (150 mg, 0.253 mmol) in DCM (2 mL) was added Dess-Martin periodinane (161 mg, 0.380 mmol). After 1 h, saturated NaHCO₃ (5 mL) was added to the reaction mixture followed by extraction with dichloromethane (5 mL×3). The combined organic layers were dried over Na₂SO₄, filtered and concentrated. The crude product was used for next step without further purification. LC-MS calculated for C₃₄H₃₁N₄O₄S (M+H)⁺: m/z=591.2; found 591.3.

Step 6: (R)-1-((7-cyano-2-(2,2'-dimethyl-3'-(4,5,6,7-tetrahydrothiazolo[5,4-c]pyridin-2-yl)biphenyl-3-yl)benzo[d]oxazol-5-yl)methyl)pyrrolidine-3-carboxylic Acid To a mixture of tert-butyl 2-(3'-(7-cyano-5-formylbenzo[d]oxazol-2-yl)-2,2'-dimethyl-[1,1'-biphenyl]-3-yl)-3a,6,7,7a-tetrahydrothiazolo[5,4-c]pyridine-5(4H)-carboxylate (55 mg, 0.093 mmol), (7?)-pyrrolidine-3-carboxylic acid (16.0 mg, 0.139 mmol) in $CH_2Cl_2$ (1.0 ml) was added sodium triacetoxyborohydride (19.7 mg, 0.093 mmol). After stirring at room temperature overnight, the reaction mixture was diluted with MeOH and then purified by prep-HPLC (pH=2, acetonitrile/water+TFA). After removing solvent, the residue was treated with 1:1 TFA/DCM (2 mL) for 1 h. The solvent was removed in vacuo. The residue was purified by prep LCMS (pH 2, acetonitrile/water+TFA) to give the desired product as its TFA salt. LC-MS calculated for $C_{34}H_{32}N_5O_3S$ $(M+H)^+$: m/z=590.2; found 590.2. $^1H$ NMR (600 MHz, DMSO) δ 8.42-8.39 (m, 1H), 8.24-8.19 (m, 1H), 8.14 (d, J=1.4 Hz, 1H), 7.76-7.67 (m, 1H), 7.64-7.56 (m, 1H), 7.51-7.44 (m, 2H), 7.33 (d, J=6.7 Hz, 1H), 4.64-4.53 (m, 4H), 3.66 (m, 2H), 3.55 (m, 2H), 3.51-3.44 (m, 3H), 3.27-3.21 (m, 2H), 3.10 (m, 2H), 2.45 (s, 3H), 2.20 (s, 3H).

Example 11

N,N'-(2-chloro-2'-methylbiphenyl-3,3'-diyl)bis(5-((2-hydroxyethylamino)methyl)picolinamide)

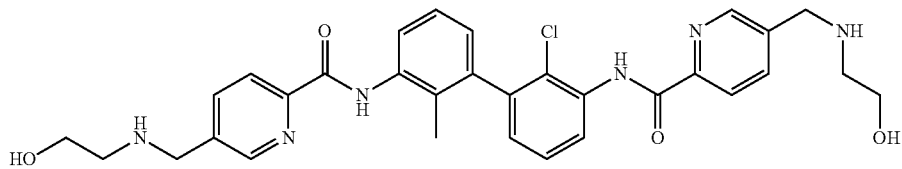 [SMILES: Cc1c(NC(=O)c2ccc(CNCCO)cn2)cccc1-c1cccc(NC(=O)c2ccc(CNCCO)cn2)c1Cl]

Step 1: 2-chloro-2'-methylbiphenyl-3,3'-diamine

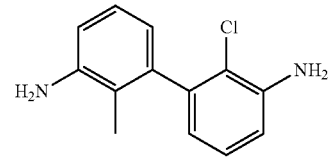 [SMILES: Cc1c(N)cccc1-c1cccc(N)c1Cl]

(1,1'-Bis(diphenylphosphino)ferrocene)-dichloropalladium(II) (28.2 mg, 0.039 mmol) was added to a mixture of 2-methyl-3-(4,4,5,5-tetramethyl-1,3,2-dioxaborolan-2-yl)aniline (Combi-Blocks, cat # PN-9127; 90 mg, 0.386 mmol), 3-bromo-2-chloroaniline (Astatech, cat # CL9068; 80 mg, 0.386 mmol), sodium carbonate (82 mg, 0.772 mmol) in 1,4-dioxane (1072 µl) and water (214 µl). The mixture was purged with $N_2$ and heated at 90° C. for 2 h. The mixture was concentrated and purified by silica gel column eluting with 0 to 20% EtOAc in DCM. LC-MS calculated for $C_{13}H_{14}ClN_2$ $(M+H)^+$: m/z=233.1; found 233.1.

Step 2: N,N'-(2-chloro-2'-methylbiphenyl-3,3'-diyl)bis(5-(dimethoxymethyl)picolinamide)

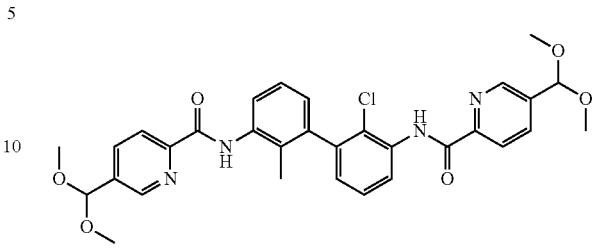

Potassium tert-butoxide in THF (851 µl, 0.851 mmol) was added to an anhydrous THF (773 µl) solution of methyl 5-(dimethoxymethyl)picolinate (Combi-Blocks, cat # QY-1318; 163 mg, 0.773 mmol) and 2-chloro-2'-methyl-[1,1'-biphenyl]-3,3'-diamine (90 mg, 0.387 mmol) under $N_2$ at room temperature. After 2 h, the mixture was quenched with water and extracted with EtOAc. The organic layers were combined, dried over $Na_2SO_4$ and concentrated to afford the desired product, which was used in next step without further purification. LC-MS calculated for $C_{31}H_{32}ClN_4O_6$ $(M+H)^+$: m/z=591.2; found 591.1.

Step 3: N,N'-(2-chloro-2'-methylbiphenyl-3,3'-diyl)bis(5-formylpicolinamide)

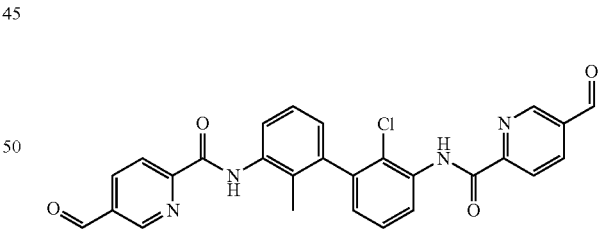

TFA (0.029 ml, 0.380 mmol) was added to a DCM (0.760 ml) solution of N,N'-(2-chloro-2'-methyl-[1,1'-biphenyl]-3,3'-diyl)bis(5-(dimethoxymethyl)picolinamide) (0.225 g, 0.38 mmol) at room temperature. The mixture was concentrated under reduced pressure after 2 h. The residue was diluted with DCM and the organic layer was washed with saturated aqueous $NaHCO_3$. The organic layers were combined and dried over $Na_2SO_4$ and concentrated to afford the desired product, which was used in next step without further purification. LC-MS calculated for $C_{27}H_{20}ClN_4O_4$ $(M+H)^+$: m/z=499.1; found 499.1.

Step 4: N,N'-(2-chloro-2'-methylbiphenyl-3,3'-diyl) bis(5-((2-hydroxyethylamino)methyl) picolinamide)

Sodium triacetoxyborohydride (0.042 g, 0.200 mmol) was added to a mixture of N,N'-(2-chloro-2'-methyl-[1,1'-biphenyl]-3,3'-diyl)bis(5-formylpicolinamide) (0.040 g, 0.08 mmol) and ethanolamine (0.019 ml, 0.320 mmol) in DCM (0.400 ml) at room temperature. After stirring at rt for 2 h, the mixture was purified by prep-HPLC (pH=2, acetonitrile/water+TFA) to give the desired product as its TFA salt. LC-MS calculated for $C_{31}H_{34}ClN_6O_4$ (M+H)$^+$: m/z=589.2; found 589.2. $^1$H NMR (500 MHz, DMSO) δ 10.73 (s, 1H), 10.41 (s, 1H), 9.07 (s, 2H), 8.84 (d, J=6.6 Hz, 2H), 8.44 (dd, J=8.2, 1.4 Hz, 1H), 8.31 (d, J=8.2 Hz, 1H), 8.26 (d, J=8.1 Hz, 2H), 8.22 (dd, J=8.1, 2.0 Hz, 1H), 7.84 (d, J=7.4 Hz, 1H), 7.54 (t, J=7.9 Hz, 1H), 7.37 (t, J=7.8 Hz, 1H), 7.16 (dd, J=7.6, 1.5 Hz, 1H), 7.09 (d, J=6.8 Hz, 1H), 4.43-4.25 (m, 4H), 3.75-3.61 (m, 4H), 3.12-2.97 (m, 4H), 2.06 (s, 3H).

Example 12

(R)-1-((2-(2'-chloro-3'-(6-isopropyl-4,5,6,7-tetrahydro-2H-pyrazolo[3,4-c]pyridin-2-yl)-2-methylbiphenyl-3-yl)-7-cyanobenzo[d]oxazol-5-yl)methyl) pyrrolidine-3-carboxylic Acid desired product. LC-MS calculated for $C_{17}H_{20}BrClN_3O_2$ (M+H)$^+$: m/z=412.0; found 412.0.

Step 2: 5-(hydroxymethyl)-2-(2-methyl-3-(4,4,5,5-tetramethyl-1,3,2-dioxaborolan-2-yl)phenyl)benzo[d]oxazole-7-carbonitrile

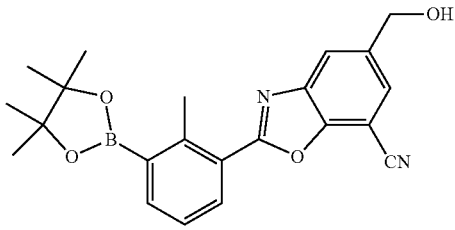

A mixture of (7-chloro-2-(2-methyl-3-(4,4,5,5-tetramethyl-1,3,2-dioxaborolan-2-yl)phenyl)benzo[d]oxazol-5-yl)methanol (Example 1, Step 5: 455 mg, 0.85 mmol), [(2-di-tert-butylphosphino-2',4',6'-triisopropyl-1,1'-biphenyl)-2-(2'-amino-1,1'-biphenyl)] palladium(II) methanesulfonate (67.8 mg, 0.085 mmol), potassium hexacyanoferrate(II)

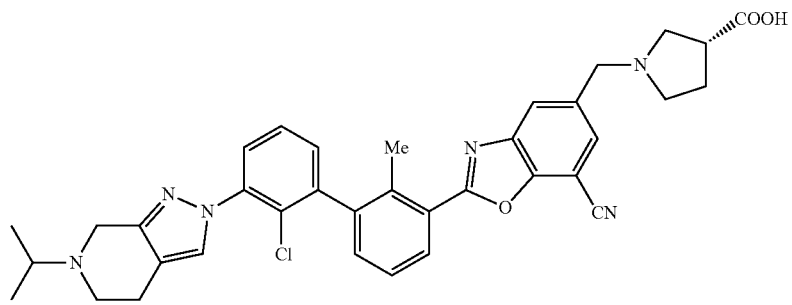 [SMILES: Cc1c(-c2nc3cc(CN4CC[C@@H](C(=O)O)C4)cc(C#N)c3o2)cccc1-c1cccc(-n2cc3c(n2)CN(C(C)C)CC3)c1Cl]

Step 1: tert-butyl 2-(3-bromo-2-chlorophenyl)-4,5-dihydro-2H-pyrazolo[3,4-c]pyridine-6(7H)-carboxylate

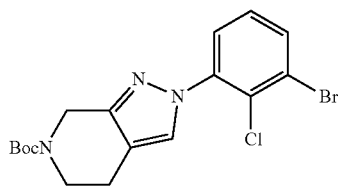 [SMILES: CC(C)(C)OC(=O)N1CCc2cn(-c3cccc(Br)c3Cl)nc2C1]

A mixture of tert-butyl 1,4,5,7-tetrahydro-6H-pyrazolo[3,4-c]pyridine-6-carboxylate (150 mg, 0.672 mmol; Astatech, cat #79248), potassium phosphate tribasic (428 mg, 2.015 mmol), 1,3-dibromo-2-chlorobenzene (363 mg, 1.344 mmol), and copper(I) iodide (12.79 mg, 0.067 mmol) was degassed and backfilled with $N_2$ 3 times. To the mixture was added trans-N,N'-dimethylcyclohexane-1,2-diamine (42.4 µl, 0.134 mmol) and toluene (2239 µl). The mixture was allowed to stir at 110° C. overnight. After cooling to rt, the mixture was filtered, concentrated and purified on silica gel column eluting with 0-80% EtOAc in hexanes to give the trihydrate (361 mg, 0.85 mmol) and potassium acetate (10.67 µl, 0.171 mmol) in 1,4-dioxane (6.0 mL) and water (6.0 mL) was purged with nitrogen and stirred at 100° C. for 1 h. After being cooled to room temperature, the reaction mixture was diluted with water and extracted with EtOAc. The combined organic layers were washed with brine, dried over $Na_2SO_4$, filtered, and concentrated under reduced pressure. The crude material was used directly for next step. LC-MS calculated for $C_{22}H_{24}BN_2O_4$ (M+H)$^+$: m/z=391.2; found 391.2.

Step 3; tert-butyl 2-(2-chloro-3'-(7-cyano-5-(hydroxymethyl)benzo[d]oxazol-2-yl)-2'-methylbiphenyl-3-yl)-4,5-dihydro-2H-pyrazolo[3,4-c]pyridine-6(7H)-carboxylate

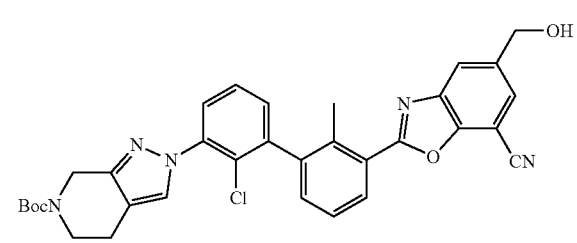 [SMILES: Cc1c(-c2nc3cc(CO)cc(C#N)c3o2)cccc1-c1cccc(-n2cc3c(n2)CN(C(=O)OC(C)(C)C)CC3)c1Cl]

(1,1'-Bis(diphenylphosphino)ferrocene)-dichloropalladium(II) (7.32 mg, 10.00 μmol) was added to a mixture of 5-(hydroxymethyl)-2-(2-methyl-3-(4,4,5,5-tetramethyl-1,3,2-dioxaborolan-2-yl)phenyl)benzo[d]oxazole-7-carbonitrile (0.039 g, 0.100 mmol), tert-butyl 2-(3-bromo-2-chlorophenyl)-4,5-dihydro-2H-pyrazolo[3,4-c]pyridine-6(7H)-carboxylate (0.041 g, 0.10 mmol), sodium carbonate (0.021 g, 0.200 mmol) in 1,4-dioxane (0.278 ml) and water (0.056 ml). The mixture was purged with $N_2$ and heated at 90° C. for 2 h. The mixture was concentrated and diluted with EtOAc and washed with water. The organic layer was dried over $Na_2SO_4$ and concentrated under reduce pressure. The residue was used in next step without further purification. LC-MS calculated for $C_{33}H_{31}ClN_5O_4$ (M+H)$^+$: m/z=596.2; found 596.3.

Step 4: tert-butyl 2-(2-chloro-3'-(7-cyano-5-formyl-benzo[d]oxazol-2-yl)-2'-methylbiphenyl-3-yl)-4,5-dihydro-2H-pyrazolo[3,4-c]pyridine-6(7H)-carboxylate

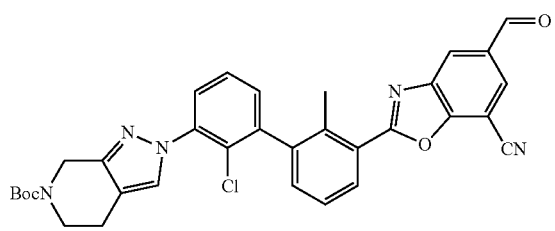 [SMILES: Cc1c(-c2nc3cc(C=O)cc(C#N)c3o2)cccc1-c1cccc(-n2cc3c(n2)CN(C(=O)OC(C)(C)C)CC3)c1Cl]

Dess-Martin periodinane (0.064 g, 0.150 mmol) was added to a DCM (0.333 ml) solution of tert-butyl 2-(2-chloro-3'-(7-cyano-5-(hydroxymethyl)benzo[d]oxazol-2-yl)-2'-methylbiphenyl-3-yl)-4,5-dihydro-2H-pyrazolo[3,4-c]pyridine-6(7H)-carboxylate (0.060 g, 0.1 mmol) and sodium bicarbonate (0.025 g, 0.300 mmol) at room temperature. After 1 h, the mixture was concentrated and purified by silica gel column eluting with 0 to 80% EtOAc in Hexanes. LC-MS calculated for $C_{33}H_{29}ClN_5O_4$ (M+H)$^+$: m/z=594.2; found 594.2.

Step 5: (R)-1-((2-(3'-(6-(tert-butoxycarbonyl)-4,5,6,7-tetrahydro-2H-pyrazolo[3,4-c]pyridin-2-yl)-2'-chloro-2-methylbiphenyl-3-yl)-7-cyanobenzo[d]oxazol-5-yl)methyl)pyrrolidine-3-carboxylic Acid

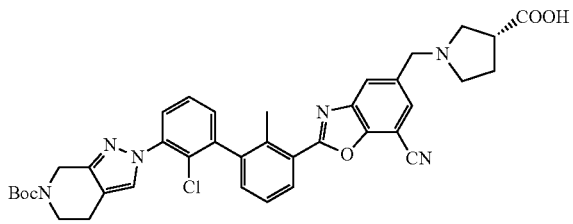 [SMILES: Cc1c(-c2nc3cc(CN4CC[C@@H](C(=O)O)C4)cc(C#N)c3o2)cccc1-c1cccc(-n2cc3c(n2)CN(C(=O)OC(C)(C)C)CC3)c1Cl]

A mixture of tert-butyl 2-(2-chloro-3'-(7-cyano-5-formyl-benzo[d]oxazol-2-yl)-2'-methylbiphenyl-3-yl)-4,5-dihydro-2H-pyrazolo[3,4-c]pyridine-6(7H)-carboxylate (15 mg, 0.025 mmol) and (R)-pyrrolidine-3-carboxylic acid (5.81 mg, 0.050 mmol), Hünig's base (8.82 μl, 0.050 mmol) in DCM (252 μl) was allowed to stir at room temperature for 2 h. Then sodium triacetoxyborohydride (8.03 mg, 0.038 mmol) was added to the mixture. After 2 h, it was diluted with DCM and washed with water and back extracted with DCM/iPrOH. The organic layers were combined and dried over sodium sulfate and concentrated and the residue was used in the next step without further purification. LC-MS calculated for $C_{38}H_{38}ClN_6O_5$ (M+H)$^+$: m/z=693.3; found 693.3.

Step 6: (R)-1-((2-(2'-chloro-2-methyl-3'-(4,5,6,7-tetrahydro-2H-pyrazolo[3,4-c]pyridin-2-yl)biphenyl-3-yl)-7-cyanobenzo[d]oxazol-5-yl)methyl)pyrrolidine-3-carboxylic Acid

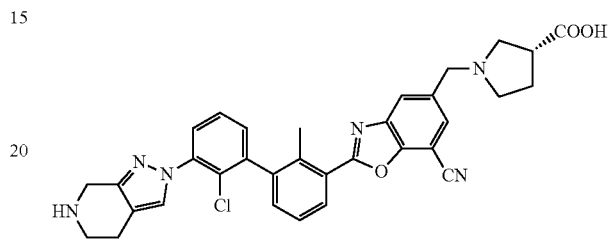

0.5 mL TFA was added to a DCM (1 mL) solution of (7?)-1-((2-(3'-(6-(tert-butoxycarbonyl)-4,5,6,7-tetrahydro-2H-pyrazolo[3,4-c]pyridin-2-yl)-2'-chloro-2-methylbiphenyl-3-yl)-7-cyanobenzo[d]oxazol-5-yl)methyl)pyrrolidine-3-carboxylic acid (14 mg, 0.025 mmol) at room temperature. After 1 h, the mixture was concentrated and used in next step without further purification. LC-MS calculated for $C_{33}H_{30}ClN_6O_3$ (M+H)$^+$: m/z=593.2; found 593.1.

Step 7: (R)-1-((2-(2'-chloro-3'-(6-isopropyl-4,5,6,7-tetrahydro-2H-pyrazolo[3,4-c]pyridin-2-yl)-2-methylbiphenyl-3-yl)-7-cyanobenzo[d]oxazol-5-yl)methyl)pyrrolidine-3-carboxylic Acid A mixture of (7?)-1-((2-(2'-chloro-2-methyl-3'-(4,5,6,7-tetrahydro-2H-pyrazolo[3,4-c]pyridin-2-yl)biphenyl-3-yl)-7-cyanobenzo[d]oxazol-5-yl)methyl)pyrrolidine-3-carboxylic acid (10 mg, 0.017 mmol) and acetone (2.4 μL, 0.034 mmol) in DCM (169 μl) was allowed to stir for 2 h. Then sodium triacetoxyborohydride (7.0 mg, 0.034 mmol) was added to the mixture. After 2 h, the mixture was concentrated and diluted with MeOH and then purified by prep-HPLC (pH=2, acetonitrile/water+TFA) to give the desired product as its TFA salt. LC-MS calculated for $C_{36}H_{36}ClN_6O_3$ (M+H)$^+$: m/z=635.2; found 635.3.

Example 13

N,N'-(2-chloro-2'-cyanobiphenyl-3,3'-diyl)bis(1-methyl-4,5,6,7-tetrahydro-1H-imidazo[4,5-c]pyridine-2-carboxamide)

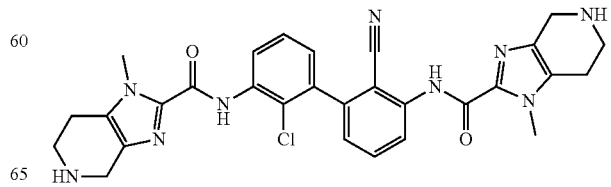

Step 1: tert-butyl 1-methyl-1,4,6,7-tetrahydro-5H-imidazo[4,5-c]pyridine-5-carboxylate

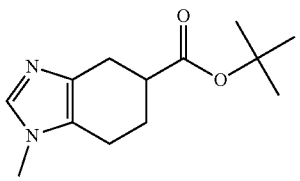 [SMILES: Cn1cnc2c1CCC(C(=O)OC(C)(C)C)C2]

A solution of 1-methyl-4,5,6,7-tetrahydro-1H-imidazo[4,5-c]pyridine (Accela, cat # SY032476: 2.0 g, 14.58 mmol), (Boc)$_2$O (3.38 mL, 14.58 mmol) in dichloromethane (60 mL) was stirred at room temperature for 1 h. The reaction was quenched with saturated aqueous NaHCO$_3$ solution, and extracted with ethyl acetate. The combined organic layers were washed with brine, dried over Na$_2$SO$_4$, filtered, and concentrated under reduced pressure. The crude product was used for next step without further purification. LCMS calculated for C$_{12}$H$_{20}$N$_3$O$_2$ (M+H)$^+$: m/z=238.2; found 238.2.

Step 2: tert-butyl 2-methyl 1-methyl-1,4,6,7-tetrahydro-5H-imidazo[4,5-c]pyridine-2,5-dicarboxylate

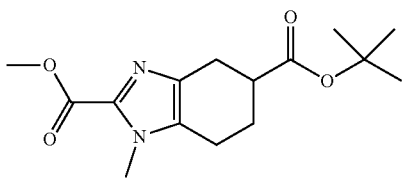

n-Butyllithium in hexanes (2.5 M, 7.0 mL, 17.49 mmol) was added to a cold (−78° C.) solution of the crude product from Step 1 in tetrahydrofuran (60.0 mL). The reaction mixture was stirred at −78° C. for 10 min prior to the addition of methyl chloroformate (1.7 mL, 21.9 mmol). After being stirred at −78° C. for 30 min, the reaction was then quenched with saturated aqueous NaHCO$_3$ solution, and extracted with ethyl acetate. The combined organic layers were washed with brine, dried over Na$_2$SO$_4$, filtered, and concentrated under reduced pressure. The residue was purified by flash chromatography on a silica gel column eluting with 80% ethyl acetate in hexanes to afford the desired product (2.1 g). LCMS calculated for C$_{14}$H$_{22}$N$_3$O$_4$ (M+H)$^+$: m/z=296.2; found 296.3.

Step 3: tert-butyl 2-((3-bromo-2-cyanophenyl)carbamoyl)-1-methyl-1,4,6,7-tetrahydro-5H-imidazo[4,5-c]pyridine-5-carboxylate

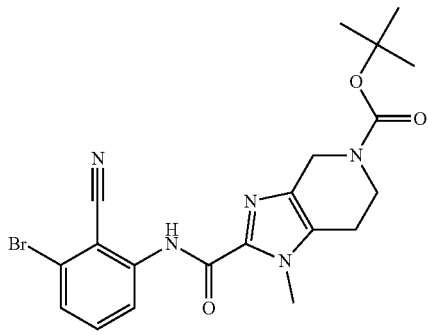 [SMILES: Cn1c(C(=O)Nc2cccc(Br)c2C#N)nc2c1CCN(C(=O)OC(C)(C)C)C2]

Potassium tert-butoxide in tetrahydrofuran (1.0 M, 0.677 mL, 0.677 mmol) was added to a solution of tert-butyl 2-methyl 1-methyl-1,4,6,7-tetrahydro-5H-imidazo[4,5-c]pyridine-2,5-dicarboxylate (Step 2: 100 mg, 0.339 mmol) and 2-amino-6-bromobenzonitrile (66.7 mg, 0.339 mmol) in tetrahydrofuran (13.5 mL). After being stirred at room temperature for 1 h, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 50% ethyl acetate in hexanes to afford the desired product (140 mg, 90% yield). LCMS calculated for C$_{20}$H$_{23}$BrN$_5$O$_3$ (M+H)$^+$: m/z=460.1/462.1; found 460.2/462.2.

Step 4: 2-chloro-3-(4,4,5,5-tetramethyl-1,3,2-dioxaborolan-2-yl)aniline

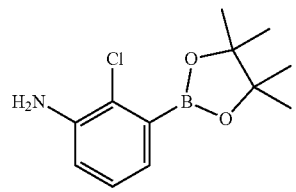 [SMILES: CC1(C)OB(c2cccc(N)c2Cl)OC1(C)C]

A mixture of 3-bromo-2-chloroaniline (1.0 g, 4.84 mmol), 4,4,5,5,4',4',5',5'-octamethyl-[2,2']bi[[1,3,2]dioxaborolanyl] (1.48 g, 5.81 mmol), [1,1'-bis(diphenylphosphino)ferrocene]dichloropalladium(II) complexed with dichloromethane (1:1) (0.40 g, 0.484 mmol) and potassium acetate (1.43 g, 14.53 mmol) in 1,4-dioxane (24.2 mL) was purged with nitrogen and then stirred at 100° C. for 2 h. The reaction mixture was cooled to room temperature, diluted with dichloromethane and then filtered through Celite. The filtrate was concentrated, and the residue was purified by flash chromatography on a silica gel column eluting with 30% ethyl acetate in hexanes to afford the desired product (0.85 g, 69% yield). LC-MS calculated for C$_{12}$H$_{18}$BClNO$_2$ (M+H)$^+$: m/z=254.1; found 254.1.

Step 5: tert-butyl 2-((3'-amino-2'-chloro-2-cyano-[1,1'-biphenyl]-3-yl)carbamoyl)-1-methyl-1,4,6,7-tetrahydro-5H-imidazo[4,5-c]pyridine-5-carboxylate

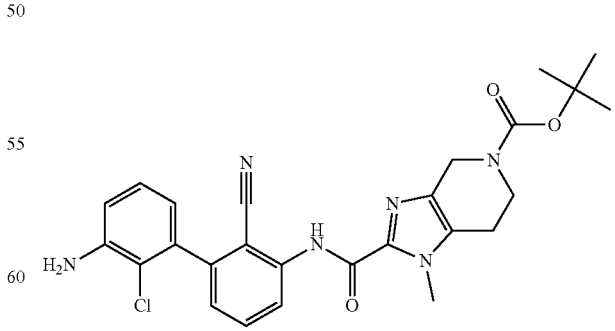

A mixture of tert-butyl 2-((3-bromo-2-cyanophenyl)carbamoyl)-1-methyl-1,4,6,7-tetrahydro-5H-imidazo[4,5-c]pyridine-5-carboxylate (Step 3: 300 mg, 0.652 mmol), 2-chloro-3-(4,4,5,5-tetramethyl-1,3,2-dioxaborolan-2-yl)

aniline (Step 4: 198 mg, 0.782 mmol), sodium carbonate (207 mg, 1.955 mmol) and [1,1'-bis(di-cyclohexylphosphino)ferrocene]dichloropalladium(II) (99 mg, 0.130 mmol) in 1,4-dioxane (3.0 mL) and water (3.0 mL) was purged with nitrogen and then stirred at 110° C. for 3 h. The reaction mixture was diluted with water and extracted with ethyl acetate. The combined organic layers were washed with brine, dried over $Na_2SO_4$, filtered, and concentrated under reduced pressure. The residue was purified by flash chromatography on a silica gel column eluting with 60% ethyl acetate in hexanes to afford the desired product (249 mg, 75% yield). LC-MS calculated for $C_{26}H_{28}ClN_6O_3$ $(M+H)^+$: m/z=507.2; found 507.2.

Step 6: N,N'-(2-chloro-2'-cyanobiphenyl-3,3'-diyl) bis(l-methyl-4,5,6,7-tetrahydro-1H-imidazo[4,5-c] pyridine-2-carboxamide)

Potassium tert-butoxide in tetrahydrofuran (1.0 M, 39.4 µL, 0.039 mmol) was added to a solution of tert-butyl 2-((3'-amino-2'-chloro-2-cyano-[1,1'-biphenyl]-3-yl)carbamoyl)-1-methyl-1,4,6,7-tetrahydro-5H-imidazo[4,5-c] pyridine-5-carboxylate (Step 5:10 mg, 0.020 mmol) and tert-butyl 2-methyl 1-methyl-1,4,6,7-tetrahydro-5H-imidazo [4,5-c]pyridine-2,5-dicarboxylate (Step 2: 7.0 mg, 0.024 mmol) in tetrahydrofuran (0.10 mL), and the reaction was stirred at room temperature for 1 h. 4.0 M hydrogen chloride in 1,4-dioxane (0.10 mL, 0.394 mmol) was added. After being stirred at 50° C. for 2 h, the reaction mixture was concentrated and purified by prep-HPLC (pH=2, acetonitrile/water+TFA) to give the desired product as the TFA salt. LCMS calculated for $C_{29}H_{29}ClN_9O_2$ $(M+H)^+$: m/z=570.2; found 570.2. $^1H$ NMR (600 MHz, DMSO-$d_6$) δ 10.53 (s, 1H), 9.97 (s, 1H), 9.21 (br, 2H), 8.34 (dd, J=8.3, 1.5 Hz, 1H), 7.92 (dd, J=8.3, 1.0 Hz, 1H), 7.83 (t, J=8.0 Hz, 1H), 7.55 (t, J=7.9 Hz, 1H), 7.37 (dd, J=7.6, 1.0 Hz, 1H), 7.27 (dd, J=7.6, 1.6 Hz, 1H), 4.23-4.20 (m, 4H), 3.96 (s, 3H), 3.92 (s, 3H), 3.49 (m, 4H), 2.99-2.93 (m, 4H) ppm.

Example 14

N-(2-chloro-2'-cyano-3'-(3-methyl-4,5,6,7-tetrahydro-3H-imidazo[4,5-c]pyridine-2-carboxamido)-[1,1'-biphenyl]-3-yl)-4,5,6,7-tetrahydrothiazolo[5,4-c]pyridine-2-carboxamide

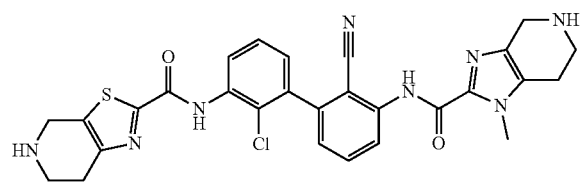 [SMILES: Cn1c(C(=O)Nc2cccc(-c3cccc(NC(=O)c4nc5c(s4)CNCC5)c3Cl)c2C#N)nc2c1CCNC2]

This compound was prepared using similar procedures as described for Example 13 with 5-(tert-butyl) 2-methyl 6,7-dihydrothiazolo[5,4-c]pyridine-2,5(4H)-dicarboxylate replacing tert-butyl 2-methyl 1-methyl-1,4,6,7-tetrahydro-5H-imidazo[4,5-c]pyridine-2,5-dicarboxylate in Step 6. The reaction mixture was purified by prep-HPLC (pH=2, acetonitrile/water+TFA) to give the desired product as the TEA salt. LCMS calculated for $C_{28}H_{26}ClN_8O_2S$ $(M+H)^+$: m/z=573.2; found 573.2.

Example 15

N-(2'-chloro-2-cyano-3'-(5,6,7,8-tetrahydroimidazo [1,2-a]pyrazine-2-carboxamido)biphenyl-3-yl)-1-methyl-4,5,6,7-tetrahydro-1H-imidazo[4,5-c]pyridine-2-carboxamide

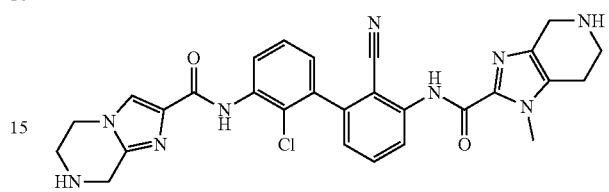

This compound was prepared using similar procedures as described for Example 13 with ethyl 5,6,7,8-tetrahydroimidazo[1,2-a]pyrazine-2-carboxylate replacing tert-butyl 2-methyl 1-methyl-1,4,6,7-tetrahydro-5H-imidazo[4,5-c] pyridine-2,5-dicarboxylate in Step 6. The reaction mixture was purified by prep-HPLC (pH=2, acetonitrile/water+TFA) to give the desired product as the TEA salt. LCMS calculated for $C_{28}H_{27}ClN_9O_2$ $(M+H)^+$: m/z=556.2; found 556.4.

Example 16

N-(2'-chloro-2-cyano-3'-(4,5,6,7-tetrahydropyrazolo [1,5-a]pyrazine-2-carboxamido)biphenyl-3-yl)-1-methyl-4,5,6,7-tetrahydro-1H-imidazo[4,5-c]pyridine-2-carboxamide

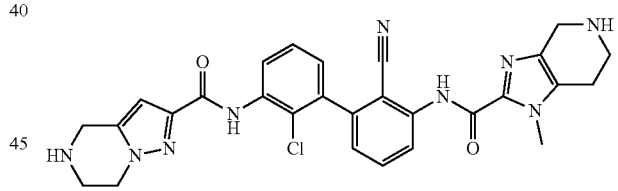

N,N-diisopropylethylamine (10.3 µL, 0.059 mmol) was added to a solution of 5-(tert-butoxycarbonyl)-4,5,6,7-tetrahydropyrazolo[1,5-a]pyrazine-2-carboxylic acid (AstaTech, cat #74720: 10.5 mg, 0.039 mmol), 1-[bis(dimethylamino) methylene]-1H-1,2,3-triazolo[4,5-b]pyridinium 3-oxide hexafluorophosphate (18.7 mg, 0.049 mmol) in DMF (0.3 mL), and the reaction mixture was stirred at room temperature for 15 min. Tert-butyl 2-((3'-amino-2'-chloro-2-cyano-[1,1'-biphenyl]-3-yl)carbamoyl)-1-methyl-1,4,6,7-tetrahydro-5H-imidazo[4,5-c]pyridine-5-carboxylate (Example 13, Step 5: 10 mg, 0.020 mmol) was added, and the reaction was stirred at room temperature for 2 h. 4.0 M hydrogen chloride in 1,4-dioxane (0.10 mL, 0.394 mmol) was added. After being stirred at 50° C. for 2 h, the reaction mixture was concentrated and purified by prep-HPLC (pH=2, acetonitrile/water+TFA) to give the desired product as the TFA salt. LCMS calculated for $C_{28}H_{27}ClN_9O_2$ $(M+H)^+$: m/z=556.2; found 556.2.

Example 17

N,N'-(2,2'-dichlorobiphenyl-3,3'-diyl)bis(1-methyl-4,5,6,7-tetrahydro-1H-imidazo[4,5-c]pyridine-2-carboxamide)

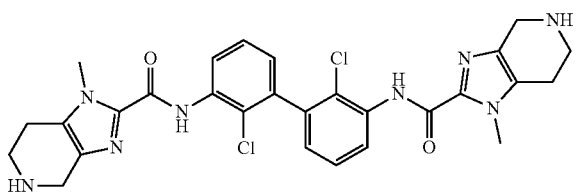 [SMILES: Cn1c(C(=O)Nc2cccc(-c3cccc(NC(=O)c4nc5c(n4C)CCNC5)c3Cl)c2Cl)nc2c1CCNC2]

This compound was prepared using similar procedures as described for Example 13 with 3-bromo-2-chloroaniline replacing 2-amino-6-bromobenzonitrile in Step 3. The reaction mixture was purified by prep-HPLC (pH=2, acetonitrile/water+TFA) to give the desired product as the TEA salt. LCMS calculated for $C_{28}H_{29}Cl_2N_8O_2$ $(M+H)^+$: m/z=579.2; found 579.3.

Example 18

N,N'-(2-chloro-2'-methyl-[1,1'-biphenyl]-3,3'-diyl)bis(l-methyl-4,5,6,7-tetrahydro-1H-imidazo[4,5-c]pyridine-2-carboxamide)

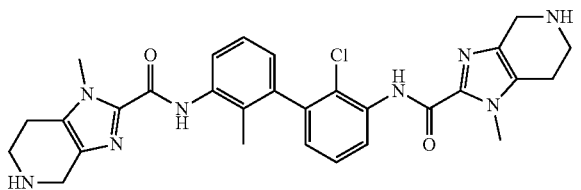 [SMILES: Cc1c(NC(=O)c2nc3c(n2C)CCNC3)cccc1-c1cccc(NC(=O)c2nc3c(n2C)CCNC3)c1Cl]

This compound was prepared using similar procedures as described for Example 13 with 3-bromo-2-chloroaniline replacing 2-amino-6-bromobenzonitrile in Step 3 and with 2-methyl-3-(4,4,5,5-tetramethyl-1,3,2-dioxaborolan-2-yl)aniline replacing 2-chloro-3-(4,4,5,5-tetramethyl-1,3,2-dioxaborolan-2-yl)aniline in Step 5. The reaction mixture was purified by prep-HPLC (pH=2, acetonitrile/water+TFA) to give the desired product as the TFA salt. LCMS calculated for $C_{29}H_{32}ClN_8O_2$ $(M+H)^+$: m/z=559.2; found 559.4.

Example 19

N-(2-chloro-2'-cyano-3'-(1,5-dimethyl-4,5,6,7-tetrahydro-1H-imidazo[4,5-c]pyridine-2-carboxamido)biphenyl-3-yl)-5-methyl-4,5,6,7-tetrahydrothiazolo[5,4-c]pyridine-2-carboxamide

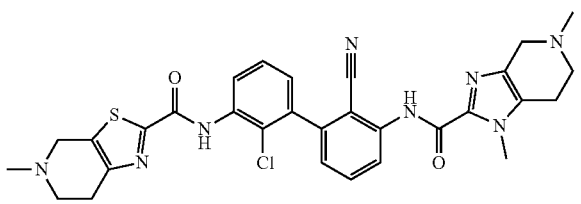

N,N-diisopropylethylamine (9.2 μL, 0.052 mmol) was added to a suspension of N-(2-chloro-2'-cyano-3'-(3-methyl-4,5,6,7-tetrahydro-3H-imidazo[4,5-c]pyridine-2-carboxamido)-[1,1'-biphenyl]-3-yl)-4,5,6,7-tetrahydrothiazolo[5,4-c]pyridine-2-carboxamide (Example 14: 6 mg, 10.47 μmol) and 37 wt. % formaldehyde in water (6.2 μL, 0.084 mmol) in tetrahydrofuran (0.10 mL). After being stirred at room temperature for 30 min, sodium triacetoxyborohydride (11.1 mg, 0.052 mmol) was added, and the reaction mixture was stirred at room temperature for 1 h. The reaction mixture was diluted with methanol and purified by prep-HPLC (pH=2, acetonitrile/water+TFA) to give the desired product as the TEA salt. LCMS calculated for $C_{30}H_{30}ClN_8O_2S$ $(M+H)^+$: m/z=601.2; found 601.3.

Example 20

N,N'-(2-chloro-2'-cyanobiphenyl-3,3'-diyl)bis(1,5-dimethyl-4,5,6,7-tetrahydro-1H-imidazo[4,5-c]pyridine-2-carboxamide)

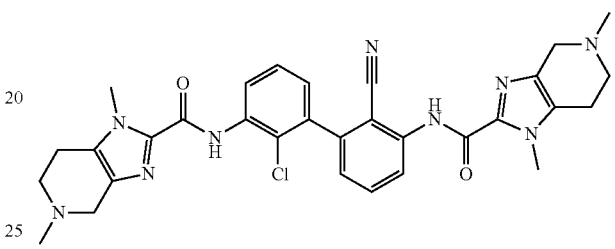

This compound was prepared using similar procedures as described for Example 19 with N,N'-(2-chloro-2'-cyanobiphenyl-3,3'-diyl)bis(l-methyl-4,5,6,7-tetrahydro-1H-imidazo[4,5-c]pyridine-2-carboxamide) (Example 13) replacing N-(2-chloro-2'-cyano-3'-(3-methyl-4,5,6,7-tetrahydro-3H-imidazo[4,5-c]pyridine-2-carboxamido)-[1,1'-biphenyl]-3-yl)-4,5,6,7-tetrahydrothiazolo[5,4-c]pyridine-2-carboxamide. The reaction mixture was purified by prep-HPLC (pH=2, acetonitrile/water+TFA) to give the desired product as the TFA salt. LCMS calculated for $C_{31}H_{33}ClN_9O_2$ $(M+H)^+$: m/z=598.2; found 598.2.

Example 21

N,N'-(2-chloro-2'-methylbiphenyl-3,3'-diyl)bis(1,5-dimethyl-4,5,6,7-tetrahydro-1H-imidazo[4,5-c]pyridine-2-carboxamide)

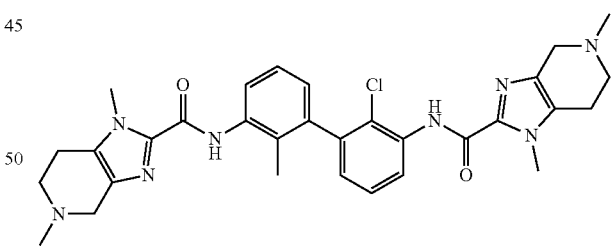

This compound was prepared using similar procedures as described for Example 19 with N,N'-(2-chloro-2'-methyl-[1,1'-biphenyl]-3,3'-diyl)bis(l-methyl-4,5,6,7-tetrahydro-1H-imidazo[4,5-c]pyridine-2-carboxamide) (Example 18) replacing N-(2-chloro-2'-cyano-3'-(3-methyl-4,5,6,7-tetrahydro-3H-imidazo[4,5-c]pyridine-2-carboxamido)-[1,1'-biphenyl]-3-yl)-4,5,6,7-tetrahydrothiazolo[5,4-c]pyridine-2-carboxamide. The reaction mixture was purified by prep-HPLC (pH=2, acetonitrile/water+TFA) to give the desired product as the TFA salt. LCMS calculated for $C_{31}H_{36}ClN_8O_2$ $(M+H)^+$: m/z=587.3; found 587.2. $^1$H NMR (500 MHz, DMSO) δ 9.95 (s, 1H), 9.92 (s, 1H), 8.22 (dd, J=8.3, 1.5 Hz, 1H), 7.61 (d, J=7.8 Hz, 1H), 7.48 (t, J=7.9 Hz, 1H), 7.31 (t, J=7.8 Hz, 1H), 7.11 (dd, J=7.6, 1.6 Hz, 1H), 7.04 (dd, J=7.7, 1.3 Hz, 1H), 4.63-4.03 (m, 4H), 3.95 (s, 3H), 3.91 (s, 3H), 3.84-3.33 (m, 4H), 3.11-2.98 (m, 4H), 2.97 (s, 3H), 2.96 (s, 3H), 1.98 (s, 3H).

Example 22

(S)—N,N'-(2-chloro-2'-methylbiphenyl-3,3'-diyl)bis(5-((S)-2-hydroxypropyl)-1-methyl-4,5,6,7-tetrahydro-1H-imidazo[4,5-c]pyridine-2-carboxamide)

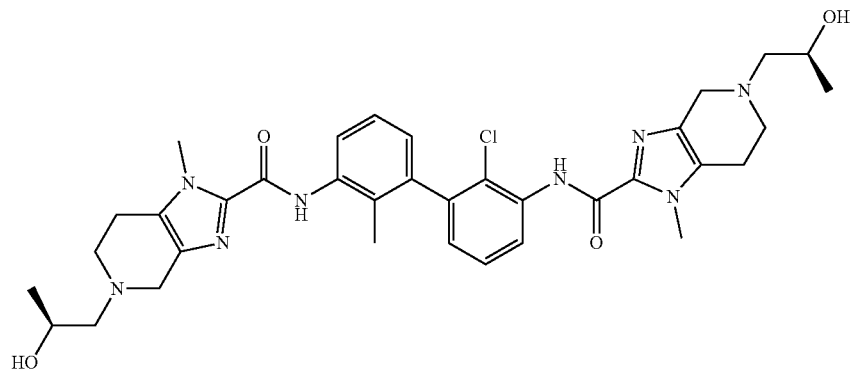 [SMILES: Cc1c(NC(=O)c2nc3c(n2C)CCN(C[C@H](C)O)C3)cccc1-c1cccc(NC(=O)c2nc3c(n2C)CCN(C[C@H](C)O)C3)c1Cl]

N,N-diisopropylethylamine (4.7 μL, 0.027 mmol) was added to a suspension of N,N'-(2-chloro-2'-methyl-[1,1'-biphenyl]-3,3'-diyl)bis(1-methyl-4,5,6,7-tetrahydro-1H-imidazo[4,5-c]pyridine-2-carboxamide) (Example 18: 5.0 mg, 8.94 μmol) and (S)-2-((tert-butyldimethylsilyl)oxy)propanal (Oakwood, cat #048933: 8.4 mg, 0.045 mmol) in tetrahydrofuran (0.05 mL), and the reaction was stirred at room temperature for 30 min. Sodium cyanoborohydride (3.0 mg, 0.045 mmol) was then added. After being stirred at room temperature for 2 h, the reaction was treated with 2 N HCl (aq.) solution (0.10 mL) and stirred at 50° C. for 30 min. The reaction was was concentrated and purified by prep-HPLC (pH=10, acetonitrile/water+NH$_4$OH) to give the desired product. LCMS calculated for C$_{35}$H44ClN$_8$O$_4$ (M+H)$^+$: m/z=675.3; found 675.3

Example 23

N,N'-(2-chloro-2'-methylbiphenyl-3,3'-diyl)bis(5-(2-hydroxyethyl)-1-methyl-4,5,6,7-tetrahydro-1H-imidazo[4,5-c]pyridine-2-carboxamide)


This compound was prepared using similar procedures as described for Example 22 with 2-((tert-butyldimethylsilyl)oxy)acetaldehyde replacing (S)-2-((tert-butyldimethylsilyl)oxy)propanal. The reaction mixture was purified by prep-HPLC (pH=2, acetonitrile/water+TFA) to give the desired product as the TFA salt. LCMS calculated for C$_{33}$H$_{40}$ClN$_8$O$_4$ (M+H)$^+$: m/z=647.3; found 647.2.

Example 24

(S)—N-(2'-chloro-3'-(1,5-dimethyl-4,5,6,7-tetrahydro-1H-imidazo[4,5-c]pyridine-2-carboxamido)-2-methylbiphenyl-3-yl)-5-(2-hydroxypropyl)-1-methyl-4,5,6,7-tetrahydro-1H-imidazo[4,5-c]pyridine-2-carboxamide

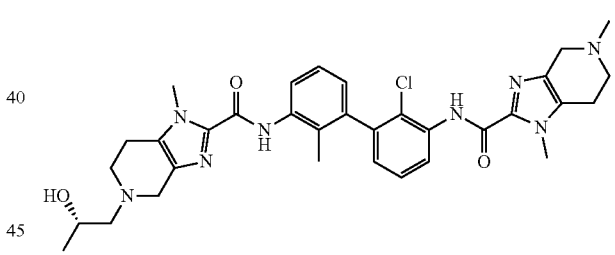

Step 1: tert-butyl 2-((3-bromo-2-chlorophenyl)car-bamoyl)-1-methyl-1,4,6,7-tetrahydro-5H-imidazo[4,5-c]pyridine-5-carboxylate

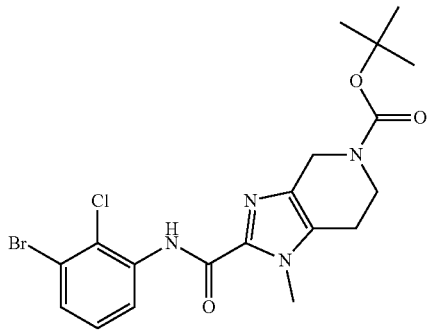

Potassium tert-butoxide in tetrahydrofuran (1.0 M, 5.42 ml, 5.42 mmol) was added to a solution of tert-butyl 2-methyl 1-methyl-1,4,6,7-tetrahydro-5H-imidazo[4,5-c]pyridine-2,5-dicarboxylate (Example 13, Step 2: 800 mg, 2.71 mmol) and 3-bromo-2-chloroaniline (559 mg, 2.71 mmol) in tetrahydrofuran (13.5 ml). After being stirred at room temperature for 1 h, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 50% ethyl acetate in hexanes to afford the desired product (1.15 g, 90% yield). LCMS calculated for C$_{19}$H$_{23}$BrClN$_4$O$_3$ (M+H)$^+$: m/z=469.1/471.1; found 469.1/471.1.

Step 2: N-(3-bromo-2-chlorophenyl)-1,5-dimethyl-4,5,6,7-tetrahydro-1H-imidazo[4,5-c]pyridine-2-carboxamide

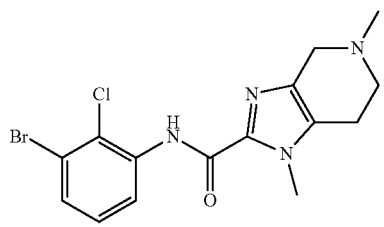 [SMILES: CN1CCc2c(nc(C(=O)Nc3cccc(Br)c3Cl)n2C)C1]

A solution of tert-butyl 2-((3-bromo-2-chlorophenyl)car-bamoyl)-1-methyl-1,4,6,7-tetrahydro-5H-imidazo[4,5-c]pyridine-5-carboxylate (Step 1: 300 mg, 0.64 mmol) in trifluoroacetic acid (0.2 mL) and dichloromethane (0.4 mL) was stirred at room temperature for 1 h. The solvent was evaporated, and the residue was dissolved in tetrahydrofuran (1.0 mL). 37 wt. % formaldehyde in water (0.48 mL, 6.39 mmol) and sodium triacetoxyborohydride (406 mg, 1.92 mmol) were successively added. After being stirred at room temperature for 1 h, the mixture was quenched with sat. NaHCO$_3$ solution, and extracted with dichloromethane. The combined organic layers were dried over Na$_2$SO$_4$, filtered and concentrated under reduced pressure. The residue was purified by flash chromatography on a silica gel column eluting with 10% methanol in dichloromethane to afford the desired product. LCMS calculated for C$_{15}$H$_{17}$BrClN$_4$O (M+H)$^+$: m/z=383.0/385.0; found 383.0/385.0.

Step 3: tert-butyl 2-((3-bromo-2-methylphenyl)car-bamoyl)-1-methyl-1,4,6,7-tetrahydro-5H-imidazo[4,5-c]pyridine-5-carboxylate

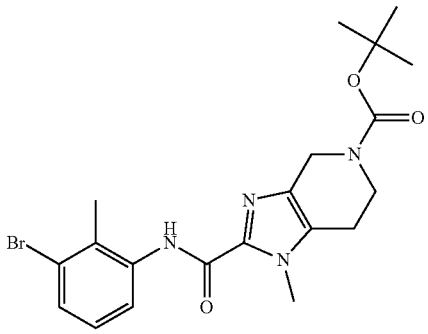 [SMILES: Cc1c(Br)cccc1NC(=O)c1nc2c(n1C)CCN(C(=O)OC(C)(C)C)C2]

Potassium tert-butoxide in tetrahydrofuran (1.0 M, 13.54 mL, 13.54 mmol) was added to a solution of tert-butyl 2-methyl 1-methyl-1,4,6,7-tetrahydro-5H-imidazo[4,5-c]pyridine-2,5-dicarboxylate (Example 13, Step 2: 2.00 g, 6.77 mmol) and 3-bromo-2-methylaniline (1.26 g, 6.77 mmol) in tetrahydrofuran (34.0 mL). After being stirred at room temperature for 1 h, the reaction mixture was quenched with water, and extracted with ethyl acetate. The combined organic layers were washed with brine, dried over Na$_2$SO$_4$, filtered, and concentrated under reduced pressure. The residue was purified by flash chromatography on a silica gel column eluting with 50% ethyl acetate in hexanes to afford the desired product (2.82 g, 93% yield). LC-MS calculated for C$_{20}$H$_{26}$BrN$_4$O$_3$ (M+H)$^+$: m/z=449.1/451.1; found 449.1/451.1.

Step 4; tert-butyl 1-methyl-2-((2-methyl-3-(4,4,5,5-tetramethyl-1,3,2-dioxaborolan-2-yl)phenyl)carbam-oyl)-1,4,6,7-tetrahydro-5H-imidazo[4,5-c]pyridine-5-carboxylate

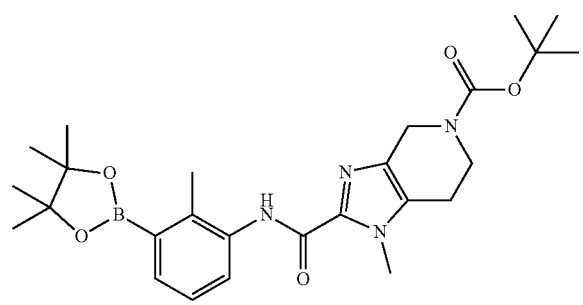 [SMILES: Cc1c(NC(=O)c2nc3c(n2C)CCN(C(=O)OC(C)(C)C)C3)cccc1B1OC(C)(C)C(C)(C)O1]

A mixture of tert-butyl 2-((3-bromo-2-methylphenyl)car-bamoyl)-1-methyl-1,4,6,7-tetrahydro-5H-imidazo[4,5-c]pyridine-5-carboxylate (Step 3: 600 mg, 1.34 mmol), 4,4,5,5,4',4',5',5'-octamethyl-[2,2']bi[[1,3,2]dioxaborolanyl] (509 mg, 2.00 mmol), [1,1'-bis(diphenylphosphino)ferrocene]di-chloropalladium(II) complexed with dichloromethane (1:1) (109 mg, 0.14 mmol) and potassium acetate (393 mg, 4.01 mmol) in 1,4-dioxane (12.5 mL) was purged with nitrogen and then stirred at 100° C. for 2 h. The reaction mixture was cooled to room temperature, diluted with dichloromethane, and then filtered through Celite. The filtrate was concentrated, and the residue was purified by flash chromatography on a silica gel column eluting with 30% ethyl acetate in hexanes to afford the desired product. LC-MS calculated for $C_{26}H_{38}BN_4O_5$ (M+H)$^+$: m/z=497.3; found 497.3.

Step 5: tert-butyl 2-((2'-chloro-3'-(1,5-dimethyl-1,4,6,7-tetrahydro-1H-imidazo[4f-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate

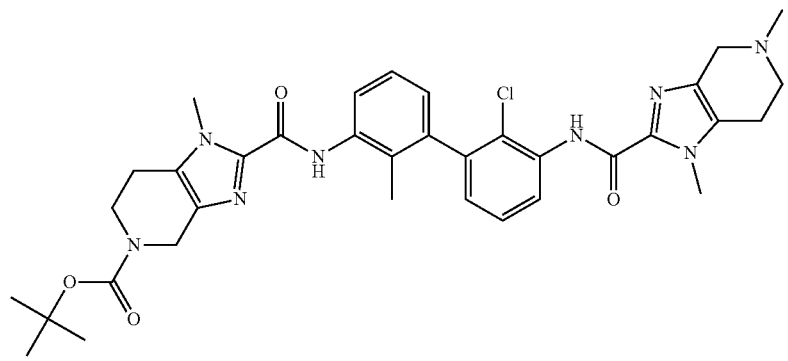 [SMILES: Cc1c(NC(=O)c2nc3c(n2C)CCN(C(=O)OC(C)(C)C)C3)cccc1-c1cccc(NC(=O)c2nc3c(n2C)CCN(C)C3)c1Cl]

A mixture of N-(3-bromo-2-chlorophenyl)-1,5-dimethyl-4,5,6,7-tetrahydro-1H-imidazo[4,5-c]pyridine-2-carboxamide (Step 2: 450 mg, 1.17 mmol), tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate (Step 4: 699 mg, 1.41 mmol), [1,1'-bis(di-cyclohexylphosphino)ferrocene]dichloropalladium (II) (89 mg, 0.12 mmol) and sodium carbonate (373 mg, 3.52 mmol) in 1,4-dioxane (6 mL) and water (6 mL) was purged with nitrogen and then stirred at 110° C. for 3 h. The reaction mixture was cooled to room temperature, diluted with water and extracted with ethyl acetate. The combined organic layers were washed with brine, dried over $Na_2SO_4$, filtered, and concentrated under reduced pressure. The residue was purified by flash chromatography on a silica gel column eluting with 10% methanol in dichloromethane to afford the desired product. LC-MS calculated for $C_{35}H_{42}ClN_8O_4$ (M+H)$^+$: m/z=673.3; found 673.3.

Step 6: (S)—N-(2'-chloro-3'-(1,5-dimethyl-4,5,6,7-tetrahydro-1H-imidazo[4,5-c]pyridine-2-carboxamido)-2-methylbiphenyl-3-yl)-5-(2-hydroxypropyl)-1-methyl-4,5,6,7-tetrahydro-1H-imidazo[4,5-c]pyridine-2-carboxamide A solution of tert-butyl 2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Step 5: 10 mg, 0.015 mmol) in dichloromethane (0.05 mL) and trifluoroacetic acid (0.05 mL) was stirred at room temperature for 30 min. The mixture was concentrated under reduced pressure. The residue was dissolved in tetrahydrofuran (0.10 mL) then successively treated with N,N-diisopropylethylamine (13.0 µL, 0.074 mmol) and (S)-2-(((tert-butyldimethylsilyl)oxy)propanal (Oakwood, cat #048933: 8.4 mg, 0.045 mmol). The reaction mixture was stirred at room temperature for 30 min. Sodium triacetoxyborohydride (9.44 mg, 0.045 mmol) was then added. After being stirred at room temperature for 2 h, the reaction mixture was treated with 2 N HCl (aq.) solution (0.20 mL) and stirred at 50° C. for 30 min. The reaction mixture was concentrated and then purified by prep-HPLC (pH=2, acetonitrile/water+TFA) to give the desired product as the TFA salt. LC-MS calculated for $C_{33}H_{40}ClN_8O_3$ (M+H)$^+$: m/z=631.3; found 631.5. $^1$H NMR (600 MHz, DMSO-$d_6$) δ 9.95 (br, 1H), 9.89 (br, 1H), 8.22 (dd, J=8.2, 1.6 Hz, 1H), 7.66-7.59 (m, 1H), 7.48 (t, J=7.9 Hz, 1H), 7.32 (t, J=7.8 Hz, 1H), 7.11 (dd, J=7.6, 1.5 Hz, 1H), 7.04 (dd, J=7.7, 1.3 Hz, 1H), 4.53-4.11 (m, 5H), 3.95 (s, 3H), 3.91 (s, 3H), 3.85-3.00 (m, 10H), 2.95 (s, 3H), 1.98 (s, 3H), 1.14 (d, 6.2 Hz, 3H).

Example 25

(R)—N-(2'-chloro-3'-(1,5-dimethyl-4,5,6,7-tetrahydro-1H-imidazo[4,5-c]pyridine-2-carboxamido)-2-methylbiphenyl-3-yl)-5-(2-hydroxypropyl)-1-methyl-4,5,6,7-tetrahydro-1H-imidazo[4,5-c]pyridine-2-carboxamide

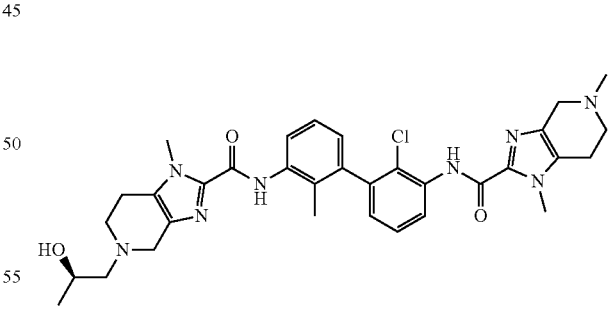

This compound was prepared using similar procedures as described for Example 24 with (R)-2-((tert-butyldimethylsilyl)oxy)propanal (Aurum, cat # U24448) replacing (S)-2-((tert-butyldimethylsilyl)oxy)propanal in Step 6. The reaction mixture was purified by prep-HPLC (pH=2, acetonitrile/water+TFA) to give the desired product as the TEA salt. LC-MS calculated for $C_{33}H_{40}ClN_8O_3$ (M+H)$^+$: m/z=631.3; found 631.4.

Example 26

(S)—N-(2-chloro-3'-(1,5-dimethyl-4,5,6,7-tetra-hydro-1H-imidazo[4,5-c]pyridine-2-carboxamido)-2'-methylbiphenyl-3-yl)-5-(2-hydroxypropyl)-1-methyl-4,5,6,7-tetrahydro-1H-imidazo[4,5-c]pyridine-2-carboxamide

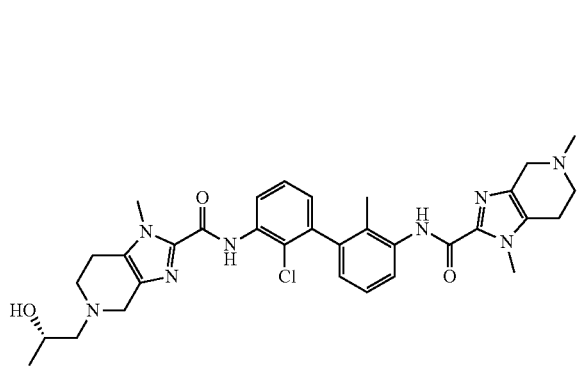 [SMILES: Cc1c(NC(=O)c2nc3c(n2C)CCN(C)C3)cccc1-c1cccc(NC(=O)c2nc3c(n2C)CCN(C[C@H](C)O)C3)c1Cl]

This compound was prepared using similar procedures as described for Example 24 with 3-bromo-2-methylaniline replacing 3-bromo-2-chloroaniline in Step 1 and 3-bromo-2-chloroaniline replacing 3-bromo-2-methylaniline in Step 3. The reaction mixture was purified by prep-HPLC (pH=2, acetonitrile/water+TFA) to give the desired product as the TFA salt. LC-MS calculated for $C_{33}H_{40}ClN_8O_3$ (M+H)$^+$: m/z=631.3; found 631.4.

Example 27

(S)—N-(2,2'-dichloro-3'-(1,5-dimethyl-4,5,6,7-tetra-hydro-1H-imidazo[4,5-c]pyridine-2-carboxamido)biphenyl-3-yl)-5-(2-hydroxypropyl)-1-methyl-4,5,6,7-tetrahydro-1H-imidazo[4,5-c]pyridine-2-carboxamide

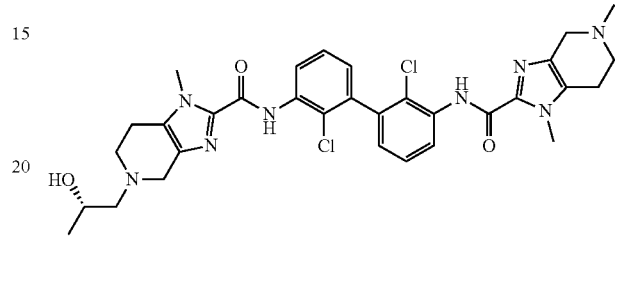

This compound was prepared using similar procedures as described for Example 24 with 3-bromo-2-chloroaniline replacing 3-bromo-2-methylaniline in Step 3. The reaction mixture was purified by prep-HPLC (pH=2, acetonitrile/water+TFA) to give the desired product as the TFA salt. LC-MS calculated for $C_{32}H_{37}Cl_2N_8O_3$ (M+H)$^+$: m/z=651.2; found 651.3.

Example 28

N-(2-chloro-2'-methyl-3'-(1-methyl-5-(1-(methylsulfonyl)piperidin-4-yl)-4,5,6,7-tetrahydro-1H-imidazo[4,5-c]pyridine-2-carboxamido)biphenyl-3-yl)-1,5-dimethyl-4,5,6,7-tetrahydro-1H-imidazo[4,5-c]pyridine-2-carboxamide

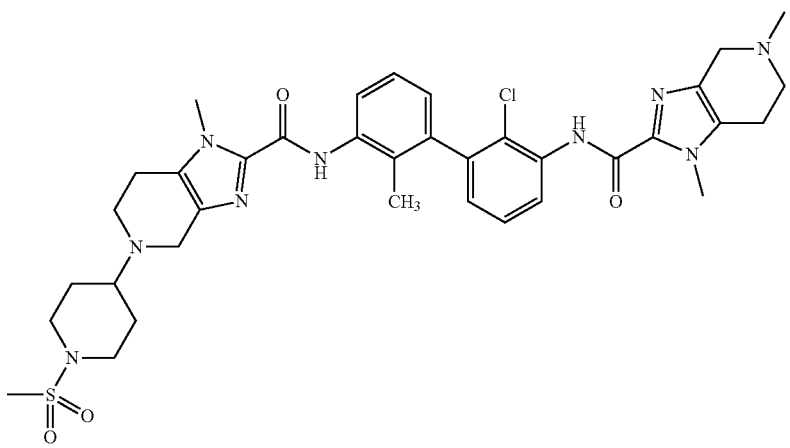

A solution of tert-butyl 2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Example 24, Step 5: 10 mg, 0.015 mmol) in dichloromethane (0.05 mL) and trifluoroacetic acid (0.05 mL) was stirred at room temperature for 30 min. The mixture was concentrated under reduced pressure. The residue was dissolved in tetrahydrofuran (0.10 mL) and successively treated with N,N-diisopropylethylamine (13.0 µL, 0.074 mmol) and 1-(methylsulfonyl)piperidin-4-one (7.9 mg, 0.045 mmol). The reaction mixture was stirred at room temperature for 1 h. Sodium triacetoxyborohydride (9.5 mg, 0.045 mmol) was then added. After being stirred at room temperature for 2 h, the reaction was diluted with MeOH, and purified by pH 2 preparative LC/MS (MeCN/water with TFA) to give the desired product as the TFA salt. LC-MS calculated for $C_{36}H_{45}ClN_9O_4S$ (M+H)$^+$: m/z=734.3; found 734.4. $^1$H NMR (500 MHz, DMSO) δ 9.95 (s, 1H), 9.88 (s, 1H), 8.22 (dd, J=8.1, 1.5 Hz, 1H), 7.65 (dd, J=8.0, 1.3 Hz, 1H), 7.48 (t, J=7.9 Hz, 1H), 7.32 (t, J=7.9 Hz, 1H), 7.11 (dd, j=7.8, 1.5 Hz, 1H), 7.04 (dd, J=7.8, 1.3 Hz, 1H), 4.53-4.13 (m, 4H), 3.95 (s, 3H), 3.93 (s, 3H), 3.93-3.36 (m, 7H), 3.82-3.69 (m, 4H), 2.96 (s, 3H), 2.93 (s, 3H), 2.86-2.76 (m, 2H), 2.30-2.13 (m, 2H), 1.98 (s, 3H), 1.91-1.78 (s, 2H).

Example 29

N-(2-chloro-2'-methyl-3'-(1-methyl-5-(tetrahydro-2H-pyran-4-yl)-4,5,6,7-tetrahydro-1H-imidazo[4,5-c]pyridine-2-carboxamido)biphenyl-3-yl)-1,5-dimethyl-4,5,6,7-tetrahydro-1H-imidazo[4,5-c]pyridine-2-carboxamide

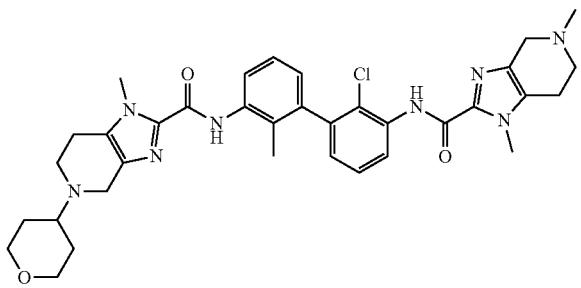 [SMILES: Cc1c(NC(=O)c2nc3c(n2C)CCN(C2CCOCC2)C3)cccc1-c1cccc(NC(=O)c2nc3c(n2C)CCN(C)C3)c1Cl]

This compound was prepared using similar procedures as described for Example 28 with tetrahydro-4H-pyran-4-one replacing 1-(methylsulfonyl)piperidin-4-one. The reaction mixture was purified by prep-HPLC (pH=2, acetonitrile/water+TFA) to give the desired product as the TFA salt. LC-MS calculated for $C_{35}H_{42}ClN_8O_3$ (M+H)$^+$: m/z=657.3; found 657.5.

Example 30

N-(2-chloro-2'-methyl-3'-(1-methyl-5-((tetrahydro-2H-pyran-4-yl)methyl)-4,5,6,7-tetrahydro-1H-imidazo[4,5-c]pyridine-2-carboxamido)biphenyl-3-yl)-1,5-dimethyl-4,5,6,7-tetrahydro-1H-imidazo[4,5-c]pyridine-2-carboxamide

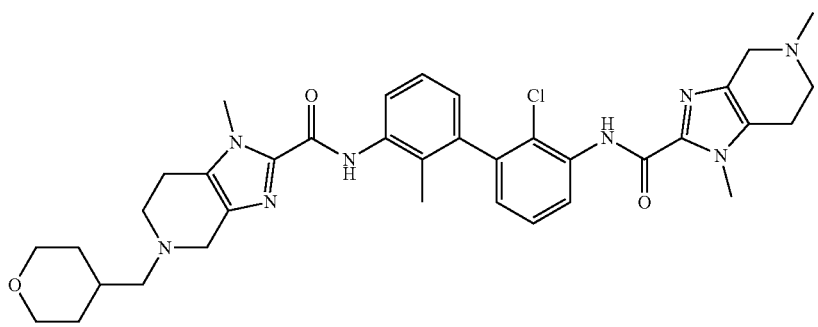 [SMILES: Cc1c(NC(=O)c2nc3c(n2C)CCN(CC2CCOCC2)C3)cccc1-c1cccc(NC(=O)c2nc3c(n2C)CCN(C)C3)c1Cl]

This compound was prepared using similar procedures as described for Example 28 with tetrahydro-2H-pyran-4-carbaldehyde replacing 1-(methylsulfonyl)piperidin-4-one. The reaction mixture was purified by prep-HPLC (pH=2, acetonitrile/water+TFA) to give the desired product as the TFA salt. LC-MS calculated for $C_{36}H_{44}ClN_8O_3$ (M+H)$^+$: m/z=671.3; found 671.3.

Example 31

N-(2'-chloro-3'-(1,5-dimethyl-4,5,6,7-tetrahydro-1H-imidazo[4,5-c]pyridine-2-carboxamido)-2-methylbiphenyl-3-yl)-5-((1-(hydroxymethyl)cyclopropyl)methyl)-1-methyl-4,5,6,7-tetrahydro-1H-imidazo[4,5-c]pyridine-2-carboxamide

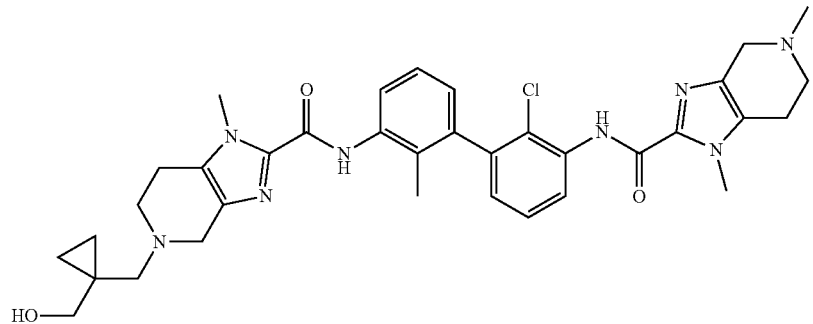 [SMILES: Cc1c(NC(=O)c2nc3c(n2C)CCN(CC2(CO)CC2)C3)cccc1-c1cccc(NC(=O)c2nc3c(n2C)CCN(C)C3)c1Cl]

Step 1: tert-butyl 2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

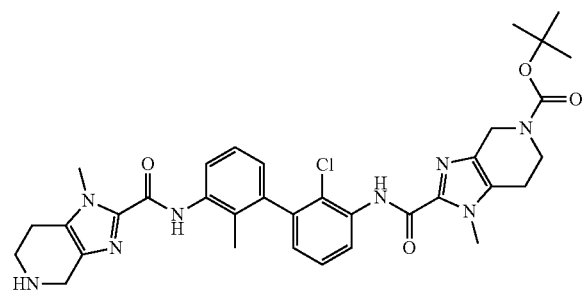 [SMILES: Cc1c(NC(=O)c2nc3c(n2C)CCNC3)cccc1-c1cccc(NC(=O)c2nc3c(n2C)CCN(C(=O)OC(C)(C)C)C3)c1Cl]

A solution of tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate (Example 24, Step 4: 254 mg, 0.511 mmol) in dichloromethane (0.5 mL) and trifluoroacetic acid (0.5 mL) was stirred at room temperature for 30 min. The reaction mixture was concentrated under reduced pressure. A mixture of the residue, tert-butyl 2-((3-bromo-2-chlorophenyl)carbamoyl)-1-methyl-1,4,6,7-tetrahydro-5H-imidazo[4,5-c]pyridine-5-carboxylate (Example 24, Step 1: 200 mg, 0.426 mmol), sodium carbonate (226 mg, 2.129 mmol) and [1,1'-bis(di-cyclohexylphosphino)ferrocene]dichloropalladium (II) (32.3 mg, 0.043 mmol) in 1,4-dioxane (2.0 mL) and water (2.0 mL) was purged with nitrogen and then stirred at 100° C. for 3 h. The reaction mixture was diluted with water and extracted with dichloromethane. The combined organic layers were washed with brine, dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{34}$H$_{40}$ClN$_8$O$_4$ (M+H)$^+$: m/z=659.3; found 659.4.

Step 2; N-(2'-chloro-3'-(1,5-dimethyl-4,5,6,7-tetrahydro-1H-imidazo[4,5-c]pyridine-2-carboxamido)-2-methylbiphenyl-3-yl)-5-((1-(hydroxymethyl)cyclopropyl)methyl)-1-methyl-4,5,6,7-tetrahydro-1H-imidazo[4,5-c]pyridine-2-carboxamide A solution of tert-butyl 2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 10 mg, 0.015 mmol), 1,1-bis(iodomethyl)cyclopropane (14.7 mg, 0.046 mmol) and potassium carbonate (6.3 mg, 0.046 mmol) in DMF (0.20 mL) was stirred at room temperature for 3 h. 2 N NaOH (aq.) solution (0.10 mL) was then added and the reaction mixture was stirred at room temperature for 1 h. The reaction mixture was extracted with dichloromethane. The combined organic layers were dried over Na$_2$SO$_4$, filtered, and concentrated under reduced pressure. The residue was treated with dichloromethane (0.05 mL) and trifluoroacetic acid (0.05 mL) at room temperature for 30 min. The mixture was concentrated under reduced pressure. The residue was dissolved in tetrahydrofuran (0.10 mL), and successively treated with 37 wt. % formaldehyde in water (5.7 µL, 0.076 mmol) and sodium triacetoxyborohydride (9.65 mg, 0.046 mmol). After being stirred at room temperature for 1 h, the reaction mixture was purified by prep-HPLC (pH=2, acetonitrile/water+TFA) to give the desired product as the TFA salt. LC-MS calculated for C$_{35}$H$_{42}$ClN$_8$O$_3$ (M+H)$^+$: m/z=657.3; found 657.5.

Example 32

(S)—N-(2'-chloro-3'-(1,5-dimethyl-4,5,6,7-tetrahydro-1H-imidazo[4,5-c]pyridine-2-carboxamido)-2-methylbiphenyl-3-yl)-5-(2,3-dihydroxypropyl)-1-methyl-4,5,6,7-tetrahydro-1H-imidazo[4,5-c]pyridine-2-carboxamide

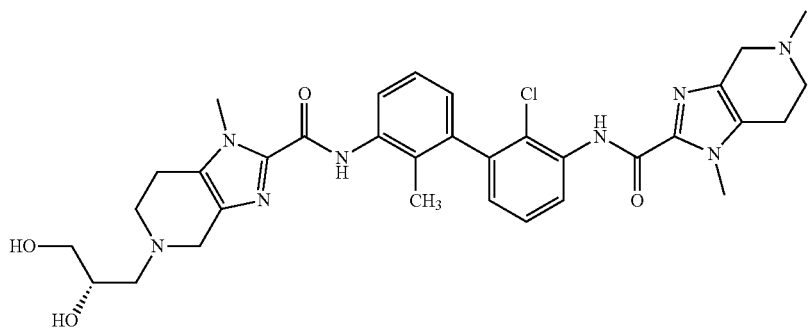 [SMILES: Cc1c(NC(=O)c2nc3c(n2C)CCN(C[C@H](O)CO)C3)cccc1-c1cccc(NC(=O)c2nc3c(n2C)CCN(C)C3)c1Cl]

This compound was prepared using similar procedures as described for Example 28 with (R)-2,3-dihydroxypropanal replacing 1-(methylsulfonyl)piperidin-4-one. The reaction mixture was purified by prep-HPLC (pH=10, acetonitrile/water+NH$_4$OH) to give the desired product. LC-MS calculated for $C_{33}H_{40}ClN_8O_4$ (M+H)$^+$: m/z=647.3; found 647.3.

Example 33

2-(2-(2'-chloro-3'-(1,5-dimethyl-4,5,6,7-tetrahydro-1H-imidazo[4,5-c]pyridine-2-carboxamido)-2-methylbiphenyl-3-ylcarbamoyl)-1-methyl-6,7-dihydro-1H-imidazo[4,5-c]pyridin-5(4H)-yl)acetic Acid

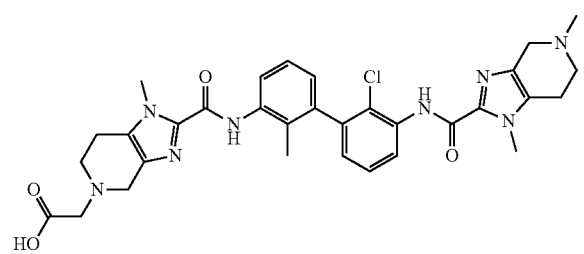 [SMILES: Cc1c(NC(=O)c2nc3c(n2C)CCN(CC(=O)O)C3)cccc1-c1cccc(NC(=O)c2nc3c(n2C)CCN(C)C3)c1Cl]

This compound was prepared using similar procedures as described for Example 28 with 2-oxoacetic acid hydrate replacing 1-(methylsulfonyl)piperidin-4-one. The reaction mixture was purified by prep-HPLC (pH=2, acetonitrile/water+TFA) to give the desired product as the TFA salt. LC-MS calculated for $C_{32}H_{36}ClN_8O_4$ (M+H)$^+$: m/z=631.3; found 631.4. $^1$H NMR (400 MHz, DMSO-d$_6$) δ 9.96 (s, 1H), 9.92 (s, 1H), 8.23 (dd, J=8.2, 1.6 Hz, 1H), 7.62 (dd, J=8.1, 1.3 Hz, 1H), 7.49 (t, J=7.9 Hz, 1H), 7.32 (t, J=7.8 Hz, 1H), 7.12 (dd, J=7.6, 1.6 Hz, 1H), 7.05 (dd, J=7.7, 1.3 Hz, 1H), 4.54-4.10 (m, 6H), 3.96 (s, 3H), 3.91 (s, 3H), 3.83-3.36 (m, 4H), 3.09-2.98 (m, 4H), 2.97 (s, 3H), 1.98 (s, 3H).

Example 34

5-(1-acetylpiperidin-4-yl)-N-(2'-chloro-3'-(1,5-dimethyl-4,5,6,7-tetrahydro-1H-imidazo[4,5-c]pyridine-2-carboxamido)-2-methylbiphenyl-3-yl)-1-methyl-4,5,6,7-tetrahydro-1H-imidazo[4,5-c]pyridine-2-carboxamide

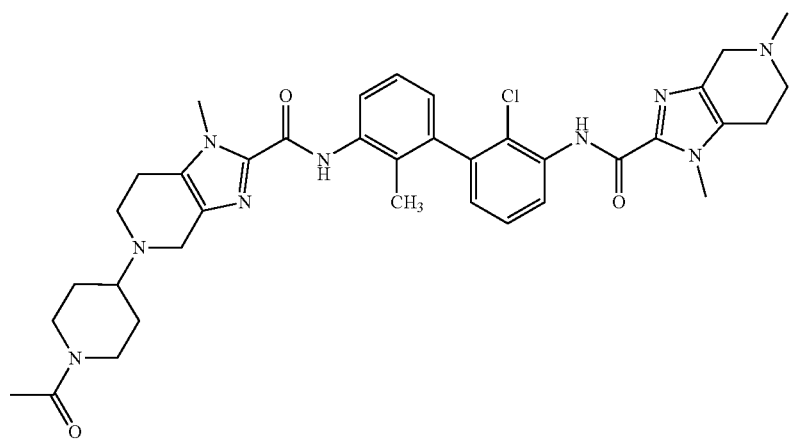 [SMILES: CC(=O)N1CCC(N2CCc3c(nc(C(=O)Nc4cccc(-c5cccc(NC(=O)c6nc7c(n6C)CCN(C)C7)c5Cl)c4C)n3C)C2)CC1]

This compound was prepared using similar procedures as described for Example 28 with 1-acetylpiperidin-4-one replacing 1-(methylsulfonyl)piperidin-4-one. The reaction mixture was purified by prep-HPLC (pH=10, acetonitrile/water+NH$_4$OH) to give the desired product. LC-MS calculated for C$_{37}$H$_{45}$ClN$_9$O$_3$ (M+H)$^+$: m/z=698.3; found 698.4.

Example 35

4-(2-(2'-chloro-3'-(1,5-dimethyl-4,5,6,7-tetrahydro-1H-imidazo[4,5-c]pyridine-2-carboxamido)-2-methylbiphenyl-3-ylcarbamoyl)-1-methyl-6,7-dihydro-1H-imidazo[4,5-c]pyridin-5(4H)-yl)-1-methylcyclohexanecarboxylic acid

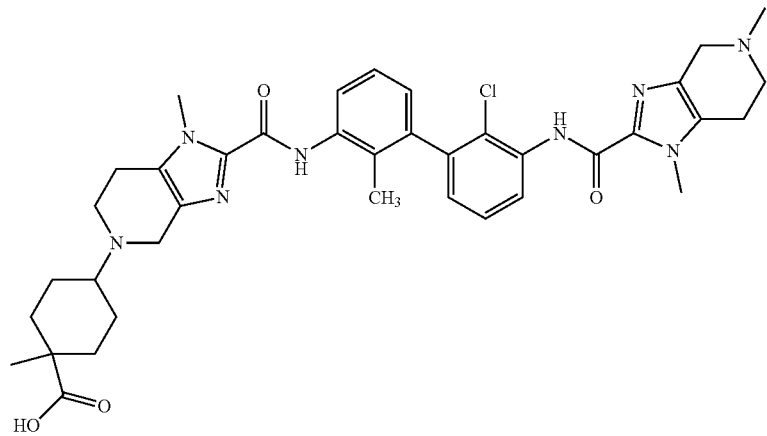

This compound was prepared using similar procedures as described for Example 28 with 1-methyl-4-oxocyclohexane-1-carboxylic acid replacing 1-(methylsulfonyl)piperidin-4-one. The reaction mixture was purified by prep-HPLC (pH=10, acetonitrile/water+NH$_4$OH) to give the desired product as a mixture of cis-/trans-isomers. LC-MS calculated for C$_{38}$H$_{46}$ClN$_8$O$_4$ (M+H)$^+$: m/z=713.3; found 713.3.

Example 36

N-(2-chloro-2'-methyl-3'-(1-methyl-5-(3-(methylsulfonamido)propyl)-4,5,6,7-tetrahydro-1H-imidazo[4,5-c]pyridine-2-carboxamido)biphenyl-3-yl)-1,5-dimethyl-4,5,6,7-tetrahydro-1H-imidazo[4,5-c]pyridine-2-carboxamide

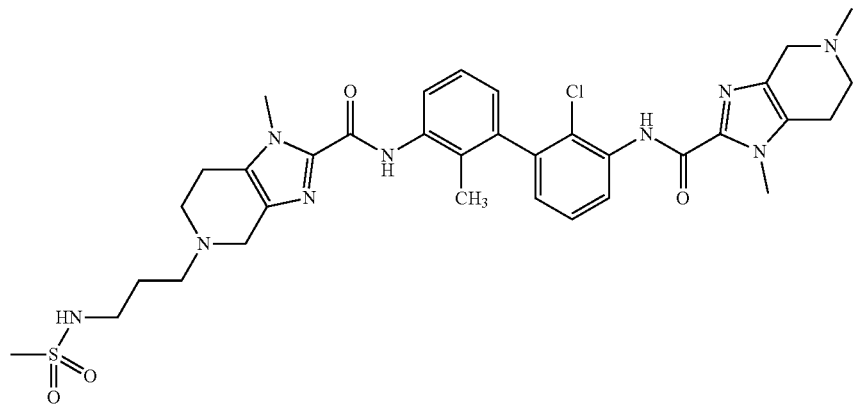

Step 1: tert-butyl 3-(2-(2'-chloro-3'-(1,5-dimethyl-4,5,6,7-tetrahydro-1H-imidazo[4,5-c]pyridine-2-carboxamido)-2-methylbiphenyl-3-ylcarbamoyl)-1-methyl-6,7-dihydro-1H-imidazo[4,5-c]pyridin-5(4H)-yl)propylcarbamate

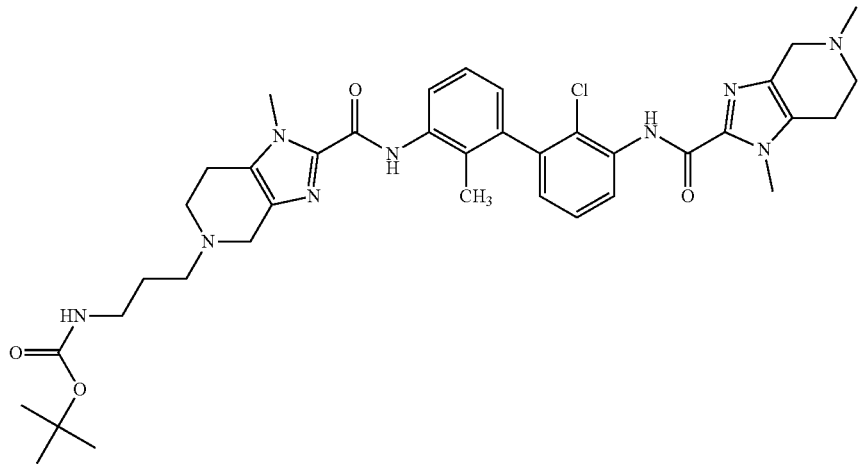 [SMILES: Cc1c(NC(=O)c2nc3c(n2C)CCN(CCCNC(=O)OC(C)(C)C)C3)cccc1-c1cccc(NC(=O)c2nc3c(n2C)CCN(C)C3)c1Cl]

A solution of tert-butyl 2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Example 24, Step 5: 200 mg, 0.297 mmol) in dichloromethane (0.80 mL) and trifluoroacetic acid (0.40 mL) was stirred at room temperature for 30 min. The mixture was concentrated under reduced pressure. The residue was dissolved in THF (3.0 mL) and successively treated with N,N-diisopropylethylamine (104 μL, 0.594 mmol) and tert-butyl (3-oxopropyl)carbamate (154 mg, 0.891 mmol). The reaction mixture was stirred at room temperature for 1 h. Sodium triacetoxyborohydride (189 mg, 0.891 mmol) was added. After being stirred at room temperature for 2 h, the reaction was quenched with sat. NaHCO$_3$ solution, and extracted with dichloromethane. The combined organic layers were washed with brine, dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{38}$H$_{49}$ClN$_9$O$_4$ (M+H)$^+$: m/z=730.4; found 730.4.

Step 2: N-(2-chloro-2'-methyl-3'-(1-methyl-5-(3-(methylsulfonamido)propyl)-4,5,6,7-tetrahydro-1H-imidazo[4,5-c]pyridine-2-carboxamido)biphenyl-3-yl)-1,5-dimethyl-4,5,6,7-tetrahydro-1H-imidazo[4,5-c]pyridine-2-carboxamide A solution of tert-butyl (3-(2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)propyl)carbamate (Step 1: 10 mg, 0.014 mmol) in dichloromethane (0.05 mL) and trifluoroacetic acid (0.05 mL) was stirred at room temperature for 30 min. The mixture was concentrated under reduced pressure. The residue was dissolved in THF (0.15 mL), and successively treated with triethylamine (9.6 μL, 0.068 mmol) and methanesulfonyl chloride (2.1 μL, 0.027 mmol) at 0° C. After being stirred at room temperature for 1 h, the reaction mixture was diluted with MeOH, and purified by pH 10 preparative LC/MS (MeCN/water with NH$_4$OH) to give the desired product. LC-MS calculated for C$_{34}$H$_{43}$ClN$_9$O$_4$S (M+H)$^+$: m/z=708.3; found 708.5.

Example 37

Trans-4-((2-(2'-chloro-3'-(1,5-dimethyl-4,5,6,7-tetrahydro-1H-imidazo[4,5-c]pyridine-2-carboxamido)-2-methylbiphenyl-3-ylcarbamoyl)-1-methyl-6,7-dihydro-1H-imidazo[4,5-c]pyridin-5(4H)-yl)methyl)cyclohexane-1-carboxylic Acid

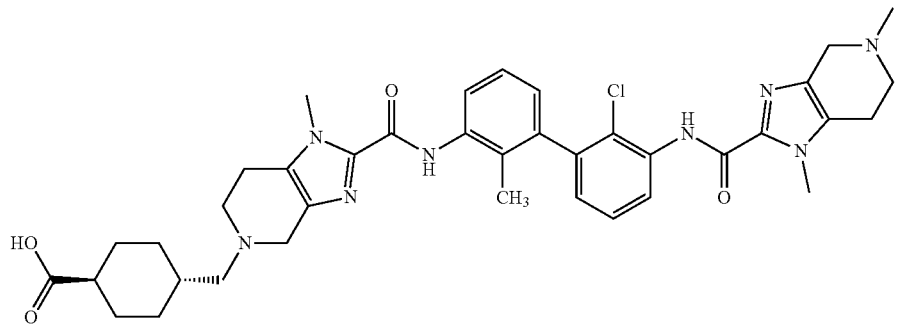 [SMILES: Cc1c(NC(=O)c2nc3c(n2C)CCN(C[C@H]2CC[C@H](C(=O)O)CC2)C3)cccc1-c1cccc(NC(=O)c2nc3c(n2C)CCN(C)C3)c1Cl]

A solution of tert-butyl 2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Example 24, Step 5: 10 mg, 0.015 mmol) in dichloromethane (0.05 mL) and trifluoroacetic acid (0.05 mL) was stirred at room temperature for 30 min. The mixture was concentrated under reduced pressure. The residue was dissolved in THF (0.15 mL) and successively treated with methyl trans-4-formylcyclohexanecarboxylate (7.58 mg, 0.045 mmol) and N,N-diisopropylethylamine (13.0 µL, 0.074 mmol). The reaction mixture was stirred at room temperature for 1 h. Sodium triacetoxyborohydride (9.44 mg, 0.045 mmol) was added. After being stirred at room temperature for 2 h, the reaction was quenched with saturated NaHCO$_3$ solution, and extracted with dichloromethane. The combined organic layers were washed with brine, dried over Na$_2$SO$_4$, filtered, and concentrated under reduced pressure. The residue was dissolved in methanol (0.20 mL) and water (0.04 mL), and treated with lithium hydroxide, monohydrate (3.12 mg, 0.074 mmol). After being stirred at room temperature for 3 h, the reaction mixture was neutralized with 2 N HCl (aq.) solution until the pH=7, diluted with MeOH, and purified by pH=2 preparative LC/MS (MeCN/water with TFA) to give the desired product as the TFA salt. LC-MS calculated for C$_{38}$H$_{46}$ClN$_8$O$_4$ (M+H)$^+$: m/z=713.3; found 713.4. $^1$H NMR (600 MHz, DMSO-d$_6$) δ 9.96 (s, 1H), 9.86 (s, 1H), 8.23 (dd, J=8.3, 1.5 Hz, 1H), 7.67 (dd, J=8.1, 1.5 Hz, 1H), 7.49 (t, J=7.9 Hz, 1H), 7.33 (t, J=7.8 Hz, 1H), 7.12 (dd, J=7.6, 1.5 Hz, 1H), 7.05 (dd, J=7.6, 1.5 Hz, 1H), 4.55-4.44 (m, 2H), 4.29-4.15 (m, 2H), 3.96 (s, 3H), 3.93 (s, 3H), 3.85-3.70 (m, 2H), 3.54-3.36 (m, 2H), 3.15-3.00 (m, 6H), 2.97 (s, 3H), 2.17 (tt, J=12.1, 3.4 Hz, 1H), 1.99 (s, 3H), 1.96-1.80 (m, 5H), 1.44-1.32 (m, 2H), 1.09-0.96 (m, 2H).

Example 38

N-(2-chloro-2'-cyano-3'-(1,5-dimethyl-4,5,6,7-tetrahydro-1H-imidazo[4,5-c]pyridine-2-carboxamido)biphenyl-3-yl)-5-(2-hydroxyethyl)-1-methyl-4,5,6,7-tetrahydro-1H-imidazo[4,5-c]pyridine-2-carboxamide

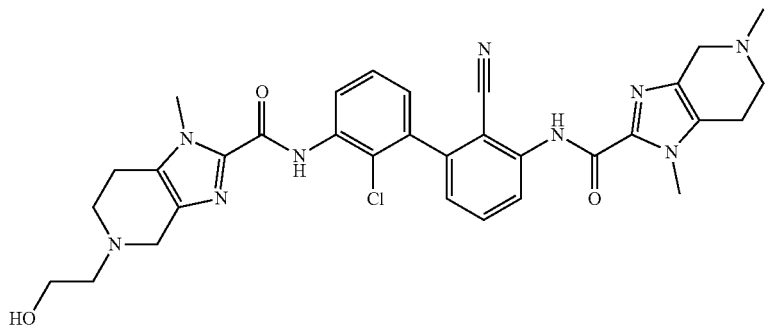 [SMILES: CN1CCc2c(nc(C(=O)Nc3cccc(-c4cccc(NC(=O)c5nc6c(n5C)CCN(CCO)C6)c4Cl)c3C#N)n2C)C1]

This compound was prepared using similar procedures as described for Example 24 with 2-amino-6-bromobenzonitrile replacing 3-bromo-2-chloroaniline in Step 1, 3-bromo-2-chloroaniline replacing 3-bromo-2-methylaniline in Step 3 and 2-((tert-butyldimethylsilyl)oxy)acetaldehyde replacing (S)-2-((tert-butyldimethylsilyl)oxy)propanal in Step 6. The reaction mixture was purified by prep-HPLC (pH=2, acetonitrile/water+TFA) to give the desired product as the TFA salt. LC-MS calculated for C$_{32}$H$_{35}$ClN$_9$O$_3$ (M+H)$^+$: m/z=628.3; found 628.3.

Example 39

(S)—N-(2-chloro-2'-cyano-3'-(1,5-dimethyl-4,5,6,7-tetrahydro-1H-imidazo[4,5-c]pyridine-2-carboxamido)biphenyl-3-yl)-5-(2-hydroxypropyl)-1-methyl-4,5,6,7-tetrahydro-1H-imidazo[4,5-c]pyridine-2-carboxamide

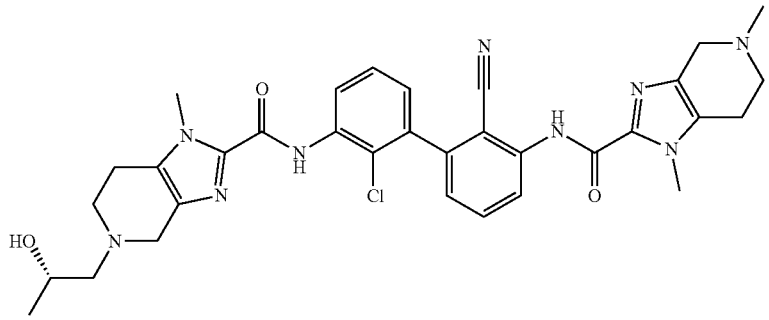 [SMILES: C[C@H](O)CN1CCc2c(nc(C(=O)Nc3cccc(-c4cccc(NC(=O)c5nc6c(n5C)CCN(C)C6)c4C#N)c3Cl)n2C)C1]

This compound was prepared using similar procedures as described for Example 24 with 2-amino-6-bromobenzonitrile replacing 3-bromo-2-chloroaniline in Step 1 and 3-bromo-2-chloroaniline replacing 3-bromo-2-methylaniline in Step 3. The reaction mixture was purified by prep-HPLC (pH=2, acetonitrile/water+TFA) to give the desired product as the TFA salt. LC-MS calculated for C$_{33}$H$_{37}$ClN$_9$O$_3$ (M+H)$^+$: m/z=642.3; found 642.3. $^1$H NMR (500 MHz, DMSO) δ 10.58 (br, 2H), 8.32 (d, J=8.1 Hz, 1H), 7.91 (dd, J=8.4, 1.1 Hz, 1H), 7.82 (t, J=8.0 Hz, 1H), 7.56 (t, J=7.9 Hz, 1H), 7.36 (dd, J=7.6, 1.1 Hz, 1H), 7.28 (dd, J=7.7, 1.5 Hz, 1H), 4.57-4.13 (m, 5H), 3.95 (s, 3H), 3.92 (s, 3H), 3.89-3.00 (m, 10H), 2.96 (s, 3H), 1.13 (d, J=6.2 Hz, 3H).

Example 40

(R)—N-(2-chloro-2'-cyano-3'-(1,5-dimethyl-4,5,6,7-tetrahydro-1H-imidazo[4,5-c]pyridine-2-carboxamido)biphenyl-3-yl)-5-(2-hydroxypropyl)-1-methyl-4,5,6,7-tetrahydro-1H-imidazo[4,5-c]pyridine-2-carboxamide N,N-Diisopropylethylamine (79 μL, 0.455 mmol) was added to a solution of tert-butyl 2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 31, Step 1: 100 mg, 0.152 mmol) and (S)-2-((tert-butyldimethylsilyl)oxy)propanal (86 mg, 0.455 mmol) in tetrahydrofuran (1.5 mL), and the mixture was stirred at room temperature for 30 min. Sodium triacetoxyborohydride (161 mg, 0.759 mmol) was added. After being stirred at room temperature for 2 h, the reaction was treated with 2 N HCl (aq.) solution (2.0 mL), and stirred at 50° C. for 30 min. The reaction mixture was concentrated and then purified by prep-HPLC (pH=10, acetonitrile/water+NH$_4$OH) to give the desired product. LC-MS calculated for C$_{32}$H$_{38}$ClN$_8$O$_3$ (M+H)$^+$: m/z=617.3; found 617.3.

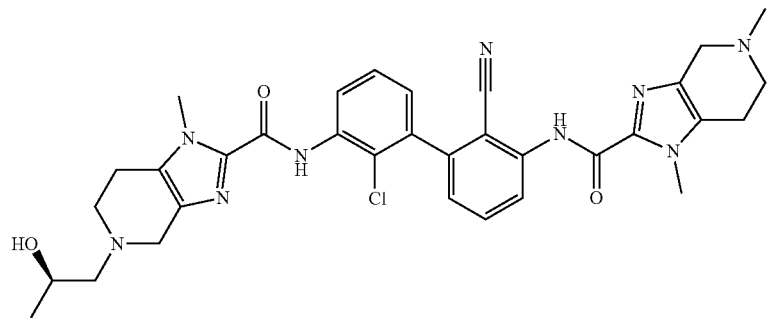 [SMILES: C[C@@H](O)CN1CCc2c(nc(C(=O)Nc3cccc(-c4cccc(NC(=O)c5nc6c(n5C)CCN(C)C6)c4C#N)c3Cl)n2C)C1]

This compound was prepared using similar procedures as described for Example 24 with 2-amino-6-bromobenzonitrile replacing 3-bromo-2-chloroaniline in Step 1, 3-bromo-2-chloroaniline replacing 3-bromo-2-methylaniline in Step 3 and (R)-2-((tert-butyldimethylsilyl)oxy)propanal replacing (S)-2-((tert-butyldimethylsilyl)oxy)propanal in Step 6. The reaction mixture was purified by prep-HPLC (pH=2, acetonitrile/water+TFA) to give the desired product as the TFA salt. LC-MS calculated for C$_{33}$H$_{37}$ClN$_9$O$_3$ (M+H)$^+$: m/z=642.3; found 642.3.

Example 41

(S)—N-(2'-chloro-2-methyl-3'-(1-methyl-4,5,6,7-tetrahydro-1H-imidazo[4,5-c]pyridine-2-carboxamido)-[1,1'-biphenyl]-3-yl)-5-(2-hydroxypropyl)-1-methyl-4,5,6,7-tetrahydro-1H-imidazo[4,5-c]pyridine-2-carboxamide

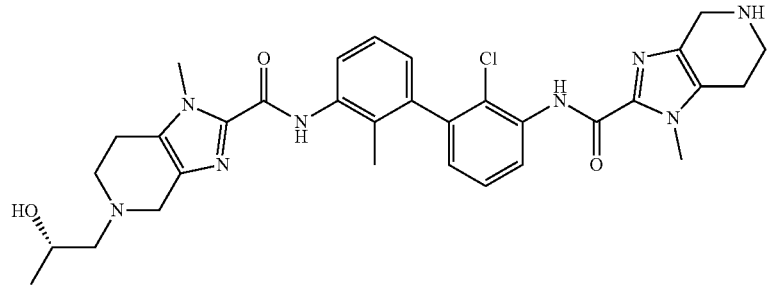 [SMILES: Cc1c(NC(=O)c2nc3c(n2C)CCN(C[C@H](C)O)C3)cccc1-c1cccc(NC(=O)c2nc3c(n2C)CCNC3)c1Cl]

Example 42

(S)—N-(2'-chloro-3'-(5-(2-hydroxyethyl)-1-methyl-4,5,6,7-tetrahydro-1H-imidazo[4,5-c]pyridine-2-carboxamido)-2-methylbiphenyl-3-yl)-5-(2-hydroxypropyl)-1-methyl-4,5,6,7-tetrahydro-1H-imidazo[4,5-c]pyridine-2-carboxamide

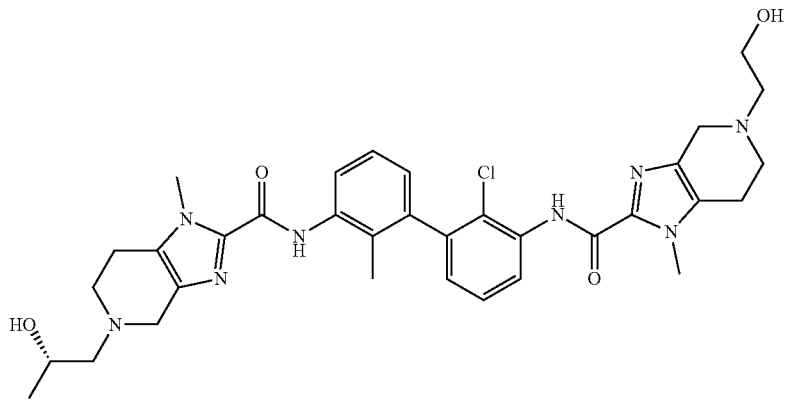 [SMILES: Cc1c(NC(=O)c2nc3c(n2C)CCN(C[C@H](C)O)C3)cccc1-c1cccc(NC(=O)c2nc3c(n2C)CCN(CCO)C3)c1Cl]

N,N-Diisopropylethylamine (8.49 µL, 0.049 mmol) was added to a solution of (S)—N-(2-chloro-2-methyl-3'-(1-methyl-4,5,6,7-tetrahydro-1H-imidazo[4,5-c]pyridine-2-carboxamido)-[1,1'-biphenyl]-3-yl)-5-(2-hydroxypropyl)-1-methyl-4,5,6,7-tetrahydro-1H-imidazo[4,5-c]pyridine-2-carboxamide (Example 41: 10 mg, 0.016 mmol) and 2-((tert-butyldimethylsilyl)oxy)acetaldehyde (8.47 mg, 0.049 mmol) in tetrahydrofuran (0.20 mL), and the mixture was stirred at room temperature for 30 min. Sodium triacetoxyborohydride (10.30 mg, 0.049 mmol) was then added. After being stirred at room temperature for 2 h, the reaction was treated with 2 N HCl (aq.) solution (0.20 mL), and stirred at 50° C. for 30 min. The reaction mixture was concentrated and then purified by prep-HPLC (pH=2, acetonitrile/water+TFA) to give the desired product as the TEA salt. LC-MS calculated for $C_{34}H_{42}ClN_8O_4$ (M+H)$^+$: m/z=661.3; found 661.4.

Example 43

(S)—N-(2'-chloro-2-methyl-3'-(1-methyl-5-(1-(methylsulfonyl)piperidin-4-yl)-4,5,6,7-tetrahydro-1H-imidazo[4,5-c]pyridine-2-carboxamido)biphenyl-3-yl)-5-(2-hydroxypropyl)-1-methyl-4,5,6,7-tetrahydro-1H-imidazo[4,5-c]pyridine-2-carboxamide

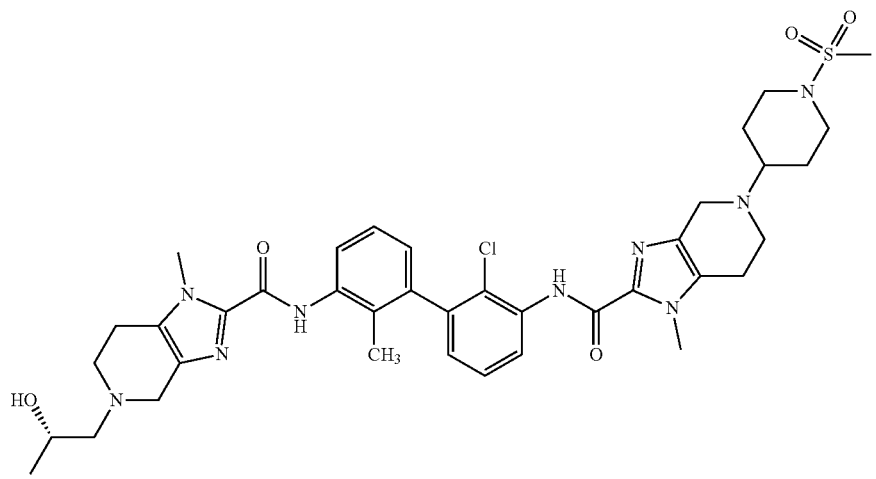 [SMILES: Cc1c(NC(=O)c2nc3c(n2C)CCN(C[C@H](C)O)C3)cccc1-c1cccc(NC(=O)c2nc3c(n2C)CCN(C2CCN(S(C)(=O)=O)CC2)C3)c1Cl]

N,N-Diisopropylethylamine (8.5 µL, 0.049 mmol) was added to a solution of (S)—N-(2'-chloro-2-methyl-3'-(1-methyl-4,5,6,7-tetrahydro-1H-imidazo[4,5-c]pyridine-2-carboxamido)-[1,1'-biphenyl]-3-yl)-5-(2-hydroxypropyl)-1-methyl-4,5,6,7-tetrahydro-1H-imidazo[4,5-c]pyridine-2-carboxamide (Example 41: 10 mg, 0.016 mmol) and 1-(methylsulfonyl)piperidin-4-one (8.6 mg, 0.049 mmol) in THE (0.15 mL), and the reaction was stirred at room temperature for 30 min. Sodium triacetoxyborohydride (10.3 mg, 0.049 mmol) was then added. After being stirred at room temperature for 2 h, the reaction mixture was purified by prep-HPLC (pH=10, acetonitrile/water+ NH₄OH) to give the desired product. LC-MS calculated for $C_{38}H_{49}ClN_9O_5S$ (M+H)⁺: m/z=778.3; found 778.3.

Example 44

(S)—N-(2-chloro-3'-(5-(2-hydroxypropyl)-1-methyl-4,5,6,7-tetrahydro-1H-imidazo[4,5-c]pyridine-2-carboxamido)-2'-methylbiphenyl-3-yl)-5-cyclobutyl-1-methyl-4,5,6,7-tetrahydro-1H-imidazo[4,5-c]pyridine-2-carboxamide

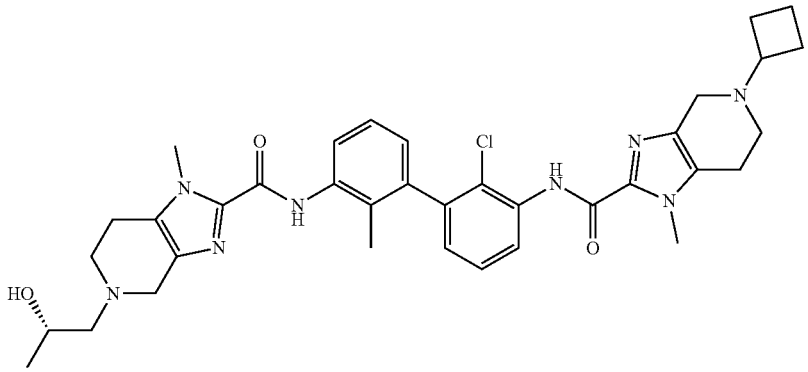 [SMILES: Cc1c(NC(=O)c2nc3c(n2C)CCN(C[C@H](C)O)C3)cccc1-c1cccc(NC(=O)c2nc3c(n2C)CCN(C2CCC2)C3)c1Cl]

A suspension of (S)—N-(2'-chloro-2-methyl-3'-(1-methyl-4,5,6,7-tetrahydro-1H-imidazo[4,5-c]pyridine-2-carboxamido)-[1,1'-biphenyl]-3-yl)-5-(2-hydroxypropyl)-1-methyl-4,5,6,7-tetrahydro-1H-imidazo[4,5-c]pyridine-2-carboxamide (Example 41: 10 mg, 0.016 mmol), bromocyclobutane (10.9 mg, 0.081 mmol) and potassium carbonate (6.7 mg, 0.049 mmol) in DMF (0.10 mL) was stirred at 90° C. for 3 h. After being cooled to room temperature, the reaction mixture was diluted with methanol and purified by prep-HPLC (pH=10, acetonitrile/water+ NH₄OH) to give the desired product. LC-MS calculated for $C_{36}H_{44}ClN_8O_3$ (M+H)⁺: m/z=671.3; found 671.3.

Example 45

(S)—N-(2-chloro-3'-(5-(2-hydroxypropyl)-1-methyl-4,5,6,7-tetrahydro-1H-imidazo[4,5-c]pyridine-2-carboxamido)-2'-methylbiphenyl-3-yl)-5-isopropyl-1-methyl-4,5,6,7-tetrahydro-1H-imidazo[4,5-c]pyridine-2-carboxamide

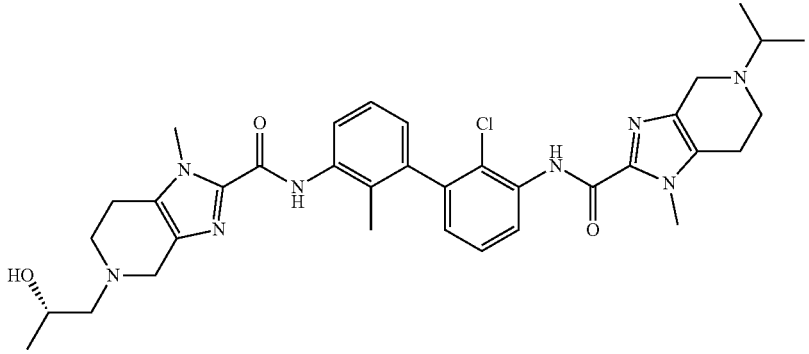 [SMILES: Cc1c(NC(=O)c2nc3c(n2C)CCN(C[C@H](C)O)C3)cccc1-c1cccc(NC(=O)c2nc3c(n2C)CCN(C(C)C)C3)c1Cl]

This compound was prepared using a similar procedure as described for Example 44 with 2-iodopropane replacing bromocyclobutane. The reaction mixture was purified by prep-HPLC (pH=10, acetonitrile/water+NH₄OH) to give the desired product. LC-MS calculated for $C_{35}H_{44}ClN_8O_3$ (M+H)⁺: m/z=659.3; found 659.4.

Example 46

(S)—N-(2-chloro-3'-(5-(2-hydroxypropyl)-1-methyl-4,5,6,7-tetrahydro-1H-imidazo[4,5-c]pyridine-2-carboxamido)-2'-methylbiphenyl-3-yl)-5-(cyclopropylmethyl)-1-methyl-4,5,6,7-tetrahydro-1H-imidazo[4,5-c]pyridine-2-carboxamide

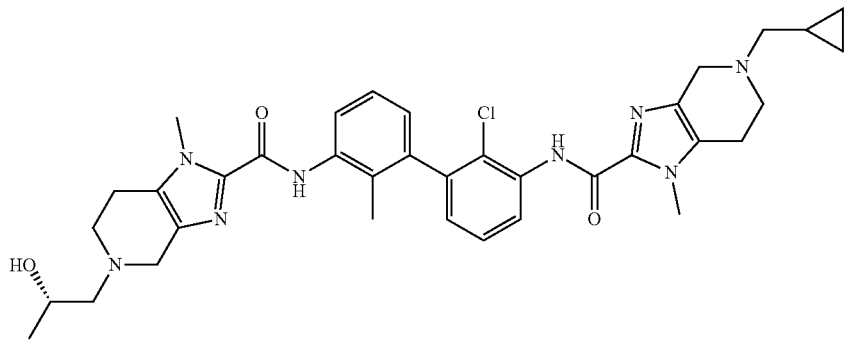 [SMILES: Cc1c(NC(=O)c2nc3c(n2C)CCN(C[C@H](C)O)C3)cccc1-c1cccc(NC(=O)c2nc3c(n2C)CCN(CC2CC2)C3)c1Cl]

This compound was prepared using a similar procedure as described for Example 44 with (iodomethyl)cyclopropane replacing bromocyclobutane. The reaction mixture was purified by prep-HPLC (pH=10, acetonitrile/water+NH₄OH) to give the desired product. LC-MS calculated for $C_{36}H_{44}ClN_8O_3$ (M+H)⁺: m/z=671.3; found 671.5.

Example 47

(S)—N-(2'-chloro-2-methyl-3'-(1-methyl-5-(tetrahydro-2H-pyran-4-yl)-4,5,6,7-tetrahydro-1H-imidazo[4,5-c]pyridine-2-carboxamido)biphenyl-3-yl)-5-(2-hydroxypropyl)-1-methyl-4,5,6,7-tetrahydro-1H-imidazo[4,5-c]pyridine-2-carboxamide

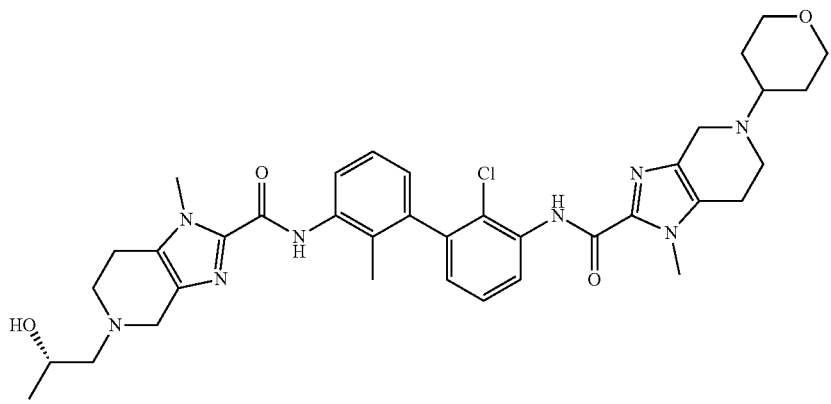 [SMILES: Cc1c(NC(=O)c2nc3c(n2C)CCN(C[C@H](C)O)C3)cccc1-c1cccc(NC(=O)c2nc3c(n2C)CCN(C2CCOCC2)C3)c1Cl]

This compound was prepared using a similar procedure as described for Example 43 with tetrahydro-4H-pyran-4-one replacing 1-(methylsulfonyl)piperidin-4-one. The reaction mixture was purified by prep-HPLC (pH=2, acetonitrile/water+TFA) to give the desired product as the TEA salt. LC-MS calculated for $C_{37}H_{46}ClN_8O_4$ (M+H)⁺: m/z=701.3; found 701.4.

Example 48

(R)—N-(2-chloro-3'-(5-((3-hydroxypyrrolidin-1-yl)methyl)-1-methyl-2-oxo-1,2-dihydropyridine-3-carboxamido)-2'-methylbiphenyl-3-yl)-1,5-dimethyl-4,5,6,7-tetrahydro-1H-imidazo[4,5-c]pyridine-2-carboxamide

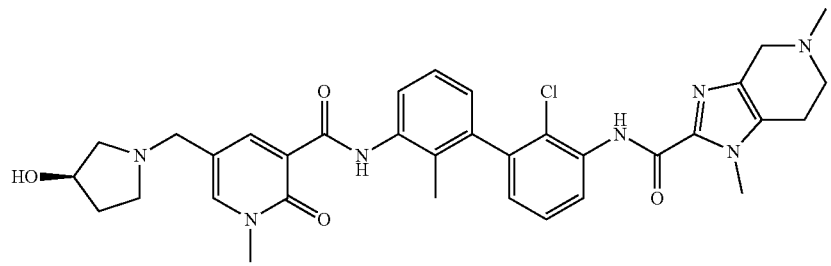 [SMILES: Cc1c(NC(=O)c2cc(CN3CC[C@@H](O)C3)cn(C)c2=O)cccc1-c1cccc(NC(=O)c2nc3c(n2C)CCN(C)C3)c1Cl]

Step 1: 5-bromo-1-methyl-2-oxo-1,2-dihydropyridine-3-carboxylic acid

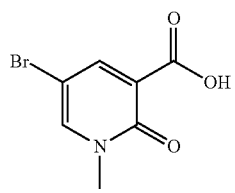

Methyl iodide (1.71 ml, 27.5 mmol) was added to a mixture of 5-bromo-2-hydroxynicotinic acid (5.0 g, 22.94 mmol) and potassium carbonate (4.75 g, 34.4 mmol) in methanol (76.0 mL). The reaction mixture was stirred at 80° C. for 10 h. The reaction was cooled to room temperature and the solvent was concentrated under reduced pressure. Water was added, and the mixture was washed with dichloromethane twice. To the aqueous phase was added 1 M aqueous solution of HCl until the pH=2. Then, the acidic aqueous layer was extracted with dichloromethane twice. The organic phase was dried over MgSO$_4$, filtered and the filtrate was concentrated. The crude residue was used directly in the next step without further purification. LC-MS calculated for $C_7H_7BrNO_3$ (M+H)$^+$: m/z=232.0/234.0; found 232.0/234.0.

Step 2: 1-methyl-2-oxo-5-vinyl-1,2-dihydropyridine-3-carboxylic acid

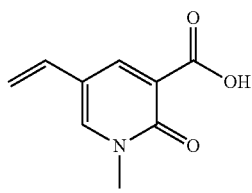

A mixture of 5-bromo-1-methyl-2-oxo-1,2-dihydropyridine-3-carboxylic acid (Step 1: 321 mg, 1.385 mmol), 4,4,5,5-tetramethyl-2-vinyl-1,3,2-dioxaborolane (213 mg, 1.385 mmol), sodium carbonate (440 mg, 4.15 mmol) and tetrakis(triphenylphosphine)palladium(0) (80 mg, 0.069 mmol) in tert-butanol (1.4 mL) and water (1.4 mL) was degassed and sealed. It was stirred at 80° C. for 2 h. The reaction was cooled to room temperature and the solvent was concentrated under reduced pressure. Water was added, and the mixture was washed with dichloromethane twice. To the aqueous phase was added 1 M aqueous solution of HCl until the pH=2. Then, the acidic aqueous layer was extracted with dichloromethane twice. The organic phase was dried over MgSO$_4$, filtered and the filtrate was concentrated. The crude residue was used directly in the next step without further purification. LC-MS calculated for $C_9H_{10}NO_3$ (M+H)$^+$: m/z=180.1; found 180.1.

Step 3: tert-butyl 2-(3'-amino-2-chloro-2'-methylbiphenyl-3-ylcarbamoyl)-1-methyl-6,7-dihydro-1H-imidazo[4,5-c]pyridine-5(4H)-carboxylate

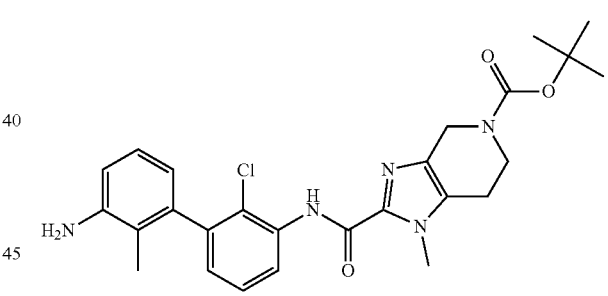

A mixture of tert-butyl 2-((3-bromo-2-chlorophenyl)carbamoyl)-1-methyl-1,4,6,7-tetrahydro-5H-imidazo[4,5-c]pyridine-5-carboxylate (Example 24, Step 1: 620.0 mg, 1.320 mmol), 2-methyl-3-(4,4,5,5-tetramethyl-1,3,2-dioxaborolan-2-yl)aniline (400 mg, 1.716 mmol), dichloro[1,1'-bis(dicyclohexylphosphino)ferrocene]palladium(II) (108 mg, 0.132 mmol) and sodium carbonate (280 mg, 2.64 mmol) in 1,4-dioxane (4.0 mL) and water (0.2 mL) was purged with nitrogen and then stirred at 110° C. for 2 h. After being cooled to room temperature, the reaction mixture was extracted with DCM. The combined organic layers were washed with brine, dried over MgSO$_4$, filtered and concentrated under reduced pressure. The residue was purified by flash chromatography on a silica gel column eluting with 60% ethyl acetate in hexanes to afford the desired product. LC-MS calculated for $C_{26}H_{31}ClN_5O_3$ (M+H)$^+$: m/z=496.2; found 496.2.

Step 4: tert-butyl 2-(2-chloro-2'-methyl-3'-(1-methyl-2-oxo-5-vinyl-1,2-dihydropyridine-3-carboxamido)biphenyl-3-ylcarbamoyl)-1-methyl-6,7-dihydro-1H-imidazo[4,5-c]pyridine-5 (4H)-carboxylate

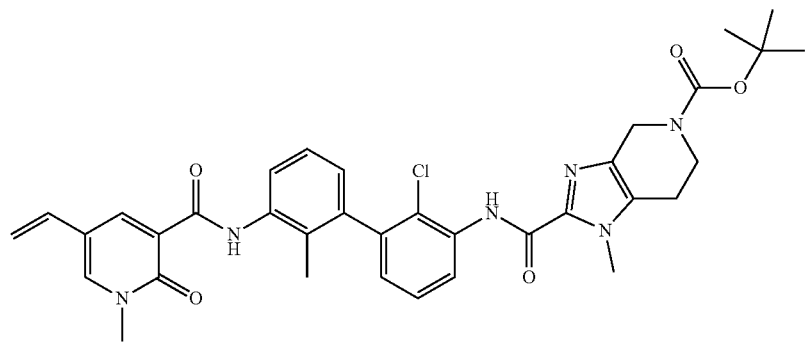 [SMILES: C=Cc1cc(C(=O)Nc2cccc(-c3cccc(NC(=O)c4nc5c(n4C)CCN(C(=O)OC(C)(C)C)C5)c3Cl)c2C)c(=O)n(C)c1]

To a solution of 1-methyl-2-oxo-5-vinyl-1,2-dihydropyridine-3-carboxylic acid (Step 2: 395.0 mg, 1.04 mmol), tert-butyl 2-(3'-amino-2-chloro-2'-methylbiphenyl-3-ylcarbamoyl)-1-methyl-6,7-dihydro-1H-imidazo[4,5-c]pyridine-5(4H)-carboxylate (Step 3: 395.0 mg, 1.04 mmol), and 1-[bis(dimethylamino)methylene]-1H-1,2,3-triazolo[4,5-b]pyridinium 3-oxide hexafluorophosphate (306 mg, 0.804 mmol) in 1,2-dichloroethane (2.2 mL) was added N,N-diisopropylethylamine (233 µL, 1.339 mmol). The mixture was stirred at room temperature for 2 h. Then, the mixture was diluted with DCM, and washed with water and brine. The organic phase was dried over MgSO$_4$ before filtering. The filtrate was concentrated and purified by flash chromatography on a silica gel column eluting with 8% methanol in dichloromethane to afford the desired product. LC-MS calculated for $C_{35}H_{38}ClN_6O_5$ (M+H)$^+$: m/z=657.3; found 657.3.

Step 5: tert-butyl 2-(2-chloro-3'-(5-formyl-1-methyl-2-oxo-1,2-dihydropyridine-3-carboxamido)-2'-methylbiphenyl-3-ylcarbamoyl)-1-methyl-6,7-dihydro-1H-imidazo[4,5-c]pyridine-5(4H)-carboxylate A vial was charged with tert-butyl 2-(2-chloro-2'-methyl-3'-(1-methyl-2-oxo-5-vinyl-1,2-dihydropyridine-3-carboxamido)biphenyl-3-ylcarbamoyl)-1-methyl-6,7-dihydro-1H-imidazo[4,5-c]pyridine-5(4H)-carboxylate (Step 4: 440 mg, 0.670 mmol), a stir bar, 1,4-dioxane (1.7 mL) and water (0.6 mL). To this suspension was added potassium osmate dihydrate (9.87 mg, 0.027 mmol). The reaction was stirred for 5 min then sodium periodate (716 mg, 3.35 mmol) was added. After stirring at room temperature for 1 h, the reaction mixture was quenched with a saturated aqueous solution of sodium thiosulfate. The mixture was then extracted with ethyl acetate, and the combined organic layers were separated, washed with brine, dried over Na$_2$SO$_4$, filtered, and concentrated in vacuo. The crude residue was purified by flash chromatography on a silica gel column eluting with 6% methanol in dichloromethane to afford the desired product. LC-MS calculated for $C_{34}H_{36}ClN_6O_6$ (M+H)$^+$: m/z=659.2; found 659.4.

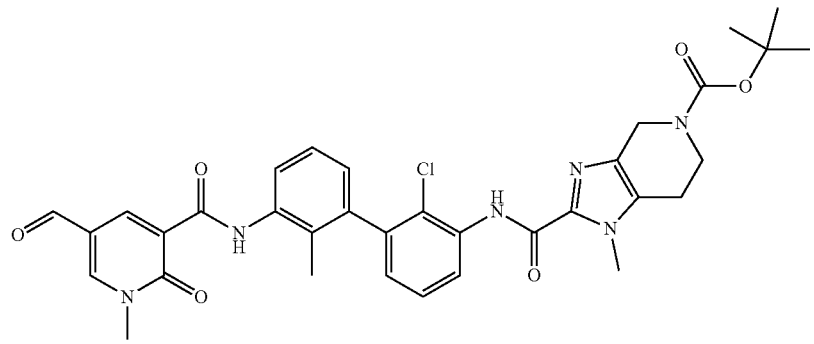 [SMILES: Cc1c(NC(=O)c2cc(C=O)cn(C)c2=O)cccc1-c1cccc(NC(=O)c2nc3c(n2C)CCN(C(=O)OC(C)(C)C)C3)c1Cl]

Step 6: (R)-tert-butyl 2-(2-chloro-3'-(5-((3-hydroxypyrrolidin-1-yl)methyl)-1-methyl-2-oxo-1,2-dihydropyridine-3-carboxamido)-2'-methylbiphenyl-3-ylcarbamoyl)-1-methyl-6,7-dihydro-1H-imidazo[4,5-c]pyridine-5(4H)-carboxylate

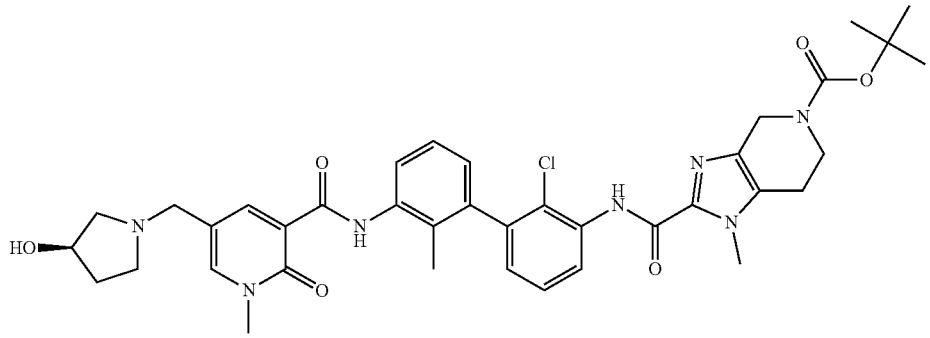 [SMILES: Cc1c(NC(=O)c2cc(CN3CC[C@@H](O)C3)cn(C)c2=O)cccc1-c1cccc(NC(=O)c2nc3c(n2C)CCN(C(=O)OC(C)(C)C)C3)c1Cl]

A mixture of tert-butyl 2-(2-chloro-3'-(5-formyl-1-methyl-2-oxo-1,2-dihydropyridine-3-carboxamido)-2'-methylbiphenyl-3-ylcarbamoyl)-1-methyl-6,7-dihydro-1H-imidazo[4,5-c]pyridine-5(4H)-carboxylate (Step 5: 12 mg, 0.018 mmol), (7?)-pyrrolidin-3-ol (8 mg, 0.092 mmol), and acetic acid (5.26 µL, 0.092 mmol) in THF (0.5 mL) was stirred at room temperature for 0.5 h. Then sodium triacetoxyborohydride (11.68 mg, 0.055 mmol) was added. The mixture was further stirred at room temperature for 1 h. The reaction mixture was quenched by $NH_4OH$ aqueous solution then extracted with DCM. The organic phases were combined and dried over $MgSO_4$, then filtered. The filtrate was concentrated and used directly in the next step without further purification. LC-MS calculated for $C_{38}H_{45}ClN_7O_6$ $(M+H)^+$: m/z=730.3; found 730.5.

Step 7: (R)—N-(2-chloro-3'-(5-((3-hydroxypyrrolidin-1-yl)methyl)-1-methyl-2-oxo-1,2-dihydropyridine-3-carboxamido)-2'-methylbiphenyl-3-yl)-1,5-dimethyl-4,5,6,7-tetrahydro-1H-imidazo[4,5-c]pyridine-2-carboxamide A solution of (R)-tert-butyl 2-(2-chloro-3'-(5-((3-hydroxypyrrolidin-1-yl)methyl)-1-methyl-2-oxo-1,2-dihydropyridine-3-carboxamido)-2'-methylbiphenyl-3-ylcarbamoyl)-1-methyl-6,7-dihydro-1H-imidazo[4,5-c]pyridine-5(4H)-carboxylate (Step 6: 10 mg, 0.014 mmol) in dichloromethane (0.05 mL) and trifluoroacetic acid (0.05 mL) was stirred at room temperature for 30 min. The solvent was evaporated, and the residue was dissolved in tetrahydrofuran (0.6 mL). 37 wt. % formaldehyde in water (0.020 mL, 0.27 mmol) and sodium triacetoxyborohydride (9.44 mg, 0.045 mmol) were successively added. After being stirred at room temperature for 1 h, the mixture was diluted with methanol, and purified by prep-HPLC (pH=10, acetonitrile/water+$NH_4OH$) to give the desired product. LC-MS calculated for $C_{34}H_{39}ClN_7O_4$ $(M+H)^+$: m/z=644.3; found 644.3.

Example 49

(R)-1-((5-(2'-chloro-3'-(1,5-dimethyl-4,5,6,7-tetrahydro-1H-imidazo[4,5-c]pyridine-2-carboxamido)-2-methylbiphenyl-3-ylcarbamoyl)-1-methyl-6-oxo-1,6-dihydropyridin-3-yl)methyl)pyrrolidine-3-carboxylic acid

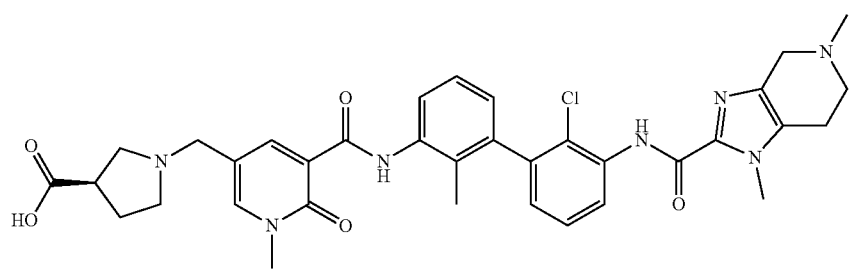 [SMILES: Cc1c(NC(=O)c2cc(CN3CC[C@@H](C(=O)O)C3)cn(C)c2=O)cccc1-c1cccc(NC(=O)c2nc3c(n2C)CCN(C)C3)c1Cl]

This compound was prepared using similar procedures as described for Example 48 with (7?J-pyrrolidine-3-carboxylic acid replacing (7?)-pyrrolidin-3-ol in Step 6. The reaction mixture was diluted with methanol and purified by prep-HPLC (pH=10, acetonitrile/water+$NH_4OH$) to give the desired product. LC-MS calculated for $C_{35}H_{39}ClN_7O_5$ $(M+H)^+$: m/z=672.3; found 672.3.

Example 50

N-(2-chloro-2'-methyl-3'-(1-methyl-2-oxo-5-(pyrrolidin-1-ylmethyl)-1,2-dihydropyridine-3-carboxamido)biphenyl-3-yl)-1,5-dimethyl-4,5,6,7-tetrahydro-1H-imidazo[4,5-c]pyridine-2-carboxamide

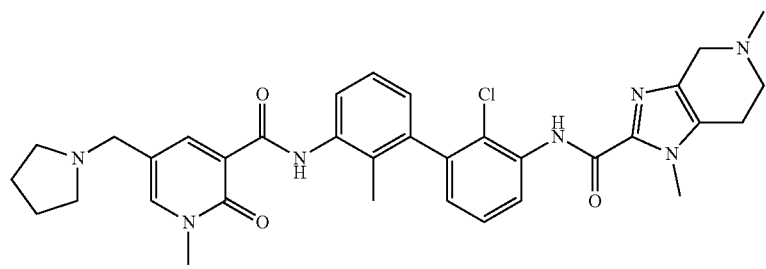 [SMILES: Cc1c(NC(=O)c2cc(CN3CCCC3)cn(C)c2=O)cccc1-c1cccc(NC(=O)c2nc3c(n2C)CCN(C)C3)c1Cl]

This compound was prepared using similar procedures as described for Example 48 with pyrrolidine replacing (R)-pyrrolidin-3-ol in Step 6. The reaction mixture was diluted with methanol and purified by prep-HPLC (pH=10, acetonitrile/water+NH$_4$OH) to give the desired product. LC-MS calculated for $C_{34}H_{39}ClN_7O_3$ (M+H)$^+$: m/z=628.3; found 628.3.

Example 51

N-(2-chloro-3'-(5-(((R)-3-hydroxypyrrolidin-1-yl)methyl)-1-methyl-2-oxo-1,2-dihydropyridine-3-carboxamido)-2'-methylbiphenyl-3-yl)-5-((S)-2-hydroxypropyl)-1-methyl-4,5,6,7-tetrahydro-1H-imidazo[4,5-c]pyridine-2-carboxamide

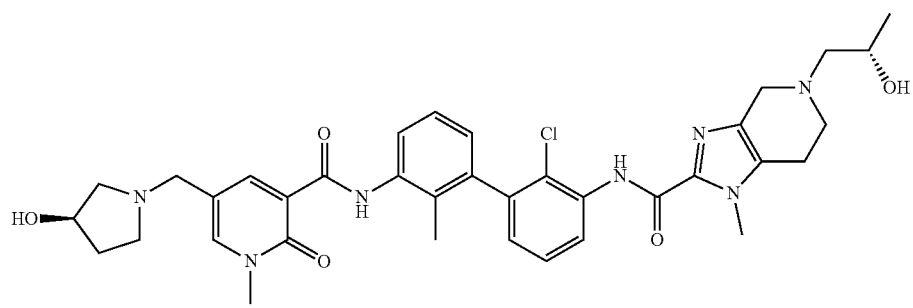 [SMILES: Cc1c(NC(=O)c2cc(CN3CC[C@@H](O)C3)cn(C)c2=O)cccc1-c1cccc(NC(=O)c2nc3c(n2C)CCN(C[C@H](C)O)C3)c1Cl]

This compound was prepared using similar procedures as described for Example 48 with (S)-2-((tert-butyldimethylsilyl)oxy)propanal replacing 37 wt. % formaldehyde in water in Step 7. After being stirred at room temperature for 1 h, the reaction was treated with 1 M HCl (aq.) solution (0.45 mL), and stirred at 60° C. for 30 min. The reaction mixture was diluted with methanol and purified by prep-HPLC (pH=10, acetonitrile/water+NH$_4$OH) to give the desired product. LC-MS calculated for $C_{36}H_{43}ClN_7O_5$ (M+H)$^+$: m/z=688.3; found 688.3.

Example 52

(S)—N-(2-chloro-2'-methyl-3'-(1-methyl-2-oxo-5-(pyrrolidin-1-ylmethyl)-1,2-dihydropyridine-3-carboxamido)biphenyl-3-yl)-5-(2-hydroxypropyl)-1-methyl-4,5,6,7-tetrahydro-1H-imidazo[4,5-c]pyridine-2-carboxamide

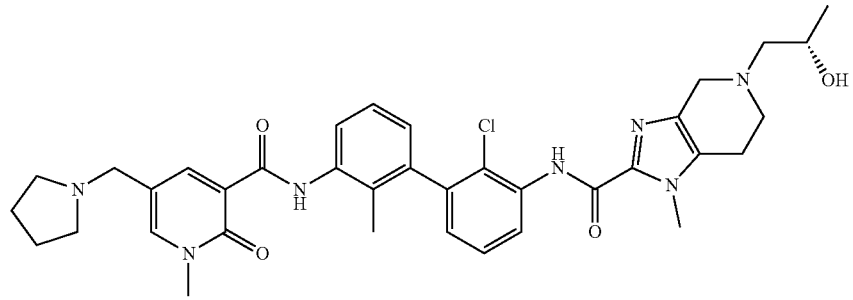 [SMILES: Cc1c(NC(=O)c2cc(CN3CCCC3)cn(C)c2=O)cccc1-c1cccc(NC(=O)c2nc3c(n2C)CCN(C[C@H](C)O)C3)c1Cl]

This compound was prepared using similar procedures as described for Example 48 with pyrrolidine replacing (R)-pyrrolidin-3-ol in Step 6, and (S)-2-((tert-butyldimethylsilyl)oxy)propanal replacing 37 wt. % formaldehyde in water in Step 7. After being stirred at room temperature for 1 h, the reaction was treated with 1 M HCl (aq.) solution (0.45 mL), and stirred at 60° C. for 30 min. The reaction mixture was diluted with methanol and purified by prep-HPLC (pH=10, acetonitrile/water+NH$_4$OH) to give the desired product. LC-MS calculated for C$_{36}$H$_{43}$ClN$_7$O$_4$ (M+H)$^+$: m/z=672.3; found 672.3.

Example 53

N-(2-chloro-3'-(5-(2-(dimethylamino)acetyl)-5,6-dihydro-4H-pyrrolo[3,4-d]thiazol-2-yl)-2'-methylbiphenyl-3-yl)-1,5-dimethyl-4,5,6,7-tetrahydro-1H-imidazo[4,5-c]pyridine-2-carboxamide

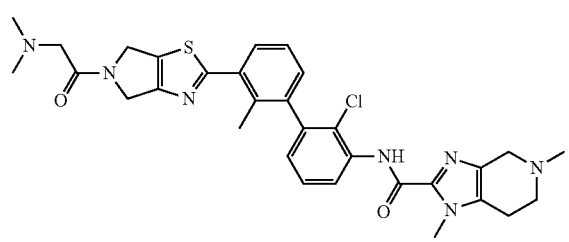

Step 1: tert-butyl 2-(3-chloro-2-methylphenyl)-4H-pyrrolo[3,4-d]thiazole-5(6H)-carboxylate

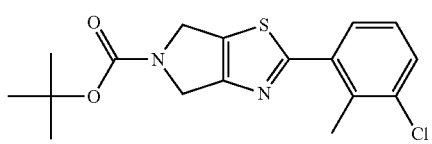 [SMILES: Cc1c(Cl)cccc1-c1nc2c(s1)CN(C(=O)OC(C)(C)C)C2]

A mixture of tert-butyl 2-bromo-4,6-dihydro-5H-pyrrolo[3,4-d]thiazole-5-carboxylate (0.30 g, 0.983 mmol), (3-chloro-2-methylphenyl)boronic acid (0.201 g, 1.180 mmol), tetrakis(triphenylphosphine)palladium(0) (0.114 g, 0.098 mmol) and potassium carbonate (0.272 g, 1.966 mmol) in 1,4-dioxane (4.5 mL) and water (1.5 mL) was degassed and stirred at 90° C. for 3 h. EtOAc and water were added and stirred over weekend. The organic layer was separated, washed with sat. NaHCO$_3$ solution and brine, dried over Na$_2$SO$_4$ and concentrated under reduced pressure. The residue was purified by flash chromatography on a silica gel column eluting with 25% ethyl acetate in hexanes to afford the desired product (228 mg, 66% yield). LCMS calculated for C$_{17}$H$_{20}$ClN$_2$O$_2$S (M+H)$^+$: m/z=351.1; found 351.1.

Step 2: tert-butyl 2-(2-methyl-3-(4,4,5,5-tetramethyl-1,3,2-dioxaborolan-2-yl)phenyl)-4H-pyrrolo[3,4-d]thiazole-5(6H)-carboxylate

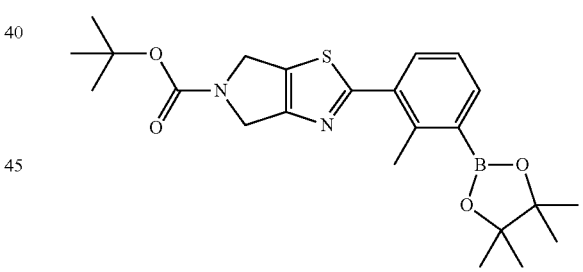

A mixture of tert-butyl 2-(3-chloro-2-methylphenyl)-4,6-dihydro-5H-pyrrolo[3,4-d]thiazole-5-carboxylate (Step 1: 228 mg, 0.650 mmol), 4,4,4',4',5,5,5',5'-octamethyl-2,2'-bi(1,3,2-dioxaborolane) (248 mg, 0.975 mmol), tris(dibenzylideneacetone)dipalladium(0) (47.6 mg, 0.052 mmol), 2-dicyclohexylphosphino-2',4',6'-tri-iso-propyl-1,1'-biphenyl (49.6 mg, 0.104 mmol) and potassium acetate (128 mg, 1.300 mmol) in 1,4-dioxane (1 mL) was degassed and stirred at 100° C. for 3 h. After being cooled to room temperature, EtOAc and water were added. The organic layer was separated, washed with sat. NaHCO$_3$ solution and brine, dried over Na$_2$SO$_4$ and concentrated under reduced pressure. The residue was purified by flash chromatography on a silica gel column eluting with 25% ethyl acetate in hexanes to afford the desired product (250 mg, 87% yield). LCMS calculated for C$_{23}$H$_{32}$BN$_2$O$_4$S (M+H)$^+$: m/z=443.2; found 443.2.

Step 3: N-(2-chloro-3'-(5,6-dihydro-4H-pyrrolo[3,4-d]thiazol-2-yl)-2'-methylbiphenyl-3-yl)-1,5-dimethyl-4,5,6,7-tetrahydro-1H-imidazo[4,5-c]pyridine-2-carboxamide

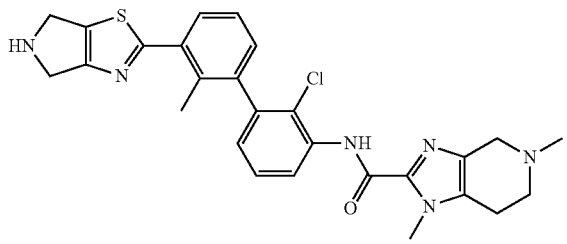 [SMILES: Cc1c(-c2nc3c(s2)CNC3)cccc1-c1cccc(NC(=O)c2nc3c(n2C)CCN(C)C3)c1Cl]

A mixture of N-(3-bromo-2-chlorophenyl)-1,5-dimethyl-4,5,6,7-tetrahydro-1H-imidazo[4,5-c]pyridine-2-carboxamide (Example 24, Step 2: 248 mg, 0.647 mmol), tert-butyl 2-(2-methyl-3-(4,4,5,5-tetramethyl-1,3,2-dioxaborolan-2-yl)phenyl)-4,6-dihydro-5H-pyrrolo[3,4-d]thiazole-5-carboxylate (Step 2: 220 mg, 0.497 mmol), sodium carbonate (117 mg, 1.100 mmol) and [1,1'-bis(di-cyclohexylphosphino)ferrocene]dichloropalladium(II) (37.7 mg, 0.050 mmol) in 1,4-dioxane (3 mL) and water (1.0 mL) was degased and stirred at 110° C. overnight. The reaction mixture was cooled to room temperature, diluted with water and extracted with ethyl acetate. The combined organic layers were washed with brine, dried over Na$_2$SO$_4$, filtered, and concentrated under reduced pressure. The residue was purified by flash chromatography on a silica gel column eluting with 10% methanol in dichloromethane to afford the crude, which was stirred in DCM (3.0 mL) and TFA (3.0 mL) for 2.5 h. The mixture was concentrated under reduced pressure to give the desired product as the TFA salt. LCMS calculated for C$_{27}$H$_{28}$ClN$_6$O (M+H)$^+$: m/z=519.2; found 519.2.

Step 4; N-(2-chloro-3'-(5-(2-(dimethylamino)acetyl)-5,6-dihydro-4H-pyrrolo[3,4-d]thiazol-2-yl)-2'-methylbiphenyl-3-yl)-1,5-dimethyl-4,5,6,7-tetrahydro-1H-imidazo[4,5-c]pyridine-2-carboxamide To a solution of N-(2-chloro-3'-(5,6-dihydro-4H-pyrrolo[3,4-d]thiazol-2-yl)-2'-methyl-[1,1'-biphenyl]-3-yl)-1,5-dimethyl-4,5,6,7-tetrahydro-1H-imidazo[4,5-c]pyridine-2-carboxamide compound with 2,2,2-trifluoroacetic acid (~1:3) (Step 3: 10.0 mg, 0.012 mmol) in THF (1.0 mL) was successively added N,N-diisopropylethylamine (0.028 mL, 0.160 mmol) and dimethylglycinoyl chloride hydrochloride (5.8 mg, 0.037 mmol). After being stirred at room temperature overnight, the reaction mixture was diluted with MeOH, and purified by pH 10 preparative LC/MS (MeCN/water with NH$_4$OH) to give the desired product. LCMS calculated for C$_{31}$H$_{35}$ClN$_7$O$_2$S (M+H)$^+$: m/z=604.2; found 604.2.

Example 54

(S)-1-(5-chloro-4-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)methoxy)-2-((5-cyanopyridin-3-yl)methoxy)benzyl)piperidine-2-carboxylic acid

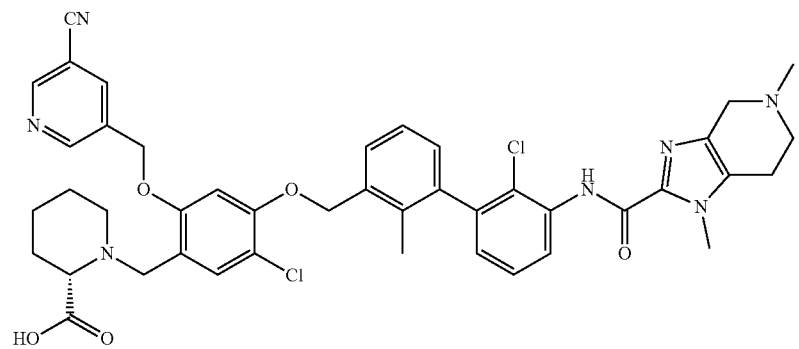 [SMILES: Cc1c(COc2cc(OCc3cncc(C#N)c3)c(CN3CCCC[C@H]3C(=O)O)cc2Cl)cccc1-c1cccc(NC(=O)c2nc3c(n2C)CCN(C)C3)c1Cl]

Step 1: 4-((3-bromo-2-methylbenzyl)oxy)-5-chloro-2-hydroxybenzaldehyde

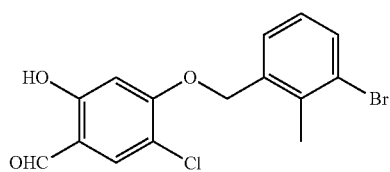 [SMILES: Cc1c(Br)cccc1COc1cc(O)c(C=O)cc1Cl]

To a mixture of (3-bromo-2-methylphenyl)methanol (2.330 g, 11.59 mmol), 5-chloro-2,4-dihydroxybenzaldehyde (2.0 g, 11.59 mmol) and triphenylphosphine (3.65 g, 13.91 mmol) in THF (10 mL) at 0° C. was added DIAD (2.93 mL, 15.07 mmol). The mixture was stirred at room temperature overnight. The mixture was concentrated and diluted with EtOAc. The solid was collected by filtration to give the desired product (2.0 g, 48.5% yield). LCMS calculated for C$_{15}$H$_{13}$BrClO$_3$ (M+H)+: m/z=355.0; found 355.0.

Step 2: 5-((5-((3-bromo-2-methylbenzyl)oxy)-4-chloro-2-formylphenoxy)methyl)nicotinonitrile

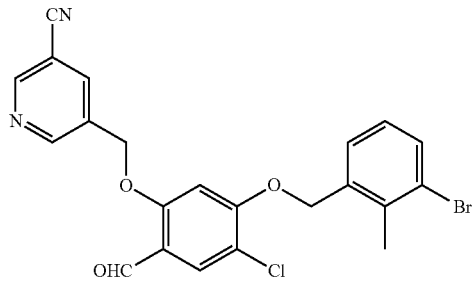 [SMILES: Cc1c(Br)cccc1COc1cc(OCc2cncc(C#N)c2)c(C=O)cc1Cl]

A mixture of 4-((3-bromo-2-methylbenzyl)oxy)-5-chloro-2-hydroxybenzaldehyde (Step 1: 2.0 g, 5.62 mmol), 5-(chloromethyl)nicotinonitrile (0.927 g, 6.07 mmol) and cesium carbonate (2.75 g, 8.44 mmol) in DMF (12 mL) was stirred at 70° C. for 3 hours. The mixture was poured into water. The solid was collected by filtration and air dried to give the desired product (2.2 g, 83% yield). LCMS calculated for $C_{22}H_{17}BrClN_2O_3$ (M+H)+: m/z=471.0; found 471.0.

Step 3: tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate

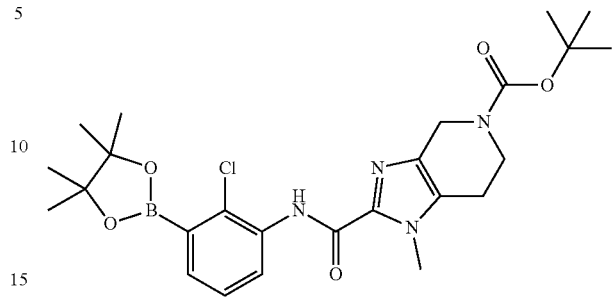

A mixture of tert-butyl 2-((3-bromo-2-chlorophenyl)carbamoyl)-1-methyl-1,4,6,7-tetrahydro-5H-imidazo[4,5-c]pyridine-5-carboxylate (Example 24, Step 1: 1.0 g, 2.129 mmol), 4,4,5,5,4',4',5',5'-octamethyl-[2,2']bi[[1,3,2]dioxaborolanyl] (0.649 g, 2.55 mmol), [1,1'-bis(diphenylphosphino)ferrocene]dichloropalladium(II) complexed with dichloromethane (1:1) (0.174 g, 0.213 mmol) and potassium acetate (0.522 g, 5.32 mmol) in 1,4-dioxane (24.0 mL) was purged with nitrogen and then stirred at 100° C. for 2 h. The reaction mixture was cooled to room temperature, diluted with dichloromethane, and then filtered through Celite. The filtrate was concentrated, and the residue was purified by flash chromatography on a silica gel column eluting with 30% ethyl acetate in hexanes to afford the desired product. LC-MS calculated for $C_{25}H_{35}BClN_4O_5$ (M+H)+: m/z=517.2; found 517.2.

Step 4: tert-butyl 2-((2-chloro-3'-((2-chloro-5-((5-cyanopyridin-3-yl)methoxy)-4-formylphenoxy)methyl)-2'-methyl-[1,1'-biphenyl]-3-yl)carbamoyl)-1-methyl-1,4,6,7-tetrahydro-5H-imidazo[4,5-c]pyridine-5-carboxylate

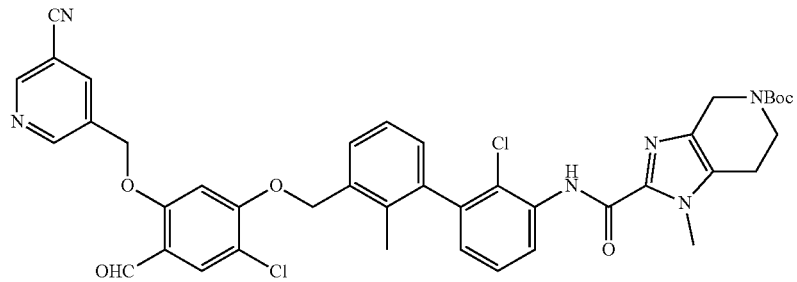 [SMILES: Cc1c(COc2cc(OCc3cncc(C#N)c3)c(C=O)cc2Cl)cccc1-c1cccc(NC(=O)c2nc3c(n2C)CCN(C(=O)OC(C)(C)C)C3)c1Cl]

A mixture of 5-((5-((3-bromo-2-methylbenzyl)oxy)-4-chloro-2-formylphenoxy)methyl)nicotinonitrile (Step 2: 90 mg, 0.191 mmol), tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Step 3:118 mg, 0.229 mmol), potassium carbonate (52.7 mg, 0.382 mmol) and tetrakis(triphenylphosphine)palladium(0) (22.05 mg, 0.019 mmol) in 1,4-dioxane (3 mL) and water (0.60 mL) was purged with nitrogen, and then heated at 100° C. overnight. The mixture was purified on silica chromatography (0-100% EtOAc/Hexanes) to give the desired product (100 mg, 67.1% yield). LCMS calculated for $C_{41}H_{39}Cl_2N_6O_6$ (M+H)+: m/z=781.2; found 781.2.

Step 5: (S)-1-(4-((3'-(5-(tert-butoxycarbonyl)-1-methyl-4,5,6,7-tetrahydro-1H-imidazo[4,5-c]pyridine-2-carboxamido)-2'-chloro-2-methyl-[1,1'-biphenyl]-3-yl)methoxy)-5-chloro-2-((5-cyanopyridin-3-yl)methoxy)benzyl)piperidine-2-carboxylic acid

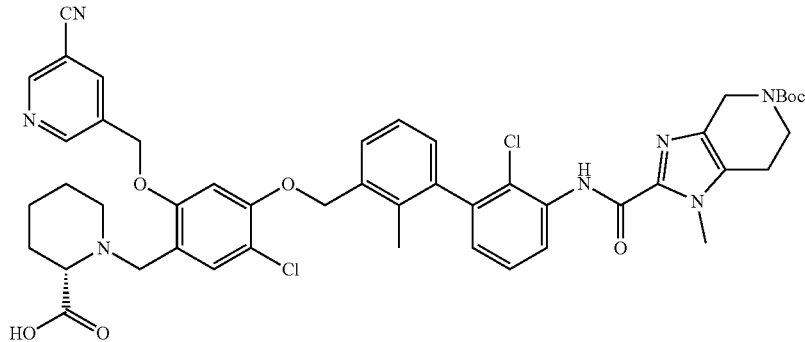 [SMILES: Cc1c(COc2cc(OCc3cncc(C#N)c3)c(CN3CCCC[C@H]3C(=O)O)cc2Cl)cccc1-c1cccc(NC(=O)c2nc3c(n2C)CCN(C(=O)OC(C)(C)C)C3)c1Cl]

Sodium triacetoxyborohydride (56.9 mg, 0.269 mmol) was added to a mixture of tert-butyl 2-((2-chloro-3'-((2-chloro-5-((5-cyanopyridin-3-yl)methoxy)-4-formylphenoxy)methyl)-2'-methyl-[1,1'-biphenyl]-3-yl)carbamoyl)-1-methyl-1,4,6,7-tetrahydro-5H-imidazo[4,5-c]pyridine-5-carboxylate (Step 4: 140 mg, 0.179 mmol), (S)-piperidine-2-carboxylic acid (41.6 mg, 0.322 mmol) and triethylamine (0.050 mL, 0.358 mmol) in DCM (3 mL) after stirring for 2 h at room temperature. After stirring at room temperature for 2 h, the mixture was diluted with DCM, washed with water, dried over $MgSO_4$ and concentrated to give the desired product (80 mg, 49.9% yield). LCMS calculated for $C_{47}H_{50}Cl_2N_7O_7$ (M+H)+: m/z=894.2; found 894.2.

Step 6: (S)-1-(5-chloro-4-((2'-chloro-2-methyl-3'-(1-methyl-4,5,6,7-tetrahydro-1H-imidazo[4,5-c]pyridine-2-carboxamido)-[1,1'-biphenyl]-3-yl)methoxy)-2-((5-cyanopyridin-3-yl)methoxy)benzyl)piperidine-2-carboxylic acid (S)-1-(4-((3'-(5-(tert-butoxycarbonyl)-1-methyl-4,5,6,7-tetrahydro-1H-imidazo[4,5-c]pyridine-2-carboxamido)-2'-chloro-2-methyl-[1,1'-biphenyl]-3-yl)methoxy)-5-chloro-2-((5-cyanopyridin-3-yl)methoxy)benzyl)piperidine-2-carboxylic acid (Step 5: 80 mg, 0.089 mmol) was treated with 4 M HCl solution in 1,4-dioxane (0.5 mL, 2.000 mmol) in DCM (1.0 mL) at room temperature for 30 min. The mixture was purified on prep-HPLC (pH=2, acetonitrile/water+TFA) to give the desired product (30 mg, 42.2% yield). LCMS calculated for $C_{42}H_{42}Cl_2N_7O_5$ (M+H)+: m/z=794.3; found 794.3.

Step 7: (S)-1-(5-chloro-4-((2'-chloro-3'-(1,5-dimethyl-4,5,6,7-tetrahydro-1H-imidazo[4,5-e]pyridine-2-carboxamido)-2-methyl-[1,1'-biphenyl]-3-yl)methoxy)-2-((5-cyanopyridin-3-yl)methoxy)benzyl)piperidine-2-carboxylic acid A mixture of (S)-1-(5-chloro-4-((2'-chloro-2-methyl-3'-(1-methyl-4,5,6,7-tetrahydro-1H-imidazo[4,5-c]pyridine-2-carboxamido)-[1,1'-biphenyl]-3-yl)methoxy)-2-((5-cyanopyridin-3-yl)methoxy)benzyl)piperidine-2-carboxylic acid (4.5 mg, 5.66 µmol) and 37 wt. % formaldehyde in water (0.92 mg, 0.011 mmol) in DCM (1.0 mL) was stirred at room temperature for 30 min. Then to the mixture was added sodium triacetoxyborohydride (2.4 mg, 0.011 mmol) and the reaction was stirred at room temperature for 2 h. The reaction mixture was purified by prep-HPLC (pH=2,

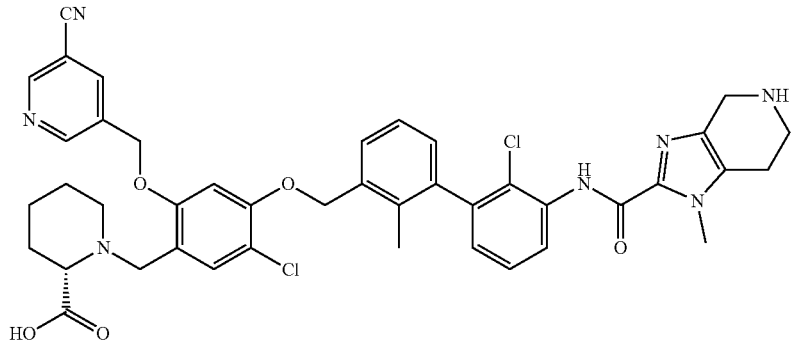 [SMILES: Cc1c(COc2cc(OCc3cncc(C#N)c3)c(CN3CCCC[C@H]3C(=O)O)cc2Cl)cccc1-c1cccc(NC(=O)c2nc3c(n2C)CCNC3)c1Cl]

acetonitrile/water+TFA) to give the desired product as the TFA salt. LCMS calculated for $C_{43}H_{44}Cl_2N_7O_5$ (M+H)+: m/z=808.3; found 808.3.

Example 55

(2S)-1-{[6-(cyanomethoxy)-2-(2-methylbiphenyl-3-yl)-1,3-benzoxazol-5-yl]methyl}piperidine-2-carboxylic acid

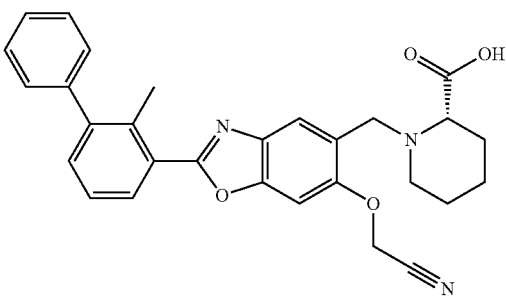 [SMILES: Cc1c(-c2ccccc2)cccc1-c1nc2cc(CN3CCCC[C@H]3C(=O)O)c(OCC#N)cc2o1]

This compound was prepared according to the procedures in US 2017/0145025.

Step 1: methyl 2,4-dihydroxy-5-nitrobenzoate

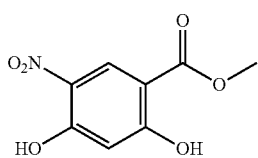

To a solution of methyl 2,4-dihydroxybenzoate (Aldrich, cat # M42505: 9.15 g, 54.4 mmol) in acetic anhydride (34 mL) and acetic acid (66 mL) was slowly added a mixture of nitric acid (3.82 mL, 63.8 mmol) in acetic acid (30 mL) at 0° C. After addition, a light brown solution was formed. Then the mixture was stirred at room temperature for 30 min, after which a suspension had formed. Water (130 mL) was added, whereupon the mixture was aged for another 30 min without stirring. The precipitate was filtered, rinsed with small amount of water, and dried under vacuum to give crude product, which was used directly in the next step without further purification. LC-MS calculated for $C_8H_8NO_6$ $(M+H)^+$: m/z=214.0; found 214.0.

Step 2: methyl 5-amino-2,4-dihydroxybenzoate

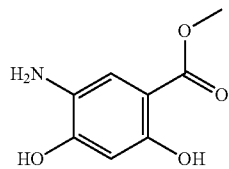

Methyl 2,4-dihydroxy-5-nitrobenzoate (592 mg, 2.78 mmol) was hydrogenated under ambient pressure of hydrogen using palladium on carbon (10 wt %, 300 mg, 0.28 mmol) in ethyl acetate (30 mL) for 3 h. The resulting suspension was filtered through a pad of Celite, washed with ethyl acetate and the solvent was removed under reduced pressure to give crude product, which was used directly without further purification. LC-MS calculated for $C_8H_{10}NO_4$ $(M+H)^+$: m/z=184.1; found 184.0.

Step 3: methyl 6-hydroxy-2-(2-methylbiphenyl-3-yl)-1,3-benzoxazole-5-carboxylate

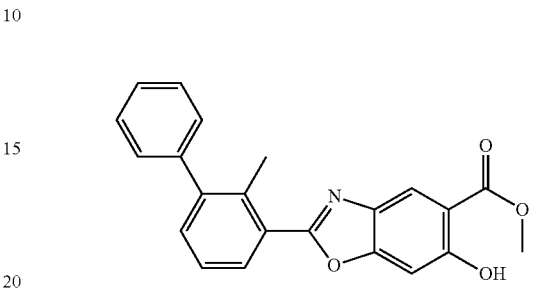

A mixture of methyl 5-amino-2,4-dihydroxybenzoate (660 mg, 3.60 mmol), 2-methylbiphenyl-3-carbaldehyde (777.8 mg, 3.96 mmol) in ethanol (23 mL) was placed in a vial and stirred at room temperature overnight. LC-MS calculated for $C_{22}H_{20}NO_4$ $(M+H)^+$: m/z=362.1; found 362.1. The mixture was then concentrated. The residue was redissovled in methylene chloride (20 mL) and dichlorodicyanoquinone (981 mg, 4.32 mmol) was added. The mixture was stirred at room temperature for 30 min. The reaction was diluted with methylene chloride and washed with a $Na_2S_2O_3$ solution and $NaHCO_3$ solution. The organic phase was dried over $MgSO_4$ and concentrated. The crude residue was purified by flash chromatography on a silica gel column eluting with 0 to 50% EtOAc/Hexanes. LC-MS calculated for $C_{22}H_{18}NO_4$ $(M+H)^+$: m/z=360.1; found 360.1.

Step 4: 5-(hydroxymethyl)-2-(2-methylbiphenyl-3-yl)-1,3-benzoxazol-6-ol

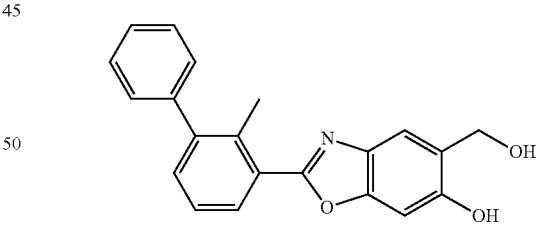

To a solution of methyl 6-hydroxy-2-(2-methylbiphenyl-3-yl)-1,3-benzoxazole-5-carboxylate (845.3 mg, 2.35 mmol) in tetrahydrofuran (20 mL) was added lithium tetrahydroaluminate in THF (1.0 M, 1600 µL) dropwise at 0° C. The mixture was slowly warmed up to room temperature. Then the mixture was quenched with ethyl acetate followed by water and sodium hydroxide solution. The mixture was extracted with ethyl acetate three times. The organic phase was combined, dried over $MgSO_4$ and concentrated. The residue was used in the next step without further purification. LC-MS calculated for $C_{21}H_{18}NO_3$ $(M+H)^+$: m/z=332.1; found 332.1.

Step 5: {[5-(hydroxymethyl)-2-(2-methylbiphenyl-3-yl)-1,3-benzoxazol-6-yl]oxy}acetonitrile

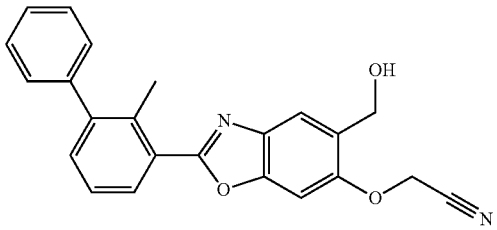 [SMILES: Cc1c(-c2ccccc2)cccc1-c1nc2cc(CO)c(OCC#N)cc2o1]

To 5-(hydroxymethyl)-2-(2-methylbiphenyl-3-yl)-1,3-benzoxazol-6-ol in N,N-dimethylformamide (0.64 mL) was added potassium carbonate (34.1 mg, 0.247 mmol) and bromoacetonitrile (17.2 μL, 0.247 mmol). The mixture was stirred at 50° C. for 40 min. The reaction was then cooled to room temperature and diluted with EtOAc, quenched with water. After extraction, the organic phase was dried over MgSO$_4$ and concentrated. The residue was used directly without further purification. LC-MS calculated for $C_{23}H_{19}N_2O_3$ (M+H)$^+$: m/z=371.1; found 371.1.

Step 6: {[5-formyl-2-(2-methylbiphenyl-3-yl)-1,3-benzoxazol-6-yl]oxy}acetonitrile

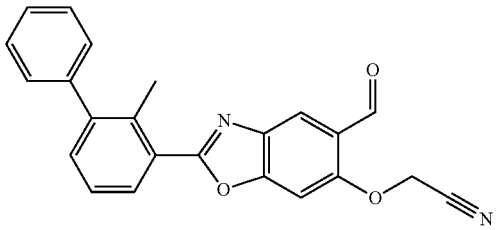 [SMILES: Cc1c(-c2ccccc2)cccc1-c1nc2cc(C=O)c(OCC#N)cc2o1]

{[5-(hydroxymethyl)-2-(2-methylbiphenyl-3-yl)-1,3-benzoxazol-6-yl]oxy}acetonitrile (52 mg, 0.14 mmol) was dissolved in methylene chloride (0.4 mL) and treated with Dess-Martin periodinane (60.1 mg, 0.142 mmol) at room temperature. The reaction was stirred at room temperature for 10 min. and then was quenched with a NaHCO$_3$ solution and Na$_2$S$_2$O$_3$ solution. The mixture was extracted with methylene chloride. The organic phase was combined, dried over MgSO$_4$ and concentrated. The residue was purified by flash chromatography on a silica gel column eluting with 0 to 45% EtOAc/Hexanes. LC-MS calculated for $C_{23}H_{17}N_2O_3$ (M+H)$^+$: m/z=369.1; found 369.2.

Step 7: (2S)-1-{[6-(cyanomethoxy)-2-(2-methylbiphenyl-3-yl)-1,3-benzoxazol-5-yl]methyl}piperidine-2-carboxylic acid This compound was prepared using similar procedures as described for Example 1 of US Publication No. 2017/0145025 with {[5-formyl-2-(2-methylbiphenyl-3-yl)-1,3-benzoxazol-6-yl]oxy}acetonitrile (product from Step 6) replacing 2-(2-methylbiphenyl-3-yl)furo[2,3-b]pyridine-6-carbaldehyde and (S)-piperidine-2-carboxylic acid replacing ethanolamine in Step 5. The reaction mixture was diluted with methanol then purified by prep-HPLC (pH=10, acetonitrile/water+NH$_4$OH) to give the desired product. LC-MS calculated for $C_{29}H_{28}N_3O_4$ (M+H)$^+$: m/z=482.2; found 482.2.

Example 56

4-[6-{[(2-hydroxy ethyl)amino]methyl}-2-(2-methylbiphenyl-3-yl) [1,2,4]triazolo[1,5-a]pyridin-8-yl]butanenitrile

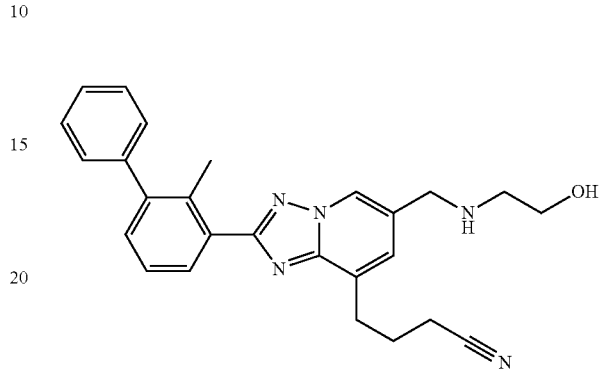

This compound was prepared according to the procedures described in US Publication 2017/0107216. Chloro(2-dicyclohexylphosphino-2',6'-diisopropoxy-1,1'-biphenyl)[2-(2'-amino-1,1'-biphenyl)]palladium(II) (RuPhos-Pd-G2, Aldrich, cat #753246: 1.6 mg, 0.0020 mmol) was added to a mixture of 2-({[8-chloro-2-(2-methylbiphenyl-3-yl)[1,2,4]triazolo[1,5-a]pyridin-6-yl]methyl} amino)ethanol (from Example 21 of US 2017/0107216: 8.0 mg, 0.02 mmol), 4-(4,4,5,5-tetramethyl-1,3,2-dioxaborolan-2-yl)butanenitrile (7.9 mg, 0.041 mmol) and cesium carbonate (13.3 mg, 0.0407 mmol) in 1,4-dioxane (94.5 μL)/water (31.1 μL). The mixture was stirred at 100° C. for 1 h. The crude was diluted with MeOH and filtered. The filtrate was purified by prep-HPLC (pH=2, acetonitrile/water+TFA) to afford the desired product as the TFA salt. LC-MS calculated for $C_{26}H_{28}N_5O$ (M+H)$^+$: m/z=426.2; found: 426.3.

Example 57

2-({[6-methoxy-2-(2-methylbiphenyl-3-yl)-1,3-benzoxazol-5-yl]methyl}amino)ethanol

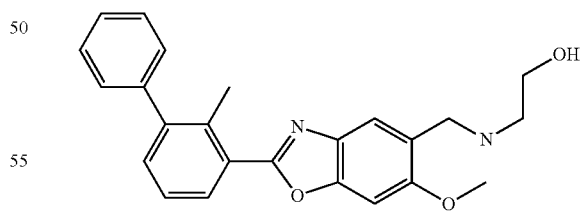

This compound was prepared using similar procedures as described for Example 26 in US Publication No. 2017/0145025 with methyl iodide replacing bromoacetonitrile in Step 5 and ethanolamine replacing (S)-piperidine-2-carboxylic acid in Step 7. The reaction mixture was diluted with methanol and then purified by prep-HPLC (pH=10, acetonitrile/water+NH$_4$OH) to give the desired product. LC-MS calculated for $C_{24}H_{25}N_2O_3$ (M+H)$^+$: m/z=389.2; found 389.2.

Example 58

(2S)-1-({6-(cyanomethoxy)-2-[3-(2,3-dihydro-1,4-benzodioxin-6-yl)-2-methylphenyl]-1,3-benzoxazol-5-yl}methyl)piperidine-2-carboxylic acid

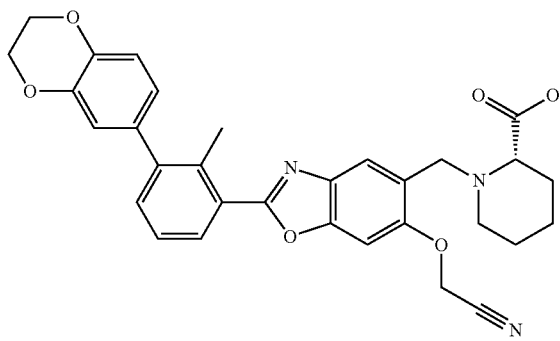

This compound was prepared using similar procedures as described for Example 26 of US Publication No. 2017/0145025 with 3-(2,3-dihydro-1,4-benzodioxin-6-yl)-2-methylbenzaldehyde (product from Step 2 in Example 15 of US 2017/0145025) replacing 2-methylbiphenyl-3-carbaldehyde in Step 3. The reaction mixture was diluted with MeOH and then purified by prep-HPLC (pH=10, acetonitrile/water+NH$_4$OH) to give the desired product. LC-MS calculated for C$_{31}$H$_{30}$N$_3$O$_6$ (M+H)$^+$: m/z=540.2; found 540.2.

Example 59

2-[2-cyano-3-(2,3-dihydro-1,4-benzodioxin-6-yl)phenyl]-6-{[(2-hydroxyethyl)amino]methyl}[1,2,4]triazolo[1,5-a]pyridine-8-carbonitrile

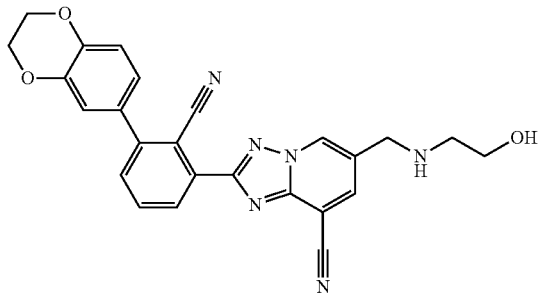 [SMILES: N#Cc1c(-c2ccc3c(c2)OCCO3)cccc1-c1nc2c(C#N)cc(CNCCO)cn2n1]

This compound was prepared according to the procedures in US Publication No. 2017/0107216. A mixture of 2-(8-chloro-6-{[(2-hydroxyethyl)amino]methyl}[1,2,4]triazolo[1,5-a]pyridin-2-yl)-6-(2,3-dihydro-1,4-benzodioxin-6-yl)benzonitrile (Example 25 of US 2017/0107216: 6.0 mg, 0.013 mmol), potassium hexacyanoferrate(II) trihydrate (5.49 mg, 0.0130 mmol), and potassium acetate (0.255 mg, 0.00260 mmol) in 1,4-dioxane (32.2 μL)/water (32.2 μL) was stirred and heated at 100° C. for 1 h. The resulting crude was diluted with MeOH and filtered. The filtrate was purified by prep-HPLC (pH=2, acetonitrile/water+TFA) to give the desired product as the TFA salt. LC-MS calculated for C$_{25}$H$_{21}$N$_6$O$_3$ (M+H)$^+$: m/z=453.2; found: 453.2.

Example 60 trans-4-((2-(2,2'-dichloro-3'-(1,5-dimethyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)cyclohexane-1-carboxylic acid

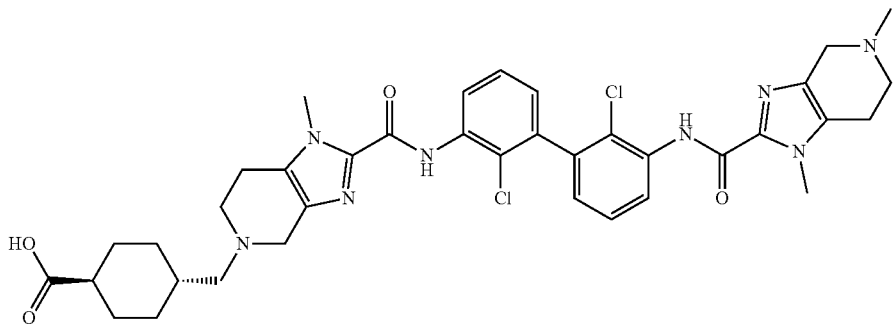 [SMILES: CN1CCc2c(nc(C(=O)Nc3cccc(-c4cccc(NC(=O)c5nc6c(n5C)CCN(C[C@H]5CC[C@H](C(=O)O)CC5)C6)c4Cl)c3Cl)n2C)C1]

Step 1: tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

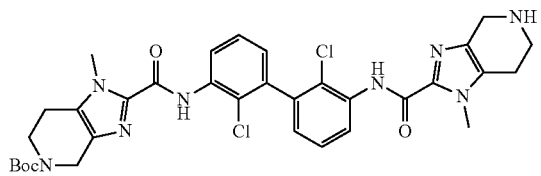 [SMILES: Cn1c(C(=O)Nc2cccc(-c3cccc(NC(=O)c4nc5c(n4C)CCN(C(=O)OC(C)(C)C)C5)c3Cl)c2Cl)nc2c1CCNC2]

A mixture of tert-butyl 2-((3-bromo-2-chlorophenyl)carbamoyl)-1-methyl-1,4,6,7-tetrahydro-5H-imidazo[4,5-c]pyridine-5-carboxylate (Example 24, Step 1: 900 mg, 1.92 mmol) in trifluoroacetic acid (2 mL) and dichloromethane (4 mL) was stirred at room temperature for 1 h. The reaction mixture was concentrated under reduced pressure. A mixture of the above residue, tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Example 54, Step 3: 1188 mg, 2.30 mmol), sodium carbonate (1015 mg, 9.58 mmol) and [1,1-bis(dicyclohexylphosphino)ferrocene]dichloropalladium(II) (145 mg, 0.19 mmol) in 1,4-dioxane (12.0 mL) and water (6.0 mL) was purged with nitrogen and then stirred at 110° C. for 2 h. After being cooled to room temperature, the reaction mixture was diluted with water and extracted with dichloromethane. The combined organic layers were dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{33}$H$_{37}$Cl$_2$N$_8$O$_4$ (M+H)$^+$: m/z=679.2; found 679.2.

Step 2: tert-butyl 2-((2,2'-dichloro-3'-(1 f-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

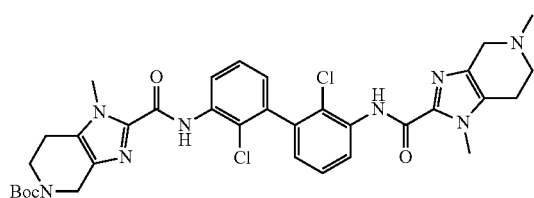

A solution of tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 500 mg, 0.736 mmol), 37 wt. % formaldehyde in water (0.274 mL, 3.68 mmol) and N,N-diisopropylethylamine (0.257 mL, 1.471 mmol) in dichloromethane (7.0 mL) was stirred at room temperature for 10 min. Sodium triacetoxyborohydride (468 mg, 2.207 mmol) was added in portions. After being stirred at room temperature for 1 h, the mixture was quenched with saturated aqueous NaHCO$_3$ solution, and extracted with dichloromethane. The combined organic layers were dried over Na$_2$SO$_4$, filtered and concentrated under reduced pressure. The residue was purified by flash chromatography on a silica gel column eluting with 10% methanol in dichloromethane to afford the desired product. LCMS calculated for C$_{34}$H$_{39}$Cl$_2$N$_8$O$_4$ (M+H)$^+$: m/z=693.2; found 693.3.

Step 3: trans-4-((2-(2,2'-dichloro-3'-(1,5-dimethyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)cyclohexane-1-carboxylic acid A solution of tert-butyl 2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 2: 20 mg, 0.029 mmol) in dichloromethane (0.05 mL) and trifluoroacetic acid (0.05 mL) was stirred at room temperature for 30 min. The mixture was concentrated under reduced pressure. The residue was dissolved in dichloromethane (0.15 mL) and sequentially treated with N,N-diisopropylethylamine (0.020 mL, 0.115 mmol), sodium triacetoxyborohydride (12.2 mg, 0.058 mmol) and methyl trans-4-formylcyclohexanecarboxylate (9.8 mg, 0.058 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, mono hydrate (6.1 mg, 0.144 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{37}$H$_{43}$Cl$_2$N$_8$O$_4$ (M+H)$^+$: m/z=733.3; found 733.3. $^1$H NMR (600 MHz, DMSO-d$_6$) δ 9.95 (s, 1H), 9.92 (s, 1H), 8.32 (d, J=8.2 Hz, 1H), 8.27 (d, 0.7=8.2 Hz, 1H), 7.52 (t, 7=8.1 Hz, 2H), 7.17-7.20 (m, 2H), 4.55-4.44 (m, 2H), 4.30-4.15 (m, 2H), 3.96 (s, 3H), 3.96 (s, 3H), 3.85-3.70 (m, 2H), 3.55-3.36 (m, 2H), 3.15-2.99 (m, 6H), 2.97 (s, 3H), 2.28-2.09 (m, 1H), 1.98-1.78 (m, 5H), 1.46-1.32 (m, 2H), 1.08-0.96 (m, 2H).

Example 61 trans-4-((2-(2,2'-dichloro-3'-(1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)cyclohexane-1-carboxylic acid

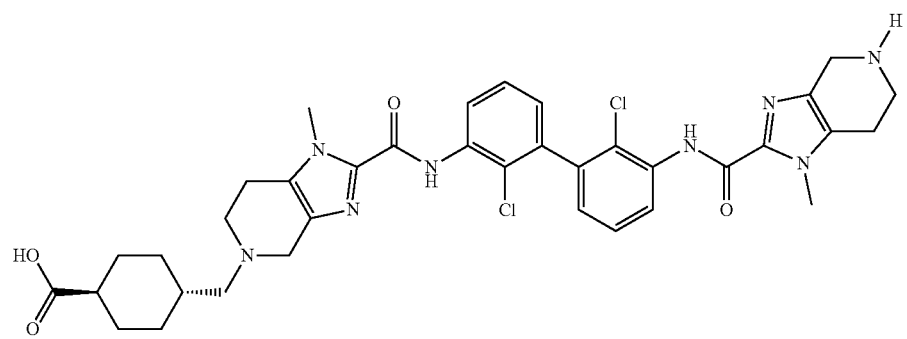 [SMILES: Cn1c(C(=O)Nc2cccc(-c3cccc(NC(=O)c4nc5c(n4C)CCN(C[C@H]4CC[C@H](C(=O)O)CC4)C5)c3Cl)c2Cl)nc2c1CCNC2]

Step 1: tert-butyl trans-2-((2,2'-dichloro-3'-(5-((4-(methoxycarbonyl)cyclohexyl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

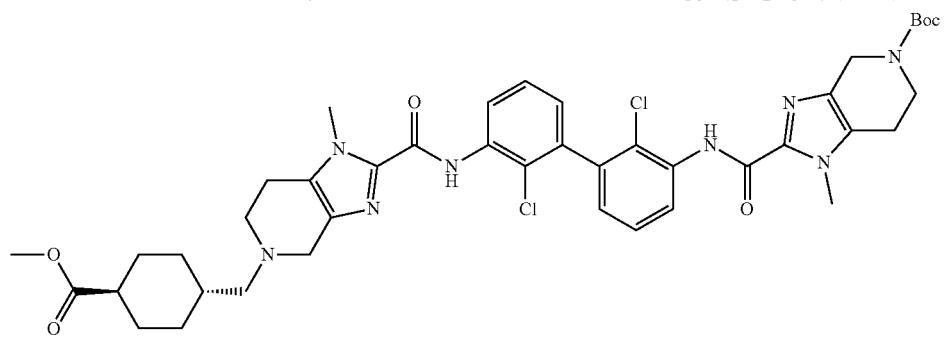 [SMILES: COC(=O)[C@H]1CC[C@H](CN2CCc3c(nc(C(=O)Nc4cccc(-c5cccc(NC(=O)c6nc7c(n6C)CCN(C(=O)OC(C)(C)C)C7)c5Cl)c4Cl)n3C)C2)CC1]

Methyl trans-4-formylcyclohexanecarboxylate (30.1 mg, 0.177 mmol) was added to a mixture of tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 60, Step 1: 80 mg, 0.118 mmol) and sodium triacetoxyborohydride (49.9 mg, 0.235 mmol) in dichloromethane (1.2 mL). After being stirred at room temperature for 2 h, the reaction was quenched with saturated aqueous NaHCO$_3$ solution and extracted with dichloromethane. The combined organic layers were dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{42}$H$_{51}$Cl$_2$N$_8$O$_6$ (M+H)$^+$: m/z=833.3; found 833.5

Step 2: trans-4-((2-(2,2'-dichloro-3'-(1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)cyclohexane-1-carboxylic acid A solution of tert-butyl trans-2-((2,2'-dichloro-3'-(5-((4-(methoxycarbonyl)cyclohexyl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 60 mg, 0.072 mmol) in dichloromethane (0.5 mL) and trifluoroacetic acid (0.5 mL) was stirred at room temperature for 30 min. The mixture was concentrated under reduced pressure. The residue was dissolved in THF/MeOH/water (0.2 mL/0.2 mL/0.1 mL), and then treated with lithium hydroxide, monohydrate (30.2 mg, 0.720 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{36}$H$_{41}$Cl$_2$N$_8$O$_4$ (M+H)$^+$: m/z=719.3; found 719.2.

Example 62 trans-4-((2-(2,2'-dichloro-3'-(5-ethyl-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)cyclohexane-1-carboxylic acid

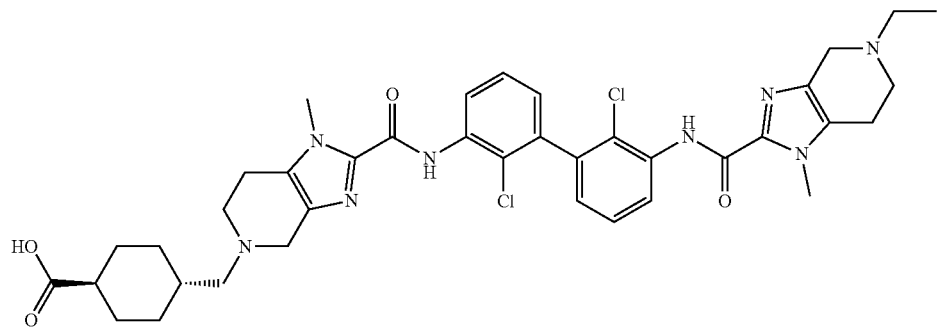 [SMILES: CCN1CCc2c(nc(C(=O)Nc3cccc(-c4cccc(NC(=O)c5nc6c(n5C)CCN(C[C@H]5CC[C@H](C(=O)O)CC5)C6)c4Cl)c3Cl)n2C)C1]

A solution of tert-butyl trans-2-((2,2'-dichloro-3'-(5-((4-(methoxycarbonyl)cyclohexyl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 61, Step 1: 20 mg, 0.024 mmol) in dichloromethane (0.1 mL) and trifluoroacetic acid (0.1 ml) was stirred at room temperature for 30 min. The mixture was concentrated under reduced pressure. The residue was dissolved in dichloromethane (0.24 mL) and sequentially treated with N,N-diisopropylethylamine (0.017 mL, 0.096 mmol), sodium triacetoxyborohydride (10.2 mg, 0.048 mmol) and acetaldehyde (2.7 μL, 0.048 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (10.1 mg, 0.240 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for $C_{38}H_{45}Cl_2N_8O_4$ (M+H)$^+$: m/z=747.3; found 747.4. $^1$H NMR (600 MHz, DMSO-4) δ 9.93 (s, 1H), 9.92 (s, 1H), 8.48-8.06 (m, 2H), 7.52 (t, J=7.9 Hz, 2H), 7.19 (d, J=7.6 Hz, 2H), 4.55-4.47 (m, 2H), 4.28-4.15 (m, 2H), 3.97 (s, 6H), 3.87-3.73 (m, 2H), 3.53-3.37 (m, 2H), 3.36-3.25 (m, 2H), 3.16-2.97 (m, 6H), 2.16 (tt, J=12.3, 3.5 Hz, 1H), 1.94-1.80 (m, 5H), 1.44-1.33 (m, 2H), 1.32 (t, 0.7=7.2 Hz, 3H), 1.07-0.95 (m, 2H).

TABLE 5

The compounds in Table 5 were prepared in accordance with the synthetic protocols set forth in Example 62 using the appropriate starting materials.

| Example # | Name/$^1$H NMR | Structure | LC-MS (M + H)$^+$ |
|---|---|---|---|
| 63 | trans-4-((2-(2,2'-dichloro-3'-(5-(cyclopropylmethyl)-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)cyclohexane-1-carboxylic acid | 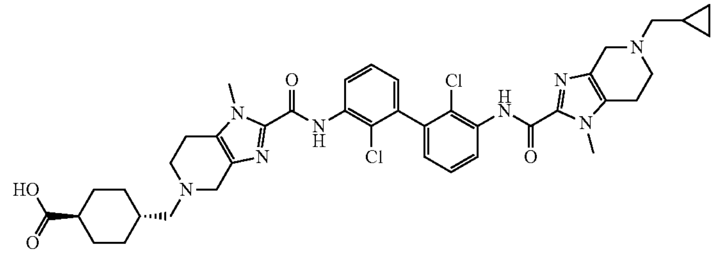 [SMILES: Cn1c(C(=O)Nc2cccc(-c3cccc(NC(=O)c4nc5c(n4C)CCN(C[C@H]4CC[C@H](C(=O)O)CC4)C5)c3Cl)c2Cl)nc2c1CCN(CC1CC1)C2] | 773.4 |
| 64 | trans-4-((2-(2,2'-dichloro-3'-(1-methyl-5-(tetrahydro-2H-pyran-4-yl)-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)cyclohexane-1-carboxylic acid<br>$^1$H NMR (600 MHz, DMSO-d$_6$)<br>δ 9.93 (s, 1H), 9.92 (s, 1H), 8.32 (d, J = 7.7 Hz, 1H), 8.31 (d, J = 7.7 Hz, 1H), 7.52 (t, J = 7.9 Hz, 2H), 7.19 (dd, J = 7.5, 1.8 Hz, 1H), 7.19 (dd, J = 7.5, 1.8 Hz, 1H), 4.52 (d, J = 14.6 Hz, 1H), 4.38 (s, 2H), 4.23 (d, J = 14.6 Hz, 1H), 4.03-3.97 (m, 2H), 3.97 (s, 3H), 3.96 (s, 3H), 3.92 (br, 1H), 3.80 (br, 1H), 3.68-3.56 (m, 1H), 3.51-3.28 (m, 4H), 3.18-2.95 (m, 6H), 2.21-1.98 (m, 3H), 1.97-1.72 (m, 7H), 1.32-1.42 (m, 2H), 1.07-0.96 (m, 2H). | 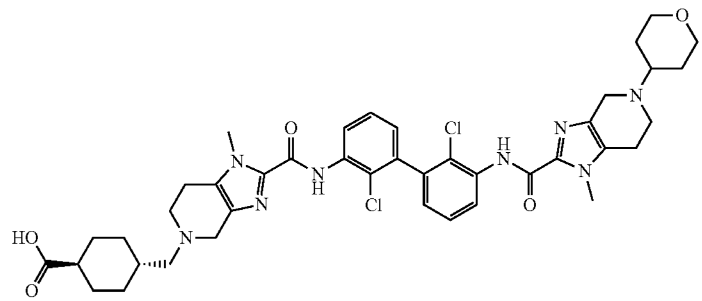 [SMILES: Cn1c(C(=O)Nc2cccc(-c3cccc(NC(=O)c4nc5c(n4C)CCN(C4CCOCC4)C5)c3Cl)c2Cl)nc2c1CCN(C[C@H]1CC[C@H](C(=O)O)CC1)C2] | 803.4 |

Example 65 trans-4-((2-((2,2'-dichloro-3'-(5-(2-hydroxyethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

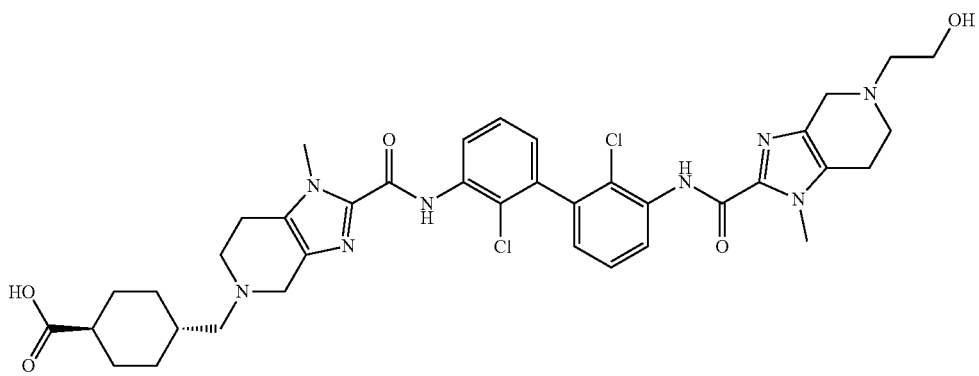 [SMILES: Cn1c(C(=O)Nc2cccc(-c3cccc(NC(=O)c4nc5c(n4C)CCN(C[C@H]4CC[C@H](C(=O)O)CC4)C5)c3Cl)c2Cl)nc2c1CCN(CCO)C2]

A solution of tert-butyl trans-2-((2,2'-dichloro-3'-(5-((4-(methoxycarbonyl)cyclohexyl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 61, Step 1: 20 mg, 0.024 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.096 mmol), sodium triacetoxyborohydride (10.2 mg, 0.048 mmol) and 2-((tert-butyldimethylsilyl)oxy)acetaldehyde (8.4 mg, 0.048 mmol). After being stirred at room temperature for 2 h, the reaction was quenched with saturated aqueous NaHCO₃ solution, and extracted with dichloromethane. The combined organic layers were dried over Na$_2$SO$_4$, filtered, and concentrated under reduced pressure. The residue was treated with 4 N HCl in 1,4-dioxane (0.12 mL, 0.480 mmol) at 30° C. for 1 h, and then the solvent was evaporated. The residue was dissolved in THF/MeOH/water (0.2 mL/0.2 mL/0.1 mL), and then treated with lithium hydroxide, monohydrate (10.1 mg, 0.240 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for $C_{38}H_{45}Cl_2N_8O_5$ (M+H)$^+$: m/z=763.3; found 763.4.

TABLE 6

The compounds in Table 6 were prepared in accordance with the synthetic protocols set forth in Example 65 using the appropriate starting materials.

| Example # | Name | Structure | LC-MS (M + H)+ |
|---|---|---|---|
| 66 | trans-4-((2-((2,2'-dichloro-3'-(5-((S)-2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 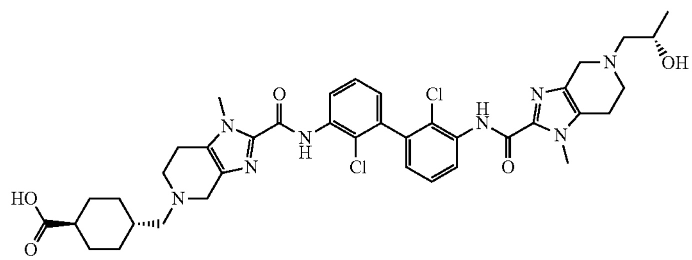 [SMILES: C[C@H](O)CN1CCc2c(nc(C(=O)Nc3cccc(-c4cccc(NC(=O)c5nc6c(n5C)CCN(C[C@H]5CC[C@H](C(=O)O)CC5)C6)c4Cl)c3Cl)n2C)C1] | 777.4 |
| 67 | trans-4-((2-((2,2'-dichloro-3'-(5-((R)-2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 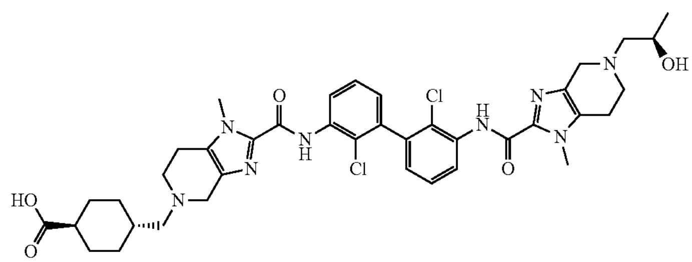 [SMILES: C[C@@H](O)CN1CCc2c(nc(C(=O)Nc3cccc(-c4cccc(NC(=O)c5nc6c(n5C)CCN(C[C@H]5CC[C@H](C(=O)O)CC5)C6)c4Cl)c3Cl)n2C)C1] | 777.4 |

Example 68 cis-4-((2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

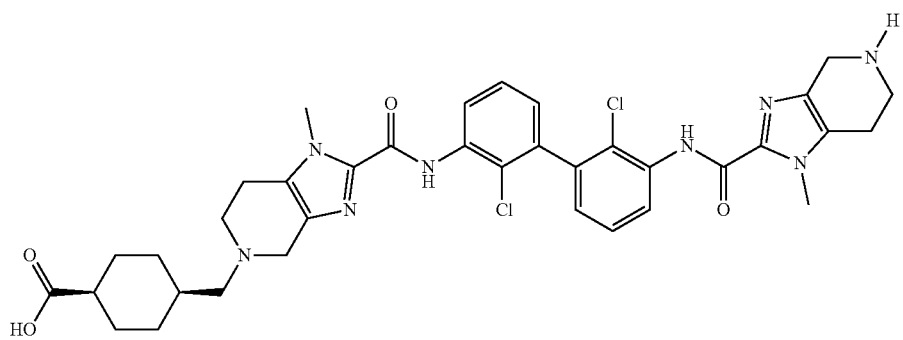 [SMILES: Cn1c(C(=O)Nc2cccc(-c3cccc(NC(=O)c4nc5c(n4C)CCN(C[C@H]4CC[C@@H](C(=O)O)CC4)C5)c3Cl)c2Cl)nc2c1CCNC2]

Step 1: methyl cis-4-(((methylsulfonyl)oxy)methyl) cyclohexane-1-carboxylate

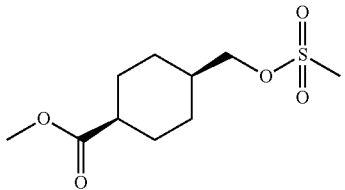

Thionyl chloride (2.77 mL, 37.9 mmol) was added dropwise to a mixture of cis-4-(hydroxymethyl)cyclohexane-1-carboxylic acid (3.0 g, 18.96 mmol) in MeOH (45.0 mL) at 0° C. The reaction was stirred at room temperature for 12 h. The mixture was concentrated under reduced pressure. The residue was dissolved in dichloromethane (45 mL) and sequentially treated with triethylamine (7.93 mL, 56.9 mmol) and methanesulfonyl chloride (1.761 mL, 22.76 mmol). After being stirred at room temperature for 1 h, the reaction was quenched with saturated aqueous NaHCO$_3$ solution, and extracted with dichloromethane. The combined organic layers were dried over Na$_2$SO$_4$, filtered, and concentrated under reduced pressure. The crude residue was used directly in the next step without further purification.

Step 2: tert-butyl cis-2-((2,2'-dichloro-3'-(5-((4-(methoxycarbonyl)cyclohexyl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate A mixture of tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 60, Step 1: 900 mg, 1.324 mmol), methyl cis-4-(((methylsulfonyl)oxy)methyl)cyclohexane-1-carboxylate (Step 1: 994 mg, 3.97 mmol), N,N-diisopropylethylamine (1.157 mL, 6.62 mmol), benzyltriethylammonium chloride (30.2 mg, 0.132 mmol) and potassium iodide (22.0 mg, 0.132 mmol) in DMF (5.9 mL) was stirred at 80° C. for 12 h. The reaction mixture was quenched with saturated aqueous NaHCO$_3$ solution, and extracted with ethyl acetate. The combined organic layers were washed with brine, dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{42}$H$_{51}$Cl$_2$N$_8$O$_6$ (M+H)$^+$: m/z=833.3; found 833.5.

Step 3: cis-4-((2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid A solution of tert-butyl cis-2-((2,2'-dichloro-3'-(5-((4-(methoxycarbonyl)cyclohexyl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 2: 10 mg, 0.012 mmol) in dichloromethane (0.1 mL) and trifluoroacetic acid (0.1 mL) was stirred at room temperature for 30 min. The mixture was concentrated under reduced pressure. The residue was dissolved in THF/MeOH/water (0.2 mL/0.2 mL/0.1 mL), and then treated with lithium hydroxide, monohydrate (5.0 mg, 0.120 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{36}$H$_{41}$Cl$_2$N$_8$O$_4$ (M+H)$^+$: m/z=719.3; found 719.3.

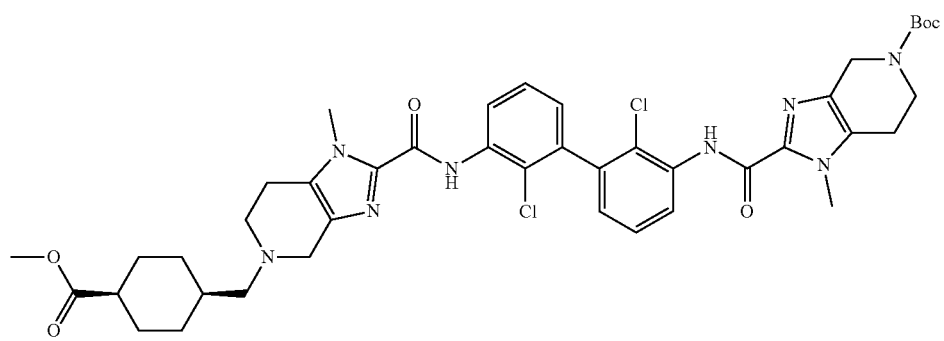 [SMILES: COC(=O)[C@H]1CC[C@@H](CN2CCc3c(nc(C(=O)Nc4cccc(-c5cccc(NC(=O)c6nc7c(n6C)CCN(C(=O)OC(C)(C)C)C7)c5Cl)c4Cl)n3C)C2)CC1]

Example 69 cis-4-((2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

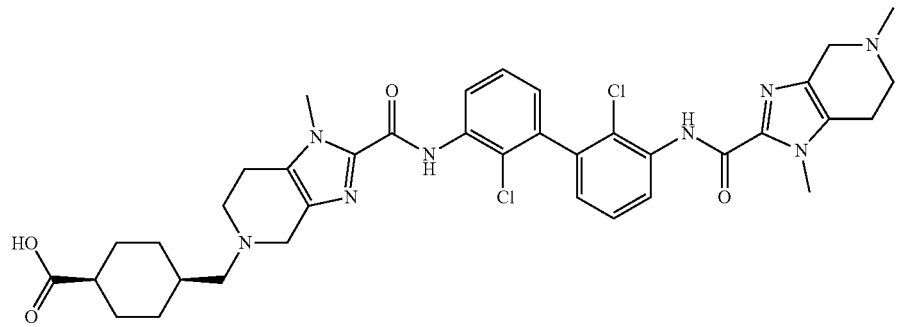 [SMILES: CN1CCc2c(nc(C(=O)Nc3cccc(-c4cccc(NC(=O)c5nc6c(n5C)CCN(C[C@H]5CC[C@@H](C(=O)O)CC5)C6)c4Cl)c3Cl)n2C)C1]

A solution of tert-butyl cis-2-((2,2'-dichloro-3'-(5-((4-(methoxycarbonyl)cyclohexyl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 68, Step 2: 20 mg, 0.024 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.096 mmol), sodium triacetoxyborohydride (10.2 mg, 0.048 mmol), and 37 wt % formaldehyde in water (8.9 μL, 0.120 mmol). After being stirred at room temperature for 2 h, the reaction was quenched with saturated aqueous NaHCO₃ solution, and extracted with dichloromethane. The combined organic layers were dried over Na₂SO₄, filtered, and concentrated under reduced pressure. The residue was dissolved in THF/MeOH/water (0.2 mL/0.2 mL/0.1 mL), and treated with lithium hydroxide, monohydrate (10.1 mg, 0.240 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for $C_{37}H_{43}Cl_2N_8O_4$ (M+H)⁺: m/z=733.3; found 733.4. ¹H NMR (500 MHz, DMSO-d₆) δ 9.95 (s, 1H), 9.92 (s, 1H), 8.32 (dd, J=8.3, 1.5 Hz, 1H), 8.27 (dd, J=8.2, 1.5 Hz, 1H), 7.52 (t, J=8.0 Hz, 1H), 7.52 (t, J=8.0 Hz, 1H), 7.20 (dd, J=7.6, 1.5 Hz, 1H), 7.18 (dd, J=7.6, 1.5 Hz, 1H), 4.51-4.42 (m, 2H), 4.23 (br, 2H), 3.96 (s, 3H), 3.96 (s, 3H), 3.79 (br, 2H), 3.46 (br, 2H), 3.16 (br, 2H), 3.05 (br, 4H), 2.97 (s, 3H), 2.52-2.47 (m, 1H), 2.02 (br, 1H), 1.97-1.78 (m, 2H), 1.72-1.50 (m, 4H), 1.33-1.18 (m, 2H).

TABLE 7

The compounds in Table 7 were prepared in accordance with the synthetic protocols set forth in Example 69 using the appropriate starting materials.

| Example # | Name | Structure | LC-MS (M + H)⁺ |
|---|---|---|---|
| 70 | cis-4-((2-((2,2'-dichloro-3'-(5-ethyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 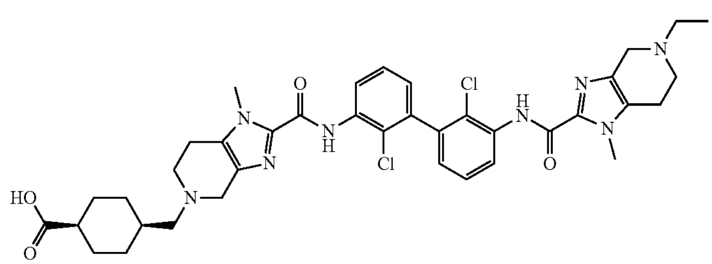 [SMILES: CCN1CCc2c(nc(C(=O)Nc3cccc(-c4cccc(NC(=O)c5nc6c(n5C)CCN(C[C@H]5CC[C@@H](C(=O)O)CC5)C6)c4Cl)c3Cl)n2C)C1] | 747.3 |
| 71 | cis-4-((2-((2,2'-dichloro-3'-(5-(cyclopropylmethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 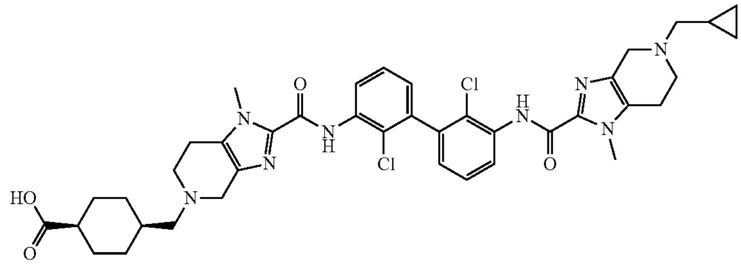 [SMILES: Cn1c(C(=O)Nc2cccc(-c3cccc(NC(=O)c4nc5c(n4C)CCN(C[C@H]4CC[C@@H](C(=O)O)CC4)C5)c3Cl)c2Cl)nc2c1CCN(CC1CC1)C2] | 773.4 |

TABLE 7-continued

The compounds in Table 7 were prepared in accordance with the synthetic protocols set forth in Example 69 using the appropriate starting materials.

| Example # | Name | Structure | LC-MS (M + H)+ |
|---|---|---|---|
| 72 | cis-4-((2-((2,2'-dichloro-3'-(5-isopropyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 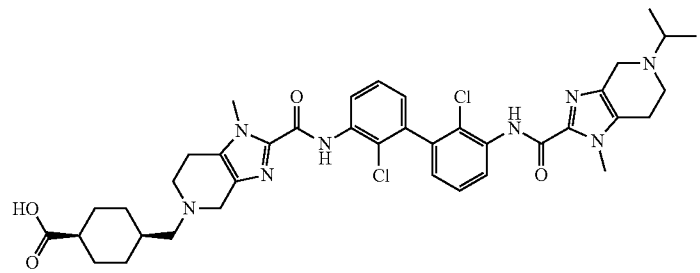 [SMILES: CC(C)N1CCc2c(nc(C(=O)Nc3cccc(-c4cccc(NC(=O)c5nc6c(n5C)CCN(C[C@H]5CC[C@@H](C(=O)O)CC5)C6)c4Cl)c3Cl)n2C)C1] | 761.3 |
| 73 | cis-4-((2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 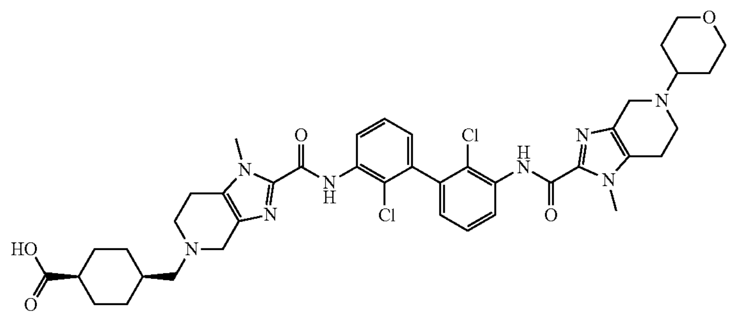 [SMILES: Cn1c(C(=O)Nc2cccc(-c3cccc(NC(=O)c4nc5c(n4C)CCN(C4CCOCC4)C5)c3Cl)c2Cl)nc2c1CCN(C[C@H]1CC[C@@H](C(=O)O)CC1)C2] | 803.5 |

Example 74 cis-4-((2-((2,2'-dichloro-3'-(5-(2-hydroxyethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

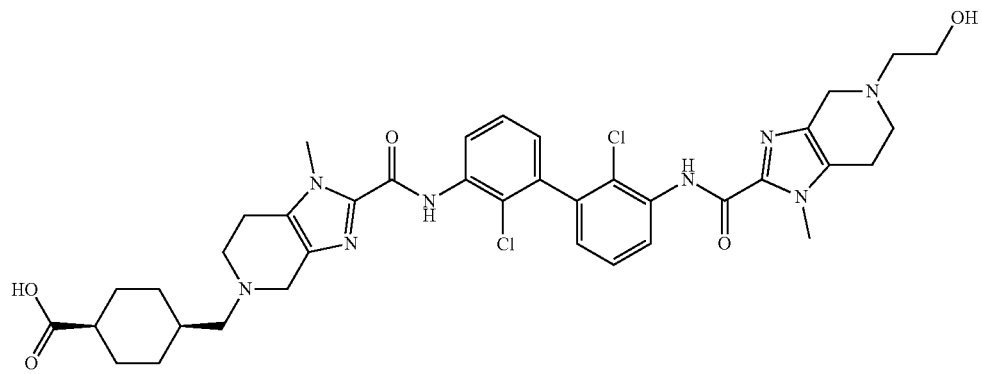 [SMILES: Cn1c(C(=O)Nc2cccc(-c3cccc(NC(=O)c4nc5c(n4C)CCN(C[C@H]4CC[C@@H](C(=O)O)CC4)C5)c3Cl)c2Cl)nc2c1CCN(CCO)C2]

A solution of tert-butyl cis-2-((2,2'-dichloro-3'-(5-((4-(methoxycarbonyl)cyclohexyl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 68, Step 2: 20 mg, 0.024 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.096 mmol), sodium triacetoxyborohydride (10.2 mg, 0.048 mmol) and 2-((tert-butyldimethylsilyl)oxy)acetaldehyde (8.4 mg, 0.048 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was treated with 4 N HCl in 1,4-dioxane (0.12 mL, 0.480 mmol) at 30° C. for 1 h, and then the solvent was evaporated. The residue was dissolved in THF/MeOH/water (0.2 mL/0.2 mL/0.1 mL), and then treated with lithium hydroxide, monohydrate (10.1 mg, 0.240 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{38}$H$_{45}$Cl$_2$N$_8$O$_5$ (M+H)$^+$: m/z=763.3; found 763.4.

TABLE 8

The compounds in Table 8 were prepared in accordance with the synthetic protocols set forth in Example 74 using the appropriate starting materials.

| Example # | Name | Structure | LC-MS (M + H)+ |
|---|---|---|---|
| 75 | cis-4-((2-((2,2'-dichloro-3'-(5-((S)-2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 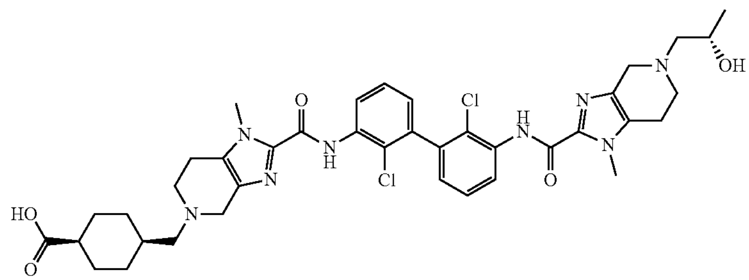 [SMILES: C[C@H](O)CN1CCc2c(nc(C(=O)Nc3cccc(-c4cccc(NC(=O)c5nc6c(n5C)CCN(C[C@H]5CC[C@@H](C(=O)O)CC5)C6)c4Cl)c3Cl)n2C)C1] | 777.4 |
| 76 | cis-4-((2-((2,2'-dichloro-3'-(5-((R)-2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 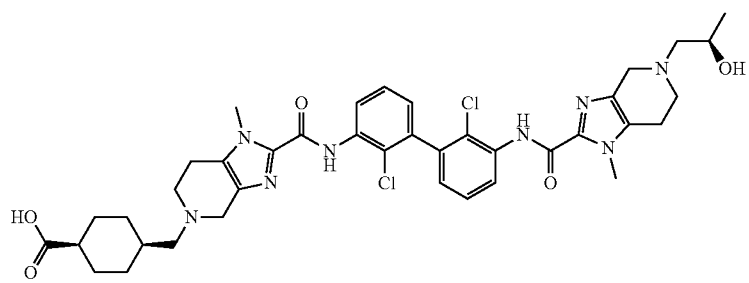 [SMILES: C[C@@H](O)CN1CCc2c(nc(C(=O)Nc3cccc(-c4cccc(NC(=O)c5nc6c(n5C)CCN(C[C@H]5CC[C@@H](C(=O)O)CC5)C6)c4Cl)c3Cl)n2C)C1] | 777.4 |

Example 77

4-(2-(2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

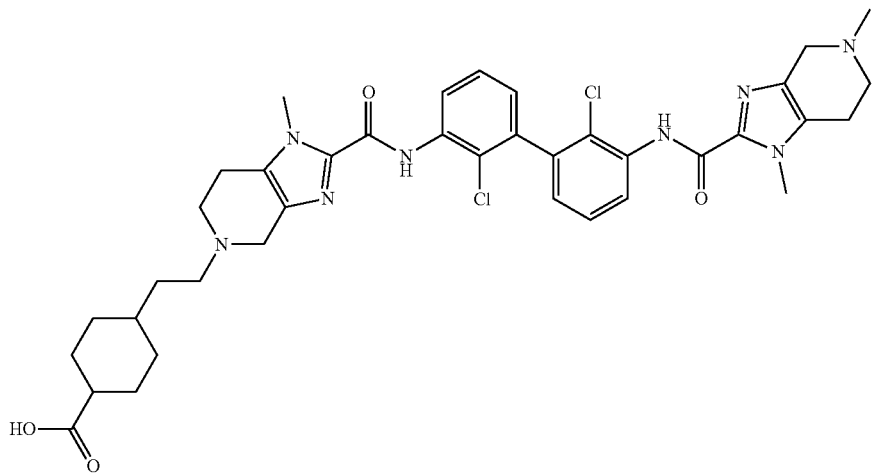 [SMILES: CN1CCc2c(nc(C(=O)Nc3cccc(-c4cccc(NC(=O)c5nc6c(n5C)CCN(CCC5CCC(C(=O)O)CC5)C6)c4Cl)c3Cl)n2C)C1]

A solution of tert-butyl 2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 60, Step 2: 10 mg, 0.014 mmol) in dichloromethane (0.10 mL) and trifluoroacetic acid (0.05 mL) was stirred at room temperature for 30 min. The mixture was concentrated under reduced pressure. The residue was dissolved in dichloromethane (0.15 mL) and sequentially treated with N,N-diisopropylethylamine (10.0 µL, 0.058 mmol), sodium triacetoxyborohydride (12.2 mg, 0.058 mmol), and methyl 4-(2-oxoethyl)cyclohexane-1-carboxylate (5.3 mg, 0.029 mmol). After being stirred at room temperature for 2 h, the reaction was quenched with saturated aqueous NaHCO₃ solution, and extracted with dichloromethane. The combined organic layers were dried over Na₂SO₄, filtered, and concentrated under reduced pressure. The residue was dissolved in THF/MeOH/water (0.2 mL/0.2 mL/0.1 mL), and treated with lithium hydroxide, monohydrate (3.0 mg, 0.072 mmol). After being stirred at 30° C. for 3 h, the reaction mixture was diluted with MeOH, and purified by prep-HPLC (pH=2, acetonitrile/water+TFA) to give two desired products as the TFA salt:

Compound 77-1 (major peak, trans-isomer): retention time on analytical LC-MS (pH=2, acetonitrile/water+TFA) $t_r$-0.95 min, LC-MS calculated for $C_{38}H_{45}Cl_2N_8O_4$ (M+H)$^+$: m/z=747.3; found 747.3; $^1$H NMR (600 MHz, DMSO-d$_6$) δ 9.95 (s, 1H), 9.93 (s, 1H), 8.30 (dd, J=8.3, 1.5 Hz, 1H), 8.27 (dd, J=8.3, 1.5 Hz, 1H), 7.62-7.44 (m, 2H), 7.20 (dd, J=3.0, 1.6 Hz, 1H), 7.18 (dd, J=3.0, 1.6 Hz, 1H), 4.45 (br, 2H), 4.21 (br, 2H), 3.96 (s, 3H), 3.96 (s, 3H), 3.88-3.20 (m, 6H), 3.06-2.96 (m, 4H), 2.94 (s, 3H), 2.14 (tt, J=12.1, 3.6 Hz, 1H), 1.96-1.85 (m, 2H), 1.82-1.72 (m, 2H), 1.66 (br, 2H), 1.35-1.22 (m, 3H), 1.03-0.93 (m, 2H).

Compound 77-2 (minor peak, cis-isomer): retention time on analytical LC-MS (pH=2, acetonitrile/water+TFA) $t_r$=0.98 min, LC-MS calculated for $C_{38}H_{45}Cl_2N_8O_4$ (M+H)$^+$: m/z=747.3; found 747.3.

TABLE 9

The compounds in Table 9 were prepared in accordance with the synthetic protocols set forth in Example 77 using the appropriate starting materials.

| Example # | Name/$^1$H NMR | Structure | LC-MS (M + H)$^+$ |
|---|---|---|---|
| 78 | 4-(2-(2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)benzoic acid $^1$H NMR (600 MHz, DMSO-d$_6$) δ 9.95 (s, 1H), 9.95 (s, 1H), 8.31 (dd, J = 8.2, 1.5 Hz, 1H), 8.27 (dd, J = 8.3, 1.5 Hz, 1H), 7.93 (d, J = 8.3 Hz, 2H), 7.53 (t, J = 7.9, Hz, 1H), 7.51 (t, J = 7.9 Hz, 1H), 7.45 (d, J = 8.3 Hz, 2H), 7.19 (dd, J = 7.6, 1.5 Hz, 1H), 7.19 (dd, J = 7.6, 1.5 Hz, 1H), 4.72-4.10 (m, 4H), 3.97 (s, 3H), 3.96 (s, 3H), 3.17-3.42 (s, 6H), 3.21 (br, 2H), 3.13-3.00 (m, 4H), 2.96 (s, 3H). | 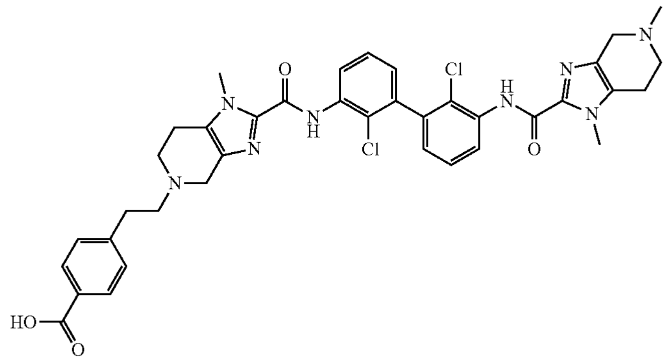 [SMILES: CN1CCc2c(nc(C(=O)Nc3cccc(-c4cccc(NC(=O)c5nc6c(n5C)CCN(CCc5ccc(C(=O)O)cc5)C6)c4Cl)c3Cl)n2C)C1] | 741.3 |
| 79 | 4-(2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)cyclohexane-1-carboxylic acid | Mixture of cis/trans isomers | 719.4 |
| 80 | 4-(2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid | Mixture of cis/trans isomers | 733.4 |

TABLE 9-continued

The compounds in Table 9 were prepared in accordance with the synthetic protocols set forth in Example 77 using the appropriate starting materials.

| Example # | Name/¹H NMR | Structure | LC-MS (M + H)⁺ |
|---|---|---|---|
| 81 | 4-((2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)bicyclo[2.2.2]octane-1-carboxylic acid | 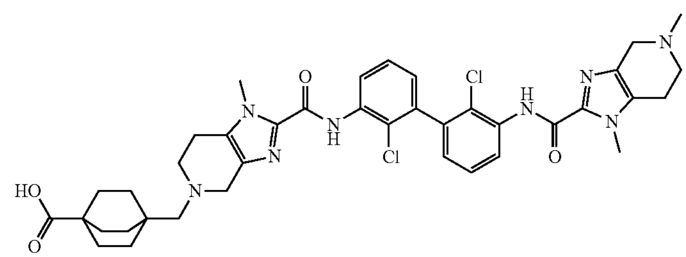 [SMILES: CN1CCc2c(nc(C(=O)Nc3cccc(-c4cccc(NC(=O)c5nc6c(n5C)CCN(CC57CCC(C(=O)O)(CC5)CC7)C6)c4Cl)c3Cl)n2C)C1] | 759.3 |
| 82 (peak 1; Compound 82-1) | 4-((2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)-1-methylcyclohexane-1-carboxylic acid | Peak 1, t_r = 1.00 min (pH = 2, acetonitrile/water + TFA) | 747.4 |
| 82 (peak 2; Compound 82-2) | 4-((2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)-1-methylcyclohexane-1-carboxylic acid | Peak 2, t_r = 1.02 min (pH = 2, acetonitrile/water + TFA) | 747.4 |

Example 83

4-(2-((2,2'-dichloro-3'-(1,5-dimethyl-4,5,6,7-tetra-hydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-ethylcyclohexane-1-carboxylic acid

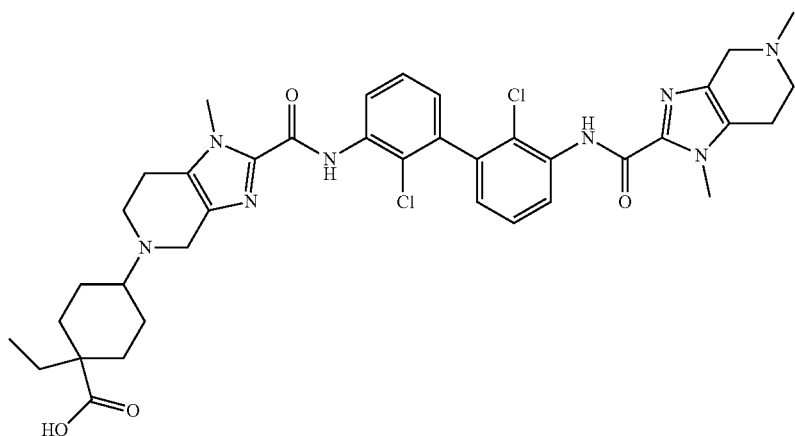 [SMILES: CCC1(C(=O)O)CCC(N2CCc3c(nc(C(=O)Nc4cccc(-c5cccc(NC(=O)c6nc7c(n6C)CCN(C)C7)c5Cl)c4Cl)n3C)C2)CC1]

Step 1: 1-ethyl-4-oxocyclohexane-1-carboxylic acid

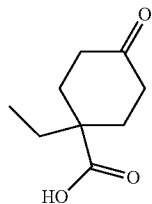

A mixture of ethyl 1-ethyl-4-oxocyclo hexane-1-carboxylate (500 mg, 2.52 mmol) and lithium hydroxide, monohydrate (529 mg, 12.61 mmol) in MeOH (20.0 mL) and water (2.0 mL) was stirred at 70° C. for 2 h. The mixture was cooled down to room temperature, and was acidified with 6 N HCl in water until pH=2. The reaction mixture was extracted with dichloromethane. The combined organic layers were dried over $Na_2SO_4$, filtered, and concentrated under reduced pressure. The crude product was used directly in the next step without further purification.

Step 2: 4-(2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-1)-1-ethylcyclohexane-1-carboxylic acid A solution of tert-butyl 2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 60, Step 2: 10 mg, 0.014 mmol) in dichloromethane (0.10 mL) and trifluoroacetic acid (0.05 mL) was stirred at room temperature for 30 min. The mixture was concentrated under reduced pressure. The residue was dissolved in dichloromethane (0.15 mL) and sequentially treated with N,N-diisopropylethylamine (10.0 µL, 0.058 mmol), sodium triacetoxyborohydride (12.2 mg, 0.058 mmol), and 1-ethyl-4-oxocyclohexane-1-carboxylic acid (Step 1: 7.4 mg, 0.043 mmol). After being stirred at room temperature for 2 h, the reaction mixture was diluted with MeOH, and purified by prep-HPLC (pH=2, acetonitrile/water+TFA) to give the desired product as a mixture of cis/trans isomers. LC-MS calculated for $C_{38}H_{45}Cl_2N_8O_4$ (M+H)$^+$: m/z=747.3; found 747.3.

Example 84

4-((2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid

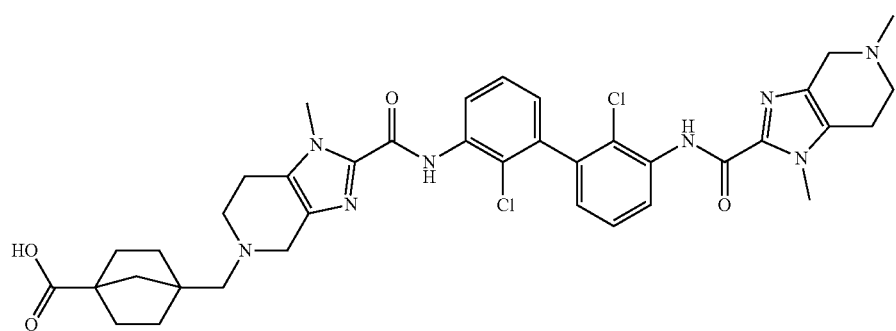 [SMILES: CN1CCc2c(nc(C(=O)Nc3cccc(-c4cccc(NC(=O)c5nc6c(n5C)CCN(CC57CCC(C(=O)O)(CC5)C7)C6)c4Cl)c3Cl)n2C)C1]

Step 1: methyl 4-formylbicyclo[2.2.1]heptane-1-carboxylate

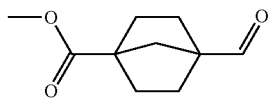

A mixture of methyl 4-(hydroxymethyl)bicyclo[2.2.1]heptane-1-carboxylate (PharmaBlock, cat # PBZ3820: 400 mg, 2.171 mmol) and Dess-Martin periodinane (1381 mg, 3.26 mmol) in dichloromethane (12.0 mL) was stirred at room temperature for 3 h. The reaction mixture was quenched with 20% aqueous $Na_2S_2O_3$ solution and saturated aqueous $NaHCO_3$ solution, and extracted with ethyl acetate. The combined organic layers were washed with brine, dried over $Na_2SO_4$, filtered, and concentrated under reduced pressure. The crude product was used directly in the next step without further purification.

Step 2: 4-((2-((2,2'-dichloro-3(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid A solution of tert-butyl 2-((2,2'-dichloro-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 60, Step 2: 10 mg, 0.014 mmol) in dichloromethane (0.05 mL) and trifluoroacetic acid (0.05 mL) was stirred at room temperature for 30 min. The mixture was concentrated under reduced pressure. The residue was dissolved in dichloromethane (0.15 mL) and sequentially treated with N,N-diisopropylethylamine (10.0 µL, 0.058 mmol), sodium triacetoxyborohydride (12.2 mg, 0.058 mmol), and methyl 4-formylbicyclo[2.2.1]heptane-1-carboxylate (Step 1: 5.3 mg, 0.029 mmol). After being stirred at room temperature for 2 h, the reaction was quenched with saturated aqueous $NaHCO_3$ solution, and extracted with dichloromethane. The combined organic layers were dried over $Na_2SO_4$, filtered, and concentrated under reduced pressure. The residue was dissolved in THF/MeOH/water (0.2 mL/0.2 mL/0.1 mL), and treated with lithium hydroxide, monohydrate (3.0 mg, 0.072 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for $C_{38}H_{43}Cl_2N_8O_4$ $(M+H)^+$: m/z=745.3; found 745.3. $^1H$ NMR (500 MHz, DMSO-$d_6$) δ 9.96 (s, 1H), 9.93 (s, 1H), 8.31 (dd, J=8.3, 1.5 Hz, 1H), 8.27 (dd, J=8.3, 1.5 Hz, 1H), 7.52 (t, J=7.9 Hz, 2H), 7.19 (dd, J=7.5, 1.5 Hz, 1H), 7.19 (dd, J=7.5, 1.5 Hz, 1H), 4.55-4.44 (m, 2H), 4.36-4.15 (m, 2H), 3.97 (s, 3H), 3.96 (s, 3H), 3.85-3.70 (m, 2H), 3.58-3.36 (m, 4H), 3.12-2.99 (m, 4H), 2.97 (s, 3H), 1.98-1.87 (m, 2H), 1.80-1.55 (m, 8H).

Example 85 trans-4-(2-(2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

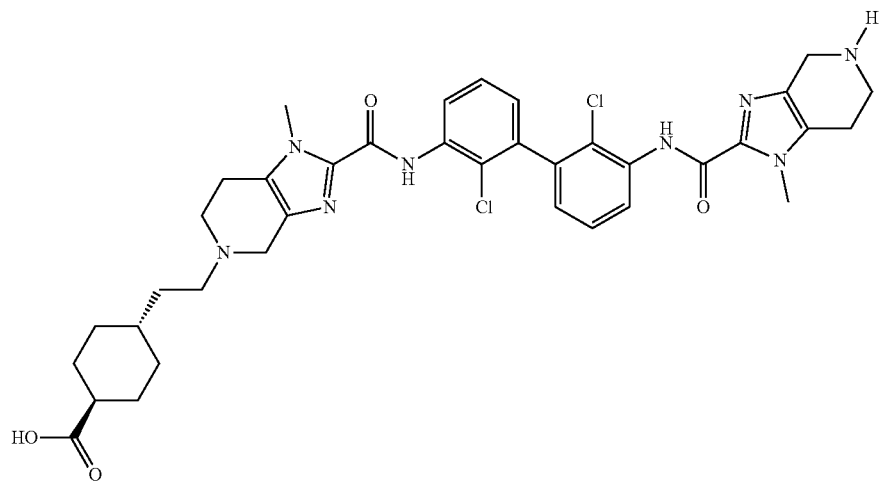 [SMILES: Cn1c(C(=O)Nc2cccc(-c3cccc(NC(=O)c4nc5c(n4C)CCN(CC[C@H]4CC[C@H](C(=O)O)CC4)C5)c3Cl)c2Cl)nc2c1CCNC2]

Step 1: tert-butyl 2-((2,2'-dichloro-3'-(5-(2-(4-(methoxycarbonyl)cyclohexyl)ethyl)-1-methyl-4,5,6,7-tetrahydro-1H-imidazo[4,5-c]pyridine-2-carboxamido)-[1,1'-biphenyl]-3-yl) carbamoyl)-1-methyl-1,4,6,7-tetrahydro-5H-imidazo[4,5-c]pyridine-5-carboxylate

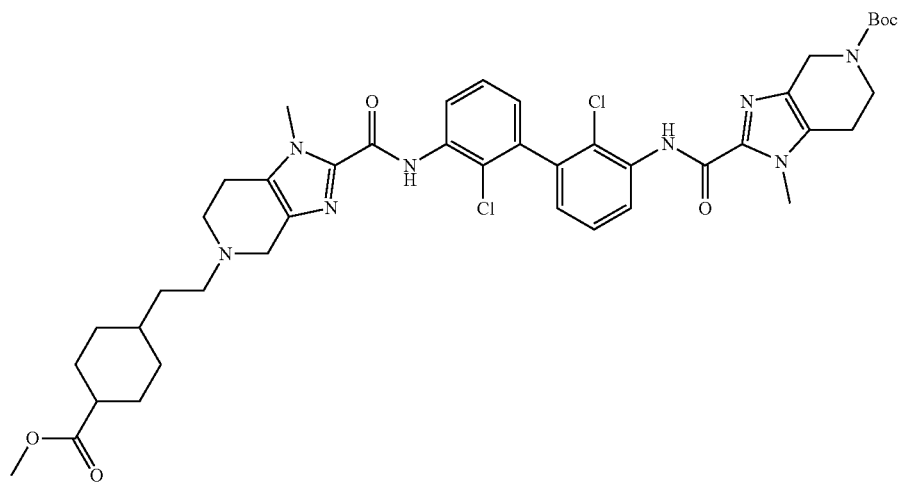 [SMILES: COC(=O)C1CCC(CCN2CCc3c(nc(C(=O)Nc4cccc(-c5cccc(NC(=O)c6nc7c(n6C)CCN(C(=O)OC(C)(C)C)C7)c5Cl)c4Cl)n3C)C2)CC1]

Methyl 4-(2-oxoethyl)cyclohexane-1-carboxylate (61.0 mg, 0.331 mmol) was added to a mixture of tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 60, Step 1: 150 mg, 0.221 mmol) and sodium triacetoxyborohydride (94 mg, 0.441 mmol) in dichloromethane (2.2 mL). After being stirred at room temperature for 2 h, the reaction was quenched with saturated aqueous NaHCO$_3$ solution and extracted with dichloromethane. The combined organic layers were dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{43}$H$_{53}$Cl$_2$N$_8$O$_6$ (M+H)$^+$: m/z=847.3; found 847.5.

Step 2: trans-4-(2-(2-((2,2'-dichloro-3'-(1-methyl-4,5,6,7-tetrahydro-1H-imidazo[4,5-c]pyridine-2-carboxamido)-[1,1'-biphenyl]-3-yl) carbamoyl)-1-methyl-1,4,6,7-tetrahydro-5H-imidazo[4,5-c]pyridin-5-yl)ethyl)cyclohexane-1-carboxylic acid A solution of tert-butyl 2-((2,2'-dichloro-3'-(5-(2-(4-(methoxycarbonyl)cyclohexyl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 20 mg, 0.024 mmol) in dichloromethane (0.05 mL) and trifluoroacetic acid (0.05 mL) was stirred at room temperature for 30 min. The mixture was concentrated under reduced pressure. The residue was dissolved in THF/MeOH/water (0.2 mL/0.2 mL/0.1 mL), and then treated with lithium hydroxide, monohydrate (5.0 mg, 0.118 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for $C_{37}H_{43}Cl_2N_8O_4$ (M+H)$^+$: m/z=733.3; found 733.4.

Example 86 trans-4-(2-(2-((2,2'-dichloro-3'-(5-ethyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid A solution of tert-butyl 2-((2,2'-dichloro-3'-(5-(2-(4-(methoxycarbonyl)cyclohexyl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 85, Step 1: 20 mg, 0.024 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.016 mL, 0.094 mmol), sodium triacetoxyborohydride (15.0 mg, 0.071 mmol), and acetaldehyde (2.7 μL, 0.047 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (5.0 mg, 0.118 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for $C_{39}H_{47}Cl_2N_8O_4$ (M+H)$^+$: m/z=761.3; found 761.4.

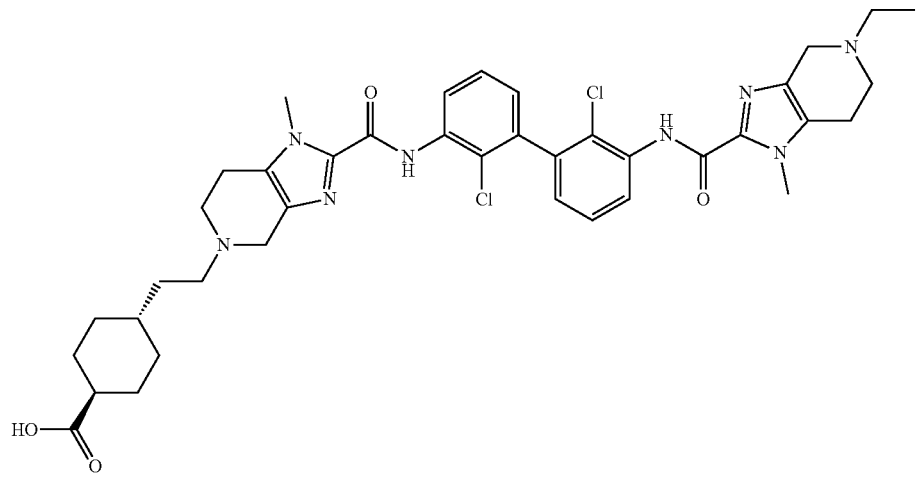 [SMILES: CCN1CCc2c(nc(C(=O)Nc3cccc(-c4cccc(NC(=O)c5nc6c(n5C)CCN(CC[C@H]5CC[C@H](C(=O)O)CC5)C6)c4Cl)c3Cl)n2C)C1]

TABLE 10

The compounds in Table 10 were prepared in accordance with the synthetic protocols set forth in Example 86 using the appropriate starting materials.

| Example # | Name | Structure | LC-MS (M + H)+ |
|---|---|---|---|
| 87 | trans-4-(2-(2-((2,2'-dichloro-3'-(5-(cyclopropylmethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 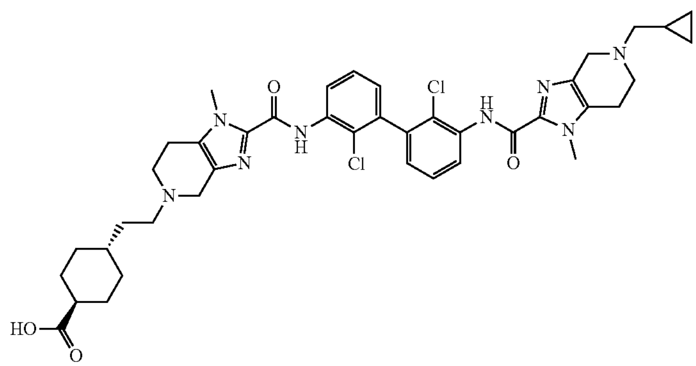 [SMILES: Cn1c(C(=O)Nc2cccc(-c3cccc(NC(=O)c4nc5c(n4C)CCN(CC4CC4)C5)c3Cl)c2Cl)nc2c1CCN(CC[C@H]1CC[C@H](C(=O)O)CC1)C2] | 787.4 |
| 88 | trans-4-(2-(2-((2,2'-dichloro-3'-(5-isopropyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 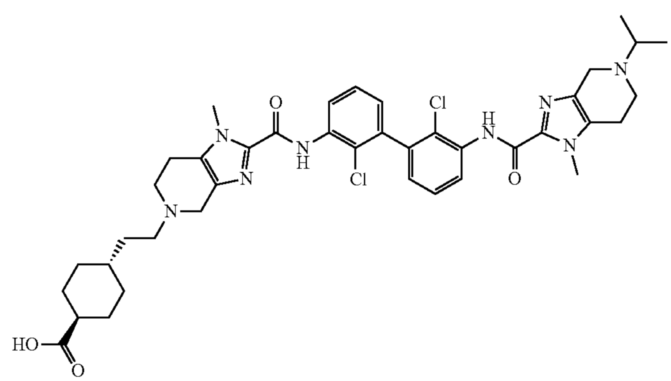 [SMILES: CC(C)N1CCc2c(nc(C(=O)Nc3cccc(-c4cccc(NC(=O)c5nc6c(n5C)CCN(CC[C@H]5CC[C@H](C(=O)O)CC5)C6)c4Cl)c3Cl)n2C)C1] | 775.3 |
| 89 | trans-4-(2-(2-((2,2'-dichloro-3'-(5-cyclobutyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 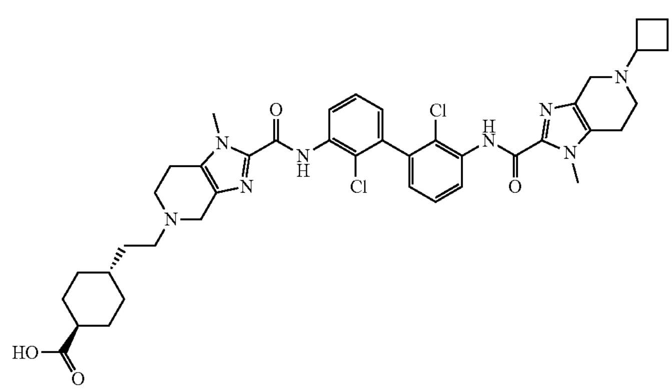 [SMILES: Cn1c(C(=O)Nc2cccc(-c3cccc(NC(=O)c4nc5c(n4C)CCN(C4CCC4)C5)c3Cl)c2Cl)nc2c1CCN(CC[C@H]1CC[C@H](C(=O)O)CC1)C2] | 787.4 |

TABLE 10-continued

The compounds in Table 10 were prepared in accordance with the synthetic protocols set forth in Example 86 using the appropriate starting materials.

| Example # | Name | Structure | LC-MS (M + H)+ |
|---|---|---|---|
| 90 | trans-4-(2-(2-((2,2'-dichloro-3'-(5-cyclopentyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 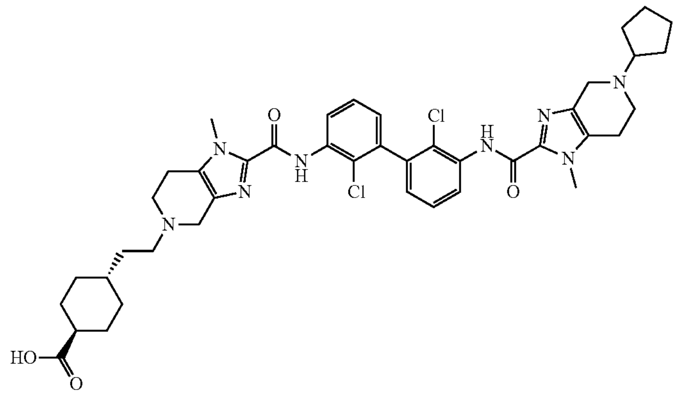 [SMILES: Cn1c(C(=O)Nc2cccc(-c3cccc(NC(=O)c4nc5c(n4C)CCN(C4CCCC4)C5)c3Cl)c2Cl)nc2c1CCN(CC[C@H]1CC[C@H](C(=O)O)CC1)C2] | 801.5 |
| 91 | trans-4-(2-(2-((2,2'-dichloro-3'-(5-cyclohexyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 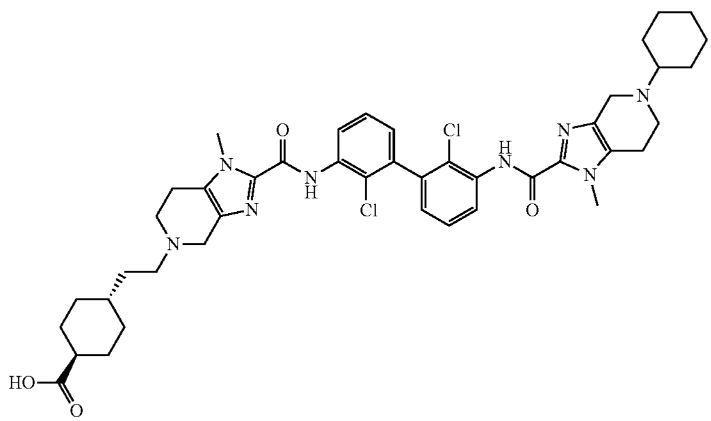 [SMILES: Cn1c(C(=O)Nc2cccc(-c3cccc(NC(=O)c4nc5c(n4C)CCN(C4CCCCC4)C5)c3Cl)c2Cl)nc2c1CCN(CC[C@H]1CC[C@H](C(=O)O)CC1)C2] | 815.5 |
| 92 | trans-4-(2-(2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 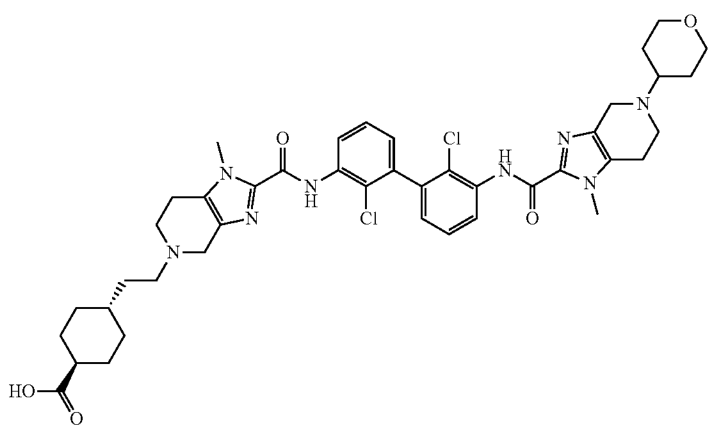 [SMILES: Cn1c(C(=O)Nc2cccc(-c3cccc(NC(=O)c4nc5c(n4C)CCN(C4CCOCC4)C5)c3Cl)c2Cl)nc2c1CCN(CC[C@H]1CC[C@H](C(=O)O)CC1)C2] | 817.4 |

Example 93 trans-4-(2-(2-((2,2'-dichloro-3'-(5-(2-hydroxyethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

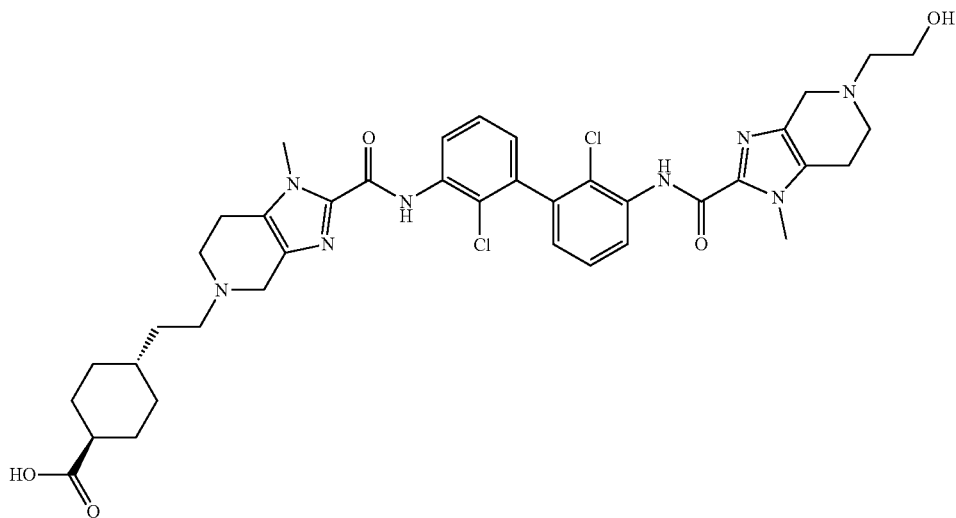 [SMILES: Cn1c(C(=O)Nc2cccc(-c3cccc(NC(=O)c4nc5c(n4C)CCN(CC[C@H]4CC[C@H](C(=O)O)CC4)C5)c3Cl)c2Cl)nc2c1CCN(CCO)C2]

A solution of tert-butyl 2-((2,2'-dichloro-3'-(5-(2-(4-(methoxycarbonyl)cyclohexyl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 85, Step 1: 20 mg, 0.024 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.096 mmol), sodium triacetoxyborohydride (10.0 mg, 0.047 mmol), and 2-((tert-butyldimethylsilyl)oxy)acetaldehyde (8.2 mg, 0.047 mmol). After being stirred at room temperature for 2 h, the reaction was quenched with saturated aqueous NaHCO₃ solution, and extracted with dichloromethane. The combined organic layers were dried over $Na_2SO_4$, filtered, and concentrated under reduced pressure. The residue was treated with 4 N HCl in 1,4-dioxane (0.12 mL, 0.480 mmol) at 30° C. for 1 h, and then the solvent was evaporated. The residue was dissolved in THF/MeOH/water (0.2 mL/0.2 mL/0.1 mL), and then treated with lithium hydroxide, monohydrate (10.1 mg, 0.240 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for $C_{39}H_{47}Cl_2N_8O_5$ $(M+H)^+$: m/z=777.3; found 777.4.

TABLE 11

The compounds in Table 11 were prepared in accordance with the synthetic protocols set forth in Example 93 using the appropriate starting materials.

| Example # | Name | Structure | LC-MS $(M + H)^+$ |
|---|---|---|---|
| 94 | trans-4-(2-(2-((2,2'-dichloro-3'-(5-((S)-2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 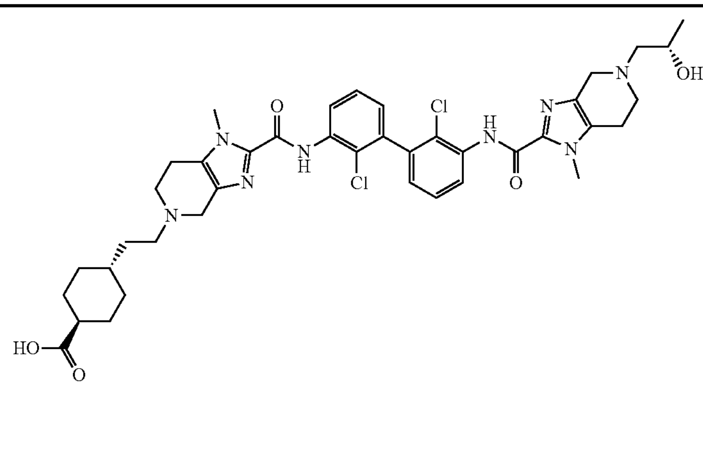 | 791.4 |

TABLE 11-continued

The compounds in Table 11 were prepared in accordance with the synthetic protocols set forth in Example 93 using the appropriate starting materials.

| Example # | Name | Structure | LC-MS (M + H)+ |
|---|---|---|---|
| 95 | trans-4-(2-(2-((2,2'-dichloro-3'-(5-((R)-2-hydroxypropyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 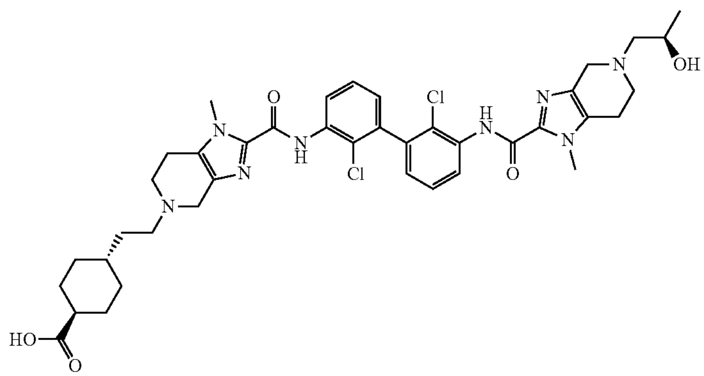 [SMILES: C[C@@H](O)CN1CCc2c(nc(C(=O)Nc3cccc(-c4cccc(NC(=O)c5nc6c(n5C)CCN(CC[C@H]5CC[C@H](C(=O)O)CC5)C6)c4Cl)c3Cl)n2C)C1] | 791.4 |

Example 96

4-(2-(2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)benzoic acid

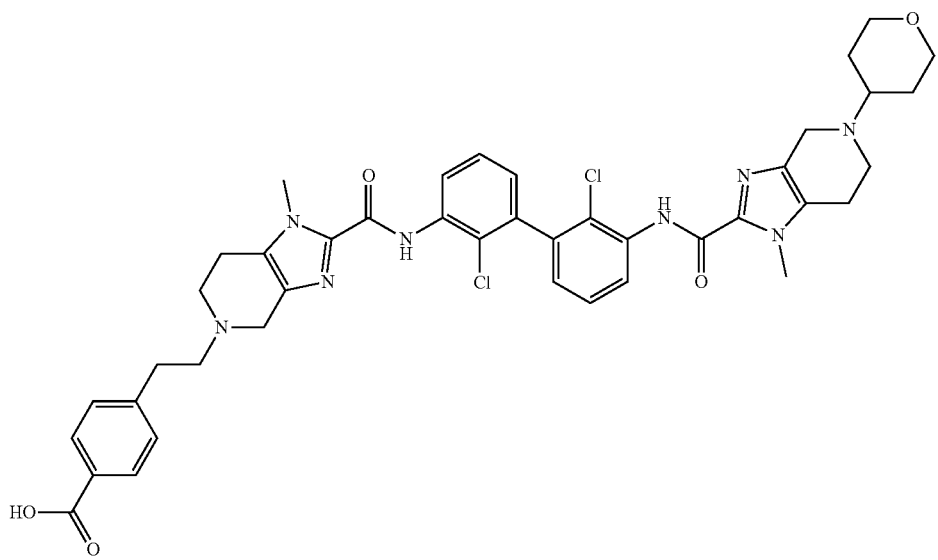 [SMILES: Cn1c(C(=O)Nc2cccc(-c3cccc(NC(=O)c4nc5c(n4C)CCN(C4CCOCC4)C5)c3Cl)c2Cl)nc2c1CCN(CCc1ccc(C(=O)O)cc1)C2]

Step 1: tert-butyl 2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

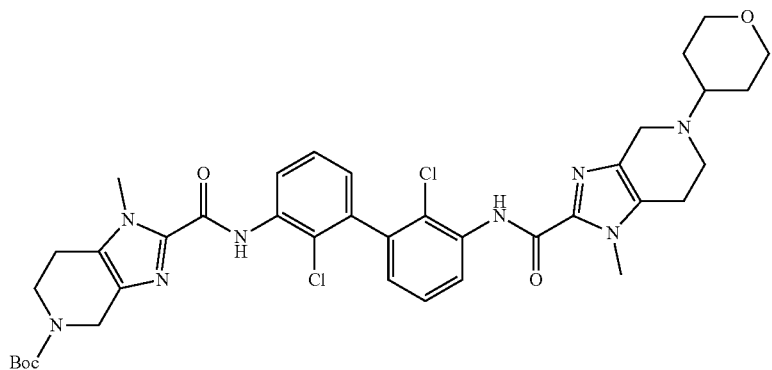 [SMILES: Cn1c(C(=O)Nc2cccc(-c3cccc(NC(=O)c4nc5c(n4C)CCN(C4CCOCC4)C5)c3Cl)c2Cl)nc2c1CCN(C(=O)OC(C)(C)C)C2]

A solution of tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 60, Step 1: 400 mg, 0.589 mmol), N,N-diisopropylethylamine (0.206 mL, 1.177 mmol) and tetrahydro-4H-pyran-4-one (0.163 mL, 1.766 mmol) in dichloromethane (4.9 mL) was stirred at room temperature for 15 min. Sodium triacetoxyborohydride (374 mg, 1.766 mmol) was added, and the mixture was further stirred at room temperature for 2 h. The reaction was quenched with saturated aqueous NaHCO₃ solution and extracted with dichloromethane. The combined organic layers were dried over $Na_2SO_4$, filtered, and concentrated under reduced pressure. The residue was purified by flash chromatography on a silica gel column eluting with 10% methanol in dichloromethane to afford the desired product. LC-MS calculated for $C_{38}H_{45}Cl_2N_8O_5$ $(M+H)^+$: m/z=763.3; found 763.3

Step 2: 4-(2-(2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)benzoic acid A solution of tert-butyl 2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 10 mg, 0.013 mmol) in dichloromethane (0.1 mL) and trifluoroacetic acid (0.05 mL) was stirred at room temperature for 30 min. The mixture was concentrated under reduced pressure. The residue was dissolved in dichloromethane (0.12 mL) and sequentially treated with N,N-diisopropylethylamine (9.2 μL, 0.052 mmol), sodium triacetoxyborohydride (8.3 mg, 0.039 mmol) and methyl 4-(2-oxoethyl)benzoate (7.0 mg, 0.039 mmol). After being stirred at room temperature for 2 h, the reaction was quenched with saturated aqueous NaHCO₃ solution, and extracted with dichloromethane. The combined organic layers were dried over $Na_2SO_4$, filtered, and concentrated under reduced pressure. The residue was dissolved in THF/MeOH/water (0.2 mL/0.2 mL/0.1 mL), and treated with lithium hydroxide, monohydrate (2.8 mg, 0.065 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for $C_{42}H_{45}Cl_2N_8O_5$ $(M+H)^+$: m/z=811.3; found 811.4.

TABLE 12

The compounds in Table 12 were prepared in accordance with the synthetic protocols set forth in Example 96 using the appropriate starting materials.

| Example # | Name | Structure | LC-MS (M + H)+ |
|---|---|---|---|
| 97 | 4-(2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)cyclohexane-1-carboxylic acid | Mixture of cis/trans isomers | 789.4 |
| 98 | 4-(2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid | Mixture of cis/trans isomers | 803.4 |

Example 99

4-(2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-ethylcyclohexane-1-carboxylic acid

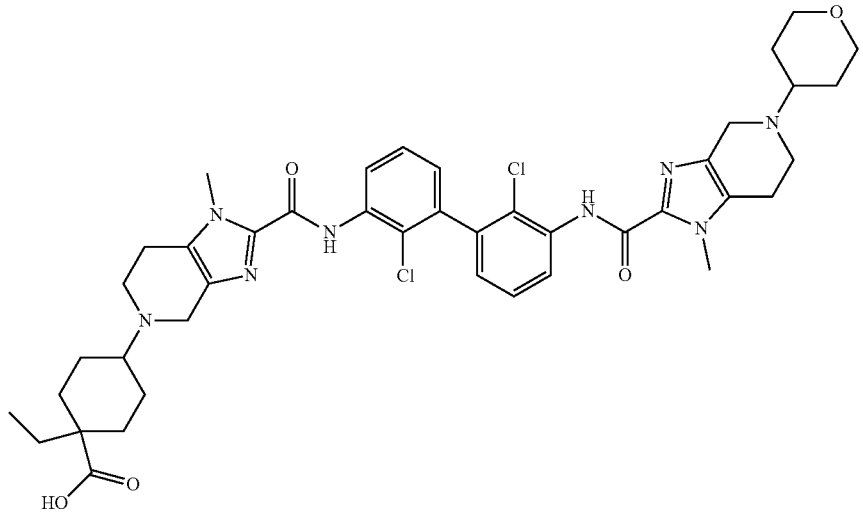

A solution of tert-butyl 2-((2,2'-dichloro-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 96, Step 1: 10 mg, 0.013 mmol) in dichloromethane (0.1 mL) and trifluoroacetic acid (0.05 mL) was stirred at room temperature for 30 min. The mixture was concentrated under reduced pressure. The residue was dissolved in dichloromethane (0.12 mL) and sequentially treated with N,N-diisopropylethylamine (9.2 µL, 0.052 mmol), sodium triacetoxyborohydride (8.3 mg, 0.039 mmol) and 1-ethyl-4-oxocyclohexane-1-carboxylic acid (Example 83, Step 1: 4.5 mg, 0.026 mmol). After being stirred at room temperature for 2 h, the reaction mixture was diluted with MeOH, and purified by prep-HPLC (pH=2, acetonitrile/water+TFA) to give the desired product as a mixture of cis/trans isomers. LC-MS calculated for $C_{42}H_{51}Cl_2N_8O_5$ $(M+H)^+$: m/z=817.3; found 817.4.

Example 100 trans-4-(2-(2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

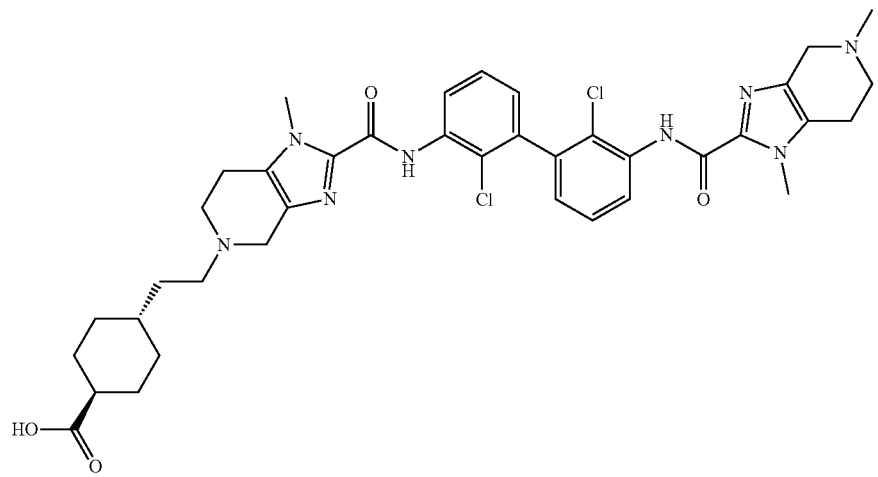 [SMILES: CN1CCc2c(nc(C(=O)Nc3cccc(-c4cccc(NC(=O)c5nc6c(n5C)CCN(CC[C@H]5CC[C@H](C(=O)O)CC5)C6)c4Cl)c3Cl)n2C)C1]

A solution of tert-butyl 2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1- methyl-1,4,6,7-tetrahydro-5H-imidazo[4,5-c]pyridine-5-carboxylate (Example 24, Step 5: 10 mg, 0.015 mmol) in dichloromethane (0.10 mL) and trifluoroacetic acid (0.05 mL) was stirred at room temperature for 30 min. The mixture was concentrated under reduced pressure. The residue was dissolved in dichloromethane (0.15 mL) and sequentially treated with N,N-diisopropylethylamine (10.4 µL, 0.059 mmol), sodium triacetoxyborohydride (9.4 mg, 0.045 mmol), and methyl 4-(2-oxoethyl)cyclohexane-1-carboxylate (5.5 mg, 0.030 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (3.2 mg, 0.074 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for C$_{39}$H$_{48}$ClN$_8$O$_4$(M+H)$^+$: m/z=727.3; found 727.4. $^1$H NMR (500 MHz, DMSO-d$_6$) δ 9.96 (s, 1H), 9.89 (s, 1H), 8.23 (dd, J=8.2, 1.6 Hz, 1H), 7.65 (d, J=8.0 Hz, 1H), 7.49 (t, J=7.9 Hz, 1H), 7.33 (t, J=7.8 Hz, 1H), 7.12 (dd, j=7.6, 1.6 Hz, 1H), 7.05 (d, j=7.3 Hz, 1H), 4.64-4.34 (m, 2H), 4.30-4.13 (m, 2H), 3.96 (s, 3H), 3.92 (s, 3H), 3.85-3.74 (m, 2H), 3.45 (br, 2H), 3.29 (br, 2H), 3.13-2.98 (m, 4H), 2.97 (s, 3H), 2.21-2.07 (m, 1H), 1.99 (s, 3H), 1.95-1.82 (m, 2H), 1.82-1.72 (m, 2H), 1.71-1.60 (m, 2H), 1.34-1.22 (m, 3H), 1.05-0.93 (m, 2H).

TABLE 13

The compounds in Table 13 were prepared in accordance with the synthetic protocols set forth in Example 100 using the appropriate starting materials.

| Example # | Name | Structure | LC-MS (M + H)$^+$ |
|---|---|---|---|
| 101 | 4-(2-(2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)benzoic acid | 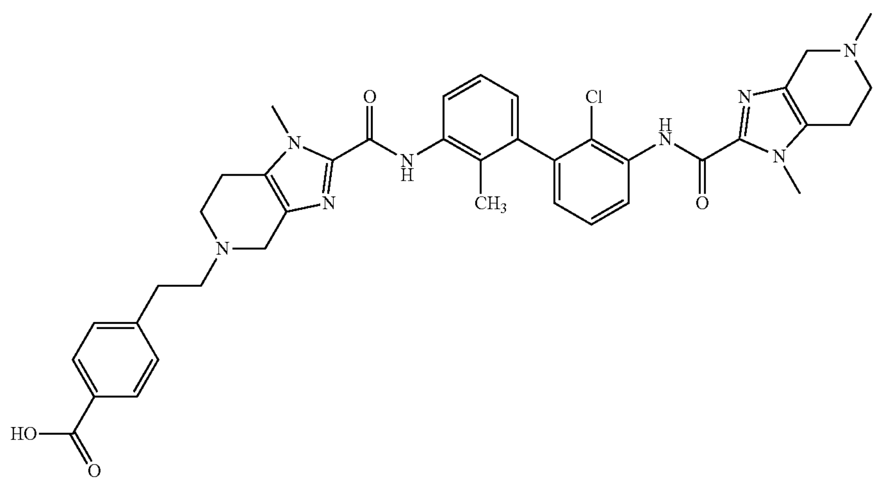 [SMILES: Cc1c(NC(=O)c2nc3c(n2C)CCN(CCc2ccc(C(=O)O)cc2)C3)cccc1-c1cccc(NC(=O)c2nc3c(n2C)CCN(C)C3)c1Cl] | 721.3 |
| 102 | 4-((2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid | 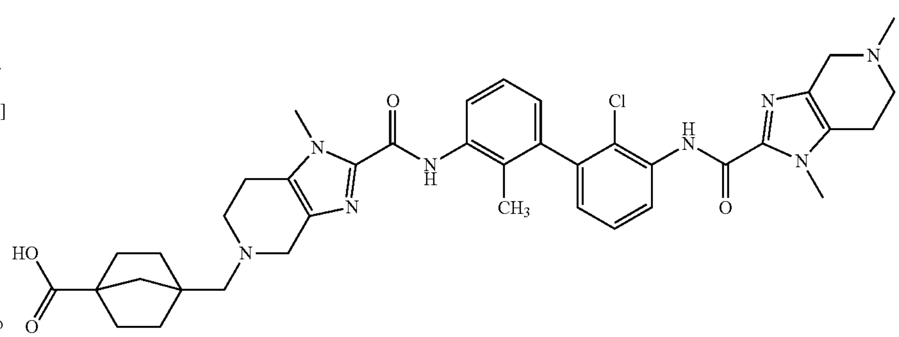 | 725.4 |

| Example # | Name | Structure | LC-MS (M + H)+ |
|---|---|---|---|
| 103 | 4-((2-(2'-chloro-3'-(1,5-dimethyl-4,5,6,7-tetrahydro-1H-imidazo[4,5-c]pyridine-2-carboxamido)-2-methylbiphenyl-3-ylcarbamoyl)-1-methyl-6,7-dihydro-1H-imidazo[4,5-c]pyridin-5(4H)-yl)methyl)bicyclo[2.2.2]octane-1-carboxylic acid | 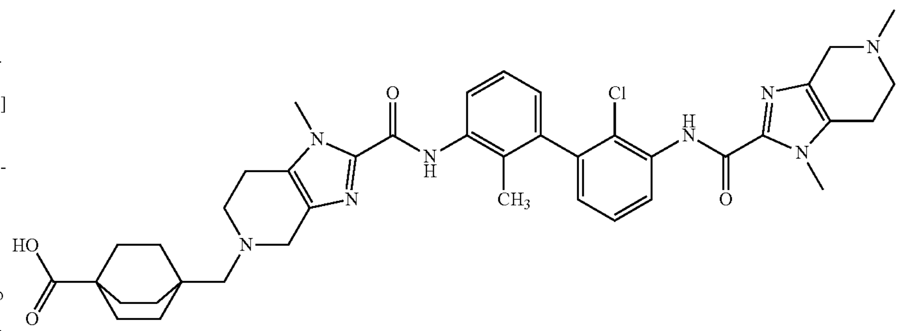 | 739.4 |

Example 104

4-(2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)-1-ethylcyclohexane-1-carboxylic acid

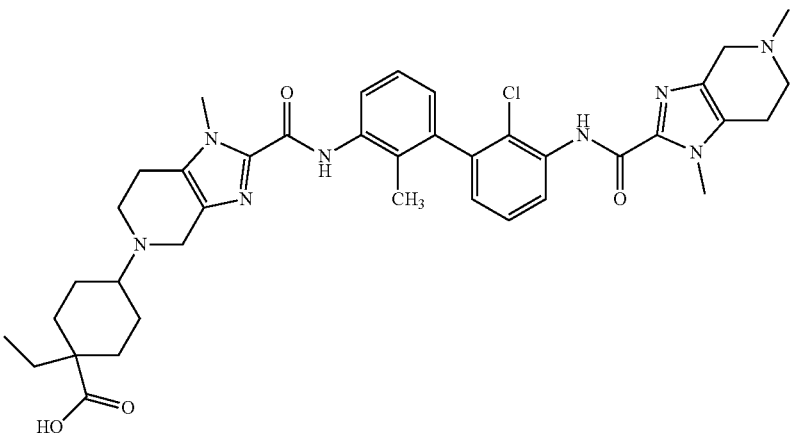

A solution of tert-butyl 2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Example 24, Step 5: 10 mg, 0.015 mmol) in dichloromethane (0.05 mL) and trifluoroacetic acid (0.05 mL) was stirred at room temperature for 30 min. The mixture was concentrated under reduced pressure. The residue was dissolved in dichloromethane (0.15 mL) and sequentially treated with N,N-diisopropylethylamine (13.0 µL, 0.074 mmol), sodium triacetoxyborohydride (9.5 mg, 0.045 mmol), and 1-ethyl-4-oxocyclohexane-1-carboxylic acid (Example 83, Step 1: 7.6 mg, 0.045 mmol). After being stirred at room temperature for 2 h, the reaction mixture was diluted with MeOH, and purified by prep-HPLC (pH=2, acetonitrile/water+TFA) to give the desired product as a mixture of cis/trans isomers. LC-MS calculated for $C_{39}H_{48}ClN_8O_4$ (M+H)+: m/z=727.3; found 727.4.

Example 105

4-(2-((2'-chloro-3'-(5-ethyl-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid

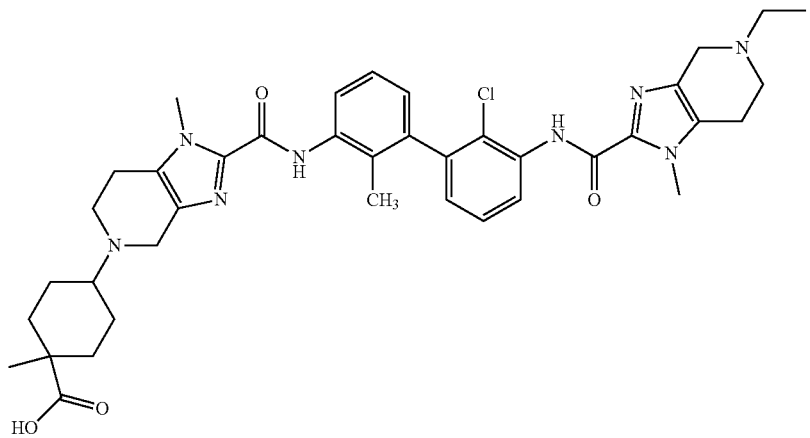 [SMILES: CCN1CCc2c(nc(C(=O)Nc3cccc(-c4cccc(NC(=O)c5nc6c(n5C)CCN(C5CCC(C)(C(=O)O)CC5)C6)c4C)c3Cl)n2C)C1]

Step 1; 4-(2-((3'-(5-(tert-butoxycarbonyl)-1-methyl-4,5,6,7-tetrahydro-1H-imidazo[4,5-c]pyridine-2-carboxamido)-2'-chloro-2-methyl-[1,1'-biphenyl]-3-yl) carbamoyl)-1-methyl-1,4,6,7-tetrahydro-5H-imidazo[4,5-c]pyridin-5-yl)-1-methylcyclohexane-1-carboxylic acid

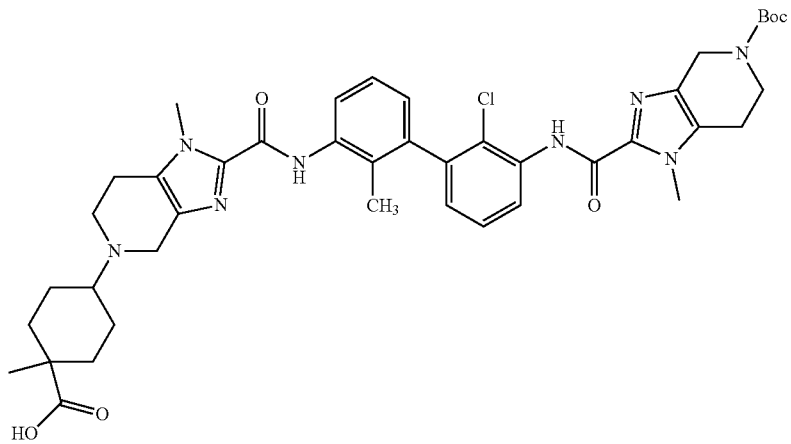 [SMILES: Cc1c(NC(=O)c2nc3c(n2C)CCN(C2CCC(C)(C(=O)O)CC2)C3)cccc1-c1cccc(NC(=O)c2nc3c(n2C)CCN(C(=O)OC(C)(C)C)C3)c1Cl]

A solution of tert-butyl 2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 31, Step 1: 200 mg, 0.303 mmol), and 1-methyl-4-oxocyclohexane-1-carboxylic acid (95 mg, 0.607 mmol) in dichloromethane (3.0 mL) was stirred at room temperature for 15 min. Sodium triacetoxyborohydride (193 mg, 0.910 mmol) was added, and the reaction was stirred at room temperature for 2 h. The reaction mixture was concentrated under reduced pressure and the residue was purified by flash chromatography on a silica gel column eluting with 20% methanol in dichloromethane to afford the desired product. LC-MS calculated for $C_{42}H_{52}ClN_8O_6$ (M+H)$^+$: m/z=799.4; found 799.4.

Step 2: 4-(2-((2'-chloro-3'-(5-ethyl-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid A solution of 4-(2-((3'-(5-(tert-butoxycarbonyl)-1-methyl-4,5,6,7-tetrahydro-1H-imidazo[4,5-c]pyridine-2-carboxamido)-2'-chloro-2-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid (Step 1: 10 mg, 0.013 mmol) in dichloromethane (0.1 mL) and trifluoroacetic acid (0.05 mL) was stirred at room temperature for 30 min. The mixture was concentrated under reduced pressure. The residue was dissolved in dichloromethane (0.12 mL) and sequentially treated with N,N-diisopropylethylamine (10.9 μL, 0.063 mmol), sodium triacetoxyborohydride (7.9 mg, 0.038 mmol), and acetaldehyde (1.7 mg, 0.038 mmol). After being stirred at room temperature for 2 h, the reaction mixture was diluted with MeOH, and purified by prep-HPLC (pH=2, acetonitrile/water+TFA) to give the desired product as a mixture of cis/trans isomers. LC-MS calculated for $C_{39}H_{48}ClN_8O_4$ (M+H)$^+$: m/z=727.3; found 727.4.

TABLE 14

The compounds in Table 14 were prepared in accordance with the synthetic protocols set forth in Example 105 using the appropriate starting materials.

| Example # | Name | Structure | LC-MS (M + H)+ |
|---|---|---|---|
| 106 | 4-(2-((2'-chloro-3'-(5-isopropyl-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid | Mixture of cis/trans isomers | 741.4 |
| 107 | 4-(2-((2'-chloro-3'-(5-cyclohexyl-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid | Mixture of cis/trans isomers | 781.4 |

TABLE 14-continued

The compounds in Table 14 were prepared in accordance with the synthetic protocols set forth in Example 105 using the appropriate starting materials.

| Example # | Name | Structure | LC-MS (M + H)+ |
|---|---|---|---|
| 108 | 4-(2-((2'-chloro-2-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid | 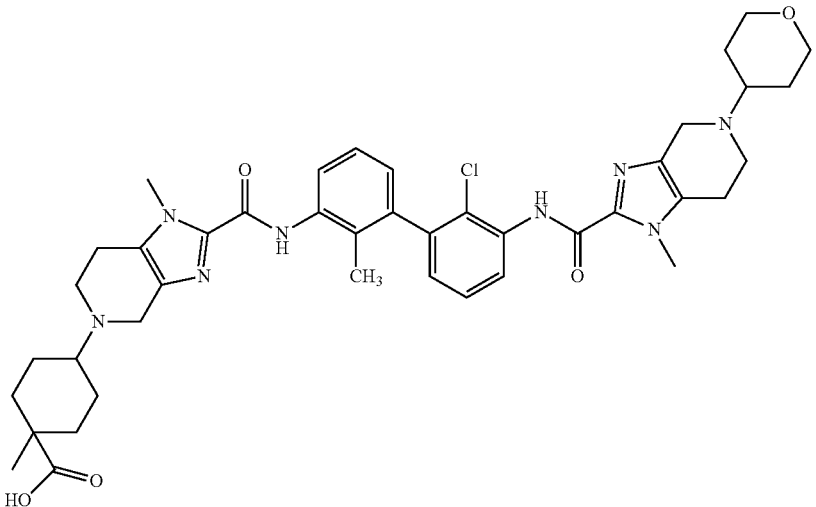 Mixture of cis/trans isomers | 783.3 |

Example 109 trans-4-(2-(2-((2'-chloro-2-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

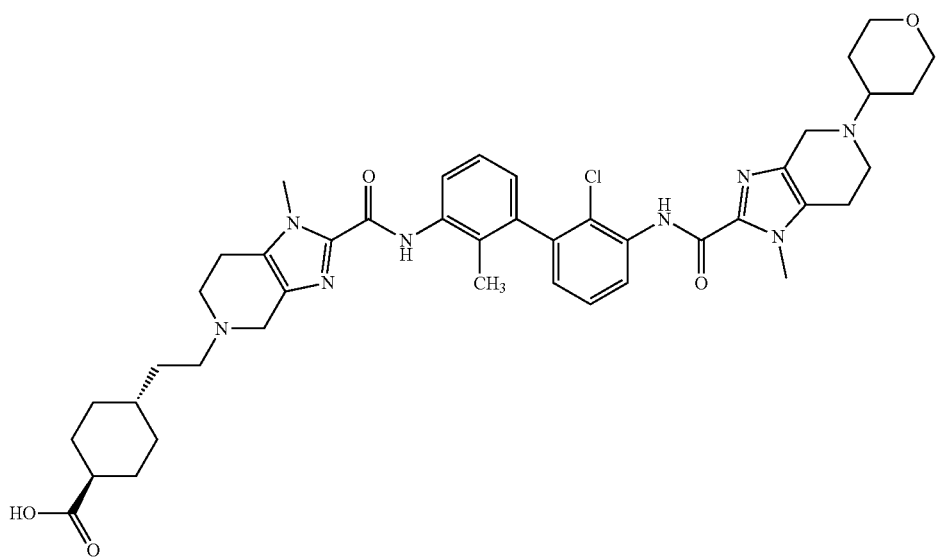 [SMILES: Cc1c(NC(=O)c2nc3c(n2C)CCN(CC[C@H]2CC[C@H](C(=O)O)CC2)C3)cccc1-c1cccc(NC(=O)c2nc3c(n2C)CCN(C2CCOCC2)C3)c1Cl]

225

Step 1: tert-butyl 2-((2'-chloro-2-methyl-3'-(1-methyl-4,5,6,7-tetrahydro-1H-imidazo[4,5-c]pyridine-2-carboxamide)-[1,1'-biphenyl]-3-yl)carbamoyl)-1-methyl-1,4,6,7-tetrahydro-5H-imidazo[4,5-c]pyridine-5-carboxylate

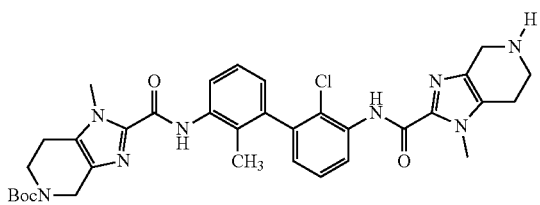 [SMILES: Cc1c(NC(=O)c2nc3c(n2C)CCN(C(=O)OC(C)(C)C)C3)cccc1-c1cccc(NC(=O)c2nc3c(n2C)CCNC3)c1Cl]

A solution of tert-butyl 2-((3-bromo-2-chlorophenyl)carbamoyl)-1-methyl-1,4,6,7-tetrahydro-5H-imidazo[4,5-c]pyridine-5-carboxylate (Example 24, Step 1: 1.0 g, 2.129 mmol) in dichloromethane (1.0 mL) and trifluoroacetic acid (0.5 mL) was stirred at room temperature for 30 min. The reaction mixture was concentrated under reduced pressure. A mixture of the above residue, tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate (Example 24, Step 4: 1.162 g, 2.342 mmol), sodium carbonate (1.023 mL, 10.64 mmol) and [1,1-bis(di-cyclohexylphosphino)ferrocene]dichloropalladium(II) (0.161 g, 0.213 mmol) in 1,4-dioxane (12.0 mL) and water (6.0 mL) was purged with nitrogen and then stirred at 100° C. for 3 h. The reaction mixture was diluted with water and extracted with dichloromethane. The combined organic layers were dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{34}$H$_{40}$ClN$_8$O$_4$ (M+H)$^+$: m/z=659.3; found 659.4.

Step 2: tert-butyl 2-((2'-chloro-2-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

226

A solution of tert-butyl 2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 200 mg, 0.303 mmol), N,N-diisopropylethylamine (0.106 mL, 0.607 mmol) and tetrahydro-4H-pyran-4-one (0.084 mL, 0.910 mmol) in dichloromethane (3.0 mL) was stirred at room temperature for 15 min. Sodium triacetoxyborohydride (193 mg, 0.910 mmol) was added, and the mixture was further stirred at room temperature for 2 h. The reaction was quenched with saturated aqueous NaHCO$_3$ solution and extracted with dichloromethane. The combined organic layers were dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{39}$H$_{48}$ClN$_8$O$_5$ (M+H)$^+$: m/z=743.3; found 743.5

Step 3: trans-4-(2-(2-((2'-chloro-2-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid A solution of tert-butyl 2-((2'-chloro-2-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 2: 20 mg, 0.027 mmol) in dichloromethane (0.1 mL) and trifluoroacetic acid (0.05 mL) was stirred at room temperature for 30 min. The mixture was concentrated under reduced pressure. The residue was dissolved in dichloromethane (0.24 mL) and sequentially treated with N,N-diisopropylethylamine (23.5 µL, 0.135 mmol), sodium triacetoxyborohydride (17.11 mg, 0.081 mmol) and methyl 4-(2-oxoethyl)cyclohexane-1-carboxylate (9.9 mg, 0.054 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (5.7 mg, 0.135 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for C$_{43}$H$_{54}$ClN$_8$O$_5$ (M+H)$^+$: m/z=797.4; found 797.4.

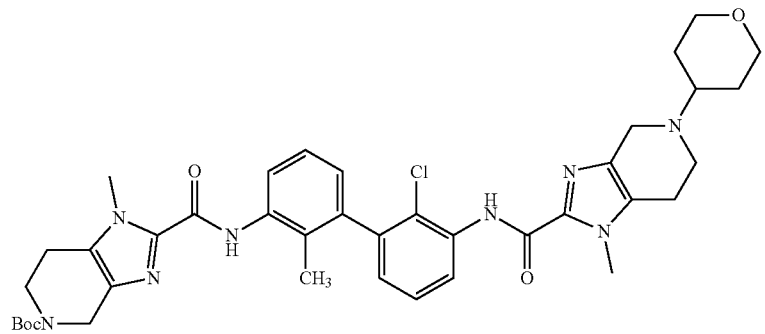 [SMILES: Cc1c(NC(=O)c2nc3c(n2C)CCN(C(=O)OC(C)(C)C)C3)cccc1-c1cccc(NC(=O)c2nc3c(n2C)CCN(C2CCOCC2)C3)c1Cl]

TABLE 15

The compounds in Table 15 were prepared in accordance with the synthetic protocols set forth in Example 109 using the appropriate starting materials.

| Example # | Name | Structure | LC-MS (M + H)+ |
|---|---|---|---|
| 110 | trans-4-((2-((2'-chloro-2-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 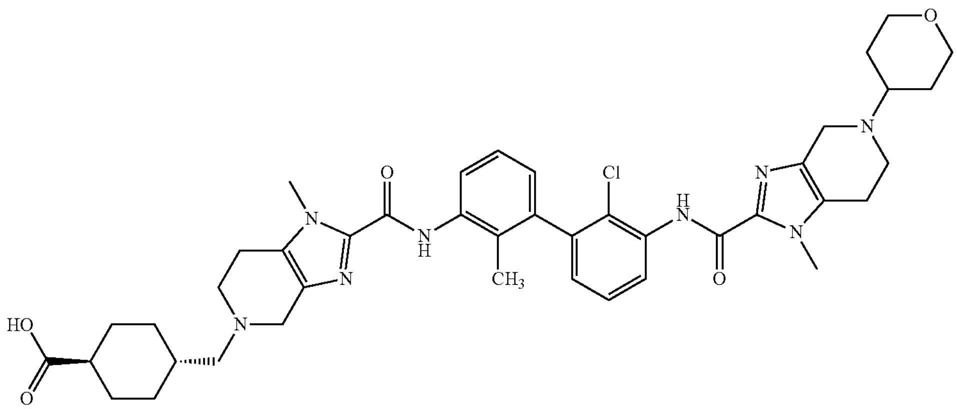 [SMILES: Cc1c(NC(=O)c2nc3c(n2C)CCN(C[C@H]2CC[C@H](C(=O)O)CC2)C3)cccc1-c1cccc(NC(=O)c2nc3c(n2C)CCN(C2CCOCC2)C3)c1Cl] | 783.4 |
| 111 | 4-(2-((2'-chloro-2-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)cyclohexane-1-carboxylic acid | Mixture of cis/trans isomers | 769.5 |

Example 112

4-(2-((2'-chloro-2-methyl-3'-(1-methyl-5-(tetra-hydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-ethylcyclohexane-1-carboxylic acid

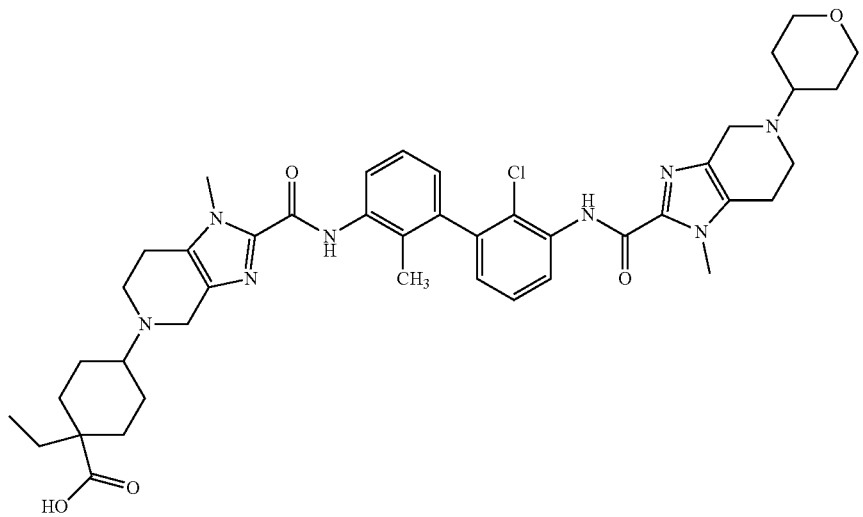

A solution of tert-butyl 2-((2'-chloro-2-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 109, Step 2: 20 mg, 0.027 mmol) in dichloromethane (0.1 mL) and trifluoroacetic acid (0.05 mL) was stirred at room temperature for 30 min. The mixture was concentrated under reduced pressure. The residue was dissolved in dichloromethane (0.24 mL) and sequentially treated with N, N-diisopropylethylamine (23.5 µL, 0.135 mmol), sodium triacetoxyborohydride (17.1 mg, 0.081 mmol) and 1-ethyl-4-oxocyclohexane-1-carboxylic acid (Example 83, Step 1: 9.2 mg, 0.054 mmol). After being stirred at room temperature for 2 h, the reaction mixture was diluted with MeOH, and purified by prep-HPLC (pH=2, acetonitrile/water+TFA) to give the desired product as the TFA salt. LC-MS calculated for $C_{43}H54ClN_8O_5$ (M+H)$^+$: m/z=797.4; found 797.4.

Example 113 cis-4-((2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

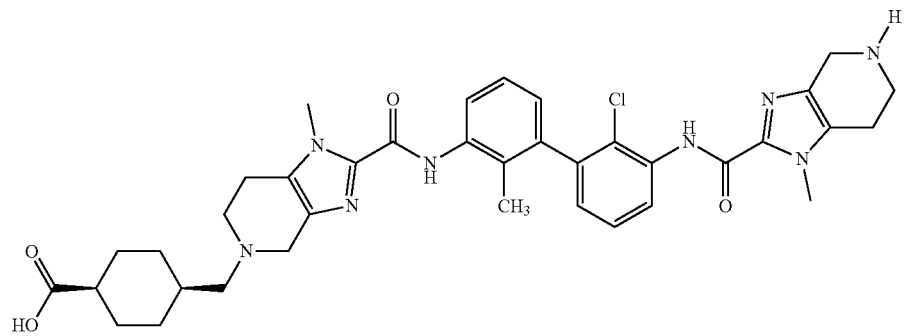 [SMILES: Cc1c(NC(=O)c2nc3c(n2C)CCN(C[C@H]2CC[C@@H](C(=O)O)CC2)C3)cccc1-c1cccc(NC(=O)c2nc3c(n2C)CCNC3)c1Cl]

Step 1: tert-butyl 2-((2-chloro-3'-(5-((cis-4-(methoxycarbonyl)cyclohexyl)methyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridine-5-carboxylate

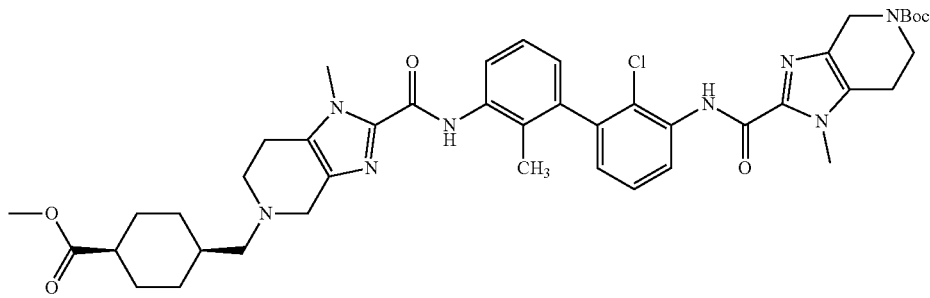 [SMILES: COC(=O)[C@H]1CC[C@@H](CN2CCc3c(nc(C(=O)Nc4cccc(-c5cccc(NC(=O)c6nc7c(n6C)CCN(C(=O)OC(C)(C)C)C7)c5Cl)c4C)n3C)C2)CC1]

A solution of tert-butyl 2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 31, Step 1: 50 mg, 0.076 mmol), methyl cis-4-(((methylsulfonyl)oxy)methyl)cyclohexane-1-carboxylate (Example 68, Step 1: 57.0 mg, 0.228 mmol), N,N-diisopropylethylamine (0.053 mL, 0.303 mmol), benzyltriethylammonium chloride (1.7 mg, 7.59 μmol) and potassium iodide (1.3 mg, 7.59 μmol) in DMF (0.30 mL) was stirred at 80° C. for 12 h. The reaction mixture was quenched with saturated aqueous NaHCO$_3$ solution, and extracted with ethyl acetate. The combined organic layers were washed with brine, dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{43}$H$_{54}$ClN$_8$O$_6$ (M+H)$^+$: m/z=813.4; found 813.4.

Step 2: cis-4-((2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid A solution of tert-butyl 2-((2-chloro-3'-(5-((cis-4-(methoxycarbonyl)cyclohexyl)methyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridine-5-carboxylate (Step 1:10 mg, 0.012 mmol) in dichloromethane (0.1 mL) and trifluoroacetic acid (0.1 mL) was stirred at room temperature for 30 min. The mixture was concentrated under reduced pressure. The residue was dissolved in THF/MeOH/water (0.2 mL/0.2 mL/0.1 mL), and then treated with lithium hydroxide, monohydrate (5.0 mg, 0.120 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{37}$H$_{44}$ClN$_8$O$_4$ (M+H)$^+$: m/z=699.3; found 699.3.

Example 114 cis-4-((2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

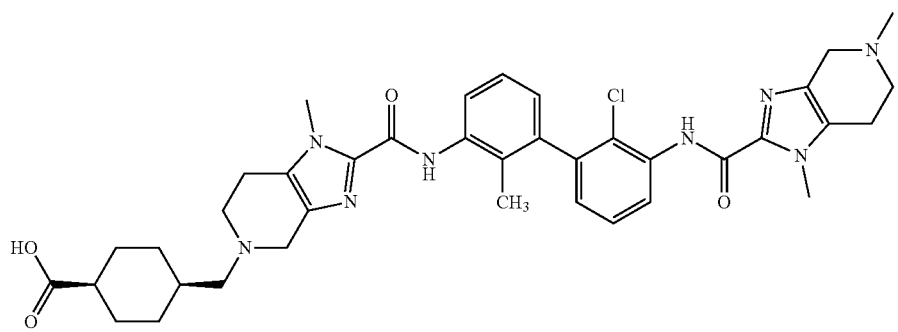 [SMILES: Cc1c(NC(=O)c2nc3c(n2C)CCN(C[C@H]2CC[C@@H](C(=O)O)CC2)C3)cccc1-c1cccc(NC(=O)c2nc3c(n2C)CCN(C)C3)c1Cl]

A solution of tert-butyl 2-((2-chloro-3'-(5-((cis-4-(methoxycarbonyl)cyclohexyl)methyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridine-5-carboxylate (Example 113, Step 1: 20 mg, 0.025 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.098 mmol), sodium triacetoxyborohydride (10.4 mg, 0.049 mmol), and 37 wt % Formaldehyde in water (9.2 µL, 0.123 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (10.3 mg, 0.246 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{38}$H$_{46}$ClN$_8$ClN$_8$O$_4$ (M+H)$^+$: m/z=713.3; found 713.4. $^1$H NMR (500 MHz, DMSO-d$_6$) δ 9.96 (s, 1H), 9.87 (s, 1H), 8.23 (dd, J=8.3, 1.6 Hz, 1H), 7.66 (dd, J=8.1, 1.3 Hz, 1H), 7.49 (t, J=7.9 Hz, 1H), 7.33 (t, J=7.8 Hz, 1H), 7.12 (dd, J=7.6, 1.6 Hz, 1H), 7.05 (dd, J=7.7, 1.3 Hz, 1H), 4.52-4.20 (m, 2H), 4.28-4.15 (m, 2H), 3.96 (s, 3H), 3.93 (s, 3H), 3.85-3.69 (m, 2H), 3.54-3.38 (m, 2H), 3.22-3.12 (m, 2H), 3.09-2.98 (m, 4H), 2.96 (s, 3H), 2.51-2.47 (m, 1H), 2.02 (br, 1H), 1.99 (s, 3H), 1.93-1.84 (m, 2H), 1.73-1.48 (m, 4H), 1.34-1.22 (m, 2H).

Example 115 trans-4-(2-(2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid Step 1; tert-butyl 2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridine-5-carboxylate

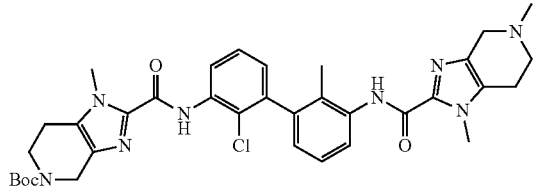

A solution of tert-butyl 2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 31, Step 1: 150 mg, 0.228 mmol), 37 wt. % formaldehyde in water (141 µL, 1.896 mmol) and N,N-diisopropylethylamine (79 µL, 0.455 mmol) in dichloromethane (2.0 mL) was stirred at room temperature for 10 min. Sodium triacetoxyborohydride (145 mg, 0.683 mmol) was added in portions. After being stirred at room temperature for 2 h, the mixture was quenched with saturated aqueous NaHCO$_3$ solution, and extracted with dichloromethane. The combined organic layers were dried over Na$_2$SO$_4$, filtered and concentrated under reduced pressure. The residue was purified by flash chromatography on a silica gel column eluting with 10% methanol in dichloromethane to afford the desired product. LCMS calculated for C$_{35}$H$_{42}$ClN$_8$O$_4$ (M+H)$^+$: m/z=673.3; found 673.3.

Step 2: trans-4-(2-(2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid A solution of tert-butyl 2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridine-5-carboxylate (Step 1: 10 mg, 0.015 mmol) in dichloromethane (0.10 mL)

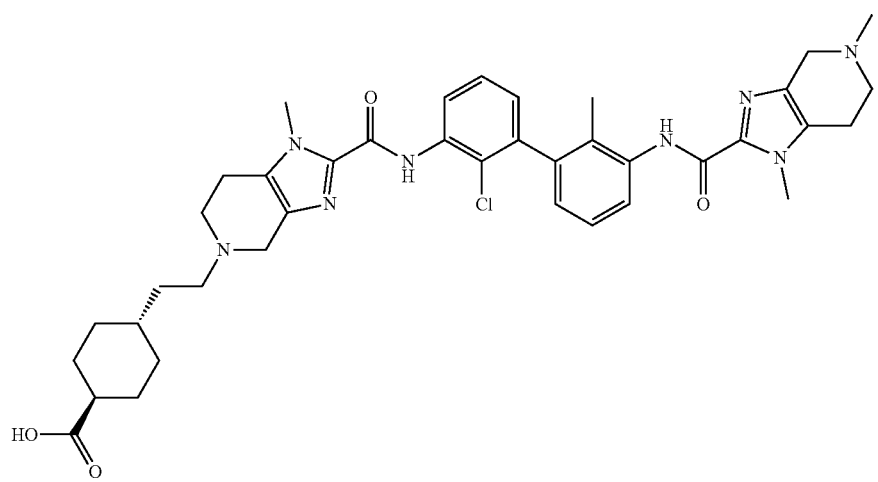 [SMILES: Cc1c(NC(=O)c2nc3c(n2C)CCN(C)C3)cccc1-c1cccc(NC(=O)c2nc3c(n2C)CCN(CC[C@H]2CC[C@H](C(=O)O)CC2)C3)c1Cl]

and trifluoroacetic acid (0.05 mL) was stirred at room temperature for 30 min. The mixture was concentrated under reduced pressure. The residue was dissolved in, dichloromethane (0.15 mL) and sequentially treated with N,N-diisopropylethylamine (10.4 μL, 0.059 mmol), sodium triacetoxyborohydride (9.4 mg, 0.045 mmol), and methyl 4-(2-oxoethyl)cyclohexane-1-carboxylate (5.5 mg, 0.030 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (3.2 mg, 0.074 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for C$_{39}$H$_4$BClN$_8$O$_4$ (M+H)$^+$: m/z=727.3; found 727.4.

TABLE 16

The compounds in Table 16 were prepared in accordance with the synthetic protocols set forth in Example 115 using the appropriate starting materials.

| Example # | Name/$^1$H NMR | Structure | LC-MS (M + H)$^+$ |
|---|---|---|---|
| 116 | trans-4-((2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid $^1$H NMR (500 MHz, DMSO-d$_6$) δ 9.90 (s, 1H), 9.75 (s, 1H), 8.34 (dd, J = 8.2, 1.6 Hz, 1H), 7.71 (d, J = 8.0 Hz, 1H), 7.46 (t, J = 7.9 Hz, 1H), 7.30 (t, J = 7.8 Hz, 1H), 7.07 (dd, J = 7.6, 1.6 Hz, 1H), 7.01 (d, J = 7.4 Hz, 1H), 3.90 (s, 3H), 3.87 (s, 3H), 3.38 (br, 4H), 2.77-2.62 (m, 8H), 2.39 (s, 3H), 2.31 (d, J = 7.1 Hz, 2H), 2.07 (tt, J = 12.2, 3.7 Hz, 1H), 1.99 (s, 3H), 1.90-1.75 (m, 4H), 1.59-1.47 (m, 1H), 1.36-1.23 (m, 2H), 0.93-0.81 (m, 2H). | purified by prep-HPLC (pH = 10, acetonitrile/water + NH$_4$OH) | 713.4 |

TABLE 16-continued

The compounds in Table 16 were prepared in accordance with the synthetic protocols set forth in Example 115 using the appropriate starting materials.

| Example # | Name/¹H NMR | Structure | LC-MS (M + H)⁺ |
|---|---|---|---|
| 117 | 4-(2-(2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)benzoic acid | 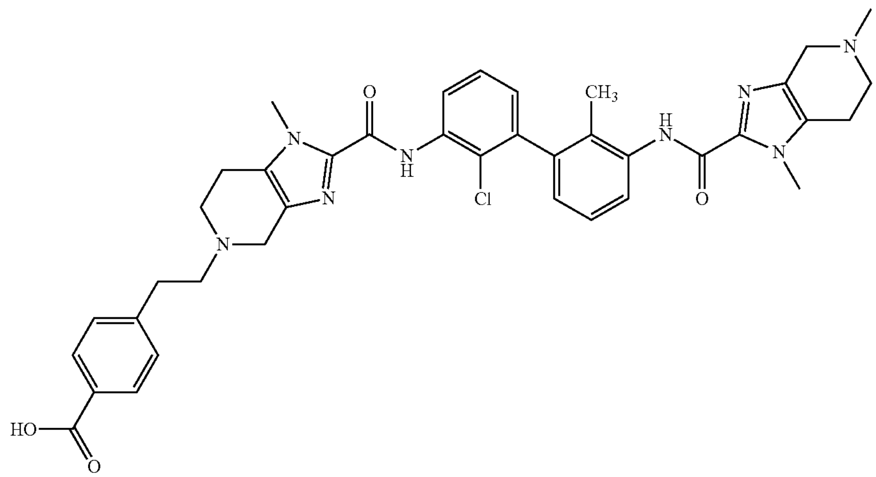 [SMILES: Cc1c(NC(=O)c2nc3c(n2C)CCN(C)C3)cccc1-c1cccc(NC(=O)c2nc3c(n2C)CCN(CCc2ccc(C(=O)O)cc2)C3)c1Cl] | 721.4 |
| 118 | 4-(2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid | Mixture of cis/trans isomers | 713.3 |
| 119 | 4-((2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylic acid | 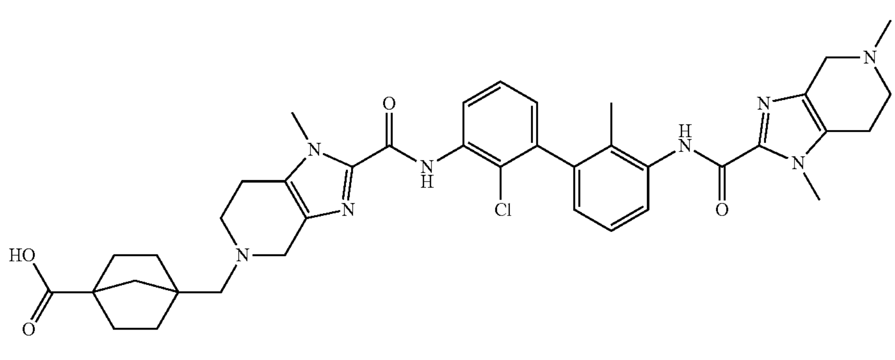 [SMILES: Cc1c(NC(=O)c2nc3c(n2C)CCN(C)C3)cccc1-c1cccc(NC(=O)c2nc3c(n2C)CCN(CC24CCC(C(=O)O)(CC2)C4)C3)c1Cl] | 725.4 |

TABLE 16-continued

The compounds in Table 16 were prepared in accordance with the synthetic protocols set forth in Example 115 using the appropriate starting materials.

| Example # | Name/¹H NMR | Structure | LC-MS (M + H)⁺ |
|---|---|---|---|
| 120 (peak 1; Compound 120-1) | 4-((2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)-1-methylcyclohexane-1-carboxylic acid | Peak 1, $t_r$ = 0.93 min (pH = 2, acetonitrile/water + TFA) | 727.4 |
| 120 (peak 2; Compound 120-2) | 4-((2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)-1-methylcyclohexane-1-carboxylic acid | Peak 2, $t_r$ = 0.95 min (pH = 2, acetonitrile/water + TFA) | 727.4 |

Example 121

4-(2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)-1-ethylcyclohexane-1-carboxylic acid

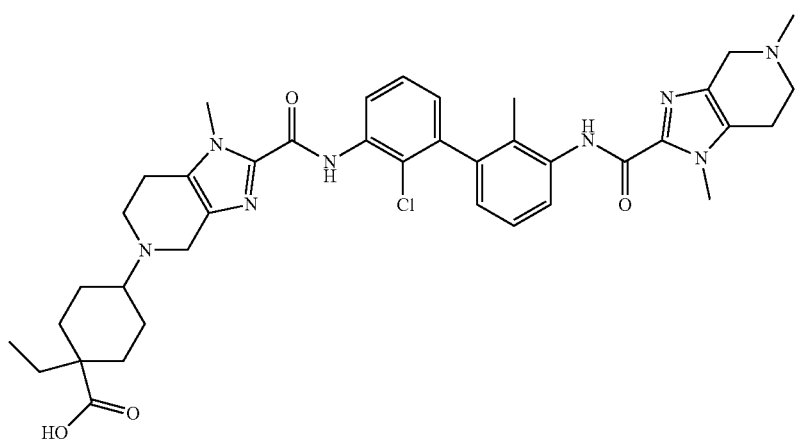 [SMILES: CCC1(C(=O)O)CCC(N2CCc3c(nc(C(=O)Nc4cccc(-c5cccc(NC(=O)c6nc7c(n6C)CCN(C)C7)c5C)c4Cl)n3C)C2)CC1]

A solution of tert-butyl 2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridine-5-carboxylate (Example 115, Step 1: 10 mg, 0.015 mmol) in dichloromethane (0.05 mL) and trifluoroacetic acid (0.05 mL) was stirred at room temperature for 30 min. The mixture was concentrated under reduced pressure. The residue was dissolved in dichloromethane (0.15 mL) and sequentially treated with N,N-diisopropylethylamine (13.0 μL, 0.074 mmol), sodium triacetoxyborohydride (9.4 mg, 0.045 mmol), and 1-ethyl-4-oxocyclohexane-1-carboxylic acid (Example 83, Step 1: 7.6 mg, 0.045 mmol). After being stirred at room temperature for 2 h, the reaction mixture was diluted with MeOH, and purified by prep-HPLC (pH=2, acetonitrile/water+TFA) to give the desired product as a mixture of cis/trans isomers. LC-MS calculated for $C_{39}H_{48}ClN_8O_4$ $(M+H)^+$: m/z=727.3; found 727.4.

Example 122 trans-4-(2-(2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

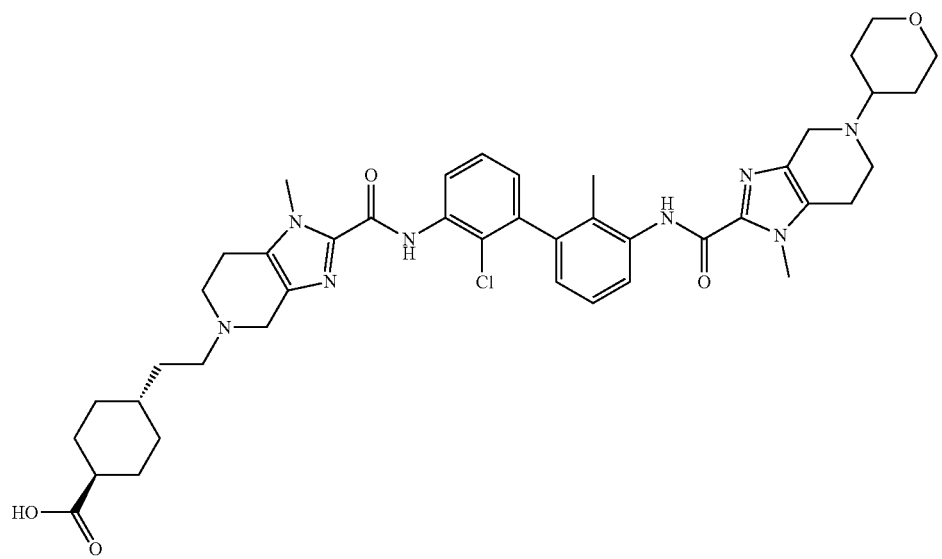 [SMILES: Cc1c(NC(=O)c2nc3c(n2C)CCN(C2CCOCC2)C3)cccc1-c1cccc(NC(=O)c2nc3c(n2C)CCN(CC[C@H]2CC[C@H](C(=O)O)CC2)C3)c1Cl]

Step 1; tert-butyl 2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

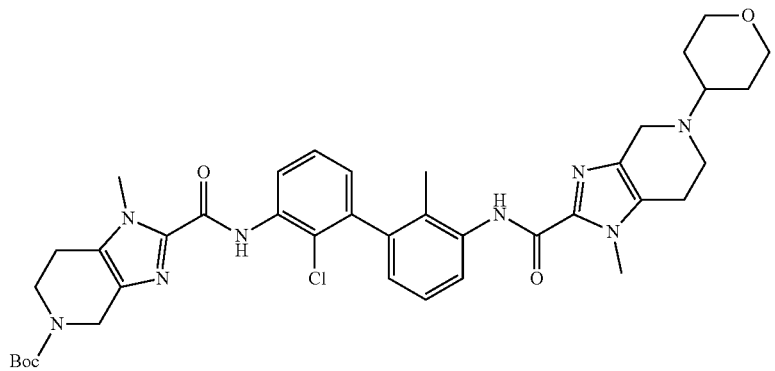 [SMILES: Cc1c(NC(=O)c2nc3c(n2C)CCN(C2CCOCC2)C3)cccc1-c1cccc(NC(=O)c2nc3c(n2C)CCN(C(=O)OC(C)(C)C)C3)c1Cl]

A solution of tert-butyl 2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 31, Step 1: 200 mg, 0.303 mmol), N,N-diisopropylethylamine (0.106 mL, 0.607 mmol) and tetrahydro-4H- pyran-4-one (0.084 mL, 0.910 mmol) in dichloromethane (3.0 mL) was stirred at room temperature for 15 min. Sodium triacetoxyborohydride (193 mg, 0.910 mmol) was added, and the mixture was further stirred at room temperature for 2 h. The reaction was quenched with saturated aqueous NaHCO$_3$ solution and extracted with dichloromethane. The combined organic layers were dried over Na$_2$SO$_4$, filtered, and concentrated under reduced pressure. The residue was purified by flash chromatography on a silica gel column eluting with 10% methanol in dichloromethane to afford the desired product. LC-MS calculated for C$_{39}$H$_{48}$ClN$_8$O$_5$ (M+H)$^+$: m/z=743.3; found 743.5

Step 2: trans-4-(2-(2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)A-methyl-1,4,6,7-tetrahydro-5H-imidazo[4,5-c]pyridin-5-yl)ethyl) cyclohexane-1-carboxylic acid A solution of tert-butyl 2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 20 mg, 0.027 mmol) in dichloromethane (0.1 mL) and trifluoroacetic acid (0.05 mL) was stirred at room temperature for 30 min. The mixture was concentrated under reduced pressure. The residue was dissolved in dichloromethane (0.24 mL) and sequentially treated with N,N-diisopropylethylamine (23.5 µL, 0.135 mmol), sodium triacetoxyborohydride (17.1 mg, 0.081 mmol) and methyl 4-(2-oxoethyl)cyclohexane-1-carboxylate (9.9 mg, 0.054 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (5.7 mg, 0.135 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for C$_{43}$H54ClN$_8$O$_5$ (M+H)$^+$: m/z=797.4; found 797.4.

TABLE 17

The compounds in Table 17 were prepared in accordance with the synthetic protocols set forth in Example 122 using the appropriate starting materials.

| Example # | Name | Structure | LC-MS (M + H)$^+$ |
|---|---|---|---|
| 123 | trans-4-((2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 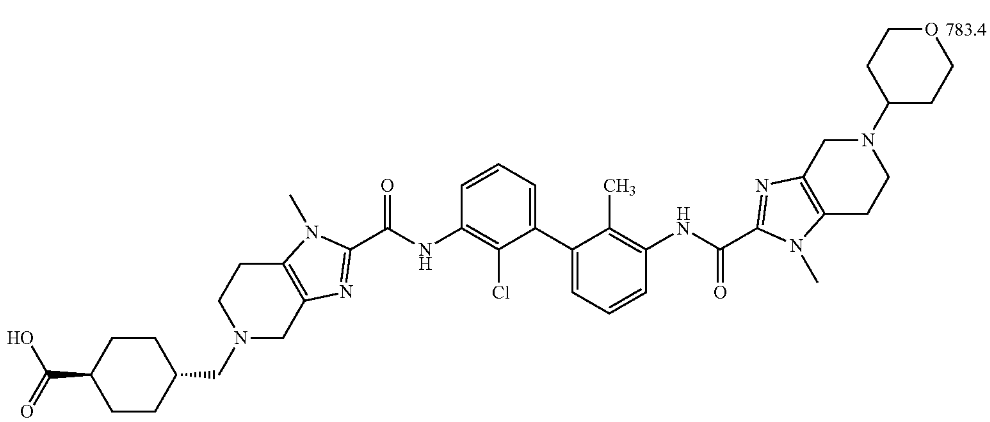 | 783.4 |

TABLE 17-continued

The compounds in Table 17 were prepared in accordance with the synthetic protocols set forth in Example 122 using the appropriate starting materials.

| Example # | Name | Structure | LC-MS (M + H)+ |
|---|---|---|---|
| 124 | 4-(2-(2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)benzoic acid | 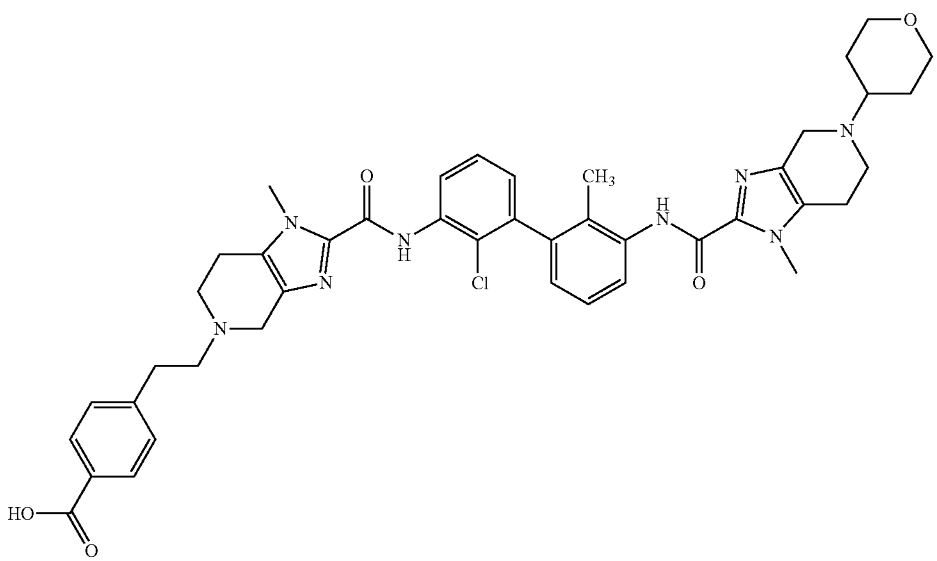 [SMILES: Cc1c(NC(=O)c2nc3c(n2C)CCN(C2CCOCC2)C3)cccc1-c1cccc(NC(=O)c2nc3c(n2C)CCN(CCc2ccc(C(=O)O)cc2)C3)c1Cl] | 791.4 |
| 125 | 4-(2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)cyclohexane-1-carboxylic acid | Mixture of cis/trans isomers | 769.4 |

Example 126 trans-4-(2-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

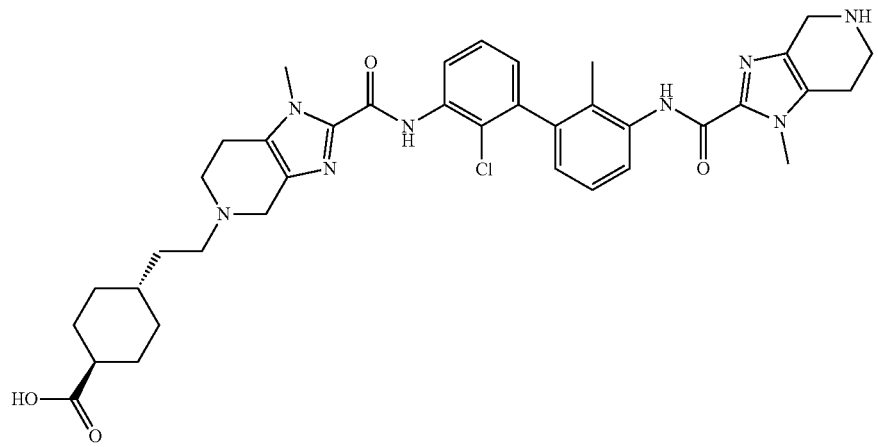 [SMILES: Cc1c(NC(=O)c2nc3c(n2C)CCNC3)cccc1-c1cccc(NC(=O)c2nc3c(n2C)CCN(CC[C@H]2CC[C@H](C(=O)O)CC2)C3)c1Cl]

Step 1: tert-butyl 2-((2'-chloro-3'-(5-(2-(4-(methoxycarbonyl)cyclohexyl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate

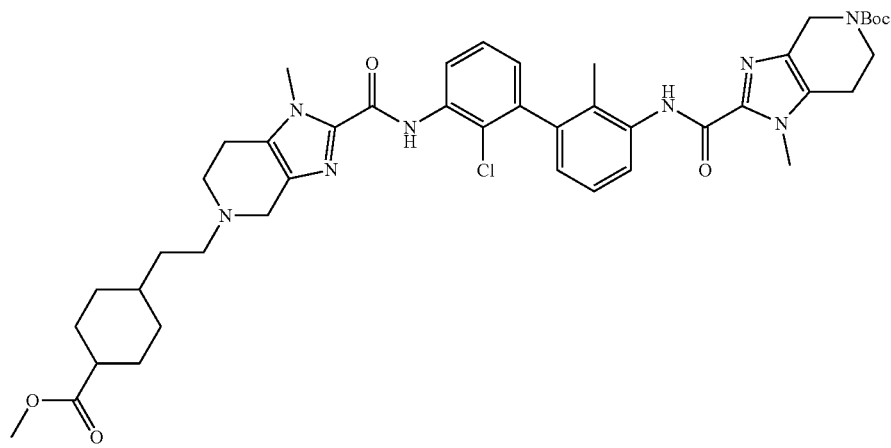 [SMILES: COC(=O)C1CCC(CCN2CCc3c(nc(C(=O)Nc4cccc(-c5cccc(NC(=O)c6nc7c(n6C)CCN(C(=O)OC(C)(C)C)C7)c5C)c4Cl)n3C)C2)CC1]

Methyl 4-(2-oxoethyl)cyclohexane-1-carboxylate (61.0 mg, 0.331 mmol) was added to a mixture of tert-butyl 2-((2'-chloro-2-methyl-3'-(1-methyl-4,5,6,7-tetrahydro-1H-imidazo[4,5-c]pyridine-2-carboxamido)-[1,1'-biphenyl]-3- yl)carbamoyl)-1-methyl-1,4,6,7-tetrahydro-5H-imidazo[4,5-c]pyridine-5-carboxylate (Example 109, Step 1: 150 mg, 0.221 mmol) and sodium triacetoxyborohydride (94 mg, 0.441 mmol) in dichloromethane (2.2 mL). After being stirred at room temperature for 2 h, the reaction was quenched with saturated aqueous NaHCO$_3$ solution and extracted with dichloromethane. The combined organic layers were dried over Na$_2$SO$_4$, filtered, and concentrated under reduced pressure. The residue was purified by flash chromatography on a silica gel column eluting with 10% methanol in dichloromethane to afford the desired product. LC-MS calculated for $C_{44}H_{56}ClN_8O_6$ (M+H)$^+$: m/z=827.4; found 827.5.

Step 2; trans-4-(2-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid A solution of tert-butyl 2-((2'-chloro-3'-(5-(2-(4-(methoxycarbonyl)cyclohexyl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Step 1: 20 mg, 0.024 mmol) in dichloromethane (0.05 mL) and trifluoroacetic acid (0.05 mL) was stirred at room temperature for 30 min. The mixture was concentrated under reduced pressure. The residue was dissolved in THF/MeOH/water (0.2 mL/0.2 mL/0.1 mL), and then treated with lithium hydroxide, monohydrate (5.0 mg, 0.118 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for $C_{38}H_{46}ClN_8O_4$ (M+H)$^+$: m/z=713.3; found 713.4.

Example 127 trans-4-(2-(2-((2-chloro-3'-(5-ethyl-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

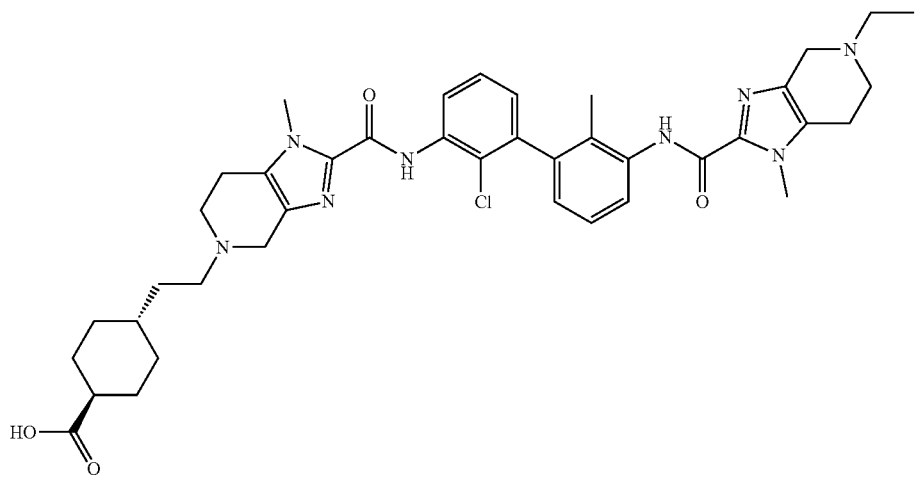 [SMILES: CCN1CCc2c(nc(C(=O)Nc3cccc(-c4cccc(NC(=O)c5nc6c(n5C)CCN(CC[C@H]5CC[C@H](C(=O)O)CC5)C6)c4Cl)c3C)n2C)C1]

A solution of tert-butyl 2-((2'-chloro-3'-(5-(2-(4-(methoxycarbonyl)cyclohexyl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Example 126, Step 1: 20 mg, 0.024 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.097 mmol), sodium triacetoxyborohydride (15.37 mg, 0.073 mmol), and acetaldehyde (2.130 mg, 0.048 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (5.1 mg, 0.121 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for $C_{40}H_{50}ClN_8O_4$ (M+H)$^+$: m/z=741.4; found 741.5.

TABLE 18

The compounds in Table 18 were prepared in accordance with the synthetic protocols set forth in Example 127 using the appropriate starting materials.

| Example # | Name | Structure | LC-MS (M + H)+ |
|---|---|---|---|
| 128 | trans-4-(2-(2-((2-chloro-3'-(5-(cyclopropylmethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 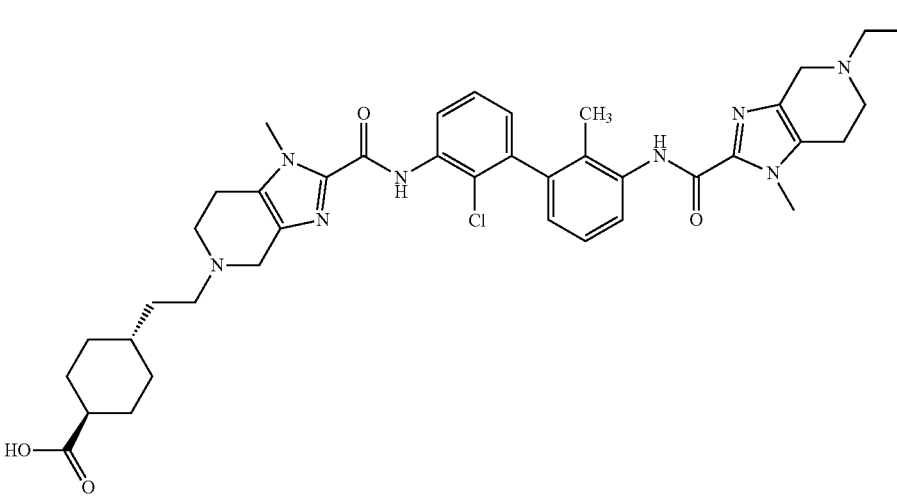 | 767.5 |
| 129 | trans-4-(2-(2-((2-chloro-3'-(5-isopropyl-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 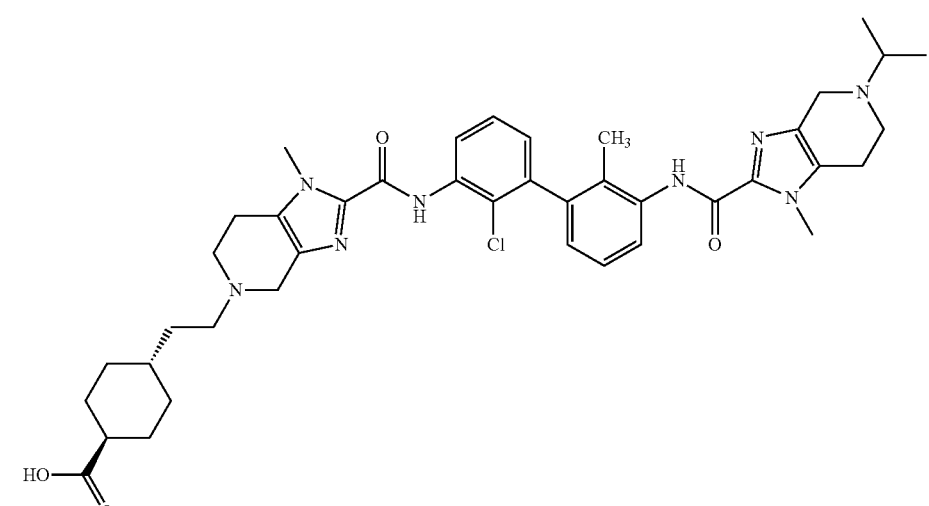 | 755.5 |

TABLE 18-continued

The compounds in Table 18 were prepared in accordance with the synthetic protocols set forth in Example 127 using the appropriate starting materials.

| Example # | Name | Structure | LC-MS (M + H)+ |
|---|---|---|---|
| 130 | trans-4-(2-(2-((2-chloro-3'-(5-cyclopentyl-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 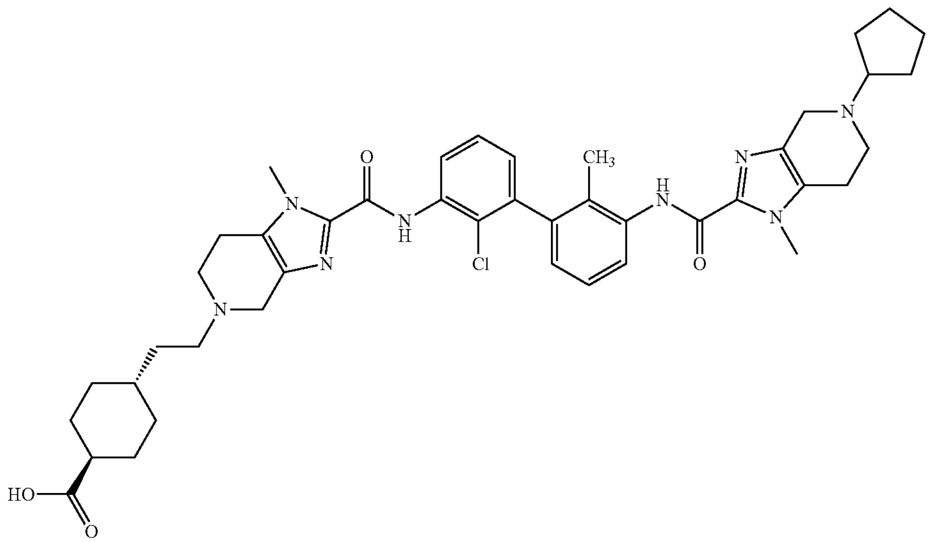 [SMILES: Cc1c(NC(=O)c2nc3c(n2C)CCN(C2CCCC2)C3)cccc1-c1cccc(NC(=O)c2nc3c(n2C)CCN(CC[C@H]2CC[C@H](C(=O)O)CC2)C3)c1Cl] | 781.4 |
| 131 | trans-4-(2-(2-((2-chloro-3'-(5-cyclohexyl-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 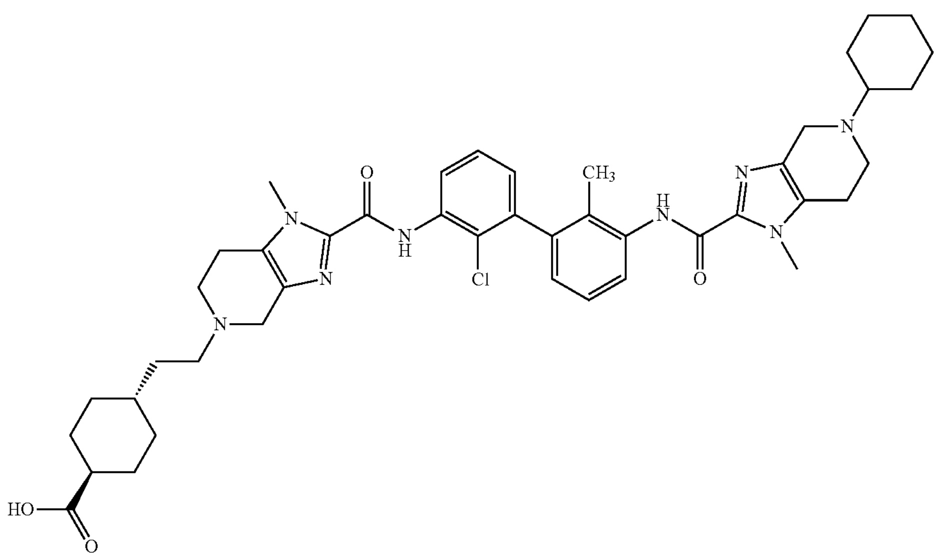 [SMILES: Cc1c(NC(=O)c2nc3c(n2C)CCN(C2CCCCC2)C3)cccc1-c1cccc(NC(=O)c2nc3c(n2C)CCN(CC[C@H]2CC[C@H](C(=O)O)CC2)C3)c1Cl] | 795.5 |

Example 132 trans-4-(2-(2-((2-chloro-3'-(5-(2-hydroxyethyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

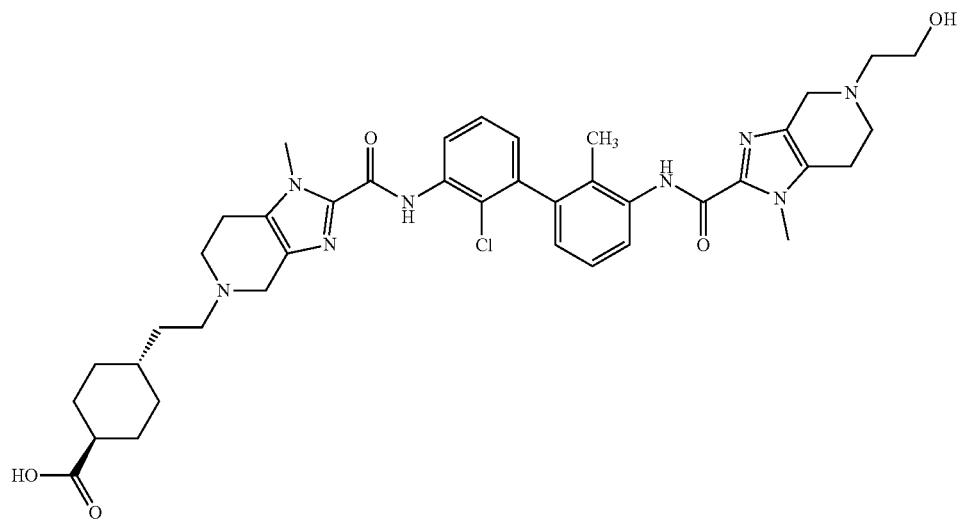 [SMILES: Cc1c(NC(=O)c2nc3c(n2C)CCN(CCO)C3)cccc1-c1cccc(NC(=O)c2nc3c(n2C)CCN(CC[C@H]2CC[C@H](C(=O)O)CC2)C3)c1Cl]

A solution of tert-butyl 2-((2'-chloro-3'-(5-(2-(4-(methoxycarbonyl)cyclohexyl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Example 126, Step 1: 20 mg, 0.024 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.097 mmol), sodium triacetoxyborohydride (15.4 mg, 0.073 mmol), and 2-((tert-butyldimethylsilyl)oxy)acetaldehyde (8.4 mg, 0.048 mmol). After being stirred at room temperature for 2 h, the reaction was quenched with saturated aqueous $NaHCO_3$ solution, and extracted with dichloromethane. The combined organic layers were dried over $Na_2SO_4$, filtered, and concentrated under reduced pressure. The residue was treated with 4 N HCl in 1,4-dioxane (0.12 mL, 0.480 mmol) at 30° C. for 1 h, and then the solvent was evaporated. The residue was dissolved in THF/MeOH/water (0.2 mL/0.2 mL/0.1 mL), and treated with lithium hydroxide, monohydrate (5.1 mg, 0.121 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for $C_{40}H_{50}ClN_8O_5$ $(M+H)^+$: m/z=757.4; found 757.5.

TABLE 19

The compound in Table 19 was prepared in accordance with the synthetic protocols set forth in Example 132 using the appropriate starting material.

| Example # | Name | Structure | LC-MS (M + H)+ |
|---|---|---|---|
| 133 | trans-4-(2-(2-(2-chloro-3'-(5-((S)-2-hydroxypropyl)-1-methyl-4,5,6,7-tetrahydro-1H-imidazo[4,5-c]pyridine-2-carboxamido)-2'-methylbiphenyl-3-ylcarbamoyl)-1-methyl-6,7-dihydro-1H-imidazo[4,5-c]pyridin-5(4H)-yl)ethyl)cyclohexane-1-carboxylic acid | 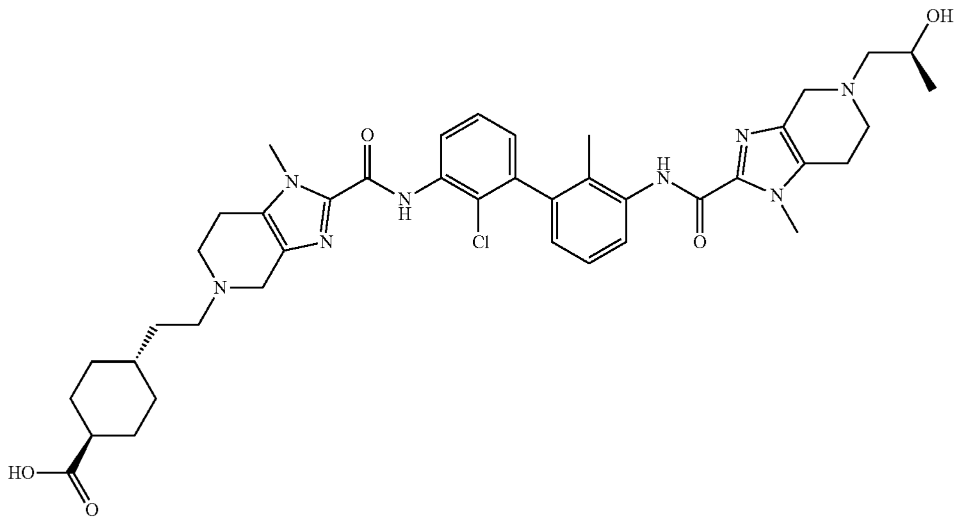 [SMILES: Cc1c(NC(=O)c2nc3c(n2C)CCN(C[C@H](C)O)C3)cccc1-c1cccc(NC(=O)c2nc3c(n2C)CCN(CC[C@H]2CC[C@H](C(=O)O)CC2)C3)c1Cl] | 771.4 |

Example 134

Trans-4-(2-(2-(2-chloro-3'-(5-(4-hydroxycyclohexyl)-1-methyl-4,5,6,7-tetrahydro-1H-imidazo[4,5-c]pyridine-2-carboxamido)-2'-methylbiphenyl-3-ylcarbamoyl)-1-methyl-6,7-dihydro-1H-imidazo[4,5-c]pyridin-5(4H)-yl)ethyl)cyclohexane-1-carboxylic Acid

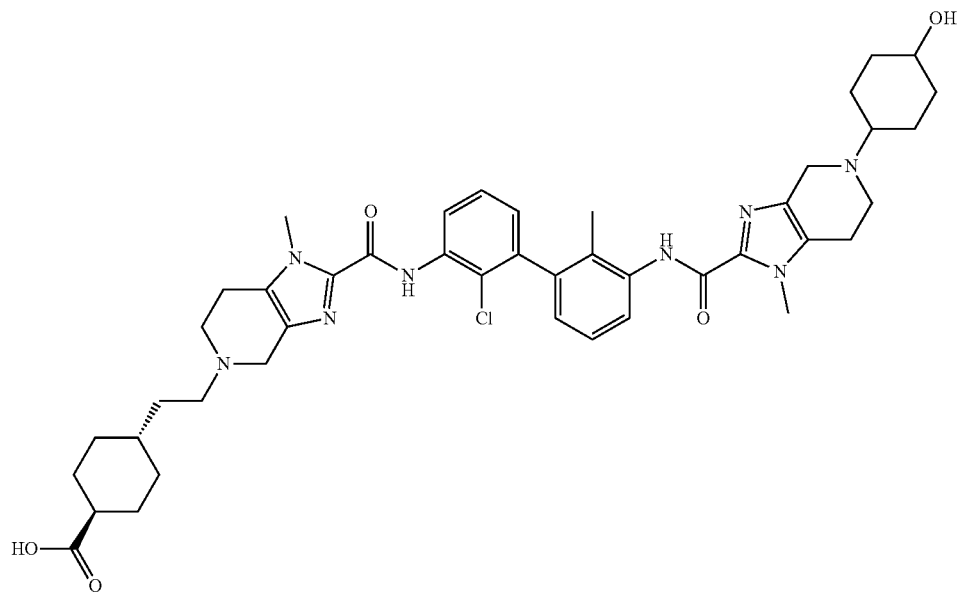 [SMILES: Cc1c(NC(=O)c2nc3c(n2C)CCN(C2CCC(O)CC2)C3)cccc1-c1cccc(NC(=O)c2nc3c(n2C)CCN(CC[C@H]2CC[C@H](C(=O)O)CC2)C3)c1Cl]

Step 1: methyl 4-(2-(2-((2-chloro-2'-methyl-3"-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylate

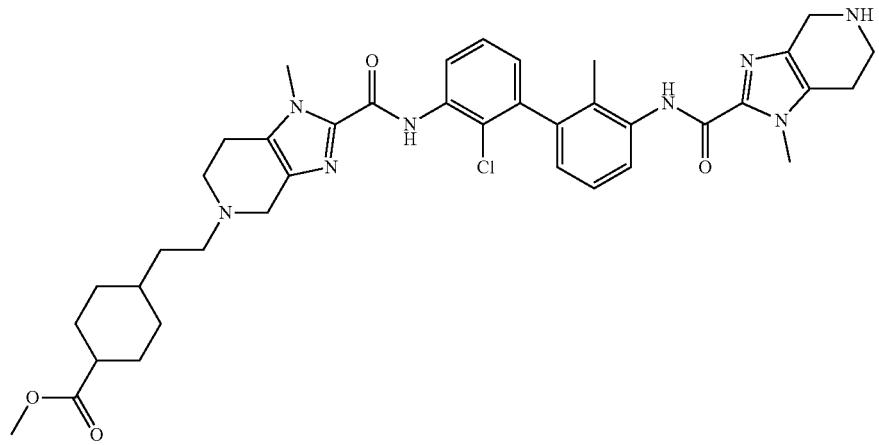 [SMILES: COC(=O)C1CCC(CCN2CCc3c(nc(C(=O)Nc4cccc(-c5cccc(NC(=O)c6nc7c(n6C)CCNC7)c5C)c4Cl)n3C)C2)CC1]

A solution of tert-butyl 2-((2'-chloro-3'-(5-(2-(4-(methoxycarbonyl)cyclohexyl)ethyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Example 126, Step 1: 260 mg, 0.314 mmol) in dichloromethane (3.0 mL) was treated with 4 N hydrochloric acid in 1,4-dioxane (3 mL, 12.00 mmol) at room temperature for 30 min. The mixture was stripped to dryness to give the desired product. LC-MS calculated for $C_{39}H_{48}ClN_8O_4$ $(M+H)^+$: m/z=727.3; found: 727.2.

Step 2; methyl 4-(2-(2-((2'-chloro-3'-(5-(4-hydroxycyclohexyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylate

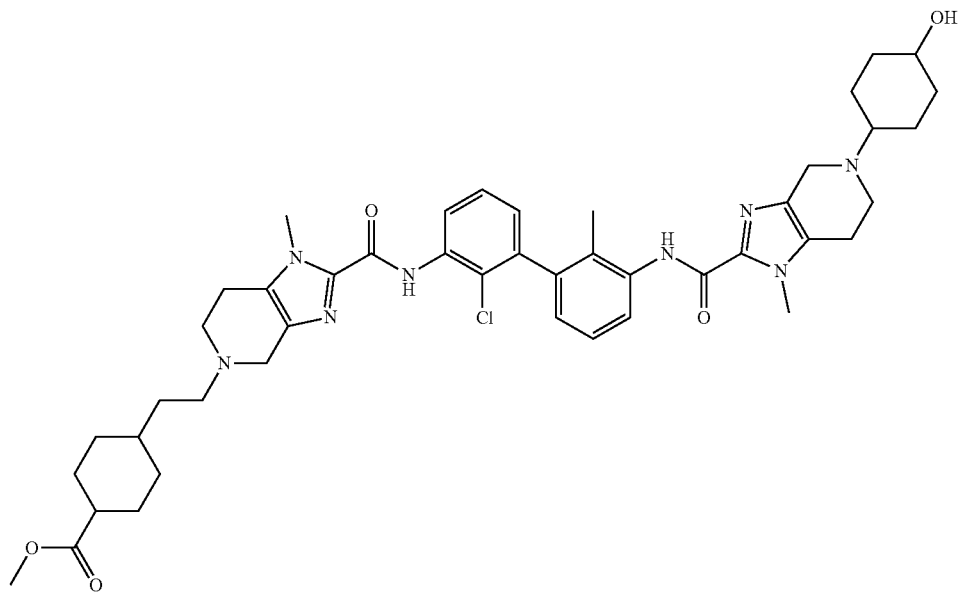 [SMILES: COC(=O)C1CCC(CCN2CCc3c(nc(C(=O)Nc4cccc(-c5cccc(NC(=O)c6nc7c(n6C)CCN(C6CCC(O)CC6)C7)c5C)c4Cl)n3C)C2)CC1]

A mixture of methyl 4-(2-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylate (Step 1: 22 mg, 0.030 mmol) and 4-hydroxycyclohexan-1-one (6.9 mg, 0.060 mmol) in dichloromethane (1 mL) was stirred at room temperature for 30 min. Then to the mixture was added sodium triacetoxyborohydride (19.2 mg, 0.091 mmol), stirring at room temperature for 2 h. The mixture was washed with saturated aqueous $NaHCO_3$ solution, concentrated and purified on prep-HPLC (pH=10, acetonitrile/water+$NH_4OH$) to give two desired products (cis/trans isomers):

Peak 1: retention time on analytical LC-MS (pH=10, acetonitrile/water+$NH_4OH$) $t_r$=3.25 min, LCMS calculated for $C_{45}H_{58}ClN_8O_5$ $(M+H)^+$: m/z=825.4; Found: 825.4;

Peak 2: retention time on analytical LC-MS (pH=10, acetonitrile/water+$NH_4OH$) $t_r$=3.30 min, LC-MS calculated for $C_{45}H_{58}ClN_8O_5$ $(M+H)^+$: m/z=825.4; Found: 825.4.

Step 3: trans-4-(2-(2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid Methyl 4-(2-(2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylate (5 mg, 6.06 μmol) from Step 2, peak 1 and peak 2 were respectively treated with lithium hydroxide (3.3 mg, 0.139 mmol) in MeOH/THF/water (0.5 mL/0.5 mL/0.25 mL) at room temperature for 3 h. The reactions were purified by prep-HPLC (pH=2, acetonitrile/water+TFA) to give the desired products as the TFA salt.

Compound 134-1 (from Step 2, peak 1): LC-MS calculated for $C_{44}H_{56}ClN_8O_5$ $(M+H)^+$: m/z=811.4; found: 811.2.

Compound 134-2 (from Step 2, peak 2): LC-MS calculated for $C_{44}H_{56}ClN_8O_5$ $(M+H)^+$: m/z=811.4; found: 811.2.

Example 135 cis-4-((2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

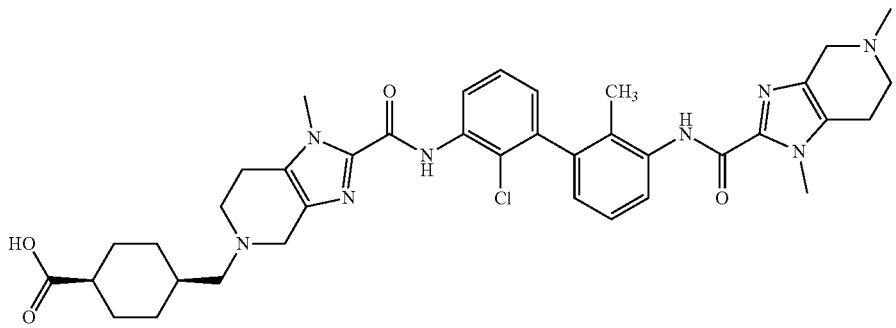 [SMILES: Cc1c(NC(=O)c2nc3c(n2C)CCN(C)C3)cccc1-c1cccc(NC(=O)c2nc3c(n2C)CCN(C[C@H]2CC[C@@H](C(=O)O)CC2)C3)c1Cl]

Step 1: tert-butyl 2-((2'-chloro-3'-(5-((cis-4-(methoxycarbonyl)cyclohexyl)methyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate

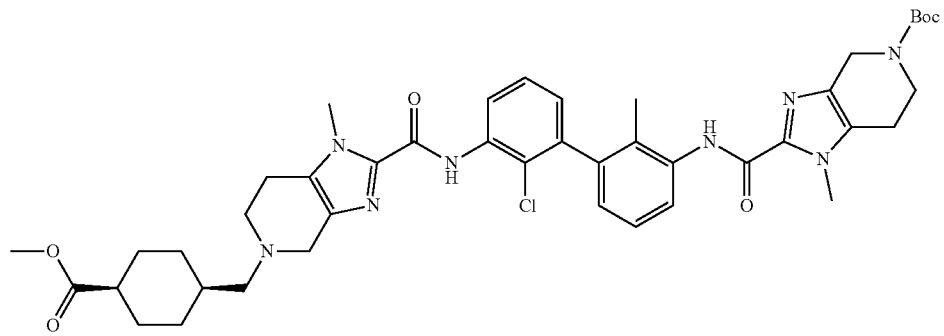

A solution of tert-butyl 2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 109, Step 1: 400 mg, 0.607 mmol), methyl cis-4-(((methylsulfonyl)oxy)methyl)cyclohexane-1-carboxylate (Example 68, Step 1: 456 mg, 1.820 mmol), N,N-diisopropylethylamine (0.530 mL, 3.03 mmol), benzyltriethylammonium chloride (13.8 mg, 0.061 mmol) and potassium iodide (10.1 mg, 0.061 mmol) in DMF (5.9 mL) was stirred at 80° C. for 12 h. The reaction mixture was quenched with saturated aqueous NaHCOs solution, and extracted with ethyl acetate. The combined organic layers were washed with brine, dried over $Na_2SO_4$, filtered, and concentrated under reduced pressure. The residue was purified by flash chromatography on a silica gel column eluting with 10% methanol in dichloromethane to afford the desired product. LC-MS calculated for $C_{43}H_{54}ClN_8O_6$ (M+H)$^+$: m/z=813.4; found: 813.2.

Step 2: cis-4-((2-((2-chloro-3'-(1,5-dimethyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid A solution of tert-butyl 2-((2'-chloro-3'-(5-((cis-4-(methoxycarbonyl)cyclohexyl)methyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Step 1: 20 mg, 0.025 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.098 mmol), sodium triacetoxyborohydride (10.4 mg, 0.049 mmol), and 37 wt % Formaldehyde in water (9.2 µL, 0.123 mmol). After being stirred at room temperature for 2 h, the reaction was quenched with saturated aqueous $NaHCO_3$ solution, and extracted with dichloromethane. The combined organic layers were dried over $Na_2SO_4$, filtered, and concentrated under reduced pressure. The residue was dissolved in THF/MeOH/water (0.2 mL/0.2 mL/0.1 mL), and treated with lithium hydroxide, monohydrate (10.3 mg, 0.246 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for $C_{38}H_{46}ClN_8O_4$ (M+H)$^+$: m/z=713.3; found 713.4. $^1$H NMR (600 MHz, DMSO-d$_6$) δ 9.95 (s, 1H), 9.93 (s, 1H), 8.28 (d, J=8.1 Hz, 1H), 7.61 (d, J=8.0 Hz, 1H), 7.49 (t, J=7.8 Hz, 1H), 7.32 (t, 7.8 Hz, 1H), 7.11 (d, J=7.5 Hz, 1H), 7.05 (d, J=7.6 Hz, 1H), 4.56-4.37 (m, 2H), 4.29-4.15 (m, 2H), 3.97 (s, 3H), 3.92 (s, 3H), 3.86-3.69 (m, 2H), 3.46 (br, 2H), 3.24-3.09 (m, 2H), 3.11-3.00 (m, 4H), 2.98 (s, 3H), 2.51 (br, 1H), 2.02 (br, 1H), 1.98 (s, 3H), 1.92-1.83 (m, 2H), 1.73-1.59 (m, 2H), 1.61-1.48 (m, 2H), 1.34-1.21 (m, 2H).

Example 136 cis-4-((2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic Acid

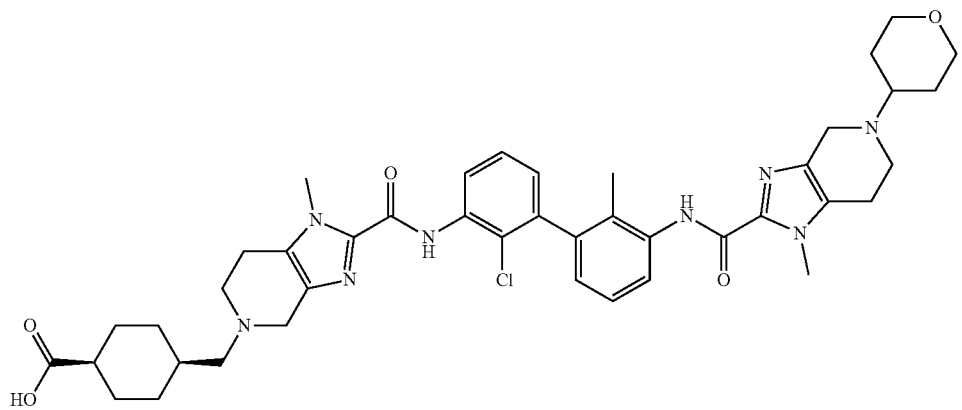 [SMILES: Cc1c(NC(=O)c2nc3c(n2C)CCN(C2CCOCC2)C3)cccc1-c1cccc(NC(=O)c2nc3c(n2C)CCN(C[C@H]2CC[C@@H](C(=O)O)CC2)C3)c1Cl]

Step 1: methyl cis-4-((2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate and tetrahydro-4H-pyran-4-one (28.1 mg, 0.280 mmol) in dichloromethane (3 mL) was stirred at room temperature for 30 min. Then to the mixture was added sodium triacetoxyborohydride (59.4 mg, 0.280 mmol), stirring at room temperature for 2 h. The mixture was washed with water, dried

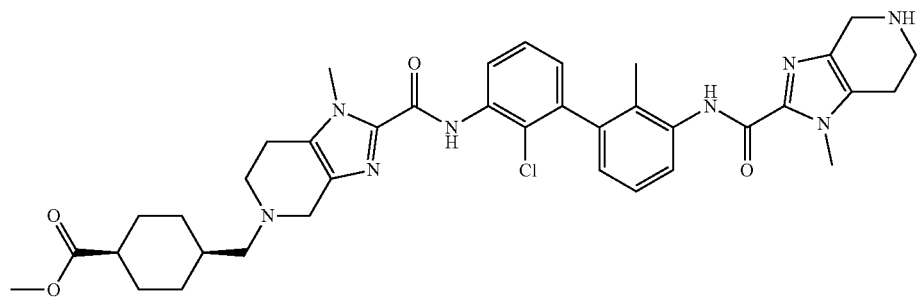 [SMILES: COC(=O)[C@H]1CC[C@@H](CN2CCc3c(nc(C(=O)Nc4cccc(-c5cccc(NC(=O)c6nc7c(n6C)CCNC7)c5C)c4Cl)n3C)C2)CC1]

tert-Butyl 2-((2'-chloro-3'-(5-((cis-4-(methoxycarbonyl)cyclohexyl)methyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Example 135, Step 1: 540 mg, 0.664 mmol) was treated with 4 N HCl in 1,4-dioxane (3 ml, 12.00 mmol) in dichloromethane (3 mL) at room temperature for 30 min. The mixture was stripped to dryness to give the desired product. LC-MS calculated for $C_{38}H_{46}ClN_8O_4$ (M+H)+: m/z=713.3; found: 713.2.

Step 2: methyl cis-4-((2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate over MgSO4 and concentrated to give the desired product. LC-MS calculated for $C_{43}H_{54}ClN_8O_5$ (M+H)+: m/z=797.4; found: 797.2.

Step 3: cis-4-((2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid Methyl cis-4-((2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate (Step 2: 100 mg, 0.130 mmol) was treated with aq. 1 N sodium

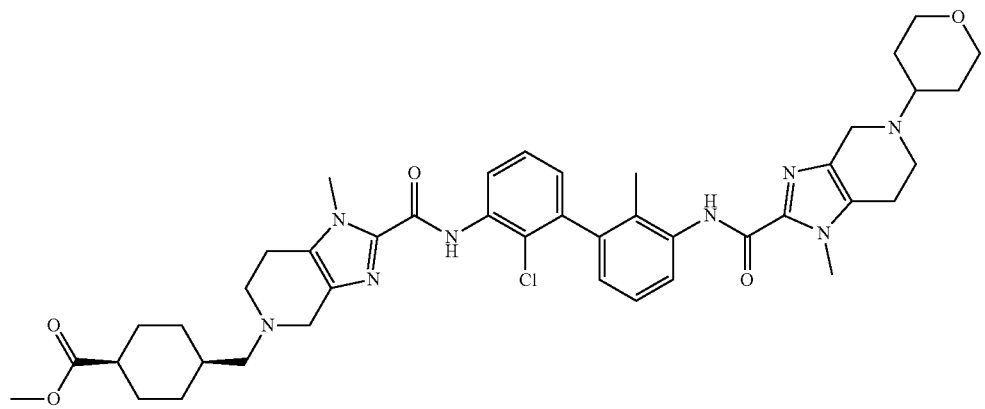 [SMILES: COC(=O)[C@H]1CC[C@@H](CN2CCc3c(nc(C(=O)Nc4cccc(-c5cccc(NC(=O)c6nc7c(n6C)CCN(C6CCOCC6)C7)c5C)c4Cl)n3C)C2)CC1]

A mixture of methyl cis-4-((2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate (step 1: 100 mg, 0.140 mmol)

hydroxide solution (0.42 mL, 0.421 mmol) in MeOH (3.0 mL) at room temperature for 2 h. The mixture was purified on prep-HPLC (pH=2, acetonitrile/water+TFA) to give the desired product as the TFA salt. LC-MS calculated for $C_{42}H_{52}ClN_8O_5$ (M+H)+: m/z=783.4; found: 783.2.

TABLE 20

The compound in Table 20 was prepared in accordance with the synthetic protocols set forth in Example 136 using the appropriate starting material.

| Example # | Name | Structure | LC-MS (M + H)+ |
|---|---|---|---|
| 137 | cis-4-((2-((2-chloro-3'-(5-((R)-2-hydroxypropyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid | 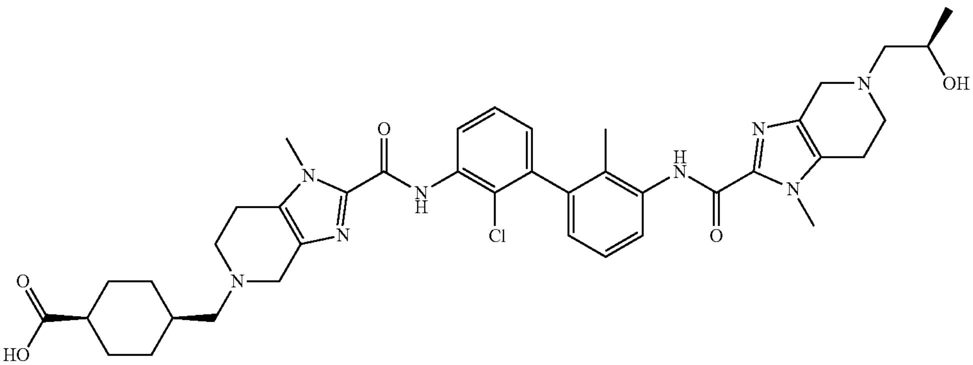 [SMILES: Cc1c(NC(=O)c2nc3c(n2C)CCN(C[C@@H](C)O)C3)cccc1-c1cccc(NC(=O)c2nc3c(n2C)CCN(C[C@H]2CC[C@@H](C(=O)O)CC2)C3)c1Cl] | 757.3 |

Example 138 cis-4-((2-((2-chloro-3'-(5-(4-hydroxy cyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic

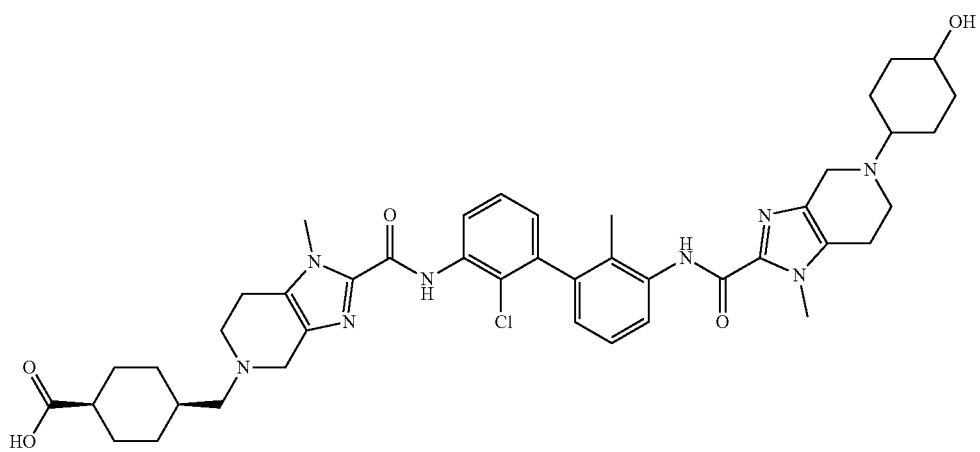 [SMILES: Cc1c(NC(=O)c2nc3c(n2C)CCN(C2CCC(O)CC2)C3)cccc1-c1cccc(NC(=O)c2nc3c(n2C)CCN(C[C@H]2CC[C@@H](C(=O)O)CC2)C3)c1Cl]

Step 1: methyl cis-4-((2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate

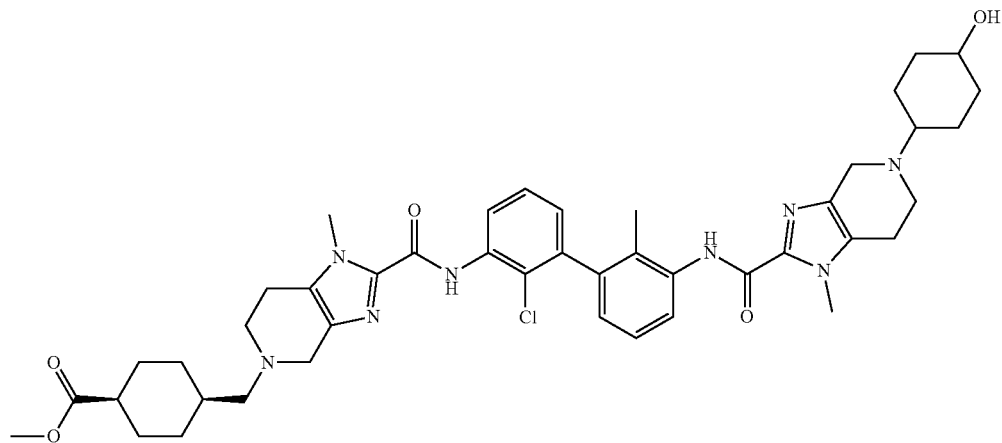 [SMILES: COC(=O)[C@H]1CC[C@@H](CN2CCc3c(nc(C(=O)Nc4cccc(-c5cccc(NC(=O)c6nc7c(n6C)CCN(C6CCC(O)CC6)C7)c5C)c4Cl)n3C)C2)CC1]

A mixture of methyl cis-4-((2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate (Example 136, Step 1: 20 mg, 0.028 mmol) and 4-hydroxycyclohexan-1-one (3.2 mg, 0.028 mmol) in dichloromethane (3 mL) was stirred at room temperature for 30 min. Then to the mixture was added sodium triacetoxyborohydride (11.89 mg, 0.056 mmol), stirring at room temperature overnight. The mixture was washed with water, concentrated and purified on prep-HPLC (pH=10, acetonitrile/water+NH$_4$OH) to give two desired products (cis/trans isomers).

Peak 1: retention time on analytical LC-MS (pH=10, acetonitrile/water+NH$_4$OH) t$_r$=3.29 min, LCMS calculated for C$_{44}$H$_{56}$ClN$_8$O$_5$ (M+H)$^+$: m/z=811.4; Found: 811.2;

Peak 2: retention time on analytical LC-MS (pH=10, acetonitrile/water+NH$_4$OH) t$_r$=3.36 min, LCMS calculated for C$_{44}$H$_{56}$ClN$_8$O$_5$ (M+H)$^+$: m/z=811.4; Found: 811.2.

Step 2: cis-4-((2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid Methyl cis-4-((2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate (5 mg, 6.16 μmol) from Step 1, peak 1 and peak 2 were respectively treated with sodium hydroxide (3.3 mg, 0.083 mmol) in MeOH/THF/water (0.5 mL/0.5 mL/0.25 mL) at room temperature for 2 h. The reactions were purified by prep-HPLC (pH=2, acetonitrile/water+TFA) to give the desired products as the TFA salt.

Compound 138-1 (from Step 1, peak 1): LC-MS calculated for C$_{43}$H$_{54}$ClN$_8$O$_5$ (M+H)$^+$: m/z=797.4; found: 797.2.

Compound 138-2 (from Step 1, peak 2): LC-MS calculated for C$_{43}$H$_{54}$ClN$_8$O$_5$ (M+H)$^+$: m/z=797.4; found: 797.2.

Example 139

4-(2-((2-chloro-3'-(5-cyclohexyl-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid

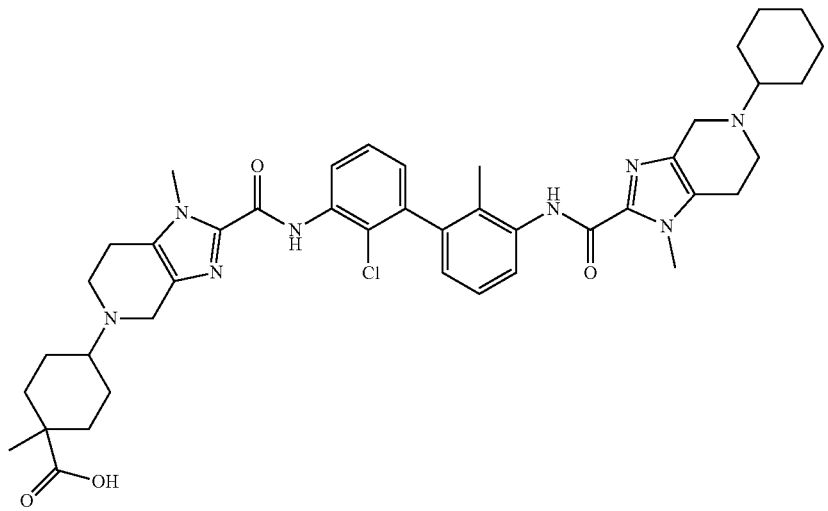 [SMILES: Cc1c(NC(=O)c2nc3c(n2C)CCN(C2CCCCC2)C3)cccc1-c1cccc(NC(=O)c2nc3c(n2C)CCN(C2CCC(C)(C(=O)O)CC2)C3)c1Cl]

Step 1: 4-(2-((3'-(5-(tert-butoxycarbonyl)-1-methyl-4,5,6,7-tetrahydro-1H-imidazo[4,5-c]pyridine-2-carboxamido)-2-chloro-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid

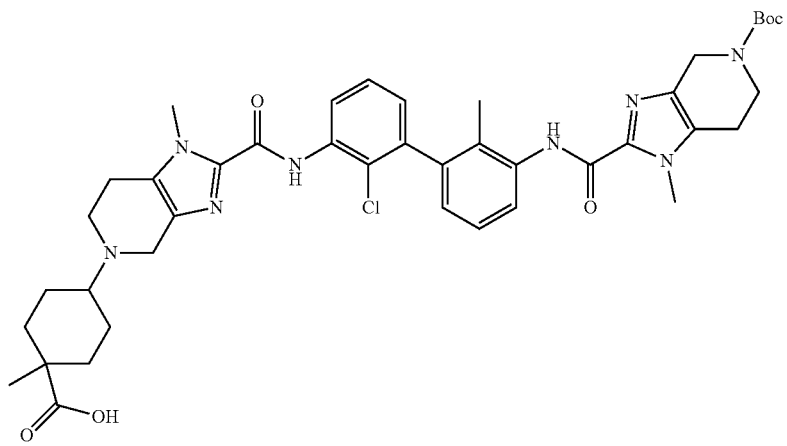 [SMILES: Cc1c(NC(=O)c2nc3c(n2C)CCN(C(=O)OC(C)(C)C)C3)cccc1-c1cccc(NC(=O)c2nc3c(n2C)CCN(C2CCC(C)(C(=O)O)CC2)C3)c1Cl]

A mixture of tert-butyl 2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 109, Step 1: 170 mg, 0.258 mmol) and 1-methyl-4-oxocyclohexane-1-carboxylic acid (81 mg, 0.516 mmol) in dichloromethane (3 mL) was stirred at room temperature for 30 min. Then to the mixture was added sodium triacetoxyborohydride (137 mg, 0.645 mmol), stirring at room temperature for 2 h. The mixture was purified by flash chromatography on a silica gel column eluting with 20% methanol in dichloromethane to afford the desired product. LC-MS calculated for $C_{42}H_{52}ClN_8O_6$ (M+H)$^+$: m/z=799.4; found: 799.2.

Step 2: 4-(2-((2-chloro-2'-methyl-3'-(1-methyl-4,5,6,
7-tetrahydro-1H-imidazo[4,5-c]pyridine-2-carbox-
amido)-[1,1'-biphenyl]-3-yl)carbamoyl)-1-methyl-1,
4,6,7-tetrahydro-5H-imidazo[4,5-c]pyridin-5-yl)-1-
methylcyclohexane-1-carboxylic acid

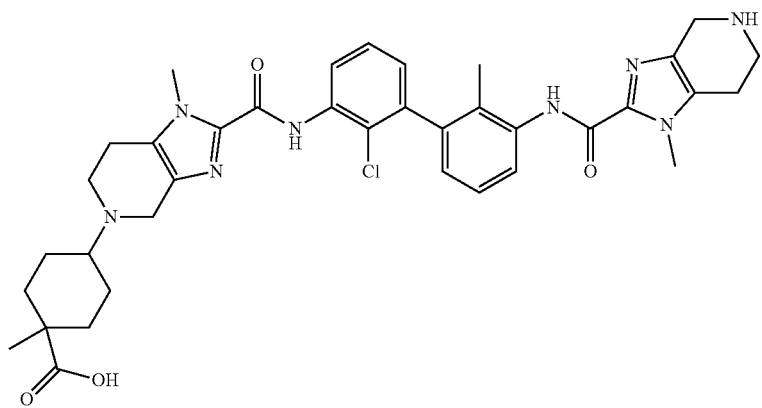 [SMILES: Cc1c(NC(=O)c2nc3c(n2C)CCNC3)cccc1-c1cccc(NC(=O)c2nc3c(n2C)CCN(C2CCC(C)(C(=O)O)CC2)C3)c1Cl]

4-(2-((3'-(5-(tert-Butoxycarbonyl)-1-methyl-4,5,6,7-tet-rahydro-1H-imidazo[4,5-c]pyridine-2-carboxamido)-2-chloro-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid (Step 1: 160 mg, 0.200 mmol) was treated with 4 N HCl in 1,4-dioxane (3 mL, 12.00 mmol) in dichloromethane (3 mL) at room temperature for 30 min. The mixture was stripped to dryness to give the desired product. LC-MS calculated for $C_{37}H_{44}ClN_8O_4$ (M+H)$^+$: m/z=699.3; found: 699.1.

Step 3: 4-(2-((2-chloro-3-(5-cyclohexyl-1-methyl-4,
5,6,7-tetrahydro-1H-imidazo[4,5-c]pyridine-2-car-
boxamido)-2'-methyl-[1,1'-biphenyl]-3-yl)carbam-
oyl)-1-methyl-1,4,6,7-tetrahydro-5H-imidazo[4,5-c]
pyridin-5-yl)-1-methylcyclohexane-1-carboxylic
acid A mixture of 4-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid (Step 2: 10 mg, 0.014 mmol) and cyclohexanone (2.8 mg, 0.029 mmol) in dichloromethane (0.3 mL) was stirred at room temperature for 30 min. Then to the mixture was added sodium triacetoxyborohydride (6.1 mg, 0.029 mmol), stirring at room temperature for 2 h. The mixture was purified on prep-HPLC (pH=2, acetonitrile/water+TFA) to give the desired product as a mixture of cis/trans isomers. LC-MS calculated for $C_{43}H_{54}ClN_8O_4$ (M+H)$^+$: m/z=781.4; found: 781.2.

TABLE 21

The compounds in Table 21 were prepared in accordance with the synthetic protocols set forth in Example 139 using the appropriate starting materials.

| Example # | Name | Structure | LC-MS (M+H)+ |
|---|---|---|---|
| 140 | 4-(2-((2-chloro-3'-(5-(4-hydroxycyclohexyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid | 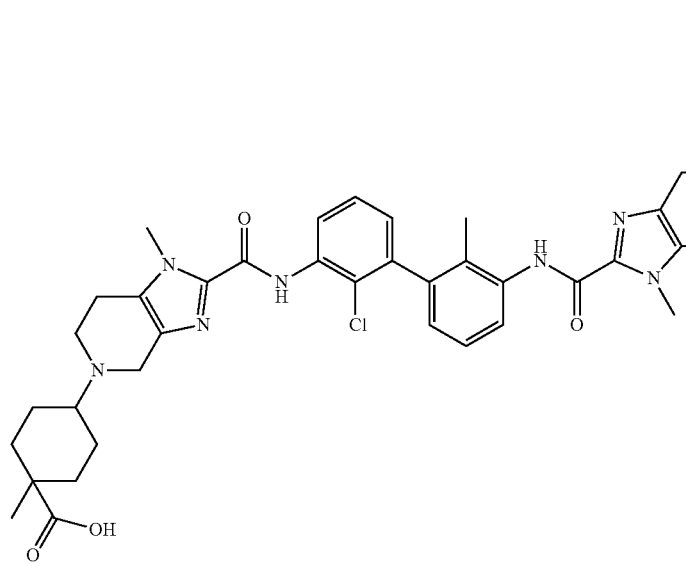 mixture of cis/trans isomers | 797.2 |
| 141 | (R)-4-(2-((2-chloro-3'-(5-(2-hydroxypropyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid | 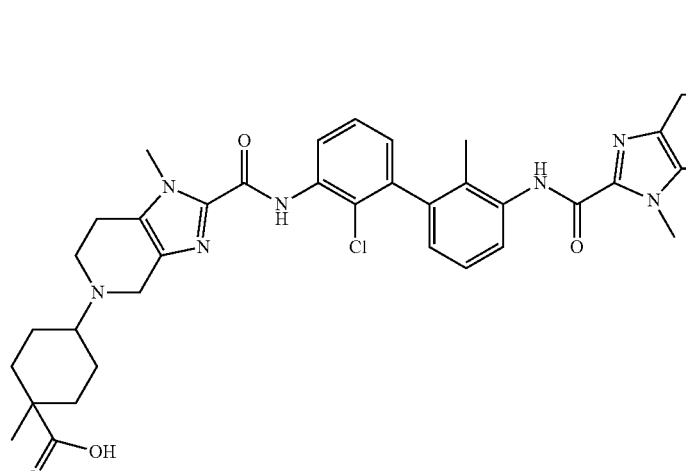 mixture of cis/trans isomers | 757.2 |

Example 142

4-(2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid

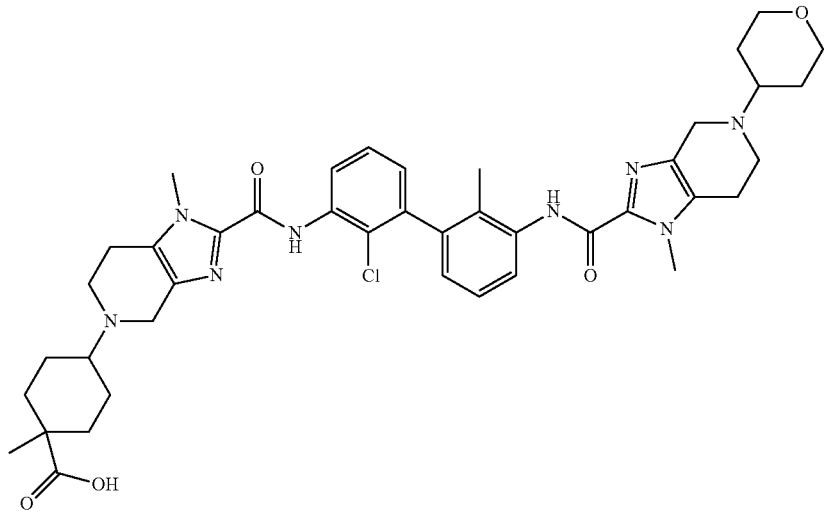 [SMILES: Cc1c(NC(=O)c2nc3c(n2C)CCN(C2CCOCC2)C3)cccc1-c1cccc(NC(=O)c2nc3c(n2C)CCN(C2CCC(C)(C(=O)O)CC2)C3)c1Cl]

Step 1; ten-butyl 2-((2'-chloro-3'-(5-(4-(methoxycarbonyl)-4-methylcyclohexyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate

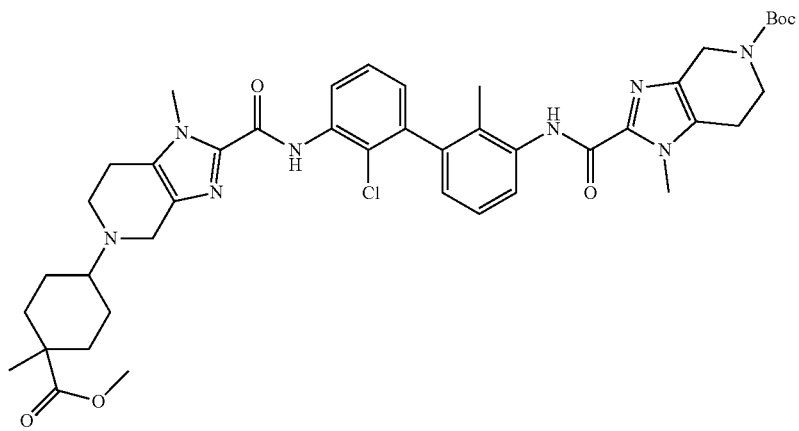 [SMILES: COC(=O)C1(C)CCC(N2CCc3c(nc(C(=O)Nc4cccc(-c5cccc(NC(=O)c6nc7c(n6C)CCN(C(=O)OC(C)(C)C)C7)c5C)c4Cl)n3C)C2)CC1]

A mixture of tert-butyl 2-((2'-chloro-2-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 109, Step 1: 440 mg, 0.667 mmol) and methyl 1-methyl-4-oxocyclohexane-1-carboxylate (261 mg, 1.535 mmol) in dichloromethane (8 mL) was stirred at room temperature for 30 min. Then to the mixture was added sodium triacetoxyborohydride (424 mg, 2.002 mmol), stirring at room temperature over weekend. The mixture was purified by flash chromatography on a silica gel column eluting with 20% methanol in dichloromethane to afford the desired product. LC-MS calculated for $C_{43}H_{54}ClN_8O_6$ (M+H)+: m/z=813.4; found: 813.2.

Step 2: methyl 4-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylate

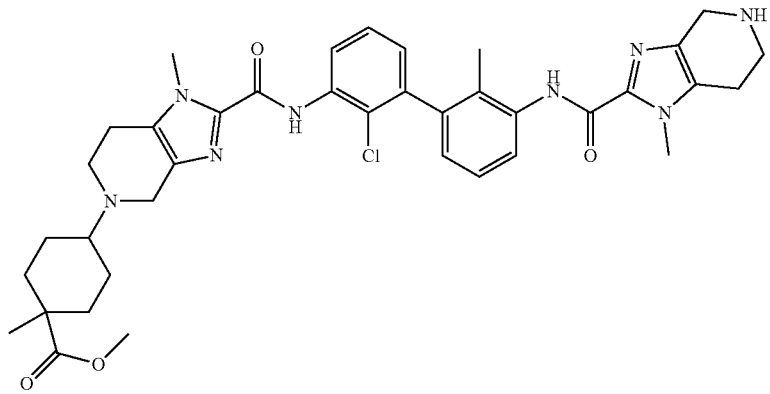 [SMILES: COC(=O)C1(C)CCC(N2CCc3c(nc(C(=O)Nc4cccc(-c5cccc(NC(=O)c6nc7c(n6C)CCNC7)c5C)c4Cl)n3C)C2)CC1]

tert-Butyl 2-((2'-chloro-3'-(5-(4-(methoxycarbonyl)-4-methylcyclohexyl)-1-methyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridine-5-carboxylate (Step 1: 480 mg, 0.590 mmol) was treated with 4 N HCl in 1,4-dioxane (3 mL, 12.00 mmol) in dichloromethane (3 mL) at room temperature for 30 min. The mixture was stripped to dryness to give the desired product. LC-MS calculated for $C_{38}H_{46}ClN_8O_4$ (M+H)+: m/z=713.3; found. 713.2.

Step 3: methyl 4-(2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylate

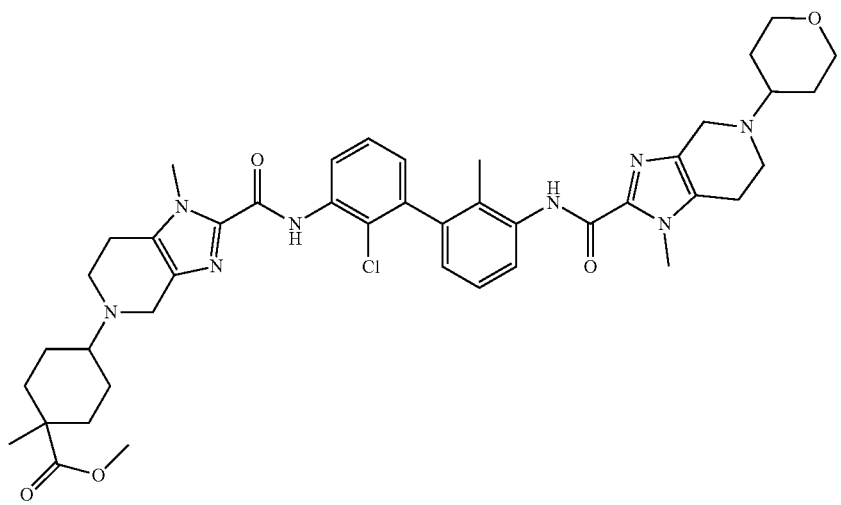 [SMILES: COC(=O)C1(C)CCC(N2CCc3c(nc(C(=O)Nc4cccc(-c5cccc(NC(=O)c6nc7c(n6C)CCN(C6CCOCC6)C7)c5C)c4Cl)n3C)C2)CC1]

A mixture of methyl 4-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylate (Step 2: 220 mg, 0.308 mmol) and tetrahydro-4H-pyran-4-one (77 mg, 0.771 mmol) in dichloromethane (3 mL) was stirred at room temperature for 30 min. Then to the mixture was added sodium triacetoxyborohydride (261 mg, 1.234 mmol), stirring at room temperature overnight. The mixture was purified on prep-HPLC (pH=2, acetonitrile/water+TFA) to give two desired products (cis/trans isomers):

Peak 1: retention time on analytical LC-MS (pH=2, acetonitrile/water+TFA) $t_r$=1.85 min, LCMS calculated for $C_{43}H_{54}ClN_8O_5$ (M+H)$^+$: m/z=797.4; found: 797.2;

Peak 2: retention time on analytical LC-MS (pH=2, acetonitrile/water+TFA) U=1.90 min, LCMS calculated for $C_{43}H_{54}ClN_8O_5$ (M+H)$^+$: m/z=797.4; found: 797.2.

Step 4: 4-(2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid Methyl 4-(2-((2-chloro-2'-methyl-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylate (8 mg, 10.03 μmol) from Step 3, peak 1 and peak 2 were respectively treated with lithium hydroxide (3.2 mg, 0.130 mmol) in MeOH/THF/water (0.5 mL/0.5 mL/0.25 mL) at 35° C. overnight. The reactions were purified by prep-HPLC (pH=2, acetonitrile/water+TFA) to give the desired products as the TFA salt.

Compound 142-1 (from Step 3, peak 1): LC-MS calculated for $C_{42}H_{52}ClN_8O_5$ (M+H)$^+$: m/z=783.4; found: 783.2.

Compound 142-2 (from Step 3, peak 2): LC-MS calculated for $C_{42}H_{52}ClN_8O_5$ (M+H)$^+$: m/z=783.4; found: 783.2.

Example 143

(S)-4-(2-((2-chloro-3'-(5-(2-hydroxypropyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid

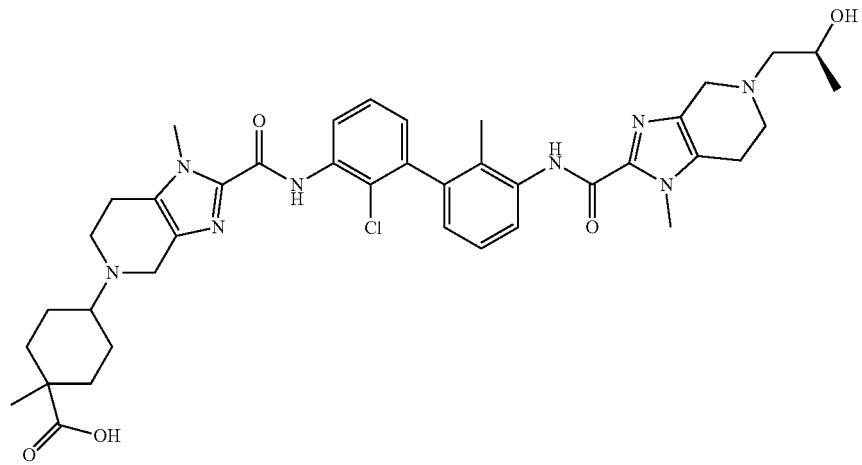 [SMILES: Cc1c(NC(=O)c2nc3c(n2C)CCN(C[C@H](C)O)C3)cccc1-c1cccc(NC(=O)c2nc3c(n2C)CCN(C2CCC(C)(C(=O)O)CC2)C3)c1Cl]

Step 1; methyl (S)-4-(2-((3'-(5-(2-((tert-butyldimethylsilyl)oxy)propyl)-1-methyl-4,5,6,7-tetrahydro-1H-imidazo[4,5-c]pyridine-2-carboxamido)-2-chloro-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylate

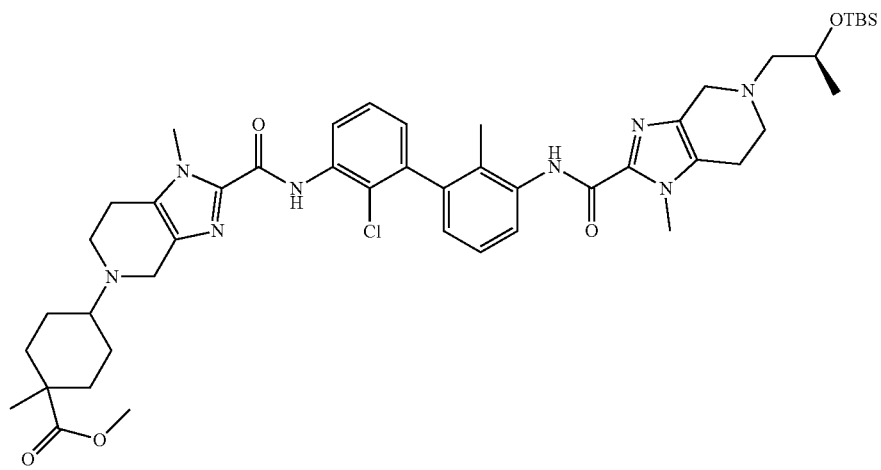 [SMILES: COC(=O)C1(C)CCC(N2CCc3c(nc(C(=O)Nc4cccc(-c5cccc(NC(=O)c6nc7c(n6C)CCN(C[C@H](C)O[Si](C)(C)C(C)(C)C)C7)c5C)c4Cl)n3C)C2)CC1]

A mixture of methyl 4-(2-((2-chloro-2'-methyl-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylate (Example 142, Step 2: 24 mg, 0.034 mmol) and (S)-2-((tert-butyldimethylsilyl)oxy)propanal (12.7 mg, 0.067 mmol) in dichloromethane (1 mL) was stirred at room temperature for 30 min. Then to the mixture was added sodium triacetoxyborohydride (14.3 mg, 0.067 mmol), stirring at room temperature for 2 h. The mixture was washed with saturated aqueous $NaHCO_3$ solution, dried over $MgSO_4$ and concentrated to give the desired product. LC-MS calculated for $C_{47}H_{66}ClN_8O_5Si$ (M+H)+: m/z=885.5; found: 885.2.

Step 2: methyl (S)-4-(2-((2-chloro-3'-(5-(2-hydroxypropyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylate

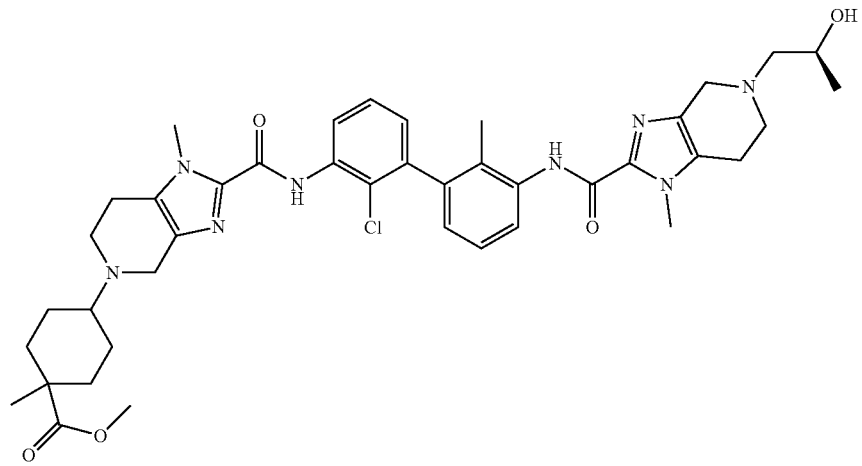 [SMILES: COC(=O)C1(C)CCC(N2CCc3c(nc(C(=O)Nc4cccc(-c5cccc(NC(=O)c6nc7c(n6C)CCN(C[C@H](C)O)C7)c5C)c4Cl)n3C)C2)CC1]

A solution of methyl (S)-4-(2-((3'-(5-(2-((tert-butyldimethylsilyl)oxy)propyl)-1-methyl-4,5,6,7-tetrahydro-1H-imidazo[4,5-c]pyridine-2-carboxamido)-2-chloro-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylate (Step 1: 20 mg, 0.023 mmol) in THF (1 mL) was treated with aq. 4 N HCl (56.5 μL, 0.34 mmol) at room temperature for 30 min. The mixture was purified on prep-HPLC (pH=2, acetonitrile/water+TFA) to give two desired products (cis/trans isomers):

Peak 1: retention time on analytical LC-MS (pH=2, acetonitrile/water+TFA) $t_r$=1.82 min, LCMS calculated for $C_{41}H_{52}ClN_8O_5$ (M+H)$^+$: m/z=771.4; found: 771.2;

Peak 2: retention time on analytical LC-MS (pH=2, acetonitrile/water+TFA) U=1.88 min, LCMS calculated for $C_{41}H_{52}ClN_8O_5$ (M+H)$^+$: m/z=771.4; found: 771.2.

Step 3: (S)-4-(2-((2-chloro-3'-(5-(2-hydroxypropyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid Methyl (S)-4-(2-((2-chloro-3'-(5-(2-hydroxypropyl)-1-methyl-4,5,6,7-tetrahydro-1H-imidazo[4,5-c]pyridine-2-carboxamido)-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylate (5 mg, 6.48 μmol) from Step 2, peak 1 and peak 2 were respectively treated with 1 N aq. sodium hydroxide (1 mL, 1.000 mmol) solution in MeOH (1 mL)/THF (1 mL) at room temperature for 30 min. The reactions were purified by prep-HPLC (pH=2, acetonitrile/water+TFA) to give the desired products as the TFA salt.

Compound 143-1 (from Step 2, peak 1): LC-MS calculated for $C_{40}H_{50}ClN_8O_5$ (M+H)$^+$: m/z=757.4; found: 757.2.

Compound 143-2 (from Step 2, peak 2): LC-MS calculated for $C_{40}H_{50}ClN_8O_5$ (M+H)$^+$: m/z=757.4; found: 757.2.

Example 144 trans-4-((2-((2,2'-dichloro-3'-(5-(4-hydroxycyclo-hexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

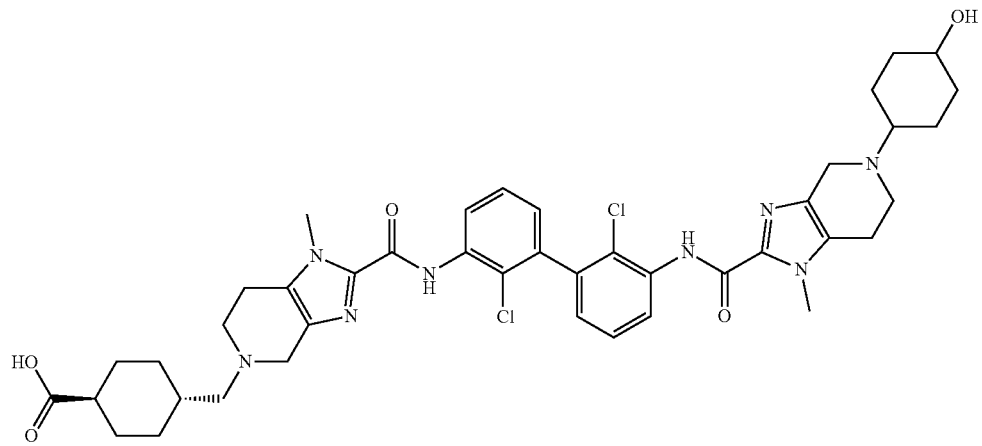 [SMILES: Cn1c(C(=O)Nc2cccc(-c3cccc(NC(=O)c4nc5c(n4C)CCN(C4CCC(O)CC4)C5)c3Cl)c2Cl)nc2c1CCN(C[C@H]1CC[C@H](C(=O)O)CC1)C2]

Step 1: methyl trans-4-((2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate

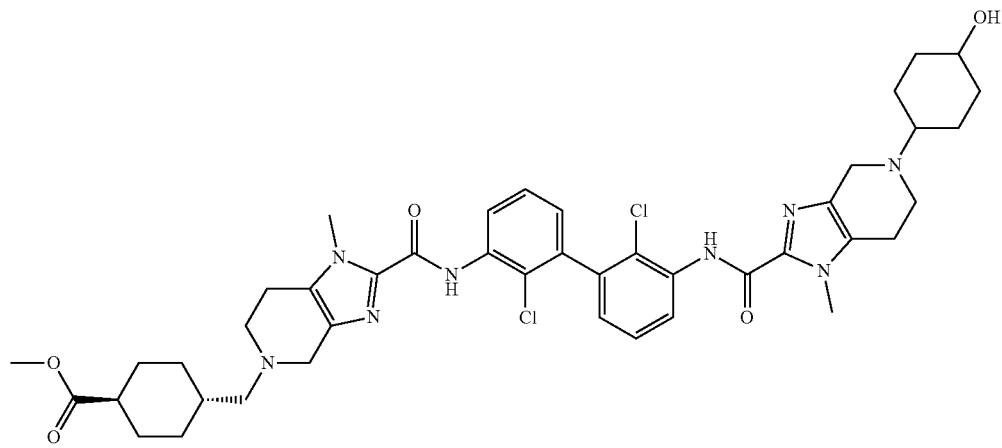 [SMILES: COC(=O)[C@H]1CC[C@H](CN2CCc3c(nc(C(=O)Nc4cccc(-c5cccc(NC(=O)c6nc7c(n6C)CCN(C6CCC(O)CC6)C7)c5Cl)c4Cl)n3C)C2)CC1]

A solution of tert-butyl trans-2-((2,2'-dichloro-3'-(5-((4-(methoxycarbonyl)cyclohexyl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 61, Step 1: 20 mg, 0.024 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.096 mmol), sodium triacetoxyborohydride (10.2 mg, 0.048 mmol) and 4-hydroxycyclohexan-1-one (5.5 mg, 0.048 mmol). After being stirred at room temperature for 2 h, the reaction mixture was diluted with MeOH, and purified by prep-HPLC (pH=10, acetonitrile/water+NH$_4$OH) to give two desired products (cis/trans isomers):

Peak 1: retention time on analytical LC-MS (pH=10, acetonitrile/water+NH$_4$OH) t$_r$=1.71 min, LCMS calculated for C$_{43}$H$_{53}$Cl$_2$N$_8$O$_5$ (M+H)$^+$: m/z=831.4; Found: 831.4;

Peak 2: retention time on analytical LC-MS (pH=10, acetonitrile/water+NH$_4$OH) t$_r$=1.73 min, LC-MS calculated for C$_{43}$H$_{53}$Cl$_2$N$_8$O$_5$ (M+H)$^+$: m/z=831.4; Found: 831.4.

Step 2: trans-4-((2-((2,2'-dichloro-3'-(5-(4-hydroxy-cyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid Methyl trans-4-((2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate (Step 1: 5 mg, 6.01 µmol) from Step 1, peak 1 and peak 2 were respectively treated with lithium hydroxide, monohydrate (1.3 mg, 0.030 mmol) in THF/MeOH/water (0.2 mL/0.2 mL/0.1 mL) at 30° C. for 3 h. The reactions were purified by prep-HPLC (pH=2, acetonitrile/water+TFA) to give the desired products as the TFA salt.

Compound 144-1 (from Step 1, peak 1): LC-MS calculated for $C_{42}H_{51}Cl_2N_8O_5$ (M+H)$^+$: m/z=817.3; found: 817.4.

Compound 144-2 (from Step 1, peak 2): LC-MS calculated for $C_{42}H_{51}Cl_2N_8O_5$ (M+H)$^+$: m/z=817.3; found: 817.4.

Example 145 cis-4-((2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

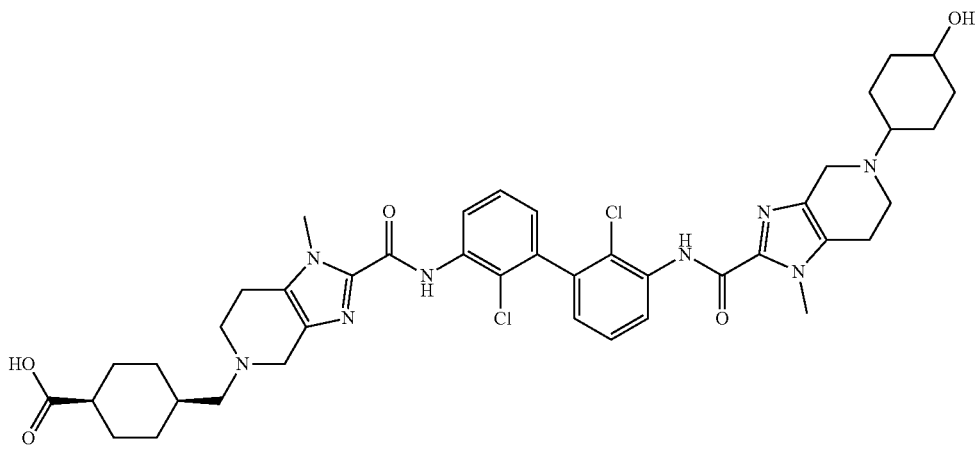 [SMILES: Cn1c(C(=O)Nc2cccc(-c3cccc(NC(=O)c4nc5c(n4C)CCN(C4CCC(O)CC4)C5)c3Cl)c2Cl)nc2c1CCN(C[C@H]1CC[C@@H](C(=O)O)CC1)C2]

Step 1: methyl cis-4-((2-((2,2'-dichloro-3'-(5-(4-Hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate

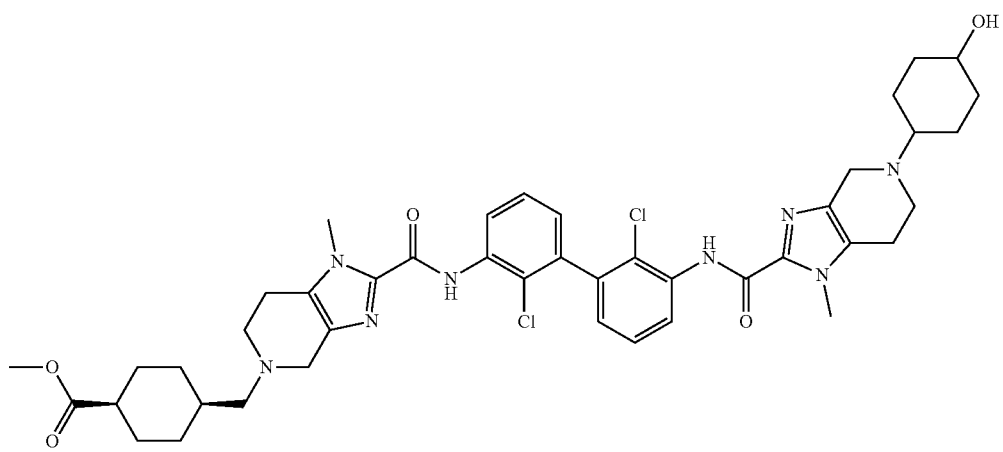 [SMILES: COC(=O)[C@H]1CC[C@@H](CN2CCc3c(nc(C(=O)Nc4cccc(-c5cccc(NC(=O)c6nc7c(n6C)CCN(C6CCC(O)CC6)C7)c5Cl)c4Cl)n3C)C2)CC1]

A solution of tert-butyl cis-2-((2,2'-dichloro-3'-(5-((4-(methoxycarbonyl)cyclohexyl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 68, Step 2: 20 mg, 0.024 mmol) in dichloromethane (0.1 ml) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.096 mmol), sodium triacetoxyborohydride (10.2 mg, 0.048 mmol) and 4-hydroxycyclohexan-1-one (5.5 mg, 0.048 mmol). After being stirred at room temperature for 2 h, the reaction mixture was diluted with MeOH, and purified by prep-HPLC (pH=10, acetonitrile/water+NH$_4$OH) to give two desired products (cis/trans isomers):

Peak 1: retention time on analytical LC-MS (pH=10, acetonitrile/water+NH$_4$OH) $t_r$=1.73 min, LCMS calculated for O$_{43}$H$_{53}$Cl$_2$N$_8$O$_5$ (M+H)$^+$: m/z=831.4; Found: 831.4;

Peak 2: retention time on analytical LC-MS (pH=10, acetonitrile/water+NH$_4$OH) $t_r$=1.75 min, LC-MS calculated for C$_{43}$H$_{53}$Cl$_2$N$_8$O$_5$ (M+H)$^+$: m/z=831.4; Found: 831.4.

Step 2; cis-4-((2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid Methyl cis-4-((2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylate (5 mg, 6.01 μmol) from Step 1, peak 1 and peak 2 were respectively treated with lithium hydroxide, monohydrate (1.3 mg, 0.030 mmol) in THF/MeOH/water (0.2 mL/0.2 mL/0.1 mL) at 30° C. for 3 h. The reactions were purified by prep-HPLC (pH=2, acetonitrile/water+TFA) to give the desired products as the TFA salt.

Compound 145-1 (from Step 1, peak 1): LC-MS calculated for C$_{42}$H$_{51}$Cl$_2$N$_8$O$_5$ (M+H)$^+$: m/z=817.3; found: 817.4.

Compound 145-2 (from Step 1, peak 2): LC-MS calculated for C$_{42}$H$_{51}$Cl$_2$N$_8$O$_5$ (M+H)$^+$: m/z=817.3; found: 817.4.

Example 146 trans-4-(2-(2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

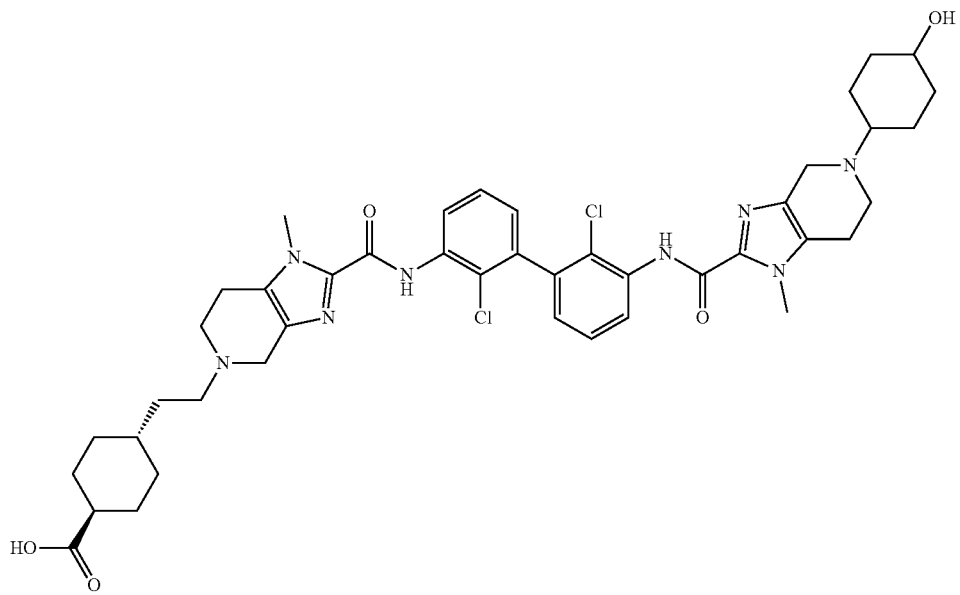

Step 1: Methyl 4-(2-(2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylate

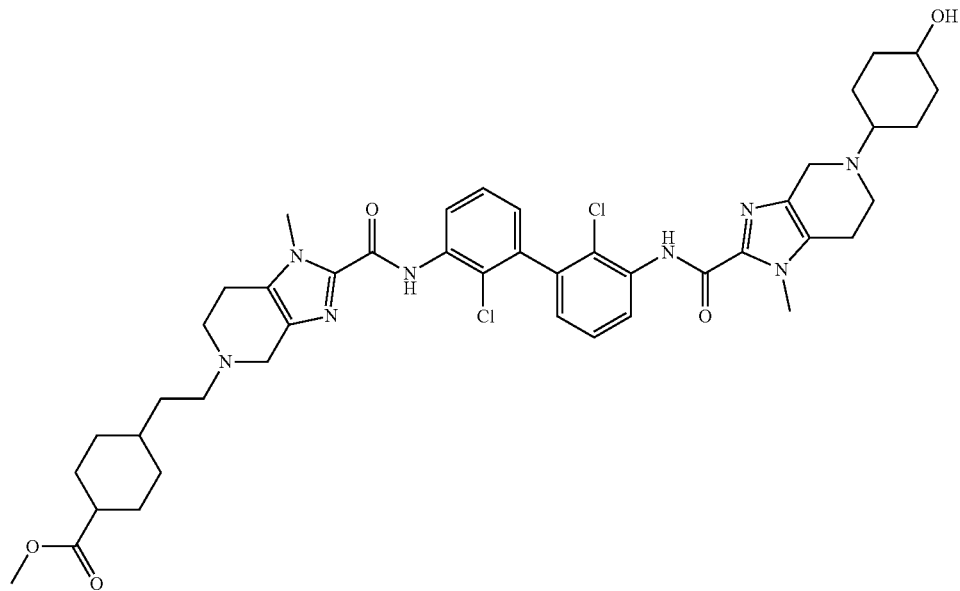

A solution of tert-butyl 2-((2,2'-dichloro-3'-(5-(2-(4-(methoxycarbonyl)cyclohexyl)ethyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 85, Step 1: 20 mg, 0.024 mmol) in dichloromethane (0.1 mL) and trifluoroacetic acid (0.1 ml) was stirred at room temperature for 30 min. The mixture was concentrated under reduced pressure. The residue was dissolved in dichloromethane (0.24 mL) and sequentially treated with N,N-diisopropylethylamine (0.016 mL, 0.094 mmol), sodium triacetoxyborohydride (15.00 mg, 0.071 mmol), and 4-hydroxycyclohexan-1-one (5.4 mg, 0.047 mmol). After being stirred at room temperature for 2 h, the reaction mixture was diluted with MeOH, and purified by prep-HPLC (pH=10, acetonitrile/water+NH$_4$OH) to give two desired products (cis/trans isomers):

Peak 1: retention time on analytical LC-MS (pH=10, acetonitrile/water+NH$_4$OH) $t_r$=1.77 min, LCMS calculated for $C_{44}H_{55}Cl_2N_8O_5$ (M+H)$^+$: m/z=845.4; Found: 845.4;

Peak 2: retention time on analytical LC-MS (pH=10, acetonitrile/water+NH$_4$OH) $t_r$=1.79 min, LCMS calculated for $C_{44}H_{55}Cl_2N_8O_5$ (M+H)$^+$: m/z=845.4; Found: 845.4.

Step 2; trans-4-(2-(2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid Methyl 4-(2-(2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylate (Step 1: 5.0 mg, 6.0 µmol) from Step 1, peak 1 and peak 2 were respectively treated with lithium hydroxide, monohydrate (1.3 mg, 0.030 mmol) in THF/MeOH/water (0.2 mL/0.2 mL/0.1 mL) at 30° C. for 3 h. The reactions were purified by prep-HPLC (pH=2, acetonitrile/water+TFA) to give the desired products (major peak) as the TFA salt.

Compound 146-1 (from Step 1, peak 1): LC-MS calculated for $C_{43}H_{53}Cl_2N_8O_5$ (M+H)$^+$: m/z=831.4; found: 831.4.

Compound 146-2 (from Step 1, peak 2): LC-MS calculated for $C_{43}H_{53}Cl_2N_8O_5$ (M+H)$^+$: m/z=831.4; found: 831.4.

Example 147 trans-4-((2-((2'-chloro-2-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

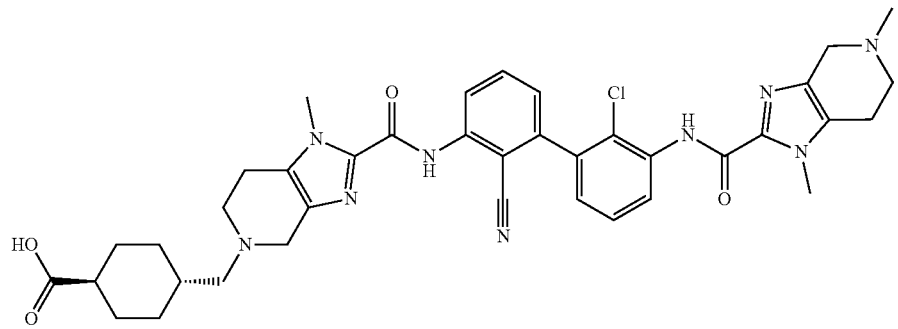 [SMILES: CN1CCc2c(nc(C(=O)Nc3cccc(-c4cccc(NC(=O)c5nc6c(n5C)CCN(C[C@H]5CC[C@H](C(=O)O)CC5)C6)c4C#N)c3Cl)n2C)C1]

Step 1: tert-butyl 2-((2'-chloro-2-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate Step 2: tert-butyl 2-((2'-chloro-2-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

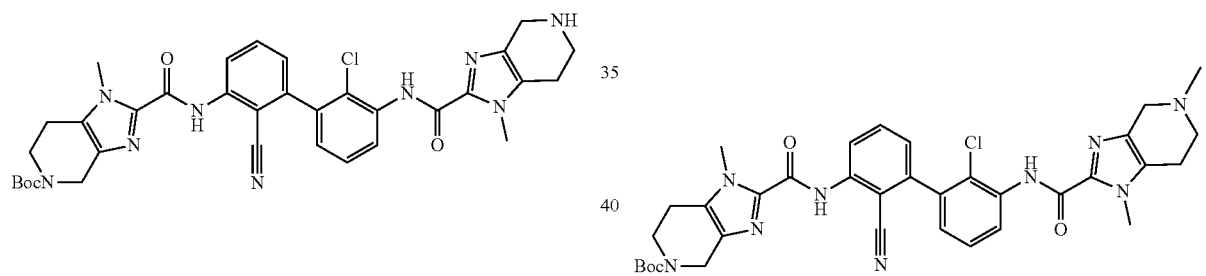

A mixture of tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Example 54, Step 3: 1078 mg, 2.085 mmol) in trifluoroacetic acid (2.0 mL) and dichloromethane (4.0 mL) was stirred at room temperature for 1 h. The reaction mixture was concentrated under reduced pressure. A mixture of the above residue, tert-butyl 2-((3-bromo-2-cyanophenyl)carbamoyl)-1-methyl-1,4,6,7-tetrahydro-5H-imidazo[4,5-c]pyridine-5-carboxylate (Example 13, Step 3: 800 mg, 1.738 mmol), sodium carbonate (921 mg, 8.69 mmol) and [1,1'-bis(di-cyclohexylphosphino)ferrocene]dichloropalladium (II) (132 mg, 0.174 mmol) in 1,4-dioxane (12.0 mL) and water (6.0 mL) was purged with nitrogen and then stirred at 110° C. for 3 h. After being cooled to room temperature, the reaction mixture was diluted with water and extracted with dichloromethane. The combined organic layers were dried over $Na_2SO_4$, filtered, and concentrated under reduced pressure. The residue was purified by flash chromatography on a silica gel column eluting with 10% methanol in dichloromethane to afford the desired product. LC-MS calculated for $C_{34}H_{37}ClN_9O_4$ $(M+H)^+$: m/z=670.3; found 670.4.

A solution of tert-butyl 2-((2'-chloro-2-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 100 mg, 0.149 mmol), 37 wt. % formaldehyde in water (55.5 µL, 0.745 mmol) and N,N-diisopropylethylamine (52.1 µL, 0.298 mmol) in dichloromethane (1.5 mL) was stirred at room temperature for 15 min. Sodium triacetoxyborohydride (95 mg, 0.448 mmol) was added in portions. After being stirred at room temperature for 1 h, the mixture was quenched with saturated aqueous $NaHCO_3$ solution, and extracted with dichloromethane. The combined organic layers were dried over $Na_2SO_4$, filtered and concentrated under reduced pressure. The residue was purified by flash chromatography on a silica gel column eluting with 10% methanol in dichloromethane to afford the desired product. LCMS calculated for $C_{35}H_{39}ClN_9O_4$ $(M+H)^+$: m/z=684.3; found 684.3.

Step 3: trans-4-((2-((2'-chloro-2-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid A solution of tert-butyl 2-((2'-chloro-2-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 2: 20 mg, 0.029 mmol) in dichloromethane (0.10 mL) and trifluoroacetic acid (0.05 mL) was stirred at room temperature for 30 min. The mixture was concentrated under reduced pressure. The residue was dissolved in dichloromethane (0.29 mL) and sequentially treated with N,N-diisopropylethylamine (0.020 mL, 0.117 mmol), sodium triacetoxyborohydride (12.2 mg, 0.058 mmol) and methyl trans-4-formylcyclohexanecarboxylate (9.9 mg, 0.058 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (6.1 mg, 0.146 mmol). After being stirred at 30° C. for 3 h, the reaction mixture was diluted with MeOH, and purified by prep-HPLC (pH=2, acetonitrile/water+TFA) to give the desired product as the TFA salt. LC-MS calculated for C$_{38}$H$_{43}$ClN$_9$O$_4$ (M+H)$^+$: m/z=724.3; found 724.4.

Example 148 trans-4-(2-(2-((2'-chloro-2-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

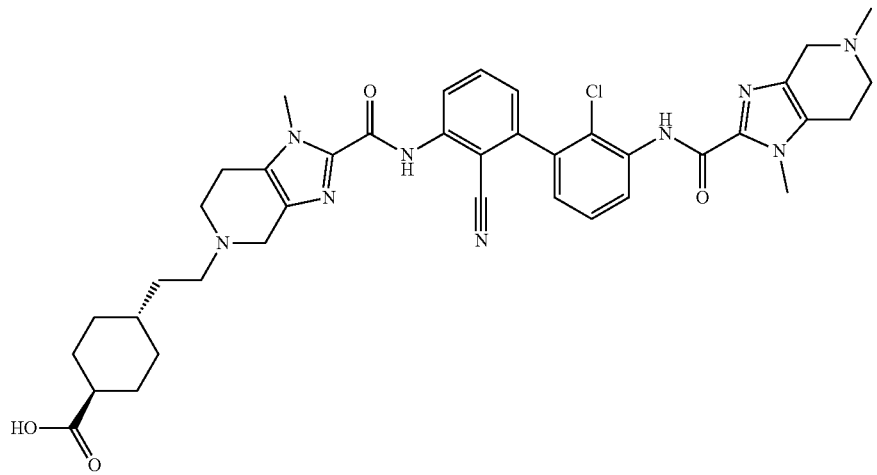 [SMILES: CN1CCc2c(nc(C(=O)Nc3cccc(-c4cccc(NC(=O)c5nc6c(n5C)CCN(CC[C@H]5CC[C@H](C(=O)O)CC5)C6)c4C#N)c3Cl)n2C)C1]

A solution of tert-butyl 2-((2'-chloro-2-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 147, Step 2: 20 mg, 0.029 mmol) in dichloromethane (0.10 mL) and trifluoroacetic acid (0.05 mL) was stirred at room temperature for 30 min. The mixture was concentrated under reduced pressure. The residue was dissolved in dichloromethane (0.29 mL) and sequentially treated with N,N-diisopropylethylamine (0.020 mL, 0.117 mmol), sodium triacetoxyborohydride (12.2 mg, 0.058 mmol) and methyl 4-(2-oxoethyl)cyclohexane-1-carboxylate (10.1 mg, 0.058 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (6.1 mg, 0.146 mmol). After being stirred at 30° C. for 3 h, the reaction mixture was diluted with MeOH, and purified by prep-HPLC (pH=2, acetonitrile/water+TFA) to give the desired product (major peak) as the TFA salt. LC-MS calculated for C$_{39}$H$_{45}$ClN$_9$O$_4$ (M+H)$^+$: m/z=738.3; found 738.4.

Example 149 trans-4-((2-((2-chloro-2'-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

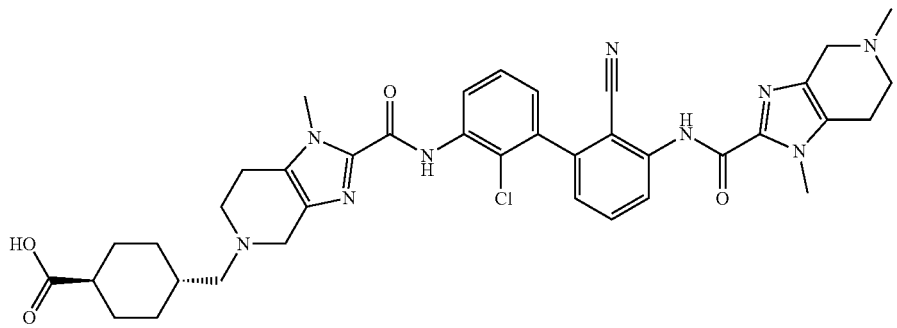 [SMILES: CN1CCc2c(nc(C(=O)Nc3cccc(-c4cccc(NC(=O)c5nc6c(n5C)CCN(C[C@H]5CC[C@H](C(=O)O)CC5)C6)c4Cl)c3C#N)n2C)C1]

Step 1: trans-4-((2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

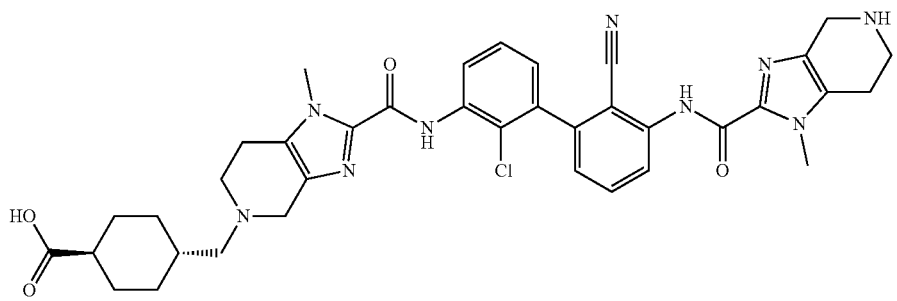 [SMILES: Cn1c(C(=O)Nc2cccc(-c3cccc(NC(=O)c4nc5c(n4C)CCNC5)c3C#N)c2Cl)nc2c1CCN(C[C@H]1CC[C@H](C(=O)O)CC1)C2]

A solution of tert-butyl 2-((2'-chloro-2-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 147, Step 1: 75 mg, 0.112 mmol), methyl trans-4-formylcyclohexane-1-carboxylate (57.1 mg, 0.336 mmol), and acetic acid (0.019 mL, 0.336 mmol) in dichloromethane (1 mL) was stirred at room temperature for 30 min. Sodium triacetoxyborohydride (83 mg, 0.392 mmol) was added. After being stirred at room temperature for 3 h, the mixture was quenched with saturated aqueous NaHCO$_3$ solution, and extracted with dichloromethane. The combined organic layers were dried over Na$_2$SO$_4$, filtered and concentrated under reduced pressure. The residue was treated with dichloromethane (1.0 mL) and TFA (1.0 mL) at room temperature for 30 min. The reaction mixture was concentrated under reduced pressure. The residue was treated with KOH (100 mg, 1.78 mmol) in THF/MeOH/water (1 mL/1 mL/0.5 mL) at room temperature for 2 h. The reaction was purified by prep-HPLC (pH=2, acetonitrile/water+TFA) to give the desired product as the TFA salt. LCMS calculated for C$_{37}$H$_{41}$ClN$_9$O$_4$ (M+H)$^+$: m/z=710.3; found 710.2.

Step 2: trans-4-((2-((2-chloro-2'-cyano-3'-(1,5-dimethyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid To a solution of trans-4-((2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid (Step 1: 6.0 mg, 5.14 µmol) was added 37 wt % formaldehyde in water (10.0 µL, 0.134 mmol). After being stirred at room temperature for 30 min, sodium triacetoxyborohydride (5.5 mg, 0.026 mmol) was added. After being further stirred at room temperature for 2 h, the reaction was purified by prep-HPLC (pH=2, acetonitrile/water+TFA) to give the desired product as the TFA salt. LCMS calculated for C$_{38}$H$_{43}$ClN$_9$O$_4$ (M+H)$^+$: m/z=724.3; found 724.2.

Example 150 trans-4-(2-(2-(2-chloro-2'-cyano-3'-(1,5-dimethyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)ethyl)cyclohexane-1-carboxylic acid

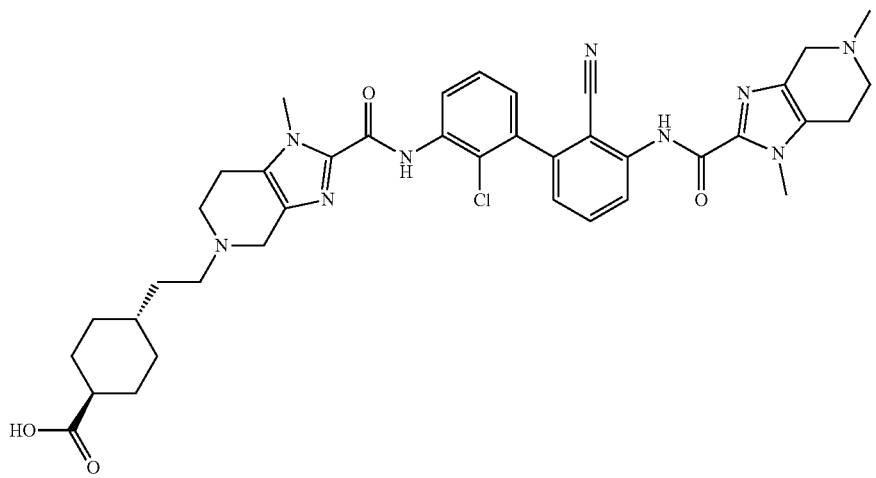 [SMILES: CN1CCc2c(nc(C(=O)Nc3cccc(-c4cccc(NC(=O)c5nc6c(n5C)CCN(CC[C@H]5CC[C@H](C(=O)O)CC5)C6)c4Cl)c3C#N)n2C)C1]

Step 1: trans-4-(2-(2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

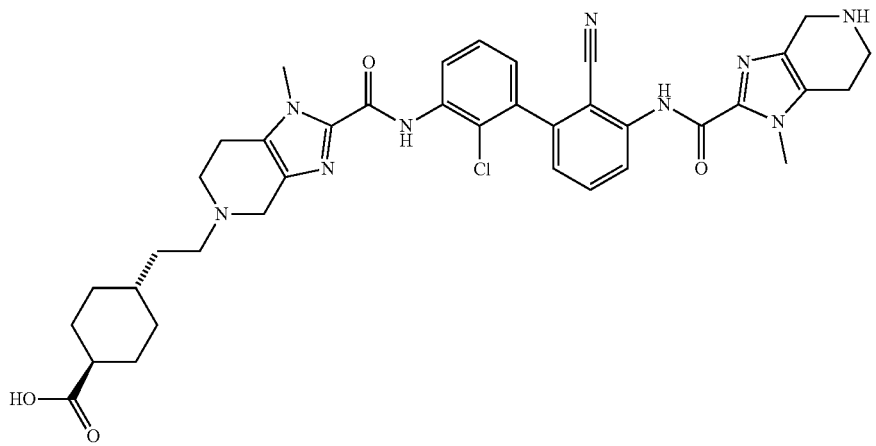 [SMILES: Cn1c(C(=O)Nc2cccc(-c3cccc(NC(=O)c4nc5c(n4C)CCNC5)c3C#N)c2Cl)nc2c1CCN(CC[C@H]1CC[C@H](C(=O)O)CC1)C2]

To a solution of tert-butyl 2-((2'-chloro-2-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 147, Step 1: 95 mg, 0.142 mmol) in dichloromethane (2 ml) was sequentially added methyl 4-(2-oxoethyl)cyclohexane-1-carboxylate (39.2 mg, 0.213 mmol), acetic acid (0.012 mL, 0.213 mmol) and sodium triacetoxyborohydride (75 mg, 0.354 mmol). After being stirred at room temperature for 2 h, the reaction mixture was quenched with saturated aqueous NaHCO₃ solution, and extracted with dichloromethane. The combined organic layers were dried over $Na_2SO_4$, filtered and concentrated under reduced pressure. The residue was treated with dichloromethane (2 mL) and TEA (2.0 mL) at room temperature for 30 min. The reaction mixture was concentrated under reduced pressure. The residue was treated with KOH (199 mg, 3.56 mmol) in THF/MeOH/water (2 mL/2 mL/1 mL) at room temperature for 4 h. The reaction was purified by prep-HPLC (pH=2, acetonitrile/water+TFA) to give the desired product (major peak) as the TFA salt. LCMS calculated for $C_{38}H_{43}ClN_9O_4$ $(M+H)^+$: m/z=724.3; found 724.2.

Step 2; trans-4-(2-(2-(2-chloro-2'-cyano-3'-(1,5-dimethyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)ethyl)cyclohexane-1-carboxylic acid To a solution of trans-4-(2-(2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid (6.0 mg, 5.08 μmol) in DMF (0.3 mL) was added 37 wt % formaldehyde in water (10.0 μL, 0.134 mmol). After being stirred at room temperature for 30 min, sodium triacetoxyborohydride (10 mg, 0.047 mmol) was added. After being further stirred at room temperature for 2 h, the reaction was purified by prep-HPLC (pH=2, acetonitrile/water+TFA) to give the desired product as the TFA salt. LCMS calculated for $C_{39}H_{45}ClN_9O_4$ (M+H)$^+$: m/z=738.3; found 738.2

TABLE 22

The compounds in Table 22 were prepared in accordance with the synthetic protocols set forth in Example 150 using the appropriate starting materials.

| Example # | Name | Structure | LC-MS (M + H)$^+$ |
|---|---|---|---|
| 151 | trans-4-(2-(2-((2-chloro-2'-cyano-3'-(5-ethyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 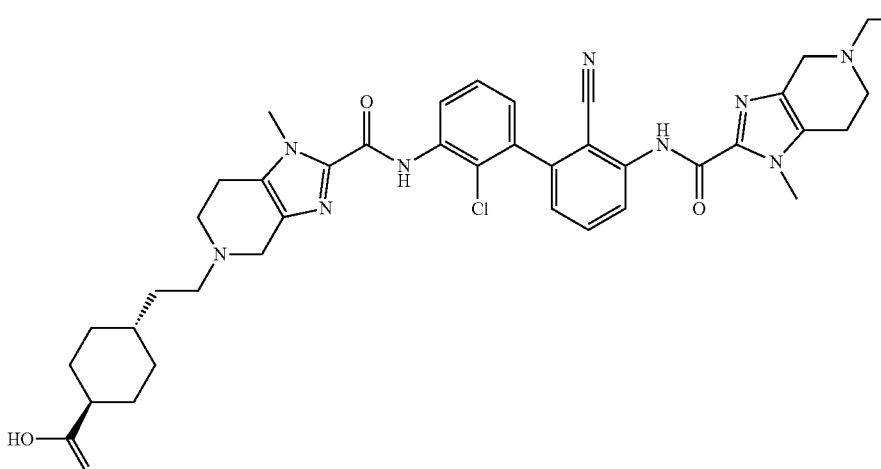 | 752.3 |
| 152 | trans-4-(2-(2-((2-chloro-2'-cyano-3'-(5-isopropyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 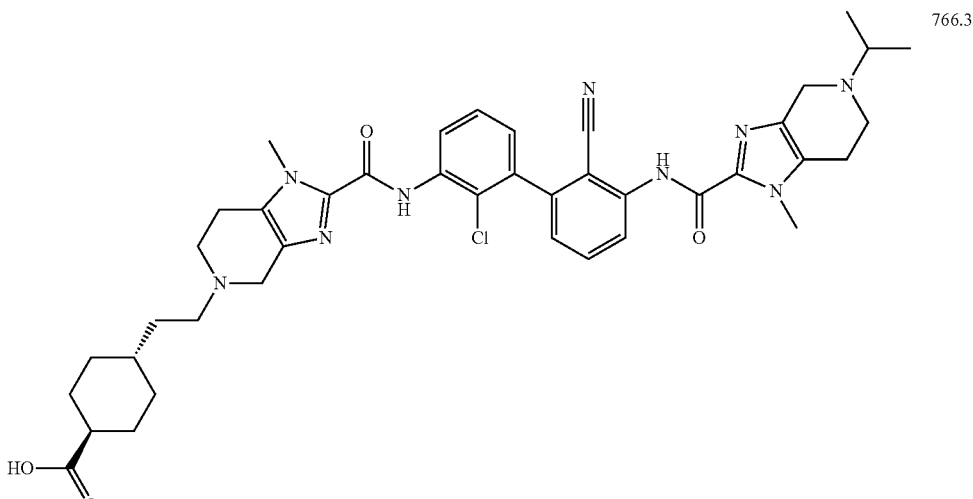 | 766.3 |

TABLE 22-continued

The compounds in Table 22 were prepared in accordance with the synthetic protocols set forth in Example 150 using the appropriate starting materials.

| Example # | Name | Structure | LC-MS (M + H)+ |
|---|---|---|---|
| 153 | trans-4-(2-(2-((2-chloro-2'-cyano-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid | 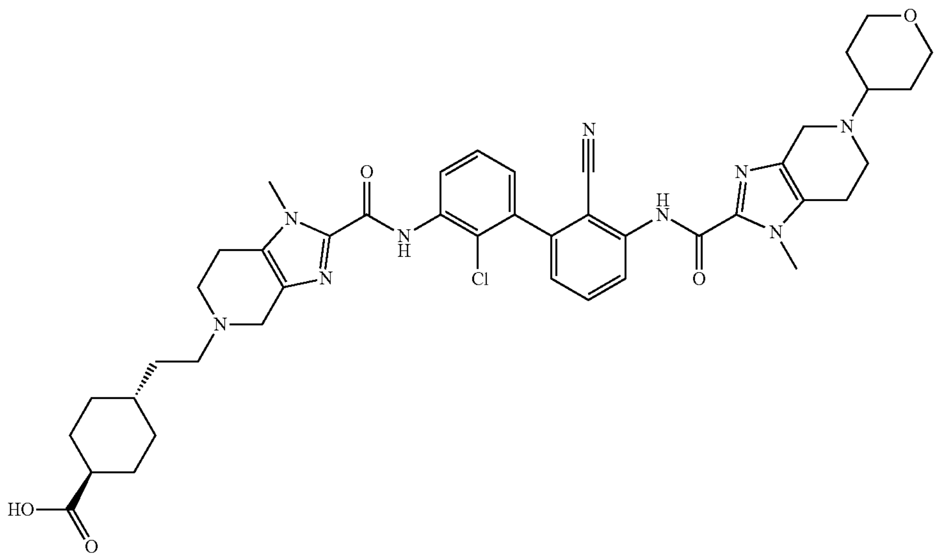 [SMILES: Cn1c(C(=O)Nc2cccc(-c3cccc(NC(=O)c4nc5c(n4C)CCN(C4CCOCC4)C5)c3C#N)c2Cl)nc2c1CCN(CC[C@H]1CC[C@H](C(=O)O)CC1)C2] | 808.3 |

Example 154 trans-4-(2-(2-((2'-chloro-2-cyano-3'-(5-ethyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

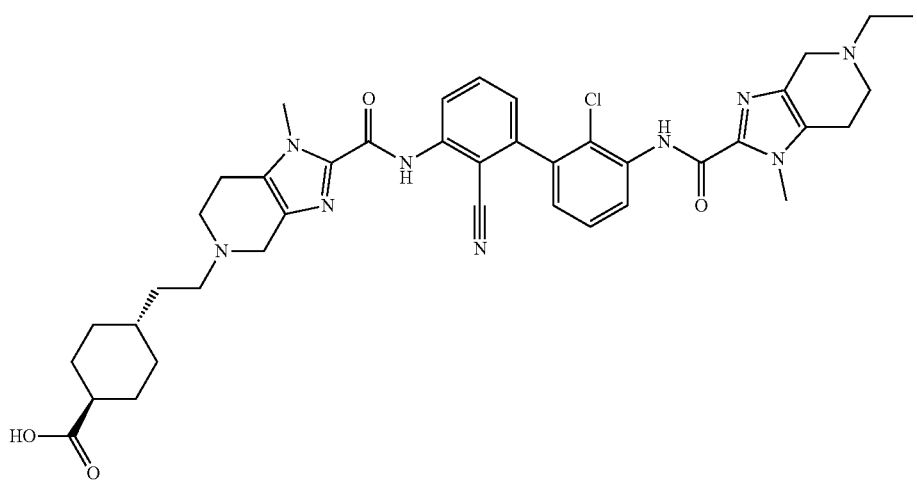 [SMILES: CCN1CCc2c(nc(C(=O)Nc3cccc(-c4cccc(NC(=O)c5nc6c(n5C)CCN(CC[C@H]5CC[C@H](C(=O)O)CC5)C6)c4C#N)c3Cl)n2C)C1]

Step 1: N-(3-bromo-2-cyanophenyl)-1-methyl-4,5,6,7-tetrahydro-1H-imidazo[4,5-c]pyridine-2-carboxamide

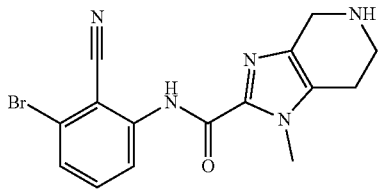 [SMILES: Cn1c(C(=O)Nc2cccc(Br)c2C#N)nc2c1CCNC2]

A solution of tert-butyl 2-((3-bromo-2-cyanophenyl)carbamoyl)-1-methyl-1,4,6,7-tetrahydro-5H-imidazo[4,5-c]pyridine-5-carboxylate (Example 13, Step 3: 0.50 g, 1.086 mmol) in dichloromethane (5.0 mL) and TEA (5.0 mL) was stirred at room temperature for 1 h. The mixture was concentrated under reduced pressure to give the desired product. LCMS calculated for $C_{15}H_{15}BrN_5O$ (M+H)$^+$: m/z=360.0; found 360.0.

Step 2: tert-butyl 2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate

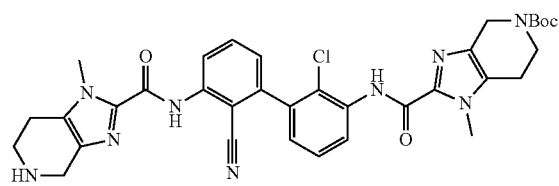 [SMILES: Cn1c(C(=O)Nc2cccc(-c3cccc(NC(=O)c4nc5c(n4C)CCNC5)c3C#N)c2Cl)nc2c1CCN(C(=O)OC(C)(C)C)C2]

A mixture of tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Example 54, Step 3: 232 mg, 0.450 mmol), N-(3-bromo-2-cyanophenyl)-1-methyl-4,5,6,7-tetrahydro-1H-imidazo[4,5-c]pyridine-2-carboxamide (Step 1: 135 mg, 0.375 mmol), [1,1-bis(di-cyclohexylphosphino)ferrocene]dichloropalladium(II) (28.4 mg, 0.037 mmol), and sodium carbonate (82.4 mg, 2.061 mmol) in 1,4-dioxane (3 mL) and water (1.0 mL) was purged with nitrogen and then stirred at 120° C. for 3 h. After being cooled to room temperature, the reaction mixture was diluted with water and extracted with dichloromethane. The combined organic layers were dried over $Na_2SO_4$, filtered, and concentrated under reduced pressure. The residue was purified by flash chromatography on a silica gel column eluting with 10% methanol in dichloromethane to afford the desired product. LCMS calculated for $C_{34}H_{37}ClN_9O_4$ (M+H)$^+$: m/z=670.3; found 670.2.

Step 3: trans-4-(2-(2-((2'-chloro-2-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

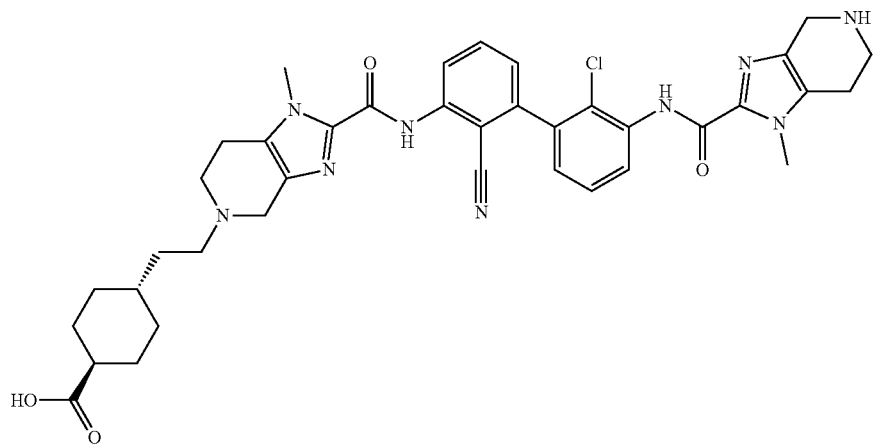 [SMILES: Cn1c(C(=O)Nc2cccc(-c3cccc(NC(=O)c4nc5c(n4C)CCN(CC[C@H]4CC[C@H](C(=O)O)CC4)C5)c3C#N)c2Cl)nc2c1CCNC2]

To a solution of tert-butyl 2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 2: 78 mg, 0.116 mmol) in dichloromethane (2 mL) was sequentially added methyl trans-4-(2-oxoethyl)cyclohexane-1-carboxylate (32.2 mg, 0.175 mmol), acetic acid (9.99 µL, 0.175 mmol) and sodium triacetoxyborohydride (61.7 mg, 0.291 mmol). After being stirred at room temperature for 2 h, the reaction mixture was quenched with saturated aqueous $NaHCO_3$ solution, and extracted with dichloromethane. The combined organic layers were dried over $Na_2SO_4$, filtered and concentrated under reduced pressure. The residue was treated with dichloromethane (2 mL) and TFA (2.0 mL) at room temperature for 30 min. The reaction mixture was concentrated under reduced pressure. The residue was treated with KOH (199 mg, 3.56 mmol) in THF/MeOH/water (2 mL/2 mL/1 mL) at room temperature for 4 h. The reaction was purified by prep-HPLC (pH=2, acetonitrile/water+TFA) to give the desired product (major peak) as the TFA salt. LCMS calculated for $C_{38}H_{43}ClN_9O_4$ (M+H)$^+$: m/z=724.3; found 724.2.

Step 4: trans-4-(2-(2-((2'-chloro-2-cyano-3'-(5-ethyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid To a solution of trans-4-(2-(2-((2'-chloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid (Step 3: 6.6 mg, 5.59 µmol) in DMF (0.3 mL) was added 1.3 M solution of acetaldehyde in DCE (60 µL, 0.078 mmol) followed by sodium triacetoxyborohydride (12.5 mg, 0.059 mmol). After being stirred at room temperature for 2 h, the reaction was purified by prep-HPLC (pH=2, acetonitrile/water+TFA) to give the desired product as the TFA salt. LCMS calculated for $C_{40}H_{47}ClN_9O_4$ (M+H)$^+$: m/z=752.3; found 752.2.

Example 155 trans-4-(2-(2-((2'-chloro-2-cyano-3'-(5-isopropyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid

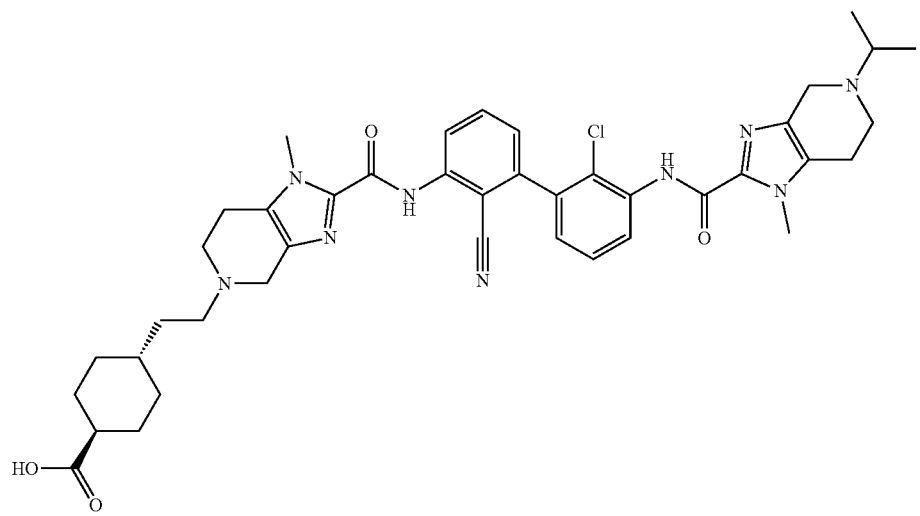 [SMILES: CC(C)N1CCc2c(nc(C(=O)Nc3cccc(-c4cccc(NC(=O)c5nc6c(n5C)CCN(CC[C@H]5CC[C@H](C(=O)O)CC5)C6)c4C#N)c3Cl)n2C)C1]

This compound was prepared using a similar procedure as described for Example 154 with acetone replacing acetaldehyde in Step 4. The reaction mixture was purified by prep-HPLC (pH=2, acetonitrile/water+TFA) to give the desired product as the TFA salt. LCMS calculated for $C_{41}H_{49}ClN_9O_4$ (M+H)$^+$: m/z=766.4; found 766.3

Example 156 trans-4-((2-((2'-chloro-2-cyano-3'-(5-ethyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

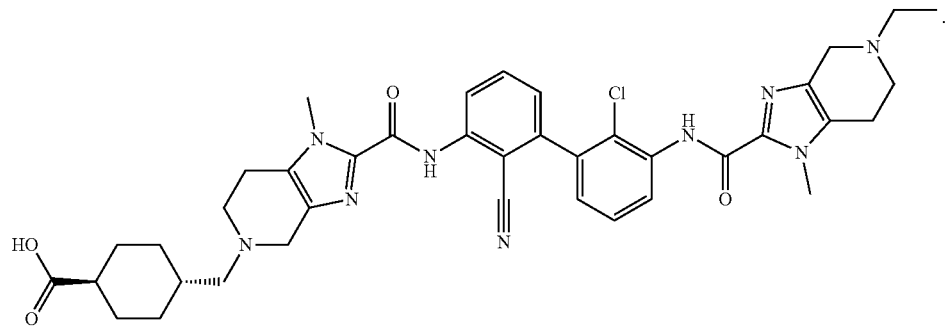 [SMILES: CCN1CCc2c(nc(C(=O)Nc3cccc(-c4cccc(NC(=O)c5nc6c(n5C)CCN(C[C@H]5CC[C@H](C(=O)O)CC5)C6)c4C#N)c3Cl)n2C)C1]

Step 1: tram-4-((2-((2'-chloro-2-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

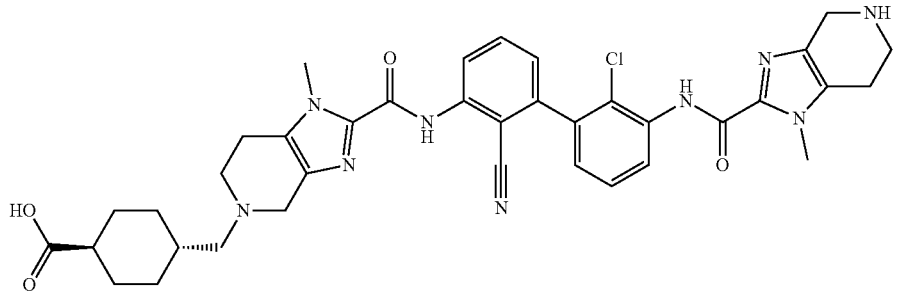 [SMILES: Cn1c(C(=O)Nc2cccc(-c3cccc(NC(=O)c4nc5c(n4C)CCN(C[C@H]4CC[C@H](C(=O)O)CC4)C5)c3C#N)c2Cl)nc2c1CCNC2]

To a solution of tert-butyl 2-((2-chloro-2'-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 154, Step 2: 40 mg, 0.060 mmol) in dichloromethane (1 mL) was sequentially added methyl trans-4-formyl-cyclohexane-1-carboxylate (16 mg, 0.094 mmol), acetic acid (5.1 µL, 0.090 mmol) and sodium triacetoxyborohydride (31.6 mg, 0.149 mmol). After being stirred at room temperature for 2 h, the reaction mixture was quenched with saturated aqueous NaHCO₃ solution, and extracted with dichloromethane. The combined organic layers were dried over Na₂SO₄, filtered and concentrated under reduced pressure. The residue was treated with dichloromethane (2.0 mL) and TEA (2.0 mL) at room temperature for 30 min. The reaction mixture was concentrated under reduced pressure. The residue was treated with KOH (99 mg, 1.78 mmol) in THF/MeOH/water (1 mL/1 mL/1 mL) at room temperature for 1 h. The reaction was purified by prep-HPLC (pH=2, acetonitrile/water+TFA) to give the desired product as the TFA salt. LCMS calculated for $C_{37}H_{41}ClN_9O_4$ (M+H)⁺: m/z=710.3; found 710.2.

Step 2: trans-4-((2-((2'-chloro-2-cyano-3'-(5-ethyl-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid To a solution of trans-4-((2-((2'-chloro-2-cyano-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid (Step 1: 6.0 mg, 5.14 µmol) in DMF (0.3 mL) was added a 1.3 M solution of acetaldehyde in DCE (80 µL, 0.104 mmol) followed by sodium triacetoxyborohydride (12.5 mg, 0.059 mmol). After being stirred at room temperature for 4 h, the reaction was purified by prep-HPLC (pH=2, acetonitrile/water+TFA) to give the desired product as the TFA salt. LCMS calculated for $C_{39}H_{45}ClN_9O_4$ (M+H)⁺: m/z=738.3; found 738.2.

Example 157 trans-4-((2-((2'-chloro-2-cyano-3'-(1-methyl-5-(tetrahydro-2H-pyran-4-yl)-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

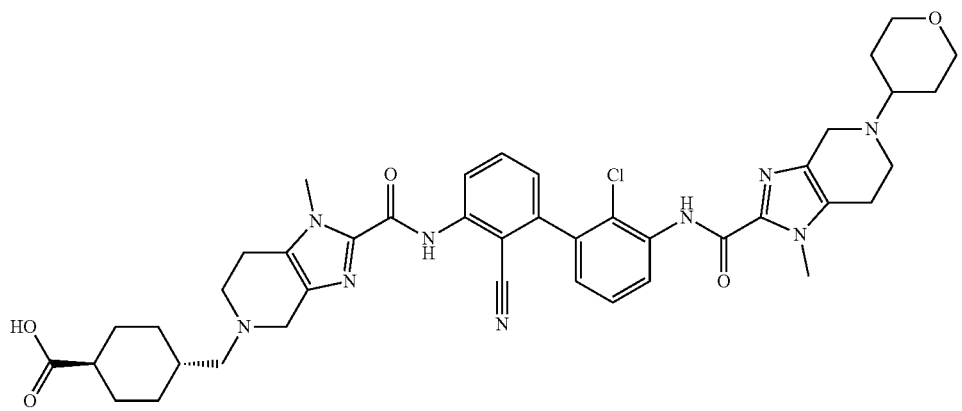 [SMILES: Cn1c(C(=O)Nc2cccc(-c3cccc(NC(=O)c4nc5c(n4C)CCN(C[C@H]4CC[C@H](C(=O)O)CC4)C5)c3C#N)c2Cl)nc2c1CCN(C1CCOCC1)C2]

This compound was prepared using a similar procedure as described for Example 156 with tetrahydro-4H-pyran-4-one replacing acetaldehyde in Step 2. The reaction mixture was purified by prep-HPLC (pH=2, acetonitrile/water+TFA) to give the desired product as the TFA salt. LCMS calculated for $C_{42}H_{49}ClN_9O_5$ (M+H)⁺: m/z=794.4; found 794.3.

Example 158 trans-4-((2-(2-chloro-3'-(5-(2-(isopropyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid

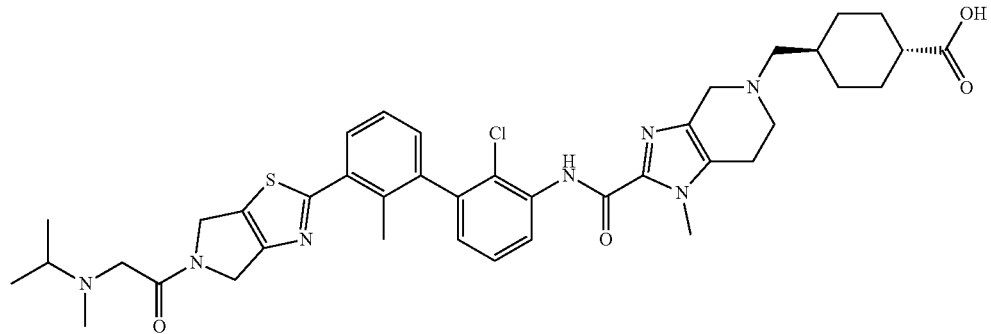 [SMILES: Cc1c(-c2nc3c(s2)CN(C(=O)CN(C)C(C)C)C3)cccc1-c1cccc(NC(=O)c2nc3c(n2C)CCN(C[C@H]2CC[C@H](C(=O)O)CC2)C3)c1Cl]

Step 1: tert-butyl 2-bromo-4H-pyrrolo[3,4-d]thiazole-5(6H)-carboxylate

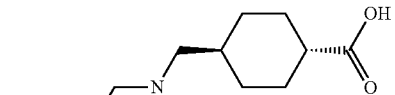

To a stirred solution of 2-bromo-5,6-dihydro-4H-pyrrolo[3,4-d]thiazole, HBr salt (Aurum Pharm, cat # MR22320: 220.0 mg, 0.769 mmol) and N,N-diisopropylethylamine (0.269 mL, 1.539 mmol) in dichloromethane (5.0 mL) was added Boc-anhydride (201 mg, 0.923 mmol) at room temperature. After 1 hour, the reaction mixture was diluted with EtOAc (100 mL), and washed with water (3×15 mL). The organic layer was dried over $Na_2SO_4$, filtered and the filtrate was concentrated to afford crude product (220 mg, 0.724 mmol, 93.6% yield), which was used directly in the next step without further purification. LC-MS calculated for $C_{10}H_{14}BrN_2O_2S$ (M+H)$^+$: m/z=305.0/307.0; found 305.0/307.0.

Step 2: tert-butyl 2-(3-chloro-2-methylphenyl)-4H-pyrrolo[3,4-d]thiazole-5(6H)-carboxylate

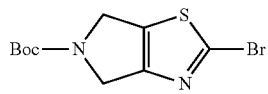

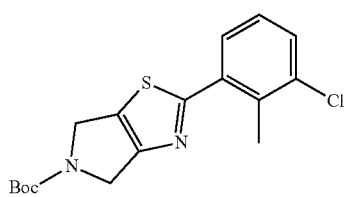 [SMILES: Cc1c(Cl)cccc1-c1nc2c(s1)CN(C(=O)OC(C)(C)C)C2]

A mixture of (3-chloro-2-methylphenyl)boronic acid (335 mg, 1.966 mmol), tert-butyl 2-bromo-4,6-dihydro-5H-pyrrolo[3,4-d]thiazole-5-carboxylate (Step 1: 600 mg, 1.966 mmol), tetrakis(triphenylphosphine)palladium(0) (114 mg, 0.098 mmol) and sodium carbonate (521 mg, 4.91 mmol) in 1,4-dioxane (8 mL) and water (2 mL) was purged with nitrogen and sealed. It was stirred at 100° C. overnight. After being cooled to room temperature, the reaction mixture was diluted with EtOAc (100 mL), and washed with water. The organic layer was dried over $Na_2SO_4$, filtered and the filtrate was concentrated. The residue was purified by chromatography on silica gel, eluting with 0-40% EtOAc/hexanes, to give the desired product. LC-MS calculated for $C_{17}H_{20}ClN_2O_2S$ (M+H)$^+$: m/z=351.1; found 351.1.

Step 3: 2-chloro-1-(2-(3-chloro-2-methylphenyl)-4H-pyrrolo[3,4-d]thiazol-5(6H)-yl)ethanone

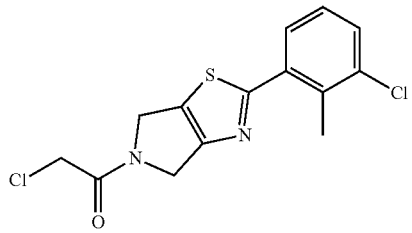 [SMILES: Cc1c(Cl)cccc1-c1nc2c(s1)CN(C(=O)CCl)C2]

To a stirred solution of tert-butyl 2-(3-chloro-2-methylphenyl)-4,6-dihydro-5H-pyrrolo[3,4-d]thiazole-5-carboxylate (Step 2: 408 mg, 1.163 mmol) in dichloromethane (2 mL) at room temperature was added TFA (2 mL). After 1 h, the volatiles were removed and the residue was dissolved in dichloromethane (3 mL). N,N-diisopropylethylamine (0.406 mL, 2.326 mmol) and 2-chloroacetyl chloride (0.102 mL, 1.279 mmol) were then added sequentially at room temperature. After another 1 h, the reaction mixture was quenched with saturated aq. $NaHCO_3$ solution, and extracted with dichloromethane (3×50 mL). The organic layers were combined, dried over $Na_2SO_4$, filtered and the filtrate was concentrated under reduced pressure. The residue was purified by chromatography on silica gel, eluting with 0-30% EtOAc/hexanes, to give the desired product (362 mg). LC-MS calculated for $C_{14}H_{13}Cl_2N_2OS$ (M+H)$^+$: m/z=327.0; found 327.0.

Step 4: 1-(2-(3-chloro-2-methylphenyl)-4H-pyrrolo[3,4-d]thiazol-5(6H)-yl)-2-(isopropyl(methyl)amino)ethanone

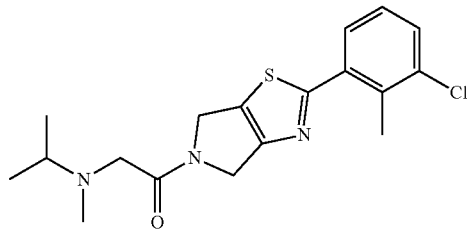 [SMILES: Cc1c(Cl)cccc1-c1nc2c(s1)CN(C(=O)CN(C)C(C)C)C2]

To a stirred solution of 2-chloro-1-(2-(3-chloro-2-methylphenyl)-4,6-dihydro-5H-pyrrolo[3,4-d]thiazol-5-yl)ethan-1-one (Step 3: 200 mg, 0.611 mmol) in acetonitrile (3.0 mL), N-methylpropan-2-amine (44.7 mg, 0.611 mmol) and N,N-diisopropylethylamine (107 µL, 0.611 mmol) were added at room temperature. The resulted mixture was heated at 60° C. After 2 h, the reaction mixture was quenched with saturated aq. NaHCO$_3$, extracted with dichloromethane (3×50 mL). The organic layers were combined, dried over Na$_2$SO$_4$, filtered and the filtrate was concentrated under reduced pressure. The residue was purified by chromatography on silica gel, eluting with 0-5% MeOH/DCM, to give the desired product (203 mg). LC-MS calculated for C$_{18}$H$_{23}$ClN$_3$OS (M+H)$^+$: m/z=364.1; found 364.1.

Step 5: 2-(isopropyl(methyl)amino)-1-(2-(2-methyl-3-(4,4,5,5-tetramethyl-1,3,2-dioxaborolan-2-yl)phenyl)-4H-pyrrolo[3,4-d]thiazol-5(6H)-yl)ethanone

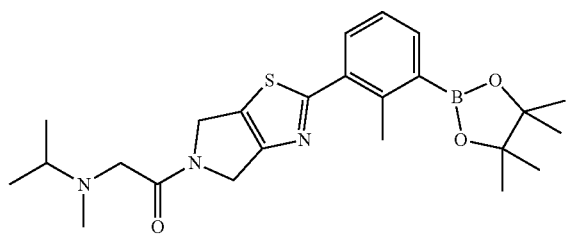 [SMILES: Cc1c(B2OC(C)(C)C(C)(C)O2)cccc1-c1nc2c(s1)CN(C(=O)CN(C)C(C)C)C2]

A mixture of 1-(2-(3-chloro-2-methylphenyl)-4,6-dihydro-5H-pyrrolo[3,4-d]thiazol-5-yl)-2-(isopropyl(methyl)amino)ethan-1-one (Step 4: 200.0 mg, 0.550 mmol), 4,4,4',4',5,5,5',5'-octamethyl-2,2'-bi(1,3,2-dioxaborolane) (209 mg, 0.824 mmol), tris(dibenzylideneacetone)dipalladium(0) (40.3 mg, 0.044 mmol), 2-dicyclohexylphosphino-2',4',6'-tri-iso-propyl-1,1'-biphenyl (41.9 mg, 0.088 mmol) and potassium acetate (108 mg, 1.099 mmol) in 1,4-dioxane (5.0 mL) was purged with nitrogen and stirred at 100° C. for 3 h. The reaction mixture was quenched with saturated aq. NH$_4$Cl solution, and extracted with dichloromethane (3×50 mL). The organic layers were combined, dried over Na$_2$SO$_4$, filtered and the filtrate was concentrated under reduced pressure. The residue was purified by chromatography on silica gel, eluting with 0-10% MeOH/DCM, to give the desired product. LC-MS calculated for C$_{24}$H$_{35}$BN$_3$O$_3$S (M+H)$^+$: m/z=456.2; found 456.3.

Step 6: tert-butyl 2-(2-chloro-3'-(5-(2-(isopropyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridine-5(4H)-carboxylate

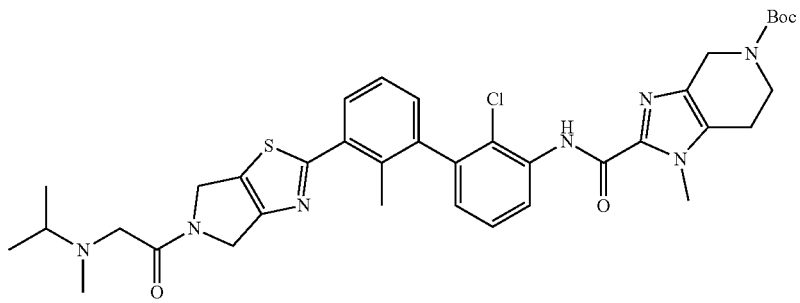 [SMILES: Cc1c(-c2nc3c(s2)CN(C(=O)CN(C)C(C)C)C3)cccc1-c1cccc(NC(=O)c2nc3c(n2C)CCN(C(=O)OC(C)(C)C)C3)c1Cl]

A degassed mixture of tert-butyl 2-((3-bromo-2-chlorophenyl)carbamoyl)-1-methyl-1,4,6,7-tetrahydro-5H-imidazo[4,5-c]pyridine-5-carboxylate (Example 24, Step 1: 50 mg, 0.106 mmol), 2-(isopropyl(methyl)amino)-1-(2-(2-methyl-3-(4,4,5,5-tetramethyl-1,3,2-dioxaborolan-2-yl)phenyl)-4,6-dihydro-5H-pyrrolo[3,4-d]thiazol-5-yl)ethan-1-one (Step 5: 50 mg, 0.110 mmol), sodium carbonate (22.56 mg, 0.213 mmol), and [1,1-bis(di-cyclohexylphosphino)ferrocene]dichloropalladium(II) (8.07 mg, 10.64 µmol) in t-BuOH (2 mL)/water (2 mL) was heated at 90° C. overnight. After being cooled to room temperature, the reaction mixture was diluted with EtOAc (50 mL), washed with water. The organic layer was dried over Na$_2$SO$_4$, filtered and the filtrate was concentrated. The residue was purified by chromatography on silica gel, eluting with 0-5% MeOH/DCM, to give the desired product. LC-MS calculated for C$_{37}$H$_{45}$ClN$_7$O$_4$S (M+H)$^+$: m/z=718.3; found 718.4.

Step 7: N-(2-chloro-3'-(5-(2-(isopropyl(methyl)amino)acetyl)-5,6-dihydro-4H-pyrrolo[3,4-d]thiazol-2-yl)-2'-methylbiphenyl-3-yl)-1-methyl-4,5,6,7-tetrahydro-1H-imidazo[4,5-c]pyridine-2-carboxamide

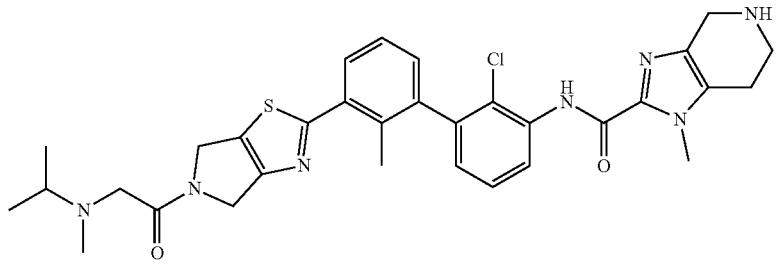 [SMILES: Cc1c(-c2nc3c(s2)CN(C(=O)CN(C)C(C)C)C3)cccc1-c1cccc(NC(=O)c2nc3c(n2C)CCNC3)c1Cl]

To a stirred solution of tert-butyl 2-(2-chloro-3'-(5-(2-(isopropyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridine-5(4H)-carboxylate (Step 6: 50 mg, 0.070 mmol) in dichloromethane (1 mL) was added TFA (1 mL) at room temperature. After 1 h, the volatiles were removed under reduced pressure to give the desired product, which was used directly in the next step without further purification. LC-MS calculated for $C_{32}H37ClN_7O_2S$ (M+H)$^+$: m/z=618.2; found 618.2.

Step 8: trans-4-((2-(2-chloro-3'-(5-(2-(isopropyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid The mixture of N-(2-chloro-3'-(5-(N-isopropyl-N-methylglycyl)-5,6-dihydro-4H-pyrrolo[3,4-d]thiazol-2-yl)-2'-methyl-[1,1'-biphenyl]-3-yl)-1-methyl-4,5,6,7-tetrahydro-1H-imidazo[4,5-c]pyridine-2-carboxamide (Step 7: 6 mg, 9.71 μmol), methyl trans-4-formylcyclohexane-1-carboxylate (2.478 mg, 0.015 mmol), and N,N-diisopropylethylamine (5.09 μL, 0.029 mmol) in N,N-dimethylformamide (1.0 mL) was stirred at room temperature. After 30 min, sodium cyanoborohydride (2.4 mg, 0.038 mmol) was added. After another 2 h, the reaction mixture was diluted with water and extracted with dichloromethane (3×10 mL). The combined organic layers were washed with brine, dried over $Na_2SO_4$, filtered and the filtrate was concentrated under reduced pressure. The residue was dissolved in THF (1.0 mL)/water (0.2 mL), followed by the addition of lithium hydroxide (0.697 mg, 0.029 mmol). The resulted mixture was heated at 60° C. for 2 h. The reaction was diluted with MeOH and purified on prep-HPLC (pH=2, acetonitrile/water+TFA) to give the desired product as its TFA salt. LC-MS calculated for $C_{40}H_{49}ClN_7O_4S$ (M+H)$^+$: m/z=758.3; found 758.2.

TABLE 23

The compounds in Table 23 were prepared in accordance with the synthetic protocols set forth in Example 158, using the appropriate starting materials.

| Example # | Name | Structure | LC-MS (M + H)$^+$ |
|---|---|---|---|
| 159 | trans-4-((2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c] | 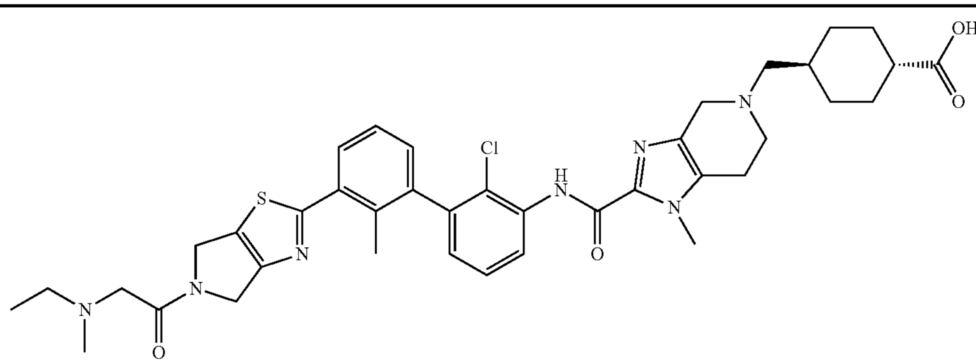 | 744.3 |

TABLE 23-continued

The compounds in Table 23 were prepared in accordance with the synthetic protocols set forth in Example 158, using the appropriate starting materials.

| Example # | Name | Structure | LC-MS (M + H)+ |
|---|---|---|---|
| | pyridin-5(4H)-yl)methyl)cyclohexane-1-carboxylic acid | | |
| 160 | cis-4-((2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid | 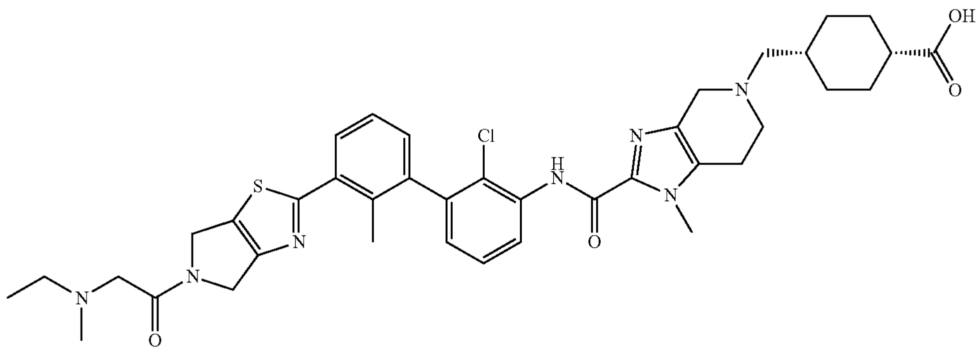 [SMILES: CCN(C)CC(=O)N1Cc2nc(-c3cccc(-c4cccc(NC(=O)c5nc6c(n5C)CCN(C[C@H]5CC[C@@H](C(=O)O)CC5)C6)c4Cl)c3C)sc2C1] | 744.3 |
| 161 | 4-(2-(2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)ethyl)cyclo- | 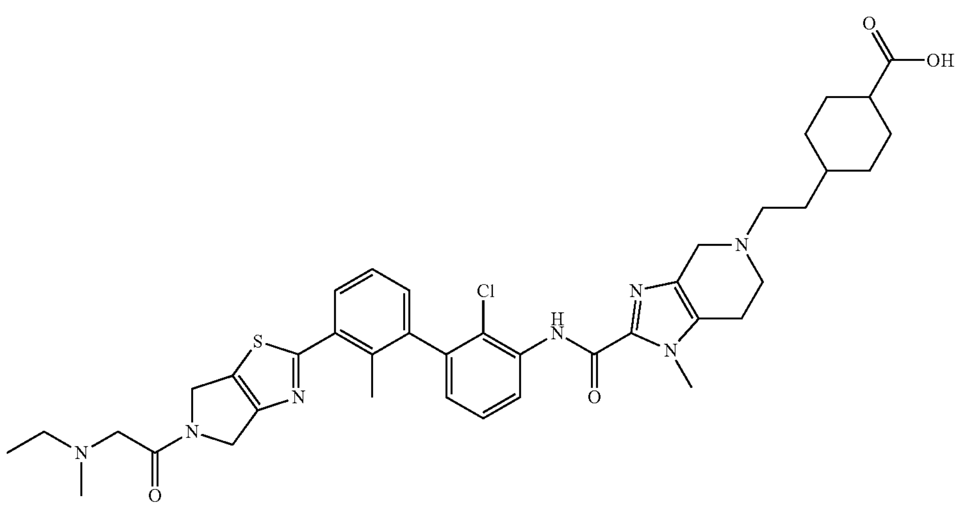 [SMILES: CCN(C)CC(=O)N1Cc2nc(-c3cccc(-c4cccc(NC(=O)c5nc6c(n5C)CCN(CCC5CCC(C(=O)O)CC5)C6)c4Cl)c3C)sc2C1] | 758.3 |

TABLE 23-continued

The compounds in Table 23 were prepared in accordance with the synthetic protocols set forth in Example 158, using the appropriate starting materials.

| Example # | Name | Structure | LC-MS (M + H)+ |
|---|---|---|---|
| | hexane-1-carboxylic acid | | |
| 162 | 4-(2-(2-(2-chloro-3'-(5-(2-(isopropyl(methyl)amino)acetyl)-5,6-dihydro-4H-pyrrolo[3,4-d]thiazol-2-yl)-2'-methyl-biphenyl-3-ylcarbamoyl)-1-methyl-6,7-dihydro-1H-imidazo[4,5-c]pyridin-5(4H)-yl)ethyl)cyclohexane-1-carboxylic acid | 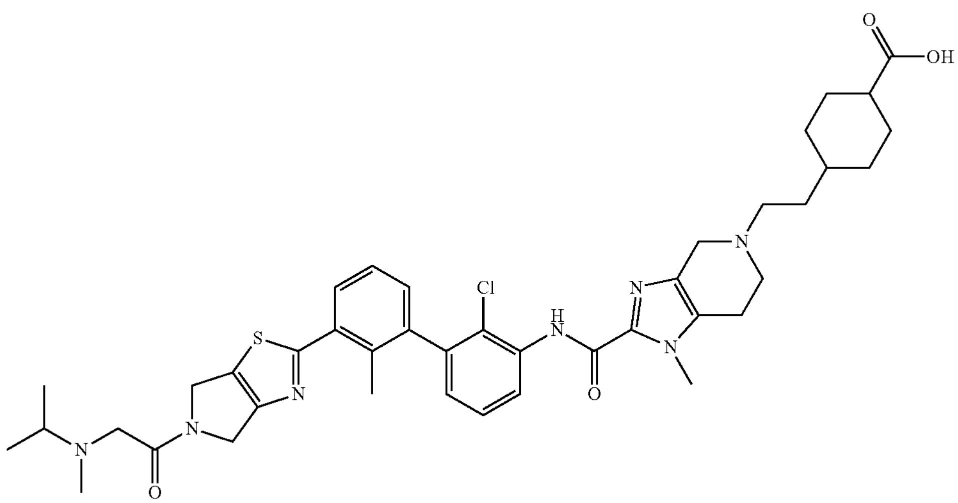 [SMILES: Cc1c(-c2nc3c(s2)CN(C(=O)CN(C)C(C)C)C3)cccc1-c1cccc(NC(=O)c2nc3c(n2C)CCN(CCC2CCC(C(=O)O)CC2)C3)c1Cl] | 772.3 |

Example 163

(S)-1-(2-(2-(2'-chloro-3'-(1,5-dimethyl-4,5,6,7-tetrahydro-1H-imidazo[4,5-c]pyridine-2-carboxamido)-2-methyl-[1,1'-biphenyl]-3-yl)-4,6-dihydro-5H-pyrrolo[3,4-d]oxazol-5-yl)-2-oxoethyl)-3-methylpyrrolidine-3-carboxylic acid

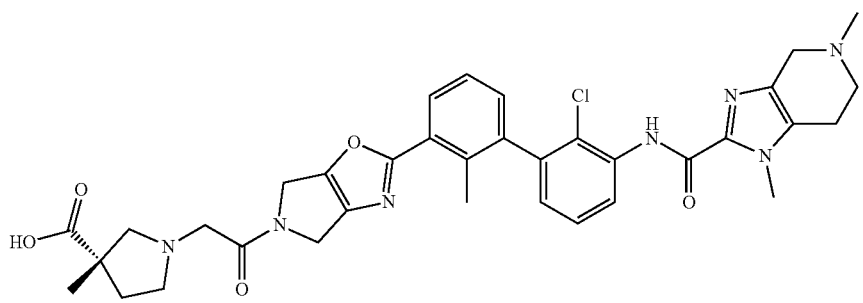 [SMILES: Cc1c(-c2nc3c(o2)CN(C(=O)CN2CC[C@](C)(C(=O)O)C2)C3)cccc1-c1cccc(NC(=O)c2nc3c(n2C)CCN(C)C3)c1Cl]

Step 1: Benzyl 6-oxa-3-azabicyclo[3.1.0]hexane-3-carboxylate

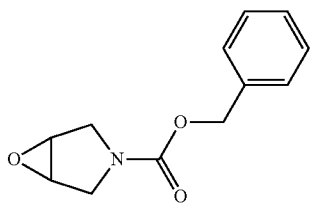 [SMILES: O=C(OCc1ccccc1)N1CC2OC2C1]

To a solution of benzyl 2,5-dihydro-1H-pyrrole-1-carboxylate (12.4 g, 61.0 mmol) in dichloromethane (200 mL) was added m-CPBA (16.20 g, 61.0 mmol). The resulting mixture was stirred at room temperature for 3 h. The reaction was quenched with saturated NaHCO$_3$ solution, the organic layer was separated and the aqueous layer was extracted with dichloromethane once. The combined organic layers were dried over Na$_2$SO$_4$, filtered and concentrated. The crude was purified with flash chromatography (eluting with 0-50% ethyl acetate in hexanes) to give the desired product as clear oil (13 g, 97%). LC-MS calculated for C$_{12}$H$_{14}$NO$_3$ (M+H)$^+$: m/z=220.1; found 220.1.

Step 2: Benzyl 3-amino-4-hydroxypyrrolidine-1-carboxylate

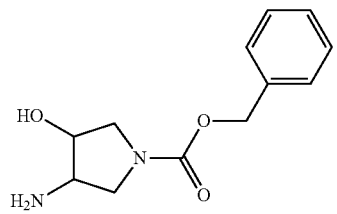 [SMILES: NC1CN(C(=O)OCc2ccccc2)CC1O]

To a flask was charged with benzyl 6-oxa-3-azabicyclo[3.1.0]hexane-3-carboxylate (Step 1: 13.0 g, 59.3 mmol) and ammonium hydroxide (115 mL, 2.96 mol). The reaction mixture was heated at 90° C. overnight. The solvent was removed. The residue was used in the next step without purification. LC-MS calculated for C$_{12}$H$_{17}$N$_2$O$_3$ (M+H)$^+$: m/z=237.1; found 237.1.

Step 3; Benzyl 3-(3-bromo-2-methylbenzamido)-4-hydroxypyrrolidine-1-carboxylate

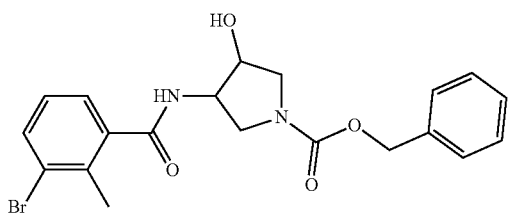 [SMILES: Cc1c(Br)cccc1C(=O)NC1CN(C(=O)OCc2ccccc2)CC1O]

To a solution of 3-bromo-2-methylbenzoic acid (9.70 g, 45.1 mmol) in N,N-dimethylformamide (226 mL) was added N,N,N',N'-tetramethyl-O-(7-azabenzotriazol-1-yl)uronium hexafluorophosphate (18.87 g, 49.6 mmol). After stirring for 5 min, benzyl 3-amino-4-hydroxypyrrolidine-1-carboxylate (Step 2: 10.66 g, 45.1 mmol) and N,N-diisopropylethylamine (23.57 mL, 135 mmol) was added. The reaction mixture was stirred at room temperature for 2 h. The reaction was diluted with water, and the aqueous layer was extracted with dichloromethane once. The combined organic layers were dried over Na$_2$SO$_4$, filtered and concentrated. The residue was purified with flash chromatography (eluting with 0-60% ethyl acetate in hexanes) to give the desired product (11.5 g, 59%). LC-MS calculated for C$_{20}$H$_{22}$BrN$_2$O$_4$ (M+H)$^+$: m/z=433.1/435.1; found 433.1/435.1.

Step 4. benzyl 3-(3-bromo-2-methylbenzamido)-4-oxopyrrolidine-1-carboxylate

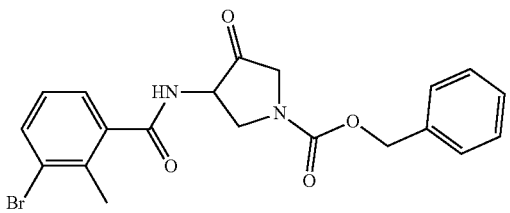 [SMILES: Cc1c(Br)cccc1C(=O)NC1CN(C(=O)OCc2ccccc2)CC1=O]

To a solution of benzyl 3-(3-bromo-2-methylbenzamido)-4-hydroxypyrrolidine-1-carboxylate (Step 3: 16.50 g, 38.1 mmol) in dichloromethane (200 mL) was added Dess-Martin periodinane (19.38 g, 45.7 mmol). The resulting mixture was stirred at room temperature for 2 h. The reaction mixture was diluted with Et$_2$O and 1 M NaOH solution. After stirring for 1 h, the organic layer was separated and dried over Na$_2$SO$_4$, filtered and concentrated. The residue was purified with flash chromatography (eluting with 0-50% ethyl acetate in hexanes) to give the desired product (9.2 g, 56%). LC-MS calculated for C$_{20}$H$_{20}$BrN$_2$O$_4$ (M+H)$^+$: m/z=431.1/433.1; found 431.1/433.1.

Step 5: benzyl 2-(3-bromo-2-methylphenyl)-4,6-dihydro-5H-pyrrolo[3,4-d]oxazole-5-carboxylate

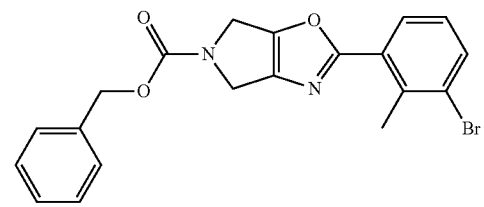 [SMILES: Cc1c(Br)cccc1-c1nc2c(o1)CN(C(=O)OCc1ccccc1)C2]

To a solution of benzyl 3-(3-bromo-2-methylbenzamido)-4-oxopyrrolidine-1-carboxylate (Step 4: 9.23 g, 21.40 mmol) in 1,4-dioxane (100 mL) was added POCl$_3$ (1.995 mL, 21.40 mmol). The resulting mixture was stirred at 110° C. for 3 h. After cooling to room temperature, the reaction mixture was diluted with saturated aqueous NaHCO$_3$ solution and ethyl acetate. The aqueous layer was extracted with ethyl acetate once. The combined organic layers were washed with brine, dried over Na$_2$SO$_4$, filtered and concentrated. The precipitate was collected via filtration and washed with ethyl acetate and hexanes to give the desired product as off white solid (4.85 g, 55%). LC-MS calculated for C$_{20}$H$_{18}$BrN$_2$O$_3$ (M+H)$^+$: m/z=413.0/415.0; found 413.0/415.0.

Step 6. 2-(3-Bromo-2-methylphenyl)-5,6-dihydro-4H-pyrrolo[3,4-d]oxazole

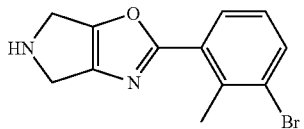 [SMILES: Cc1c(Br)cccc1-c1nc2c(o1)CNC2]

To a solution of benzyl 2-(3-bromo-2-methylphenyl)-4,6-dihydro-5H-pyrrolo[3,4-d]oxazole-5-carboxylate (Step 5: 3.70 g, 8.95 mmol) in dichloromethane (60 mL) was added 1 M BBr$_3$ in dichloromethane solution (17.9 mL, 17.91 mmol) at 0° C. After stirring at same temperature for 1 h, the reaction mixture was diluted with dichloromethane and saturated aqueous NaHCO$_3$ solution. The resultant precipitate was collected via filtration and dried under vacuum to give the desired product as white solid (2.0 g, 80%). LC-MS calculated for C$_{12}$H$_{12}$BrN$_2$O (M+H)$^+$: m/z=279.0/281.0; found 279.0/281.0.

Step 7: 1-(2-(3-bromo-2-methylphenyl)-4,6-dihydro-5H-pyrrolo[3,4-d]oxazol-5-yl)-2-chloroethan-1-one

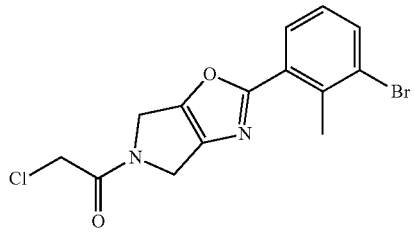 [SMILES: Cc1c(Br)cccc1-c1nc2c(o1)CN(C(=O)CCl)C2]

To a solution of 2-(3-bromo-2-methylphenyl)-5,6-dihydro-4H-pyrrolo[3,4-d]oxazole (Step 6: 1.04 g, 3.73 mmol) in dichloromethane (18 mL) was added 2-chloroacetyl chloride (0.421 g, 3.73 mmol) and N,N-diisopropylethylamine (1.947 mL, 11.18 mmol) at 0° C. The reaction mixture was stirred at room temperature for 2 h. The reaction was diluted with water, and the aqueous layer was extracted with dichloromethane once. The combined organic layers were dried over Na$_2$SO$_4$, filtered and concentrated. The residue was purified with flash chromatography (eluting with 0-60% ethyl acetate in hexanes) to give the desired product as white solid (0.65 g, 49%). LC-MS calculated for C$_{14}$H$_{13}$BrClN$_2$O$_2$ (M+H)$^+$: m/z=355.0/357.0; found 355.0/357.0.

Step 8. (S)-1-(2-(2-(3-bromo-2-methylphenyl)-4,6-dihydro-5H-pyrrolo[3,4-d]oxazol-5-yl)-2-oxoethyl)-3-methylpyrrolidine-3-carboxylic acid

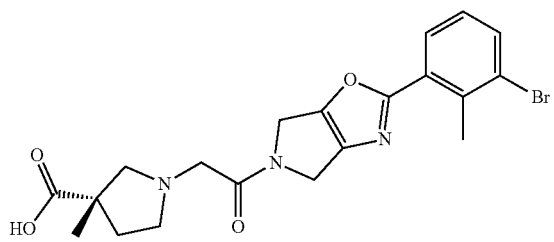 [SMILES: Cc1c(Br)cccc1-c1nc2c(o1)CN(C(=O)CN1CC[C@](C)(C(=O)O)C1)C2]

The mixture of 1-(2-(3-bromo-2-methylphenyl)-4,6-dihydro-5H-pyrrolo[3,4-d]oxazol-5-yl)-2-chloroethan-1-one (Step 7: 85 mg, 0.239 mmol), (S)-3-methylpyrrolidine-3-carboxylic acid (46.3 mg, 0.359 mmol), TEA (0.100 ml, 0.717 mmol) and N,N-Dimethylformamide (1.0 ml) was heated at 60° C. for 2 h. The reaction mixture was diluted with methanol and 1 N HCl, then purified via prep-HPLC (pH=2, acetonitrile/water+TFA) to give the desired product (52 mg, 48%). LC-MS calculated for C$_{20}$H$_{23}$BrN$_3$O$_4$ (M+H)$^+$: m/z=448.1/450.1; found 448.1/450.1.

Step 9. N-(2-Chloro-3-(4,4,5,5-tetramethyl-1,3,2-dioxaborolan-2-yl)phenyl)-1,5-dimethyl-4,5,6,7-tetrahydro-1H-imidazo[4,5-c]pyridine-2-carboxamide

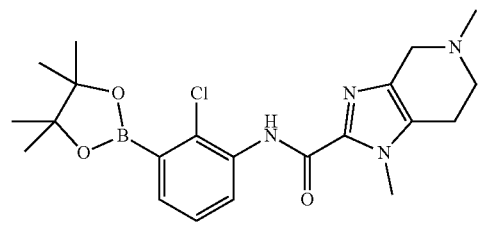

A mixture of N-(3-bromo-2-chlorophenyl)-1,5-dimethyl-4,5,6,7-tetrahydro-1H-imidazo[4,5-c]pyridine-2-carboxamide (Example 24, Step 2: 615 mg, 1.603 mmol), bis(pinacolato)diboron (488 mg, 1.924 mmol), dichloro[1,1'-bis(diphenylphosphino)ferrocene]palladium (II) dichloromethane adduct (131 mg, 0.160 mmol) and potassium acetate (346 mg, 3.53 mmol) was charged with nitrogen and stirred at 100° C. for 12 h. The crude was diluted with DCM, and then filtered through Celite. The filtrate was concentrated. The residue was purified by chromatography on silica gel (0-20% methanol in dichloromethane) to give the desired product (0.35 g, 50%). LC-MS calculated for C$_{21}$H$_{29}$BClN$_4$O$_3$ (M+H)$^+$: m/z=431.2; found 431.2.

Step 10: (S)-1-(2-(2-(2'-chloro-3'-(1,5-dimethyl-4,5,6,7-tetrahydro-1H-imidazo[4,5-c]pyridine-2-carboxamido)-2-methyl-[1,1'-biphenyl]-3-yl)-4,6-dihydro-5H-pyrrolo[3,4-d]oxazol-5-yl)-2-oxoethyl)-3-methylpyrrolidine-3-carboxylic acid (1,1'-Bis(diphenylphosphino)ferrocene)-dichloropalladium(II) (1.632 mg, 2.231 µmol) was added to a mixture of (S)-1-(2-(2-(3-bromo-2-methylphenyl)-4,6-dihydro-5H-pyrrolo[3,4-d]oxazol-5-yl)-2-oxoethyl)-3-methylpyrrolidine-3-carboxylic acid (Step 8: 10 mg, 0.022 mmol), N-(2-chloro-3-(4,4,5,5-tetramethyl-1,3,2-dioxaborolan-2-yl)phenyl)-1,5-dimethyl-4,5,6,7-tetrahydro-1H-imidazo[4,5-c]pyridine-2-carboxamide (Step 9: 9.6 mg, 0.022 mmol), sodium carbonate (5.9 mg, 0.056 mmol) in 1,4-dioxane (1.0 mL) and water (0.2 mL). The mixture was purged with N$_2$ and heated at 90° C. for 2 h. The mixture was diluted with methanol and 1 N HCl (0.5 mL), filtered and purified with prep-HPLC (pH=2, acetonitrile/water+TFA) to give the desired product as TFA salt. LC-MS calculated for C$_{35}$H$_{39}$ClN$_7$O$_5$ (M+H)$^+$: m/z=672.3; found 672.3. $^1$H NMR (500 MHz, DMSO) δ 9.97 (s, 1H), 8.25 (d, J=8.1 Hz, 1H), 7.99 (m, 1H), 7.50 (m, 2H), 7.35 (m, 1H), 7.18 (m, 1H), 4.83 (s, 1H), 4.72 (s, 1H), 4.64 (s, 1H), 4.54 (s, 1H), 4.45 (d, J=9.6

Hz, 2H), 4.42-4.14 (m, 4H), 3.96 (s, 3H), 3.84-3.29 (m, 4H), 3.04 (m, 2H), 2.97 (s, 3H), 2.44 (m, 1H), 2.36 (s, 3H), 1.99 (m, 1H), 1.40 (s, 3H).

Example 164

(S)—N-(2-chloro-3'-(5-((S)-(1-hydroxypropan-2-yl)glycyl)-5,6-dihydro-4H-pyrrolo[3,4-d]oxazol-2-yl)-2'-methyl-[1,1'-biphenyl]-3-yl)-1,5-dimethyl-4,5,6,7-tetrahydro-1H-imidazo[4,5-c]pyridine-2-carboxamide

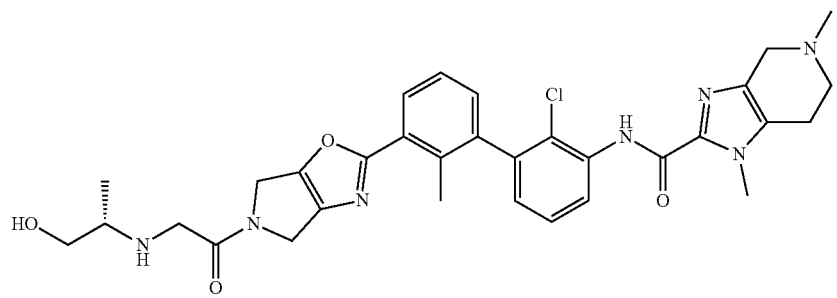 [SMILES: Cc1c(-c2nc3c(o2)CN(C(=O)CN[C@@H](C)CO)C3)cccc1-c1cccc(NC(=O)c2nc3c(n2C)CCN(C)C3)c1Cl]

Step 1: (S)-1-(2-(3-bromo-2-methylphenyl)-4,6-dihydro-5H-pyrrolo[3,4-d]oxazol-5-yl)-2-((1-hydroxypropan-2-yl)amino)ethan-1-one

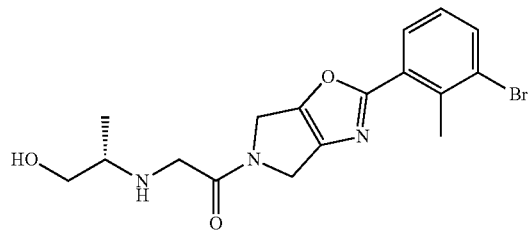 [SMILES: Cc1c(Br)cccc1-c1nc2c(o1)CN(C(=O)CN[C@@H](C)CO)C2]

The mixture of 1-(2-(3-bromo-2-methylphenyl)-4,6-dihydro-5H-pyrrolo[3,4-d]oxazol-5-yl)-2-chloroethan-1-one (Example 163, Step 7: 16 mg, 0.045 mmol), (S)-2-aminopropan-1-ol (3.38 mg, 0.045 mmol), TEA (0.019 mL, 0.135 mmol) and N,N-dimethylformamide (1.0 mL) was heated at 60° C. for 2 h. The reaction mixture was diluted with methanol and 1 N HCl, and purified with prep-HPLC (pH=2, acetonitrile/water+TFA) to give the desired product (16 mg, 90%). LC-MS calculated for $C_{17}H_{21}BrN_3O_3$ (M+H)$^+$: m/z=394.1/396.1; found 394.1/396.1.

Step 2: (S)—N-(2-chloro-3'-(5f(S)-(1-hydroxypropan-2-yl)glycyl)-5,6-dihydro-4H-pyrrolo[3N-d]oxazol-2-yl)-2'-methyl-[1,1'-biphenyl]-3-yl)-1,5-dimethyl-4,5,6,7-tetrahydro-1H-imidazo[4,5-c]pyridine-2-carboxamide This compound was prepared using similar procedures as described for Example 163 with (S)-1-(2-(3-bromo-2-methylphenyl)-4,6-dihydro-5H-pyrrolo[3,4-d]oxazol-5-yl)-2-((l-hydroxypropan-2-yl)amino)ethan-1-one (Step 1) replacing (S)-1-(2-(2-(3-bromo-2-methylphenyl)-4,6-dihydro-5H-pyrrolo[3,4-d]oxazol-5-yl)-2-oxoethyl)-3-methylpyrrolidine-3-carboxylic acid in Step 10. The reaction mixture was purified by prep-HPLC (pH=2, acetonitrile/water+TFA) to give the desired product as TEA salt. LC-MS calculated for $C_{32}H_{37}ClN_7O_4$ (M+H)$^+$: m/z=618.3; found 618.3.

TABLE 24

The compounds in Table 24 were prepared in accordance with the synthetic protocols set forth in Example 164, using the appropriate starting materials.

| Example # | Name | Structure | LC-MS (M + H)$^+$ |
|---|---|---|---|
| 165 | N-(2-chloro-3'-(5-((cis-3-hydroxycyclobutyl)glycyl)-5,6-dihydro-4H-pyrrolo[3,4-d]oxazol-2-yl)-2'-methyl-[1,1'-biphenyl]-3-yl)-1,5-dimethyl-4,5,6,7-tetrahydro-1H-imidazo[4,5-c]pyridine-2-carboxamide | 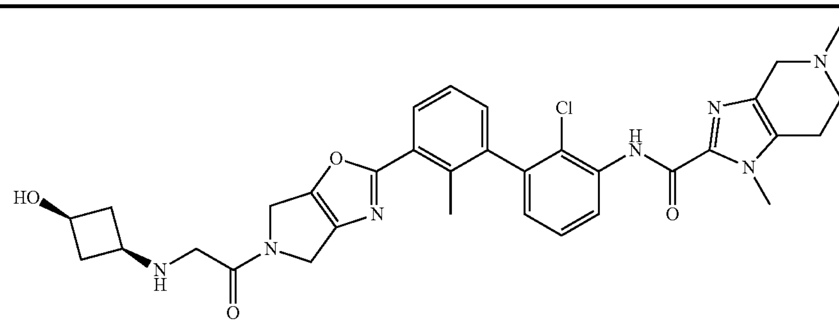 | 630.3 |

TABLE 24-continued

The compounds in Table 24 were prepared in accordance with the synthetic protocols set forth in Example 164, using the appropriate starting materials.

| Example # | Name | Structure | LC-MS (M + H)+ |
|---|---|---|---|
| 166 | N-(2-chloro-3'-(5-((trans-3-hydroxycyclobutyl)glycyl)-5,6-dihydro-4H-pyrrolo[3,4-d]oxazol-2-yl)-2'-methyl-[1,1'-biphenyl]-3-yl)-1,5-dimethyl-4,5,6,7-tetrahydro-1H-imidazo[4,5-c]pyridine-2-carboxamide | 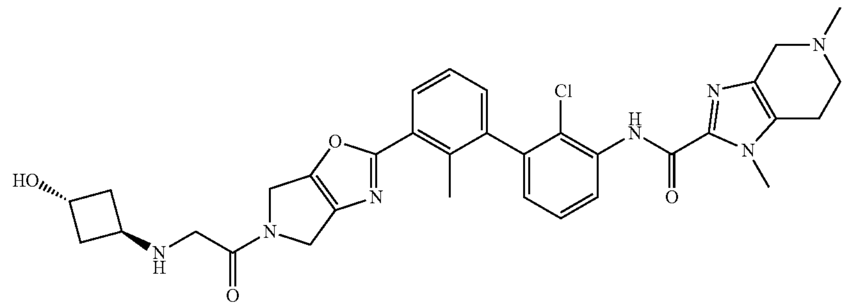 [SMILES: Cc1c(-c2nc3c(o2)CN(C(=O)CN[C@H]2C[C@H](O)C2)C3)cccc1-c1cccc(NC(=O)c2nc3c(n2C)CCN(C)C3)c1Cl] | 630.3 |
| 167 | 1-(2-(2-(2'-chloro-3'-(1,5-dimethyl-4,5,6,7-tetrahydro-1H-imidazo[4,5-c]pyridine-2-carboxamido)-2-methyl-[1,1'-biphenyl]-3-yl)-4,6-dihydro-5H-pyrrolo[3,4-d]oxazol-5-yl)-2-oxoethyl)piperidine-4-carboxylic acid | 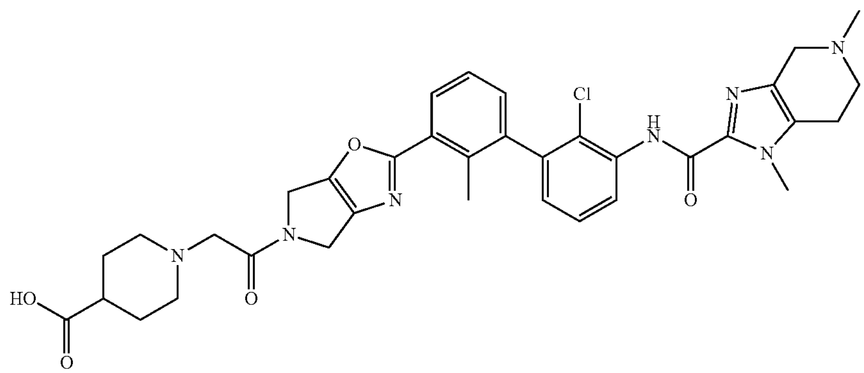 [SMILES: Cc1c(-c2nc3c(o2)CN(C(=O)CN2CCC(C(=O)O)CC2)C3)cccc1-c1cccc(NC(=O)c2nc3c(n2C)CCN(C)C3)c1Cl] | 672.2 |

Example 168

4-(2-((2-chloro-3'-(5-(dimethylglycyl)-5,6-dihydro-4H-pyrrolo[3,4-d]oxazol-2-yl)-2'-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid

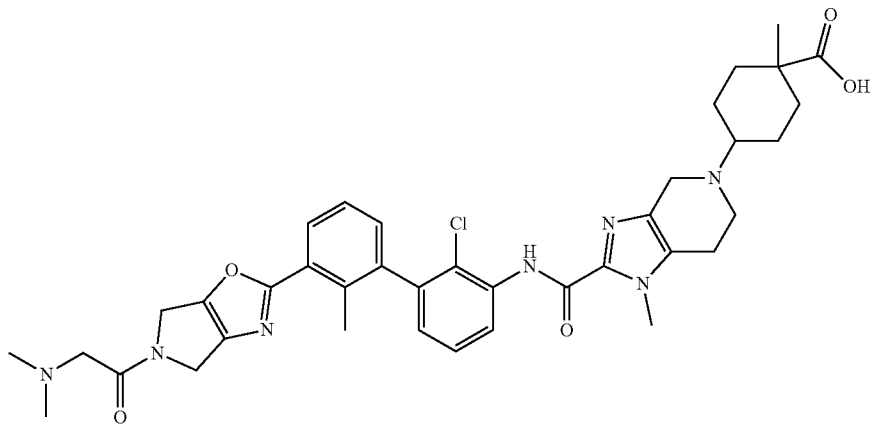 [SMILES: Cc1c(-c2nc3c(o2)CN(C(=O)CN(C)C)C3)cccc1-c1cccc(NC(=O)c2nc3c(n2C)CCN(C2CCC(C)(C(=O)O)CC2)C3)c1Cl]

329

Step 1. 1-(2-(3-Bromo-2-methylphenyl)-4,6-dihydro-5H-pyrrolo[3,4-d]oxazol-5-yl)-2-(dimethylamino)ethan-1-one

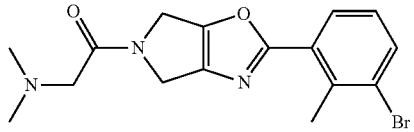 [SMILES: Cc1c(Br)cccc1-c1nc2c(o1)CN(C(=O)CN(C)C)C2]

To a solution of dimethylglycine (20.5 mg, 0.199 mmol) in N,N-dimethylformamide (1 mL) was added N,N,N',N'-tetramethyl-O-(7-azabenzotriazol-1-yl)uronium hexafluorophosphate (104 mg, 0.274 mmol). After stirring for 5 min, 2-(3-bromo-2-methylphenyl)-5,6-dihydro-4H-pyrrolo[3,4-d]oxazole (Example 163, Step 6: 55.5 mg, 0.199 mmol) and N,N-diisopropylethylamine (104 μL, 0.596 mmol). The reaction mixture was stirred at room temperature for 2 h. The reaction mixture was diluted with water, and the aqueous layer was extracted with dichloromethane once. The combined organic layers were dried over Na$_2$SO$_4$, filtered and concentrated. The residue was purified with silica gel column (eluting with 0-30% MeOH in DCM) to give the desired product (35 mg, 49%). LC-MS calculated for C$_{16}$H$_{19}$BrN$_3$O$_2$ (M+H)$^+$: m/z=364.1/366.1; found 364.1/366.1.

Step 2: tert-butyl 2-((2-chloro-3'-(5-(dimethylglycyl)-5,6-dihydro-4H-pyrrolo[3,4-d]oxazol-2-yl)-2'-methyl-[1,1'-biphenyl]-3-yl)carbamoyl)-1-methyl-1,4,6,7-tetrahydro-5H-imidazo[4,5-c]pyridine-5-carboxylate

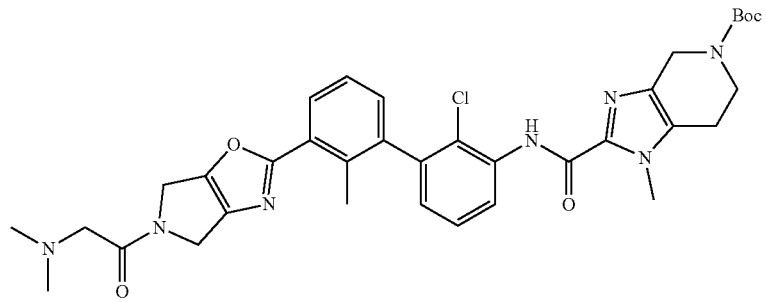 [SMILES: Cc1c(-c2nc3c(o2)CN(C(=O)CN(C)C)C3)cccc1-c1cccc(NC(=O)c2nc3c(n2C)CCN(C(=O)OC(C)(C)C)C3)c1Cl]

(1,1'-Bis(diphenylphosphino)ferrocene)-dichloropalladium(II) (69.3 mg, 0.095 mmol) was added to a mixture of 1-(2-(3-bromo-2-methylphenyl)-4,6-dihydro-5H-pyrrolo[3,4-d]oxazol-5-yl)-2-(dimethylamino)ethan-1-one (Step 1: 345 mg, 0.947 mmol), tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Example 54, step 3: 538 mg, 1.042 mmol), sodium carbonate (251 mg, 2.368 mmol) in 1,4-dioxane (5.0 mL) and water (1.0 mL). The mixture was purged with N$_2$ and heated at 100° C. for 3 h. The mixture was diluted with methanol and 1 N HCl (0.5 mL), filtered and purified by prep-HPLC (pH=2, acetonitrile/water+TFA) to give the desired product (0.59 g, 92%). LC-MS calculated for C$_{35}$H$_{41}$ClN$_7$O$_5$ (M+H)$^+$: m/z=674.3; found 674.2.

330

Step 3: N-(2-chloro-3'-(5-(dimethylglycyl)-5,6-dihydro-4H-pyrrolo[3,4-d]oxazol-2-yl)-2'-methyl-[1,1'-biphenyl]-3-yl)-1-methyl-4,5,6,7-tetrahydro-1H-imidazo[4,5-c]pyridine-2-carboxamide

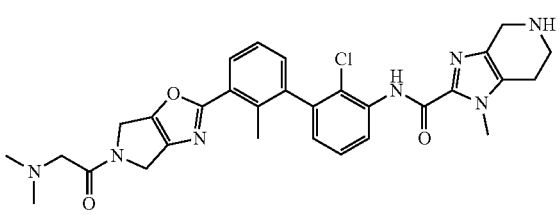 [SMILES: Cc1c(-c2nc3c(o2)CN(C(=O)CN(C)C)C3)cccc1-c1cccc(NC(=O)c2nc3c(n2C)CCNC3)c1Cl]

To a solution of tert-butyl 2-((2-chloro-3'-(5-(dimethylglycyl)-5,6-dihydro-4H-pyrrolo[3,4-d]oxazol-2-yl)-2'-methyl-[1,1'-biphenyl]-3-yl)carbamoyl)-1-methyl-1,4,6,7-tetrahydro-5H-imidazo[4,5-c]pyridine-5-carboxylate (Step 2: 590 mg, 0.875 mmol) in dichloromethane (4 mL) was added 4 M HCl in 1,4-dioxane (1.3 mL, 5.25 mmol). The resulting mixture was stirred at room temperature for 1 h. The solvent was removed in vacuo. The crude product was used in the next step without purification. LC-MS calculated for C$_{30}$H$_{33}$ClN$_7$O$_3$ (M+H)$^+$: m/z=574.2; found 574.2.

Step 4: 4-(2-((2-chloro-3-(5-(dimethylglycyl)-5,6-dihydro-4H-pyrrolo[3,4M]oxazol-2-yl)-2-methyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid To a mixture of 1-methyl-4-oxocyclohexane-1-carboxylic acid (4.08 mg, 0.026 mmol), N-(2-chloro-3'-(5-(dimethylglycyl)-5,6-dihydro-4H-pyrrolo[3,4-d]oxazol-2-yl)-2'-methyl-[1,1'-biphenyl]-3-yl)-1-methyl-4,5,6,7-tetrahydro-1H-imidazo[4,5-c]pyridine-2-carboxamide (Step 3: 10 mg, 0.017 mmol) in DCM (1 mL) was added DIEA (6.08 μL, 0.035 mmol). After stirring at room temperature for 2.5 h, sodium triacetoxyborohydride (7.38 mg, 0.035 mmol) was added and stirred overnight. The solvent was removed in vacuo, the residue was dissolved in methanol and water and purified by prep-HPLC (pH=2, acetonitrile/water+TFA) to give the desired product as a mixture of cis/trans isomers. LC-MS calculated for C$_{38}$H$_{45}$ClN$_7$O$_5$ (M+H)$^+$: m/z=714.3; found 714.2.

Example 169

4-(2-(2-((2,2'-dichloro-3'-(5-(N-ethyl-N-methylgly-cyl)-5,6-dihydro-4H-pyrrolo[3,4-d]oxazol-2-yl)-[1,1'-biphenyl]-3-yl)carbamoyl)-1-methyl-1,4,6,7-tetra-hydro-5H-imidazo[4,5-c]pyridin-5-yl)ethyl)cyclohexane-1-carboxylic acid

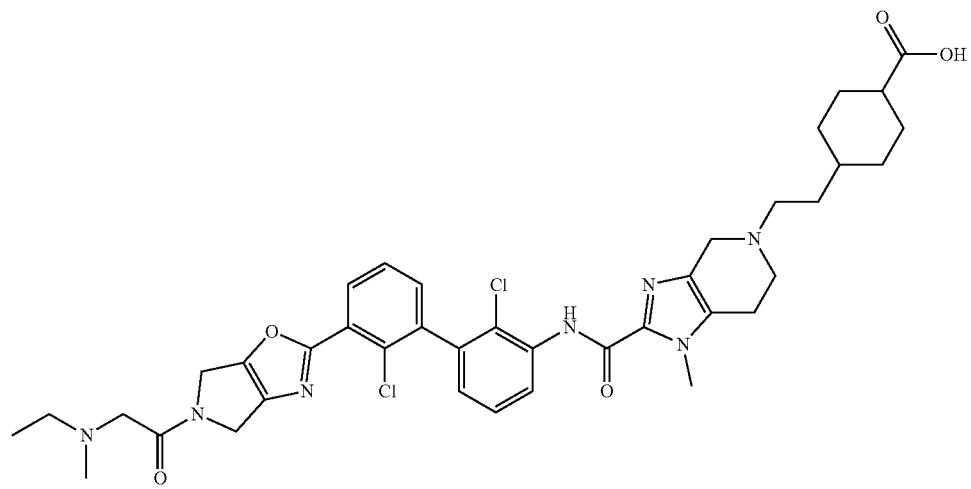 [SMILES: CCN(C)CC(=O)N1Cc2nc(-c3cccc(-c4cccc(NC(=O)c5nc6c(n5C)CCN(CCC5CCC(C(=O)O)CC5)C6)c4Cl)c3Cl)oc2C1]

Step 1. 2-(3-bromo-2-chlorophenyl)-5,6-dihydro-4H-pyrrolo[3,4-d]oxazole

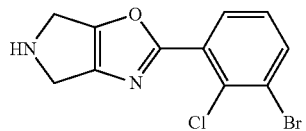 [SMILES: Clc1c(Br)cccc1-c1nc2c(o1)CNC2]

This compound was prepared using similar procedures as described for Example 163, Step 1-6 with 3-bromo-2-chlorobenzoic acid replacing 3-bromo-2-methylbenzoic acid in Step 3. LC-MS calculated for $C_{11}H_9BrClN_2O$ (M+H)$^+$: m/z=299.0/301.0; found 299.0/301.0.

Step 2. 1-(2-(3-bromo-2-chlorophenyl)-4,6-dihydro-5H-pyrrolo[3,4-d]oxazol-5-yl)-2-chloroethan-1-one

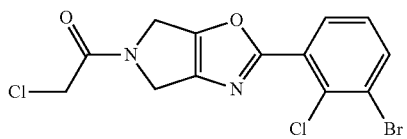 [SMILES: O=C(CCl)N1Cc2nc(-c3cccc(Br)c3Cl)oc2C1]

This compound was prepared using similar procedures as described for Example 163 with 2-(3-bromo-2-chlorophenyl)-5,6-dihydro-4H-pyrrolo[3,4-d]oxazole (Step 1) replacing 2-(3-bromo-2-methylphenyl)-5,6-dihydro-4H-pyrrolo[3,4-d]oxazole in Step 7. LC-MS calculated for $C_{13}H_{10}BrCl_2N_2O_2$ (M+H)$^+$: m/z=374.9/376.9; found 374.9/376.9.

Step 3: 1-(2-(3-bromo-2-chlorophenyl)-4,6-dihydro-5H-pyrrolo[3,4-d]oxazol-5-yl)-2-(ethyl(methyl)amino)ethan-1-one

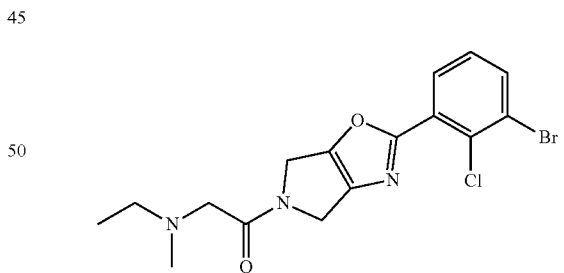

The mixture of 1-(2-(3-bromo-2-chlorophenyl)-4,6-dihydro-5H-pyrrolo[3,4-d]oxazol-5-yl)-2-chloroethan-1-one (Step 2: 15 mg, 0.040 mmol), N-methylethanamine (2.358 mg, 0.040 mmol), TEA (0.017 mL, 0.120 mmol) and N,N-dimethylformamide (1.0 mL) was heated at 60° C. for 2 h. The reaction mixture was diluted with methanol and 1 N HCl and purified with prep-HPLC (pH=2, acetonitrile/water+TFA) to give the desired product (14 mg, 88%). LC-MS calculated for $C_{16}H_{18}BrClN_3O_2$ (M+H)$^+$: m/z=398.0/400.0; found 398.0/400.0.

Step 4: tert-butyl 2-((2,2'-dichloro-3'-(5-(N-ethyl-N-methylglycyl)-5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridine-5-carboxylate

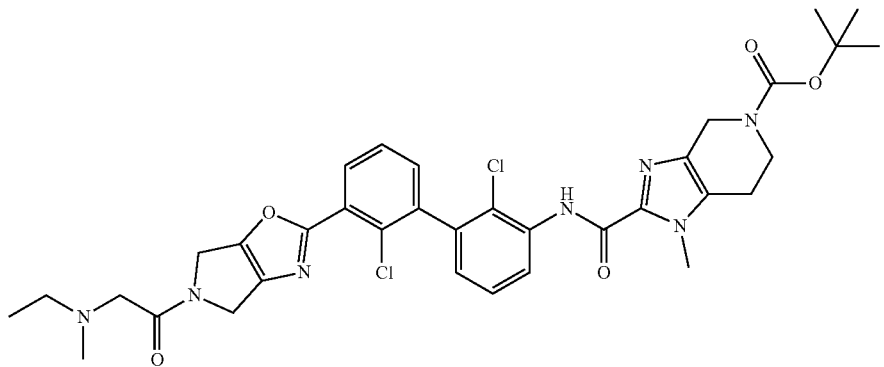 [SMILES: CCN(C)CC(=O)N1Cc2nc(-c3cccc(-c4cccc(NC(=O)c5nc6c(n5C)CCN(C(=O)OC(C)(C)C)C6)c4Cl)c3Cl)oc2C1]

To a microwave vial was charged 1-(2-(3-bromo-2-chlorophenyl)-4,6-dihydro-5H-pyrrolo[3,4-d]oxazol-5-yl)-2-(ethyl(methyl)amino)ethan-1-one (Step 3: 58 mg, 0.145 mmol), tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Example 54, step 3: 83 mg, 0.160 mmol), (1,1'-bis(diphenylphosphino)ferrocene)-dichloropalladium(II) (10.64 mg, 0.015 mmol), sodium carbonate (38.5 mg, 0.364 mmol) in 1,4-dioxane (2.0 mL) and water (0.400 mL). The mixture was purged with $N_2$ and heated at 100° C. for 3 h. The reaction mixture was purified by prep-HPLC (pH=2, acetonitrile/water+TFA) to give the desired product (85 mg, 82%). LC-MS calculated for $C_{35}H_{40}Cl_2N_7O_5$ $(M+H)^+$: m/z=708.2; found 708.2.

Step 5: N-(2,2'-dichloro-3'-(5-(N-ethyl-N-methylglycyl)-5,6-dihydro-4H-pyrrolo[3,4-d]oxazol-2-yl)-[1,1'-biphenyl]-3-yl)-1-methyl-4,5,6,7-tetrahydro-1H-imidazo[4,5-c]pyridine-2-carboxamide To a solution of tert-butyl 2-((2,2'-dichloro-3'-(5-(N-ethyl-N-methylglycyl)-5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridine-5-carboxylate (Step 4: 59 mg, 0.083 mmol) in DCM (1 mL) was added 4 M HCl in 1,4-dioxane (125 µL, 0.500 mmol). The resulting mixture was stirred at room temperature for 2 h. The solvent was removed in vacuo. The crude was used in the next step without purification. LC-MS calculated for $C_{30}H_{32}Cl_2N_7O_3$ $(M+H)^+$: m/z=608.2; found 608.2.

Step 6: 4-(2-(2-((2,2'-dichloro-3'-(5-(N-ethyl-N-methylglycyl)-5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridin-5-yl)ethyl)cyclohexane-1-carboxylic acid To a mixture of methyl 4-(2-oxoethyl)cyclohexane-1-carboxylate (4.5 mg, 0.025 mmol), N-(2,2'-dichloro-3'-(5-(N-ethyl-N-methylglycyl)-5,6-dihydro-4H-pyrrolo[3,4-d]oxazol-2-yl)-[1,1'-biphenyl]-3-yl)-1-methyl-4,5,6,7-tetrahydro-1H-imidazo[4,5-c]pyridine-2-carboxamide (Step 5: 10 mg, 0.016 mmol) in DCM (1 mL) was added DIEA (5.8 µL, 0.033 mmol). After stirring at room temperature for 2.5 h, sodium triacetoxyborohydride (7.0 mg, 0.033 mmol) was added and stirred overnight. After removing the solvent in vacuo, the residue was dissolved in methanol (0.5 ml) and 1 N aq. NaOH solution (0.1 mL, 0.100 mmol), and the mixture was stirred at 60° C. for 1 h, the reaction mixture was purified by prep-HPLC (pH=2, acetonitrile/water+TFA) to give the desired product as TFA salt. LC-MS calculated for $C_{39}H_{46}Cl_2N_7O_5$ $(M+H)^+$: m/z=762.3; found 762.3.

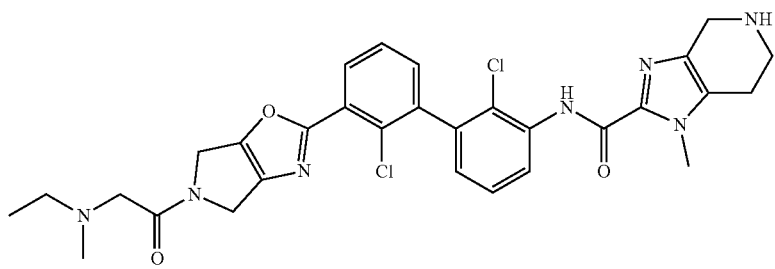 [SMILES: CCN(C)CC(=O)N1Cc2nc(-c3cccc(-c4cccc(NC(=O)c5nc6c(n5C)CCNC6)c4Cl)c3Cl)oc2C1]

TABLE 25

The compounds in Table 25 were prepared in accordance with the synthetic protocols set forth in Example 169, using the appropriate starting materials.

| Example # | Name | Structure | LC-MS (M + H)+ |
|---|---|---|---|
| 170 | 4-(2-(2-(2,2'-dichloro-3'-(5-(2-(3-hydroxyazetidin-1-yl)acetyl)-5,6-dihydro-4H-pyrrolo[3,4-d]oxazol-2-yl)biphenyl-3-ylcarbamoyl)-1-methyl-6,7-dihydro-1H-imidazo[4,5-c]pyridin-5(4H)-yl)ethyl)cyclohexane-1-carboxylic acid | 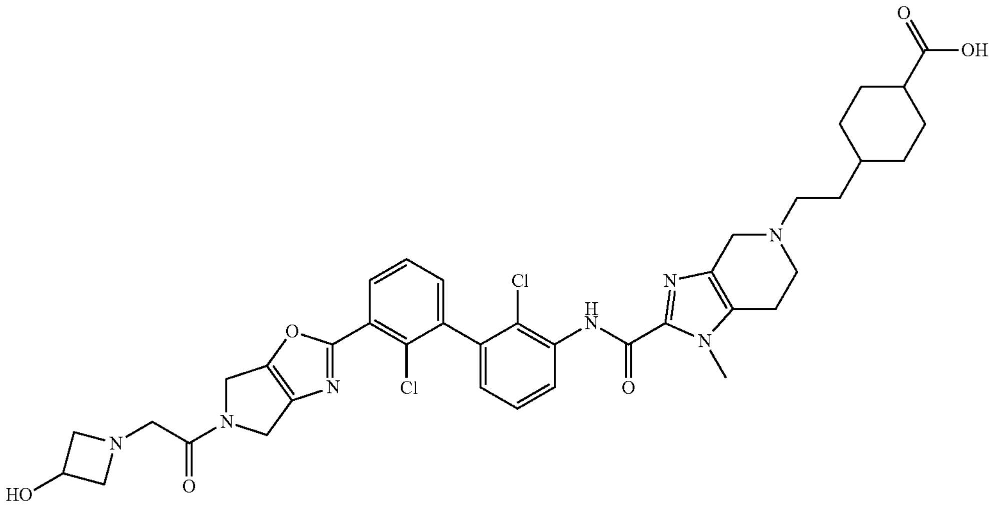 [SMILES: Cn1c(C(=O)Nc2cccc(-c3cccc(-c4nc5c(o4)CN(C(=O)CN4CC(O)C4)C5)c3Cl)c2Cl)nc2c1CCN(CCC1CCC(C(=O)O)CC1)C2] | 776.5 |
| 171 | (R)-4-(2-(2-(2,2'-dichloro-3'-(5-(2-(3-hydroxypyrrolidin-1-yl)acetyl)-5,6-dihydro-4H-pyrrolo[3,4-d]oxazol-2-yl)biphenyl-3-ylcarbamoyl)-1-methyl-6,7-dihydro-1H-imidazo[4,5-c]pyridin-5(4H)-yl)ethyl) | 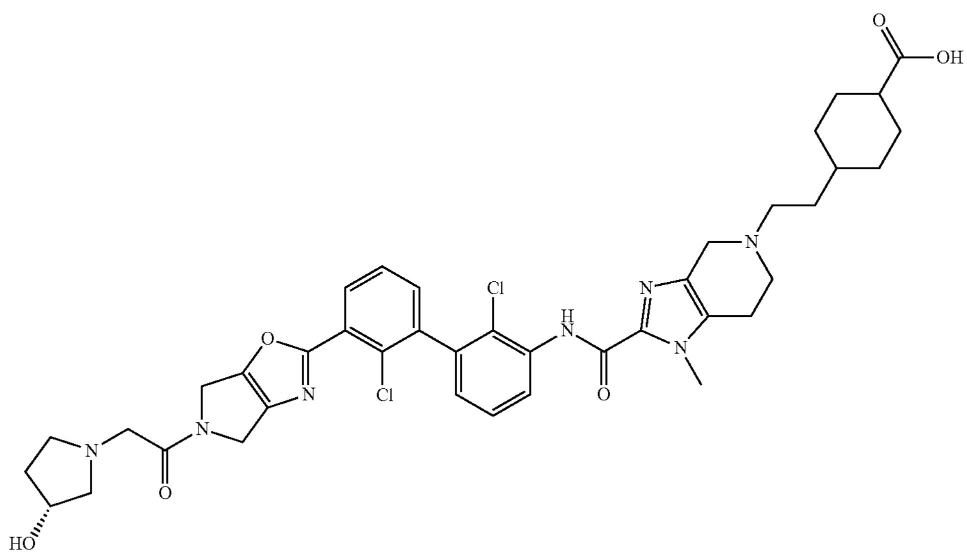 [SMILES: Cn1c(C(=O)Nc2cccc(-c3cccc(-c4nc5c(o4)CN(C(=O)CN4CC[C@@H](O)C4)C5)c3Cl)c2Cl)nc2c1CCN(CCC1CCC(C(=O)O)CC1)C2] | 790.5 |

| Example # | Name | Structure | LC-MS (M+H)+ |
|---|---|---|---|
| | cyclohexane-1-carboxylic acid | | |

Example 172 trans-4-((2-((2,2'-dichloro-3'-(5-(N-ethyl-N-methyl-glycyl)-5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridin-5-yl)methyl)cyclohexane-1-carboxylic acid

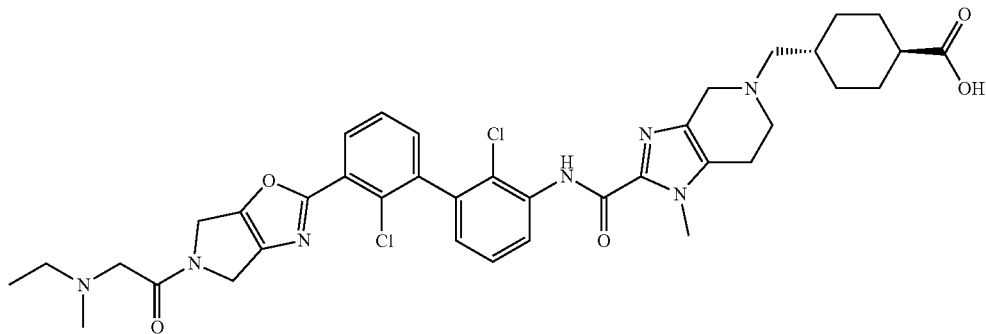 [SMILES: CCN(C)CC(=O)N1Cc2nc(-c3cccc(-c4cccc(NC(=O)c5nc6c(n5C)CCN(C[C@H]5CC[C@H](C(=O)O)CC5)C6)c4Cl)c3Cl)oc2C1]

This compound was prepared using similar procedures as described for Example 169 with methyl trans-4-formylcyclohexane-1-carboxylate replacing methyl 4-(2-oxoethyl)cyclohexane-1-carboxylate in Step 6. The reaction mixture was purified by prep-HPLC (pH=2, acetonitrile/water+TFA) to give the desired product as TEA salt. LC-MS calculated for $C_{38}H_{44}Cl_2N_7O_5$ (M+H)+: m/z=748.3; found 748.3.

Example 173

4-(2-((3'-(5-(N-ethyl-N-methylglycyl)-5,6-dihydro-4H-pyrrolo[3,4-d]oxazol-2-yl)-2,2'-dimethyl-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid

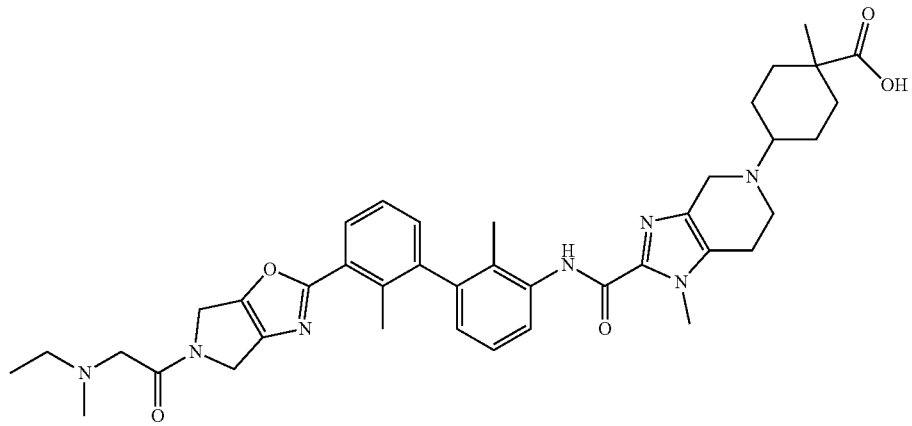 [SMILES: CCN(C)CC(=O)N1Cc2nc(-c3cccc(-c4cccc(NC(=O)c5nc6c(n5C)CCN(C5CCC(C)(C(=O)O)CC5)C6)c4C)c3C)oc2C1]

Step 1: tert-butyl 2-((3'-(5,6-dihydro-4H-pyrrolo[3,4-d]oxazol-2-yl)-2,2'-dimethyl-[1,1'-biphenyl]-3-yl)carbamoyl)-1-methyl-1,4,6,7-tetrahydro-5H-imidazo[4,5-c]pyridine-5-carboxylate

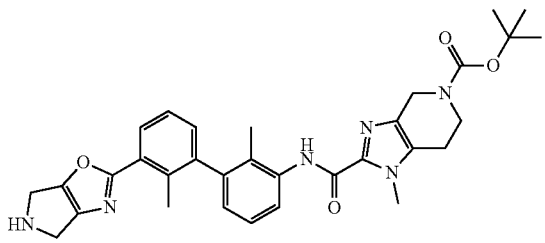 [SMILES: Cc1c(NC(=O)c2nc3c(n2C)CCN(C(=O)OC(C)(C)C)C3)cccc1-c1cccc(-c2nc3c(o2)CNC3)c1C]

A mixture of 2-(3-bromo-2-methylphenyl)-5,6-dihydro-4H-pyrrolo[3,4-d]oxazole (Example 163, Step 6: 135 mg, 0.484 mmol), tert-butyl 1-methyl-2-((2-methyl-3-(4,4,5,5-tetramethyl-1,3,2-dioxaborolan-2-yl)phenyl)carbamoyl)-1,4,6,7-tetrahydro-5H-imidazo[4,5-c]pyridine-5-carboxylate (Example 24, Step 4: 240 mg, 0.484 mmol), dicyclohexyl (2',4',6'-triisopropylbiphenyl-2-yl)phosphine-(2'-aminobiphenyl-2-yl)(chloro)palladium (1:1) (38.1 mg, 0.048 mmol) and tripotassium phosphate hydrate (245 mg, 1.064 mmol) in 1,4-dioxane (6 mL) and water (2 mL) was stirred at 80° C. for 1 h. The reaction was diluted with DCM and water, and the aqueous layer was extracted with DCM once. The combined organic layer was washed with brine, dried over $Na_2SO_4$, filtered and concentrated. The crude was used in the next step without further purification. LC-MS calculated for $C_{32}H_{37}N_6O_4$ (M+H)$^+$: m/z=569.3; found 569.3.

Step 2: ten-butyl 2-((3'-(5-(2-chloroacetyl)-5,6-dihydro-4H-pyrrolo[3,4-d]oxazol-2-yl)-2,2'-dimethyl-[1,1'-biphenyl]-3-yl)carbamoyl)-1-methyl-1,4,6,7-tetrahydro-5H-imidazo[4,5-c]pyridine-5-carboxylate

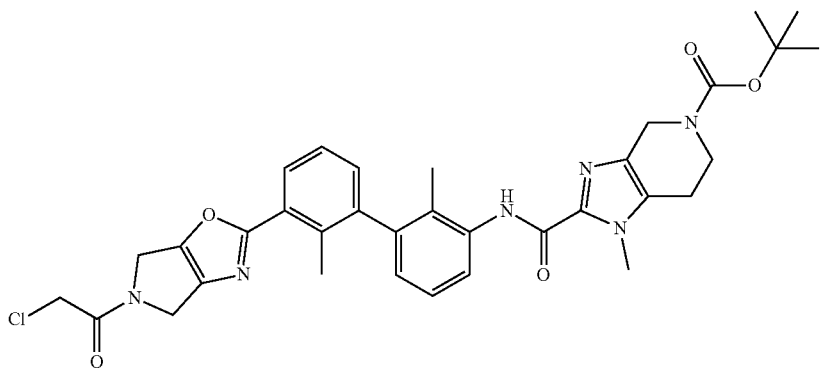 [SMILES: Cc1c(NC(=O)c2nc3c(n2C)CCN(C(=O)OC(C)(C)C)C3)cccc1-c1cccc(-c2nc3c(o2)CN(C(=O)CCl)C3)c1C]

To a solution of tert-butyl 2-((3'-(5,6-dihydro-4H-pyrrolo[3,4-d]oxazol-2-yl)-2,2'-dimethyl-[1,1-biphenyl]-3-yl)carbamoyl)-1-methyl-1,4,6,7-tetrahydro-5H-imidazo[4,5-c]pyridine-5-carboxylate (Step 1: 125 mg, 0.220 mmol) in DCM (1 mL) was added 2-chloroacetyl chloride (21 µL, 0.264 mmol) and N,N-diisopropylethylamine (115 µL, 0.659 mmol) at 0° C. The reaction mixture was stirred at room temperature for 2 h. The reaction mixture was diluted with water, and the aqueous layer was extracted with DCM once. The combined organic layers were dried over $Na_2SO_4$, filtered and concentrated. The residue was purified with flash chromatography (eluting with 50% ethyl acetate in hexanes) to give the desired product (135 mg, 95%). LC-MS calculated for $C_{34}H_3BClN_6O_5$ (M+H)$^+$: m/z=645.3; found 645.3.

Step 3; tert-butyl 2-((3'-(5-(N-ethyl-N-methylglycyl)-5,6-dihydro-4H-pyrrolo[3,4-d]oxazol-2-yl)-2,2'-dimethyl-[1,1'-biphenyl]-3-yl)carbamoyl)-1-methyl-1,4,6,7-tetrahydro-5H-imidazo[4,5-c]pyridine-5-carboxylate HCl in 1,4-dioxane (40.4 μL, 0.162 mmol). The resulting mixture was stirred at room temperature for 2 h. The solvent was removed and the residue was used in the next step without purification. LC-MS calculated for $C_{32}H_{38}N_7O_3$ $(M+H)^+$: m/z=568.3; found 568.3.

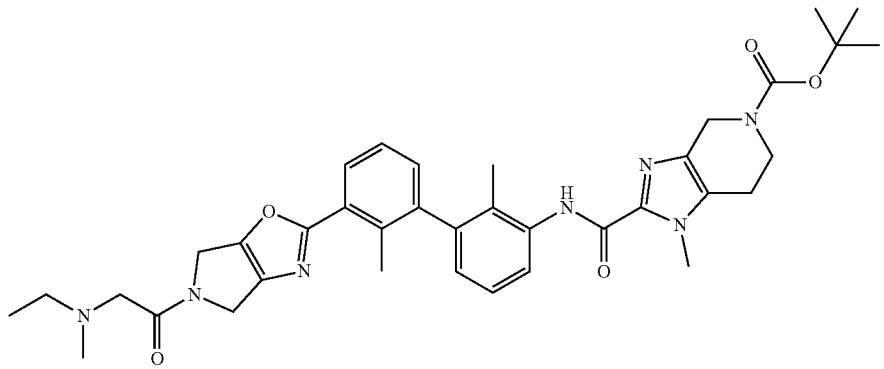 [SMILES: CCN(C)CC(=O)N1Cc2nc(-c3cccc(-c4cccc(NC(=O)c5nc6c(n5C)CCN(C(=O)OC(C)(C)C)C6)c4C)c3C)oc2C1]

The mixture of tert-butyl 2-((3'-(5-(2-chloroacetyl)-5,6-dihydro-4H-pyrrolo[3,4-d]oxazol-2-yl)-2,2'-dimethyl-[1,1'-biphenyl]-3-yl)carbamoyl)-1-methyl-1,4,6,7-tetrahydro-5H-imidazo[4,5-c]pyridine-5-carboxylate (Step 2: 20.0 mg, 0.031 mmol), N-methylethanamine (2.75 mg, 0.047 mmol), TEA (0.013 mL, 0.093 mmol) and DMF (1.0 mL) was heated at 60° C. for 2 h. The reaction mixture was diluted with methanol and 1 N HCl (1 mL), and purified with prep-HPLC (pH=2, acetonitrile/water+TFA) to give the desired product as TEA salt. LC-MS calculated for $C_{37}H_{46}N_7O_5$ $(M+H)^+$: m/z=668.4; found 668.5.

Step 4: N-(3'-(5-(N-ethyl-N-methylglycyl)-5,6-dihydro-4H-pyrrolo[3,4-d]oxazol-2-yl)-2,2 dimethyl-[1,1'-biphenyl]-3-yl)-1-methyl-4,5,6,7-tetrahydro-1H-imidazo[4,5-c]pyridine-2-carboxamide To a solution of tert-butyl 2-((3'-(5-(N-ethyl-N-methylglycyl)-5,6-dihydro-4H-pyrrolo[3,4-d]oxazol-2-yl)-2,2'-dimethyl-[1,1'-biphenyl]-3-yl)carbamoyl)-1-methyl-1,4,6,7-tetrahydro-5H-imidazo[4,5-c]pyridine-5-carboxylate (Step 3: 18 mg, 0.027 mmol) in DCM (0.5 mL) was added 4 M Step 5; 4-(2-((3'-(5-(N-ethyl-N-methylglycyl)-5,6-dihydro-4H-pyrrolo[3,4-d]oxazol-2-yl)-2,2'-dimethyl-[1,1'-biphenyl]-3-yl) carbamoyl)-1-methyl-1,4,6,7-tetrahydro-5H-imidazo[4,5-c]pyridin-5-yl)-1-methylcyclohexane-1-carboxylic acid To a mixture of 1-methyl-4-oxocyclohexane-1-carboxylic acid (4.13 mg, 0.026 mmol), N-(3'-(5-(N-ethyl-N-methylglycyl)-5,6-dihydro-4H-pyrrolo[3,4-d]oxazol-2-yl)-2,2'-dimethyl-[1,1'-biphenyl]-3-yl)-1-methyl-4,5,6,7-tetrahydro-1H-imidazo[4,5-c]pyridine-2-carboxamide (Step 4: 10 mg, 0.018 mmol) in DCM (1 mL) was added DIEA (6.15 μL, 0.035 mmol). After stirring at room temperature for 2.5 h, sodium triacetoxyborohydride (7.5 mg, 0.035 mmol) was added and stirred overnight. After removing the solvent in vacuo, the residue was dissolved in methanol and 1 N HCl and purified with prep-HPLC (pH=2, acetonitrile/water+TFA) to give the desired product as a mixture of cis/trans isomers. LC-MS calculated for $C_{40}H_{50}N_7O_5$ $(M+H)^+$: m/z=708.4; found 708.4.

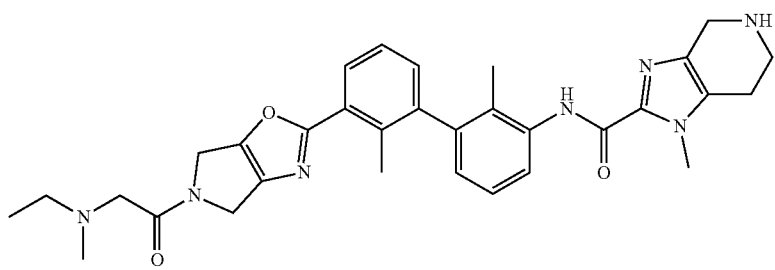 [SMILES: CCN(C)CC(=O)N1Cc2nc(-c3cccc(-c4cccc(NC(=O)c5nc6c(n5C)CCNC6)c4C)c3C)oc2C1]

Example 174

4-(2-((2,2'-dichloro-3'-(5-(3-(ethyl(methyl)amino)propanoyl)-5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid

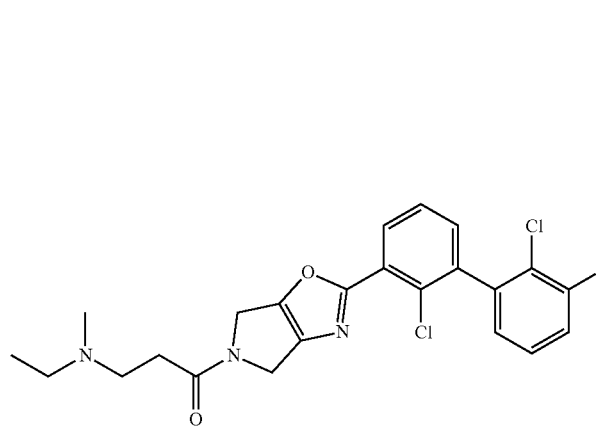

Step 1: tert-butyl 2-((2,2'-dichloro-3'-(5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridine-5-carboxylate

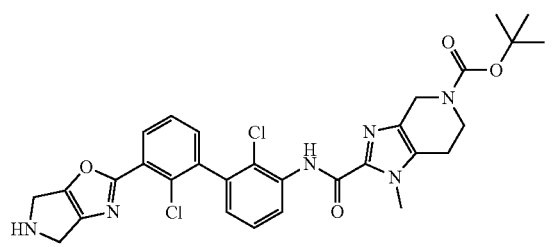 [SMILES: Cn1c(C(=O)Nc2cccc(-c3cccc(-c4nc5c(o4)CNC5)c3Cl)c2Cl)nc2c1CCN(C(=O)OC(C)(C)C)C2]

A mixture of 2-(3-bromo-2-chlorophenyl)-5,6-dihydro-4H-pyrrolo[3,4-d]oxazole (Example 169, Step 1: 235 mg, 0.785 mmol), tert-butyl 2-((2-chloro-3-(4,4,5,5-tetramethyl-1,3,2-dioxaborolan-2-yl)phenyl)carbamoyl)-1-methyl-1,4,6,7-tetrahydro-5H-imidazo[4,5-c]pyridine-5-carboxylate (Example 54, step 3: 405 mg, 0.785 mmol), dichloro[1,1'-bis(diphenylphosphino)ferrocene]palladium (II) dichloromethane adduct (64.1 mg, 0.078 mmol) and sodium carbonate (166 mg, 1.569 mmol) in 1,4-dioxane (6 mL) and water (2 mL) was stirred at 105° C. under nitrogen atmosphere for 1 h. The reaction was diluted with DCM and water, the aqueous layer was extracted with DCM once. The combined organic layer was washed with brine, dried over Na$_2$SO$_4$, filtered and concentrated. The crude was used in the next step without further purification. LC-MS calculated for C$_{30}$H$_{31}$Cl$_2$N$_6$O$_4$ (M+H)$^+$: m/z=609.2; found 609.2.

Step 2: tert-butyl 2-((2,2'-dichloro-3'-(5-(3-chloropropanoyl)-5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridine-5-carboxylate

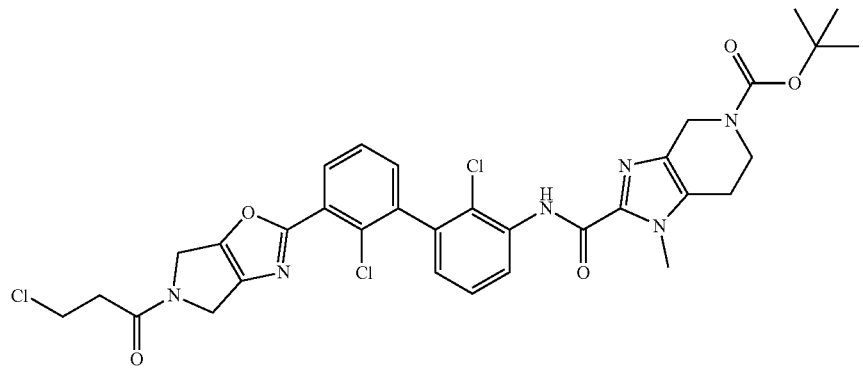 [SMILES: Cn1c(C(=O)Nc2cccc(-c3cccc(-c4nc5c(o4)CN(C(=O)CCCl)C5)c3Cl)c2Cl)nc2c1CCN(C(=O)OC(C)(C)C)C2]

A solution of tert-butyl 2-((2,2'-dichloro-3'-(5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridine-5-carboxylate (Step 1: 245 mg, 0.402 mmol) in DCM (2 mL) was added 3-chloropropanoyl chloride (61.2 mg, 0.482 mmol) and DIEA (210 μL, 1.206 mmol) at 0° C. The reaction mixture was stirred at room temperature for 2 h. The reaction was diluted with water, and the aqueous layer was extracted with DCM once. The combined organic layers were dried over $Na_2SO_4$, filtered and concentrated. The residue was purified with flash chromatography (eluting with 70% ethyl acetate in hexanes) to give the desired product (105 mg, 37%). LC-MS calculated for $C_{33}H_{34}Cl_3N_6O_5$ $(M+H)^+$: m/z=699.2; found 699.2.

Step 3: tert-butyl 2-((2,2'-dichloro-3'-(5-(3-(ethyl(methyl)amino)propanoyl)-5,6-dihydro-4H-pyrrolo[3,4-d]oxazol-2-yl)-[1,1'-biphenyl]-3-yl) carbamoyl)-1-methyl-1,4,6,7-tetrahydro-5H-imidazo[4,5-c]pyridine-5-carboxylate To a solution of tert-butyl 2-((2,2'-dichloro-3'-(5-(3-(ethyl(methyl)amino)propanoyl)-5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridine-5-carboxylate (Step 3: 20 mg, 0.028 mmol) in DCM (1.0 mL) was added trifluoroacetic acid (0.021 ml, 0.277 mmol). The resultant mixture was stirred at room temperature for 1 h. The solvent was removed in vacuo. The crude was used in the next step without further purification. LC-MS calculated for $C_{31}H_{34}Cl_2N_7O_3$ $(M+H)^+$: m/z=622.2; found 622.2.

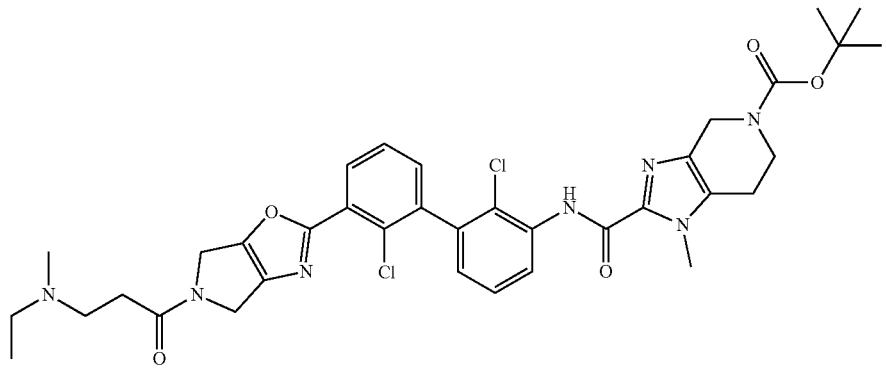 [SMILES: CCN(C)CCC(=O)N1Cc2nc(-c3cccc(-c4cccc(NC(=O)c5nc6c(n5C)CCN(C(=O)OC(C)(C)C)C6)c4Cl)c3Cl)oc2C1]

The mixture of tert-butyl 2-((2,2'-dichloro-3'-(5-(3-chloropropanoyl)-5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridine-5-carboxylate (Step 2: 50.0 mg, 0.071 mmol), N-methylethanamine (6.33 mg, 0.107 mmol), TEA (0.030 ml, 0.214 mmol) in DMF (1.0 mL) was heated at 60° C. for 2 h. The reaction mixture was diluted with methanol and 1 N HCl, then purified with prep-HPLC (pH=2, acetonitrile/water+TFA) to give the desired product. LC-MS calculated for $C_{36}H_{42}Cl_2N_7O_5$ $(M+H)^+$: m/z=722.3; found 722.3.

Step 4: N-(2,2'-dichloro-3'-5-(3-(ethyl(methyl)amino)propanoyl)-5,6-dihydro-4H-pyrrolo[3,4-d]oxazol-2-yl)-[1,1'-biphenyl]-3-yl)-1-methyl-4,5,6,7-tetrahydro-1H-imidazo[4,5-c]pyridine-2-carboxamide Step 5: 4-(2-((2,2'-dichloro-3'-(5-(3-(ethyl(methyl)amino)propanoyl)-5,6-dihydro-4H-pyrrolo[3,4-d]oxazol-2-yl)-[1,1'-biphenyl]-3-yl)carbamoyl)-1-methyl-1,4,6,7-tetrahydro-5H-imidazo[4,5-c]pyridin-5-yl)-1-methylcyclohexane-1-carboxylic acid A mixture of 1-methyl-4-oxocyclohexane-1-carboxylic acid (3.8 mg, 0.024 mmol), N-(2,2'-dichloro-3'-(5-(3-(ethyl(methyl)amino)propanoyl)-5,6-dihydro-4H-pyrrolo[3,4-d]oxazol-2-yl)-[1,1'-biphenyl]-3-yl)-1-methyl-4,5,6,7-tetrahydro-1H-imidazo[4,5-c]pyridine-2-carboxamide (Step 4: 10 mg, 0.016 mmol) in DCM (1 mL) was added DIEA (5.6 μL, 0.032 mmol). After stirring at room temperature for 2.5 h, sodium triacetoxyborohydride (7.0 mg, 0.032 mmol) was added and stirred overnight. After removing the solvent in vacuo, the residue was dissolved in methanol and 1 N HCl and purified with prep-HPLC (pH=2, acetonitrile/water+

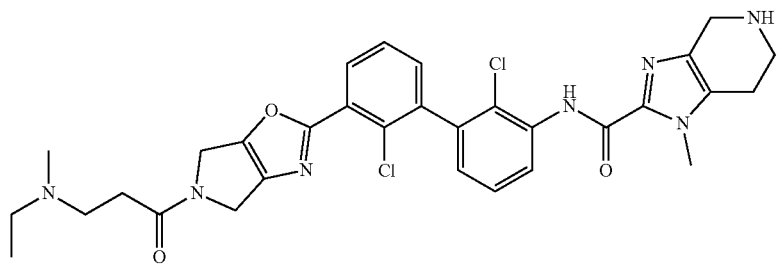 [SMILES: CCN(C)CCC(=O)N1Cc2nc(-c3cccc(-c4cccc(NC(=O)c5nc6c(n5C)CCNC6)c4Cl)c3Cl)oc2C1]

TFA) to give the desired product as a mixture of cis/trans isomers. LC-MS calculated for $C_{39}H_{46}Cl_2N_7O_5$ (M+H)$^+$: m/z=762.3; found 762.3.

Example 175

4-(2-((2'-chloro-3'-(1,5-dimethyl-4,5,6,7-tetrahydro-1H-imidazo[4,5-c]pyridine-2-carboxamido)-2-methyl-[1,1'-biphenyl]-3-yl)carbamoyl)-1-methyl-1,4,6,7-tetrahydro-5H-imidazo[4,5-c]pyridin-5-yl)adamantane-1-carboxylic acid

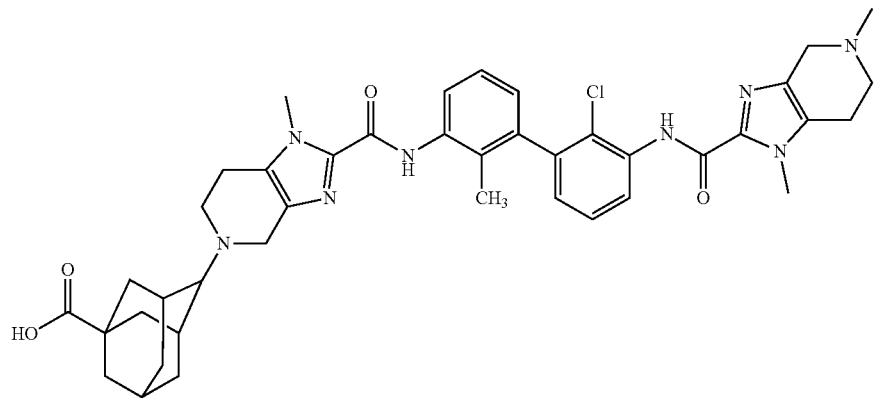 [SMILES: Cc1c(NC(=O)c2nc3c(n2C)CCN(C2C4CC5CC2CC(C(=O)O)(C5)C4)C3)cccc1-c1cccc(NC(=O)c2nc3c(n2C)CCN(C)C3)c1Cl]

This compound was prepared using similar procedures as described for Example 104 with 4-oxoadamantane-1-carboxylic acid replacing 1-ethyl-4-oxocyclohexane-1-carboxylic acid. The reaction mixture was purified by prep-HPLC (pH=2, acetonitrile/water+TFA) to give two desired products as the TFA salt:

Compound 175-1: retention time on analytical LC-MS (pH=2, acetonitrile/water+TFA) $t_r$-0.93 min, LCMS calculated for $C_{41}H_{48}ClN_8O_4$ (M+H)$^+$: m/z=751.3; found: 751.3;

Compound 175-2: retention time on analytical LC-MS (pH=2, acetonitrile/water+TFA) $t_r$=0.98 min, LCMS calculated for $C_{41}H_{48}ClN_8O_4$ (M+H)$^+$: m/z=751.3; found: 751.3;

Example 176

4-((2-(2,2'-dichloro-3'-(5-ethyl-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)bicyclo[2.2.1]heptane-1-carboxylic acid

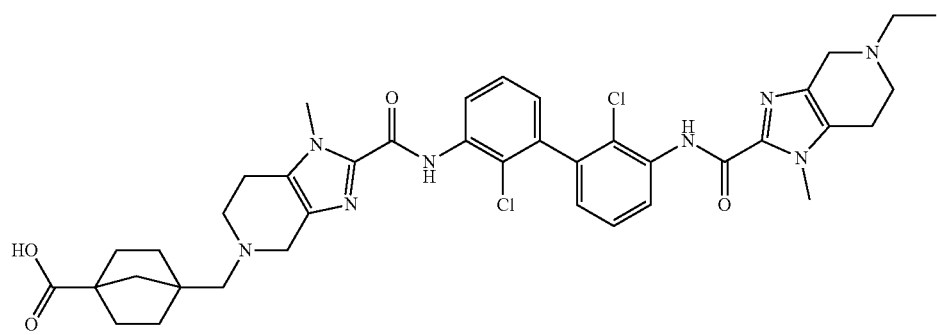 [SMILES: CCN1CCc2c(nc(C(=O)Nc3cccc(-c4cccc(NC(=O)c5nc6c(n5C)CCN(CC57CCC(C(=O)O)(CC5)C7)C6)c4Cl)c3Cl)n2C)C1]

Step 1: tert-butyl 2-((2,2'-dichloro-3'-(5-((4-(methoxycarbonyl)bicyclo[2.2H]heptan-1-yl)methyl)-1-methyl-4,5,6,7-tetrahydro-1H-imidazo[4,5-c]pyridine-2-carboxamido)-[1,1-biphenyl]-3-yl)carbamoyl)-1-methyl-1,4,6,7-tetrahydro-5H-imidazo[4,5-c]pyridine-5-carboxylate

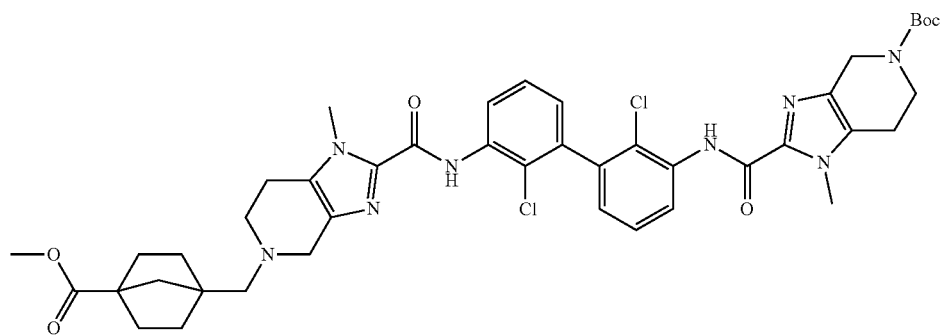 [SMILES: COC(=O)C12CCC(CN3CCc4c(nc(C(=O)Nc5cccc(-c6cccc(NC(=O)c7nc8c(n7C)CCN(C(=O)OC(C)(C)C)C8)c6Cl)c5Cl)n4C)C3)(CC1)C2]

Methyl 4-formylbicyclo[2.2.1]heptane-1-carboxylate (Example 84, Step 1: 53.6 mg, 0.294 mmol) was added to a mixture of tert-butyl 2-((2,2'-dichloro-3'-(1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 60, Step 1: 100 mg, 0.147 mmol) and sodium triacetoxyborohydride (94 mg, 0.441 mmol) in dichloromethane (1.5 mL). After being stirred at room temperature for 2 h, the reaction was quenched with saturated aqueous NaHCO$_3$ solution and extracted with dichloromethane. The combined organic layers were dried over Na$_2$SO$_4$, filtered, and concentrated under reduced pressure. The residue was purified by flash chromatography on a silica gel column eluting with 10% methanol in dichloromethane to afford the desired product. LC-MS calculated for $C_{43}H_{51}Cl_2NO_6$ (M+H)$^+$: m/z=845.3; found 845.4

Step 2: 4-((2-(2,2'-dichloro-3'-(5-ethyl-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)bicyclo[2.2.7]heptane-1-carboxylic acid A solution of tert-butyl 2-((2,2'-dichloro-3'-(5-((4-(methoxycarbonyl)bicyclo[2.2.1]heptan-1-yl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Step 1: 20 mg, 0.024 mmol) in trifluoroacetic acid (0.05 mL) and dichloromethane (0.1 mL) was stirred at room temperature for 1 h. The mixture was concentrated under reduced pressure. The residue was dissolved in dichloromethane (0.24 mL) and sequentially treated with N,N-diisopropylethylamine (16.5 µL, 0.095 mmol), sodium triacetoxyborohydride (15.0 mg, 0.071 mmol) and acetaldehyde (2.1 mg, 0.047 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was dissolved in THF/MeOH/water (0.2 mL/0.2 mL/0.1 mL), and treated with lithium hydroxide, monohydrate (5.0 mg, 0.118 mmol). After being stirred at 30° C. for 3 h, the reaction mixture was diluted with MeOH, and purified by prep-HPLC (pH=10, acetonitrile/water+ NH$_4$OH) to give the desired product. LC-MS calculated for $C_{39}H_{45}Cl_2N_8O_4$ (M+H)$^+$: m/z=759.3; found 759.4

TABLE 26

The compounds in Table 26 were prepared in accordance with the synthetic protocols set forth in Example 176 using the appropriate starting materials.

| Example # | Name | Structure | LC-MS (M + H)+ |
|---|---|---|---|
| 177 | 4-((2-(2,2'-dichloro-3'-(5-isopropyl-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)bicyclo[2.2.1]heptane-1-carboxylic acid | 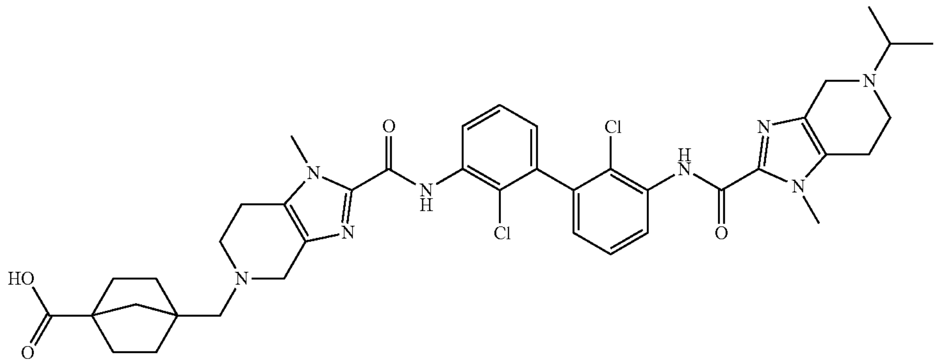 [SMILES: CC(C)N1CCc2c(nc(C(=O)Nc3cccc(-c4cccc(NC(=O)c5nc6c(n5C)CCN(CC57CCC(C(=O)O)(CC5)C7)C6)c4Cl)c3Cl)n2C)C1] | 773.4 |
| 178 | 4-((2-(2,2'-dichloro-3'-(5-cyclobutyl-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)bicyclo[2.2.1]heptane-1-carboxylic acid | 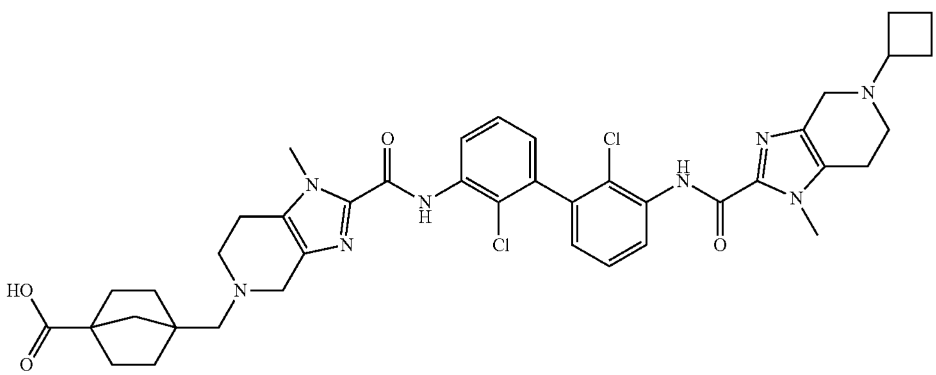 [SMILES: Cn1c(C(=O)Nc2cccc(-c3cccc(NC(=O)c4nc5c(n4C)CCN(C4CCC4)C5)c3Cl)c2Cl)nc2c1CCN(CC13CCC(C(=O)O)(CC1)C3)C2] | 785.4 |
| 179 | 4-((2-(2,2'-dichloro-3'-(1-methyl-5-(tetrahydro-2H-pyran-4-yl)-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin- | 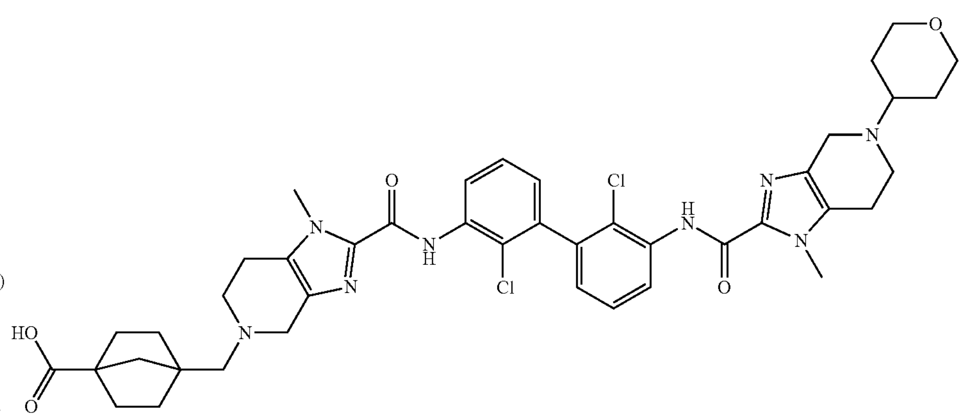 | 815.3 |

TABLE 26-continued

The compounds in Table 26 were prepared in accordance with the synthetic protocols set forth in Example 176 using the appropriate starting materials.

| Example # | Name | Structure | LC-MS (M + H)+ |
|---|---|---|---|
| | 5(4H)-yl)methyl)bicyclo[2.2.1]heptane-1-carboxylic acid | | |

Example 180

4-((2-(2,2'-dichloro-3'-(5-(2-hydroxyethyl)-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)bicyclo[2.2.1]heptane-1-carboxylic acid

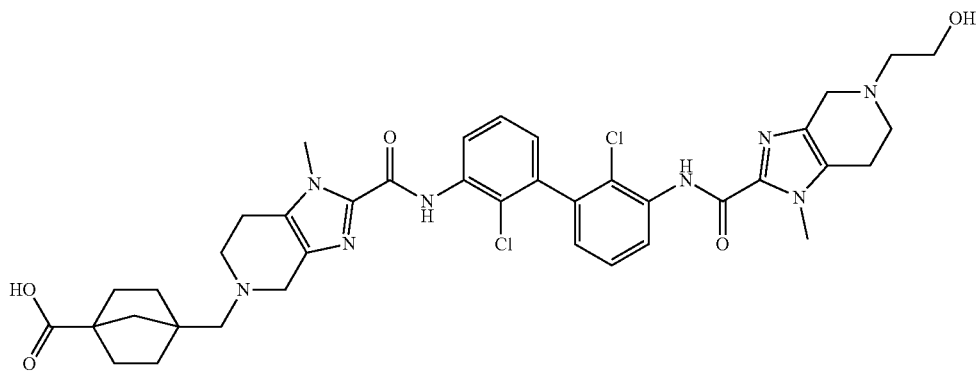 [SMILES: Cn1c(C(=O)Nc2cccc(-c3cccc(NC(=O)c4nc5c(n4C)CCN(CC46CCC(C(=O)O)(CC4)C6)C5)c3Cl)c2Cl)nc2c1CCN(CCO)C2]

A solution of tert-butyl 2-((2,2'-dichloro-3'-(5-((4-(methoxycarbonyl)bicyclo[2.2.1]heptan-1-yl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 176, Step 1: 20 mg, 0.024 mmol) in dichloromethane (0.1 mL) and trifluoroacetic acid (0.1 mL) was stirred at room temperature for 30 min. The mixture was concentrated under reduced pressure. The residue was dissolved in dichloromethane (0.24 mL) and sequentially treated with N,N-diisopropylethylamine (0.017 mL, 0.095 mmol), sodium triacetoxyborohydride (15.0 mg, 0.071 mmol) and 2-((tert-butyldimethylsilyl)oxy)acetaldehyde (8.2 mg, 0.047 mmol). After being stirred at room temperature for 2 h, the reaction was quenched with saturated aqueous NaHCO$_3$ solution, and extracted with dichloromethane. The combined organic layers were dried over Na$_2$SO$_4$, filtered, and concentrated under reduced pressure. The residue was treated with 4 N HCl in 1,4-dioxane (0.177 mL, 0.709 mmol) at 30° C. for 1 h, and then the solvent was evaporated. The residue was dissolved in THF/MeOH/water (0.2 mL/0.2 mL/0.1 mL), and then treated with lithium hydroxide, monohydrate (9.9 mg, 0.236 mmol). After being stirred at 30° C. for 3 h, the reaction mixture was diluted with MeOH, and purified by prep-HPLC (pH=10, acetonitrile/water+NH$_4$OH) to give the desired product. LC-MS calculated for C$_{39}$H$_{45}$Cl$_2$N$_8$O$_5$ (M+H)$^+$: m/z=775.3; found 775.4.

TABLE 27

The compounds in Table 27 were prepared in accordance with the synthetic protocols set forth in Example 180 using the appropriate starting materials.

| Example # | Name | Structure | LC-MS (M + H)+ |
|---|---|---|---|
| 181 | (S)-4-((2-(2,2'-dichloro-3'-(5-(2-hydroxypropyl)-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)bicyclo[2.2.1]heptane-1-carboxylic acid | 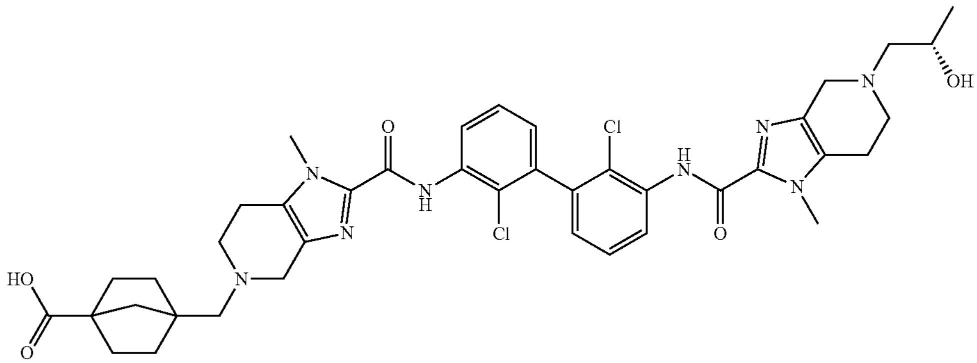 [SMILES: C[C@H](O)CN1CCc2c(nc(C(=O)Nc3cccc(-c4cccc(NC(=O)c5nc6c(n5C)CCN(CC57CCC(C(=O)O)(CC5)C7)C6)c4Cl)c3Cl)n2C)C1] | 789.4 |
| 182 | (R)-4-((2-(2,2'-dichloro-3'-(5-(2-hydroxypropyl)-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)bicyclo[2.2.1]heptane-1-carboxylic acid | 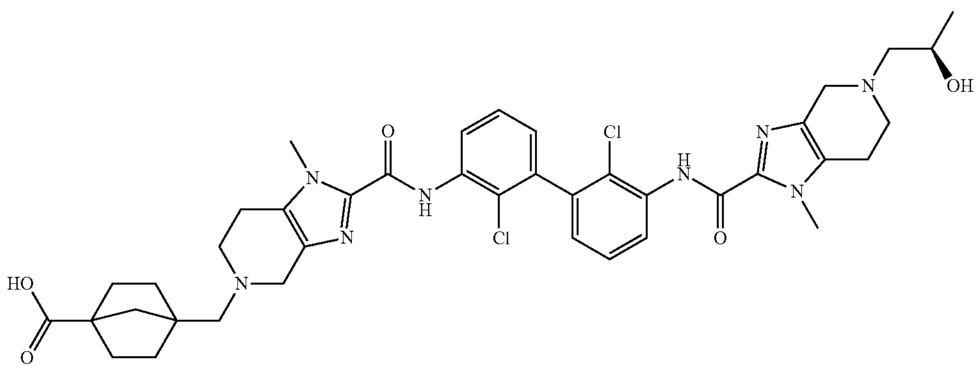 [SMILES: C[C@@H](O)CN1CCc2c(nc(C(=O)Nc3cccc(-c4cccc(NC(=O)c5nc6c(n5C)CCN(CC57CCC(C(=O)O)(CC5)C7)C6)c4Cl)c3Cl)n2C)C1] | 789.4 |

Example 183

4-((2-(2,2'-dichloro-3'-(5-(4-hydroxycyclohexyl)-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)bicyclo[2.2.1]heptane-1-carboxylic acid diisopropylethylamine (16.5 µL, 0.095 mmol), sodium triacetoxyborohydride (15.0 mg, 0.071 mmol) and 4-hydroxycyclohexan-1-one (5.4 mg, 0.047 mmol). After being stirred at room temperature for 2 h, the reaction mixture was diluted with MeOH, and purified by prep-HPLC (pH=10, acetonitrile/water+NH$_4$OH) to give two desired products (cis/trans isomers):

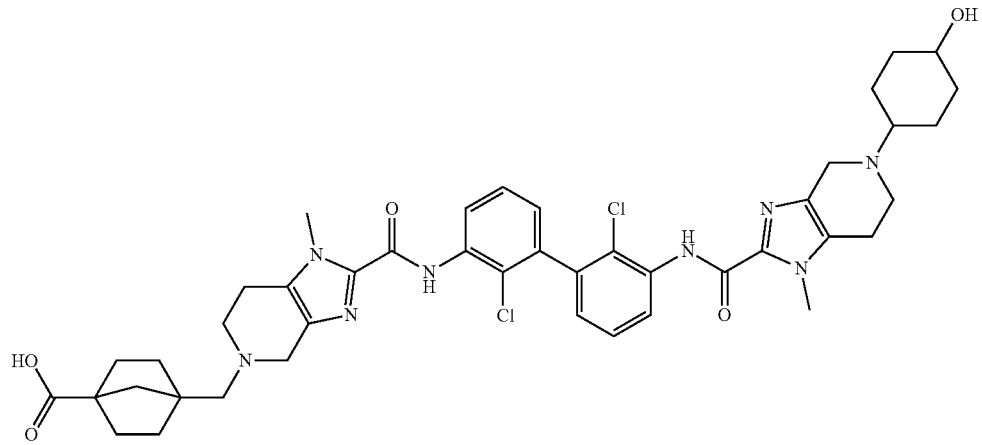 [SMILES: Cn1c(C(=O)Nc2cccc(-c3cccc(NC(=O)c4nc5c(n4C)CCN(C4CCC(O)CC4)C5)c3Cl)c2Cl)nc2c1CCN(CC13CCC(C(=O)O)(CC1)C3)C2]

Step 1: Methyl 4-((2((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridin-5-yl)methyl)bicyclo[2.2.1]heptane-1-carboxylate Peak 1: retention time on analytical LC-MS (pH=10, acetonitrile/water+NH$_4$OH) t$_r$=1.81 min, LCMS calculated for C$_{44}$H$_{53}$Cl$_2$N$_8$O$_5$ (M+H)$^+$: m/z=843.4; Found: 843.4;

Peak 2: retention time on analytical LC-MS (pH=10, acetonitrile/water+NH$_4$OH) U=1.84 min, LCMS calculated for C$_{44}$H$_{53}$Cl$_2$N$_8$O$_5$ (M+H)$^+$: m/z=843.4; Found: 843.4.

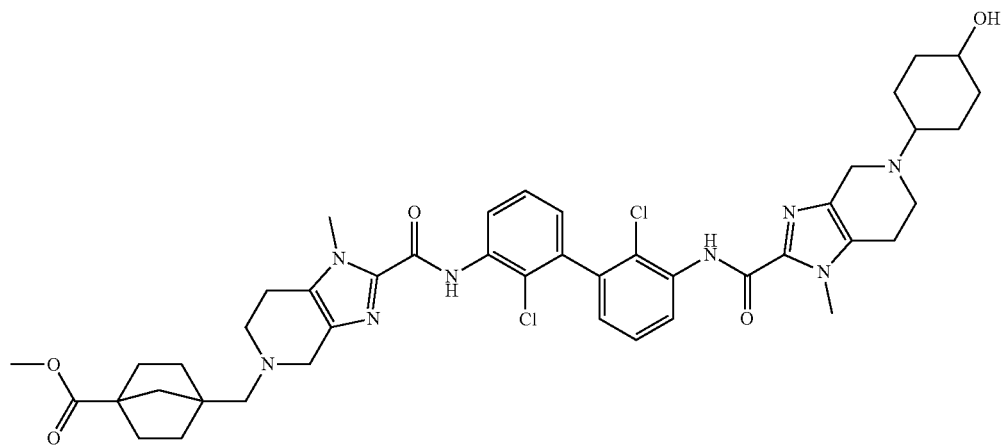 [SMILES: COC(=O)C12CCC(CN3CCc4c(nc(C(=O)Nc5cccc(-c6cccc(NC(=O)c7nc8c(n7C)CCN(C7CCC(O)CC7)C8)c6Cl)c5Cl)n4C)C3)(CC1)C2]

A solution of tert-butyl 2-((2,2'-dichloro-3'-(5-((4-(methoxycarbonyl)bicyclo[2.2.1]heptan-1-yl)methyl)-1-methyl-4,5,6,7-tetrahydro-1H-imidazo[4,5-c]pyridine-2-carboxamido)-[1,1'-biphenyl]-3-yl)carbamoyl)-1-methyl-1,4,6,7-tetrahydro-5H-imidazo[4,5-c]pyridine-5-carboxylate (Example 176, Step 1: 20 mg, 0.024 mmol) in trifluoroacetic acid (0.05 mL) and dichloromethane (0.1 mL) was stirred at room temperature for 1 h. The mixture was concentrated under reduced pressure. The residue was dissolved in dichloromethane (0.24 mL) and sequentially treated with N,N-

Step 2: 4-((2-(2,2'-dichloro-3'-(5-(4-hydroxycyclohexyl)-1-methyl-4,5,6,7-tetrahydro-1H-imidazo[4,5-c]pyridine-2-carboxamido)biphenyl-3-ylcarbamoyl)-1-methyl-6,7-dihydro-1H-imidazo[4,5-c]pyridin-5(4H)-yl)methyl)bicyclo[2.2.1]heptane-1-carboxylic acid Methyl 4-((2-((2,2'-dichloro-3'-(5-(4-hydroxycyclohexyl)-1-methyl-4,5,6,7-tetrahydro-1H-imidazo[4,5-c]pyridine-2-carboxamido)-[1,1'-biphenyl]-3-yl)carbamoyl)-1- methyl-1,4,6,7-tetrahydro-5H-imidazo[4,5-c]pyridin-5-yl)methyl)bicyclo[2.2.1]heptane-1-carboxylate (5 mg, 5.93 µmol) from Step 1, peak 1 and peak 2 were respectively treated with lithium hydroxide, monohydrate (1.3 mg, 0.030 mmol) in THF/MeOH/water (0.2 mL/0.2 mL/0.1 mL) at 30° C. for 3 h. The reactions were purified by prep-HPLC (pH=10, acetonitrile/water+TFA) to give the desired products.

Compound 183-1 (from Step 1, peak 1): LC-MS calculated for $C_{43}H_{51}Cl_2N_8O_5$ $(M+H)^+$: m/z=829.3; found: 829.4.

Compound 183-2 (from Step 1, peak 2): LC-MS calculated for $C_{43}H_{51}Cl_2N_8O_5$ $(M+H)^+$: m/z=829.3; found: 829.4.

Example 184

2-(2-(3-(2,3-dihydrobenzo[b][1,4]dioxin-6-yl)-2-methylphenyl)-6-(((2-hydroxyethyl)amino)methyl)-[1,2,4]triazolo[1,5-a]pyridin-8-yl)acetonitrile

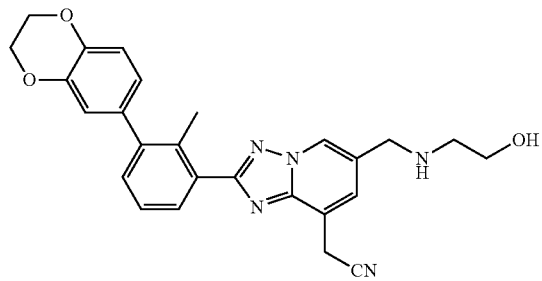 [SMILES: Cc1c(-c2ccc3c(c2)OCCO3)cccc1-c1nc2c(CC#N)cc(CNCCO)cn2n1]

Step 1: 6-(3-bromo-2-methylphenyl)-2,3-dihydrobenzo[b][1,4]dioxine

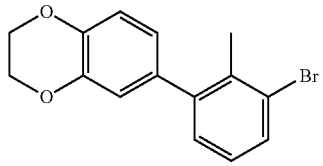 [SMILES: Cc1c(Br)cccc1-c1ccc2c(c1)OCCO2]

A mixture of 2-(2,3-dihydrobenzo[b][1,4]dioxin-6-yl)-4,4,5,5-tetramethyl-1,3,2-dioxaborolane (2.00 g, 7.63 mmol), 1-bromo-3-iodo-2-methylbenzene (2.72 g, 9.16 mmol), 1,1'-Bis(diphenylphosphino)ferrocene-palladium(II)dichloride dichloromethane complex (0.62 g, 0.76 mmol) and potassium phosphate, tribasic (4.54 g, 21.4 mmol) in 1,4-dioxane (34.7 ml)/Water (3.47 ml) was stirred at 80° C. for 6 h. The crude was diluted with DCM, dried and filtered. The filtrate was concentrated. The residue was purified with chromatography (4-10% EtOAc/Hex) on silica gel to give the desired product. LC-MS calculated for $C_{15}H_{14}BrO_2$ $(M+H)^+$: m/z=305.0; found 304.9.

Step 2: 6-[2-methyl-3-(4,4,5,5-tetramethyl-1,3,2-dioxaborolan-2-yl)phenyl]-2,3-dihydro-1,4-benzodioxine

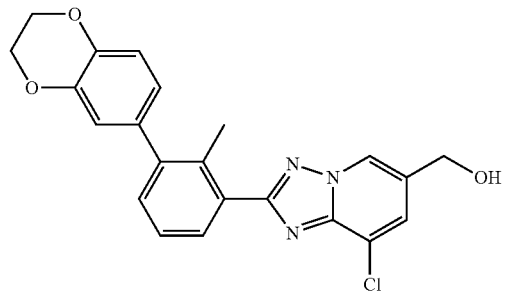 [SMILES: Cc1c(-c2ccc3c(c2)OCCO3)cccc1-c1nc2c(Cl)cc(CO)cn2n1]

A mixture of 6-(3-bromo-2-methylphenyl)-2,3-dihydrobenzo[b][1,4]dioxine (2.3 g, 7.6 mmol), bis(pinacolato)diboron (Step 1: 2.7 g, 10.7 mmol), dichloro[1,1'-bis(diphenylphosphino)ferrocene]palladium (II) dichloromethane adduct (0.62 g, 0.76 mmol) and potassium acetate (2.1 g, 21.4 mmol) was charged with nitrogen and stirred at 110° C. for 1 h. The crude was diluted with DCM, and then filtered through Celite. The filtrate was concentrated. The residue was purified by chromatography (1-8% EtOAc/Hex) on silica gel to give the desired product (2.36 g, 88% yield). LC-MS calculated for $C_{21}H_{26}BO_4$ $(M+H)^+$: m/z=353.2; found 353.2.

Step 3: {8-chloro-2-[3-(2,3-dihydro-1,4-benzodioxin-6-yl)-2-methylphenyl][1,2,4]triazolo[1,5-a]pyridin-6-yl}methanol A mixture of (2-bromo-8-chloro[1,2,4]triazolo[1,5-a]pyridin-6-yl)methanol (prepared according to the procedures in US Publication No. 2017/0107216: 339 mg, 1.29 mmol), 6-[2-methyl-3-(4,4,5,5-tetramethyl-1,3,2-dioxaborolan-2-yl)phenyl]-2,3-dihydro-1,4-benzodioxine (Step 2: 501 mg, 1.42 mmol), $K_3PO_4$ (494 mg, 2.33 mmol) and [1,1'-Bis(diphenylphosphino)ferrocene]dichloropalladium (II), complex with dichloromethane (1:1) (100 mg, 0.13 mmol) in 1,4-Dioxane/Water was stirred and heated at 100° C. for 2 h. The crude was dried, filtered and concentrated. The residue was purified by chromatography (50-90% EtOAc/Hex) on silica gel to give the desired product (335 mg, 64% yield). LC-MS calculated for $C_{22}H_{19}ClN_3O_3$ $(M+H)^+$: m/z=408.1; found 408.1.

Step 4: 8-chloro-2-[3-(2,3-dihydro-1,4-benzodioxin-6-yl)-2-methylphenyl][1,2,4]triazolo[1,5-a]pyridine-6-carbaldehyde

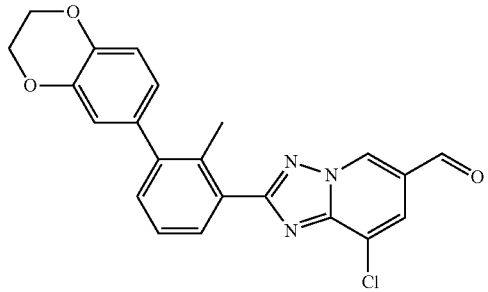 [SMILES: Cc1c(-c2ccc3c(c2)OCCO3)cccc1-c1nc2c(Cl)cc(C=O)cn2n1]

Dess-Martin periodinane (627 mg, 1.48 mmol) was added to the solution of {8-chloro-2-[3-(2,3-dihydro-1,4-benzodioxin-6-yl)-2-methylphenyl][1,2,4]triazolo[1,5-a]pyridin-6-yl}methanol (Step 3: 335 mg, 0.82 mmol) in methylene chloride. The mixture was stirred at room temperature for 1 h. The mixture was quenched with aq. sodium bisulfite, extracted with DCM. The combined extracts were dried over $Na_2SO_4$, filtered and concentrated. The residue was purified by chromatography (15-30% EtOAc/Hex) to give the desired product (114 mg, 34% yield). LC-MS calculated for $C_{22}H_{17}ClN_3O_3$ $(M+H)^+$: m/z=406.1; found 406.1.

Step 5: 2-[({8-chloro-2-[3-(2,3-dihydro-1,4-benzodioxin-6-yl)-2-methylphenyl][1,2,4]triazolo[1,5-a]pyridin-6-yl}methyl)amino]ethanol

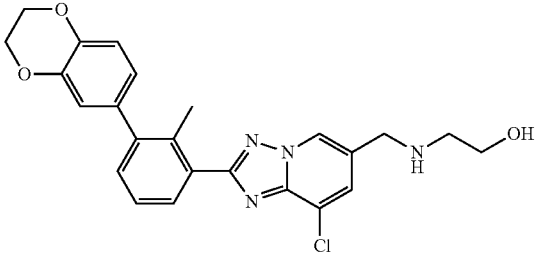 [SMILES: Cc1c(-c2ccc3c(c2)OCCO3)cccc1-c1nc2c(Cl)cc(CNCCO)cn2n1]

Ethanolamine (15 mg, 0.25 mmol) was added to a solution of 8-chloro-2-[3-(2,3-dihydro-1,4-benzodioxin-6-yl)-2-methylphenyl][1,2,4]triazolo[1,5-a]pyridine-6-carbaldehyde (Step 4: 34 mg, 0.084 mmol) in N,N-Dimethylformamide, followed by trifluoroacetic Acid (0.25 mmol). The reaction mixture was stirred at room temperature for 10 min. Then sodium triacetoxyborohydride (62 mg, 0.29 mmol) was added in two portions. The reaction mixture was stirred at room temperature overnight. The crude was diluted with water and extracted with EtOAc. The organic phase was concentrated. The residue was purified by chromatography on silica gel to give the desired product (31 mg, 82% yield). LC-MS calculated for $C_{24}H_{24}ClN_4O_3$ $(M+H)^+$: m/z=451.2; found 451.1.

Step 6: 2-(2-(3-(2,3-dihydrobenzo[b][1,4]dioxin-6-yl)-2-methylphenyl)-6-(((2-hydroxyethyl)amino)methyl)-[1,2,4]triazolo[L5-a]pyridin-8-yl)acetonitrile (2'-Aminobiphenyl-2-yl)(chloro)[dicyclohexyl(2',4',6'-triisopropylbiphenyl-2-yl)phosphoranylidene]palladium (3.4 mg, 0.0043 mmol) was added to the mixture of 2-[({8-chloro-2-[3-(2,3-dihydro-1,4-benzodioxin-6-yl)-2-methylphenyl][1,2,4]triazolo[1,5-a]pyridin-6-yl}methyl)amino]ethanol (Step 5: 10 mg, 0.02 mmol), 4-(4,4,5,5-tetramethyl-1,3,2-dioxaborolan-2-yl)isoxazole (7.6 mg, 0.039 mmol) and Potassium phosphate (14 mg, 0.065 mmol) in 1,4-Dioxane/Water. The mixture was stirred at 100° C. for 1 h. The crude was diluted with MeOH and filtered through Celite. The filtrate was purified with prep-HPLC (pH=2, acetonitrile/water+TFA) to give the desired product as the TFA salt. LCMS calculated for $C_{26}H_{26}N_5O_3$ $(M+H)^+$: m/z=456.2; found 456.2.

Example 185

(R)-1-((7-chloro-2-(2'-cyano-3'-(1,5-dimethyl-4,5,6,7-tetrahydro-1H-imidazo[4,5-c]pyridine-2-carboxamido)-2-methylbiphenyl-3-yl)benzo[d]oxazol-5-yl)methyl)pyrrolidine-3-carboxylic acid

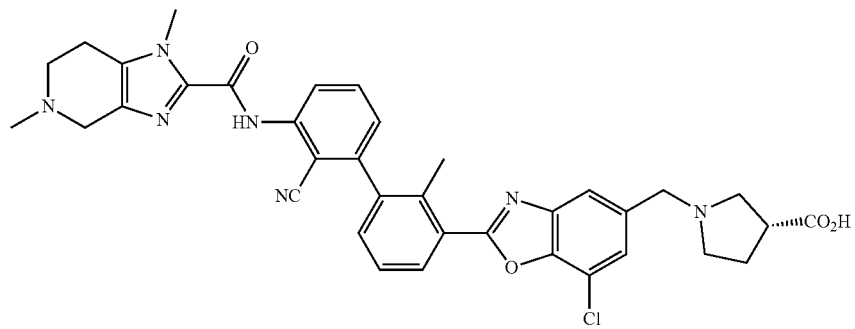 [SMILES: Cc1c(-c2nc3cc(CN4CC[C@@H](C(=O)O)C4)cc(Cl)c3o2)cccc1-c1cccc(NC(=O)c2nc3c(n2C)CCN(C)C3)c1C#N]

Step 1: N-(3'-(7-chloro-5-(hydroxymethyl)benzo[d]oxazol-2-yl)-2-cyano-2'-methyl-[1,1'-biphenyl]-3-yl)-1,5-dimethyl-4,5,6,7-tetrahydro-1H-imidazo[4,5-c]pyridine-2-carboxamide

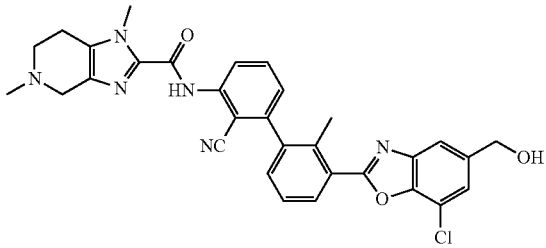 [SMILES: Cc1c(-c2nc3cc(CO)cc(Cl)c3o2)cccc1-c1cccc(NC(=O)c2nc3c(n2C)CCN(C)C3)c1C#N]

This compound was prepared using similar procedures as described for Example 1, Step 1-10 with 2-amino-6-bromobenzonitrile replacing 3-bromo-2-chloroaniline in Step 8. LCMS calculated for $C_{31}H_{28}ClN_6O_3$ (M+H)$^+$: m/z=567.2; found 567.2.

Step 2: N-(3'-(7-chloro-5-formylbenzo[d]oxazol-2-yl)-2-cyano-2'-methyl-[1,1'-biphenyl]-3-yl)-1,5-dimethyl-4,5,6,7-tetrahydro-1H-imidazo[4,5-c]pyridine-2-carboxamide

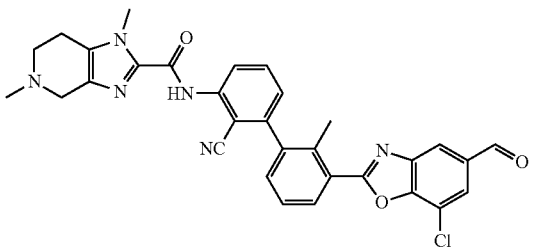 [SMILES: Cc1c(-c2nc3cc(C=O)cc(Cl)c3o2)cccc1-c1cccc(NC(=O)c2nc3c(n2C)CCN(C)C3)c1C#N]

To a stirred solution of N-(3'-(7-chloro-5-(hydroxymethyl)benzo[d]oxazol-2-yl)-2-cyano-2'-methyl-[1,1'-biphenyl]-3-yl)-1,5-dimethyl-4,5,6,7-tetrahydro-1H-imidazo[4,5-c]pyridine-2-carboxamide (76 mg, 0.13 mmol) in DCM (3.0 mL) was added sodium bicarbonate (113 mg, 1.34 mmol) and Dess-Martin periodinane (85 mg, 0.2 mmol). The resulted mixture was stirred at room temperature for 2 hours, and then filtered. The filtrate was concentrated under reduced pressure. The residue was used in the next step without further purification. LCMS calculated for $C_{31}H_{26}ClN_6O_3$ (M+H)$^+$: m/z=565.2; found 565.1.

Step 3: (R)-1-((7-chloro-2-(2'-cyano-3(1,5-dimethyl-4,5,6,7-tetrahydro-1H-imidazo[4,5-c]pyridine-2-carboxamido)-2-methylbiphenyl-3-yl)benzo[d]oxazol-5-yl)methyl)pyrrolidine-3-carboxylic acid To a solution of N-(3'-(7-chloro-5-formylbenzo[d]oxazol-2-yl)-2-cyano-2'-methyl-[1,1'-biphenyl]-3-yl)-1,5-dimethyl-4,5,6,7-tetrahydro-1H-imidazo[4,5-c]pyridine-2-carboxamide (10 mg, 0.018 mmol) in DCM (1 mL) was added (R)-pyrrolidine-3-carboxylic acid (10 mg, 0.087 mmol) and DIEA (0.025 mL, 0.142 mmol). The mixture was stirred at room temperature for 1 hour, and then sodium triacetoxyborohydride (11.25 mg, 0.053 mmol) was added. The resulting mixture was stirred at room temperature overnight then concentrated. The residue was dissolved in MeOH then purified by prep-HPLC (pH=2, acetonitrile/water+TFA) to give the desired product as the TFA salt. LCMS calculated for $C_{36}H_{35}ClN_7O_4$ (M+H)$^+$: m/z=664.2; found 664.2.

Example 186

(R)-1-((8-chloro-2-(3'-(3-(((R)-3-hydroxypyrrolidin-1-yl)methyl)-1,7-naphthyridin-8-ylamino)-2,2'-dimethylbiphenyl-3-yl)-[1,2,4]triazolo[1,5-a]pyridin-6-yl)methyl)pyrrolidine-3-carboxylic acid

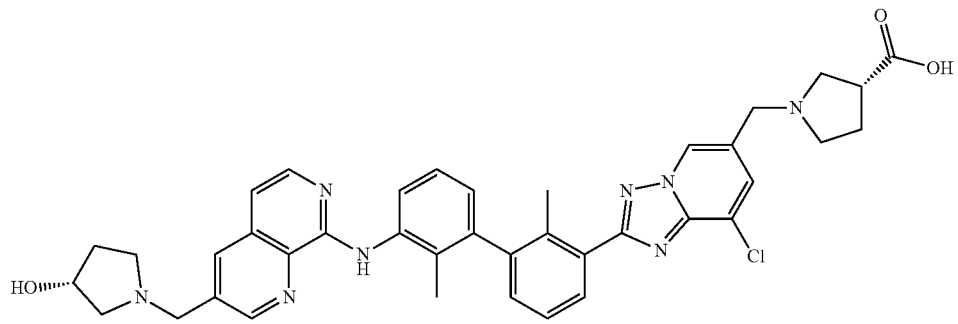 [SMILES: Cc1c(Nc2nccc3cc(CN4CC[C@@H](O)C4)cnc23)cccc1-c1cccc(-c2nc3c(Cl)cc(CN4CC[C@@H](C(=O)O)C4)cn3n2)c1C]

Step 1: ethyl ({[3-chloro-5-(hydroxymethyl)pyridin-2-yl]amino}carbonothioyl)carbamate

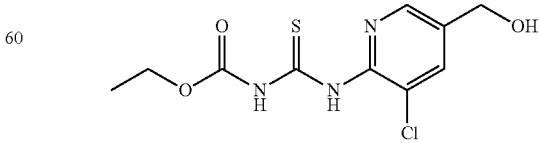

To a solution of (6-amino-5-chloropyridin-3-yl)methanol (649 mg, 4.09 mmol) in 1,4-dioxane (26.5 mL) was added ethoxycarbonyl isothiocyanate (0.694 mL, 6.14 mmol). The reaction mixture was stirred at 50° C. for 2 h. The crude was concentrated. The residue was directly used for the next step. LC-MS calculated for $C_{10}H_{13}ClN_3O_3S$ $(M+H)^+$: m/z=290.0; found: 290.0.

Step 2: (2-amino-8-chloro[1,2,4]triazolo[1,5-a]pyridin-6-yl)methanol

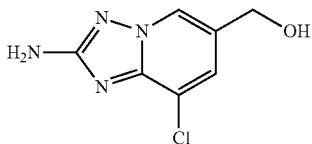 [SMILES: Nc1nc2c(Cl)cc(CO)cn2n1]

Hydroxylamine hydrochloride (0.566 g, 8.14 mmol) was added to a solution of ethyl ({[3-chloro-5-(hydroxymethyl)pyridin-2-yl]amino}carbonothioyl)carbamate (1.18 g, 4.07 mmol) in methanol (15 mL, 370 mmol)/ethanol (15 mL, 260 mmol), followed by N,N-diisopropylethylamine (1.42 mL, 8.14 mmol). The reaction mixture was then stirred at 50° C. for 3 h. The crude was cooled. The precipitate was filtered to give the desired product (728 mg, 90% yield, two steps). LC-MS calculated for $C_7H_8ClN_4O$ $(M+H)^+$: m/z=199.0; found: 199.0.

Step 3: (2-bromo-8-chloro[1,2,4]triazolo[1,5-a]pyridin-6-yl)methanol

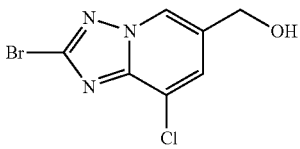 [SMILES: OCc1cc(Cl)c2nc(Br)nn2c1]

tert-Butyl nitrite (0.728 mL, 6.12 mmol) was added to a suspension of (2-amino-8-chloro[1,2,4]triazolo[1,5-a]pyridin-6-yl)methanol (0.811 g, 4.08 mmol) and copper(II) bromide (1.37 g, 6.12 mmol) in acetonitrile (19.1 mL, 365 mmol). The mixture was stirred at room temperature for 1 h. The reaction mixture was diluted with DCM and washed with water. The organic phase was dried, filtered and concentrated to almost dry. The residue was filtered to give the pure product. The filtrate also contained some product and was purified by chromatography on silica gel to give the desired product (combined, 1.06 g, 99% yield). LC-MS calculated for $C_7H_6BrClN_3O$ $(M+H)^+$: m/z=261.9/263.9; found: 261.9/263.9.

Step 4: (2-(3-bromo-2-methylphenyl)-8-chloro-[1,2,4]triazolo[1,5-a]pyridin-6-yl)methanol

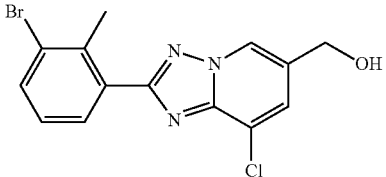 [SMILES: Cc1c(Br)cccc1-c1nc2c(Cl)cc(CO)cn2n1]

A mixture of 2-(3-bromo-2-methylphenyl)-4,4,5,5-tetramethyl-1,3,2-dioxaborolane (727 mg, 2.448 mmol), (2-bromo-8-chloro-[1,2,4]triazolo[1,5-a]pyridin-6-yl)methanol (612 mg, 2.332 mmol), Pd(PPh$_3$)$_4$ (539 mg, 0.466 mmol) and potassium phosphate, tribasic (990 mg, 4.66 mmol) in 1,4-dioxane (11.1 mL)/water (555 µL) was stirred at 90° C. for 1 h. The crude was diluted with DCM, dried, filtered and concentrated. The residue was purified by chromatography on silica gel to give the desired product (516 mg, 63% yield). LC-MS calculated for $C_{14}H_{12}BrClN_3O$ $(M+H)^+$: m/z=352.0; found: 352.1.

Step 5: (8-chloro-2-(2-methyl-3-(4,4,5,5-tetramethyl-1,3,2-dioxaborolan-2-yl)phenyl)-[1,2,4]triazolo[1,5-a]pyridin-6-yl)methanol

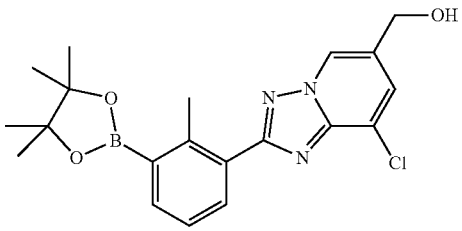 [SMILES: Cc1c(B2OC(C)(C)C(C)(C)O2)cccc1-c1nc2c(Cl)cc(CO)cn2n1]

A mixture of (2-(3-bromo-2-methylphenyl)-8-chloro-[1,2,4]triazolo[1,5-a]pyridin-6-yl)methanol (0.300 g, 0.851 mmol), bis(pinacolato)diboron (0.259 g, 1.021 mmol), dichloro[1,1'-bis(diphenylphosphino)ferrocene]palladium(II) dichloromethane adduct (0.069 g, 0.085 mmol) and potassium acetate (0.209 g, 2.127 mmol) in 1,4-dioxane (5 mL) was charged with nitrogen and stirred at 110° C. for 2 h. The crude was diluted with DCM, and then filtered through Celite®. The filtrate was concentrated. The residue was used directly without further purification. LC-MS calculated for $C_{20}H_{24}BClN_3O_3$ $(M+H)^+$: m/z=400.2; found 400.2.

Step 6: (R)-1-((8-(3'-(8-chloro-6-(hydroxymethyl)-[1,2,4]triazolo[1,5-a]pyridin-2-yl)-2,2-dimethylbiphenyl-3-ylamino)-1,7-naphthyridin-3-yl)methyl)pyrrolidin-3-ol

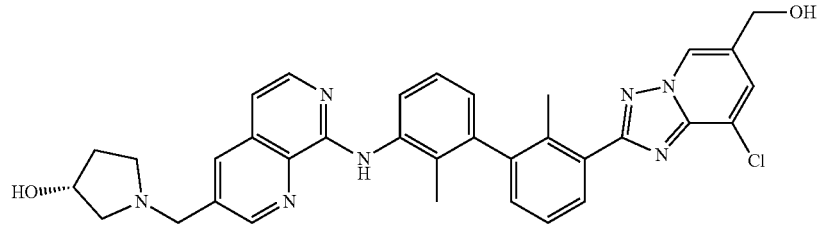 [SMILES: Cc1c(Nc2nccc3cc(CN4CC[C@@H](O)C4)cnc23)cccc1-c1cccc(-c2nc3c(Cl)cc(CO)cn3n2)c1C]

To a vial was added (8-chloro-2-(2-methyl-3-(4,4,5,5-tetramethyl-1,3,2-dioxaborolan-2-yl)phenyl)-[1,2,4]triazolo[1,5-a]pyridin-6-yl)methanol (0.129 g, 0.322 mmol), (R)-1-((8-((3-bromo-2-methylphenyl)amino)-1,7-naphthyridin-3-yl)methyl)pyrrolidin-3-ol (Example 3, Step 4: 0.121 g, 0.293 mmol), 1 M aqueous sodium carbonate (0.586 mmol), tetrakis(triphenylphosphine) palladium(O) (0.034 g, 0.029 mmol), and 1,4-dioxane (2.6 mL). The mixture was degassed, sealed, and heated to 90° C. whilst stirring for 2 h. The mixture was cooled, diluted with EtOAc and filtered through Celite®. The filtrate was concentrated and used directly in the next step without further purification. LC-MS calculated for $C_{34}H_{33}ClN_7O_2$ (M+H): m/z=606.2, found 606.2.

Step 7: (R)-8-chloro-2-(3'-(3-((3-hydroxypyrrolidin-1-yl)methyl)-1,7-naphthyridin-8-ylamino)-2,2'-dimethylbiphenyl-3-yl)-[1,2,4]triazolo[1,5-a]pyridine-6-carbaldehyde

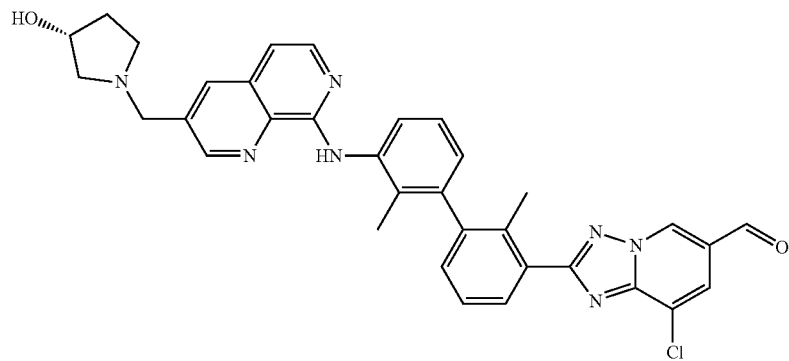 [SMILES: Cc1c(Nc2nccc3cc(CN4CC[C@@H](O)C4)cnc23)cccc1-c1cccc(-c2nc3c(Cl)cc(C=O)cn3n2)c1C]

A suspension of (R)-1-((8-((3'-(8-chloro-6-(hydroxymethyl)-[1,2,4]triazolo[1,5-a]pyridin-2-yl)-2,2'-dimethyl-[1,1'-biphenyl]-3-yl)amino)-1,7-naphthyridin-3-yl)methyl)pyrrolidin-3-ol(40 mg, 0.066 mmol) and manganese dioxide (115 mg, 1.320 mmol) in DCM (660 μL) was stirred at 45°c for 1 h. The reaction was filtered through a pad of Celite® and then concentrated to yield the desired product, which was used directly in the next step without further purification. LC-MS calculated for $C_{34}H_{31}ClN_7O_2$ (M+H)[+]: m/z=604.2; found 604.4.

Step 8: (R)-1-((8-chloro-2-(3'-(3-(((R)-3-hydroxypyrrolidin-1-yl)methyl)-1,7-naphthyridin-8-ylamino)-2,2'-dimethylbiphenyl-3-yl)-[1,2,4]triazolo[1,5-a]pyridin-6-yl)methyl)pyrrolidine-3-carboxylic acid To a vial was added (R)-8-chloro-2-(3'-(3-((3-hydroxypyrrolidin-1-yl)methyl)-1,7-naphthyridin-8-yl)amino)-2,2'-dimethyl-[U'-biphenyl]-3-yl)-[1,2,4]triazolo[1,5-a]pyridine-6-carbaldehyde (0.012 g, 0.020 mmol), (R)-pyrrolidine-3- carboxylic acid (Combi-Blocks, cat # ST-7698: 6.86 mg, 0.060 mmol), dichloromethane (0.3 mL) and triethylamine (0.016 mL, 0.115 mmol). The reaction was stirred at room temperature for 2 h, then sodium triacetoxyborohydride (0.021 g, 0.099 mmol) and acetic acid (3.41 µL, 0.060 mmol) were added. The reaction was stirred for 2 h, then the mixture was diluted with methanol and purified by prep-HPLC (pH=2, acetonitrile/water+TFA) to provide the desired compound as its TFA salt. LC-MS calculated for $C_{39}H_{40}ClN_8O_3$ (M+H)$^+$: m/z=703.3; found 703.2.

Example 187

(R)-1-((7-chloro-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)azetidine-3-carboxylic acid

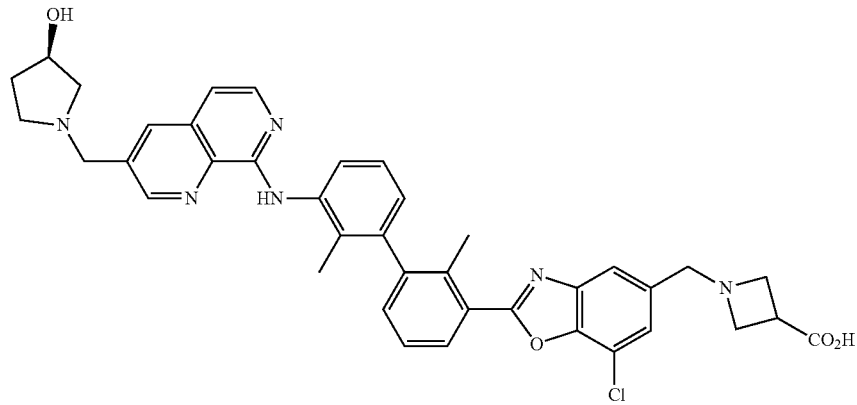 [SMILES: Cc1c(Nc2nccc3cc(CN4CC[C@@H](O)C4)cnc23)cccc1-c1cccc(-c2nc3cc(CN4CC(C(=O)O)C4)cc(Cl)c3o2)c1C]

Step 1: (R)-7-chloro-2-(3'-(3-((3-hydroxypyrrolidin-1-yl)methyl)-1,7-naphthyridin-8-ylamino)-2,2'-dimethyl biphenyl-3-yl)benzo[d]oxazole-5-carbaldehyde

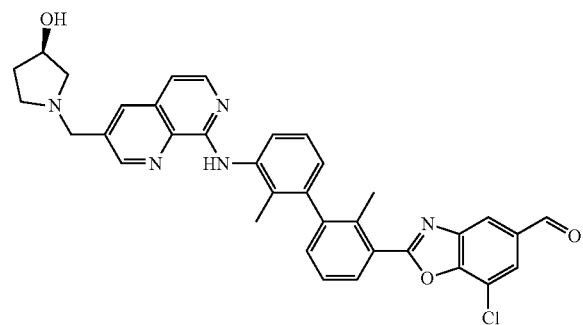 [SMILES: Cc1c(Nc2nccc3cc(CN4CC[C@@H](O)C4)cnc23)cccc1-c1cccc(-c2nc3cc(C=O)cc(Cl)c3o2)c1C]

A suspension of (R)-1-((8-((3'-(7-chloro-5-(hydroxymethyl)benzo[d]oxazol-2-yl)-2,2'-dimethyl-[1,1'-biphenyl]-3-yl)amino)-1,7-naphthyridin-3-yl)methyl)pyrrolidin-3-ol (Example 3, Step 5: 1.0 g, 1.65 mmol) and manganese dioxide (2.87 g, 33.0 mmol) in DCM (11 mL) was stirred at 45° C. for 15 min. The reaction mixture was cooled to room temperature, filtered through a short pad of celite and then concentrated to yield a crude residue, which was used directly without further purification. LC-MS calculated for $C_{35}H_{31}ClN_5O_3$ (M+H)$^+$: m/z=604.2; found 604.4.

Step 2: (R)-1-((7-chloro-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazol-5-yl)methyl)azetidine-3-carboxylic acid A mixture of (R)-7-chloro-2-(3'-((3-((3-hydroxypyrrolidin-1-yl)methyl)-1,7-naphthyridin-8-yl)amino)-2,2'-dimethyl-[1,1'-biphenyl]-3-yl)benzo[d]oxazole-5-carbaldehyde (10 mg, 0.017 mmol), azetidine-3-carboxylic acid (1.674 mg, 0.017 mmol), and DIPEA (8.7 µL, 0.050 mmol) in DMF (1 mL) was stirred at room temperature for 2 h. Then sodium cyanoborohydride (3.2 mg, 0.050 mmol) and acetic acid (5.7 µL, 0.099 mmol) was added. The mixture was further stirred at room temperature for 1 h. The reaction mixture was diluted with MeOH then purified by prep-HPLC (pH=2, acetonitrile/water+TFA) to give the desired product as TFA salt. LC-MS calculated for $C_{39}H_{38}ClN_6O_5$ (M+H)$^+$: m/z=689.3; found 689.3.

Example 188

(R)-1-((2-(3'-(8-chloro-6-(((R)-3-hydroxypyrrolidin-1-yl)methyl)-[1,2,4]triazolo[1,5-a]pyridin-2-yl)-2,2'-dimethylbiphenyl-3-yl)-7-cyanobenzo[d]oxazol-5-yl)methyl)pyrrolidine-3-carboxylic acid

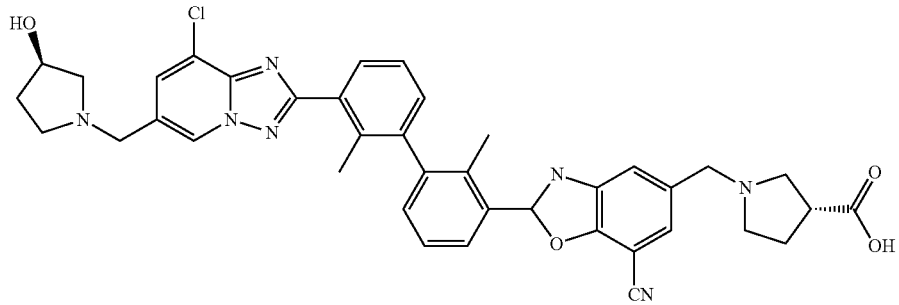 [SMILES: Cc1c(-c2nc3c(Cl)cc(CN4CC[C@@H](O)C4)cn3n2)cccc1-c1cccc(C2Nc3cc(CN4CC[C@@H](C(=O)O)C4)cc(C#N)c3O2)c1C]

Step 1: 2-(3-bromo-2-methylphenyl)-8-chloro-[1,2,4]triazolo[1,5-a]pyridine-6-carbaldehyde

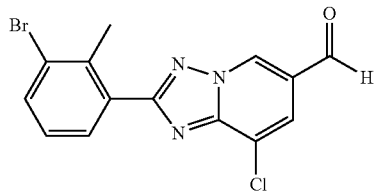 [SMILES: Cc1c(Br)cccc1-c1nc2c(Cl)cc(C=O)cn2n1]

Dess-Martin periodinane (722 mg, 1.7 mmol) was added to the suspension of (2-(3-bromo-2-methylphenyl)-8-chloro-[1,2,4]triazolo[1,5-a]pyridin-6-yl)methanol (Example 186, Step 4: 500 mg, 1.418 mmol) in DCM (7.09 mL). The mixture was stirred at 50° C. for 1 h. The crude was quenched with aq. Na$_2$S$_2$O$_3$ and NaHCO$_3$ and extracted with DCM. The organic phase was dried, filtered and concentrated. The residue was purified by chromatography on silica (10-30% EtOAc/Hex) gel to give the desired product 495 mg (100% yield). LC-MS calculated for C$_{14}$H$_{10}$BrClN$_3$O (M+H)+: m/z=350.0 and 352.0; found 350.0 and 352.0.

Step 2: (R)-1-((2-(3-bromo-2-methylphenyl)-8-chloro-[1,2,4]triazolo[1,5-a]pyridin-6-yl)methyl)pyrrolidin-3-ol

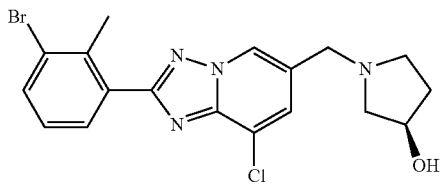 [SMILES: Cc1c(Br)cccc1-c1nc2c(Cl)cc(CN3CC[C@@H](O)C3)cn2n1]

A mixture of 2-(3-bromo-2-methylphenyl)-8-chloro-[1,2,4]triazolo[1,5-a]pyridine-6-carbaldehyde (89.0 mg, 0.254 mmol), (R)-pyrrolidin-3-ol (66.3 mg, 0.762 mmol) and TEA (58.7 μL, 0.762 mmol) in DMF (2.54 mL) was stirred at room temperature overnight. Sodium triacetoxyborohydride (161 mg, 0.762 mmol) was added at 0° C. The mixture was stirred at room temperature for 1 h. The crude was quenched with aq. NaHCO$_3$ and extracted with DCM. The organic phase was dried, filtered and concentrated. The residue was directly used for the next step. LC-MS calculated for C$_{18}$H$_{19}$BrClN$_4$O (M+H)+: m/z=421.0 and 423.0; found 421.1 and 423.0.

Step 3: (R)-2-(3'-(8-chloro-6-((3-hydroxypyrrolidin-1-yl)methyl)-[1,2,4]triazolo[1,5-a]pyridin-2-yl)-2,2'-dimethylbiphenyl-3-yl)-5-(hydroxymethyl)benzo[d]oxazole-7-carbonitrile

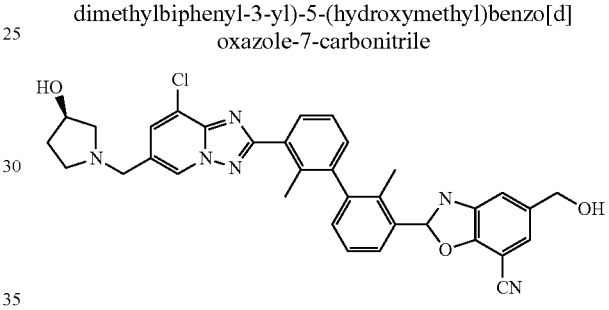

A mixture of 5-(hydroxymethyl)-2-(2-methyl-3-(4,4,5,5-tetramethyl-1,3,2-dioxaborolan-2-yl)phenyl)benzo[d]oxazole-7-carbonitrile (Example 12, Step 2: 58.9 mg, 0.151 mmol), (R)-1-((2-(3-bromo-2-methylphenyl)-8-chloro-[1,2,4]triazolo[1,5-a]pyridin-6-yl)methyl)pyrrolidin-3-ol (53.0 mg, 0.126 mmol), tetrakis(triphenylphosphine)palladium(0) (29.0 mg, 0.025 mmol) and potassium phosphate, tribasic (53.4 mg, 0.251 mmol) in 1,4-dioxane (598 μl) and water (29.9 μl) was stirred at 90° C. for 3 h. The crude was diluted with DCM, filtered and concentrated. The residue was purified by chromatography (5-15% MeOH/DCM) on silica gel to give the desired product 61.6 mg (81% yield). LC-MS calculated for C$_{34}$H$_{30}$ClN$_6$O$_3$ (M+H)+: m/z=605.2; found 605.2.

Step 4: (R)-2-(3'-(8-chloro-6-((3-hydroxypyrrolidin-1-yl)methyl)-[1,2,4]triazolo[1,5-a]pyridin-2-yl)-2,2'-dimethylbiphenyl-3-yl)-5-formylbenzo[d]oxazole-7-carbonitrile

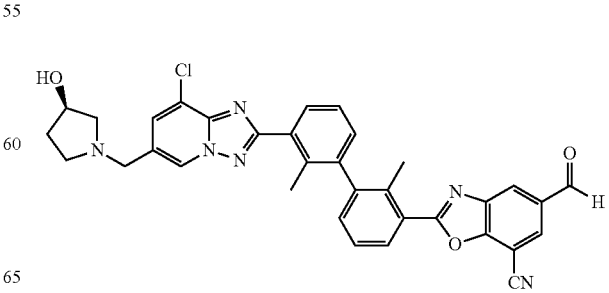

Manganese dioxide (177 mg, 2.036 mmol) was added to the solution of (R)-2-(3'-(8-chloro-6-((3-hydroxypyrrolidin-1-yl)methyl)-[1,2,4]triazolo[1,5-a]pyridin-2-yl)-2,2'-dimethyl-[1,1'-biphenyl]-3-yl)-5-(hydroxymethyl)benzo[d]oxazole-7-carbonitrile (61.6 mg, 0.102 mmol) in DCM (509 µl). The mixture was stirred at 50° C. for 1 h. The crude was filtered. The residue was purified with chromatography on silica gel to give the desired product 55.2 mg (90% yield). LC-MS calculated for $C_{34}H28ClN_6O_3$ (M+H)$^+$: m/z=603.2; found 603.2.

Step 5: (R)-1-(2-(3'-(8-chloro-6-(((R)-3-hydroxypyrrolidin-1-yl)methyl)-[1,2,4]triazolo[1,5-a]pyridin-2-yl)-2,2'-dimethylbiphenyl-3-yl)-7-cyanobenzo[d]oxazol-5-yl)methyl)pyrrolidine-3-carboxylic acid A mixture of (R)-2-(3'-(8-chloro-6-((3-hydroxypyrrolidin-1-yl)methyl)-[1,2,4]triazolo[1,5-a]pyridin-2-yl)-2,2'-dimethyl-[1,1'-biphenyl]-3-yl)-5-formylbenzo[d]oxazole-7-carbonitrile (19.0 mg, 0.032 mmol) and (R)-pyrrolidine-3-carboxylic acid (10.88 mg, 0.095 mmol) in DMF (315 µl) was stirred at room temperature overnight. Sodium triacetoxyborohydride (20.03 mg, 0.095 mmol) was added at 0° C. The reaction was stirred at room temperature for 1 h. The crude was diluted with MeOH and purified by prep-HPLC (pH=2, acetonitrile/water+TFA) to give the desired product as the TFA salt. LC-MS calculated for $C_{39}H_{37}ClN_7O_4$ (M+H)$^+$: m/z=702.3; found 702.4.

Example 189

(R)-1-((7-cyano-2-(3'-(8-cyano-6-(((R)-3-hydroxypyrrolidin-1-yl)methyl)-[1,2,4]triazolo[1,5-a]pyridin-2-yl)-2,2'-dimethylbiphenyl-3-yl)benzo[d]oxazol-5-yl)methyl)pyrrolidine-3-carboxylic acid Example 9A: T Cell Activation Assay Using Artificial Antigen Presenting Cell (aAPC)

Mononuclear blood cells were isolated from leucopaks from normal donors using Ficoll gradient separation. T cells were enriched using Pan T Cell Isolation Negative selection kit (Miltenyi) using manufacturer's protocol. The isolated T cells were confirmed by anti-CD3 staining (>95% by flow cytometry) and frozen in Cryostor Freezing Media CS10 (BioLife Solutions) until use.

10,000 PDL1 aAPC/CHO-K1 (Promega) cells were seeded into 96-well tissue culture plates in 100 ul of F-12 Media with 10% FBS and allowed to attach overnight in a 37 C/5% CO2 incubator. The next day, frozen T cells were thawed and resuspended to 1×10$^6$ cells/ml in T cell medium (IMDM with 10% HI FBS, 1× Glutamine, 1× Non-essential amino acid, 1000× Mercaptoethanol, and 1× Sodium Pyruvate). The media from the CHOK1 cell plates was replaced with 130 ul of T Cell Media. Inhibitors were serially diluted in DMSO and spotted into plates. The dots were resuspended in 100× volume of T cell media, and 20 ul of each compound was added each well of the cell plate. Then 50,000 T cells were transferred into each well and incubated at 37 C/5% CO2 for 72 hrs. After 3 days, the conditioned medium was harvested. The levels of hIFNg and hIL2 were assayed using a ProCartaplex 2 plex kit (Life Technologies) for hIFNg and hIL2 according to the manufacturer's protocols and analyzed on a Luminex Flexmap 3D instrument. DMSO treated cells were used as the control. Data for tested compounds are shown in Table 28 below. + refers to <10 nM; ++refers to >=10 nM to <100 nM; +++refers to >=100 nM to <=500 nM; and ++++refers to >500 nM.

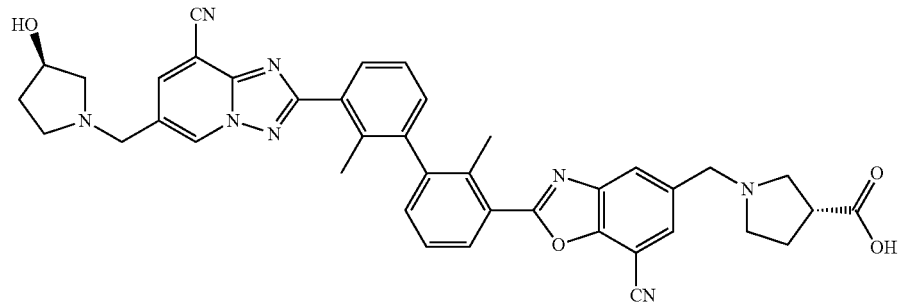 [SMILES: Cc1c(-c2nc3c(C#N)cc(CN4CC[C@@H](O)C4)cn3n2)cccc1-c1cccc(-c2nc3cc(CN4CC[C@@H](C(=O)O)C4)cc(C#N)c3o2)c1C]

A mixture of (R)-1-((2-(3'-(8-chloro-6-(((R)-3-hydroxypyrrolidin-1-yl)methyl)-[1,2,4]triazolo[1,5-a]pyridin-2-yl)-2,2'-dimethylbiphenyl-3-yl)-7-cyanobenzo[d]oxazol-5-yl)methyl)pyrrolidine-3-carboxylic acid (Example 188: 6.0 mg, 8.54 µmol), potassium ferrocyanide(II) trihydrate (3.61 mg, 8.54 µmol), potassium acetate (0.084 mg, 0.854 µmol) and [(2-di-tert-butylphosphino-2',4',6'-triisopropyl-1,1'-biphenyl)-2-(2'-amino-1,1'-biphenyl)]palladium(II) methanesulfonate (0.68 mg, 0.85 µmol) in 1,4-dioxane (21.4 µl) and water (21.4 µl) was stirred at 90° C. for 30 min. The crude was diluted with MeOH and purified by prep-HPLC (pH=2, acetonitrile/water+TFA) to give the desired product as the TFA salt. LC-MS calculated for $C_{40}H_{37}N_8O_4$ (M+H)$^+$: m/z=693.3; found 693.3.

TABLE 28

| Compound from Table 2 | T cell IFNg secretion median EC$_{50}$ (nM) |
| --- | --- |
| 7 | ++ |
| 8 | ++ |
| 9 | ++ |
| 10 | ++ |
| 11 | + |
| 12 | ++ |
| 13 | ++ |
| 14 | ++ |
| 15 | +++ |
| 16 | ++ |
| 17 | +++ |
| 18 | ++ |
| 19 | +++ |
| 20 | ++ |

TABLE 28-continued

| Compound from Table 2 | T cell IFNg secretion median $EC_{50}$ (nM) |
|---|---|
| 21 | +++ |
| 22 | + |
| 23 | +++ |
| 24 | ++ |
| 25 | ++ |
| 26 | ++ |

Example 10A: Results of Binding Assay

Several compounds were assessed in the PD-1-PD-L1 HTRF binding assay (Example 1B). The results obtained for the tested compounds are shown in Table 29. The cutoffs for ranges of values observed the assay is shown in Table 1.

TABLE 29

| Compound from Example Number | PD-1-PD-L1 Binding $IC_{50}$ (nM) (HTRF) |
|---|---|
| 60 | + |
| 61 | + |
| 62 | + |
| 63 | + |
| 64 | + |
| 65 | + |
| 66 | + |
| 67 | + |
| 68 | + |
| 69 | + |
| 70 | + |
| 71 | + |
| 72 | + |
| 73 | + |
| 74 | + |
| 75 | + |
| 76 | + |
| 77 (compound 77-1) | + |
| 77 (compound 77-2) | + |
| 78 | + |
| 79 | + |
| 80 | + |
| 81 | + |
| 82 (compound 82-1) | + |
| 82 (compound 82-2) | + |
| 83 | + |
| 84 | + |
| 85 | + |
| 86 | + |
| 87 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 99 | + |
| 100 | + |
| 101 | + |
| 102 | + |
| 103 | + |
| 104 | + |
| 105 | + |
| 106 | + |
| 107 | + |
| 108 | + |
| 109 | + |
| 110 | + |
| 111 | + |

TABLE 29-continued

| Compound from Example Number | PD-1-PD-L1 Binding $IC_{50}$ (nM) (HTRF) |
|---|---|
| 112 | + |
| 113 | + |
| 114 | + |
| 115 | + |
| 116 | + |
| 117 | + |
| 118 | + |
| 119 | + |
| 120 (compound 120-1) | + |
| 120 (compound 120-2) | + |
| 121 | + |
| 122 | + |
| 123 | + |
| 124 | + |
| 125 | + |
| 126 | + |
| 127 | + |
| 128 | + |
| 129 | + |
| 130 | + |
| 131 | + |
| 132 | + |
| 133 | + |
| 134 (compound 134-1) | + |
| 134 (compound 134-2) | + |
| 135 | + |
| 136 | + |
| 137 | + |
| 138 (compound 138-1) | + |
| 138 (compound 138-2) | + |
| 139 | + |
| 140 | + |
| 141 | + |
| 142 (compound 142-1) | + |
| 142 (compound 142-2) | + |
| 143 (compound 143-1) | + |
| 143 (compound 143-2) | + |
| 144 (compound 144-1) | + |
| 144 (compound 144-2) | + |
| 145 (compound 145-1) | + |
| 145 (compound 145-2) | + |
| 146 (compound 146-1) | + |
| 146 (compound 1462) | + |
| 147 | + |
| 148 | + |
| 149 | + |
| 150 | + |
| 151 | + |
| 152 | + |
| 153 | + |
| 154 | + |
| 155 | + |
| 156 | + |
| 157 | + |
| 158 | + |
| 159 | + |
| 160 | + |
| 161 | + |
| 162 | + |
| 163 | + |
| 164 | + |
| 165 | + |
| 166 | + |
| 167 | + |
| 168 | + |
| 169 | + |
| 170 | + |
| 171 | + |
| 172 | + |
| 173 | + |
| 174 | + |
| 175 (compound 175-1) | + |
| 175 (compound 175-2) | + |
| 176 | + |
| 177 | + |
| 178 | + |
| 179 | ++ |

TABLE 29-continued

| Compound from Example Number | PD-1-PD-L1 Binding IC$_{50}$ (nM) (HTRF) |
|---|---|
| 180 | + |
| 181 | + |
| 182 | + |
| 183 (compound 183-1) | + |
| 183 (compound 183-2) | + |

Example 11A: Malignant Pleural Effusion from Non-Small Cell Lung Cancer Patients Human patients were recruited and staged radio graphically. Patients then underwent insertion of a tunneled intrapleural catheter under local anesthesia as an outpatient. If this was not technically feasible, a pleural catheter was inserted via thoracoscopy under general anesthesia by thoracic surgery or via image-guided placement by interventional radiology. Pleural effusion fluids obtained were used in the methods of Example 12A.

Example 12A: Determination of Macrophage PD-L1 Internalization Induced by a Compound of the Invention as Exemplified in Table 2

Pleural effusion fluids were spun down at 1200 rpm for 7 min to form cell pellet, followed by resuspending with AIM-V culture medium at the cell density of 5×10$^6$/mL. To determine the effect of the PD-L1 inhibitors on pleural effusion macrophage surface PD-L1, 10 μL of a compound in Table 2 at appropriate dilutions was added to a 96 well Assay Block (Costar). Pleural effusion cells (190 μL; 1×10$^6$ cells) were then transferred to the Assay Block. In some studies, human IFNγ (R&D) was added to the cell suspension to reach the final concentration of 1 ng/mL prior to the transfer. A negative control with no IFNγ was also included. Plates were incubated at 37° C., 5% CO$_2$ for 18-20 hr. After overnight incubation, cells were collected, washed with phosphate buffered saline, and then stained with BV421 viability dye (BD Bioscience) for 15 min in dark. Cells were then washed with PBS again, followed by addition of 11 μL of Ab mixture (3 μL of PE conjugated anti-CD274 (clone M1H1; BD Bioscience)+1 μL of APC-conjugated anti-CD14 (clone MHCD1405; Life Technologies)+1 μL of BUV395 conjugated anti-CD11b (clone D12, BD Biosciences)+2 μL of PercP-Cy5.5 conjugated anti-PD-L2 (clone M1H18, BD Bioscience)+2 μL of BV785 conjugated anti-EpCAM and 2 μL V500 conjugated anti-CD45 (clone HI30; BD Bioscience)) was added and incubated 30 minutes in the dark. Prewarmed fixation buffer (BD Bioscience) was added and incubated for 10 min at 37° C., plates centrifuged at 1600 rpm for 5 min and 500 μL staining buffer was added to the pellet. Flow cytometric analysis was performed. Cells were gated on CD14+ and read on PD-L1 mean fluorescence intensity (BD LSRFortessa™ X-20). The data was converted to percent inhibition relative to DMSO control and the compound in Table 2. IC$_{50}$ determination was performed by fitting the curve of percent inhibition versus the log of the inhibitor concentration using GraphPad Prism 6.0 software.

Figure 2:
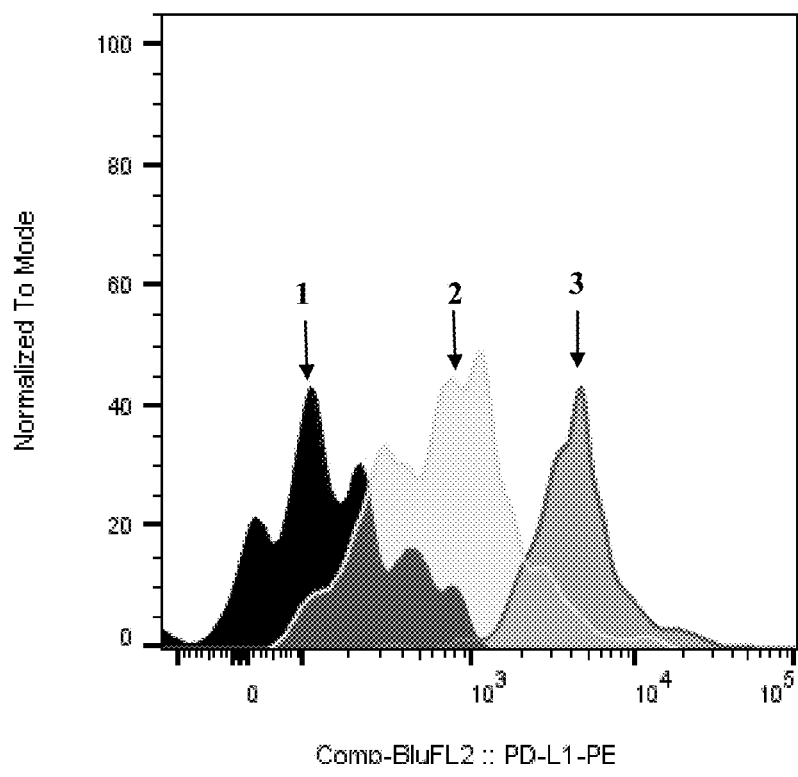
FIG. 2 is a graph depicting the internalization of a compound of the invention as exemplified in Table 2 using pleural effusion macrophages from a NSCLC patient treated with or without IFNg.

Results of this study are shown in FIG. 2. Ex vivo stimulation of the macrophages with IFNg resulted in an increase in surface PDL1. Comparing the potency of a PDL1 inhibitor to induce PDL1 internalization between unstimulated and stimulated cells showed that the compound was more potent in macrophages stimulated with IFNg.

Example 13A: Efficacy Study

A compound of the invention as exemplified in Table 2 was suspended in 5% DMAC in 0.5% (w/v) methylcellulose (Sigma catalog # MC430) for oral dosing of huCD34 engrafted NSG mice (The Jackson Laboratory, Bar Harbor, Me.). The 5% DMAC in 0.5% methylcellulose solution without the compound was included in all studies as a control. For the in vivo assessment of the compound in Table 2, female human CD34+ reconstituted mice (33 weeks of age; The Jackson Laboratory, Bar Harbor, Me.) were inoculated subcutaneously with 3×10$^6$ MDA-MB-231 cells (ATCC # HTB-26). The treatment of tumor-bearing mice was started 7 days post inoculation when tumor volume reached approximately 160 mm$^3$. Dosing continued until day 33 post inoculation. Tumor measurements were taken twice weekly to assess efficacy.

Figure 3:
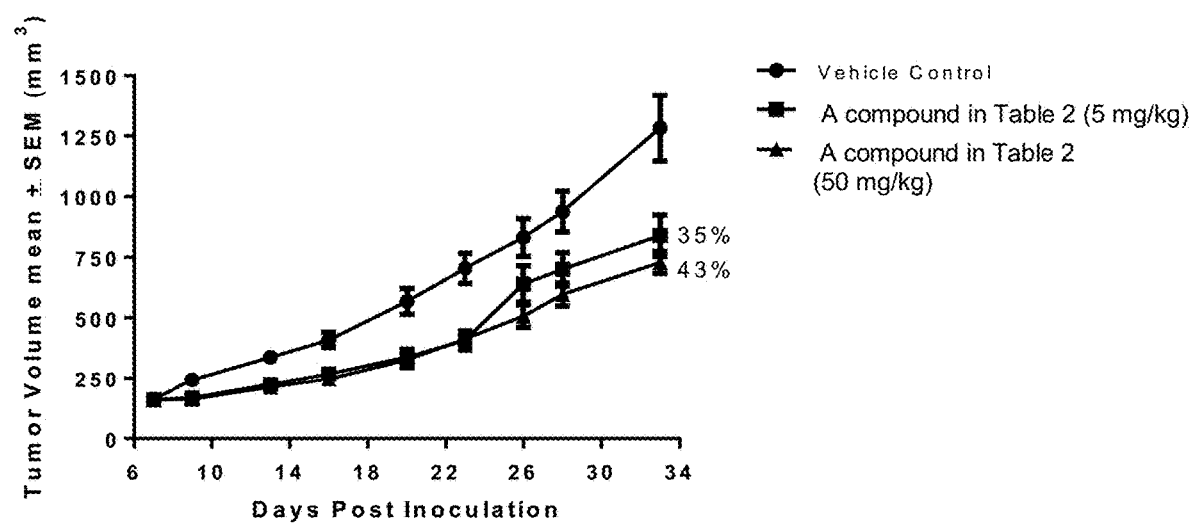
FIG. 3 is a graph depicting efficacy of a compound of the invention as exemplified in Table 2 in the MDA-MB-231 tumor model grafted into human CD34+ reconstituted NSG mice.

Results of this study are shown in FIG. 3.

Example 14A: Internalization of a Compound of the Invention as Exemplified in Table 2 Using CHOK1-PDL1 Cells Expressing High or Moderate Levels of PDL1

Figure 4A:
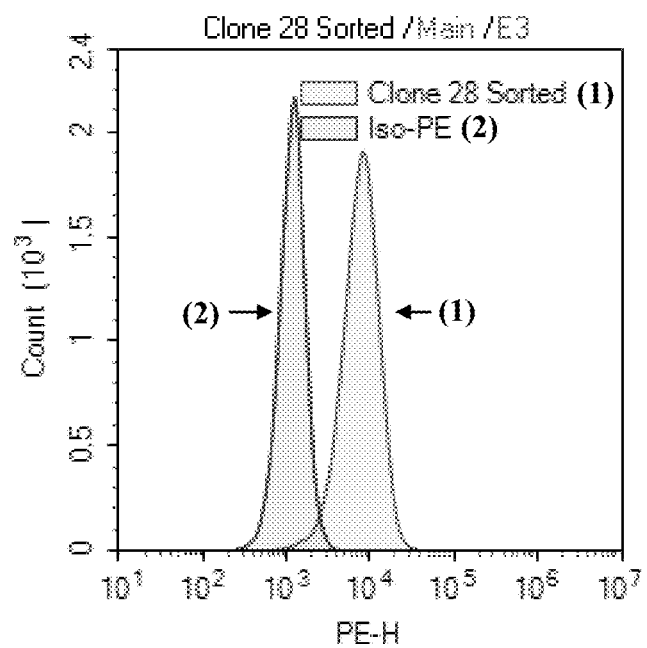
FIGS. 4A and 4B are graphs depicting internalization of a compound of the invention as exemplified in Table 2 using CHOK1-PDL1 cells expressing moderate (FIG. 4A) and high (FIG. 4B) levels of PDL1.
Figure 4B:
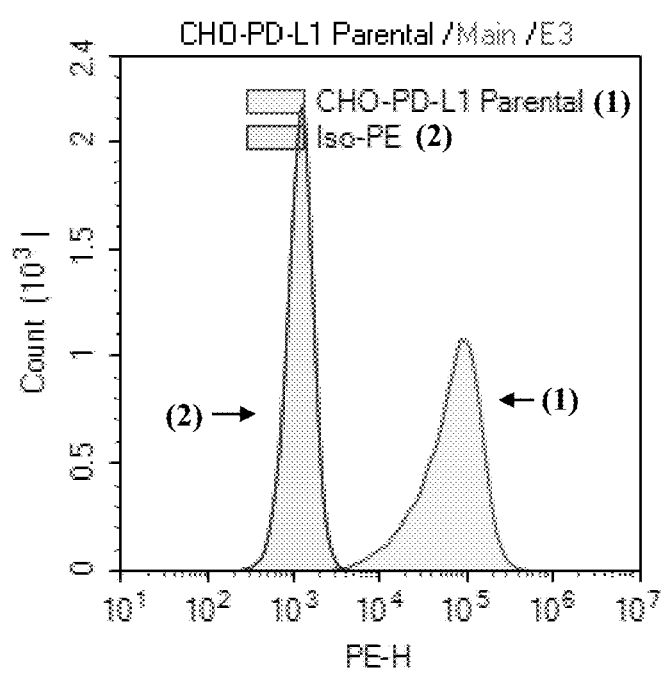

Results of the internalization of a compound in Table 2 using CHOK1-PDL1 cells expressing high or moderate levels of PDL1 are shown in FIG. 4. The EC$_{50}$ value for PDL1 internalization by the PDL1 inhibitor decreases as the density of PDL1 on the target cell increases. In the example, CHOK1 cells with high expression of PDL1 had a lower EC$_{50}$ value for PDL1 internalization than CHOK1 cells with lower levels of expression. This result suggests that the potency of the compound is not fixed but is related to the levels of the target protein (PDL1).

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A compound selected from:
trans-4-((2-(2-chloro-3'-(5-(2-(ethyl(methyl)amino) acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl) cyclohexane-1-carboxylic acid;
cis-4-((2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid;
4-(2-(2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)ethyl)cyclohexane-1-carboxylic acid; and
4-(2-(2-(2-chloro-3'-(5-(2-(isopropyl(methyl)amino) acetyl)-5,6-dihydro-4H-pyrrolo[3,4-d]thiazol-2-yl)-2'-methylbiphenyl-3-ylcarbamoyl)-1-methyl-6,7-di- hydro-1H-imidazo[4,5-c]pyridin-5(4H)-yl)ethyl)
cyclohexane-1-carboxylic acid;
or a pharmaceutically acceptable salt thereof.

2. The compound of claim 1, which is trans-4-((2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid, or a pharmaceutically acceptable salt thereof.

3. The compound of claim 1, which is trans-4-((2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid.

4. The compound of claim 1, which is cis-4-((2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid, or a pharmaceutically acceptable salt thereof.

5. The compound of claim 1, which is cis-4-((2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)methyl)cyclohexane-1-carboxylic acid.

6. The compound of claim 1, which is 4-(2-(2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)ethyl)cyclohexane-1-carboxylic acid, or a pharmaceutically acceptable salt thereof.

7. The compound of claim 1, which is 4-(2-(2-(2-chloro-3'-(5-(2-(ethyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)ethyl)cyclohexane-1-carboxylic acid.

8. The compound of claim 1, which is 4-(2-(2-(2-chloro-3'-(5-(2-(isopropyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)ethyl)cyclohexane-1-carboxylic acid, or a pharmaceutically acceptable salt thereof.

9. The compound of claim 1, which is 4-(2-(2-(2-chloro-3'-(5-(2-(isopropyl(methyl)amino)acetyl)-5,6-dihydro-4H-pyrrolo[3,4-d]thiazol-2-yl)-2'-methylbiphenyl-3-ylcarbamoyl)-1-methyl-6,7-dihydro-1H-imidazo[4,5-c]pyridin-5(4H)-yl)ethyl)cyclohexane-1-carboxylic acid.

10. A pharmaceutical composition comprising the compound of claim 2, or a pharmaceutically acceptable salt thereof, and a pharmaceutically acceptable carrier or excipient.

11. A pharmaceutical composition comprising the compound of claim 3 and a pharmaceutically acceptable carrier or excipient.

12. A pharmaceutical composition comprising the compound of claim 4, or a pharmaceutically acceptable salt thereof, and a pharmaceutically acceptable carrier or excipient.

13. A pharmaceutical composition comprising the compound of claim 5 and a pharmaceutically acceptable carrier or excipient.

14. A pharmaceutical composition comprising the compound of claim 6, or a pharmaceutically acceptable salt thereof, and a pharmaceutically acceptable carrier or excipient.

15. A pharmaceutical composition comprising the compound of claim 7 and a pharmaceutically acceptable carrier or excipient.

16. A pharmaceutical composition comprising the compound of claim 8, or a pharmaceutically acceptable salt thereof, and a pharmaceutically acceptable carrier or excipient.

17. A pharmaceutical composition comprising the compound of claim 9 and a pharmaceutically acceptable carrier or excipient.

* * * * *

UNITED STATES PATENT AND TRADEMARK OFFICE
CERTIFICATE OF CORRECTION

PATENT NO. : 10,806,785 B2
APPLICATION NO. : 15/851497
DATED : October 20, 2020
INVENTOR(S) : Liang Lu et al.

It is certified that error appears in the above-identified patent and that said Letters Patent is hereby corrected as shown below:

On the Title Page

Column 2, Line 2, delete "acylation" and insert -- arylation --.

Signed and Sealed this
Twentieth Day of April, 2021

Drew Hirshfeld
*Performing the Functions and Duties of the*
*Under Secretary of Commerce for Intellectual Property and*
*Director of the United States Patent and Trademark Office*